United States Patent
Yamada et al.

(10) Patent No.: US 12,024,549 B2
(45) Date of Patent: Jul. 2, 2024

(54) COMPOUND HAVING AFFINITY SUBSTANCE TO SOLUBLE PROTEIN, CLEAVABLE PORTION AND REACTIVE GROUP, OR SALT THEREOF

(71) Applicant: Ajinomoto Co., Inc., Tokyo (JP)

(72) Inventors: Kei Yamada, Kawasaki (JP); Yutaka Matsuda, Kawasaki (JP); Tomohiro Fujii, Kawasaki (JP); Natsuki Shikida, Kawasaki (JP); Reiko Yuji, Kawasaki (JP); Kazutaka Shimbo, Kawasaki (JP); Yuji Ito, Kagoshima (JP)

(73) Assignee: Ajinomoto Co., Inc., Tokyo (JP)

(*) Notice: Subject to any disclaimer, the term of this patent is extended or adjusted under 35 U.S.C. 154(b) by 1066 days.

(21) Appl. No.: 16/663,791

(22) Filed: Oct. 25, 2019

(65) Prior Publication Data

US 2020/0190165 A1 Jun. 18, 2020

Related U.S. Application Data

(63) Continuation of application No. PCT/JP2018/017345, filed on Apr. 27, 2018.

(30) Foreign Application Priority Data

Apr. 28, 2017 (JP) ................................. 2017-090679

(51) Int. Cl.
  *C07K 16/00* (2006.01)
  *C07K 19/00* (2006.01)

(52) U.S. Cl.
  CPC .............. *C07K 16/00* (2013.01); *C07K 19/00* (2013.01); *C07K 2317/52* (2013.01)

(58) Field of Classification Search
  None
  See application file for complete search history.

(56) References Cited

U.S. PATENT DOCUMENTS

| | | | |
|---|---|---|---|
| 9,732,161 B2 | 8/2017 | Thanos et al. | |
| 2004/0234377 A1 | 11/2004 | Bolt | |
| 2006/0205670 A1 | 9/2006 | Bradshaw et al. | |
| 2009/0041674 A1 | 2/2009 | Jones et al. | |
| 2016/0000933 A1* | 1/2016 | Polukhtin ............ | C07D 223/24 562/44 |
| 2017/0081400 A1* | 3/2017 | Poulton ................ | C07K 16/241 |
| 2018/0141976 A1* | 5/2018 | Ito ......................... | C07K 7/08 |

FOREIGN PATENT DOCUMENTS

| | | |
|---|---|---|
| CN | 105377307 A | 3/2016 |
| EP | 1 056 474 A | 12/2000 |
| EP | 1 757 311 | 2/2009 |
| EP | 3 015 116 A1 | 5/2016 |
| EP | 3 299 383 A1 | 3/2018 |
| JP | 2005513340 | 5/2005 |
| JP | 2009-531302 | 9/2009 |
| JP | 2016-523900 | 8/2016 |
| KR | 10-2018-0002734 A | 1/2018 |
| WO | WO 2008/056346 | 5/2008 |
| WO | WO-2011121560 A2 * | 10/2011 ............. A61K 47/26 |
| WO | 2015/191883 A1 | 12/2015 |
| WO | 2016/186206 A1 | 11/2016 |
| WO | WO2017106643 | 6/2017 |
| WO | 2017/191817 A1 | 11/2017 |
| WO | 2017/217347 A1 | 12/2017 |

OTHER PUBLICATIONS

Yao et al. Methods to design and synthesize antibody-drug conjugates (ADCs) Int. J. Mol. Sci. 2016, 17, 194 (Year: 2016).*
Bellucci et al. "A noncanonical function of sortase enables site-specific conjugation of small molecules to Lysine residues in proteins" Angew. Chem. Int. Ed. 2015, 54, 441-445 (Year: 2015).*
Extended European Search Report issued Nov. 12, 2020 in European Patent Application No. 18791007.0, 10 pages.
Zimmerman, E.S., et al., "Production of Site-Specific Antibody-Drug Conjugates Using Optimized Non-Natural Amino Acids in a Cell-Free Expression System", Bioconjugate Chemistry, Jan. 17, 2014, vol. 25, No. 2, XP055107336, pp. 351-361.
Yao, H., et al., "Methods to Design and Synthesize Antibody-Drug Conjugates (ADCs)", International Journal of Molecular Sciences, Feb. 2, 2016, vol. 17, No. 2, XP055549886, pp. 1-16.
International Search Report issued Aug. 7, 2018 in Application No. PCT/JP2018/017345.
Reichert JM, et al., "Monoclonal antibody successes in the clinic", Nat Biotechnol 2005; 23: p. 1073-1078.
Tsuchikama, K., et al., "Antibody-drug conjugates: recent advances in conjugation and linker chemistries", Protein Cell, Jan. 2018, vol. 9, No. 1, pp. 33-46.
Kubota T, et al., "Engineered therapeutic antibodies with improved effector functions", Cancer Sci 2009; 100: p. 1566-1572.

(Continued)

*Primary Examiner* — Sharon X Wen
(74) *Attorney, Agent, or Firm* — Oblon, McClelland, Maier & Neustadt, L.L.P.

(57) ABSTRACT

The present invention provides a technique enabling modification of a soluble protein and in particular regioselective modification of a soluble protein. More specifically, the present invention provides a compound having an affinity substance to a soluble protein, a cleavable portion, and a reactive group represented by the following Formula (I):

$$A\text{-}L\text{-}B\text{-}R \qquad (I)$$

wherein
  A is an affinity substance to a soluble protein;
  L is a cleavable linker which is a divalent group comprising a cleavable portion;
  B is (a) a divalent group comprising a bioorthogonal functional group or (b) a divalent group comprising no bioorthogonal functional group; and
  R is a reactive group to the soluble protein; or
a salt thereof.

14 Claims, 73 Drawing Sheets

Specification includes a Sequence Listing.

(56) References Cited

OTHER PUBLICATIONS

Wu AM, et al., "Arming antibodies: prospects and challenges for immunoconjugates", Nat Biotechnol 2005; 23: p. 1137-1146.
Junutula JR, et al., "Site-specific conjugation of a cytotoxic drug to an antibody improves the therapeutic index", Nat Biotechnol 2008; 26: p. 925-932.
Shen BQ, et al., "Conjugation site modulates the in vivo stability and therapeutic activity of antibody-drug conjugates", Nat Biotechnol 2012; 30: p. 184-189.
Hofer T, et al., "Molecularly defined antibody conjugation through a selenocysteine interface", Biochemistry 2009; 48: p. 12047-12057.
Liu W, et al., "Genetic incorporation of unnatural amino acids into proteins in mammalian cells", Nat Methods 2007; 4: p. 239-244.
S.T. Laughlin, et al., "In Vivo Imaging of Membrane-Associated Glycans in Developing Zebrafish", Science 2008; 320, 664.
A.E. Speers, et al., "Chemical Strategies for Activity-Based Proteomics", ChemBioChem 2004; 5, 41.
Y Takaoka, et al., "Protein Organic Chemistry and Applications for Labeling and Engineering in Live-Cell Systems", Angew. Chem. Int. Ed. 2013; 52, 4088.
Isotope News, 2018, February edition, No. 755, pp. 22-24, non-official translation (Ito, Yuji et al., "Development of radiopharmaceuticals using antibody site-specific modification method").
Korean Official Communication and Observation issued Jun. 12, 2023 in Korean Patent Application No. 10-2019-7031664 (with English Translation), 105 pages.
Korean Official Communication and Observation issued Jun. 12, 2023 in Korean Patent Application No. 10-2019-7031664 (with English Translation), 56 pages.
Hayashi et al., "Traceless Affinity Labeling of Endogenous Proteins for Functional Analysis in Living Cells", Accounts of Chemical Research, vol. 45, No. 9, Jun. 8, 2012, pp. 1460-1469.
Feng et al., "Conjugates of Small Molecule Drugs with Antibodies and Other Proteins", Biomedicines, 2014, vol. 2, pp. 1-13.
Rader, "Chemical Programmed Antibodies", Trends in Biotech, 2014, vol. 32, No. 4, pp. 186-197.
Biochemical Dictionary, (4th edition), Oct. 1, 2015, pp. 1222-1225, with English translation—19 pages.
Mueller et al., "Determination of the number of e-Amino groups available for conjugation of effector molecules to monoclonal Antibodies", Hybridoma, 1988, vol. 7, pp. 453-456 (5 pages).
Imahori, "Chemistry of Immunoglobin", Biophysical Chemistry, 1968, vol. 13, No. 3, pp. 177-180, with English translation—15 pages.
Zhu et al., "Direct Observation of an Enamine Intermediate in Amine catalysis", J. Am. Chem. Soc., 2009, vol. 132, pp. 18206-18207.
Hoffmann et al., "Aldolase Antibodies of Remarkable Scope", J. Am. Chem. Soc., 1998, vol. 120, pp. 2768-2779.
Sang et al., "Conjugation site analysis o antibody-drug-conjugates (ADCs) by signature ion fingerprinting and normalized area quantitation approach using nano-liquid chromatography coupled to high resolution mass spectrometry", Analytica Chimica Acta, 2017, vol. 955 pp. 67-78.
Ito, "Development of Advanced functional antibody drugs using techniques of specific chemical modification to human IgG antibody", Cell, 2016, vol. 48, No. 4 . . . w/ English translation—18 pages.
Gavrilyuk et al., "Beta-lactam-based approach for the chemical programming of aldolase antibody 38C2", Bioorganic & Medicinal Chemistry Letters, 2009, vol. 19, pp. 1421-1424 w/ English equivalent—11 pages.
Tanaka et al, "Reconstructing Aldolase Antibodies to Alter their substrate specificity and turnover", J. Am. Chem. Soc. 2000, vol. 122, pp. 4835-4836 w/ English equivalent—19 pages.
Rader et al., "A Humanized Aldolase Antibody for Selective Chemotherapy and Adaptor Immunotherapy", J. Mol. Biiol., 2003, vol. 332 pp. 889-899.
Panowski et al., "Site-specific antibody drug conjugates for cancer therany", mAbs, 2014, vol. 6, No. 1, pp. 34-45.
Wang et al., "Structural characterization of the maytansinoid-monoclonal antibody immunoconjugate, huN901-DM1, by mass spectrometry", Protein Science, 2005, vol. 14, pp. 2436-2446—12 pages.
Liu, "Antibody glycosylation and its impact on the pharmacokinetics and Pharmacodynamics of monoclonal antibodies and Fc-fusion proteins", Journal of Pharmaceutical Sciences, 2015, vol. 104, pp. 1866-1884—20 pages.
Chugai Pharmaceutical Co., Ltd., Main Products, https://www.chugaipharm.co.jp/ir/product/product/pdf/jChugai_Main_Products.pdf?20231024 Publication date: Oct. 24, 2023—with English translation 32 pages.

\* cited by examiner

FIG. 8

(1) Amino acid sequence of heavy chain of trastuzumab with sugar chain cleaved with PNGase EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKT
KPREEQYDSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPG (SEQ ID NO: 2)

(2) Amino acid sequence of IgG1 Fc region with sugar chain cleaved with PNGase

IEGRMDPKSCDKTHTCPPCPAPEAEGAPSVFLFPPKPKDTLMISRTPEVTCVVVDVSHE
DPEVKFNWYVDGVEVHNAKTKPREEQYDSTYRVVSVLTVLHQDWLNGKEYKCKVSN
KALPAPIEKTISKAKGQPREPQVYTLPPSRDELTKNQVSLTCLVKGFYPSDIAVEWESNG
QPENNYKATPPVLDSDGSFFLYSKLTVDKSRWQQGNVFSCSVMHEALHNHYTQKSLS
LSPGK (SEQ ID NO: 3)

(3) Amino acid sequence of light chain of trastuzumab

DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ ID NO: 4)

FIG. 17

PKSCDKTHTCPPCPAPEXXGXPSVFLFPPKPKDTLMISRTPEVTCVVVDVSHEDPEVKF
NWYVDGVEVHNAKTKPREEQYDSTYRVVSVLTVLHQDWLNGKEYKCKVSNKALPAPI
EKTISKAKGQPREPQVYTLPPSRXEXTKNQVSLTCLVKGFYPSDIAVEWESNGQPENNY
KXTPPVLDSDGSFFLYSKLTVDKSRWQQGNVFSCSVMHEALHNHYTQKSLSLSPG
(SEQ ID NO:1)

FIG. 18

FIG. 19
(1)
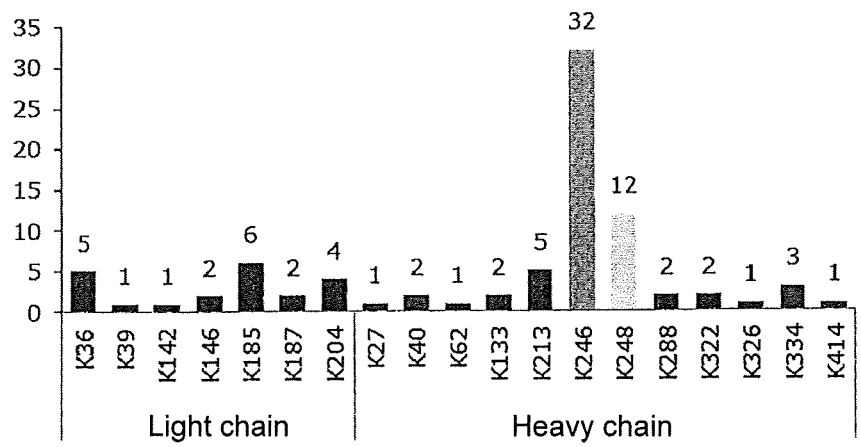
(2)
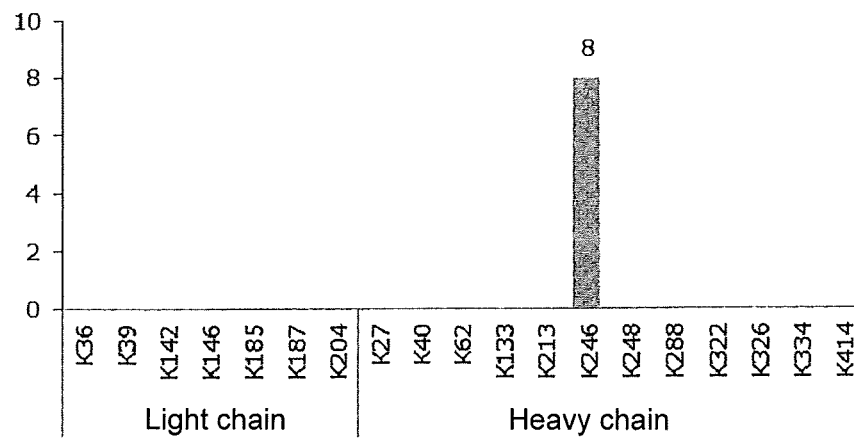

FIG. 21

| #1 | b+ | b2+ | b3+ | b4+ | Seq. | y+ | y2+ | y3+ | y4+ | #2 |
|---|---|---|---|---|---|---|---|---|---|---|
| 1 | 102.05496 | 51.53112 | 34.68994 | 26.26920 | T | 3813.92842 | 1907.46785 | 1271.98099 | 954.23756 | 33 |
| 2 | 239.11387 | 120.06057 | 80.37614 | 60.53392 | H | 3676.86951 | 1838.93839 | 1226.29469 | 919.97283 | 32 |
| 3 | 340.16155 | 170.58441 | 114.05870 | 85.79584 | T | 3575.82183 | 1788.41455 | 1192.61213 | 894.71091 | 31 |
| 4 | 500.19220 | 250.59974 | 167.40225 | 125.80351 | C-Carbami- | 3415.79118 | 1708.39923 | 1139.26958 | 854.70325 | 30 |
| 5 | 597.24497 | 299.12612 | 199.75317 | 150.06670 | P | 3318.73841 | 1659.87284 | 1106.91765 | 830.44006 | 29 |
| 6 | 694.29774 | 347.65251 | 232.10410 | 174.32959 | P | 3221.68564 | 1611.34646 | 1074.56673 | 806.17687 | 28 |
| 7 | 854.32839 | 427.66784 | 285.44765 | 214.33756 | C-Carbami- | 3061.65498 | 1531.33113 | 1021.22318 | 766.16320 | 27 |
| 8 | 951.38116 | 476.19422 | 317.79857 | 238.60075 | P | 2964.60221 | 1482.80474 | 988.87225 | 741.90601 | 26 |
| 9 | 1022.41828 | 511.71278 | 341.47761 | 256.36003 | A | 2893.56509 | 1447.28618 | 965.19321 | 724.14673 | 25 |
| 10 | 1119.47105 | 560.23917 | 373.82854 | 280.62322 | P | 2796.51232 | 1398.75980 | 932.84229 | 699.88354 | 24 |
| 11 | 1248.51365 | 624.76047 | 416.84274 | 312.88387 | E | 2667.46972 | 1334.23850 | 889.82809 | 667.62289 | 23 |
| 12 | 1361.59772 | 681.30250 | 454.53743 | 341.15488 | L | 2554.38565 | 1277.69546 | 852.13340 | 639.35187 | 22 |
| 13 | 1474.68179 | 737.84454 | 492.23212 | 369.42591 | L | 2441.30158 | 1221.15443 | 814.43871 | 611.08085 | 21 |
| 14 | 1531.70326 | 766.35527 | 511.23927 | 383.68127 | G | 2384.28011 | 1192.64369 | 795.43155 | 596.82549 | 20 |
| 15 | 1588.72473 | 794.86601 | 530.24643 | 397.93664 | G | 2327.25864 | 1164.13296 | 776.42440 | 582.57012 | 19 |
| 16 | 1685.77750 | 843.39239 | 562.59735 | 422.19993 | P | 2230.20587 | 1115.60657 | 744.07347 | 558.30633 | 18 |
| 17 | 1772.80953 | 886.90841 | 591.60803 | 443.95784 | S | 2143.17384 | 1072.09056 | 715.06280 | 536.54892 | 17 |
| 18 | 1871.87795 | 936.44262 | 624.63084 | 468.72495 | V | 2044.10542 | 1022.55635 | 682.03993 | 511.78181 | 16 |
| 19 | 2018.94637 | 1009.97683 | 673.65364 | 505.49205 | F | 1897.03700 | 949.02214 | 633.01718 | 475.01471 | 15 |
| 20 | 2132.03044 | 1066.51886 | 711.34833 | 533.76307 | L | 1783.95293 | 892.48010 | 595.32249 | 446.74363 | 14 |
| 21 | 2279.09886 | 1140.05307 | 760.37114 | 570.53017 | F | 1636.88451 | 818.94589 | 546.29969 | 409.96759 | 13 |
| 22 | 2376.15163 | 1188.57946 | 792.72206 | 594.79337 | P | 1539.83174 | 770.41951 | 513.94876 | 385.71339 | 12 |
| 23 | 2473.20440 | 1237.10584 | 825.07299 | 619.05656 | P | 1442.77897 | 721.89312 | 481.59784 | 361.45020 | 11 |
| 24 | 2855.40137 | 1428.20433 | 952.47198 | 714.60590 | K-Azide-L- | 1060.58200 | 530.79464 | 354.19885 | 265.90096 | 10 |
| 25 | 2952.45414 | 1476.73071 | 984.82290 | 738.88399 | P | 963.52323 | 482.26825 | 321.84793 | 241.63777 | 9 |
| 26 | 3049.54911 | 1540.77820 | 1027.52122 | 770.89274 | P | 835.43426 | 418.22077 | 279.14960 | 209.61402 | 8 |
| 27 | 3195.57606 | 1598.29167 | 1065.86354 | 799.64947 | K | 963.52323 | 418.22077 | 279.14960 | 209.61402 | 7 |
| 28 | 3296.62374 | 1648.81551 | 1099.54610 | 824.91139 | D | 720.40731 | 360.70729 | 240.80729 | 180.85729 | 6 |
| 29 | 3409.70781 | 1705.35755 | 1137.24079 | 853.18241 | T | 619.35963 | 310.18345 | 207.12473 | 155.59537 | 5 |
| 30 | 3540.74831 | 1770.87780 | 1180.92096 | 885.94254 | M | 506.27556 | 253.64142 | 169.43004 | 127.32435 | 4 |
| 31 | 3653.83238 | 1827.41983 | 1218.61565 | 914.21355 | I | 375.23506 | 188.12117 | 125.74987 | 94.56422 | 3 |
| 32 | 3740.86441 | 1870.93585 | 1247.62632 | 935.97156 | S | 262.15099 | 131.57913 | 88.05518 | 66.29321 | 2 |
| 33 |  |  |  |  | R | 175.11896 | 88.06312 | 59.04450 | 44.53520 | 1 |

FIG. 24

(1) >Trastuzumab Light chain

DIQMTQSPSS LSASVGDRVT ITCRASQDVN TAVAWYQQKP GKAPKLLIYS ASFLYSGVPS
RFSGSRSGTD FTLTISSLQP EDFATYYCQQ HYTTPPTFGQ GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC                (SEQ ID NO: 4)

(2) > Trastuzumab Heavy chain

EVQLVESGGG LVQPGGSLRL SCAASGFNIK DTYIHWVRQA PGKGLEWVAR IYPTNGYTRY
ADSVKGRFTI SADTSKNTAY LQMNSLRAED TAVYYCSRWG GDGFYAMDYW GQGTLVTVSS
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKKVEP KSCDKTHTCP PCPAPELLGG
PSVFLFPPKP KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPG                      (SEQ ID NO: 53)

(3) > Trastuzumab Heavy chain (N300D)

EVQLVESGGG LVQPGGSLRL SCAASGFNIK DTYIHWVRQA PGKGLEWVAR IYPTNGYTRY
ADSVKGRFTI SADTSKNTAY LQMNSLRAED TAVYYCSRWG GDGFYAMDYW GQGTLVTVSS
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKKVEP KSCDKTHTCP PCPAPELLGG
PSVFLFPPKP KDTLMISRTP EVTCVVVDVS HEDPEVKFNW YVDGVEVHNA KTKPREEQYD
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPG                      (SEQ ID NO: 2)

FIG. 27
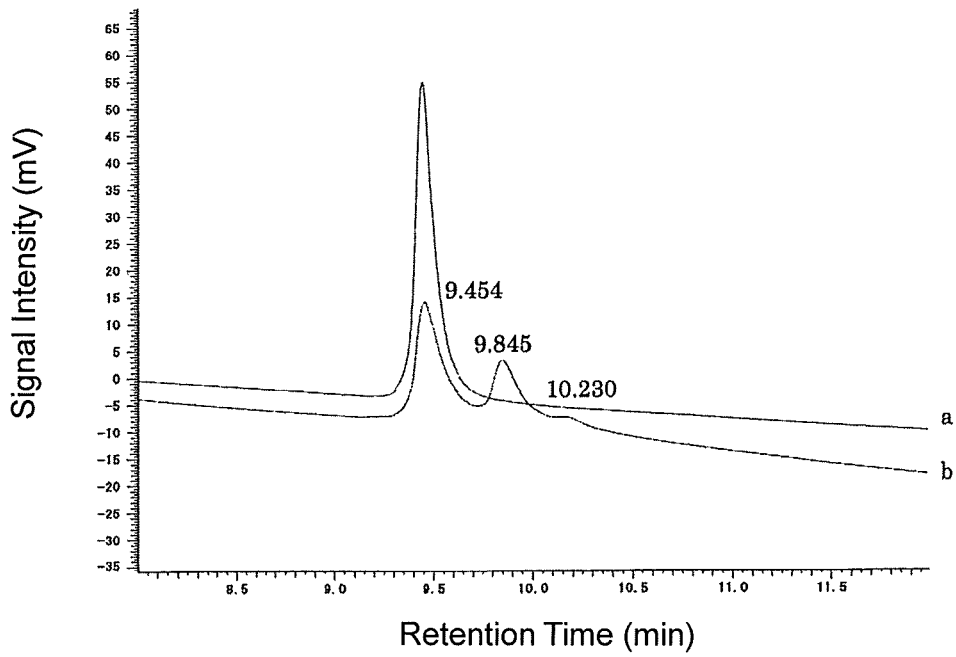
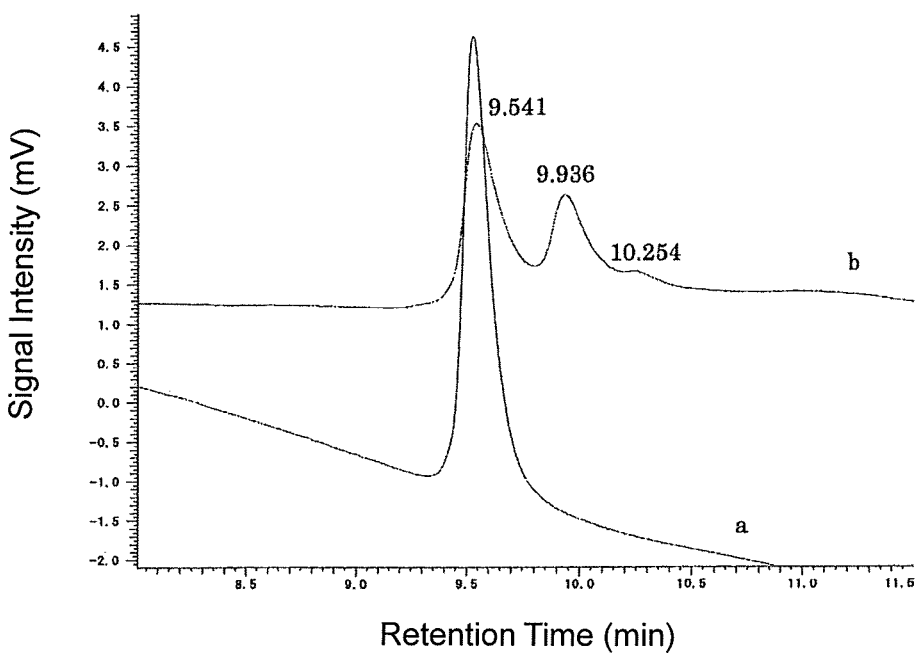

FIG. 28
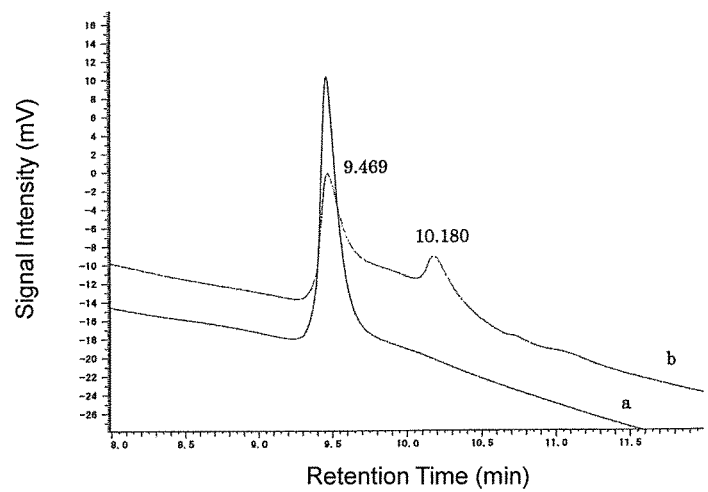
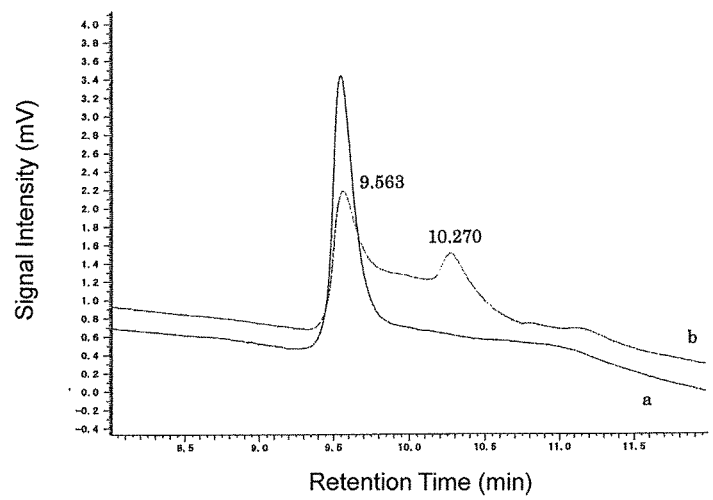

FIG. 29
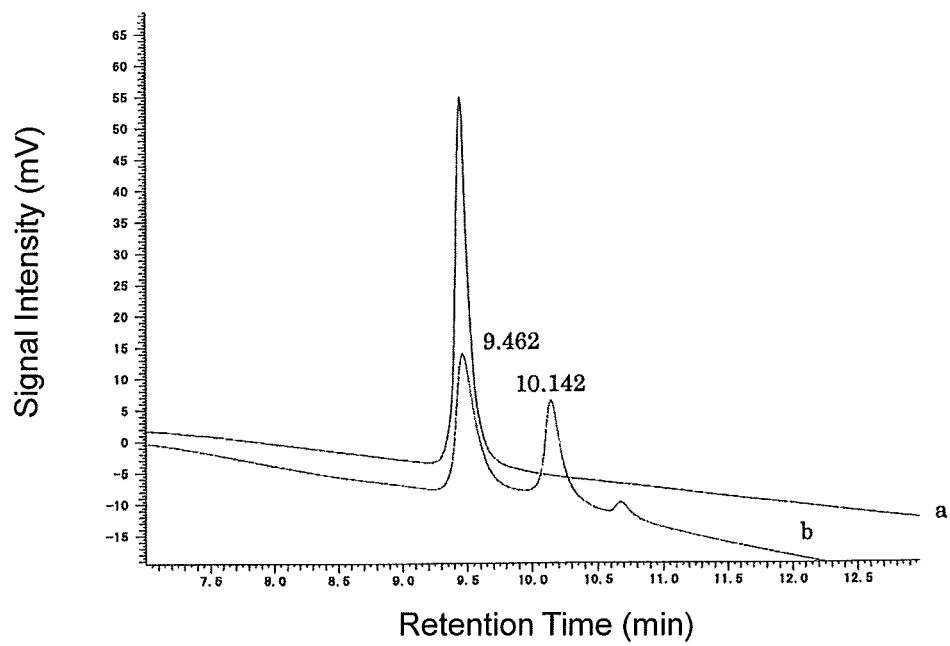
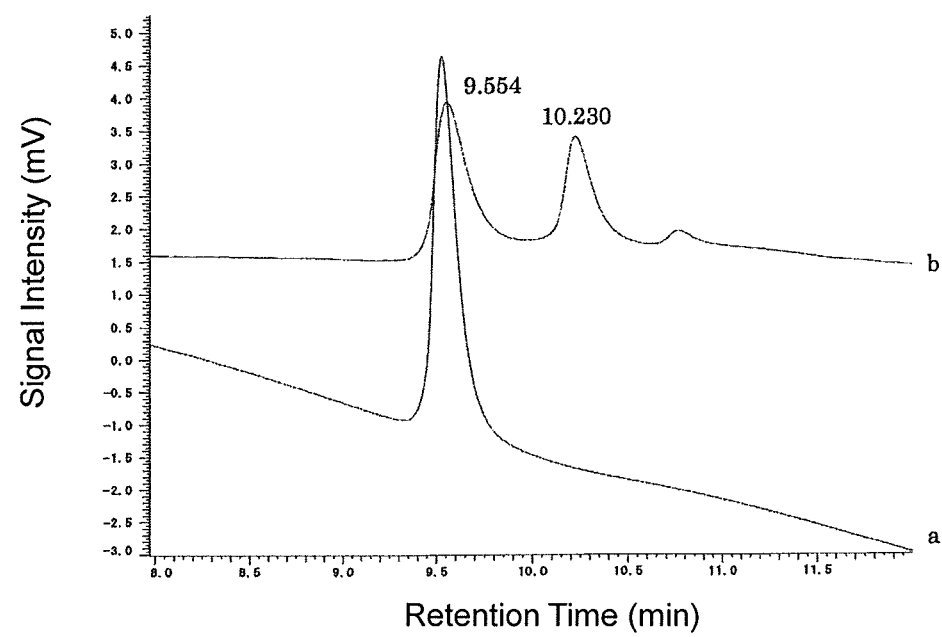

FIG. 30
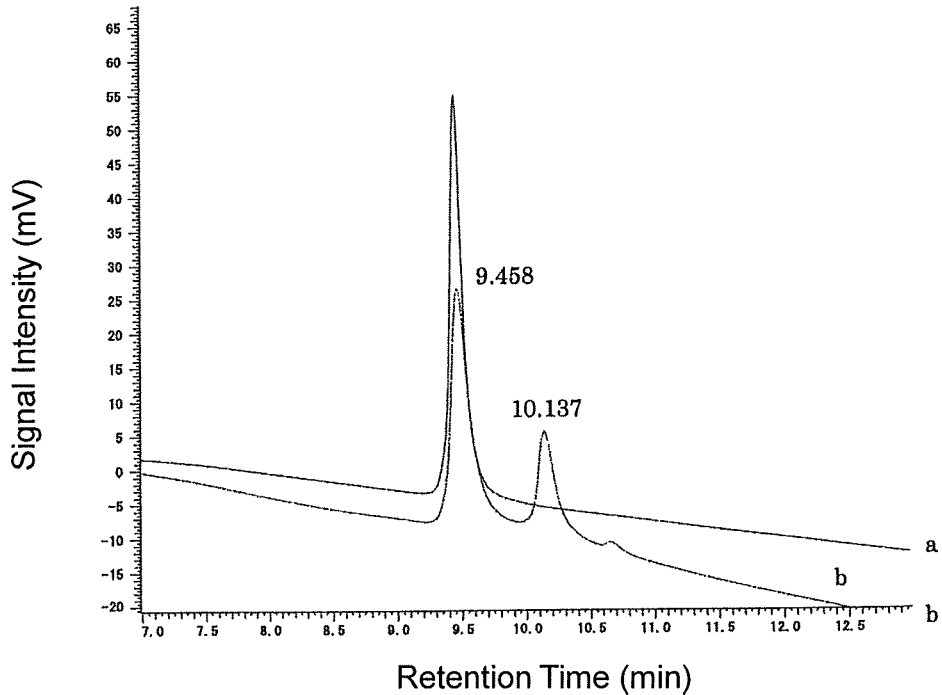
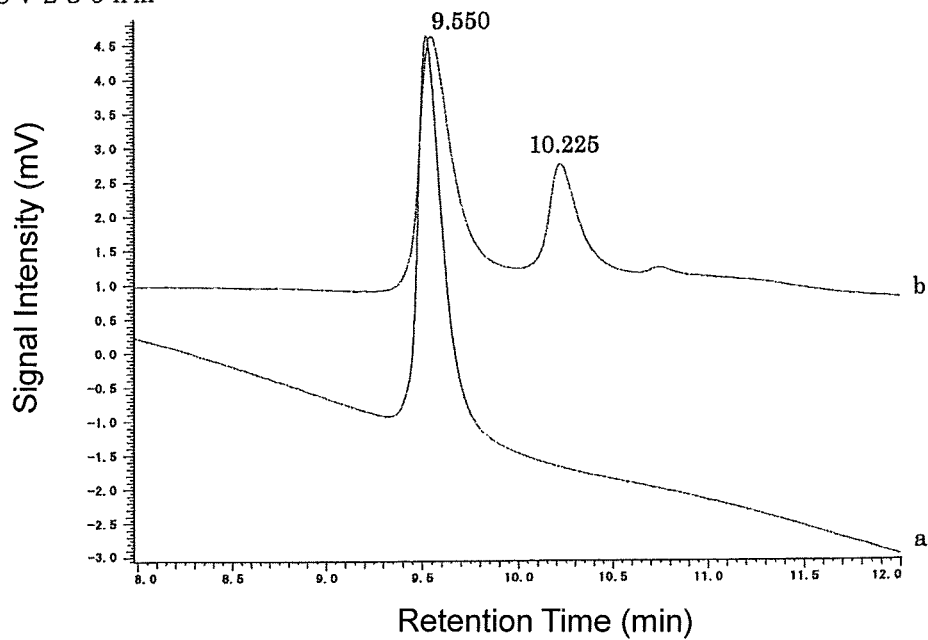

FIG. 31
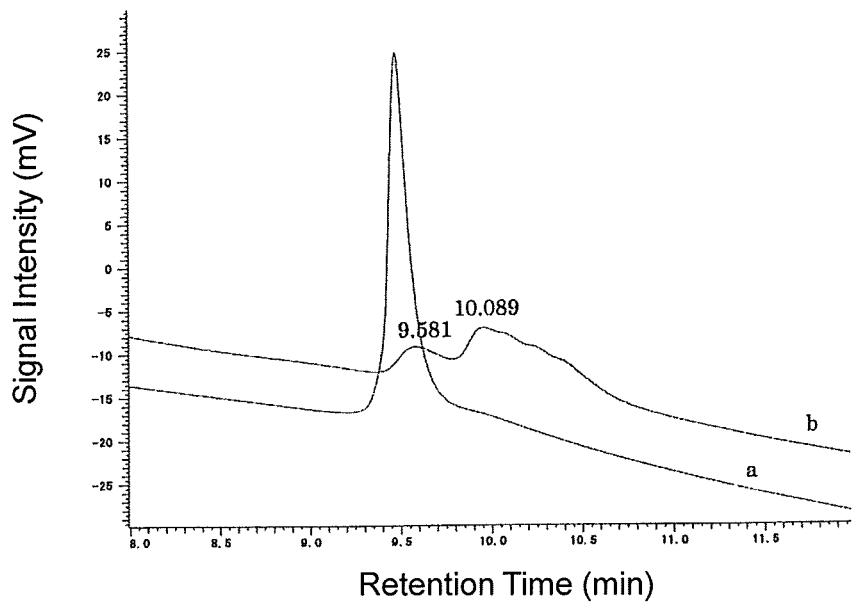
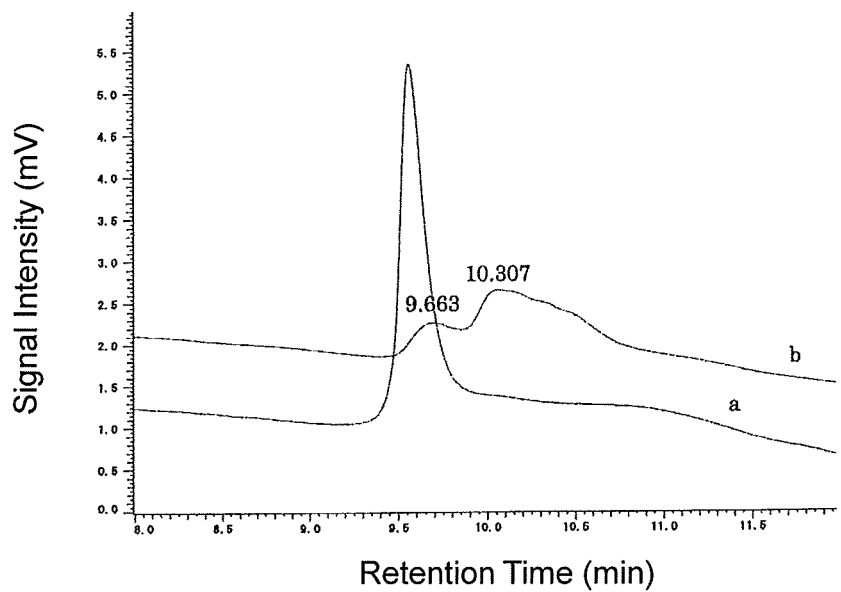

FIG. 32
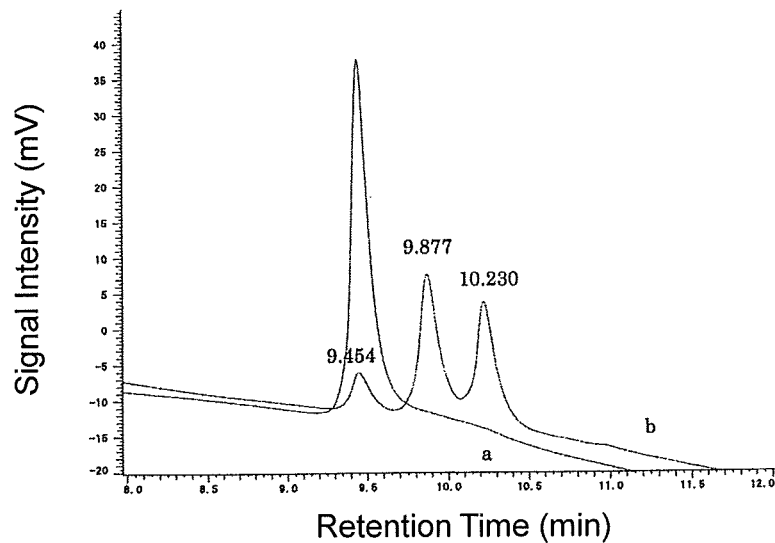
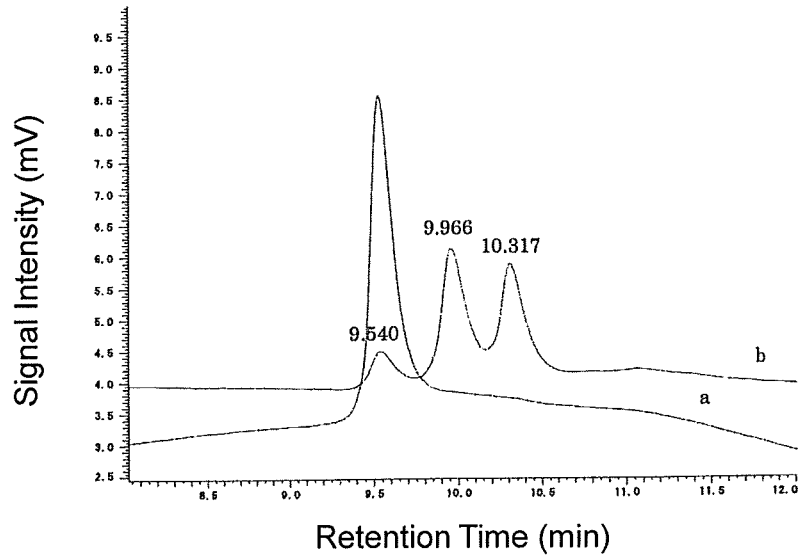

FIG. 33
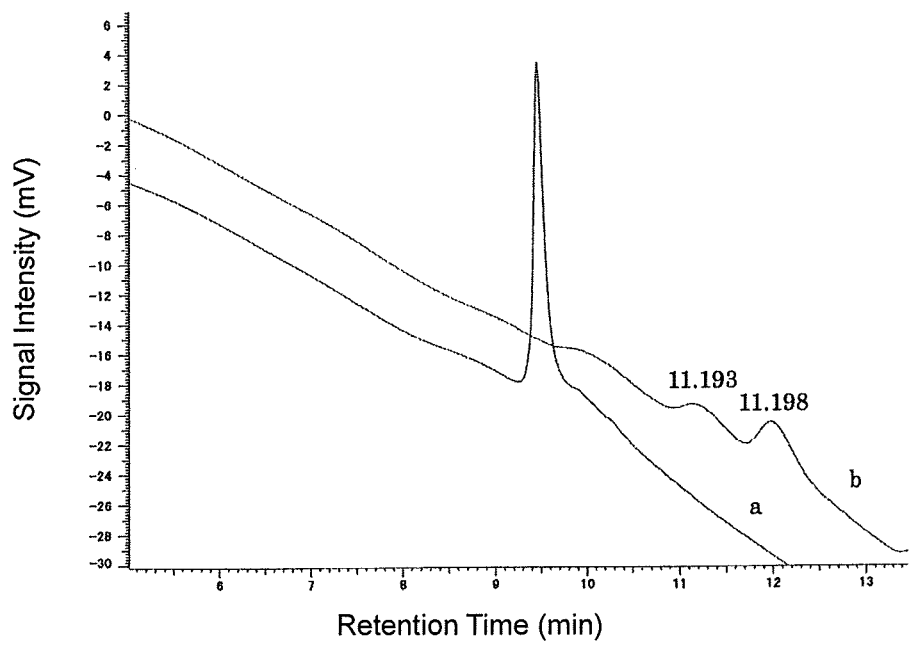
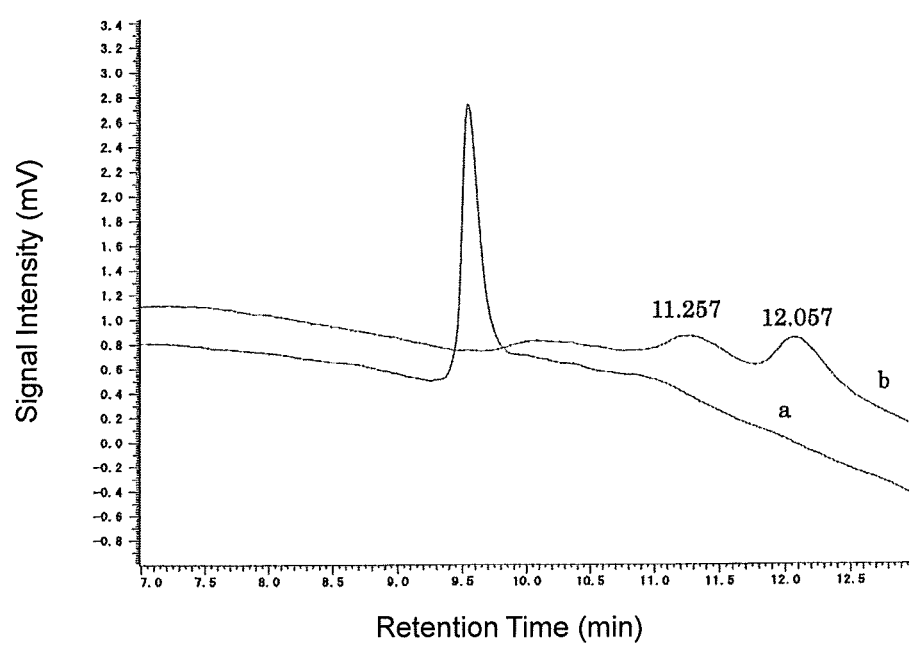

FIG. 34
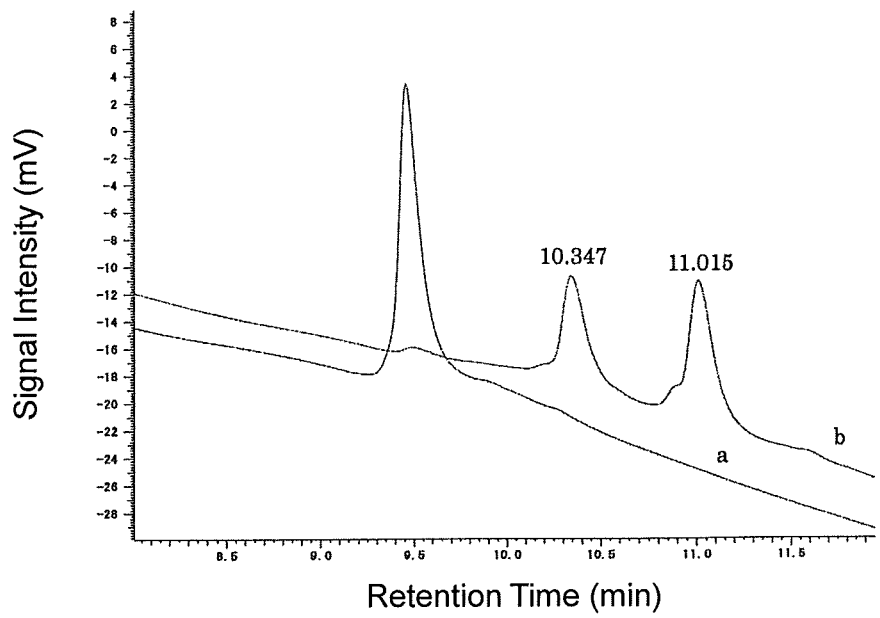
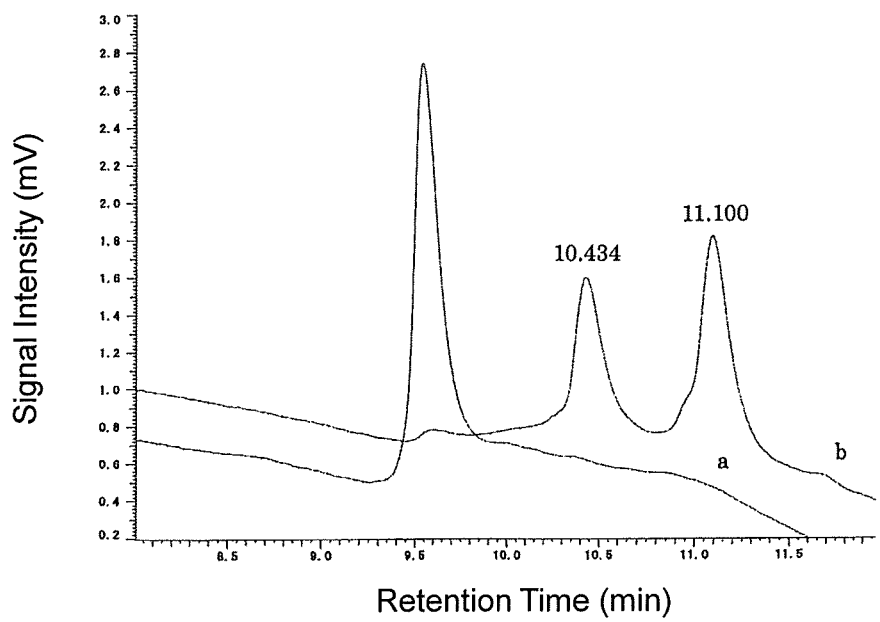

FIG. 35
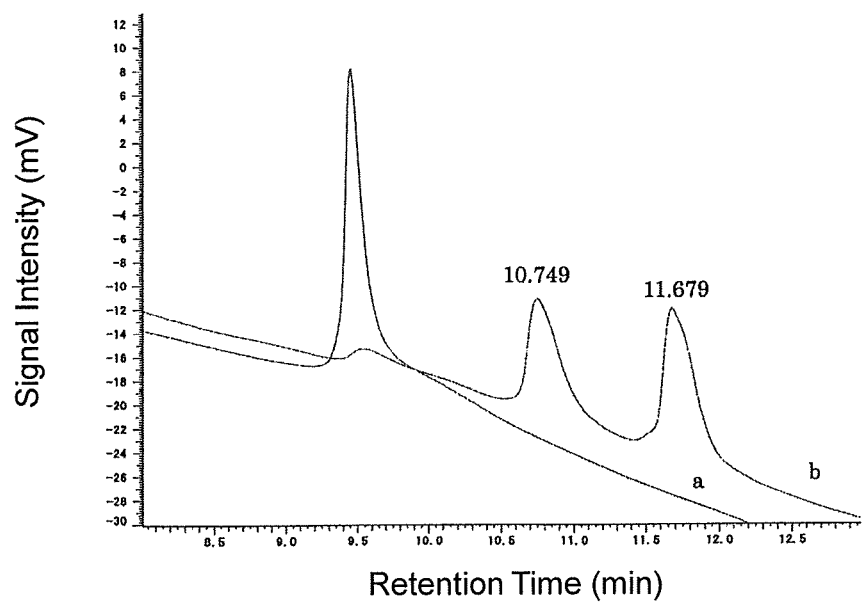
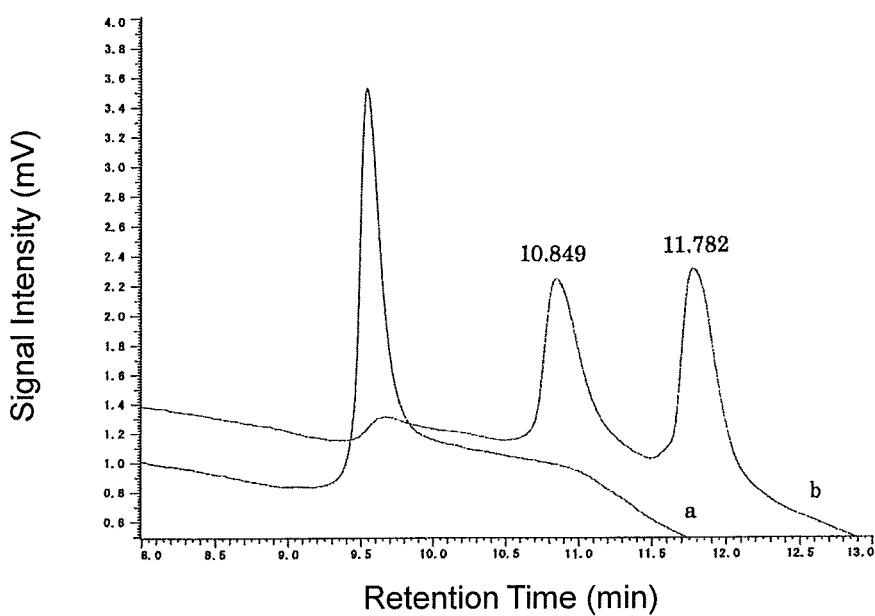

FIG. 36
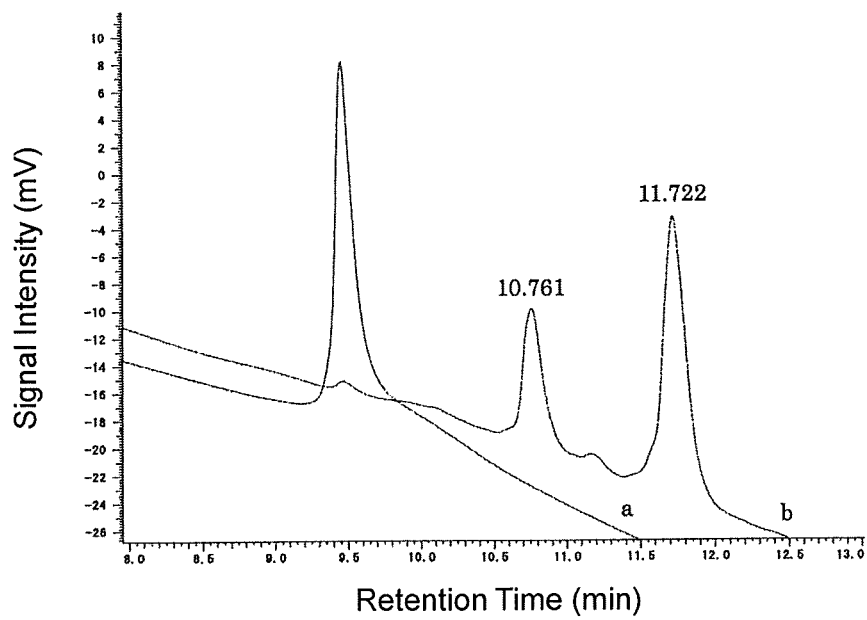
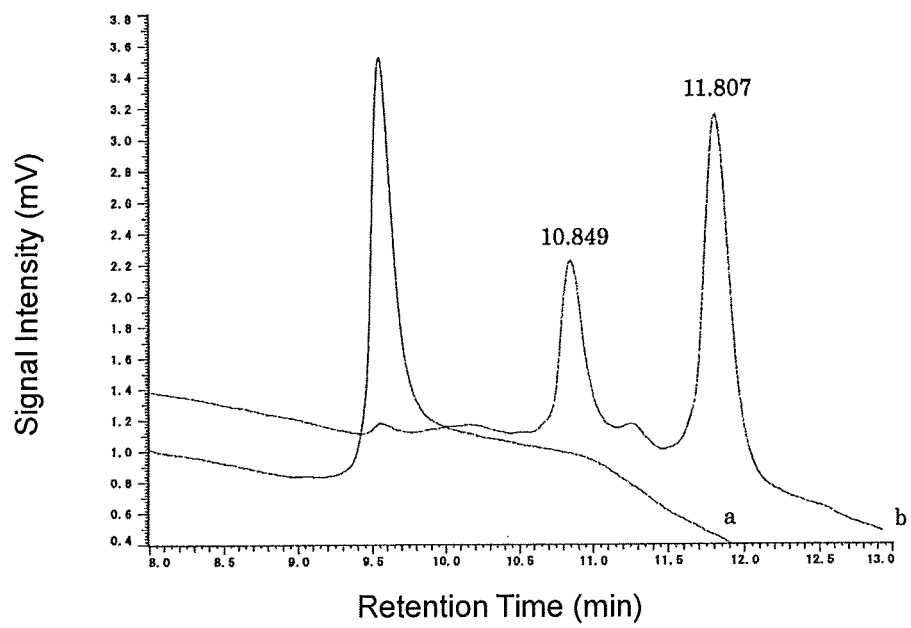

FIG. 37
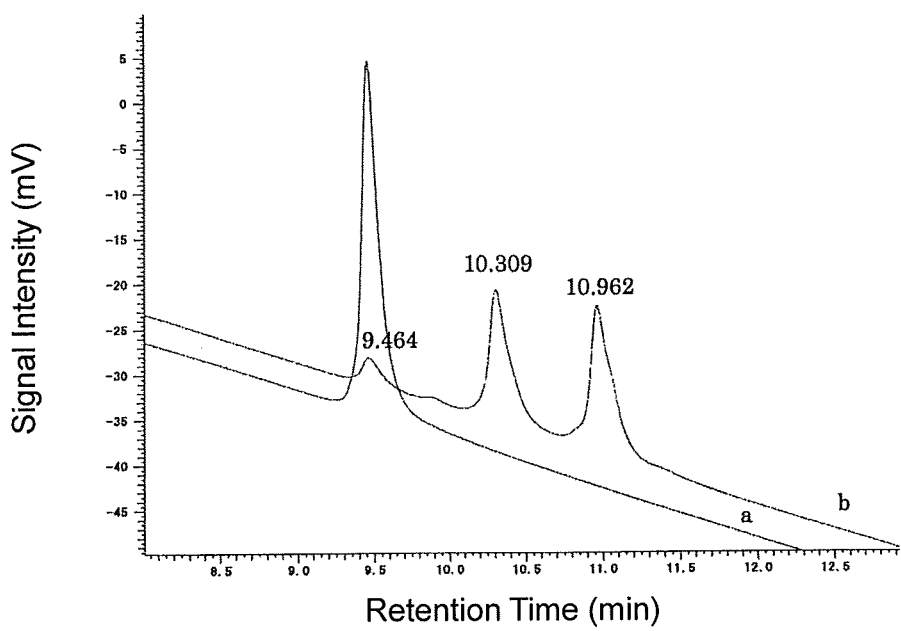
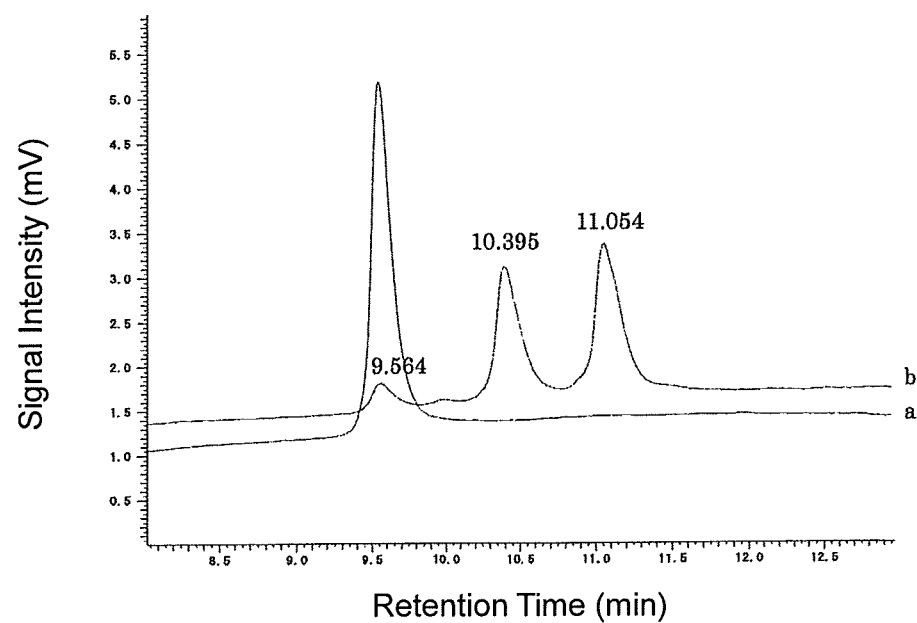

FIG. 38
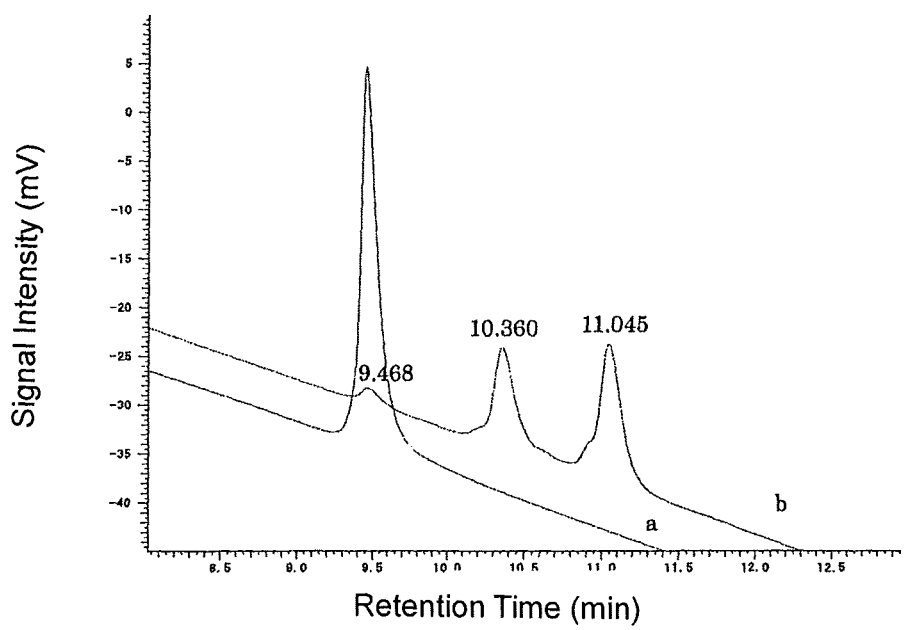
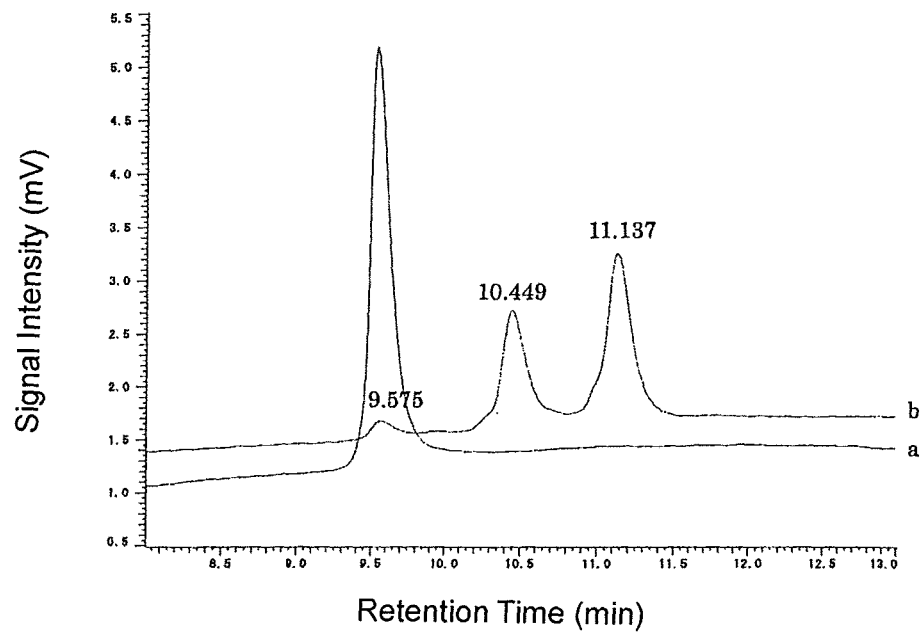

FIG. 39
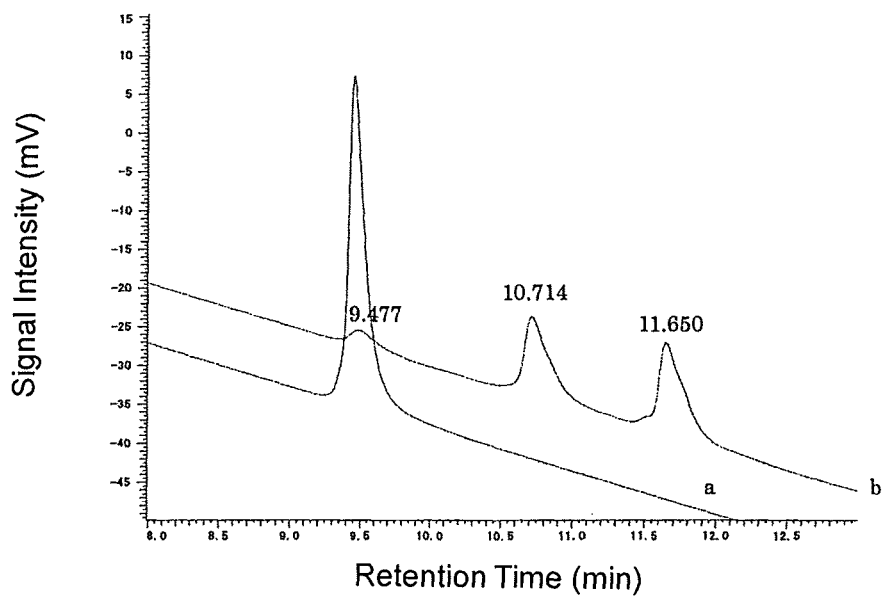
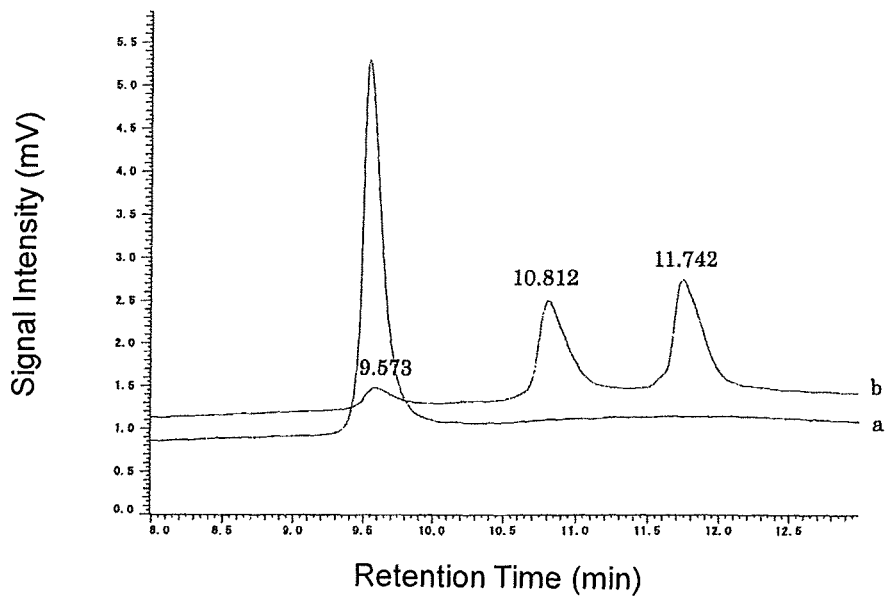

FIG. 40
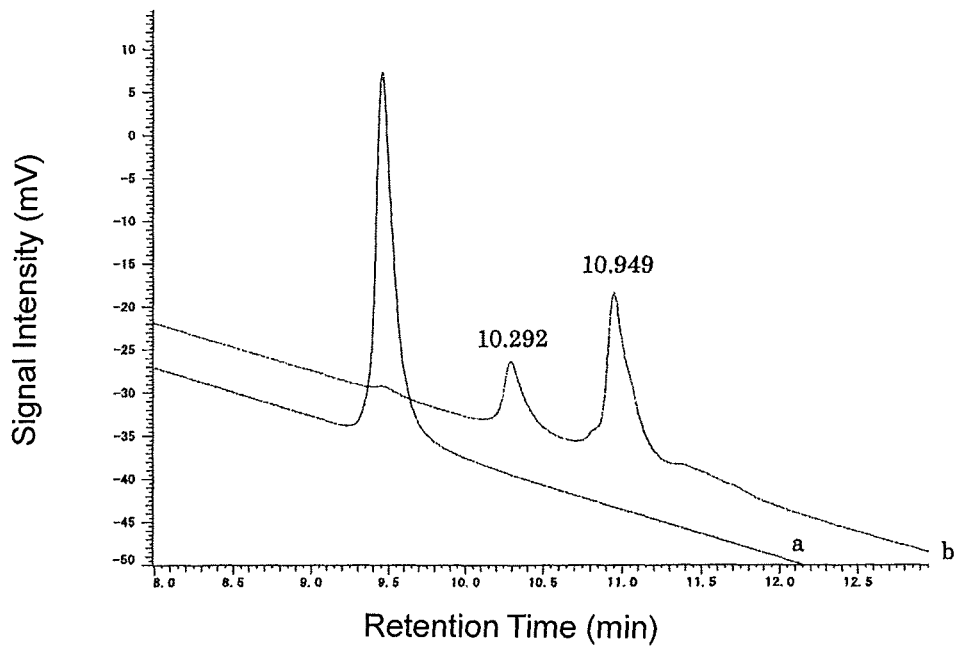
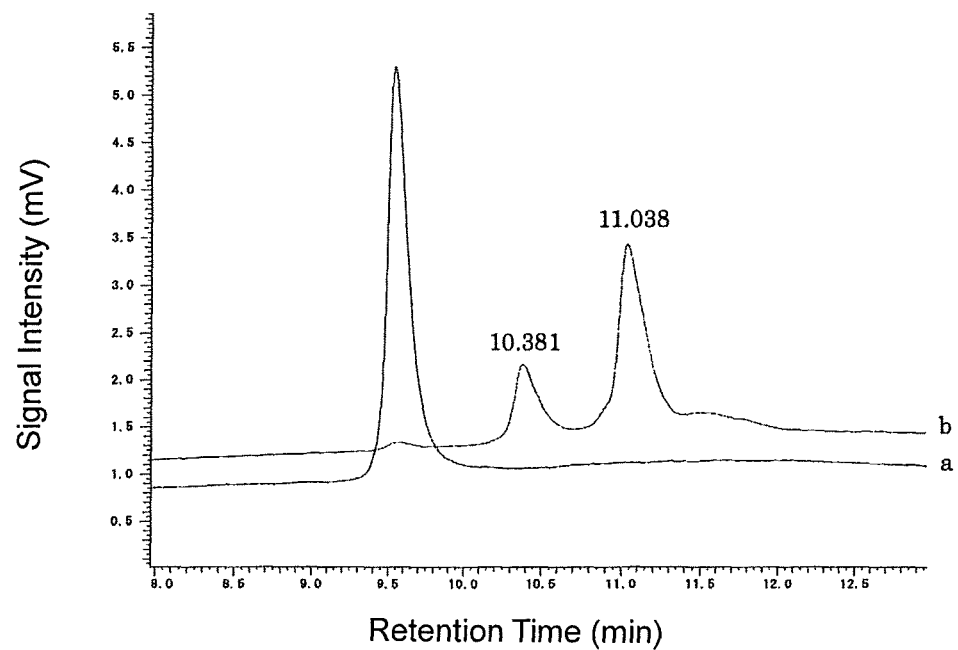

FIG. 41
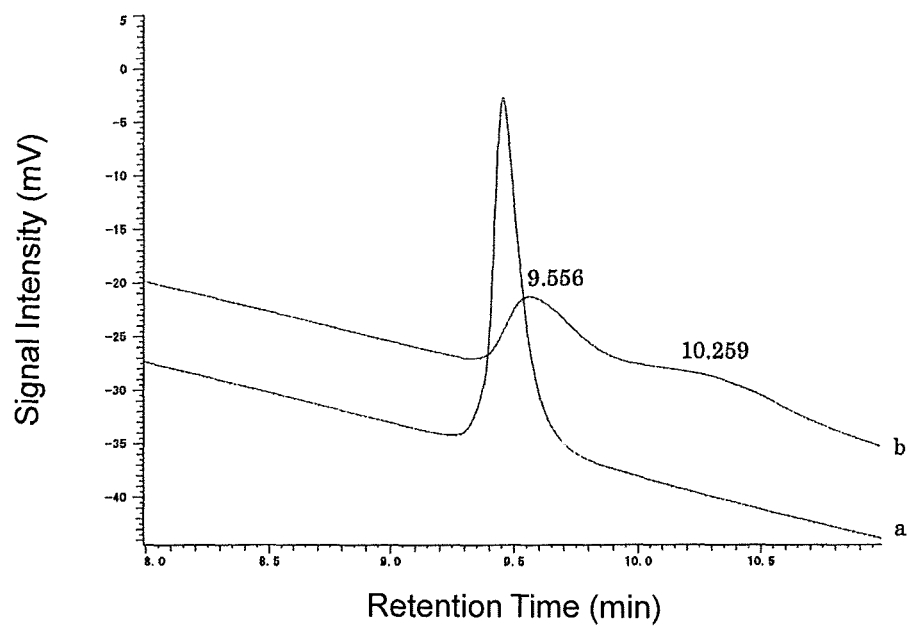
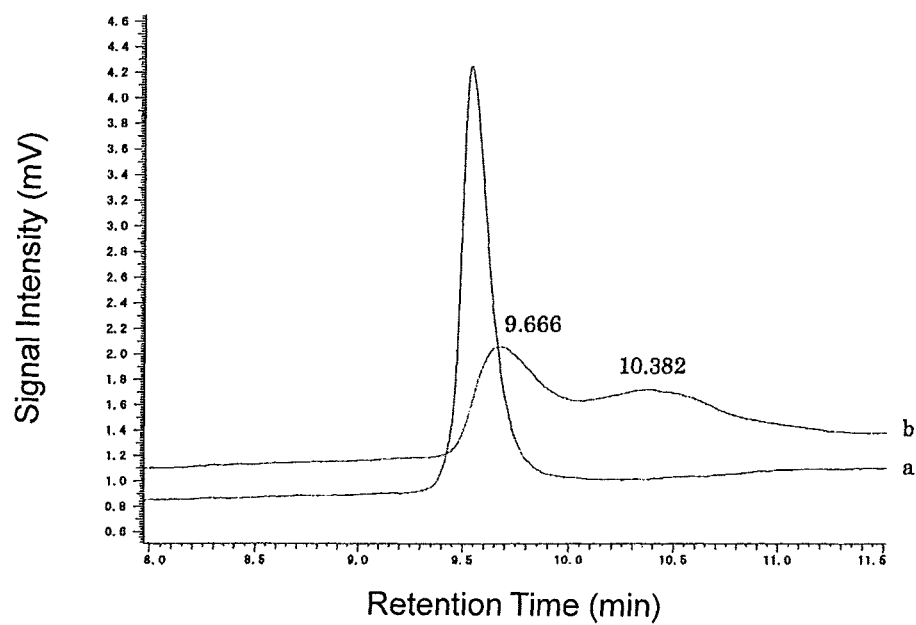

COMPOUND HAVING AFFINITY SUBSTANCE TO SOLUBLE PROTEIN, CLEAVABLE PORTION AND REACTIVE GROUP, OR SALT THEREOF

CROSS REFERENCES TO RELATED APPLICATIONS

This application is a continuation of International Patent Application No. PCT/JP2018/017345, filed on Apr. 27, 2018, and claims priority to Japanese Patent Application No. 2017-090679, filed on Apr. 28, 2017, both of which are incorporated herein by reference in their entireties.

BACKGROUND OF THE INVENTION

Field of the Invention

The present invention relates to compounds having an affinity substance to a soluble protein, a cleavable portion and a reactive group, or a salt thereof, and the like.

Discussion of the Background

In recent years, research and development of antibody drug conjugates (ADCs) have been actively conducted. An ADC, as implied by the name, is a medicine in which a drug (e.g., an anti-cancer agent) is conjugated with an antibody and has a direct cytotoxic activity on cancer cells and the like. Examples of representative ADCs include T-DM1 (product name: Kadcyla (registered trademark)) jointly developed by Immunogene, Inc. and F. Hoffmann-La Roche, Ltd (see Reichert J M et al., Nat Biotechnol 2005; 23: 1073-8; Kubota T et al., Cancer Sci 2009; 100: 1566-72; and Wu A M et al., Nat Biotechnol 2005; 23: 1137-46, all of which are incorporated herein by reference in their entireties).

ADCs including T-DM1 have had the problem of their nonuniformity from the beginning of their development. That is, a small drug is randomly reacted with about 70 to 80 Lys residues in an antibody, and thus a drug antibody ratio (DAR) and a conjugation position are not constant. It is known that such a random conjugation method normally provides a DAR within a range of 0 to 8, producing a plurality of medicines having different numbers of bonds of a drug. In recent years, it has been reported that when the number of bonds and the bond positions of a drug of an ADC are changed, pharmacokinetics, and a releasing rate and effects of the drug change. Given these circumstances, next-generation ADCs are required to control the number and positions of a drug to be conjugated. It is believed that when the number and positions are fixed, the problems of expected efficacy, variations in conjugation medicines, and lot difference, or what is called regulation, will be solved (see Junutula J R et al., Nat Biotechnol 2008; 26: 925-32, which is incorporated herein by reference in its entirety).

Although methods for regioselectively modifying antibodies are being investigated worldwide, most of them are methods of modification using genetic engineering techniques or enzymes. For the genetic engineering methods of modification, problems have been pointed out such as reductions in the expression efficiency of antibodies themselves (reductions in total yield when ADCs are prepared), although regioselectivity and number selectivity can be controlled. In addition, there is a problem in that it takes long years to construct an antibody expression system and the like (see Shen B Q et al., Nat Biotechnol 2012; 30: 184-9; Hofer T et al., Biochemistry 2009; 48: 12047-57; and Liu W et al., Nat Methods 2007; 4: 239-44, all of which are incorporated herein by reference in their entireties).

In recent years, methods that chemically modify proteins under complicated environments such as intracellular ones using a small molecule probe have been reported. The methods are used for imaging or identification of receptors in repositioning small compound drugs. In the field of chemical biology, organic chemical methods of protein modification using a synthesized small molecule probe are attracting attention (see S. T. Laughlin et al., Science 2008; 320, 664; A. E. Speers et al., ChemBioChem 2004; 5, 41; and Y. Takaoka et al., Angew. Chem. Int. Ed. 2013; 52, 4088, all of which are incorporated herein by reference in their entireties).

Chemical conjugation by affinity peptide (C-CAP) has recently been developed. This method has succeeded in regioselective modification of antibodies by a method that reacts a peptide reagent in which an NHS-activated ester and a drug are coupled to an affinity peptide with an antibody (that is, a method for producing an ADC through a linker comprising a peptide portion). This method has succeeded in regioselectively modifying an antibody Fc region with a drug by a chemical synthetic technique first in the world, and besides, practically favorable results [reaction time: 30 minutes, yield: 70% (for DAR 1), and regioselectivity: 100%] have been determined. It has been demonstrated that control with a DAR of 2 can be achieved by adding about five equivalents of the peptide reagent, which is epoch-making in that a modified position can also be controlled (see WO 2016/186206, which is incorporated herein by reference in its entirety).

SUMMARY OF THE INVENTION

Accordingly, it is one object of the present invention to provide novel techniques that enable modification of a soluble protein and, in particular, regioselective modification of a soluble protein.

These and other objects, which will become apparent during the following detailed description, have been achieved by the inventors' discovery that a compound developed based on a novel and original design concept having a structural feature comprising (1) an affinity substance to a soluble protein, (2) a reactive group to an amino acid residue constituting the soluble protein, and (3) a cleavable portion between the affinity substance and the reactive group, and capable of producing (4) a structural unit having a bioorthogonal functional group or bioorthogonal functional groups (hereinafter, optionally abbreviated as "a bioorthogonal functional group(s)"), on a reactive group side (that is, a structural unit comprising a bioorthogonal functional group and a reactive group) by cleavage at the cleavable portion is useful for regiospecific modification of a soluble protein (e.g., FIG. 1-1, FIG. 1-2, FIG. 1-3, and FIG. 2). The inventors of the present invention have also found out that using such a compound can prepare a soluble protein regioselectively having a functional substance or functional substances (hereinafter, optionally abbreviated as "a functional substance(s)"), (e.g., a drug or drugs) comprising no peptide portion as a linker (e.g., an antibody drug conjugate (ADC)). Avoidance of use of a linker comprising a peptide portion, which has potential immunogenicity and is easily hydrolyzed in the blood, is desirable in the clinical candidate of ADC. That is, it can be said that the method developed by the inventors of the present invention has succeeded first in the world in regioselectively modifying an antibody Fc region with a drug by a chemical synthetic technique, and besides, without using any linker comprising a peptide portion. The inventors of the present invention have also succeeded in developing various compounds having the above (1) to (4) structural features (e.g., FIG. 1-1, FIG. 1-2, FIG. 1-3, and FIG. 2) to complete the present invention.

Specifically, the present invention is as follows.

In a first embodiment, the present invention provides a compound having an affinity substance to a soluble protein, a cleavable portion, and a reactive group, and a reagent of modifying an antibody regioselectively, comprising the compound or a salt thereof.

(1) A compound having an affinity substance to a soluble protein, a cleavable portion, and a reactive group represented by the following Formula (I):

A-L-B-R    (I)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R is a reactive group to a soluble protein; or
a salt thereof.

(2) The compound or salt thereof according to (1), wherein L is (i) a cleavable linker which is a divalent group comprising a cleavable portion having an ability to form a bioorthogonal functional group on a reactive group side by cleavage or (ii) a cleavable linker which is a divalent group comprising a cleavable portion having no ability to form a bioorthogonal functional group on a reactive group side by cleavage.

(3) The compound or salt thereof according to (2), wherein L is the cleavable linker (i).

(4) The compound or salt thereof according to (2) or (3), wherein
L is the cleavable linker (i), and
B is the divalent group (b).

(5) The compound or salt thereof according to (2), wherein L is the cleavable linker (ii); and
B is the divalent group (a).

(6) The compound or salt thereof according to any one of (1) to (5), wherein the affinity substance to the soluble protein is a peptide.

(7) The compound or salt thereof according to (6), wherein the peptide is a binding peptide to an Fc region of a monoclonal antibody.

(8) The compound or salt thereof according to (7), wherein the binding peptide is a binding peptide to an Fc region of IgG.

(9) The compound or salt thereof according to any one of (1) to (8), wherein the affinity substance is an affinity substance to an antibody comprising any one Fc region protein selected from the group consisting of the following (A) to (C) and having antigen-binding ability:
(A) an Fc region protein comprising the amino acid sequence of SEQ ID NO: 1;
(B) an Fc region protein comprising an amino acid sequence with one or several amino acid residues inserted, added, deleted, or substituted in the amino acid sequence of SEQ ID NO: 1; and
(C) an Fc region protein comprising an amino acid sequence having 90% or more identity to the amino acid sequence of SEQ ID NO: 1.

(10) The compound or salt thereof according to any one of (7) to (9), wherein the binding peptide is a peptide comprising an amino acid sequence consisting of 13 to 17 amino acid residues represented by the following Formula (i):

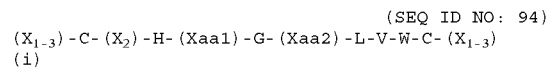

wherein
Xs are the same or different from each other, and are each any amino acid residue other than cysteine;
C is a cysteine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue; and
W is a tryptophan residue; and
capable of binding to human IgG and/or rabbit IgG, or a salt thereof.

(11) The compound or salt thereof according to any one of (7) to (9), wherein the binding peptide is a peptide comprising an amino acid sequence consisting of 13 to 17 amino acid residues represented by the following Formula (i-1):

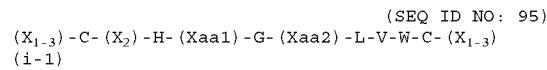

wherein
Xs are the same or different from each other, and are each any amino acid residue other than cysteine;
C is a cysteine residue;
H is a histidine residue;
Xaa1 is a lysine residue, a cysteine residue, an aspartic acid residue, a glutamic acid residue, a 2-amino suberic acid residue, or a diaminopropionic acid residue;
G is a glycine residue;
Xaa2 is a glutamic acid residue or an aspartic acid residue;
L is a leucine residue;
V is a valine residue; and
W is a tryptophan residue; and
capable of binding to human IgG and/or rabbit IgG, or a salt thereof.

(12) The compound or salt thereof according to any one of (7) to (10), wherein the binding peptide is a peptide comprising an amino acid sequence consisting of 13 to 17 amino acid residues represented by the following Formula (i-2):

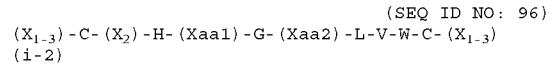

wherein
Xs are the same or different from each other, and are each any amino acid residue other than cysteine;

C is a cysteine residue;
H is a histidine residue;
Xaa1 is an arginine residue or a leucine residue;
G is a glycine residue;
Xaa2 is a lysine residue, a glutamine residue, or an aspartic acid residue;
L is a leucine residue;
V is a valine residue; and
W is a tryptophan residue; and
capable of binding to human IgG and/or rabbit IgG, or a salt thereof.

(13) The compound or salt thereof according to any one of (7) to (12), wherein the binding peptide is a peptide comprising an amino acid sequence consisting of 13 to 17 amino acid residues represented by the following Formula (v):

```
                                          (SEQ ID NO: 102)
(X_{1-3})-C-(Xaa3)-(xaa4)-H-(Xaa1)-G-(Xaa2)-L-V-W-C-

(Xaa5)-(Xaa6)-(Xaa7)
(v)
``` wherein
Xs are the same or different from each other, and are each any amino acid residue other than cysteine;
C is a cysteine residue;
Xaa3 is an alanine residue or a lysine residue;
Xaa4 is a tryptophan residue or a tyrosine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue;
W is a tryptophan residue;
Xaa5 is a threonine residue or a lysine residue;
Xaa6 is a tyrosine residue, a lysine residue, or absent; and
Xaa7 is a histidine residue, a lysine residue, or absent; and
capable of binding to human IgG and/or rabbit IgG, or a salt thereof.

(14) The compound or salt thereof according to any one of (7) to (13), wherein the binding peptide is a peptide comprising an amino acid sequence consisting of 13 to 15 amino acid residues represented by the following Formula (vi):

```
                                          (SEQ ID NO: 103)
D-C-(Xaa3)-(Xaa4)-H-(Xaa1)-G-(Xaa2)-L-V-W-C-

(Xaa5)-(Xaa6)-(Xaa7)
(vi)
``` wherein
D is an aspartic acid residue;
C is a cysteine residue;
Xaa3 is an alanine residue or a lysine residue;
Xaa4 is a tryptophan residue or a tyrosine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue;
W is a tryptophan residue;
Xaa5 is a threonine residue or a lysine residue;
Xaa6 is a tyrosine residue, a lysine residue, or absent; and
Xaa7 is a histidine residue, a lysine residue, or absent; and
capable of binding to human IgG and/or rabbit IgG, or a salt thereof.

(15) The compound or salt thereof according to any one of (7) to (14), wherein the binding peptide is a peptide comprising an amino acid sequence consisting of 13 amino acid residues represented by the following Formula (vii):

```
                                          (SEQ ID NO: 104)
D-C-(Xaa3)-(Xaa4)-H-(Xaa1)-G-(Xaa2)-L-V-W-C-T
(vii)
``` wherein
D is an aspartic acid residue;
C is a cysteine residue;
Xaa3 is an alanine residue or a lysine residue;
Xaa4 is a tryptophan residue or a tyrosine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue;
W is a tryptophan residue; and
T is a threonine residue; and
capable of binding to human IgG and/or rabbit IgG, or a salt thereof.

(16) The compound or salt thereof according to any one of (7) to (13), wherein the binding peptide is a peptide comprising an amino acid sequence consisting of 13 to 15 amino acid residues represented by the following Formula (viii):

```
                                          (SEQ ID NO: 105)
R-G-N-C-(Xaa3)-(Xaa4)-H-(Xaa1)-G-(Xaa2)-L-V-W-C-

(Xaa5)-(Xaa6)-(Xaa7)
(viii)
``` wherein
R is an arginine residue;
G is a glycine residue;
N is an asparagine residue;
C is a cysteine residue;
Xaa3 is an alanine residue or a lysine residue;
Xaa4 is a tryptophan residue or a tyrosine residue;
H is a histidine residue;

Xaa1 is an arginine residue, a leucine residue, a lysine residue, an aspartic acid residue, a glutamic acid residue, a 2-amino suberic acid residue, or a diaminopropionic acid residue;

G is a glycine residue;

Xaa2 is a lysine residue, a glutamine residue, a glutamic acid residue, an asparagine residue, or an aspartic acid residue;

L is a leucine residue;

V is a valine residue;

W is a tryptophan residue; and

Xaa5 is a threonine residue or a lysine residue;

Xaa6 is a tyrosine residue, a lysine residue, or absent; and

Xaa7 is a histidine residue, a lysine residue, or absent; and capable of binding to human IgG and/or rabbit IgG, or a salt thereof.

(17) The compound or salt thereof according to any one of (7) to (16), wherein the binding peptide is capable of binding to human IgG.

(18) The compound or salt thereof according to any one of (7) to (9), wherein the binding peptide is an affinity peptide comprising an amino acid sequence (a) in which any amino acid residue is substituted with one amino acid residue selected from the group consisting of a lysine residue, an aspartic acid residue, a glutamic acid residue, a 2-amino suberic acid residue, and a diaminopropionic acid residue in the amino acid sequence of FNMQCQRRF-YEALHDPNLNEEQRNARIRSIRDDC (SEQ ID NO: 92), and (b) having 90% or more identity to the amino acid sequence of SEQ ID NO: 92, or a salt thereof.

(19) The compound or salt thereof according to any one of (1) to (18), wherein the cleavable portion is a portion cleavable by any of (a) treatment with one or more substances selected from the group consisting of an acidic substance, a basic substance, a reducing agent, an oxidizing agent, and an enzyme, (b) treatment by physicochemical stimulus selected from the group consisting of light, and (c) being left when a cleavable linker comprising a self-decomposing cleavable portion is used.

(20) The compound or salt thereof according to any one of (1) to (19), wherein the cleavable portion is selected from the group consisting of a disulfide residue, an acetal residue, a ketal residue, an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue.

(21) The compound or salt thereof according to any one of (2) to (20), wherein the cleavable portion of (i) is selected from the group consisting of a disulfide residue, an ester residue, an acetal residue, a ketal residue, an imine residue, and a vicinal diol residue.

(22) The compound or salt thereof according to any one of (2) to (20), wherein the cleavable portion of (ii) is selected from the group consisting of an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue.

(23) The compound or salt thereof according to any one of (1) to (20), wherein the cleavable portion corresponds to any one chemical structure selected from the group consisting of the following:

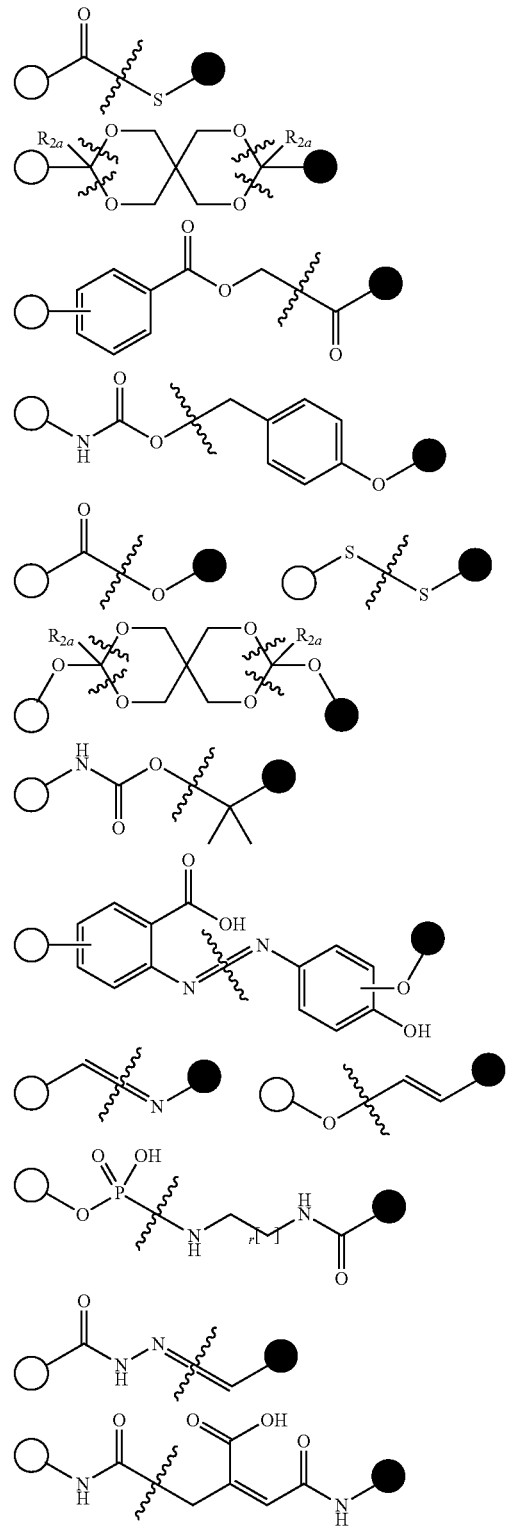

-continued

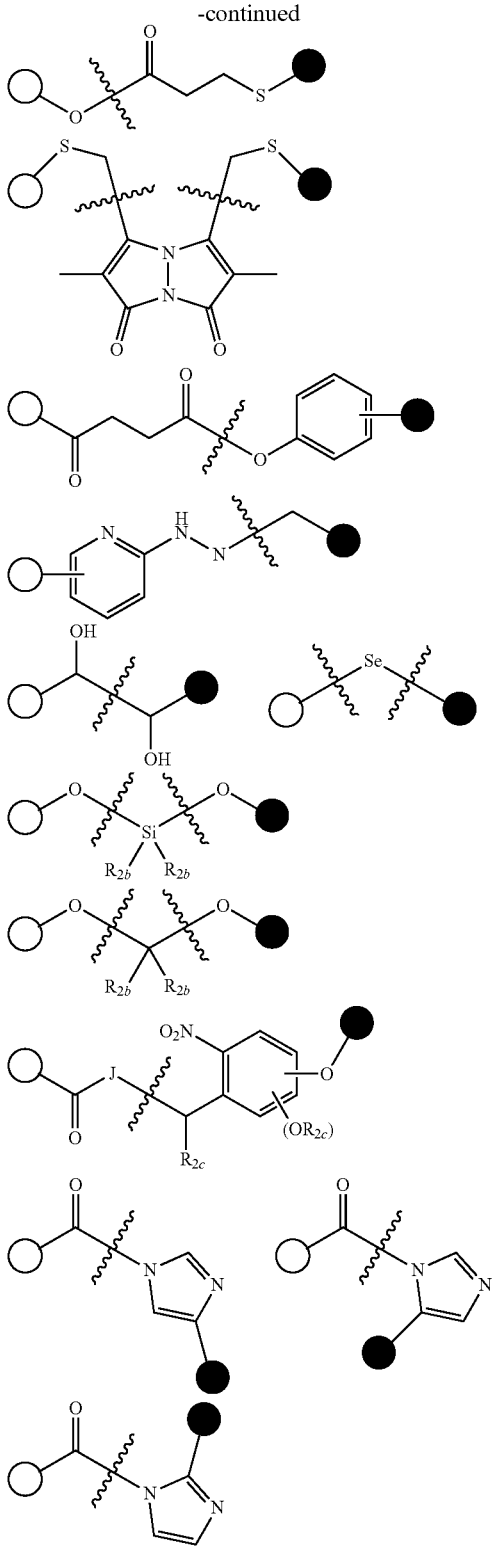

where a wavy line orthogonal to a bond indicates a cleavage site;
a plurality of $R_{2a}$, a plurality of $R_{2b}$, and a plurality of $R_{2c}$ are the same or different from each other, and are selected from the group consisting of:
(i) a hydrogen atom or a halogen atom;
(ii) a monovalent hydrocarbon group;
(iii) aralkyl;
(iv) a monovalent heterocyclic group;
(v) $R_c$—O—, $R_c$—C(=O)—, $R_c$—O—C(=O)—, or $R_c$—C(=O)—O— wherein $R_c$ indicates a hydrogen atom or a monovalent hydrocarbon group;
(vi) $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and indicate a hydrogen atom or a monovalent hydrocarbon group; and
(vii) a nitro group, a sulfuric acid group, a sulfonic acid group, a cyano group, or a carboxy group;
J is —$CH_2$—, —O—, or —S—;
r is any integer of 1 to 4;
a symbol of "white circle" indicates a bond to A, and a symbol of "black circle" indicates a bond to B; and
when a chemical structure is asymmetrical with respect to the cleavage site, a symbol of "black circle" may indicate a bond to A, and a symbol of "white circle" may indicate a bond to B.

(24) The compound or salt thereof according to any one of (2) to (19), (21), and (23), wherein the cleavable portion of (i) corresponds to any one chemical structure selected from the group consisting of the following:

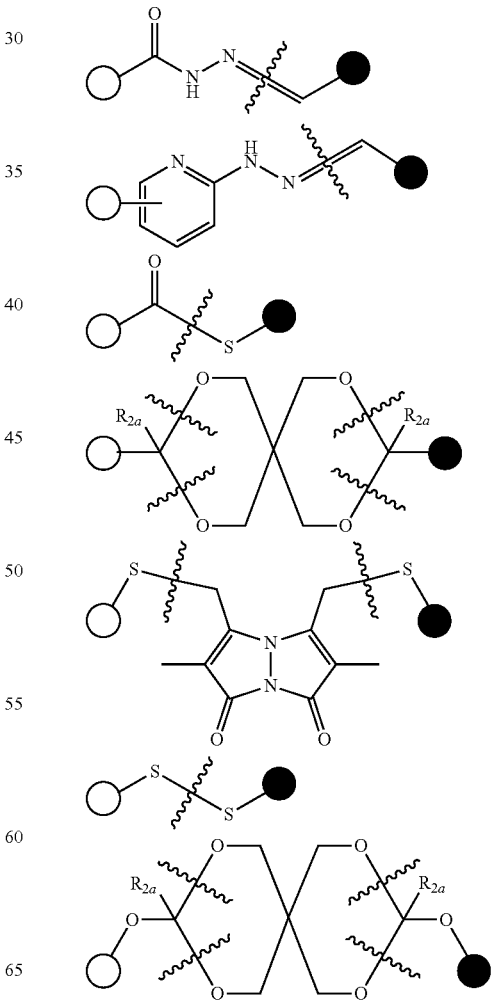

-continued

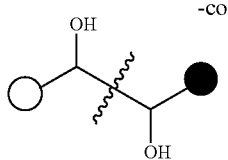

where a wavy line orthogonal to a bond indicates a cleavage site;
$R_{2a}$ are the same as that of [23];
a symbol of "white circle" indicates a bond to A, and a symbol of "black circle" indicates a bond to B; and
when a chemical structure is asymmetrical with respect to the cleavage site, a symbol of "black circle" may indicate a bond to A, and a symbol of "white circle" may indicate a bond to B.

(25) The compound or salt thereof according to any one of (2) to (19), (22), and (23), wherein the cleavable portion of (ii) corresponds to any one chemical structure selected from the group consisting of the following:

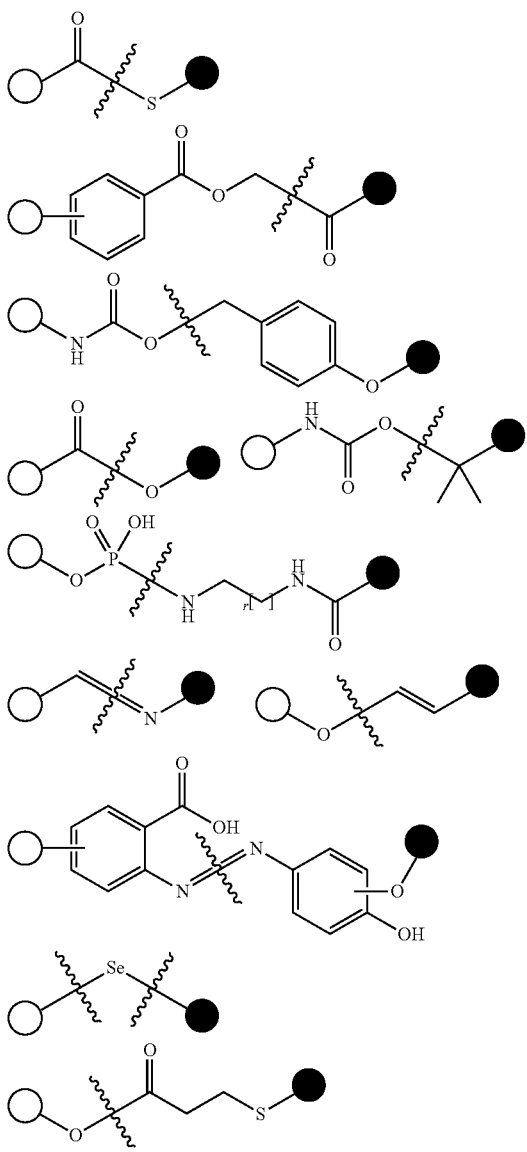

-continued

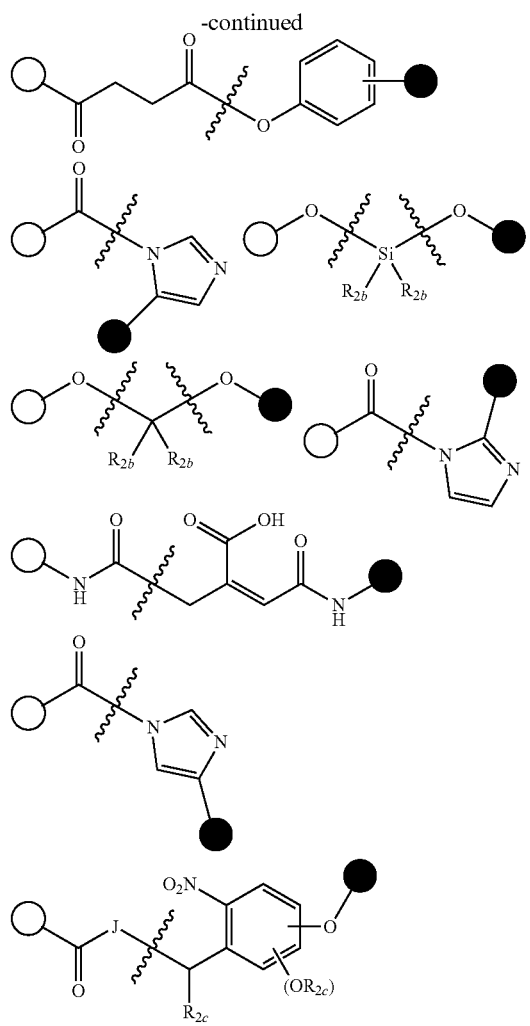

where a wavy line orthogonal to a bond indicates a cleavage site;
$R_{2b}$, $R_{2c}$, J, and r are the same as those of [23];
a symbol of "white circle" indicates a bond to A, and a symbol of "black circle" indicates a bond to B; and
when a chemical structure is asymmetrical with respect to the cleavage site, a symbol of "black circle" may indicate a bond to A, and a symbol of "white circle" may indicate a bond to B.

(26) The compound or salt thereof according to any one of (1) to (25), wherein L is represented by any one of the following Formulae (L1) to (L3):

La-C-Lb        (L1)

La-C           (L2)

C-Lb           (L3)

wherein
La and Lb are each a divalent group; and
C is a cleavable portion.

(27) The compound or salt thereof according to (26), wherein La and Lb are represented by the following (La') and (Lb'), respectively:

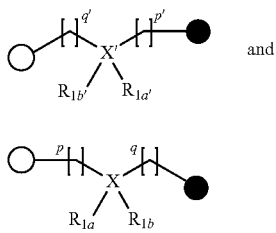

and

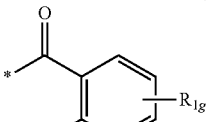

wherein
p and p' are the same or different from each other, and are each any integer of 0 to 10;
q and q' are the same or different from each other, and are each any integer of 0 to 10;
X and X' are the same or different from each other, and are each a carbon atom, a nitrogen atom, or a single bond; wherein when X is a nitrogen atom, $R_{1b}$ is absent; when X' is a nitrogen atom, $R_{1b'}$ is absent; when X is a single bond, $R_{1a}$ and $R_{1b}$ are absent; and when X' is a single bond, $R_{1a'}$ and $R_{1b'}$ are absent; and
$R_{1a}$, $R_{1b}$, $R_{1a'}$, and $R_{1b'}$ are the same or different from each other, and are each an atom or a group selected from the group consisting of the (i) to (vii).

(28) The compound or salt thereof according to any one of (1) to (27), wherein the divalent group comprising a bioorthogonal function group is a divalent group comprising a bioorthogonal functional group selected from the group consisting of an azide residue, an aldehyde residue, a thiol residue, an alkyne residue, an alkene residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue in a main chain thereof.

(29) The compound or salt thereof according to any one of (1) to (27), wherein the divalent group comprising a bioorthogonal function group is a divalent group comprising a bioorthogonal function group selected from the group consisting of an azide residue, an aldehyde residue, a thiol residue, an alkyne residue, an alkene residue, a halogen residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue in a side chain thereof.

(30) The compound or salt thereof according to any one of (1) to (29), wherein the bioorthogonal functional group is any one represented by the following:

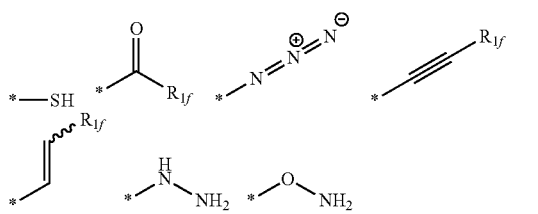

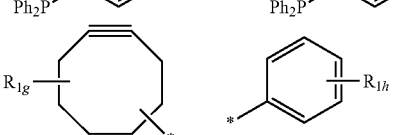

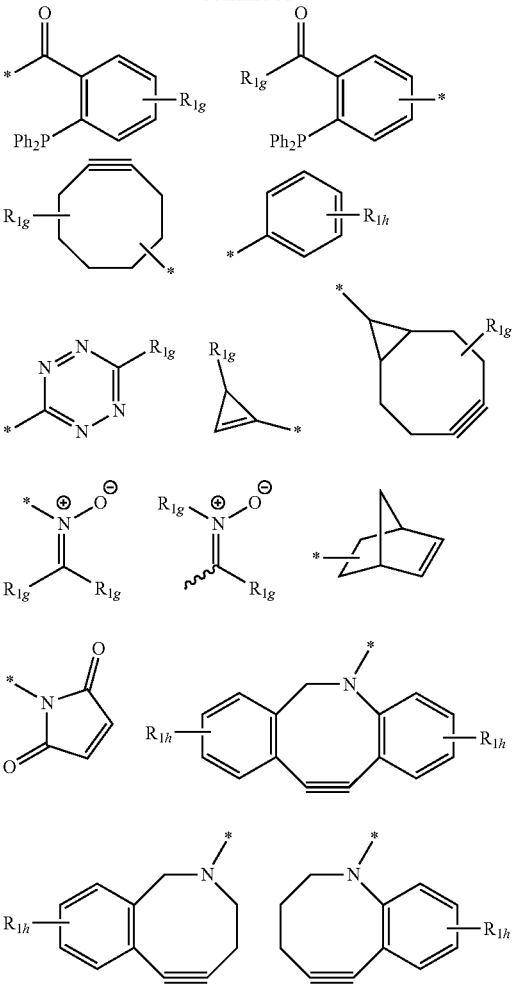

wherein
$R_{1f}$, one or a plurality of $R_{1g}$, and one or a plurality of $R_{1h}$ are the same or different from each other, and are each an atom or a group selected from the group consisting of the (i) to (vii) or an electron-withdrawing group; and
• is a bond.

(31) The compound or salt thereof according to any one of (1) to (30), wherein the divalent group (b) is selected from the group consisting of optionally substituted alkylene, optionally substituted cycloalkylene, optionally substituted aryl, an optionally substituted divalent heterocyclic group, —$NR_a$— ($R_a$ indicates a hydrogen atom or a substituent), —O—, and a combination of two or more of these.

(32) The compound or salt thereof according to any one of (1) to (31), wherein B is represented by the following Formula (B-1):

(B-1)

wherein

Y is —NH—, —O—, —CH$_2$—, or the following Formula (B-2):

(B-2)

wherein
V and V' are the same or different from each other, and are each —NH—, —O—, —CH$_2$—, or a single bond;
V1 is a divalent group comprising a bioorthogonal functional group;
s is any integer of 0 to 10;
a symbol of "white circle" and a symbol of "black circle" in Formula (B-2) have the same orientation as a symbol of "white circle" and a symbol of "black circle" in Formula (B-1), respectively;
Z is an oxygen atom, a sulfur atom, or a hydrogen atom wherein when Z is a hydrogen atom, —C(=Z)— indicates —CH$_2$—; and
a symbol of "white circle" in Formula (B-1) indicates a bond to an L-side portion, and a symbol of "black circle" indicates a bond to an R-side portion.

(33) The compound or salt thereof according to any one of (1) to (32), wherein the reactive group is a reactive group specific to a side chain of any one of a lysine residue, a tyrosine residue, and a tryptophan residue.

(34) The compound or salt thereof according to (33), wherein the reactive group is a reactive group specific to a side chain of a lysine residue.

(35) The compound or salt thereof according to any one of (1) to (34), wherein the reactive group corresponds to any one chemical structure selected from the group consisting of the following:

where
$R_{5a}$ and $R_{5c}$ are each an atom or a group selected from the group consisting of (i) to (vii);
$R_{5b}$ is an electron-withdrawing group;
j is any integer of 1 to 5; and
k is any integer of 1 to 4.

(36) The compound or salt thereof according to any one of (1) to (35), wherein the number of atoms of a main chain linking A and R is 4 to 20.

(37) The compound or salt thereof according to any one of (1) to (36), wherein a main chain linking A and R comprises no cyclic structure.

(38) The compound or salt thereof according to any one of (1) to (37), wherein a partial structure represented by L-B comprises no peptide portion.

(39) The compound or salt thereof according to any one of (1) to (38), wherein the compound represented by Formula (I) is a compound represented by the following Formula (I')

A-B2-L'-B1-R      (I')

wherein
A and R are the same as those of Formula (I);
L' is a cleavable linker which is a divalent group comprising a cleavable portion;
B1 and B2 are the same or different from each other, and are each (a) a divalent group comprising a bioorthogonal functional group or (b) a divalent group comprising no bioorthogonal functional group; and
B1 and B2 may have a symmetrical structure with respect to L'.

(40) The compound or salt thereof according to (39), wherein the compound represented by Formula (I') is represented by the following formula (I''):

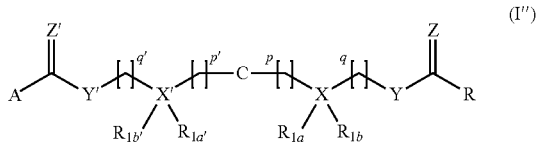

wherein
   A and R are the same as those of Formula (I) according to (1);
   C is a cleavable portion;
   p, p', q, q', X, X', $R_{1a}$, $R_{1a'}$, $R_{1b}$, and $R_{1b'}$ are the same as those of Formulae (La') and (Lb') according to (27);
   Y and Y' are the same or different from each other, and are the same as Y of Formula (B-1) according to (32); and
   Z and Z' are the same or different from each other, and are the same as Z of Formula (B-1).

(41) A reagent of modifying a soluble protein regioselectively, comprising a compound having an affinity substance to a soluble protein, a cleavable portion, and a reactive group represented by the following Formula (I):

A-L-B-R    (I)

wherein
   A is an affinity substance to a soluble protein;
   L is a cleavable linker which is a divalent group comprising a cleavable portion;
   B is (a) a divalent group comprising a bioorthogonal functional group or (b) a divalent group comprising no bioorthogonal functional group; and
   R is a reactive group to a soluble protein; or
   a salt thereof.

(42) A compound having an affinity substance to an antibody, a cleavable portion, and a reactive group represented by the following Formula (I):

A-L-B-R    (I)

wherein
   A is an affinity substance to an antibody;
   L is a cleavable linker which is a divalent group comprising a cleavable portion;
   B is (a) a divalent group comprising a bioorthogonal functional group or (b) a divalent group comprising no bioorthogonal functional group; and
   R is a reactive group specific to a side chain of a lysine residue; or
   a salt thereof.

(43) A reagent of modifying an antibody regioselectively, comprising a compound having an affinity substance to an antibody, a cleavable portion, and a reactive group represented by the following Formula (I):

A-L-B-R    (I)

wherein
   A is an affinity substance to an antibody;
   L is a cleavable linker which is a divalent group comprising a cleavable portion;
   B is (a) a divalent group comprising a bioorthogonal functional group or (b) a divalent group comprising no bioorthogonal functional group; and
   R is a reactive group specific to a side chain of a lysine residue; or
   a salt thereof.

Second, the present invention provides a soluble protein having an affinity substance to a soluble protein, and a cleavable portion, or a salt thereof, and a method for producing the same.

(A Soluble Protein Having an Affinity Substance to a Soluble Protein, and a Cleavable Portion, or a Salt Thereof)

(44) A soluble protein having an affinity substance to a soluble protein, and a cleavable portion represented by the following Formula (II):

A-L-B-R'-T    (II)

wherein
   A is an affinity substance to a soluble protein;
   L is a cleavable linker which is a divalent group comprising a cleavable portion;
   B is (a) a divalent group comprising a bioorthogonal functional group or (b) a divalent group comprising no bioorthogonal functional group; and
   R' is a portion formed by a reaction between a soluble protein and a reactive group; and
   T is a soluble protein; or
   a salt thereof.

(45) The soluble protein or salt thereof according to (44), wherein the soluble protein is a monoclonal antibody.

(46) The soluble protein or salt thereof according to (44) or (45), wherein the soluble protein is an IgG antibody.

(47) The soluble protein or salt thereof according to any one of (44) to (46), wherein the soluble protein is derived from a human.

(48) The soluble protein or salt thereof according to any one of (44) to (47), wherein the soluble protein is an antibody comprising any one Fc region protein selected from the group consisting of the following (A) to (C) and having antigen-binding ability:
   (A) an Fc region protein comprising the amino acid sequence of SEQ ID NO: 1;
   (B) an Fc region protein comprising an amino acid sequence with one or several amino acid residues inserted, added, deleted, or substituted in the amino acid sequence of SEQ ID NO: 1; and
   (C) an Fc region protein comprising an amino acid sequence having 90% or more identity to the amino acid sequence of SEQ ID NO: 1.

(49) The soluble protein or salt thereof according to any one of (44) to (48),
   wherein the soluble protein comprises one or more specific amino acid residues in a target region consisting of 1 to 50 continuous amino acid residues, and five or more of the specific amino acid residues in a non-target region other than the target region, and
   a structural unit represented by A-L-B-R' binds to the one or more specific amino acid residues contained in the target region with 30% or more regioselectivity.

(50) The soluble protein or salt thereof according to (49), wherein the target region is a region consisting of one to ten continuous amino acid residues.

(51) The soluble protein or salt thereof according to (50), wherein the target region is a region consisting of one to three continuous amino acid residues.

(52) The soluble protein or salt thereof according to (51), wherein the target region is (a) a region consisting of amino acid residues at positions 246 to 248 in an human IgG Fc region, (b) a region consisting of amino acid residues at positions 288 to 290 in the human IgG Fc region, or (c) a region consisting of an amino acid residue at position 317 in the human IgG Fc region.

(53) The soluble protein or salt thereof according to any one of (49) to (52), wherein the regioselectivity is 50% or more.

(54) The soluble protein or salt thereof according to (53), wherein the regioselectivity is 70% or more.

(55) The soluble protein or salt thereof according to (54), wherein the regioselectivity is 90% or more.

(56) The soluble protein or salt thereof according to any one of (49) to (55), wherein the target region does not comprise the same kind of amino acid residue as the specific amino acid residue other than the specific amino acid residue present at the specific position in a region up to a remote position of "a" (where "a" is any integer of 1 to 10) amino acid residues to an N-terminus side and a C-terminus side each with respect to the specific amino acid present at the specific position.

(57) The soluble protein or salt thereof according to any one of (44) to (56), wherein
the soluble protein is a multimeric protein comprising a plurality of monomeric proteins, and
T has a structural unit represented by A-L-B-R' in a plurality of corresponding target regions in the monomeric proteins such that the multimeric protein has a plurality of structural units represented by A-L-B-R'.

(58) The soluble protein or salt thereof according to any one of (44) to (57), wherein
the soluble protein is an antibody comprising a plurality of heavy chains, and
T has a structural unit represented by A-L-B-R' in a plurality of corresponding target regions in the heavy chains such that the antibody has a plurality of structural units represented by A-L-B-R'.

(59) The soluble protein or salt thereof according to (58), wherein the number of the heavy chains is two.

(60) The soluble protein or salt thereof according to any one of (44) to (59), wherein the portion formed by a reaction between a soluble protein and a reactive group is a portion formed by a reaction of a reactive group specific to any one side chain of a lysine residue, a tyrosine residue, and a tryptophan residue to a lysine residue, a tyrosine residue, or a tryptophan residue.

(61) The soluble protein or salt thereof according to any one of (44) to (60), wherein the portion formed by a reaction between a soluble protein and a reactive group is a portion formed by a reaction between a lysine residue and a reactive group specific to a side chain of a lysine residue.

(62) The soluble protein or salt thereof according to any one of (44) to (61), wherein the portion formed by a reaction corresponds to any one chemical structure selected from the group consisting of the following:

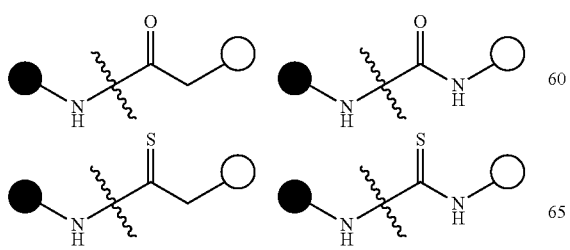

where a symbol of "black circle" indicates a bond to a T-side portion, and a symbol of "white circle" indicates a bond to a B-side portion; and a straight line orthogonal to a bond indicates a bond formed by the reaction.

(63) The soluble protein or salt thereof according to any one of (44) to (62]) wherein the number of atoms of a main chain linking A and R' is 4 to 20.

(64) The soluble protein or salt thereof according to any one of (44) to (63), wherein a main chain linking A and R comprises no cyclic structure.

(65) The soluble protein or salt thereof according to any one of (44) to (64), wherein a partial structure represented by L-B comprises no peptide portion.

(66) The soluble protein or salt thereof according to any one of (44) to (65), wherein the compound represented by Formula (II) is a compound represented by the following (II'):

A-B2-L'-B1-R'-T     (II')

wherein
A, R', and T are the same as those of Formula (II);
L' is a cleavable linker which is a divalent group comprising a cleavable portion;
B1 and B2 are the same or different from each other, and are each (a) a divalent group comprising a bioorthogonal functional group or (b) a divalent group comprising no bioorthogonal functional group; and
B1 and B2 may have a symmetrical structure with respect to L'.

(67) The soluble protein or salt thereof according to (66), wherein the compound represented by Formula (II') is represented by the following Formula (II'):

(II‴)

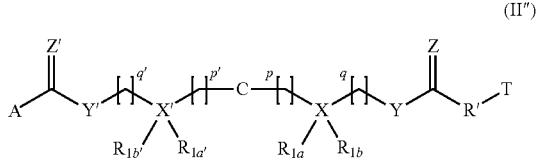

wherein
A, R' and T are the same as those of Formula (II) according to (44);
C is a cleavable portion;
p and p' are the same or different from each other, and are each any integer of 0 to 10;
q and q' are the same or different from each other, and are each any integer of 0 to 10;
X and X' are the same or different from each other, and are each a carbon atom, a nitrogen atom, or a single bond;
wherein
when X is a nitrogen atom, $R_{1b}$ is absent;
when X' is a nitrogen atom, $R_{1b'}$ is absent;
when X is a single bond, $R_{1a}$ and $R_{1b}$ are absent; and
when X' is a single bond, $R_{1a'}$ and $R_{1b'}$ are absent;
$R_{1a}$, $R_{1b}$, $R_{1a'}$, and $R_{1b'}$ are the same or different from each other, and are selected from the group consisting of
(i) a hydrogen atom or a halogen atom;
(ii) a monovalent hydrocarbon group;
(iii) aralkyl;
(iv) a monovalent heterocyclic group;
(v) $R_c$—O—, $R_c$—C(=O)—, $R_c$—O—C(=O)—, or $R_c$—C(=O)—O— wherein $R_c$ indicates a hydrogen atom or a monovalent hydrocarbon group;
(vi) $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and each indicate a hydrogen atom or a monovalent hydrocarbon group; and
(vii) a nitro group, a sulfuric acid group, a sulfonic acid group, a cyano group, or a carboxy group;
Y and Y' are the same or different from each other, and are the same as Y of Formula (B-1) according to [32]; and
Z and Z' are the same or different from each other, and are the same as Z of the above-Formula (B-1).
(68) An antibody having an affinity substance to an antibody and a cleavable portion represented by the following Formula (II):

A-L-B-R'-T (II)

wherein
A is an affinity substance to an antibody;
L is a cleavable linker which is a divalent group comprising a cleavable portion;
B is (a) a divalent group comprising a bioorthogonal functional group or (b) a divalent group comprising no bioorthogonal functional group; and
R' is a portion formed by a reaction between an antibody and a reactive group specific to a side chain of a lysine residue; and
T is an antibody; or
a salt thereof.

(A Method for Producing a Soluble Protein Having an Affinity Substance to a Soluble Protein, and a Cleavable Portion, or a Salt Thereof)
(69) A method for producing a soluble protein having an affinity substance to the soluble protein, and a cleavable portion, or a salt thereof,
the method comprising
reacting a compound having an affinity substance to a soluble protein, a cleavable portion, and a reactive group represented by the following Formula (I):

A-L-B-R (I)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R is a reactive group to a soluble protein; or
a salt thereof
with the soluble protein
to form a soluble protein having an affinity substance to a soluble protein, and a cleavable portion represented by the following Formula (II):

A-L-B-R'-T (II)

wherein
A, L, and B are the same as those of Formula (I);
R' is a portion formed by a reaction between a soluble protein and a reactive group; and
T is a soluble protein; or
a salt thereof.
(70) The method according to (69),
wherein the soluble protein is an antibody, and
the reactive group is a reactive group specific to a side chain of a lysine residue.
Third, the present invention provides a conjugate having an affinity substance to a soluble protein, a cleavable portion, a functional substance(s), and a soluble protein, or a salt thereof, and a method for producing the same.
(A Conjugate Having an Affinity Substance to a Soluble Protein, a Cleavable Portion, a Functional Substance(s), and a Soluble Protein, or a Salt Thereof)
(71) A conjugate having an affinity substance to a soluble protein, a cleavable portion, a functional substance(s), and a soluble protein represented by the following Formula (III):

A-L-B'(-F)-R'-T (III)

wherein
A is an affinity substance to a soluble protein;
L is a cleavable linker which is a divalent group comprising a cleavable portion;
B' is a divalent group comprising a portion formed by a reaction between a functional substance and a bioorthogonal functional group;
F is a functional substance;
R' is a portion formed by a reaction between a soluble protein and a reactive group; and
T is a soluble protein; or
a salt thereof.
(72) The conjugate or salt thereof according to (71), wherein the soluble protein is a monoclonal antibody.
(73) The conjugate or salt thereof according to (71) or (72), wherein the soluble protein is an IgG antibody.
(74) The conjugate or salt thereof according to any one of (71) to (73), wherein the soluble protein is derived from a human.

(75) The conjugate or salt thereof according to any one of (71) to (74), wherein the soluble protein is an antibody comprising any one Fc region protein selected from the group consisting of the following (A) to (C) and having antigen-binding ability:
  (A) an Fc region protein comprising the amino acid sequence of SEQ ID NO: 1;
  (B) an Fc region protein comprising an amino acid sequence with one or several amino acid residues inserted, added, deleted, or substituted in the amino acid sequence of SEQ ID NO: 1; and
  (C) an Fc region protein comprising an amino acid sequence having 90% or more identity to the amino acid sequence of SEQ ID NO: 1.

(76) The conjugate or salt thereof according to any one of (71) to (75),
  wherein the soluble protein comprises one or more specific amino acid residues in a target region consisting of 1 to 50 continuous amino acid residues, and five or more of the specific amino acid residues in a non-target region other than the target region, and
  a structural unit represented by A-L-B'(-F)-R' binds to the one or more of the specific amino acid residues contained in the target region with 30% or more regioselectivity.

(77) The conjugate or salt thereof according to (76), wherein the target region does not comprise the same kind of amino acid residue as the specific amino acid residue other than the specific amino acid residue present at the specific position in a region up to a remote position of "a" (where "a" is any integer of 1 to 10) amino acid residues to an N-terminus side and a C-terminus side each with respect to the specific amino acid present at the specific position.

(78) The conjugate or salt thereof according to any one of (71) to (77),
  wherein the soluble protein is a multimeric protein comprising a plurality of monomeric proteins, and
  T has a structural unit represented by A-L-B'(-F)-R' in a plurality of corresponding target regions in the monomeric proteins such that the multimeric protein has a plurality of structural units represented by A-L-B'(-F)-R'.

(79) The conjugate or salt thereof according to any one of (71) to (78),
  wherein the soluble protein is an antibody comprising a plurality of heavy chains, and
  T has a structural unit represented by A-L-B'(-F)-R' in a plurality of corresponding target regions in the heavy chains such that the antibody has a plurality of structural units represented by A-L-B'(-F)-R'.

(80) The conjugate or salt thereof according to any one of (71) to (79), wherein the divalent group comprising a portion formed by a reaction between a functional substance and a bioorthogonal functional group is a divalent group comprising a reaction portion selected from the group consisting of a disulfide residue, an acetal residue, a ketal residue, an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue.

(81) The conjugate or salt thereof according to any one of (71) to (80), wherein the portion formed by a reaction corresponds to any one chemical structure selected from the group consisting of the following:

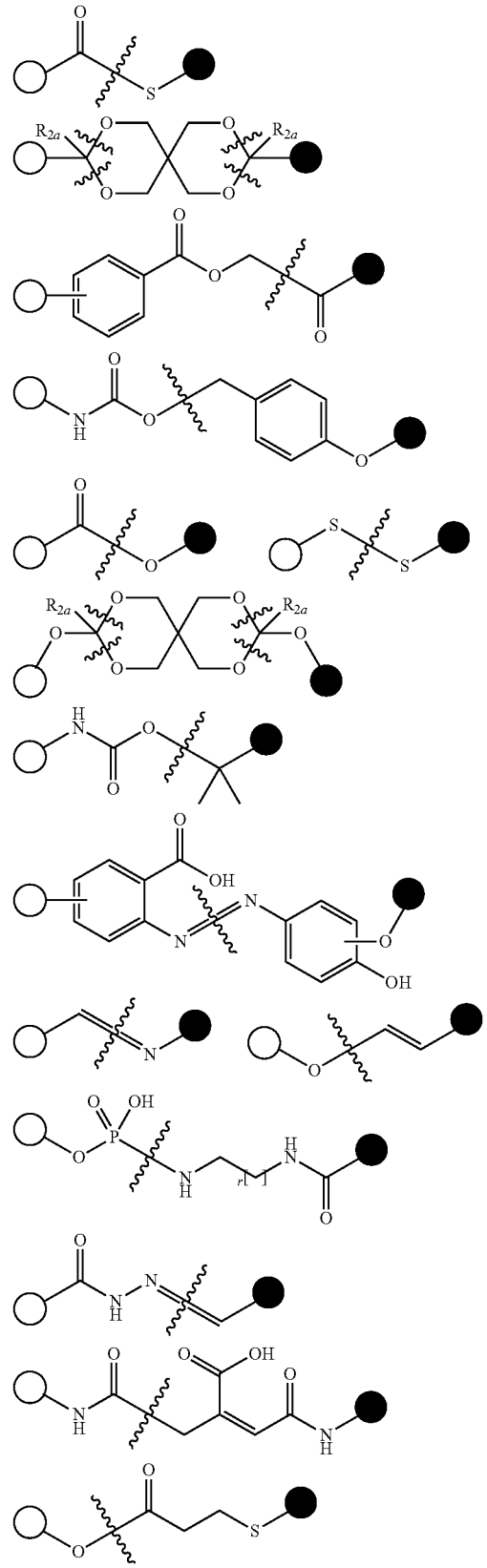

-continued

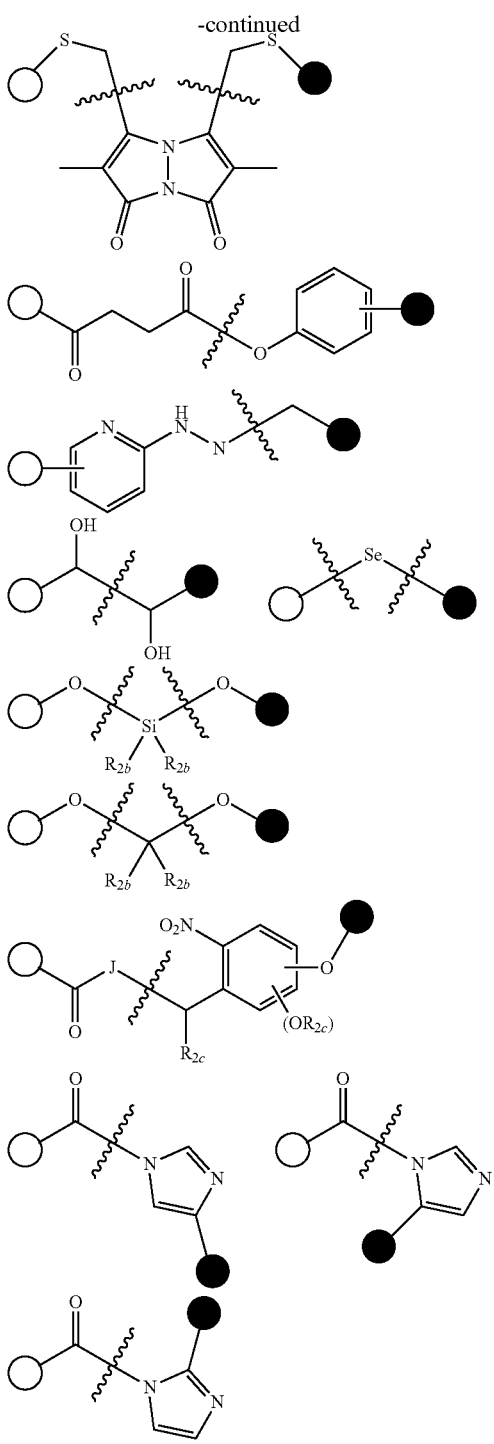

wherein a wavy line orthogonal to a bond indicates a bond formed by a reaction;
a plurality of $R_{2a}$, a plurality of $R_{2b}$, and a plurality of $R_{2c}$ are the same or different from each other, and are selected from the group consisting of:
(i) a hydrogen atom or a halogen atom;
(ii) a monovalent hydrocarbon group;
(iii) aralkyl;
(iv) a monovalent heterocyclic group;
(v) $R_c$—O—, $R_c$—C(=O)—, $R_c$—O—C(=O)—, or $R_c$—C(=O)—O— wherein $R_c$ indicates a hydrogen atom or a monovalent hydrocarbon group;

(vi) $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and each indicate a hydrogen atom or a monovalent hydrocarbon group; and (vii) a nitro group, a sulfuric acid group, a sulfonic acid group, a cyano group, or a carboxy group;

J is —CH$_2$—, —O—, or —S—;

r is any integer of 1 to 4;

a symbol of "white circle" indicates a bond to A, and a symbol of "black circle" indicates a bond to B; and when a chemical structure is asymmetrical with respect to the cleavage site, a symbol of "black circle" may indicate a bond to A, and a symbol of "white circle" may indicate a bond to B.

(82) The conjugate or salt thereof according to any one of (71) to (81), wherein the portion formed by a reaction between a soluble protein and a reactive group is a portion formed by a reaction between a lysine residue, a tyrosine residue, or a tryptophan residue and a reactive group specific to any one side chain of a lysine residue, tyrosine residue, and tryptophan residue.

(83) The conjugate or salt thereof according to any one of (71) to (82), wherein the portion formed by a reaction between a soluble protein and a reactive group is a portion formed by a reaction between a lysine residue and a reactive group specific to a side chain of a lysine residue.

(84) The conjugate or salt thereof according to any one of (71) to (83), wherein the portion formed by a reaction corresponds to any one chemical structure selected from the group consisting of the following:

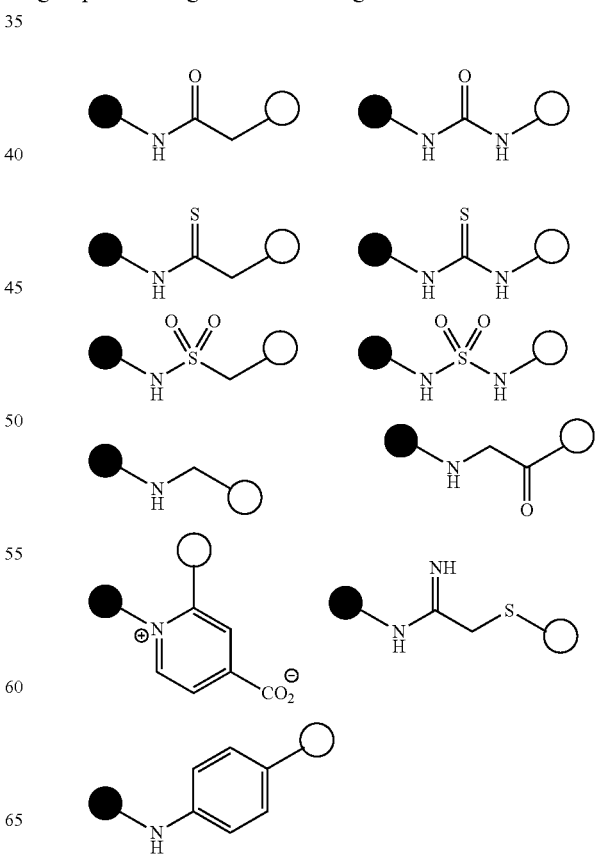

-continued

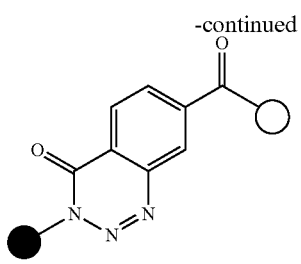

where a symbol of "black circle" indicates a bond to a T-side portion, and a symbol of "white circle" indicates a bond to a B-side portion.

(85) The conjugate or salt thereof according to any one of (71) to (84), wherein the functional substance is a drug or a labelling substance.

(86) The conjugate or salt thereof according to any one of (71) to (85), wherein the functional substance is a small compound.

(87) The conjugate or salt thereof according to (85) or (86), wherein the drug is an anti-cancer agent.

(88) The conjugate or salt thereof according to any one of (71) to (87), wherein the number of atoms of a main chain linking A and R' is 4 to 20.

(89) The conjugate or salt thereof according to any one of (71) to (88), wherein a main chain linking A and R comprises no cyclic structure.

(90) The conjugate or salt thereof according to any one of (71) to (89), wherein a partial structure represented by L-B comprises no peptide portion.

(91) The conjugate or salt thereof according to any one of (71) to (90), wherein the compound represented by Formula (III) is represented by the following Formula (III'):

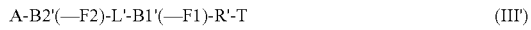
A-B2'(—F2)-L'-B1'(—F1)-R'-T        (III')

wherein
A, R', and T are the same as those of Formula (II);
L' is a cleavable linker which is a divalent group comprising a cleavable portion;
B1' and B2' are the same or different from each other, and are each a divalent group comprising a portion formed by a reaction between a functional substance and a bioorthogonal functional group;
F1 and F2 are the same or different from each other, and are each a functional substance; and
B1'(—F1) and B2'(—F2) may have a symmetrical structure with respect to L'.

(92) The conjugate or salt thereof according to (91), wherein the compound represented by Formula (III') is represented by the following Formula (III"):

(III")
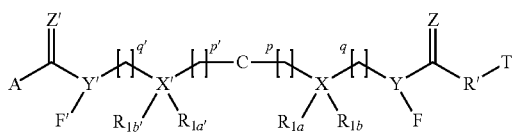

wherein
A, R', and T are the same as those of Formula (III) according to (71);
C is a cleavable portion;
p and p' are the same or different from each other, and are each any integer of 0 to 10;

q and q' are the same or different from each other, and are each any integer of 0 to 10;
X and X' are the same or different from each other, and are each a carbon atom, a nitrogen atom, or a single bond;
wherein
when X is a nitrogen atom, $R_{1b}$ is absent;
when X' is a nitrogen atom, $R_{1b'}$ is absent;
when X is a single bond, $R_{1a}$ and $R_{1b}$ are absent; and
when X' is a single bond, $R_{1a'}$ and $R_{1b'}$ are absent;
$R_{1a}$, $R_{1b}$, $R_{1a'}$, and $R_{1b'}$ are the same or different from each other, are selected from the group consisting of (i) to (vii);
Y and Y' are the same or different from each other, and are each a residue obtained by removing one hydrogen atom from Y of Formula (B-1) according to [32];
Z and Z' are the same or different from each other, and are the same as Z of the above-Formula (B-1); and
F and F' are the same or different from each other, and are each a functional substance.

(93) A conjugate having an affinity substance, a functional substance(s), and an antibody represented by the following Formula (III):

A-L-B'(-F)-R'-T        (III)

wherein
A is an affinity substance to an antibody;
L is a cleavable linker which is a divalent group comprising a cleavable portion;
B' is a divalent group comprising a portion formed by a reaction between a functional substance and a bioorthogonal functional group;
F is a functional substance;
R' is a portion formed by a reaction between an antibody and a reactive group specific to a side chain of a lysine residue; and
T is an antibody; or
a salt thereof.

(A Method for Producing a Conjugate Having an Affinity Substance to a Soluble Protein, a Cleavable Portion, a Functional Substance(s), and a Soluble Protein, or a Salt Thereof)

(94) A method for producing a conjugate having an affinity substance to a soluble protein, a cleavable portion, a functional substance(s), and a soluble protein, or a salt thereof,
the method comprising
reacting a soluble protein having an affinity substance to a soluble protein, and a cleavable portion represented by the following Formula (II):

A-L-B-R'-T        (II)

wherein
A is an affinity substance to a soluble protein;
L is a cleavable linker which is a divalent group comprising a cleavable portion;
B is (a) a divalent group comprising a bioorthogonal functional group;
R' is a portion formed by a reaction between a soluble protein and a reactive group; and
T is a soluble protein; or
a salt thereof
with a functional substance(s)

to form a conjugate having an affinity substance to a soluble protein, a cleavable portion, a functional substance(s), and a soluble protein represented by the following Formula (III):

A-L-B'(-F)-R'-T  (III)

wherein
A, L, R', and T are the same as those of Formula (II);
B' is a divalent group comprising a portion formed by a reaction between a functional substance and a bioorthogonal functional group; and
F is a functional group; or
a salt thereof.

(95) The method according to (94),
wherein the soluble protein is an antibody, and
the reactive group is a reactive group specific to a side chain of a lysine residue.

(96) A method for producing a conjugate having an affinity substance to a soluble protein, a cleavable portion, a functional substance(s), and a soluble protein, or a salt thereof,
the method comprising:
(A) reacting a compound represented by the following Formula (I):

A-L-B-R  (I)

wherein
A is an affinity substance to a soluble protein;
L is a cleavable linker which is a divalent group comprising a cleavable portion;
B is (a) a divalent group comprising a bioorthogonal functional group; and
R is a reactive group to a soluble protein; or
a salt thereof
with a soluble protein
to form a soluble protein having an affinity substance to a soluble protein, and a cleavable portion represented by the following Formula (II):

A-L-B-R'-T  (II)

wherein
A, L, and B are the same as those of Formula (I);
R' is a portion formed by a reaction between a soluble protein and a reactive group; and
T is a soluble protein; or
a salt thereof; and
(B) reacting a soluble protein having an affinity substance to a soluble protein, and a cleavable portion, or a salt thereof
with a functional substance(s)
to form a conjugate having an affinity substance to a soluble protein, a cleavable portion, a functional substance(s), and a soluble protein represented by the following Formula (III):

A-L-B'(-F)-R'-T  (III)

wherein
A and L are the same as those of Formula (I);
R' and T are the same as those of Formula (II);
B' is a divalent group comprising a portion formed by a reaction between a functional substance and a bioorthogonal functional group; and
F is a functional substance; or
a salt thereof.

Fourth, the present invention provides a method for producing a soluble protein having a bioorthogonal functional group(s), or a salt thereof.

(97) A method for producing a soluble protein having a bioorthogonal functional group, or a salt thereof,
the method comprising
cleaving a cleavable portion of a soluble protein having an affinity substance to a soluble protein, and a cleavable portion represented by the following Formula (II):

A-L-B-R'-T  (II)

wherein
A is a affinity substance to a soluble protein;
L is a cleavable linker which is a divalent group comprising a cleavable portion;
B is (a) a divalent group comprising a bioorthogonal functional group or (b) a divalent group comprising no bioorthogonal functional group;
R' is a portion formed by a reaction between a soluble protein and a reactive group; and
T is a soluble protein; or
a salt thereof
to form a soluble protein having a bioorthogonal functional group represented by the following Formula (IV):

L1-B-R'-T  (IV)

wherein
B, R', and T are the same as those of Formula (II); and
L1 is (i') a monovalent group comprising a bioorthogonal functional group or (ii') a monovalent group comprising no bioorthogonal functional group; or
a salt thereof.

(98) The method according to (97), wherein L is (i) a cleavable linker which is a divalent group comprising a cleavable portion having the ability to form a bioorthogonal functional group on a reactive group side by cleavage or (ii) a cleavable linker which is a divalent group comprising a cleavable portion having no ability to form a bioorthogonal functional group on a reactive group side by cleavage.

(99) The method according to (98), wherein
L is the cleavable linker (i);
L1 is (i') the monovalent group comprising a bioorthogonal functional group, and
B is the divalent group (a) or (b).

(100) The method according to (98) or (99), wherein
L is the cleavable linker (i);
L1 is (i') the monovalent group comprising a bioorthogonal functional group, and
B is the divalent group (b).

(101) The method according to (98),
wherein
L is the cleavable linker (ii);
L1 is (ii') the monovalent group comprising no bioorthogonal functional group, and
B is the divalent group (a).

(102) The method according to any one of (97) to (101),
wherein
the soluble protein is an antibody, and
the reactive group is a reactive group specific to a side chain of a lysine residue.

(103) A method for producing a soluble protein having a bioorthogonal functional group, or a salt thereof,
the method comprising:
(A) reacting a compound represented by the following Formula (I):

A-L-B-R  (I)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R is a reactive group to a soluble protein; or
a salt thereof
with a soluble protein
to form a soluble protein having an affinity substance to a soluble protein, and a cleavable portion represented by the following Formula (II):

A-L-B-R'-T  (II)

wherein
A, L, and B are the same as those of Formula (I);
R' is a portion formed by a reaction between a soluble protein and a reactive group; and
T is a soluble protein; or
a salt thereof; and
(B) cleaving the cleavable portion of a soluble protein having an affinity substance to a soluble protein, and a cleavable portion, or a salt thereof
to form a soluble protein having a bioorthogonal functional group(s) represented by the Formula (IV):

L1-B-R'-T  (IV)

wherein
B, R', and T are the same as those of Formula (II); and
L1 is (i') a monovalent group comprising a bioorthogonal functional group or (ii') a monovalent group comprising no bioorthogonal functional group; or
a salt thereof.

Fifth, the present invention provides a method for producing a soluble protein having a functional substance(s), or a salt thereof.

(104) A method for producing a soluble protein having a functional substance(s), or a salt thereof,
the method comprising
cleaving a cleavable portion of a conjugate having an affinity substance to a soluble protein, a cleavable portion, a functional substance(s), and a soluble protein represented by the following Formula (III):

A-L-B'(-F)-R'-T  (III)

wherein
A is an affinity substance to a soluble protein;
L is a cleavable linker which is a divalent group comprising a cleavable portion;
B' is a divalent group comprising a portion formed by a reaction between a functional substance and a bioorthogonal functional group;
F is a functional substance;
R' is a portion formed by a reaction between a soluble protein and a reactive group; and
T is a soluble protein; or
a salt thereof, or
reacting a soluble protein having a bioorthogonal functional group(s) represented by the following Formula (IV):

L1-B-R'-T  (IV)

wherein
L1 is (i') a monovalent group comprising the bioorthogonal functional group or (ii') a monovalent group comprising no bioorthogonal functional group;
B is (a) a divalent group comprising a bioorthogonal functional group or (b) a divalent group comprising no bioorthogonal functional group;
R' is a portion formed by a reaction between a soluble protein and a reactive group; and
T is a soluble protein; or
a salt thereof
with a functional substance(s)
to form a soluble protein having a functional substance(s) represented by the following Formula (V):

F-(L1-B)'—R'-T  (V)

wherein
L1 is (i') a monovalent group comprising the bioorthogonal functional group or (ii') a monovalent group comprising no bioorthogonal functional group;
B is (a) a divalent group comprising the bioorthogonal functional group or (b) a divalent group comprising no bioorthogonal functional group;
a structural unit represented by (L1-B)' is a divalent structural unit comprising a portion formed by a reaction between a functional substance and either one or both of the bioorthogonal functional groups in (i') and (a);
F is a functional substance;
R' is a portion formed by a reaction between a soluble protein and a reactive group; and
T is a soluble protein; or
a salt thereof.

(105) The method according to (104), the method comprising cleaving a cleavable portion of a conjugate having an affinity substance to a soluble protein, a cleavable portion, a functional substance(s), and a soluble protein, or a salt thereof
to form a soluble protein having a functional substance(s) represented by the following Formula (V1):

L1-B'(-F)-R'-T  (V1)

wherein
L1 is (i') a monovalent group comprising a bioorthogonal functional group or (ii') a monovalent group comprising no bioorthogonal functional group; and
B', F, R', and T are the same as those of Formula (III); or
a salt thereof.

(106) The method according to (104), the method comprising reacting the soluble protein having a bioorthogonal functional group(s), or a salt thereof
with one or two functional substances
to form a soluble protein having a functional substance(s) represented by the following Formula (V2):

F-L1'-B-R'-T  (V2)

wherein
B, R', and T are the same as those of Formula (IV);
L1' is a divalent group comprising a portion formed by a reaction between a functional substance and (i') a monovalent group comprising a bioorthogonal functional group; and
F is a functional group; or the following Formula (V3):

Fa-L1'-B'(-Fb)-R'-T  (V3)

wherein
R' and T are the same as those of Formula (IV);
L1' is the same as that of Formula (V2);
B' is a divalent group comprising a portion formed by a reaction between a functional substance and a bioorthogonal functional group; and
Fa and Fb are functional substances which are the same or different from each other; or
a salt thereof.

(107) The method according to any one of (104) to (106), wherein
the soluble protein is an antibody, and
the reactive group is a reactive group specific to a side chain of a lysine residue.

(108) A method for producing a soluble protein having a functional substance(s), or a salt thereof,
the method comprising:
(A) reacting a soluble protein having an affinity substance to a soluble protein, and a cleavable portion represented by the following Formula (II):

A-L-B-R'-T    (II)

wherein
A is an affinity substance to a soluble protein;
L is a cleavable linker which is a divalent group comprising a cleavable portion;
B is (a) a divalent group comprising a bioorthogonal functional group;
R' is a portion formed by a reaction between a soluble protein and a reactive group; and
T is a soluble protein; or
a salt thereof
with a functional substance(s)
to form a conjugate having an affinity substance to a soluble protein, a cleavable portion, a functional substance(s), and a soluble protein represented by the following Formula (III):

A-L-B'(-F)-R'-T    (III)

wherein
A, L, R', and T are the same as those of Formula (II);
B' is a divalent group comprising a portion formed by a reaction between a functional substance and a bioorthogonal functional group; and
F is a functional substance; or
a salt thereof; and
(B) cleaving a cleavable portion of a conjugate having an affinity substance to a soluble protein, a cleavable portion, a functional substance(s), and a soluble protein, or a salt thereof
to form a soluble protein having a functional substance(s) represented by the following Formula (VI):

L1-B'(-F)-R'-T    (V1)

wherein
L1 is (i') a monovalent group comprising the bioorthogonal functional group or (ii') a monovalent group comprising no bioorthogonal functional group; and
B', F, R', and T are the same as those of Formula (III); or
a salt thereof.

(109) A method for producing a soluble protein having a functional substance(s) or a salt thereof,
the method comprising:
(A) reacting a compound having an affinity substance to a soluble protein, a cleavable portion, and a reactive group represented by the following Formula (I):

A-L-B-R    (I)

wherein
A is an affinity substance to a soluble protein;
L is a cleavable linker which is a divalent group comprising the cleavable portion;
B is (a) a divalent group comprising a bioorthogonal functional group; and
R is a reactive group to the soluble protein; or
a salt thereof
with a soluble protein
to form a soluble protein having an affinity substance to a soluble protein, and a cleavable portion represented by the following Formula (II):

A-L-B-R'-T    (II)

wherein
A, L, and B are the same as those of Formula (I);
R' is a portion formed by a reaction between a soluble protein and a reactive group; and
T is a soluble protein; or
a salt thereof;
(B) reacting a soluble protein having an affinity substance to a soluble protein, and a cleavable portion, or a salt thereof with a functional substance(s)
to form a conjugate having an affinity substance to a soluble protein, a cleavable portion, a functional substance(s), and a soluble protein represented by the following Formula (III):

A-L-B'(-F)-R'-T    (III)

wherein
A and L are the same as those of Formula (I);
R' and T are the same as those of Formula (II);
B' is a divalent group comprising a portion formed by a reaction between a functional substance and a bioorthogonal functional group; and
F is a functional substance; or
a salt thereof; and
(C) cleaving a cleavable portion of a conjugate having an affinity substance to a soluble protein, a cleavable portion, a functional substance(s), and a soluble protein, or a salt thereof
to form a soluble protein having a functional substance(s) represented by the following Formula (V1):

L1-B'(-F)-R'-T    (V1)

wherein
L1 is (i') a monovalent group comprising a bioorthogonal functional group or (ii') a monovalent group comprising no bioorthogonal functional group; and
B', F, R', and T are the same as those of Formula (III); or
a salt thereof.

(110) A method for producing a soluble protein having a functional substance(s), or a salt thereof,
the method comprising:
(A) cleaving a cleavable portion of a soluble protein having an affinity substance to a soluble protein, and a cleavable portion represented by the following Formula (II):

A-L-B-R'-T    (II)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R' is a portion formed by a reaction between a soluble protein and a reactive group; and
T is a soluble protein; or
a salt thereof
to form a soluble protein having a bioorthogonal functional group(s) represented by the following Formula (IV):

L1-B-R'-T    (IV)

wherein
B, R', and T are the same as those of Formula (II); and
L1 is (i') a monovalent group comprising the bioorthogonal functional group or (ii') a monovalent group comprising no bioorthogonal functional group; or
a salt thereof; and
(B) reacting a soluble protein having a bioorthogonal functional group(s), or a salt thereof
with one or two or more functional substances
to form a soluble protein having a functional substance(s) represented by the following Formula (V2):

F-L1'-B-R'-T (V2)

wherein
B, R', and T are the same as those of Formula (IV);
L1' is a divalent group comprising a portion formed by a reaction between the functional substance and (i') the monovalent group comprising the bioorthogonal functional group; and
F is a functional substance; or
the following Formula (V3):

Fa-L1'-B'(-Fb)-R'-T (V3)

wherein
R' and T are the same as those of Formula (IV);
L1' is the same as that of Formula (V2);
B' is a divalent group comprising a portion formed by a reaction between a functional substance and a bioorthogonal functional group; and
Fa and Fb are functional substances which are the same or different from each other; or
a salt thereof.
(111) A method for producing a soluble protein having a functional substance(s), or a salt thereof,
the method comprising:
(A) reacting a compound represented by the following Formula (I):

A-L-B-R (I)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R is a reactive group to a soluble protein; or
a salt thereof
with a soluble protein
to form a soluble protein having an affinity substance to a soluble protein, and a cleavable portion represented by the following Formula (II):

A-L-B-R'-T (II)

wherein
A, L, and B are the same as those of Formula (I);
R' is a portion formed by a reaction between a soluble protein and a reactive group; and
T is the soluble protein; or
a salt thereof;
(B) cleaving a cleavable portion of a soluble protein having an affinity substance to a soluble protein, and a cleavable portion, or a salt thereof
to form a soluble protein having a bioorthogonal functional group(s) represented by the following Formula (IV):

L1-B-R'-T (IV)

wherein
B, R', and T are the same as those of Formula (II); and
L1 is (i') a monovalent group comprising a bioorthogonal functional group or (ii') a monovalent group comprising no bioorthogonal functional group; or
a salt thereof; and
(C) reacting a soluble protein having a bioorthogonal functional group(s), or a salt thereof
with one or two or more functional substances
to form a soluble protein having a functional substance(s) represented by the following Formula (V2):

F-L1'-B-R'-T (V2)

wherein
B, R', and T are the same as those of Formula (IV);
L1' is a divalent group comprising a portion formed by a reaction between a functional substance and (i') a monovalent group comprising a bioorthogonal functional group; and
F is a functional substance; or
the following Formula (V3):

Fa-L1'-B'(-Fb)-R'-T (V3)

wherein
R' and T are the same as those of Formula (IV);
L1' is the same as that of Formula (V2);
B' is a divalent group comprising a portion formed by a reaction between a functional substance and a bioorthogonal functional group; and
Fa and Fb are functional substances which are the same or different from each other; or
a salt thereof.
Sixth, the present invention provides a soluble protein regioselectively having a bioorthogonal functional group(s), or a salt thereof, and a method for producing the same.
(A Soluble Protein Regioselectively Having a Bioorthogonal Functional Group(s), or a Salt Thereof)
(1) A soluble protein regioselectively having a bioorthogonal functional group(s), or a salt thereof,
wherein the soluble protein comprises one or more specific amino acid residues in a target region consisting of 1 to 50 continuous amino acid residues, and five or more of the specific amino acid residues in a non-target region other than the target region, and
the bioorthogonal functional group(s) binds to the one or more specific amino acid residues in the target region with 30% or more regioselectivity through a linker comprising no peptide portion.
(2) A soluble protein regioselectively having a bioorthogonal functional group(s) represented by the following Formula (IV):

L1-B-R'-T (IV)

wherein
L1 is (i') a monovalent group comprising a bioorthogonal functional group or (ii') a monovalent group comprising no bioorthogonal functional group;
B is (a) a divalent group comprising a bioorthogonal functional group or (b) a divalent group comprising no bioorthogonal functional group;
R' is a portion formed by a reaction between a soluble protein and a reactive group; and
T is a soluble protein; or
a salt thereof,
wherein the soluble protein comprising one or more specific amino acid residues in a target region consisting of 1 to 50 continuous amino acid residues and comprising five or more of the specific amino acid residues in a non-target region other than the target region, and
a structural unit represented by L1-B-R' binding to one or more of the specific amino acid residues contained in the target region of the soluble protein with 30% or more regioselectivity.

(3) The soluble protein or salt thereof according to (1) or (2), wherein the soluble protein is a monoclonal antibody.

(4) The soluble protein or salt thereof according to any one of (1) to (3), wherein the soluble protein is an IgG antibody.

(5) The soluble protein or salt thereof according to any one of (1) to (4), wherein the soluble protein is derived from a human.

(6) The soluble protein or salt thereof according to any one of (1) to (5), wherein the soluble protein is an antibody comprising any one Fc region protein selected from the group consisting of the following (A) to (C) and having antigen-binding ability:
  (A) an Fc region protein comprising the amino acid sequence of SEQ ID NO: 1;
  (B) an Fc region protein comprising an amino acid sequence with one or several amino acid residues inserted, added, deleted, or substituted in the amino acid sequence of SEQ ID NO: 1; and
  (C) an Fc region protein comprising an amino acid sequence having 90% or more identity to the amino acid sequence of SEQ ID NO: 1.

(7) The soluble protein or salt thereof according to any one of (1) to (6), wherein the target region is a region consisting of one to ten continuous amino acid residues.

(8) The soluble protein or salt thereof according to any one of (1) to (7), wherein the target region is a region consisting of one to three continuous amino acid residues.

(9) The soluble protein or salt thereof according to (8), wherein the target region is (a) a region consisting of amino acid residues at positions 246 to 248 in an human IgG Fc region, (b) a region consisting of amino acid residues at positions 288 to 290 in the human IgG Fc region, or (c) a region consisting of an amino acid residue at position 317 in the human IgG Fc region.

(10) The soluble protein or salt thereof according to any one of (1) to (9), wherein the regioselectivity is 50% or more.

(11) The soluble protein or salt thereof according to (10), wherein the regioselectivity is 70% or more.

(12) The soluble protein or salt thereof according to (11), wherein the regioselectivity is 90% or more.

(13) The soluble protein or salt thereof according to any one of (1) to (12), wherein the target region does not comprise the same kind of amino acid residue as the specific amino acid residue other than the specific amino acid residue present at the specific position in a region up to a remote position of "a" (where "a" is any integer of 1 to 10) amino acid residues to an N-terminus side and a C-terminus side each with respect to the specific amino acid present at the specific position.

(14) The soluble protein or salt thereof according to any one of (1), (3) to (13),
  wherein the soluble protein is a multimeric protein comprising a plurality of monomeric proteins, and
  the bioorthogonal functional groups are present in positions of the one or more specific amino acid residues in a plurality of monomeric proteins such that the multimeric protein has a plurality of bioorthogonal functional groups.

(15) The soluble protein or salt thereof according to any one of (1), (3) to (14),
  wherein the soluble protein is an antibody comprising a plurality of heavy chains, and
  the bioorthogonal functional groups are present in positions of the one or more specific amino acid residues in a plurality of heavy chains such that the antibody has a plurality of bioorthogonal functional groups.

(16) The soluble protein or salt thereof according to any one of (2) to (13),
  wherein the soluble protein is a multimeric protein comprising a plurality of monomeric proteins, and
  T has a structural unit represented by A-L-B-R' in a plurality of corresponding target regions in the monomeric proteins such that the multimeric protein has a plurality of structural units represented by A-L-B-R'.

(17) The soluble protein or salt thereof according to any one of (2) to (13) and (16),
  wherein the soluble protein is an antibody comprising a plurality of heavy chains, and
  T has a structural unit represented by A-L-B-R' in a plurality of corresponding target regions in the heavy chains such that the antibody has a plurality of structural units represented by A-L-B-R'.

(18) The soluble protein or salt thereof according to (15) or (17), wherein the number of the heavy chains is two.

(19) The soluble protein or salt thereof according to any one of (2) to (13) and (16) to (18), wherein L1 is represented by any one of the following Formulae (L1-1) to (L1-2):

$$C1\text{-}Lb \quad (L1\text{-}1)$$

$$C1 \quad (L1\text{-}2)$$

wherein
  Lb is a divalent group; and
  C1 is a bioorthogonal functional group, or a group other than a bioorthogonal functional group.

(20) The soluble protein or salt thereof according to (19), wherein Lb is represented by the following (Lb'):

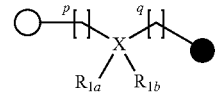

(Lb')

wherein
  p is any integer of 0 to 10;
  q is any integer of 0 to 10;
  X is a carbon atom, a nitrogen atom, or a single bond;
    wherein when X is a nitrogen atom, $R_{1b}$ is absent;
    when X is a single bond, $R_{1a}$ and $R_{1b}$ are absent;
  $R_{1a}$ and $R_{1b}$ are the same or different from each other, and are each an atom or a group selected from the group consisting of the above-substituent; and
  a symbol of "white circle" indicates a bond to C1, and a symbol of "black circle" indicates a bond to B.

(21) The soluble protein thereof according to any one of (1) to (20), wherein the divalent group comprising a bioorthogonal function group is a divalent group comprising a bioorthogonal functional group selected from the group consisting of an azide residue, an aldehyde residue, a thiol residue, an alkyne residue, an alkene residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue in a main chain thereof.

(22) The soluble protein or salt thereof according to any one of (1) to (20), wherein the divalent group comprising a bioorthogonal function group is a divalent group comprising a bioorthogonal function group selected from the group consisting of an azide residue, an aldehyde residue, a thiol residue, an alkyne residue, an alkene residue, a halogen residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue in a side chain thereof.

(23) The soluble protein or salt thereof according to any one of (1) to (22), wherein the bioorthogonal functional group is any one represented by the following:

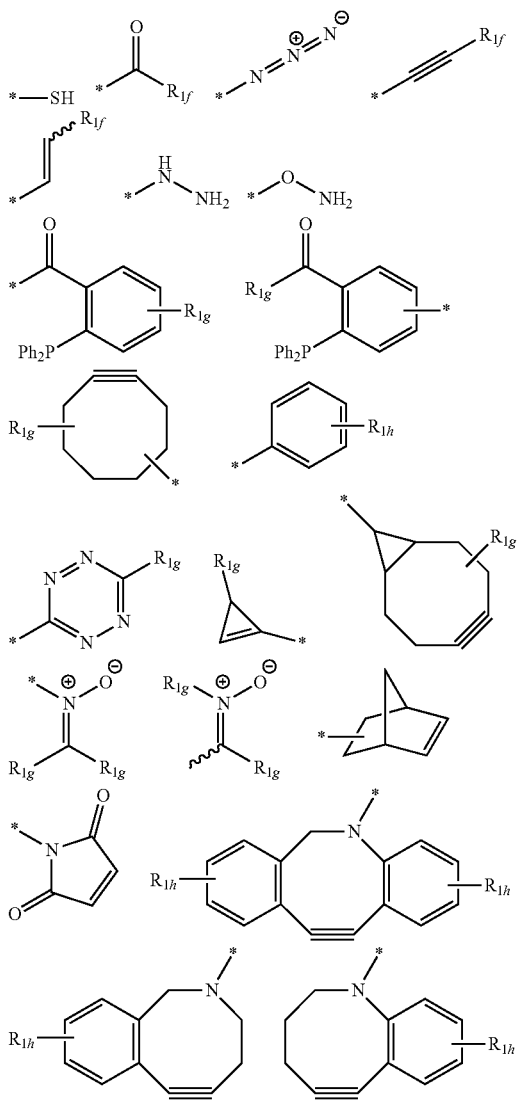

wherein
$R_{1f}$, one or a plurality of $R_{1g}$, and one or a plurality of $R_{1h}$ are the same or different from each other, and are each an atom or a group selected from the group consisting of the (i) to (vii) or an electron-withdrawing group; and
• is a bond.

(24) The soluble protein or salt thereof according to any one of (2) to (13) and (16) to (23), wherein the divalent group (b) is selected from the group consisting of optionally substituted alkylene, optionally substituted cycloalkylene, optionally substituted aryl, an optionally substituted divalent heterocyclic group, —$NR_a$— ($R_a$ indicates a hydrogen atom or a substituent), —O—, and a combination of two or more of these.

(25) The soluble protein or salt thereof according to any one of (2) to (13) and (16) to (24), wherein B is represented by the following Formula (B-1):

wherein
Y is —NH—, —O—, —$CH_2$—, or the following Formula (B-2):

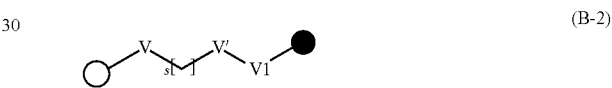

wherein
V and V' are the same or different from each other, and are each —NH—, —O—, —$CH_2$—, or a single bond;
V1 is a divalent group comprising a bioorthogonal functional group;
s is any integer of 0 to 10;
a symbol of "white circle" and a symbol of "black circle" in Formula (B-2) have the same orientation as a symbol of "white circle" and a symbol of "black circle" in Formula (B-1), respectively;
Z is an oxygen atom, a sulfur atom, or a hydrogen atom wherein when Z is a hydrogen atom, —C(=Z)— indicates —$CH_2$—; and
a symbol of "white circle" in Formula (B-1) indicates a bond to an L-side portion, and a symbol of "black circle" indicates a bond to an R-side portion.

(26) The soluble protein or salt thereof according to any one of (1) to (25), wherein the bioorthogonal functional group(s) binds to the soluble protein via a side chain of any one of a lysine residue, a tyrosine residue, and a tryptophan residue.

(27) The soluble protein or salt thereof according to (26), wherein the bioorthogonal functional group(s) binds to the soluble protein via a side chain of a lysine residue.

(28) The soluble protein or salt thereof according to any one of (2) to (13) and (16) to (26), wherein the reactive group is a reactive group specific to a side chain of any one of a lysine residue, a tyrosine residue, and a tryptophan residue.

(29) The soluble protein or salt thereof according to (2) to (13) and (16) to (28), wherein the reactive group is a reactive group specific to a side chain of a lysine residue.

(30) The soluble protein or salt thereof according to any one of (2) to (13) and (16) to (29), wherein the reactive group corresponds to any one chemical structure selected from the group consisting of the following:

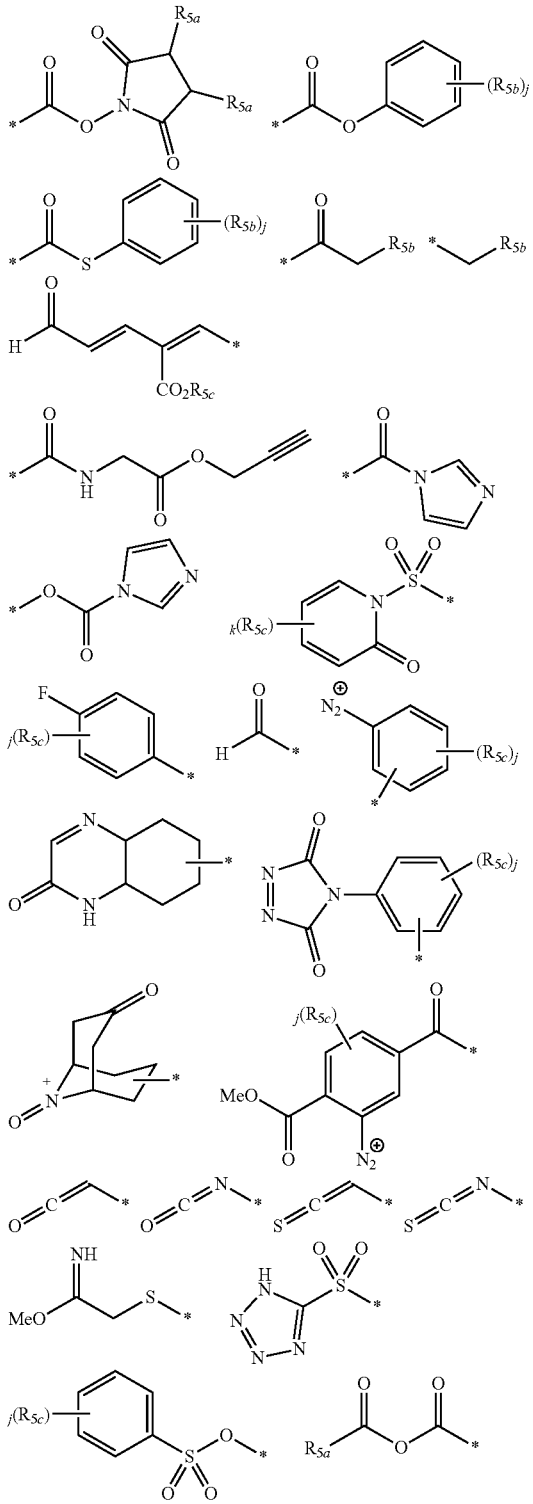

where
R$_{5a}$ and R$_{5c}$ are each an atom or a group selected from the group consisting of (i) to (vii);

R$_{5b}$ is an electron-withdrawing group;
j is any integer of 1 to 5; and
k is any integer of 1 to 4.

(31) The soluble protein or salt thereof according to any one of (1) to (30), wherein the bioorthogonal functional group(s) binds to the soluble protein via a linker comprising 2 to 10 atoms of a main chain linking the bioorthogonal functional group and the side chain of the specific amino acid residue.

(32) The soluble protein or salt thereof according to any one of (1) to (31), wherein the bioorthogonal functional group(s) binds to the soluble protein via a linker comprising no cyclic structure in a main chain linking the bioorthogonal functional group and the side chain of the specific amino acid residue.

(33) The soluble protein or salt thereof according to any one of (2) to (13) and (16) to (32), wherein the number of atoms of a main chain linking L1 terminal portion and R' is 2 to 10.

(34) The soluble protein or salt thereof according to any one of (2) to (13) and (16) to (33), wherein a main chain linking A and R comprises no cyclic structure.

(35) The soluble protein or salt thereof according to any one of (2) to (13) and (16) to (34), wherein a partial structure represented by L1-B comprises no peptide portion.

(36) The soluble protein or salt thereof according to any one of (2) to (13) and (16) to (35), wherein the soluble protein represented by the Formula (IV) is the following Formula (IV'):

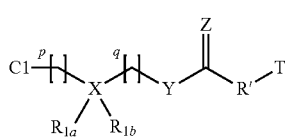

(IV')

wherein
C1 is a bioorthogonal group, or a group other than a bioorthogonal group;
p, q, X, R$_{1a}$ and R$_{1b}$ are the same as those of the Formula (Lb');
Y and Z are the same as those described above; and
R' and T are the same as those of the Formula (IV).

(37) A soluble protein regioselectively having bioorthogonal functional groups, or a salt thereof,
wherein the soluble protein comprises one or more specific amino acid residues in a target region consisting of 1 to 50 continuous amino acid residues, and five or more of the specific amino acid residues in a non-target region other than the target region, and
the bioorthogonal functional groups bind to the one or more specific amino acid residues in the target region with 30% or more regioselectivity through a linker comprising no peptide portion,
the bioorthogonal functional groups bind to the soluble protein via a side chain of a lysine residue,
the soluble protein is an antibody comprising a plurality of heavy chains, and
the bioorthogonal functional groups are present in positions of the one or more specific amino acid residues in a plurality of heavy chains such that the antibody has a plurality of bioorthogonal functional groups.

(38) A soluble protein regioselectively having a bioorthogonal functional group(s) represented by the following Formula (IV):

L1-B-R'-T (IV)

wherein
L1 is (i') a monovalent group comprising a bioorthogonal functional group or (ii') a monovalent group comprising no bioorthogonal functional group;
B is (a) a divalent group comprising a bioorthogonal functional group or (b) a divalent group comprising no bioorthogonal functional group;
R' is a portion formed by a reaction between a soluble protein and a reactive group; and
T is a soluble protein; or
a salt thereof,
wherein the soluble protein comprising one or more specific amino acid residues in a target region consisting of 1 to 50 continuous amino acid residues and comprising five or more of the specific amino acid residues in a non-target region other than the target region, and
a structural unit represented by L1-B-R' binding to one or more of the specific amino acid residues contained in the target region of the soluble protein with 30% or more regioselectivity.

(A Method for Producing a Soluble Protein Regioselectively Having a Bioorthogonal Functional Group(s), or a Salt Thereof)

The present invention also provides a method for producing a soluble protein regioselectively having a bioorthogonal functional group(s), or a salt thereof, wherein the soluble protein is to be specified by Formula (IV) or species Formula thereof among the above-soluble protein (1) to (38).

(39) A method for producing a soluble protein regioselectively having a bioorthogonal functional group(s) or a salt thereof,
the method comprising
cleaving a cleavable portion of a soluble protein regioselectively having an affinity substance to a soluble protein, and a cleavable portion represented by the following Formula (II):

A-L-B-R'-T (II)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group;
R' is a portion formed by a reaction between a soluble protein and a reactive group; and
T is a soluble protein,
the soluble protein comprising one or more specific amino acid residues in a target region consisting of 1 to 50 continuous amino acid residues and comprising five or more of the specific amino acid residues in a non-target region other than the target region, and
a structural unit represented by L1-B-R' binding to the one or more specific amino acid residues contained in the target region of the soluble protein with 30% or more regioselectivity, or
a salt thereof
to form a soluble protein regioselectively having a bioorthogonal functional group(s) represented by the following Formula (IV):

L1-B-R'-T (IV)

wherein
B, R', and T are the same as those of Formula (II); and
L1 is (i') a monovalent group comprising a bioorthogonal functional group or (ii') a monovalent group comprising no bioorthogonal functional group, and
a structural unit represented by L1-B-R' binding to the one or more specific amino acid residues contained in the target region of the soluble protein with 30% or more regioselectivity, or
a salt thereof.

Preferably, the method of (39) may be the following.

(40) The method according to (39), wherein the soluble protein is an antibody, and the reactive group is a reactive group specific to a side chain of a lysine residue.

(41) A method for producing a soluble protein regioselectively having a bioorthogonal functional group(s), or a salt thereof,
the method comprising:
(A) reacting a compound represented by the following Formula (I):

A-L-B-R (I)

wherein
A is an affinity substance to a soluble protein;
L is a cleavable linker which is a divalent group comprising a cleavable portion;
B is (a) a divalent group comprising the bioorthogonal functional group or (b) a divalent group comprising no bioorthogonal functional group; and
R is a reactive group to the soluble protein,
the soluble protein comprising one or more specific amino acid residues in a target region consisting of 1 to 50 continuous amino acid residues and comprising five or more of the specific amino acid residues in a non-target region other than the target region, or
a salt thereof
with a soluble protein
to form a soluble protein regioselectively having an affinity substance to a soluble protein, and a cleavable portion represented by the following Formula (II):

A-L-B-R'-T (II)

wherein
A, L, and B are the same as those of Formula (I);
R' is a portion formed by a reaction between the soluble protein and a reactive group; and
T is the soluble protein,
a structural unit represented by L1-B-R' binding to the one or more specific amino acid residues contained in the target region of the soluble protein with 30% or more regioselectivity, or
a salt thereof, and
(B) cleaving a cleavable portion of the soluble protein regioselectively having an affinity substance to a soluble protein, and a cleavable portion, or a salt thereof
to form the soluble protein regioselectively having a bioorthogonal functional group(s) represented by the Formula (IV):

L1-B-R'-T (IV)

wherein
B, R', and T are the same as those of Formula (II); and
L1 is (i') a monovalent group comprising the bioorthogonal functional group or (ii') a monovalent group comprising no bioorthogonal functional group,
a structural unit represented by L1-B-R' binding to the one or more specific amino acid residues contained in the target region of the soluble protein with 30% or more regioselectivity, or
a salt thereof.

Seventh, the present invention provides a soluble protein regioselectively having a functional substance(s), or a salt thereof, and a method for producing the same.

(A Soluble Protein Regioselectively Having a Functional Substance(s), or a Salt Thereof)

(1) A soluble protein regioselectively having a functional substance(s), or a salt thereof,
wherein the soluble protein comprises one or more specific amino acid residues in a target region consisting of 1 to 50 continuous amino acid residues, and five or more of the specific amino acid residues in a non-target region other than the target region, and
the a functional substance(s) binds to the one or more specific amino acid residues in the target region with 30% or more regioselectivity through a linker comprising no peptide portion.

(2) A soluble protein regioselectively having a functional substance(s) represented by the following Formula (V):

F-(L1-B)'—R'-T           (V)

wherein
L1 is (i') a monovalent group comprising a bioorthogonal functional group or (ii') a monovalent group comprising no bioorthogonal functional group;
B is (a) a divalent group comprising a bioorthogonal functional group or (b) a divalent group comprising no bioorthogonal functional group;
a structural unit represented by (L1-B)' is a divalent structural unit comprising a portion formed by a reaction between a functional substance and either one or both of the bioorthogonal functional groups in (i') and (a);
F is a functional substance;
R' is a portion formed by a reaction between a soluble protein and a reactive group;
T is a soluble protein; and
the soluble protein comprising one or more specific amino acid residues in a target region consisting of 1 to 50 continuous amino acid residues and comprising five or more of the specific amino acid residues in a non-target region other than the target region, and
a structural unit represented by F-(L1-B)'—R' binding to the one or more specific amino acid residues contained in the target region of the soluble protein with 30% or more regioselectivity, or
a salt thereof.

(3) The soluble protein or salt thereof according to (2), wherein the soluble protein or salt thereof is a soluble protein regioselectively having a functional substance(s) represented by the following Formula (V1):

L1-B'(-F)-R'-T           (V1)

wherein
L1, F, R', and T are the same as those of Formula (V),
B' is a divalent group comprising a portion formed by a reaction between a functional substance and a bioorthogonal functional group,
a structural unit represented by L1-B'(-F)-R' binding to the one or more specific amino acid residues contained in the target region of the soluble protein with 30% or more regioselectivity, or
a salt thereof.

(4) The soluble protein or salt thereof according to (2), wherein the soluble protein or salt thereof is a soluble protein regioselectively having a functional substance(s) represented by the following Formula (V2):

F-L1'-B-R'-T           (V2)

wherein
F, B, R', and T are the same as those of Formula (V);
L1' is a divalent group comprising a portion formed by a reaction between a functional substance and (i') a monovalent group comprising a bioorthogonal functional group, and
a structural unit represented by F-L1'-B-R' binding to the one or more specific amino acid residues contained in the target region of the soluble protein with 30% or more regioselectivity, or
the following Formula (V3):

Fa-L1'-B'(-Fb)-R'-T           (V3)

wherein
R' and T are the same as those of Formula (V);
L1' is the same as that of Formula (V2);
B' is a divalent group comprising a portion formed by a reaction between a functional substance and a bioorthogonal functional group; and
Fa and Fb are functional substances which are the same or different from each other, and
a structural unit represented by Fa-L1'-B'(-Fb)-R' binding to the one or more specific amino acid residues contained in the target region of the soluble protein with 30% or more regioselectivity, or
a salt thereof.

(5) The soluble protein or salt thereof according to any one of (1) to (4), wherein the soluble protein is a monoclonal antibody.

(6) The soluble protein or salt thereof according to any one of (1) to (5), wherein the soluble protein is an IgG antibody.

(7) The soluble protein or salt thereof according to any one of (1) to (6), wherein the soluble protein is derived from a human.

(8) The soluble protein or salt thereof according to any one of (1) to (7), wherein the soluble protein is an antibody comprising any one Fc region protein selected from the group consisting of the following (A) to (C) and having antigen-binding ability:
(A) an Fc region protein comprising the amino acid sequence of SEQ ID NO: 1;
(B) an Fc region protein comprising an amino acid sequence with one or several amino acid residues inserted, added, deleted, or substituted in the amino acid sequence of SEQ ID NO: 1; and
(C) an Fc region protein comprising an amino acid sequence having 90% or more identity to the amino acid sequence of SEQ ID NO: 1.

(9) The soluble protein or salt thereof according to any one of (1) to (8), wherein the target region is a region consisting of one to ten continuous amino acid residues.

(10) The soluble protein or salt thereof according to any one of (1) to (9), wherein the target region is a region consisting of one to three continuous amino acid residues.

(11) The soluble protein or salt thereof according to (10), wherein the target region is (a) a region consisting of amino acid residues at positions 246 to 248 in an human IgG Fc region, (b) a region consisting of amino acid residues at positions 288 to 290 in the human IgG Fc region, or (c) a region consisting of an amino acid residue at position 317 in the human IgG Fc region.

(12) The soluble protein or salt thereof according to any one of (1) to (11), wherein the regioselectivity is 50% or more.

(13) The soluble protein or salt thereof according to (12), wherein the regioselectivity is 70% or more.

(14) The soluble protein or salt thereof according to (13), wherein the regioselectivity is 90% or more.

(15) The soluble protein or salt thereof according to any one of (1) to (14), wherein the target region does not comprise the same kind of amino acid residue as the specific amino acid residue other than the specific amino acid residue present at the specific position in a region up to a remote position of "a" (where "a" is any integer of 1 to 10) amino acid residues to an N-terminus side and a C-terminus side each with respect to the specific amino acid present at the specific position.

(16) The soluble protein or salt thereof according to any one of (1), (5) to (15),
wherein the soluble protein is a multimeric protein comprising a plurality of monomeric proteins, and
the functional substances are present in positions of the one or more specific amino acid residues in a plurality of monomeric proteins such that the multimeric protein has a plurality of functional substances.

(17) The soluble protein or salt thereof according to any one of (1), (5) to (16),
wherein the soluble protein is an antibody comprising a plurality of heavy chains, and
the functional substances are present in positions of the one or more specific amino acid residues in a plurality of heavy chains such that the antibody has a plurality of functional substances.

(18) The soluble protein or salt thereof according to any one of (2) to (15),
wherein the soluble protein is a multimeric protein comprising a plurality of monomeric proteins, and
T has a structural unit represented by A-L-B-R' in a plurality of corresponding target regions in the monomeric proteins such that the multimeric protein has a plurality of structural units represented by A-L-B-R'.

(19) The soluble protein or salt thereof according to any one of (2) to (15) and (18),
wherein the soluble protein is an antibody comprising a plurality of heavy chains, and
T has a structural unit represented by A-L-B-R' in a plurality of corresponding target regions in the heavy chains such that the antibody has a plurality of structural units represented by A-L-B-R'.

(20) The soluble protein or salt thereof according to (17) or (19), wherein the number of the heavy chains is two.

(21) The soluble protein or salt thereof according to any one of (2) to (15) and (18) to (20), wherein L1 is represented by any one of the following Formulae (L1-1) to (L1-2):

C1-Lb (L1-1)

C1 (L1-2)

wherein
Lb is a divalent group; and
C1 is a bioorthogonal functional group, or a group other than a bioorthogonal functional group.

(22) The soluble protein or salt thereof according to (21), wherein Lb is represented by the following (Lb'):

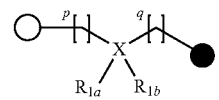

wherein
p is any integer of 0 to 10;
q is any integer of 0 to 10;
X is a carbon atom, a nitrogen atom, or a single bond;
wherein when X is a nitrogen atom, $R_{1b}$ is absent;
when X is a single bond, $R_{1a}$ and $R_{1b}$ are absent;
$R_{1a}$ and $R_{1b}$ are the same or different from each other, and are each an atom or a group selected from the group consisting of the above-substituent; and
a symbol of "white circle" indicates a bond to C1, and a symbol of "black circle" indicates a bond to B.

(23) The soluble protein thereof according to any one of (1) to (22), wherein the divalent group comprising a bioorthogonal function group is a divalent group comprising a bioorthogonal functional group selected from the group consisting of an azide residue, an aldehyde residue, a thiol residue, an alkyne residue, an alkene residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue in a main chain thereof.

(24) The soluble protein or salt thereof according to any one of (1) to (22), wherein the divalent group comprising a bioorthogonal function group is a divalent group comprising a bioorthogonal function group selected from the group consisting of an azide residue, an aldehyde residue, a thiol residue, an alkyne residue, an alkene residue, a halogen residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue in a side chain thereof.

(25) The soluble protein or salt thereof according to any one of (1) to (24), wherein the bioorthogonal functional group is any one represented by the following:

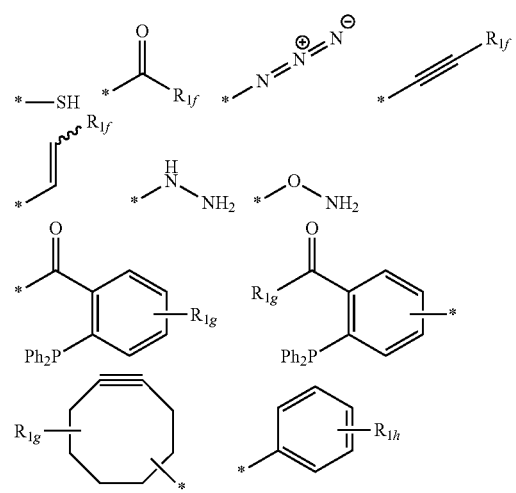

-continued

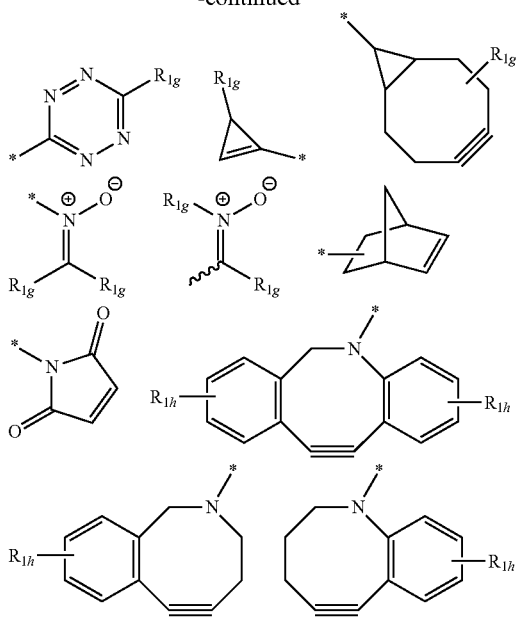

wherein
- $R_{1f}$, one or a plurality of $R_{1g}$, and one or a plurality of $R_{1h}$ are the same or different from each other, and are each an atom or a group selected from the group consisting of the (i) to (vii) or an electron-withdrawing group; and
- • is a bond.

(26) The soluble protein or salt thereof according to any one of (1) to (25), wherein the divalent group (b) is selected from the group consisting of optionally substituted alkylene, optionally substituted cycloalkylene, optionally substituted aryl, an optionally substituted divalent heterocyclic group, —$NR_a$— ($R_a$ indicates a hydrogen atom or a substituent), —O—, and a combination of two or more of these.

(27) The soluble protein or salt thereof according to any one of (2) to (15) and (18) to (26), wherein B is represented by the following Formula (B-1):

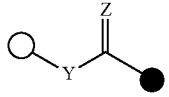 (B-1)

wherein
Y is —NH—, —O—, —$CH_2$—, or the following Formula (B-2):

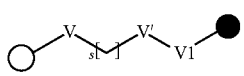 (B-2)

wherein
- V and V' are the same or different from each other, and are each —NH—, —O—, —$CH_2$—, or a single bond;
- V1 is a divalent group comprising a bioorthogonal functional group;

s is any integer of 0 to 10;
a symbol of "white circle" and a symbol of "black circle" in Formula (B-2) have the same orientation as a symbol of "white circle" and a symbol of "black circle" in Formula (B-1), respectively;
Z is an oxygen atom, a sulfur atom, or a hydrogen atom wherein when Z is a hydrogen atom, —C(=Z)— indicates —$CH_2$—; and
a symbol of "white circle" in Formula (B-1) indicates a bond to an L-side portion, and a symbol of "black circle" indicates a bond to an R-side portion.

(28) The soluble protein or salt thereof according to any one of (2) to (15) and (18) to (27), wherein the reactive group is a reactive group specific to a side chain of any one of a lysine residue, a tyrosine residue, and a tryptophan residue.

(29) The soluble protein or salt thereof according to (2) to (15) and (18) to (28), wherein the reactive group is a reactive group specific to a side chain of a lysine residue.

(30) The soluble protein or salt thereof according to any one of (2) to (15) and (18) to (29), wherein the reactive group corresponds to any one chemical structure selected from the group consisting of the following:

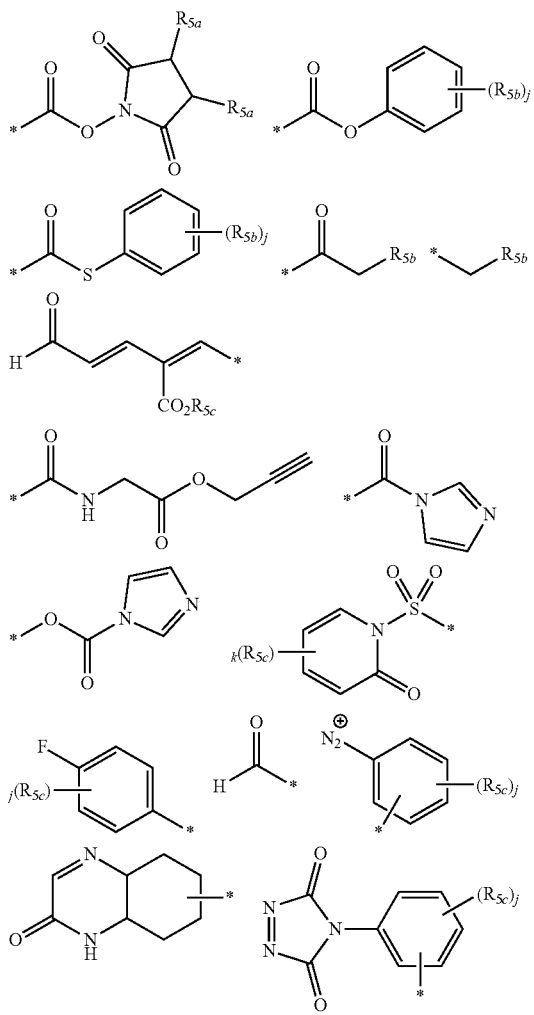

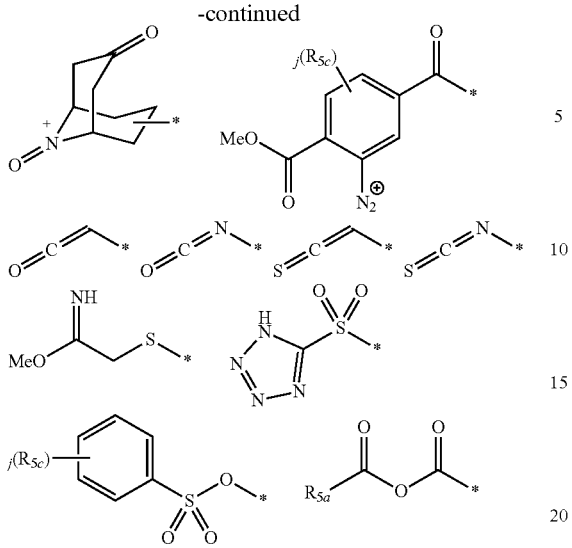

where
R$_{5a}$ and R$_{5c}$ are each an atom or a group selected from the group consisting of (i) to (vii);
R$_{5b}$ is an electron-withdrawing group;
j is any integer of 1 to 5; and
k is any integer of 1 to 4.

(31) The soluble protein or salt thereof according to any one of (1) to (30), wherein the a functional substance(s) binds to the soluble protein via a linker comprising 2 to 10 atoms of a main chain linking the functional substance and the side chain of the specific amino acid residue.

(32) The soluble protein or salt thereof according to any one of (1) to (31), wherein the a functional substance(s) binds to the soluble protein via a linker comprising no cyclic structure in a main chain linking the functional substance and the side chain of the specific amino acid residue.

(33) The soluble protein or salt thereof according to any one of (2) to (15) and (18) to (32), wherein the number of atoms of a main chain linking L1 terminal portion and R' is 2 to 10.

(34) The soluble protein or salt thereof according to any one of (2) to (15) and (18) to (33), wherein a main chain linking A and R comprises no cyclic structure.

(35) The soluble protein or salt thereof according to any one of (2) to (15) and (18) to (34), wherein a partial structure represented by L1-B comprises no peptide portion.

(36) The soluble protein or salt thereof according to any one of (2) to (15) and (18) to (35), wherein the soluble proteins represented by the Formula (V1), (V2) and (V3) are the following Formula (V1'), (V2') and (V3'), respectively:

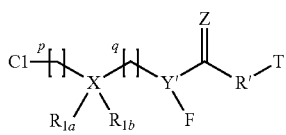

(V1')

wherein
C1 is a bioorthogonal group, or a group other than a bioorthogonal group;
p, q, X, R$_{1a}$ and R$_{1b}$ are the same as those of the Formula (Lb');
Y' is a residue obtained by removing one hydrogen atom from Y of Formula (B-1);
Z are the same as that of Formula (B-1); and
F, R' and T are the same as those of Formula (V),

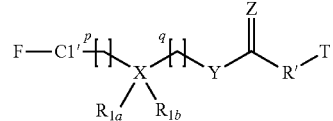

(V2')

wherein
C1' is a portion formed by a reaction between a functional substance and a bioorthogonal functional group;
p, q, X, R$_{1a}$ and R$_{1b}$ are the same as those of the Formula (Lb');
Y and Z are the same as those of Formula (B-1); and
F, R' and T are the same as those of the Formula (V), and

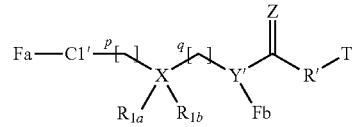

(V3')

wherein
C1' is a portion formed by a reaction between a functional substance and a bioorthogonal functional group;
p, q, X, R$_{1a}$ and R$_{1b}$ are the same as those of the Formula (Lb');
Y' is a residue obtained by removing one hydrogen atom from Y of Formula (B-1);
Z is the same as that of Formula (B-1);
Fa and Fb are functional substances which are the same or different from each other; and
R' and T are the same as those of Formula (V).

(37) A soluble protein regioselectively having functional substances, or a salt thereof,
wherein the soluble protein comprises one or more specific amino acid residues in a target region consisting of 1 to 50 continuous amino acid residues, and five or more of the specific amino acid residues in a non-target region other than the target region, and
the functional substances bind to the one or more specific amino acid residues in the target region with 30% or more regioselectivity through a linker comprising no peptide portion,
wherein the functional substances bind to the soluble protein via a side chain of a lysine residue,
wherein the soluble protein is an antibody comprising a plurality of heavy chains, and
the functional substances are present in positions of the one or more specific amino acid residues in a plurality of heavy chains such that the antibody has a plurality of functional substances.

(38) A soluble protein regioselectively having a functional substance(s) represented by the following Formula (V):

F-(L1-B)'—R'-T      (V)

wherein
L1 is (i') a monovalent group comprising a bioorthogonal functional group or (ii') a monovalent group comprising no bioorthogonal functional group;
B is (a) a divalent group comprising a bioorthogonal functional group or (b) a divalent group comprising no bioorthogonal functional group;
a structural unit represented by (L1-B)' is a divalent structural unit comprising a portion formed by a reaction between a functional substance and either one or both of the bioorthogonal functional groups in (i') and (a);
F is a functional substance;
R' is a portion formed by a reaction between a lysine residue of an antibody and a reactive group specific to a side chain of a lysine residue;
T is an antibody; and
the antibody comprising one or more specific amino acid residues in a target region consisting of 1 to 50 continuous amino acid residues and comprising five or more of the specific amino acid residues in a non-target region other than the target region, and
a structural unit represented by F-(L1-B)'—R' binding to the one or more specific amino acid residues contained in the target region of the soluble protein with 30% or more regioselectivity, or
a salt thereof.

(39) The soluble protein or salt thereof according to (38), wherein the soluble protein or salt thereof is a soluble protein regioselectively having a functional substance(s) represented by the following Formula (V1):

L1-B'(-F)-R'-T    (V1)

wherein
L1, F, R', and T are the same as those of Formula (V),
B' is a divalent group comprising a portion formed by a reaction between a functional substance and a bioorthogonal functional group,
a structural unit represented by L1-B'(-F)-R' binding to the one or more specific amino acid residues contained in the target region of the soluble protein with 30% or more regioselectivity, or
a salt thereof.

(40) The soluble protein or salt thereof according to (38), wherein the soluble protein or salt thereof is a soluble protein regioselectively having a functional substance(s) represented by the following Formula (V2):

F-L1'-B-R'-T    (V2)

wherein
F, B, R', and T are the same as those of Formula (V);
L1' is a divalent group comprising a portion formed by a reaction between a functional substance and (i') a monovalent group comprising a bioorthogonal functional group, and
a structural unit represented by F-L1'-B-R' binding to the one or more specific amino acid residues contained in the target region of the soluble protein with 30% or more regioselectivity, or
the following Formula (V3):

Fa-L1'-B'(-Fb)-R'-T    (V3)

wherein
R' and T are the same as those of Formula (V);
L1' is the same as that of Formula (V2);
B' is a divalent group comprising a portion formed by a reaction between a functional substance and a bioorthogonal functional group; and Fa and Fb are functional substances which are the same or different from each other, and
a structural unit represented by Fa-L1'-B'(-Fb)-R' binding to the one or more specific amino acid residues contained in the target region of the soluble protein with 30% or more regioselectivity, or
a salt thereof.

(A Method for Producing a Soluble Protein Regioselectively Having a Functional Substance(s), or a Salt Thereof)

The present invention also provides a method for producing a soluble protein regioselectively having a functional substance(s), or a salt thereof, wherein the soluble protein is to be specified by Formula (V) or species Formula thereof among the above-soluble protein (1) to (40).

(41) A method for producing a soluble protein regioselectively having a functional substance(s), or a salt thereof, the method comprising
cleaving a cleavable portion of a conjugate regioselectively having an affinity substance to a soluble protein, a cleavable portion, a functional substance(s), and a soluble protein represented by the following Formula (III):

A-L-B'(-F)-R'-T    (III)

wherein
A is an affinity substance to a soluble protein;
L is a cleavable linker which is a divalent group comprising a cleavable portion;
B' is a divalent group comprising a portion formed by a reaction between a functional substance and a bioorthogonal functional group;
F is a functional substance;
R' is a portion formed by a reaction between a soluble protein and a reactive group; and
T is a soluble protein,
the soluble protein comprising one or more specific amino acid residues in a target region consisting of 1 to 50 continuous amino acid residues and comprising five or more of the specific amino acid residues in a non-target region other than the target region, and
a structural unit represented by A-L-B'(-F)-R' binding to the one or more specific amino acid residues contained in the target region of the soluble protein with 30% or more regioselectivity, or
a salt thereof, or
reacting a soluble protein regioselectively having a bioorthogonal functional group(s) represented by the following Formula (IV):

L1-B-R'-T    (IV)

wherein
L1 is (i') a monovalent group comprising a bioorthogonal functional group or (ii') a monovalent group comprising no bioorthogonal functional group;
B is (a) a divalent group comprising a bioorthogonal functional group or (b) a divalent group comprising no bioorthogonal functional group;
R' is a portion formed by a reaction between a soluble protein and a reactive group; and
T is a soluble protein comprising one or more specific amino acid residues in a target region consisting of 1 to 50 continuous amino acid residues and comprising five or more of the specific amino acid residues in a non-target region other than the target region, and a structural unit represented by A-L-B'(-F)-R' binding to the one or more specific amino acid residues contained in the target region of the soluble protein with 30% or more regioselectivity, or a salt thereof with a functional substance(s)

to form a soluble protein regioselectively having a functional substance(s) represented by the following Formula (V):

F-(L1-B)'—R'-T  (V)

wherein

L1 is (i') a monovalent group comprising a bioorthogonal functional group or (ii') a monovalent group comprising no bioorthogonal functional group;

B is (a) a divalent group comprising a bioorthogonal functional group or (b) a divalent group comprising no bioorthogonal functional group;

a structural unit represented by (L1-B)' is a divalent structural unit comprising a portion formed by a reaction between a functional substance and either one or both of the bioorthogonal functional groups in (i') and (a);

F is a functional substance; and

R' and T are the same as those of Formula (III) or (IV), and a structural unit represented by F-(L1-B)'—R' binding to the one or more specific amino acid residues contained in the target region of the soluble protein with 30% or more regioselectivity, or a salt thereof.

Preferably, the method of (41) may be the followings.

(42) The method according to (41), the method comprising cleaving a cleavable portion of a conjugate regioselectively having an affinity substance to a soluble protein, a cleavable portion, a functional substance(s), and a soluble protein, or a salt thereof to form a soluble protein regioselectively having a functional substance(s) represented by the following Formula (V1):

L1-B'(-F)-R'-T  (V1)

wherein

L1 is (i') a monovalent group comprising a bioorthogonal functional group or (ii') a monovalent group comprising no bioorthogonal functional group; and B', F, R', and T are the same as those of Formula (III), a structural unit represented by L1-B'(-F)-R' binding to the one or more specific amino acid residues contained in the target region of the soluble protein with 30% or more regioselectivity, or a salt thereof.

(43) The method according to (41), the method comprising:

reacting the soluble protein regioselectively having a bioorthogonal functional group(s), or a salt thereof with one or two or more functional substances to form a soluble protein regioselectively having a functional substance(s) represented by the following Formula (V2):

F-L1'-B-R'-T  (V2)

wherein

B, R', and T are the same as those of Formula (IV);

L1' is a divalent group comprising a portion formed by a reaction between a functional substance and (i') a monovalent group comprising a bioorthogonal functional group; and F is a functional substance, and a structural unit represented by F-L1'-B-R' binding to the one or more specific amino acid residues contained in the target region of the soluble protein with 30% or more regioselectivity, or the following Formula (V3):

Fa-L1'-B'(-Fb)-R'-T  (V3)

wherein

R' and T are the same as those of Formula (IV);

L1' is the same as that of Formula (V2);

B' is a divalent group comprising a portion formed by a reaction between a functional substance and a bioorthogonal functional group; and Fa and Fb are functional substances which are the same or different from each other, and a structural unit represented by Fa-L1'-B'(-Fb)-R' binding to the one or more specific amino acid residues contained in the target region of the soluble protein with 30% or more regioselectivity, or a salt thereof.

(44) The method according to any one of (41) to (43), wherein the soluble protein is an antibody, and the reactive group is a reactive group specific to a side chain of a lysine residue.

(45) A method for producing a soluble protein regioselectively having a functional substance(s), or a salt thereof, the method comprising:

(A) reacting a soluble protein regioselectively having an affinity substance to a soluble protein, and a cleavable portion represented by the following Formula (II):

A-L-B-R'-T  (II)

wherein

A is an affinity substance to a soluble protein;

L is a cleavable linker which is a divalent group comprising a cleavable portion;

B is (a) a divalent group comprising a bioorthogonal functional group;

R' is a portion formed by a reaction between a soluble protein and a reactive group; and T is a soluble protein, the soluble protein comprising one or more specific amino acid residues in a target region consisting of 1 to 50 continuous amino acid residues and comprising five or more of the specific amino acid residues in a non-target region other than the target region, and a structural unit represented by A-L-B-R' binding to the one or more specific amino acid residues contained in the target region of the soluble protein with 30% or more regioselectivity, or a salt thereof with a functional substance(s)

to form a conjugate regioselectively having an affinity substance to a soluble protein, a cleavable portion, a functional substance(s), and a soluble protein represented by the following Formula (III):

A-L-B'(-F)-R'-T  (III)

wherein

A, L, R', and T are the same as those of Formula (II);

B' is a divalent group comprising a portion formed by a reaction between a functional substance and a bioorthogonal functional group; and F is a functional substance, and a structural unit represented by A-L-B'(-F)-R' binding to the one or more specific amino acid residues contained in the target region of the soluble protein with 30% or more regioselectivity, or
a salt thereof; and
(B) cleaving a cleavable portion of a conjugate regioselectively having an affinity substance to a soluble protein, a cleavable portion, a functional substance(s), and a soluble protein, or a salt thereof
to form a soluble protein regioselectively having a functional substance(s) represented by the following Formula (VI):

L1-B'(-F)-R'-T (VI)

wherein
L1 is (i') a monovalent group comprising a bioorthogonal functional group or (ii') a monovalent group comprising no bioorthogonal functional group; and
B', F, R', and T are the same as those of Formula (III), and
a structural unit represented by L1-B'(-F)-R' binding to the one or more specific amino acid residues contained in the target region of the soluble protein with 30% or more regioselectivity, or
a salt thereof.

(46) A method for producing a soluble protein regioselectively having a functional substance(s) or a salt thereof, the method comprising:
(A) reacting a compound regioselectively having an affinity substance to a soluble protein, a cleavable portion, and a reactive group represented by the following Formula (I):

A-L-B-R (I)

wherein
A is an affinity substance to a soluble protein;
L is a cleavable linker which is a divalent group comprising the cleavable portion;
B is (a) a divalent group comprising a bioorthogonal functional group; and
R is a reactive group to the soluble protein; or
a salt thereof
with a soluble protein, wherein the soluble protein comprises one or more specific amino acid residues in a target region consisting of 1 to 50 continuous amino acid residues and comprising five or more of the specific amino acid residues in a non-target region other than the target region,
to form a soluble protein regioselectively having an affinity substance to a soluble protein, and a cleavable portion represented by the following Formula (II):

A-L-B-R'-T (II)

wherein
A, L, and B are the same as those of Formula (I);
R' is a portion formed by a reaction between a soluble protein and a reactive group; and
T is a soluble protein, and
a structural unit represented by A-L-B-R' binding to the one or more specific amino acid residues contained in the target region of the soluble protein with 30% or more regioselectivity, or
a salt thereof;
(B) reacting a soluble protein regioselectively having an affinity substance to a soluble protein, and a cleavable portion, or a salt thereof
with a functional substance(s)
to form a conjugate regioselectively having an affinity substance to a soluble protein, a cleavable portion, a functional substance(s), and a soluble protein represented by the following Formula (III):

A-L-B'(-F)-R'-T (III)

wherein
A and L are the same as those of Formula (I);
R' and T are the same as those of Formula (II);
B' is a divalent group comprising a portion formed by a reaction between a functional substance and a bioorthogonal functional group; and
F is a functional substance, and
a structural unit represented by A-L-B'(-F)-R' binding to the one or more specific amino acid residues contained in the target region of the soluble protein with 30% or more regioselectivity, or
a salt thereof; and
(C) cleaving a cleavable portion of a conjugate regioselectively having an affinity substance to a soluble protein, a cleavable portion, a functional substance(s), and a soluble protein, or a salt thereof
to form a soluble protein regioselectively having a functional substance(s) represented by the following Formula (V1):

L1-B'(-F)-R'-T (V1)

wherein
L1 is (i') a monovalent group comprising a bioorthogonal functional group or (ii') a monovalent group comprising no bioorthogonal functional group; and
B', F, R', and T are the same as those of Formula (III), and
a structural unit represented by L1-B'(-F)-R' binding to the one or more specific amino acid residues contained in the target region of the soluble protein with 30% or more regioselectivity, or
a salt thereof.

(47) A method for producing a soluble protein regioselectively having a functional substance(s), or a salt thereof, the method comprising:
(A) cleaving a cleavable portion of a soluble protein regioselectively having an affinity substance to a soluble protein, and a cleavable portion represented by the following Formula (II):

A-L-B-R'-T (II)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R' is a portion formed by a reaction between a soluble protein and a reactive group; and
T is a soluble protein,
the soluble protein comprising one or more specific amino acid residues in a target region consisting of 1 to 50 continuous amino acid residues and comprising five or more of the specific amino acid residues in a non-target region other than the target region, and
a structural unit represented by A-L-B-R' binding to the one or more specific amino acid residues contained in the target region of the soluble protein with 30% or more regioselectivity, or
a salt thereof
to form a soluble protein regioselectively having a bioorthogonal functional group(s) represented by the following Formula (IV):

L1-B-R'-T (IV)

wherein
B, R', and T are the same as those of Formula (II); and
L1 is (i') a monovalent group comprising the bioorthogonal functional group or (ii') a monovalent group comprising no bioorthogonal functional group, and
a structural unit represented by L1-B-R' binding to the one or more specific amino acid residues contained in the target region of the soluble protein with 30% or more regioselectivity, or
a salt thereof; and
(B) reacting a soluble protein regioselectively having a bioorthogonal functional group(s), or a salt thereof
with one or two or more functional substances
to form a soluble protein regioselectively having a functional substance(s) represented by the following Formula (V2):

F-L1'-B-R'-T (V2)

wherein
B, R', and T are the same as those of Formula (IV);
L1' is a divalent group comprising a portion formed by a reaction between the functional substance and (i') the monovalent group comprising the bioorthogonal functional group; and
F is a functional substance, and
a structural unit represented by F-L1'-B-R' binding to the one or more specific amino acid residues contained in the target region of the soluble protein with 30% or more regioselectivity, or
the following Formula (V3):

Fa-L1'-B'(-Fb)-R'-T (V3)

wherein
R' and T are the same as those of Formula (IV);
L1' is the same as that of Formula (V2);
B' is a divalent group comprising a portion formed by a reaction between a functional substance and a bioorthogonal functional group; and
Fa and Fb are functional substances which are the same or different from each other, and
a structural unit represented by Fa-L1'-B'(-Fb)-R' binding to the one or more specific amino acid residues contained in the target region of the soluble protein with 30% or more regioselectivity, or
a salt thereof.

(48) A method for producing a soluble protein regioselectively having a functional substance(s), or a salt thereof, the method comprising:
(A) reacting a compound represented by the following Formula (I):

A-L-B-R (I)

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R is a reactive group to a soluble protein; or
a salt thereof
with a soluble protein, wherein the soluble protein comprising one or more specific amino acid residues in a target region consisting of 1 to 50 continuous amino acid residues and comprising five or more of the specific amino acid residues in a non-target region other than the target region,
to form a soluble protein regioselectively having an affinity substance to a soluble protein, and a cleavable portion represented by the following Formula (II):

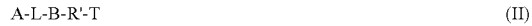

A-L-B-R'-T (II)

wherein
A, L, and B are the same as those of Formula (I);
R' is a portion formed by a reaction between a soluble protein and a reactive group; and
T is the soluble protein, and
a structural unit represented by A-L-B-R' binding to the one or more specific amino acid residues contained in the target region of the soluble protein with 30% or more regioselectivity, or
a salt thereof;
(B) cleaving a cleavable portion of a soluble protein regioselectively having an affinity substance to a soluble protein, and a cleavable portion, or a salt thereof
to form a soluble protein regioselectively having a bioorthogonal functional group(s) represented by the following Formula (IV):

L1-B-R'-T (IV)

wherein
B, R', and T are the same as those of Formula (II); and
L1 is (i') a monovalent group comprising a bioorthogonal functional group or (ii') a monovalent group comprising no bioorthogonal functional group, and
a structural unit represented by L1-B-R' binding to the one or more specific amino acid residues contained in the target region of the soluble protein with 30% or more regioselectivity, or
a salt thereof; and
(C) reacting a soluble protein regioselectively having a bioorthogonal functional group(s), or a salt thereof
with one or two or more functional substances
to form a soluble protein regioselectively having a functional substance(s) represented by the following Formula (V2):

F-L1'-B-R'-T (V2)

wherein
B, R', and T are the same as those of Formula (IV);
L1' is a divalent group comprising a portion formed by a reaction between a functional substance(s) and (i') a monovalent group comprising a bioorthogonal functional group; and
F is a functional substance, and
a structural unit represented by F-L1'-B-R' binding to the one or more specific amino acid residues contained in the target region of the soluble protein with 30% or more regioselectivity, or
the following Formula (V3):

Fa-L1'-B'(-Fb)-R'-T (V3)

wherein
R' and T are the same as those of Formula (IV);
L1' is the same as that of Formula (V2);
B' is a divalent group comprising a portion formed by a reaction between a functional substance and a bioorthogonal functional group; and
Fa and Fb are functional substances which are the same or different from each other, and
a structural unit represented by Fa-L1'-B'(-Fb)-R' binding to the one or more specific amino acid residues contained in the target region of the soluble protein with 30% or more regioselectivity, or a salt thereof.

Effect of the Invention (I) The compound or salt thereof of the present invention having an affinity substance to a soluble protein, a cleavable portion, and a reactive group is useful for regioselective modification of a soluble protein, for example.

(II) The soluble protein or salt thereof of the present invention (regioselectively) having an affinity substance to a soluble protein, and a cleavable portion, (III) the conjugate or salt thereof of the present invention (regioselectively) having an affinity substance to a soluble protein, a cleavable portion, a functional substance(s), and a soluble protein, and (IV) the soluble protein or salt thereof of the present invention (regioselectively) having a bioorthogonal functional group(s) are useful as intermediates for preparing a soluble protein (regioselectively) having a functional substance(s) or a salt thereof, for example.

(V) The soluble protein or salt thereof of the present invention (regioselectively) having a functional substance(s) is useful as pharmaceuticals or reagents (e.g., diagnostic reagents and reagents for research), for example. When the soluble protein is an antibody in particular, the antibody or salt thereof of the present invention (regioselectively) having a functional substance(s) is suitable for these uses.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1-2 is a schematic diagram (No. 2) of the concept of regioselective modification of a soluble protein (e.g., an antibody) with the compound of the present invention. Cleavage of a cleavable portion in a linker (L) produces a soluble protein (e.g., an antibody) regiospecifically modified with bioorthogonal functional groups.

FIG. 1-3 is a schematic diagram (No. 3) of the concept of regioselective modification of a soluble protein (e.g., an antibody) with the compound of the present invention. A reaction of bioorthogonal functional groups and functional substances (e.g., drugs) produces a soluble protein (e.g., an antibody) regiospecifically modified with functional substances.

FIG. 2 is a diagram of the relation among the inventions of the present invention (the expression of salts is omitted). In Reaction (1), a compound having an affinity substance to a soluble protein, a cleavable portion, and a reactive group is reacted with a soluble protein to form a soluble protein having an affinity substance to a soluble protein, and a cleavable portion. In Reaction (2), the soluble protein having an affinity substance to a soluble protein, and a cleavable portion is reacted with a functional substance(s) to form a conjugate having an affinity substance to a soluble protein, a cleavable portion, a functional substance(s), and a soluble protein. In Reaction (3), the cleavable portion of the conjugate having an affinity substance to a soluble protein, a cleavable portion, a functional substance(s), and a soluble protein is cleaved to form a soluble protein having a functional substance(s) (in this process, an affinity substance-containing portion is produced as a by-product). In Reaction (4), the cleavable portion of the soluble protein having an affinity substance to a soluble protein, and a cleavable portion is cleaved to form a soluble protein having a bioorthogonal functional group(s) (in this process, an affinity substance-containing portion is produced as a by-product). In Reaction (5), the soluble protein having a bioorthogonal functional group(s) is reacted with a functional substance(s) to form a soluble protein having a functional substance(s). Reaction (2) and Reaction (5) can be conducted in a similar manner. Reaction (3) and Reaction (5) can also be conducted in a similar manner.

FIG. 3 is a diagram of hydrophobic interaction chromatography-high-performance liquid chromatography (HIC-HPLC) analysis (detection: 225 nm) of anti-HER2 IgG antibody trastuzumab specifically modified with a peptide reagent (a peptide- and disulfide linker-coupled NHS-activation compound). Samples were reacted under the following conditions: a: trastuzumab+12 equivalents of the peptide reagent (solvent substitution with Amicon 10K after reaction); b: trastuzumab+12 equivalents of the peptide reagent; c: trastuzumab+6 equivalents of the peptide reagent; d: a trastuzumab raw material; e: the peptide reagent alone; and f: DMF alone.

FIG. 8 is diagrams of (1) an amino acid sequence of a heavy chain of trastuzumab with a sugar chain cleaved with PNGase; (2) an amino acid sequence of an IgG1 Fc region with a sugar chain cleaved with PNGase; and (3) an amino acid sequence of a light chain of trastuzumab.

FIG. 17 is a diagram of a consensus amino acid sequence between an Fc region in the heavy chain of trastuzumab and an IgG1 Fc region (SEQ ID NO: 1).

FIG. 18 is a diagram of amino acid sequences and modifications identified for modified trastuzumab (IgG1). The grey portions are the identified amino acid sequences. The identified modifications are expressed above the amino acid sequences. Regioselective modification of an azide-introduced compound was determined only at the surrounded two lysine residues (positions 246 and 248 by EU numbering).

FIG. 19 is diagrams of a modified site of an azide-introduced trastuzumab. Peptide spectrum matches (PSMs) refer to the number of times a spectrum matching a corresponding peptide was observed; a larger number of times indicates higher probability. By applying a filter about signal intensity, a modification was identified only for the lysine residue at position 246 as in (2). It is believed that the modified sites identified only in (1) are highly probably noise.

FIG. 21 is a diagram of b/y ion the CID spectrum of which has been identified. The b/y ion identified in FIG. 20 is illustrated. b25 Ion is identified, and thus it is revealed that position 246 by EU numbering is highly probably modified.

FIG. 24 is a diagram of amino acid sequence data used for search. It is known that deglycosylation changes N at the 300th residue of the heavy chain of trastuzumab into D, and hence two types of amino acid sequences of the heavy chain were used for analysis.

FIG. 27 is a diagram of results of hydrophobic interaction chromatography-ultra performance liquid chromatography (HIC-UPLC) analysis of specific modification of trastuzumab (detection wavelength: UV 225 nm and UV 280 nm) (Example 16).

FIG. 28 is a diagram of results of HIC-UPLC analysis of specific modification of trastuzumab (detection wavelength: UV 225 nm and UV 280 nm) (Example 17).

FIG. 29 is a diagram of results of HIC-UPLC analysis of specific modification of trastuzumab (detection wavelength: UV 225 nm and UV 280 nm) (Example 18).

FIG. 30 is a diagram of results of HIC-UPLC analysis of specific modification of trastuzumab (detection wavelength: UV 225 nm and UV 280 nm) (Example 19).

FIG. 31 is a diagram of results of HIC-UPLC analysis of specific modification of trastuzumab (detection wavelength: UV 225 nm and UV 280 nm) (Example 20).

FIG. 32 is a diagram of results of HIC-UPLC analysis of specific modification of trastuzumab (detection wavelength: UV 225 nm and UV 280 nm) (Example 21).

FIG. 33 is a diagram of results of HIC-UPLC analysis of specific modification of trastuzumab (detection wavelength: UV 225 nm and UV 280 nm) (Example 22).

FIG. 34 is a diagram of results of HIC-UPLC analysis of specific modification of trastuzumab (detection wavelength: UV 225 nm and UV 280 nm) (Example 23).

FIG. 35 is a diagram of results of HIC-UPLC analysis of specific modification of trastuzumab (detection wavelength: UV 225 nm and UV 280 nm) (Example 24).

FIG. 36 is a diagram of results of HIC-UPLC analysis of specific modification of trastuzumab (detection wavelength: UV 225 nm and UV 280 nm) (Example 25).

FIG. 37 is a diagram of results of HIC-UPLC analysis of specific modification of trastuzumab (detection wavelength: UV 225 nm and UV 280 nm) (Example 26).

FIG. 38 is a diagram of results of HIC-UPLC analysis (detection wavelength: UV 225 nm and UV 280 nm) of specific modification of trastuzumab (Example 27).

FIG. 39 is a diagram of results of HIC-UPLC analysis of specific modification of trastuzumab (detection wavelength: UV 225 nm and UV 280 nm) (Example 28).

FIG. 40 is a diagram of results of HIC-UPLC analysis of specific modification of trastuzumab (detection wavelength: UV 225 nm and UV 280 nm) (Example 29).

FIG. 41 is a diagram of results of HIC-UPLC analysis of specific modification of trastuzumab (detection wavelength: UV 225 nm and UV 280 nm) (Example 30).

DETAILED DESCRIPTION OF THE PREFERRED EMBODIMENTS

Figure 1:
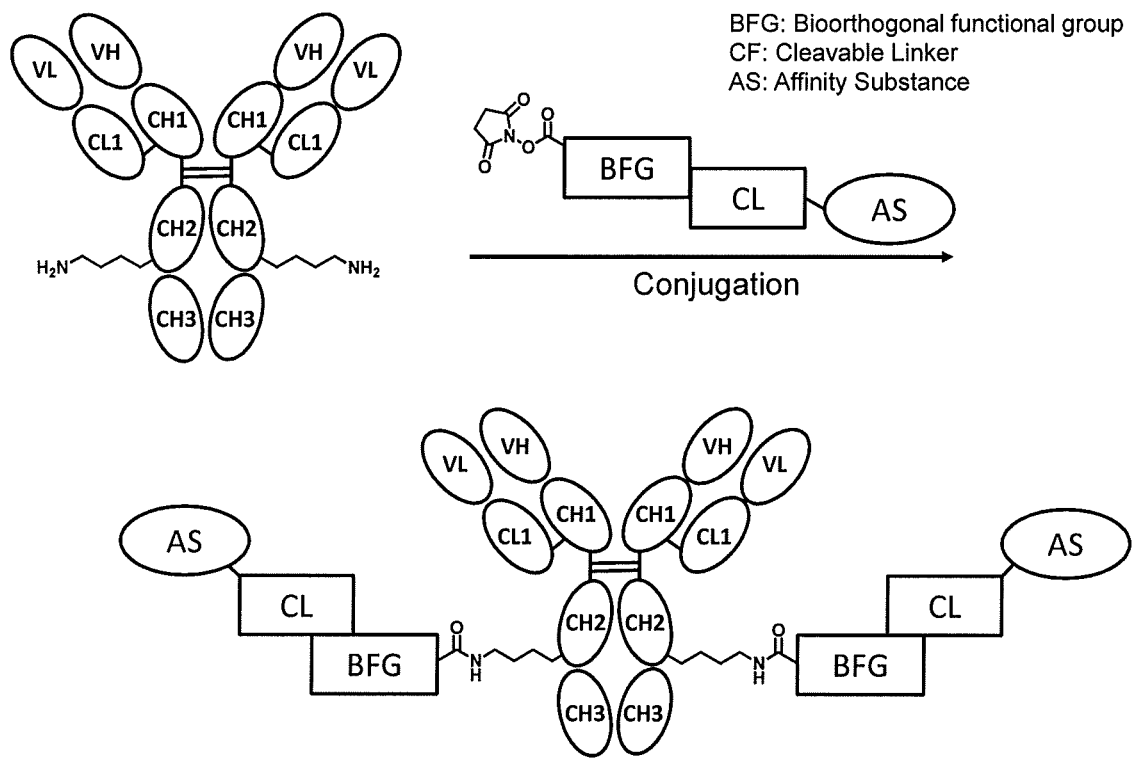
FIG. 1-1 is a schematic diagram (No. 1) of the concept of regioselective modification of a soluble protein (e.g., an antibody) with a compound of the present invention [a compound having an affinity substance to a soluble protein, a cleavable portion, and a reactive group: A-L-B-R (I)]. First, the compound of the present invention associates with a soluble protein (T) such as an antibody through an affinity substance (A) to a soluble protein. Next, the compound of the present invention reacts with a side chain of a specific amino acid residue (a side chain of a lysine residue in the drawing) in a target region present near an association site of the affinity substance and the soluble protein through a reactive group (R) (an activated ester in the drawing) to form a conjugate between the compound of the present invention and the soluble protein [a soluble protein regioselectively having structural units comprising an affinity substance to a soluble protein, and a cleavable portion: A-L-B-R'-T (II)].

1. Compound Comprising Affinity Substance to Soluble Protein, Cleavable Portion, and Reactive Group or Salt Thereof 1-1. Outline The present invention provides a compound comprising an affinity substance to a soluble protein, a cleavable portion, and a reactive group represented by Formula (I):

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R is a reactive group to the soluble protein; or
a salt thereof.

In Formula (I) and other formulae presented in relation to the present invention, - (a hyphen) indicates that two units present on both sides thereof covalently bind to each other. Consequently, in Formula (I), A covalently binds to L, L covalently binds to A and B, B covalently binds to L and R, and R covalently binds to B.

1-2. Affinity Substance (A) to Soluble Protein

In Formula (I), A is an affinity substance to a soluble protein. The affinity substance is a substance having binding ability through a noncovalent bond to a target.

The affinity substance used in the present invention targets a soluble protein also called a secretory protein. Examples of such a soluble protein include antibodies, soluble receptors, ligands, albumin, erythropoietin (EPO), vascular endothelial cell growth factors (Anti-VEGFs), bone morphogenetic proteins, follicle-stimulating hormones (FSHs), glucagon, granulocyte colony-stimulating factors, granulocyte macrophage colony-stimulating factors, ciliated gonadotrophin, insulin, interleukin, interferon, platelet-derived growth factors (PDGFs), and growth factors (TGF family and FGF family). The soluble protein may be a protein modified with a biomolecule (e.g., a sugar) (e.g., a glycoprotein) or a protein unmodified with a biomolecule.

The soluble protein as the target of the affinity substance is a natural protein or an artificial protein.

Examples of the natural protein include bio-derived and virus-derived proteins. Examples of bio-derived proteins include proteins derived from animals such as mammals and birds (e.g., chickens), insects, microorganisms, plants, fungi, and fishes. The natural protein is preferably a protein derived from mammals. Examples of mammals include primates (e.g., humans, monkeys, and chimpanzees), rodents (e.g., mice, rats, guinea pigs, hamsters, and rabbits), pets (e.g., dogs and cats), domestic animals (e.g., cows, pigs, and goats), and work animals (e.g., horses and sheep). The natural protein is more preferably a protein derived from primates or rodents, and even more preferably a human-derived protein in view of the clinical application of the present invention. Examples of virus-derived proteins include influenza viruses (e.g., avian influenza viruses and swine influenza viruses), AIDS virus, Ebola virus, and phage viruses.

Examples of the artificial protein include modified proteins of the natural protein (e.g., a protein obtained by introducing one or more variations of amino acid residues selected from the group consisting of substitution, deletion, and insertion to the natural protein), fusion proteins, and artificially designed monoclonal antibodies. Examples of artificially designed monoclonal antibodies include chimeric antibodies, humanized antibodies, human antibodies, antibodies with a certain sugar chain added (e.g., an antibody modified so as to have a sugar chain-binding consensus sequence such as an N-type sugar chain-binding consensus sequence), bi-specific antibodies, scFv antibodies, Fab antibodies, F(ab')$_2$ antibodies, VHH antibodies, Fc region proteins, and Fc-fusion proteins.

The soluble protein as the target of the affinity substance may further be a monomeric protein or a multimeric protein (e.g., dimer, trimer, or tetramer). When the protein as the target of the affinity substance is a multimeric protein, the multimeric protein is a homomultimer or a heteromultimer. The multimeric protein may be a protein forming a polymer through a covalent bond (e.g., a disulfide bond) (e.g., an antibody having a structure in which two units consisting of a light chain and a heavy chain are coupled to each other through a disulfide bond) or a protein forming a multimer through a noncovalent bond (that is, association) and is preferably a protein forming a multimer through a covalent bond. Examples of the multimeric protein as a target of the affinity substance include divalent antibodies (e.g., IgG, IgD, and IgE), tetravalent or more antibodies (e.g., IgA antibodies and IgM antibodies), and albumin.

The soluble protein as the target of the affinity substance may comprise any amino acid residues and preferably comprises 20 natural L-α-amino acid residues normally contained in proteins. Examples of such amino acid residues include L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), L-lysine (K), and glycine (G) (hereinafter, the expression of L is omitted). The soluble protein may comprise e.g., 100 or more, preferably 120 or more, more preferably 150 or more, even more preferably 180 or more, and particularly preferably 200 or more amino acid residues. The soluble protein may comprise e.g., 1,000 or less, preferably 900 or less, more preferably 800 or less, even more preferably 700 or less, and particularly preferably 600 or less amino acid residues. More specifically, the soluble protein may comprise e.g., 100 to 1,000, preferably 120 to 900, more preferably 150 to 800, even more preferably 180 to 700, and particularly preferably 200 to 600 amino acid residues. When the soluble protein is an antibody (e.g., the artificially designed monoclonal antibody described above), the above number of amino acid residues may correspond to amino acid residues of a heavy chain of the antibody.

The soluble protein as the target of the affinity substance is further a protein comprising specific amino acid residues having a side chain or a terminus (an N-terminus and/or a C-terminus), preferably a side chain, with which a reactive group described below is capable of reacting at one position or a plurality of positions (preferably a plurality of positions). Examples of such specific amino acid residues include 14 amino acid residues described below; preferred are amino acid residues selected from the group consisting of a lysine residue, a tyrosine residue, a tryptophan residue, and a cysteine residue. Considering that the compound of the present invention can regioselectively modify the soluble protein, preferred is a soluble protein comprising such specific amino acid residues at a plurality of positions. The positions are not limited to particular positions so long as they are two or more positions and may be e.g., three or more positions, preferably five or more positions, more preferably ten or more positions, even more preferably 20 or more positions, and particularly preferably 30 or more positions. The positions may be e.g., 200 or less positions, preferably 180 or less positions, more preferably 150 or less positions, even more preferably 120 or less positions, and particularly preferably 100 or less positions. More specifically, the positions may be e.g., 3 to 200 positions, preferably 5 to 180 positions, more preferably 10 to 150 positions, even more preferably 20 to 120 positions, and particularly preferably 30 to 100 positions. Even for such a soluble protein comprising the specific amino acid residues at a plurality of positions, the compound of the present invention can regioselectively modify a specific amino acid residue present at one specific position. It is said that the number of lysine residues of human IgG1 is generally about 70 to 90, for example, although it depends on an amino acid composition in a variable region. The present invention has succeeded in regioselectively modifying such lysine residues present at specific positions of human IgG1.

More specifically, in the present invention, in view of, while maintaining the function of a protein such as an antibody (that is, while maintaining native folding without denaturing the protein), modifying amino acid residues present at specific positions in the protein, preferred is regioselective modification of amino acid residues exposed to the surface of the protein. In human IgG such as human IgG1, for example, exposed lysine residues and exposed tyrosine residues are present at the following positions (refer to http://www.imgt.org/IMGTScientificChart/Numbering/HuIGHGnb er.html by EU numbering).

(1) Exposed Lysine Residues
CH2 domain (position 246, position 248, position 274, position 288, position 290, position 317, position 320, position 322, and position 338) CH3 domain (position 360, position 414, and position 439)

(2) Exposed Tyrosine Residues
CH2 domain (position 278, position 296, and position 300) CH3 domain (position 436)
Consequently, when human IgG such as human IgG1 is modified with a lysine residue or a tyrosine residue, modification at the above positions is preferred.

When human IgG such as human IgG1 is modified with a lysine residue or a tyrosine residue, among the positions of (1) and (2), lysine residues or tyrosine residues present at the following positions, which are high in the degree of exposure to the surface, may be preferably modified.

(1') Exposed Lysine Residues
CH2 domain (position 246, position 248, position 274, position 288, position 290, position 317, position 320, and position 322)
CH3 domain (position 360, position 414, and position 439)

(2') Exposed Tyrosine Residues
CH2 domain (position 278, position 296, and position 300) CH3 domain (position 436)
Consequently, when human IgG such as human IgG1 is modified with a lysine residue or a tyrosine residue, modification at the above positions is more preferred.

When human IgG such as human IgG1 is modified with a lysine residue, among (1) the positions, lysine residues present at certain positions (e.g., position 246, position 248, position 288, position 290, and position 317) in the CH2 domain, which can be efficiently modified in the present invention, may be more preferably modified.

In a specific embodiment, the soluble protein as the target of the affinity substance, when comprising the specific amino acid residues at a plurality of positions as described above, may comprise one or more specific amino acid residues in a target region consisting of 1 to 50 continuous amino acid residues and comprise five or more of the specific amino acid residues in a non-target region other than the target region. The target region may consist of preferably 1 to 30, more preferably 1 to 20, and even more preferably one to ten, one to five, or one to three (that is, one, two, or three) amino acid residues. The target region may be particularly preferably a region consisting of a specific amino acid residue present at a specific position. Such a specific position, which varies depending on the types of the target protein and the affinity substance and the like, may be e.g., a specific position in a specific region of a constant region of an antibody (e.g., CH1, CH2, and CH3) and preferably a position in CH2 of an antibody. The target region may be more specifically the following residues following Eu numbering in human IgG Fc:

(1) a Lys248 residue (hereinafter, also referred to simply as "Lys248" in the present specification and corresponding to the 18th residue in a human IgG CH2 region (SEQ ID NO: 1)) or a Lys246 residue (hereinafter, also referred to simply as "Lys246" in the present specification and corresponding to the 16th residue in the human IgG CH2 region (SEQ ID NO: 1));

(2) a Lys288 residue (hereinafter, also referred to simply as "Lys288" in the present specification and corresponding to the 58th residue in the human IgG CH2 region (SEQ ID NO: 1)) or a Lys290 residue (hereinafter, also referred to simply as "Lys290" in the present specification and corresponding to the 60th residue in the human IgG CH2 region (SEQ ID NO: 1)); and (3) a Lys317 residue (hereinafter, also referred to simply as "Lys317" in the present specification and corresponding to the 87th residue in the human IgG CH2 region (SEQ ID NO: 1)).

The present invention can modify the specific amino acid residue in the target region highly regioselectively. Such regioselectivity may be e.g., 30% or more, preferably 40% or more, more preferably 50% or more, even more preferably 60% or more, and particularly preferably 70% or more, 80% or more, 90% or more, 95% or more, 96% or more, 97% or more, 98% or more, 99% or more, or 100% or more.

The target region also may not comprise the same kind of amino acid residue as the specific amino acid residue other than the specific amino acid residue present at the specific position in a region up to a remote position of "a" (where "a" is any integer of 1 to 10) amino acid residues to an N-terminus side and a C-terminus side each with respect to the specific amino acid present at the specific position. The symbol "a" is preferably an integer of 1 to 5, more preferably an integer of 1 to 3, even more preferably 1 or 2, and particularly preferably 1.

In a preferred embodiment, the affinity substance to a soluble protein is an affinity substance to an antibody. The antibody is a polyclonal antibody or a monoclonal antibody. Examples of the isotype of the antibody include IgG (e.g., IgG1, IgG2, IgG3, and IgG4), IgM, IgA, IgD, IgE, and IgY. The antibody is a full-length antibody or an antibody fragment (e.g., F(ab')₂, Fab', Fab, Fv, and a single-chain antibody); the full-length antibody is preferred.

The antibody is an antibody to any antigen. Such an antigen may be a component found in organisms and viruses described above, for example. Examples of such an antigen include proteins [comprising oligopeptides and polypeptides, which may be proteins modified with biomolecules such as sugars (e.g., glycoproteins)], sugar chains, nucleic acids, and small compounds.

The antibody may be preferably an antibody with a protein as an antigen. Examples of the protein include cell membrane receptors, cell membrane proteins other than cell membrane receptors (e.g., extracellular matrix proteins), ligands, and soluble receptors.

More specifically, the protein as the antigen of the antibody may be a disease target protein. Examples of the disease target protein include the following.

(1) Cancerous Region

PD-L1, GD2, PDGFRα (a platelet-derived growth factor receptor), CD22, HER2, phosphatidyl serine (PS), EpCAM, fibronectin, PD-1, VEGFR-2, CD33, HGF, gpNMB, CD27, DEC-205, folic acid receptors, CD37, CD19, Trop2, CEACAM5, S1P, HER3, IGF-1R, DLL4, TNT-1/B, CPAAs, PSMA, CD20, CD105 (Endoglin), ICAM-1, CD30, CD16A, CD38, MUC1, EGFR, KIR2DL1, KIR2DL2, NKG2A, tenascin-C, IGF (insulin-like growth factor), CTLA-4, mesothelin, CD138, c-Met, Ang2, VEGF-A, CD79b, ENPD3, folic acid receptor a, TEM-1, GM2, Glypican 3, macrophage inhibitory factor, CD74, Notch1, Notch2, Notch3, CD37, TLR-2, CD3, CSF-1R, FGFR2b, HLA-DR, GM-CSF, EphA3, B7-H3, CD123, gpA33, Frizzled7 receptor, DLL4, VEGF, RSPO, LIV-1, SLITRK6, Nectin-4, CD70, CD40, CD19, SEMA4D (CD100), CD25, MET, Tissue Factor, IL-8, EGFR, cMet, KIR3DL2, Bst1 (CD157), P-Cadherin, CEA, GITR, TAM (tumor associated macrophage), CEA, DLL4, Ang2, CD73, FGFR2, CXCR4, LAG-3, GITR, Fucosyl GM1, IGF-1, Angiopoietin 2, CSF-1R, FGFR3, OX40, BCMA, ErbB3, CD137 (4-1BB), PTK7, EFNA4, FAP, DR5, CEA, Ly6E, CA6, CEACAM5, LAMP1, tissue factor, EPHA2, DR5, B7-H3, FGFR4, FGFR2, a2-PI, A33, GDF15, CAIX, CD166, ROR1, GITR, BCMA, TBA, LAG-3, EphA2, TIM-3, CD-200, EGFRvIII, CD16A, CD32B, PIGF, Axl, MICA/B, Thomsen-Friedenreich, CD39, CD37, CD73, CLEC12A, Lgr3, transferrin receptors, TGFβ, IL-17, 5T4, RTK, Immune Suppressor Protein, NaPi2b, Lewis blood group B antigen, A34, Lysil-Oxidase, DLK-1, TROP-2, a9 Integrin, TAG-72 (CA72-4), and CD70.

(2) Autoimmune Diseases and Inflammatory Diseases

IL-17, IL-6R, IL-17R, INF-α, IL-5R, IL-13, IL-23, IL-6, ActRIIB, β7-Integrin, IL-4αR, HAS, Eotaxin-1, CD3, CD19, TNF-α, IL-15, CD3E, Fibronectin, IL-1β, IL-1α, IL-17, TSLP (Thymic Stromal Lymphopoietin), LAMP (Alpha4 Beta7 Integrin), IL-23, GM-CSFR, TSLP, CD28, CD40, TLR-3, BAFF-R, MAdCAM, IL-31R, IL-33, CD74, CD32B, CD79B, IgE (immunoglobulin E), IL-17A, IL-17F, C5, FcRn, CD28, TLR4, MCAM, B7RP1, CXCR1/2 Ligands, IL-21, Cadherin-11, CX3CL1, CCL20, IL-36R, IL-10R, CD86, TNF-α, IL-7R, Kv1.3, α9 Integrin, and LIFHT.

(3) Cranial Nerve Diseases

CGRP, CD20, β amyloid, β amyloid protofibril, Calcitonin Gene-Related Peptide Receptor, LINGO (Ig Domain Containing 1), α Synuclein, extracellular tau, CD52, insulin receptors, tau protein, TDP-43, SOD1, TauC3, and JC virus.

(4) Infectious Diseases

*Clostridium Difficile* toxin B, cytomegalovirus, RS viruses, LPS, *S. Aureus* Alpha-toxin, M2e protein, Psl, PcrV, *S. Aureus* toxin, influenza A, Alginate, *Staphylococcus aureus*, PD-L1, influenza B, *Acinetobacter*, F-protein, Env, CD3, enteropathogenic *Escherichia coli*, *Klebsiella*, and *Streptococcus pneumoniae*.

(5) Hereditary Rare Diseases amyloid AL, SEMA4D (CD100), insulin receptors, ANGPTL3, IL4, IL13, FGF23, adrenocorticotropic hormone, transthyretin, and huntingtin.

(6) Eye Diseases

Factor D, IGF-1R, PGDFR, Ang2, VEGF-A, CD-105 (Endoglin), IGF-1R, and β amyloid.

(7) Bone and Orthopedic Region

Sclerostin, Myostatin, Dickkopf-1, GDF8, RNAKL, HAS, and Siglec-15.

(8) Blood Diseases vWF, Factor IXa, Factor X, IFNγ, C5, BMP-6, Ferroportin, and TFPI.

(9) Other Diseases

BAFF (B cell activating factor), IL-1β, PCSK9, NGF, CD45, TLR-2, GLP-1, TNFR1, C5, CD40, LPA, prolactin receptors, VEGFR-1, CB1, Endoglin, PTH1R, CXCL1, CXCL8, IL-1β, AT2-R, and IAPP.

In a more preferred embodiment, the affinity substance to a soluble protein is an affinity substance to a monoclonal antibody. The isotype of the monoclonal antibody is similar to those described above for the antibody; IgG (e.g., IgG1, IgG2, IgG3, and IgG4) is preferred. The monoclonal antibody is preferably a full-length monoclonal antibody.

In an even more preferred embodiment, the affinity substance to a soluble protein is an affinity substance to a chimeric antibody, a humanized antibody, or a human antibody (e.g., IgG including IgG1, IgG2, IgG3, and IgG4) as a full-length monoclonal antibody.

In a particularly preferred embodiment, the affinity substance to a soluble protein is an affinity substance to an antibody comprising any one Fc region protein selected from the group consisting of the following (A) to (C) and having antigen-binding ability:
- (A) an Fc region protein comprising the amino acid sequence of SEQ ID NO: 1;
- (B) an Fc region protein comprising an amino acid sequence with one or several amino acid residues inserted, added, deleted, or substituted in the amino acid sequence of SEQ ID NO: 1; and
- (C) an Fc region protein comprising an amino acid sequence having 90% or more identity to the amino acid sequence of SEQ ID NO: 1.

The amino acid sequence of SEQ ID NO: 1 is an Fc region protein. It is known that such an Fc region protein has secretion ability. Consequently, (A) to (C) the Fc proteins can have secretion ability. An antibody comprising such an Fc region protein can have antigen-binding ability. The amino acid residue at position 18 in SEQ ID NO: 1 is any amino acid residue, preferably a neutral amino acid, more preferably an amino acid having a nonpolar side chain described below, and even more preferably leucine, isoleucine, or alanine, and particularly preferably leucine or alanine. The amino acid residue at position 19 in SEQ ID NO: 1 is any amino acid residue, preferably a neutral amino acid residue or an acidic amino acid residue, more preferably an amino acid residue having a nonpolar side chain or an acidic amino acid residue, and even more preferably leucine or glutamic acid. The amino acid residue at position 21 in SEQ ID NO: 1 is any amino acid residue, preferably a neutral amino acid residue, more preferably an amino acid residue having a nonpolar side chain, and even more preferably glycine or alanine. The amino acid residue at position 140 in SEQ ID NO: 1 is any amino acid residue, preferably an acidic amino acid residue, and more preferably glutamic acid or aspartic acid. The amino acid residue at position 142 in SEQ ID NO: 1 is any amino acid residue, preferably a neutral amino acid residue, more preferably an amino acid residue having a nonpolar side chain, even more preferably methionine, leucine, or isoleucine, and particularly preferably methionine or leucine. The amino acid residue at position 177 in SEQ ID NO: 1 is any amino acid residue, preferably a neutral amino acid residue, more preferably an amino acid residue having an uncharged polar side chain or an amino acid residue having a nonpolar side chain described below, even more preferably threonine, alanine, or glycine, and particularly preferably threonine or alanine.

In a preferred embodiment, the amino acid sequence of SEQ ID NO: 1 may be an amino acid sequence consisting of the amino acid residues at positions 220 to 449 in the amino acid sequence of SEQ ID NO: 2 or SEQ ID NO: 41.

In another preferred embodiment, the amino acid sequence of SEQ ID NO: 1 may be an amino acid sequence consisting of the amino acid residues at positions 7 to 236 in the amino acid sequence of SEQ ID NO: 3.

In a specific embodiment, the antibody comprising the Fc region protein comprising the amino acid sequence described above may be an antibody comprising the Fc region protein comprising the amino acid sequence described above and a constant region of an antibody. Such a constant region of an antibody may be a constant region of a chimeric antibody, a humanized antibody, or a human antibody (e.g., IgG including IgG1, IgG2, IgG3, and IgG4).

In (B) the Fc region protein, one or several amino acid residues can be modified by one, two, three, or four variations selected from the group consisting of deletion, substitution, addition, and insertion of amino acid residues. The variations of amino acid residues may be introduced to one region in the amino acid sequence or intruded to a plurality of different regions. The term "one or several" indicates a number that does not significantly impair protein activity. The number indicated by the term "one or several" is e.g., 1 to 100, preferably 1 to 80, more preferably 1 to 50, 1 to 30, 1 to 20, 1 to 10, or 1 to 5 (e.g., one, two, three, four, or five).

In (C) the Fc region protein, the percent identity with the amino acid sequence of SEQ ID NO: 1 may be 70% or more, 75% or more, 80% or more, 85% or more, 90% or more, 91% or more, 92% or more, 93% or more, 94% or more, 95% or more, 96% or more, 97% or more, 98% or more, or 99% or more. In the present invention, calculation of the percent identity of peptides and polypeptides (proteins) can be performed by Algorithm blastp. More specifically, calculation of the percent identity of polypeptides can be performed using Scoring Parameters (Matrix: BLOSUM62; Gap Costs: Existence=11 Extension=1; Compositional Adjustments: Conditional compositional score matrix adjustment) as default settings in Algorithm blastp provided in National Center for Biotechnology Information (NCBI). Calculation of the percent identity of polynucleotides (genes) can be performed by Algorithm blastn. More specifically, calculation of the percent identity of polynucleotides can be performed using Scoring Parameters (Match/Mismatch Scores=1, −2; Gap Costs=Linear) as default settings in Algorithm blastn provided in NCBI.

Secretion in secretion ability has the same meaning as the secretion (what is called solubility) of the secretory protein. Consequently, "having secretion ability" means functioning as a soluble protein in a manner similar to normal antibodies.

In the antibody comprising the Fc region protein, a variation may be introduced to a specific site so long as target characteristics (e.g., secretion ability and antigen-binding ability) are maintained. The position of an amino acid residue to which a variation may be introduced that can maintain the target characteristics is obvious to a person skilled in the art. Specifically, a person skilled in the art can 1) compare amino acid sequences of a plurality of proteins having homogeneous characteristics with each other, 2) clarify a relatively preserved region and a relatively non-preserved region, and then 3) predict a region capable of playing an important role for a function and a region incapable of playing an important role for a function from the relatively preserved region and the relatively non-preserved region each and can thus recognize structure-function correlation. Consequently, a person skilled in the art can identify the position of an amino acid residue to which a variation may be introduced in the amino acid sequence of the antibody comprising the Fc region protein.

When an amino acid residue is varied by substitution, the substitution of the amino acid residue may be preservative substitution. The term "preservative substitution" when used in the present specification refers to substituting a certain amino acid residue with an amino acid residue having a similar side chain. Families of amino acid residues having a similar side chain are known in the field concerned. Examples of such families include amino acids having a basic side chain (e.g., lysine, arginine, and histidine), amino acids having an acidic side chain (e.g., aspartic acid, and glutamic acid), amino acids having an uncharged polar side chain (e.g., asparagine, glutamine, serine, threonine, tyrosine, and cysteine), amino acids having a nonpolar side chain (e.g., glycine, alanine, valine, leucine, isoleucine, proline, phenylalanine, methionine, and tryptophan), amino acids having a β-position-branched side chain (e.g., threonine, valine, and isoleucine), amino acids having an aromatic side chain (e.g., tyrosine, phenylalanine, tryptophan, and histidine), amino acids having a hydroxy group (e.g., alcoholic and phenolic)-containing side chain (e.g., serine, threonine, tyrosine), and amino acids having a sulfur-containing side chain (e.g., cysteine and methionine). The preservative substitution of the amino acid may be preferably substitution between aspartic acid and glutamic acid, substation among arginine, lysine, and histidine, substitution between tryptophan and phenylalanine, substitution between phenylalanine and valine, substitution among leucine, isoleucine, and alanine, and substitution between glycine and alanine.

Examples of the antibody comprising any one Fc region selected from the group consisting of (A) to (C) include chimeric antibodies (e.g., rituximab, basiliximab, infliximab, cetuximab, siltuximab, dinutuximab, and altertoxaximab), humanized antibodies (e.g., daclizumab, palivizumab, trastuzumab, alemtuzumab, omalizumab, efalizumab, bevacizumab, natalizumab (IgG4), tocilizumab, eculizumab (IgG2), mogamulizumab, pertuzumab, obinutuzumab, vedolizumab, pembrolizumab (IgG4), mepolizumab, elotuzumab, daratumumab, ixekizumab (IgG4), reslizumab (IgG4), and atezolizumab), and human antibodies (e.g., adalimumab, panitumumab, golimumab, ustekinumab, canakinumab, ofatumumab, denosumab (IgG2), ipilimumab, belimumab, raxibacumab, ramucirumab, nivolumab (IgG4), secukinumab, evolocumab (IgG2), alirocumab, necitumumab, brodalumab (IgG2), and olaratumab) (cases not referring to the IgG subtype indicate that they are IgG1).

Examples of the affinity substance to a soluble protein described above include peptides (comprising oligopeptides, polypeptides, and proteins), small compounds, nucleic acids, nucleic acid-peptide conjugates, peptide-small compound conjugates, and nucleic acid-small compound conjugates.

In a specific embodiment, the affinity substance to a soluble protein described above may be a peptide (comprising an oligopeptide, a polypeptide, and a protein, which may be a glycoprotein). The following are reported examples of such a peptide:

(1) IgG-binding peptides having affinity to a specific region (a CH2 region) of the entire human IgG (that is, human IgG1, IgG2, IgG3, and IgG4; hereinafter the same) (e.g., refer to WO 2016/186206, WO 2013/027796, and WO 2008/054030);

(2) Protein A Mimetic (PAM) peptide having affinity to the specific region (the CH2 region) of the entire human IgG (e.g., refer to Fassina G et al., JOURNAL OF MOLECULAR RECOGNITION, 1996, VOL. 6, 564-569);

(3) EPIHRSTLTALL (SEQ ID NO: 9) having affinity to the specific region (the CH2 region) of the entire human IgG (e.g., refer to Ehrlich G. K et al., J. Biochem. Biophys. Methods, 2001, VOL. 49, 443-454);

(4) (NH2-Cys1-X1-X2-X3-X4)2-Lys-Gly-OH having affinity to the specific region (an Fc region) of the entire human IgG (e.g., refer to Ruvo M et al., ChemBioChem, 2005, VOL. 6, 1242-1253);

(5) FARLVSSIRY (SEQ ID NO: 10), FGRLVSSIRY (SEQ ID NO: 11), and TWKTSRISIF (SEQ ID NO: 12) having affinity to the specific region (the Fc region) of the entire human IgG (e.g., refer to Krook M et al., Journal of Immunological Methods, 1998, VOL. 221, 151-157);

(6) QSYP (SEQ ID NO: 13) having affinity to the specific region of the entire human IgG (e.g., refer to Jacobs J. M. et al., Bio. Techniques, 2003, VOL. 34, 132-141);

(7) HWRGWV (SEQ ID NO: 14), HYFKFD (SEQ ID NO: 15), and HFRRHL (SEQ ID NO: 16) having affinity to the specific region (the Fc region) of the entire human IgG (e.g., refer to Carbonell R. G. et al., Journal of Chromatography A, 2009, VOL. 1216, 910-918);

(8) DAAG (SEQ ID NO: 17) having affinity to the specific region (the Fc region) of the entire human IgG (e.g., refer to Lund L. N. et al., Journal of Chromatography A, 2012, VOL. 1225, 158-167);

(9) Fc-I, Fc-II, and Fc-III having affinity to the specific region (the Fc region) of the entire human IgG (e.g., refer to Warren L. Delano et al., Science, 2000, VOL. 287, 1279-1283 and WO 2001/045746); and

(10) NARKFYKG (SEQ ID NO: 18) and NKFRGKYK (SEQ ID NO: 19) having affinity to the specific region (the Fc region) of the entire human IgG (e.g., refer to Biochemical Engineering Journal, 2013, VOL. 79, 33-40).

In another specific embodiment, the affinity substance to a soluble protein described above may be a substance other than the peptide. Reported examples of such a substance include an aptamer having affinity to a specific region (the CH2 region, especially a side chain of Lys340) of human IgG (e.g., human IgG1 to 4) [e.g., GGUG(C/A)(U/T) motif-containing aptamers such as GGUGCU and GGUGAU] (e.g., refer to WO 2007/004748; Nomura Y et al., Nucleic Acids Res., 2010 November; 38(21): 7822-9; and Miyakawa S et al., RNA., 2008 June; 14(6): 1154-63).

The affinity substance to a soluble protein described above can be obtained by any known method in the field concerned. The affinity substance to a soluble protein can be obtained by producing an antibody (e.g., the hybridoma method) using the entire soluble protein or a partial peptide in the soluble protein (e.g., when a protein surface exposed region is known, a partial peptide present in the region) or screening the affinity substance (e.g., the phage display method, the systematic evolution of ligands with exponential enrichment (SELEX) method, the mRNA display method, the ribosome display method, the cDNA display method, and the yeast display method) from a library from which the affinity substance is available (e.g., peptide libraries, antibody libraries, antibody-forming cell libraries, aptamer libraries, phage libraries, mRNA libraries, and cDNA libraries), for example. When the affinity substance to a soluble protein is an affinity substance to an Fc region (a soluble region) of an antibody, a partial peptide present in a specific region (e.g., CH1, CH2, and CH3) of the Fc region of various kinds of antibodies (e.g., IgG, IgA, IgM, IgD, and IgE) is used, whereby an affinity substance (e.g., an antibody and an aptamer) capable of selectively binding to any portion in the Fc region of the antibody can be efficiently obtained. The thus obtained affinity substances comprise a mixture of substances relatively strong and weak in affinitive binding ability. However, even an affinity substance weak in affinitive biding ability can strengthen its affinitive binding ability by using it in an excessive amount.

The affinity substance to a soluble protein described above may be an IgG-binding peptide represented by the following Formula (i) or a salt thereof (e.g., Examples and WO 2016/186206).

A peptide comprising an amino acid sequence consisting of 13 to 17 amino acid residues represented by

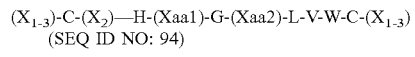

$(X_{1-3})$-C-$(X_2)$—H-(Xaa1)-G-(Xaa2)-L-V-W-C-$(X_{1-3})$
(SEQ ID NO: 94)     (i)

wherein
- Xs are the same or different from each other, and are each any amino acid residue other than cysteine;
- C is a cysteine residue;
- H is a histidine residue;
- Xaa1 is an arginine residue, a leucine residue, a lysine residue, an aspartic acid residue, a glutamic acid residue, a 2-amino suberic acid residue, or a diaminopropionic acid residue;
- G is a glycine residue;
- Xaa2 is a lysine residue, a glutamine residue, a glutamic acid residue, an asparagine residue, or an aspartic acid residue;
- L is a leucine residue;
- V is a valine residue; and
- W is a tryptophan residue; and
- capable of binding to human IgG and/or rabbit IgG, or a salt thereof.

Xaa1 and Xaa2 are preferably amino acid residues different from each other.

In the present specification, the expression $X_{1-3}$ at the N-terminus or the C-terminus means that independently one to three of any amino acid residues X other than cysteine (C or Cys) are continuous; the amino acid residues contained therein are the same or different residues and preferably consist of an arrangement in which all the three are not the same residue. Similarly, X2 means that independently two of any amino acid residues X other than cysteine (C or Cys) are continuous; the amino acid residues contained therein are the same or different residues and preferably consist of an arrangement in which the two continuous amino acid residues are not the same residue. X1 described below also means that independently one of any amino acid residue X other than cysteine (C or Cys) is present.

In the present specification, at least two cysteine residues separated from each other in each amino acid sequence of a peptide can form a cyclic peptide through a disulfide bond. In the peptide of a formula such as Formula (i), the outside two cysteine residues normally form a disulfide bond. Alternatively, in the peptide of a formula such as Formula (i), the sulfide groups in the outside two cysteine residues may be coupled with each other through a carbonyl group-containing linker represented by the following.

The broken line portions of the carbonyl group-containing linker represented by the above mean bond portions with the sulfide groups. The linker is more stable than a normal disulfide bond against a reduction reaction and the like. This peptide can be prepared by a method described in WO 2016/186206, for example.

In a specific embodiment, the affinity substance of Formula (i) may be an IgG-biding peptide represented by the following Formula (i-1) or a salt thereof (e.g., WO 2016/186206).

A peptide comprising an amino acid sequence consisting of 13 to 17 amino acid residues represented by (SEQ ID NO: 95)
$(X_{1-3})$-C-$(X_2)$-H-(Xaa1)-G-(Xaa2)-L-V-W-C-$(X_{1-3})$ (i-1)

wherein
- Xs are the same or different from each other, and are each any amino acid residue other than cysteine;
- C is a cysteine residue;
- H is a histidine residue;
- Xaa1 is a lysine residue, a cysteine residue, an aspartic acid residue, a glutamic acid residue, a 2-amino suberic acid residue, or a diaminopropionic acid residue;
- G is a glycine residue;
- Xaa2 is a glutamic acid residue or an asparagine residue;
- L is a leucine residue;
- V is a valine residue; and
- W is a tryptophan residue and capable of binding to human IgG and/or rabbit IgG, or a salt thereof.

Xaa1 and Xaa2 are preferably amino acid residues different from each other.

In another specific embodiment, the affinity substance to the soluble protein described above may be an IgG-biding peptide represented by the following Formula (i-2) or a salt thereof (e.g., Examples).

A peptide comprising an amino acid sequence consisting of 13 to 17 amino acid residues represented by (SEQ ID NO: 96)
$(X_{1-3})$-C-$(X_2)$-H-(Xaa1)-G-(Xaa2)-L-V-W-C-$(X_{1-3})$ (i-2)

wherein
- Xs are the same or different from each other, and are each any amino acid residue other than cysteine;
- C is a cysteine residue;
- H is a histidine residue;
- Xaa1 is an arginine residue or a leucine residue;
- G is a glycine residue;
- Xaa2 is a lysine residue, a glutamine residue, or an aspartic acid residue;
- L is a leucine residue;
- V is a valine residue; and
- W is a tryptophan residue; and
- capable of binding to human IgG and/or rabbit IgG, or a salt thereof.

The affinity substance undisclosed in WO 2016/186206 having such a specific structure is useful for regioselective modification of the Lys248 residue or the Lys246 residue or other amino acid residues other than the Lys248 residue or the Lys246 residue following Eu numbering in human IgG Fc (Examples).

The following describes peptides represented by Formula (i-1') and Formula (i-1"), which further satisfy the amino acid residue X in the amino acid sequence of the peptide of Formula (i-1).

That is, the peptide represented by Formula (i-1') comprises an amino acid sequence consisting of 13 to 17 amino acid residues represented by (SEQ ID NO: 97)
$(X_{1-3})$-C-(X1)-Y-H-(Xaa1)-G-N-L-V-W-C-$(X_{1-3})$ (i-1')

wherein
- Xs are the same or different from each other, and are each any amino acid residue other than cysteine;
- C is a cysteine residue;
- Y is a tyrosine residue;
- H is a histidine residue;

Xaa1 is a lysine residue, a cysteine residue, an aspartic acid residue, a glutamic acid residue, a 2-amino suberic acid residue, or a diaminopropionic acid residue;
G is a glycine residue;
N is an asparagine residue;
L is a leucine residue;
V is a valine residue; and
W is a tryptophan residue; and
capable of binding to human IgG and/or rabbit IgG.

The peptide represented by Formula (i-1″) comprises an amino acid sequence consisting of 13 to 17 amino acid residues represented by $$(X_{1-3})\text{-C-A-}(X1)\text{-H-}(Xaa1)\text{-G-E-L-V-W-C-}(X_{1-3}) \quad \text{(i-1″)} \quad \text{(SEQ ID NO: 98)}$$

wherein
Xs are the same or different from each other, and are each any amino acid residue other than cysteine;
C is a cysteine residue;
A is an alanine residue;
H is a histidine residue;
Xaa1 is a lysine residue, a cysteine residue, an aspartic acid residue, a glutamic acid residue, a 2-amino suberic acid residue, or a diaminopropionic acid residue;
G is a glycine residue;
E is a glutamic acid residue:
L is a leucine residue;
V is a valine residue; and
W is a tryptophan residue; and
capable of binding to human IgG and/or rabbit IgG.

The following describes a peptide represented by Formula (ii), which further satisfies the amino acid residue X in the amino acid sequence of the peptide of Formula (i-1).

That is, the peptide represented by Formula (ii) comprises an amino acid sequence consisting of 13 to 17 amino acid residues represented by $$(X_{1-3})\text{-C-}(Xaa3)\text{-}(Xaa4)\text{-H-}(Xaa1)\text{-G-}(Xaa2)\text{-L-V-W-C-}(X_{1-3}) \quad \text{(ii)} \quad \text{(SEQ ID NO: 99)}$$

wherein
Xs are the same or different from each other, and are each any amino acid residue other than cysteine;
C is a cysteine residue;
H is a histidine residue;
Xaa1 is a lysine residue, a cysteine residue, an aspartic acid residue, a glutamic acid residue, a 2-amino suberic acid residue, or a diaminopropionic acid residue;
G is a glycine residue;
Xaa2 is a glutamic acid residue or an asparagine residue;
L is a leucine residue;
V is a valine residue;
W is a tryptophan residue;
Xaa3 is an alanine residue, a serine residue, or a threonine residue; and
Xaa4 is a tyrosine residue or a tryptophan residue; and
capable of binding to human IgG and/or rabbit IgG.

In the amino acid sequence of the peptide of a formula such as Formula (i), in the case of 17 amino acid residues, the first, second, 16th, and 17th amino acid residues X from the N-terminus may be deleted, and such a peptide consists of 13 amino acid length.

"In the case of 17 amino acid residues" used in the present specification is a term represented for convenience's sake in order to number 17 residues, which is the longest amino acid length for the peptide of Formula (i) and the like, from the first to the 17th in order from the N-terminus when the amino acid residues of the peptide are called by amino acid numbers.

The following describes a peptide represented by Formula (iii), which further satisfies the amino acid residue X in the amino acid sequence of the peptide of Formula (i-1).

That is, the peptide represented by Formula (iii) comprises an amino acid sequence consisting of 13 to 17 amino acid residues represented by $$(X_{1-3})\text{-C-A-Y-H-}(Xaa1)\text{-G-E-L-V-W-C-}(X_{1-3}) \quad \text{(iii)} \quad \text{(SEQ ID NO: 100)}$$

wherein
Xs are the same or different from each other, and are each any amino acid residue other than cysteine;
C is a cysteine residue;
A is an alanine residue;
Y is a tyrosine residue;
H is a histidine residue;
Xaa1 is a lysine residue, a cysteine residue, an aspartic acid residue, a glutamic acid residue, a 2-amino suberic acid residue, or a diaminopropionic acid residue;
G is a glycine residue;
E is a glutamic acid residue:
L is a leucine residue;
V is a valine residue; and
W is a tryptophan residue; and
capable of binding to human IgG and/or rabbit IgG.

In the amino acid sequence of the peptide of Formula (iii), in the case of 17 amino acid residues, the first, second, 16th, and 17th amino acid residues X from the N-terminus may be deleted, and such a peptide consists of 13 amino acid length.

Furthermore, the amino acid residues other than cysteine (C) of the amino acid sequence of the peptide of each of the above formulae, that is, in the case of 17 amino acid residues, the first to third, fifth, sixth, and 15th to 17th amino acid residues from the N-terminus are preferably selected from the following, where each capital letter of the alphabet is single-letter notation of an amino acid:
the first amino acid residue=S, G, F, or absent
the second amino acid residue=D, G, A, S, P, homocysteine, or absent
the third amino acid residue=S, D, T, N, E, or R
the 15th amino acid residue=S, T, or D
the 16th amino acid residue=H, G, Y, T, N, D, F, homocysteine, or absent
the 17th amino acid residue=Y, F, H, M, or absent
the fifth amino acid residue=A or T
the sixth amino acid residue=Y or W The following describes a peptide represented by Formula (iv), which further satisfies the amino acid residue X in the amino acid sequence of the peptide of Formula (i-1).

That is, the peptide represented by Formula (iv) comprises an amino acid sequence consisting of 13 amino acid residues represented by

```
                                                    (SEQ ID NO: 101)
D-C-(Xaa3)-(Xaa4)-H-(Xaa1)-G-(Xaa2)-L-V-W-C-T
                                                    (iv)
``` wherein
- D is an asparagine residue;
- C is a cysteine residue;
- H is a histidine residue;
- Xaa1 is a lysine residue, a cysteine residue, an aspartic acid residue, a glutamic acid residue, a 2-amino suberic acid residue, or a diaminopropionic acid residue;
- G is a glycine residue;
- Xaa2 is a glutamic acid residue or an asparagine residue;
- L is a leucine residue;
- V is a valine residue;
- W is a tryptophan residue;
- T is a threonine residue;
- Xaa3 is an alanine residue or a threonine residue; and
- Xaa4 is a tyrosine residue or a tryptophan residue; and
- capable of binding to human IgG and/or rabbit IgG.

Some specific examples of the peptide of Formula (i-1) are enumerated in the following (1) to (19); it is understood that these are not limited examples:

```
                                    (SEQ ID NO: 20)
(1)  DCAYH(Xaa1)GELVWCT;
                                    (SEQ ID NO: 21)
(2)  GPDCAYH(Xaa1)GELVWCTFH;
                                    (SEQ ID NO: 22)
(3)  RCAYH(Xaa1)GELVWCS;
                                    (SEQ ID NO: 23)
(4)  GPRCAYH(Xaa1)GELVWCSFH;
                                    (SEQ ID NO: 24)
(5)  SPDCAYH(Xaa1)GELVWCTFH;
                                    (SEQ ID NO: 25)
(6)  GDDCAYH(Xaa1)GELVWCTFH;
                                    (SEQ ID NO: 26)
(7)  GPSCAYH(Xaa1)GELVWCTFH;
                                    (SEQ ID NO: 27)
(8)  GPDCAYH(Xaa1)GELVWCSFH;
                                    (SEQ ID NO: 28)
(9)  GPDCAYH(Xaa1)GELVWCTHH;
                                    (SEQ ID NO: 29)
(10) GPDCAYH(Xaa1)GELVWCTFY;
                                    (SEQ ID NO: 30)
(11) SPDCAYH(Xaa1)GELVWCTFY;
                                    (SEQ ID NO: 31)
(12) SDDCAYH(Xaa1)GELVWCTFY;
                                    (SEQ ID NO: 32)
(13) RGNCAYH(Xaa1)GQLVWCTYH;
                                    (SEQ ID NO: 33)
(14) G(Xaa2)DCAYH(Xaa1)GELVWCT(Xaa2)H;
                                    (SEQ ID NO: 34)
(15) RRGPDCAYH(Xaa1)GELVWCTFH;
                                    (SEQ ID NO: 35)
(16) DCTYH(Xaa1)GNLVWCT;
                                    (SEQ ID NO: 36)
(17) DCAYH(Xaa1)GNLVWCT;
                                    (SEQ ID NO: 37)
(18) DCTYH(Xaa1)GELVWCT
and
                                    (SEQ ID NO: 38
(19) DCAWH(Xaa1)GELVWCT
``` wherein
- Xaa1 is a lysine residue, a cysteine residue, an aspartic acid residue, a glutamic acid residue, a 2-amino suberic acid residue, or a diaminopropionic acid residue;
- Xaa2 is a homocysteine; and
- the homocysteines preferably form a disulfide bond with each other.

Preferred specific examples of the peptide of Formula (i-1) include the following:

```
                                    (SEQ ID NO: 20)
(1)  DCAYH(Xaa1)GELVWCT;
                                    (SEQ ID NO: 21)
(2)  GPDCAYH(Xaa1)GELVWCTFH;
                                    (SEQ ID NO: 22)
(13) RGNCAYH(Xaa1)GQLVWCTYH;
                                    (SEQ ID NO: 33)
(14) G(Xaa2)DCAYH(Xaa1)GELVWCT(Xaa2)H;
and
                                    (SEQ ID NO: 34)
(15) RRGPDCAYH(Xaa1)GELVWCTFH.
``` wherein
- Xaa1 is a lysine residue;
- Xaa2 is homocysteine; and
- cysteines and/or homocysteines preferably form a disulfide bond with each other.

The (13) peptide may be RGNCAYHKGQLVWCTYH (SEQ ID NO: 39).

In another specific embodiment, the affinity substance of Formula (i) may be an IgG-binding peptide represented by the following Formula (v) or a salt thereof (e.g., Examples). A peptide comprising an amino acid sequence consisting of 13 to 17 amino acid residues represented by

```
                                                    (SEQ ID NO: 102)
(X_{1-3})-C-(Xaa3)-(xaa4)-H-(Xaa1)-G-(Xaa2)-L-V-W-C-
(Xaa5)-(Xaa6)-(Xaa7) (v)
``` wherein
- Xs are the same or different from each other, and are each any amino acid residue other than cysteine;
- C is a cysteine residue;
- Xaa3 is an alanine residue or a lysine residue;
- Xaa4 is a tryptophan residue or a tyrosine residue;
- H is a histidine residue;
- Xaa1 is an arginine residue, a leucine residue, a lysine residue, an aspartic acid residue, a glutamic acid residue, a 2-amino suberic acid residue, or a diaminopropionic acid residue;
- G s a glycine residue;
- Xaa2 is a lysine residue, a glutamine residue, a glutamic acid residue, an asparagine residue, or an aspartic acid residue;
- L is a leucine residue;

V is a valine residue;
W is a tryptophan residue;
Xaa5 is a threonine residue or a lysine residue;
Xaa6 is a tyrosine residue, a lysine residue, or absent; and
Xaa7 is a histidine residue, a lysine residue, or absent; and
capable of binding to human IgG, or a salt thereof.

The affinity substance undisclosed in WO 2016/186206 having such a specific structure is useful for regioselective modification of the Lys248 residue or the Lys246 residue or other amino acid residues other than the Lys248 residue or the Lys246 residue following Eu numbering in human IgG Fc (Examples). Any one of Xaa3, Xaa1, Xaa2, Xaa5, Xaa6, and Xaa7 is preferably a lysine residue. Xaa1 may be preferably an arginine residue or a leucine residue. Alternatively, Xaa1 may be preferably a lysine residue, an aspartic acid residue, a glutamic acid residue, a 2-amino suberic acid residue, or a diaminopropionic acid residue and more preferably a lysine residue, an aspartic acid residue, or a glutamic acid residue.

In the amino acid sequence of the peptide of Formula (v), in the case of 17 amino acid residues, the first, second, 16th, and 17th amino acid residues X from the N-terminus may be deleted, and such a peptide consists of 13 amino acid length.

Furthermore, the amino acid residues other than cysteine (C) of the amino acid sequence of the peptide of Formula (v), that is, in the case of 17 amino acid residues, the first to third amino acid residues from the N-terminus are preferably selected from the following, where each capital letter of the alphabet is single-letter notation of an amino acid:
the first amino acid residue=R, S, G, F, or absent (preferably R or absent)
the second amino acid residue=D, G, A, S, P, homocysteine, or absent (preferably G or absent)
the third amino acid residue=S, D, T, N, E, or R (preferably N or D)

Some specific examples of the peptide of Formula (v) are enumerated in the following (16) to (34); it is understood that these are not limited examples:

```
                                          (SEQ ID NO: 73)
(16)  RGNCAYH(Xaa1)GQLVWCTYH (SEQ ID NO: 74)
(17)  RGNCAWH(Xaa1)GQLVWCTYH (SEQ ID NO: 75)
(18)  RGNCAWH(Xaa1)GELVWCTYH (SEQ ID NO: 76)
(19)  RGNCKWH(Xaa1)GQLVWCTYH (SEQ ID NO: 77)
(20)  RGNCKYH(Xaa1)GELVWCTYH (SEQ ID NO: 78)
(21)  RGNCKYH(Xaa1)GQLVWCTYH (SEQ ID NO: 79)
(22)  DCKWH(Xaa1)GELVWCT (SEQ ID NO: 80)
(23)  DCKYH(Xaa1)GELVWCT (SEQ ID NO: 81)
(24)  DCKWH(Xaa1)GELVWCT (SEQ ID NO: 82)
(25)  DCKWH(Xaa1)GQLVWCT (SEQ ID NO: 83)
(26)  DCKYH(Xaa1)GELVWCT (SEQ ID NO: 84)
(27)  DCKYH(Xaa1)GQLVWCT (SEQ ID NO: 85)
(28)  DCKWH(Xaa1)GQLVWCT (SEQ ID NO: 86)
(29)  DCKYH(Xaa1)GQLVWCT (SEQ ID NO: 87)
(30)  RGNCAWH(Xaa1)GQLVWCKYH (SEQ ID NO: 88)
(31)  RGNCAWH(Xaa1)GELVWCKYH (SEQ ID NO: 89)
(32)  RGNCAYH(Xaa1)GQLVWCTKH (SEQ ID NO: 90)
(33)  RGNCAYH(Xaa1)GQLVWCTYK (SEQ ID NO: 91)
(34)  RGNCAYH(Xaa1)GQLVWCTKH
``` wherein
Xaa1 is an arginine residue, a leucine residue, a lysine residue, an aspartic acid residue, a glutamic acid residue, a 2-amino suberic acid residue, or a diaminopropionic acid residue.

Xaa1 is preferably an arginine residue, a leucine residue, or a lysine residue and more preferably a lysine residue.

The IgG-binding peptide is, as a primary structure in a broad sense, a peptide comprising an amino acid sequence consisting of 13 to 15 amino acid residues represented by the following Formula (vi):

```
                                         (SEQ ID NO: 103)
D-C-(Xaa3)-(Xaa4)-H-(Xaa1)-G-(Xaa2)-L-V-W-C-
(Xaa5)-(Xaa6)-(Xaa7)(vi)
``` wherein
D is an aspartic acid residue;
C is a cysteine residue;
Xaa3 is an alanine residue or a lysine residue;
Xaa4 is a tryptophan residue or a tyrosine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue;
W is a tryptophan residue;
Xaa5 is a threonine residue or a lysine residue;
Xaa6 is a tyrosine residue, a lysine residue, or absent; and
Xaa7 is a histidine residue, a lysine residue, or absent; and
capable of binding to human IgG and/or rabbit IgG (e.g., Examples and WO 2016/186206).

Any one of Xaa3, Xaa1, Xaa2, Xaa5, Xaa6, and Xaa7 is preferably a lysine residue. Xaa1 is preferably a lysine residue, an arginine residue, or a leucine residue; and Xaa2 is preferably a lysine residue, a glutamine residue, or a glutamic acid residue.

In a specific embodiment, the IgG-binding peptide is a peptide comprising an amino acid sequence consisting of 13 amino acid residues represented by the following Formula (vii):

```
                                          (SEQ ID NO: 104)
D-C-(Xaa3)-(Xaa4)-H-(Xaa1)-G-(Xaa2)-L-V-W-C-T
(vii)
``` wherein
D is an aspartic acid residue;
C is a cysteine residue;
Xaa3 is an alanine residue or a lysine residue;
Xaa4 is a tryptophan residue or a tyrosine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue;
W is a tryptophan residue; and
T is a threonine residue; and
capable of binding to human IgG and/or rabbit IgG (e.g., WO 2016/186206). Any one of Xaa3, Xaa1, and Xaa2 is preferably a lysine residue. Xaa1 is preferably a lysine residue, an arginine residue, or a leucine residue; and Xaa2 is preferably a lysine residue, a glutamine residue, or a glutamic acid residue.

In another specific embodiment, the IgG-binding peptide is a peptide comprising an amino acid sequence consisting of 13 to 15 amino acid residues represented by the following Formula (viii):

```
                                          (SEQ ID NO: 105)
R-G-N-C-(Xaa3)-(Xaa4)-H-(Xaa1)-G-(Xaa2)-L-V-W-C-
(Xaa5)-(Xaa6)-(Xaa7)(viii)
``` wherein
R is an arginine residue;
G is a glycine residue;
N is an asparagine residue;
C is a cysteine residue;
Xaa3 is an alanine residue or a lysine residue;
Xaa4 is a tryptophan residue or a tyrosine residue;
H is a histidine residue;
Xaa1 is an arginine residue, a leucine residue, a lysine residue, an aspartic acid residue, a glutamic acid residue, a 2-amino suberic acid residue, or a diaminopropionic acid residue;
G is a glycine residue;
Xaa2 is a lysine residue, a glutamine residue, a glutamic acid residue, an asparagine residue, or an aspartic acid residue;
L is a leucine residue;
V is a valine residue;
W is a tryptophan residue; and
Xaa5 is a threonine residue or a lysine residue;
Xaa6 is a tyrosine residue, a lysine residue, or absent; and Xaa7 is a histidine residue, a lysine residue, or absent; and
capable of binding to human IgG and/or rabbit IgG (e.g., Examples). The compound undisclosed in WO 2016/186206 having such a specific structure is useful for regioselective modification of the Lys248 residue or the Lys246 residue or other amino acid residues other than the Lys248 residue or the Lys246 residue following Eu numbering in human IgG Fc (Examples). Any one of Xaa3, Xaa1, Xaa2, Xaa5, Xaa6, and Xaa7 is preferably a lysine residue. Xaa1 may be preferably an arginine residue or a leucine residue. Alternatively, Xaa1 is preferably a lysine residue, an arginine residue, or a leucine residue; and Xaa2 is preferably a lysine residue, a glutamine residue, or a glutamic acid residue.

The peptide may form a cyclic peptide through a disulfide bond by at least two cysteine (C) residues separated in each amino acid sequence and have any one or two amino acid residues other than cysteine on the N-terminus side and the C-terminus side of each cysteine residue. When the peptide has one or two amino acid residues on the N-terminus side and the C-terminus side of each cysteine residue, in the case of 17 amino acid residues, the first to second and 16th to 17th amino acid residues from the N-terminus are each that exemplified above. The amino acids forming the peptide may each be an L-body or a D-body; an L-body is preferred (in Examples, the amino acid residues forming the peptides are all L-bodies).

As described above, in the IgG-binding peptide, when the Xaa amino acid residue is an amino acid residue capable of being easily modified with a cross-linking agent (a protein-forming amino acid such as a lysine residue, a cysteine residue, an aspartic acid residue, or a glutamic acid residue or a non-protein-forming amino acid such as a diaminopropionic acid residue or a 2-amino suberic acid residue), a lysine residue is preferred among these amino acids. Examples of such a cross-linking agent include cross-linking agents comprising preferably two or more succinimidyl groups such as disuccinimidyl glutarate (DSG) and disuccinimidyl suberate (DSS); cross-linking agents comprising preferably two or more imide acid portions such as dimethyl adipimidate·2HCl (DMA), dimethyl pimelimidate·2HCl (DMP), and dimethyl suberimidate*2HCl (DMS); and cross-linking agents having an SS bond such as dimethyl 3,3'-dithiobispropionimidate*2HCl (DTBP) and dithiobis (succinimidyl propionate) (DSP) (e.g., WO 2016/186206). To increase site specificity when the IgG binding-peptide is modified with the cross-linking agent, the IgG-biding peptide preferably has no or few (e.g., has only one or two) residues the same as Xaa1 in the sequence. When Xaa1 is a lysine residue, for example, the IgG-binding peptide preferably has no or few lysine residues at positions other than Xaa1 in the sequence.

The IgG-biding peptide binds to the Fc domain of IgG. The IgG-binding peptide is close to a specific region of IgG Fc, that is, the Lys248 residue or the Lys246 residue and preferably Lys248 following Eu numbering in human IgG Fc in the Xaa amino acid residue such as Xaa1 (refer to Examples and WO 2016/186206). Alternatively, in the IgG-binding peptide, the Xaa amino acid residue can be close to other amino acid residues other than the Lys248 residue or the Lys246 residue following Eu numbering in human IgG Fc.

More specifically, the peptides represented by Formulae (i) to (viii) are as follows:

```
(1')  RGNCAYHKGQLVWCTYH       (SEQ ID NO: 39)

(2')  RGNCKYHRGQLVWCTYH       (SEQ ID NO: 42)

(3')  RGNCAWHRGKLVWCTYH       (SEQ ID NO: 43)

(4')  RGNCKWHRGELVWCTYH       (SEQ ID NO: 44)

(5')  RGNCKWHRGQLVWCTYH       (SEQ ID NO: 45)

(6')  RGNCKYHLGELVWCTYH       (SEQ ID NO: 46)

(7')  RGNCKYHLGQLVWCTYH       (SEQ ID NO: 47)

(8')  DCKWHLGELVWCT           (SEQ ID NO: 48)

(9')  DCKYHLGELVWCT           (SEQ ID NO: 49)

(10') DCKWHRGELVWCT           (SEQ ID NO: 50)

(11') DCKWHLGQLVWCT           (SEQ ID NO: 51)

(12') DCKYHRGELVWCT           (SEQ ID NO: 52)

(13') DCKYHLGQLVWCT           (SEQ ID NO: 53)

(14') DCKWHRGQLVWCT           (SEQ ID NO: 54)

(15') DCKYHRGQLVWCT           (SEQ ID NO: 55)

(16') RGNCAWHLGQLVWCKYH       (SEQ ID NO: 56)

(17') RGNCAWHLGELVWCKYH       (SEQ ID NO: 57)

(18') RGNCAYHLGQLVWCTKH       (SEQ ID NO: 58)

(19') RGNCAYHLGQLVWCTYK       (SEQ ID NO: 59)

(20') RGNCAYHRGQLVWCTKH       (SEQ ID NO: 60)
```

The affinity substance to the soluble protein described above may be an affinity peptide comprising an amino acid sequence (a) in which any amino acid residue is substituted with one amino acid residue selected from the group consisting of a lysine residue, an aspartic acid residue, a glutamic acid residue, a 2-amino suberic acid residue, and a diaminopropionic acid residue (an amino acid residue which can be easily modified with a cross-linking agent) (preferably a lysine residue, an aspartic acid residue, or a glutamic acid residue, and more preferably a lysine residue) in the amino acid sequence of FNMQCQRRFYEALHDPNLNEEQRNARIRSIRDDC (SEQ ID NO: 92), and (b) having 90% or more identity to the amino acid sequence of SEQ ID NO: 92.

The amino acid sequence having the characteristics of (a) and (b) is preferably capable of binding to human IgG described in the present specification.

The peptide consisting of the amino acid sequence of SEQ ID NO: 92 is obtained by changing two K (lysine) of the 26th and 28th counted from the N-terminus to R (arginine) in the affinity peptide known as Z34C for peptide reagent synthetic reasons and can be used by further acetylating the N-terminus and amidating the C-terminus. More specifically, examples of such an affinity peptide include Ac-FNMQCQRRFYEALHDPNLNEEQRNARIRSIRDDC-NH$_2$ (SEQ ID NO: 92). The affinity substance having such a specific structure is useful for regioselective modification of the Lys248 residue or the Lys246 residue, Lys288, Lys290, Lys 317, or other amino acid residues other than these residues following Eu numbering in human IgG Fc (Examples). The amino acid sequence of Z34C is FNMQCQRRFYEALHDPNLNEEQRNAKIKSIRDDC (SEQ ID NO: 93) (e.g., refer to Starovasnik, M. A. et al., Structural mimicry of a native protein by a minimized binding domain., Proc. Natl. Acad. Sci. USA., 94, 10080-10085 (1997)).

The affinity peptide can have affinity to human IgG (e.g., human IgG described above, preferably human IgG1). The affinity peptide may form a cyclic peptide through a disulfide bond by the cysteine residues at position 5 and position 34.

For a position to which the amino acid residue easily modified with a cross-linking agent is introduced, any position can be used so long as it has affinity to human IgG such as human IgG1. A person skilled in the art can easily identify such a position. The position to which the amino acid residue capable of being easily modified with a cross-linking agent is introduced is preferably any amino acid residue other than the cysteine residues at position 5 and position 34 that may form a disulfide bond. The position to which the amino acid residue capable of being easily modified with a cross-linking agent is introduced is more preferably the amino acid residues at position 1, position 3, position 6, position 7, position 13, position 20, position 24, position 31, and position 32, for example.

The amino acid sequence having the characteristics of (a) and (b) also preferably has one specific amino acid residue selected from the group consisting of a lysine residue, an aspartic acid residue, a glutamic acid residue, a 2-amino suberic acid residue, and a diaminopropionic acid residue (the amino acid residue capable of being easily modified with a cross-linking agent) (preferably a lysine residue, an aspartic acid residue, or a glutamic acid residue, and more preferably a lysine residue) at a certain position and has variations of the normal 20 amino acid residues forming natural proteins (preferably 17 amino acid residues other than a lysine residue, an aspartic acid residue, and a glutamic acid residue, and more preferably 19 amino acid residues other than a lysine residue) at positions other than the certain position. Such a certain position is not limited to a particular position; examples thereof include position 1, position 3, position 6, position 7, position 13, position 20, position 24, position 31, and position 32. The amino acid sequence having the characteristics of (a) and (b) maintains the two cysteine residues at position 5 and position 34, and these two cysteine residues may bond to each other through a disulfide bond. The amino acid sequence having 90% or more identity to the amino acid sequence of SEQ ID NO: 92 may comprise one to three (preferably one or two, and more preferably one) modified amino acid residues by one, two, three, or four variations selected from the group consisting of deletion, substitution, addition, and insertion (preferably substitution) of amino acid residues. The variations of amino acid residues may be introduced to one region in the amino acid sequence or introduced to a plurality of different regions.

The amino acid sequence having the characteristics of (a) and (b) may be more preferably the following (c) or (d). (c)

an amino acid sequence selected from the group consisting of the following (1) to (9) amino acid sequences:
(1) KNMQCQRRFYEALHDPNLNEEQRNARIR-SIRDDC (SEQ ID NO: 61);
(2) FNMQCQKRFYEALHDPNLNEEQRNARIR-SIRDDC (SEQ ID NO: 62);
(3) FNMQCQRRFYEAKHDPNLNEEQRNARIR-SIRDDC (SEQ ID NO: 63);
(4) FNMQCQRRFYEALHDPNLNEEQRKARIR-SIRDDC (SEQ ID NO: 64);
(5) FNMQCQRRFYEALHDPNLNKEQRNARIR-SIRDDC (SEQ ID NO: 65);
(6) FNMQCQRRFYEALHDPNLNEEQRNARIR-SIKDDC (SEQ ID NO: 68);
(7) FNKQCQRRFYEALHDPNLNEEQRNARIR-SIRDDC (SEQ ID NO: 70);
(8) FNMQCKRRFYEALHDPNLNEEQRNARIR-SIRDDC (SEQ ID NO: 71); and
(9) FNMQCQRRFYEALHDPNLNEEQRNARIR-SIRKDC (SEQ ID NO: 72); or
(d) an amino acid sequence having 90% or more identity to any of the amino acid sequences of (1) to (9) (may be modification of the number of amino acid residues described above) having variations of 19 amino acid residues other than a lysin residue at positions other than the one lysine residue and the two cysteine residues (e.g., position 1, position 3, position 6, position 7, position 13, position 20, position 24, position 31, and position 32) in any of the amino acid sequences of (1) to (9). (d) The amino acid sequence preferably maintains the two cysteine residues at position 5 and position 34, and these two cysteine residues may bond to each other through a disulfide bond. The affinity peptide having (d) the amino acid sequence is preferably capable of binding to human IgG described in the present specification.

The affinity peptide may have additional variations of amino acid residues other than the introduction of one amino acid residue easily modified with a cross-linking agent so long as it has 90% or more identity with respect to the amino acid sequence of SEQ ID NO: 92 or the amino acid sequences of (1) to (9). A person skilled in the art can easily identify a position to which the additional variations of amino acid residues can be introduced. For such positions, positions other than the cysteine residues at position 5 and position 34 can be used, for example. The phenylalanine residue at position 1, the arginine residue at position 6, the leucine residue at position 13, the glutamic acid residue at position 20, the asparagine residue at position 24, or the arginine residue at position 31 (except the position to which the amino acid residue capable of being easily modified with a cross-linking agent has already been introduced) can also be used, for example. Examples of amino acid residues that can be introduced by the additional variations of amino acid residues include alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), valine (V), aspartic acid (D), glutamic acid (E), arginine (R), histidine (H), and lysine (L). These 19 amino acids other than lysine may be preferably used. The amino acids may each be an L-body or a D-body; an L-body is preferred (in Examples, the amino acid residues forming the peptides are all L-bodies).

The degree of percent identity to the amino acid sequence of SEQ ID NO: 92 or the amino acid sequences of (1) to (9) can be determined as described above. The degree of percent identity may be preferably 92% or more, more preferably 94% or more, even more preferably 95% or more, and particularly 97% or more (that is, an amino acid sequence having only one variation of an amino acid residue selected from the group consisting of a lysine residue, an aspartic acid residue, a glutamic acid residue, a 2-amino suberic acid residue, and a diaminopropionic acid residue with respect to the amino acid sequence of SEQ ID NO: 92).

When the affinity substance is a peptide, the amino group and the carboxy group at the ends of the peptide may be protected. Examples of a protecting group for the N-terminal amino group include an alkylcarbonyl group (an acyl group) (e.g., an acetyl group, a propoxy group, and a butoxycarbonyl group such as a tert-butoxycarbonyl group), an alkyloxycarbonyl group (e.g., a fluorenylmethoxycarbonyl group), an aryloxycarbonyl group, and an arylalkyl(aralkyl) oxycarbonyl group (e.g., a benzyloxycarbonyl group). The protecting group for the N-terminal amino group is preferably an acetyl group. Examples of a protecting group for the C-terminal carboxy group include a group capable of forming an ester or an amide. Examples of the group capable of forming an ester or an amide include an alkyloxy group (e.g., methyloxy, ethyloxy, propyloxy, butyloxy, pentyloxy, and hexyloxy), an aryloxy group (e.g., phenyloxy and naphthyloxy), an aralkyloxy group (e.g., benzyloxy), and an amino group. The protecting group for the C-terminal carboxy group is preferably an amino group. When the affinity substance is a peptide comprising two or more cysteine residues, a disulfide bond may be formed through thiol residues at the side chains of the cysteine residues.

1-3. Linker (L)

In Formula (I), L is a cleavable linker which is a divalent group comprising a cleavable portion.

The cleavable linker represented by L is a divalent group comprising a cleavable portion. The cleavable portion is a site cleavable by specific treatment under a condition incapable of causing denaturation or decomposition (e.g., cleavage of an amide bond) of proteins (a mild condition). Consequently, it can be said that the cleavable portion is a site cleavable by specific cleaving treatment under a mild condition (a bond other than the amide bond). Examples of such specific treatment include (a) treatment with one or more substances selected from the group consisting of an acidic substance, a basic substance, a reducing agent, an oxidizing agent, and an enzyme, (b) treatment by physicochemical stimulus selected from the group consisting of light, and (c) being left when a cleavable linker comprising a self-decomposing cleavable portion is used. Such a cleavable linker and a cleavage condition thereof are a common technical knowledge in the field concerned (e.g., G. Leriche, L. Chisholm, A. Wagner, Bioorganic & Medicinal Chemistry 20, 571 (2012); Feng P. et al., Journal of American Chemical Society. 132, 1500 (2010); Bessodes M. et al., Journal of Controlled Release, 99, 423 (2004); DeSimone, J. M., Journal of American Chemical Society 132, 17928 (2010); Thompson, D. H., Journal of Controlled Release, 91, 187 (2003); and Schoenmarks, R. G., Journal of Controlled Release, 95, 291 (2004)). Examples of such a cleavable portion include a disulfide residue, an acetal residue, a ketal residue, an ester residue, a carbamoyl residue, an alkoxyalkyl residue, an imine residue, a tertiary alkyloxy carbamate residue (e.g., a tert-butyloxy carbamate residue), a silane residue, a hydrazone-containing residue (e.g., a hydrazone residue, an acyl hydrazone residue, and a bisaryl hydrazone residue), a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue.

The aromatic ring group having an electron-withdrawing group preferably has an aromatic ring group selected from the group consisting of aryl, aralkyl, an aromatic heterocyclic group, and alkyl having an aromatic heterocyclic group and more preferably aralkyl and alkyl having an aromatic heterocyclic group. The electron-withdrawing group preferably binds to the 2-position of the ring. The aromatic ring-containing residue having an electron-withdrawing group is even more preferably aralkyl having an electron-withdrawing group at the 2-position thereof (e.g., benzyl), for example. Examples of the electron-withdrawing group include a halogen atom, halogen atom-substituted alkyl (e.g., trifluoromethyl), a boronic acid residue, mesyl, tosyl, triflate, nitro, cyano, a phenyl group, and a keto group (e.g., acyl).

The definitions, examples, and preferred examples of groups such as alkyl, acyl (that is, alkylcarbonyl), alkoxy (that is, alkyloxy), aryl, and aralkyl found as terms such as a prefix and a suffix in relation to the names of the residues as the cleavable portion are similar to those described below.

Examples of the ester residue include normal ester residues comprising carbon atoms and oxygen atoms [e.g., alkyl esters (e.g., tertiary alkyl oxycarbonyls such as tert-butyl oxycarbonyl), aryl eaters (e.g., phenacyl ester, 2-(diphenylphosphino)benzoate)], a glycosyl ester residue, an orthoester residue, ester residues comprising a sulfur atom and an oxygen atom (e.g., thioester residues such as an α-thiophenyl ester residue and an alkyl thioester residue), ester residues comprising a phosphorous atom and an oxygen atom (e.g., a phosphodiester residue and a phosphotriester residue), and an activated ester residue (e.g., an N-hydroxysuccinimide residue).

Examples of the sulfone-containing residue include a sulfone residue and a quinolinyl benzenesulfonate residue.

The silane residue is preferably a silane residue having a group selected from the group consisting of alkyl, aryl, aralkyl, and alkoxy. Examples of such a silane residue include a dialkyldialkoxysilane residue (e.g., dimethyldialkoxysilane and diethyldialkoxysilane) and a diaryldialkoxysilane residue (e.g., diphenyldialkoxysilane).

The alkoxyalkyl (that is, alkyloxyalkyl) residue is a group obtained by combining alkyloxy and alkyl described below (the definitions, examples, and preferred examples of alkyloxy and alkyl are similar to those described below); examples thereof include, but are not limited to, a methoxymethyl residue, an ethoxymethyl residue, a methoxyethyl residue, and an ethoxyethyl residue.

The unsaturated bond-containing chain residue is a residue comprising an unsaturated bond portion consisting of only carbon atoms (e.g., vinyl (ethenyl) as the minimum unit having a carbon-carbon double bond or acetylenyl (ethynyl) as the minimum unit having a carbon-carbon triple bond) or a residue comprising an unsaturated bond portion consisting of a carbon atom and a hetero atom (e.g., a nitrogen atom, a sulfur atom and an oxygen atom) (e.g., aldehyde and cyano). Examples of the unsaturated bond-containing chain residue include a vinyl ether residue, a cyanoethyl residue, an ethylene residue, and a malondialdehyde residue.

Examples of the acidic substance (also referred to as an electrophilic reagent) include inorganic acidic substances such as hydrochloric acid, sulfuric acid, and nitric acid; and organic acidic substances such as formic acid, acetic acid, 4-(2-hydroxyethyl)-1-piperazinepropane sulfonic acid, 3-morpholinopropane sulfonic acid, sodium dihydrogenphosphate, citric acid, dodecyl sulfuric acid, N-dodecanoyl sarcosine acid, and trifluoroacetic acid.

Examples of a site cleavable with the acidic substance include an alkyloxyarylalkyl residue, a tertiary alkyloxy carbamate residue, an acetal residue, a silane residue, an imine residue, a vinyl ether residue, a β-thiopropionate residue, a trityl residue, a hydrazone residue, an aconityl residue, an orthoester residue, a carbamoyl residue, a 2-(diphenylphosphino)benzoate residue.

Examples of the basic substance (also referred to as a nucleophilic reagent) include inorganic basic substances such as sodium hydroxide, potassium hydroxide, sodium acetate, potassium acetate, and ammonium acetate; and organic basis substances such as triethylamine and N,N'-diisopropylamine. Examples of a site cleavable with the basic substance include a silane residue, a cyanoethyl residue, a sulfone residue, an ethylene residue, a glycosyl disuccinate residue, an α-thiophenyl ester residue, an unsaturated vinylsulfide residue, a malondialdehyde residue, an acylhydrazone residue, and an alkyl thioester residue.

Examples of the reducing agent include cysteine, dithiothreitol, reduced glutathione, hydroxyamine, and β-mercaptoethanol. Examples of a site cleavable with the reducing agent include a disulfide residue, an alkoxyalkyl residue, and an azo residue.

Examples of the oxidizing agent include sodium periodate and oxidized glutathione. Examples of a site cleavable with the oxidizing agent include a vicinal diol residue and a selenium residue.

Examples of the enzyme include trypsin, papain, TEV, thrombin, cathepsin B, cathepsin D, cathepsin K, caspase, protease, matrix metalloproteinase, lipase, endoglycosidase, and PNGase F. Examples of a site cleavable with the enzyme include an ester residue, a phosphodiester residue, and a glycosyl residue.

Examples of a site cleavable with light include a 2-nitrobenzyl residue, a phenacyl ester residue, an 8-quinoline benzenesulfonate residue, a coumarin residue, a phosphotriester residue, a bisarylhydrazone residue, and a bimane dithiopropionic acid residue.

Examples of the self-decomposing cleavable portion include an activated ester residue (e.g., an N-hydroxysuccinimide residue).

More specifically, the cleavable portion may correspond to any one chemical structure selected from the group consisting of the following:

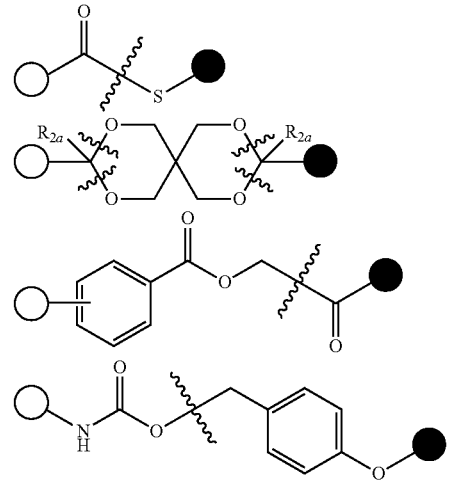

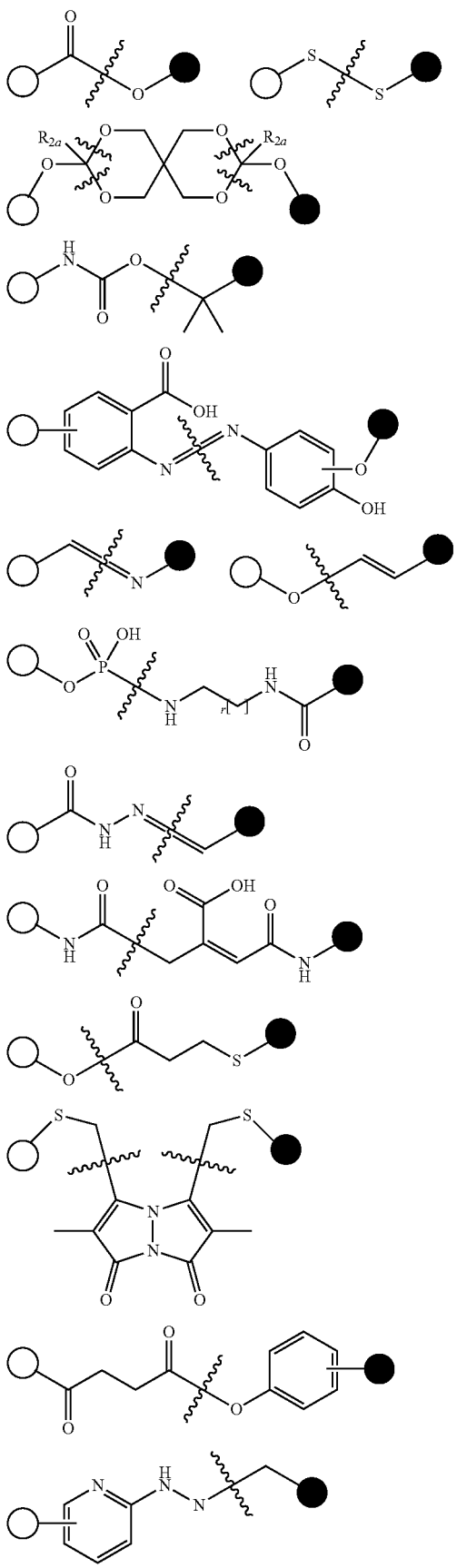
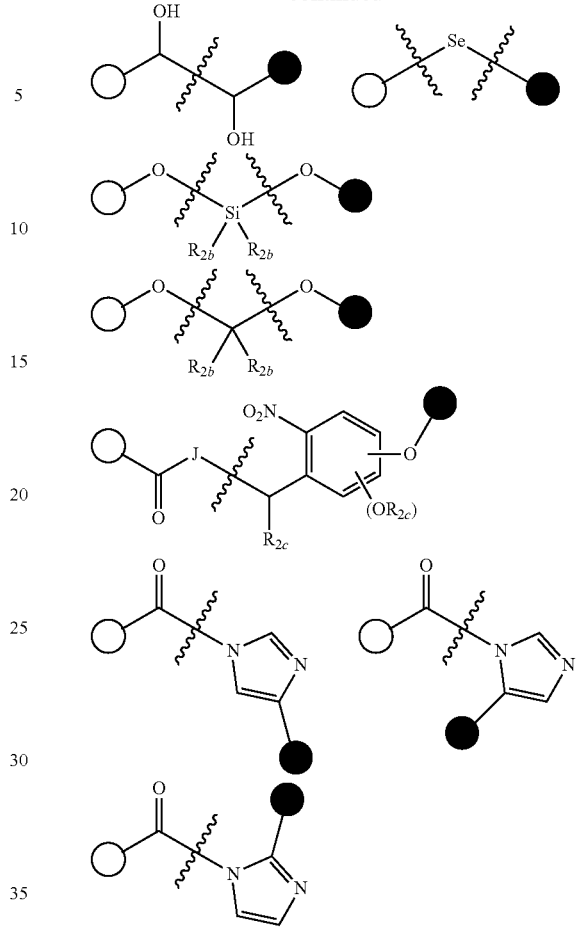

where a wavy line orthogonal to a bond indicates a cleavage site;
a plurality of $R_{2a}$, a plurality of $R_{2b}$, and a plurality of $R_{2c}$ are the same or different from each other, and are selected from a hydrogen atom or the group consisting of the following substituents;
J is —$CH_2$—, —O—, or —S—;
r is any integer of 1 to 4;
a symbol of "white circle" indicates a bond to A (or La described below), and a symbol of "black circle" indicates a bond to B (or Lb described below); and when a chemical structure is asymmetrical with respect to the cleavage site, a symbol of "black circle" may indicate a bond to A (or La described below), and a symbol of "white circle" may indicate a bond to B (or Lb described below).

J is —$CH_2$—, —O—, or —S—. J is preferably —$CH_2$— or —O— and more preferably —$CH_2$—.

The letter r is any integer of 1 to 4, preferably any integer of 1 to 3, and more preferably 1 or 2.

In an embodiment, the cleavable linker may be (i) a cleavable linker which is a divalent group comprising a cleavable portion having the ability to form a bioorthogonal functional group on a reactive group side by cleavage or (ii) a cleavable linker which is a divalent group comprising a cleavable portion having no ability to form a bioorthogonal functional group on a reactive group side by cleavage.

Examples of the cleavable portion of (i) include a disulfide residue, an ester residue, an acetal residue, a ketal residue, an imine residue, and a vicinal diol residue.

More specifically, the cleavable portion of (i) may correspond to any one chemical structure selected from the group consisting of the following:

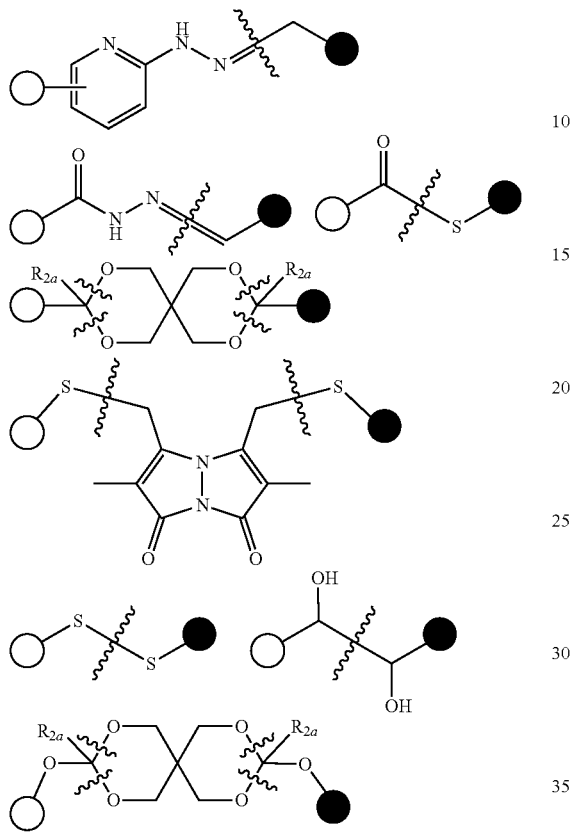

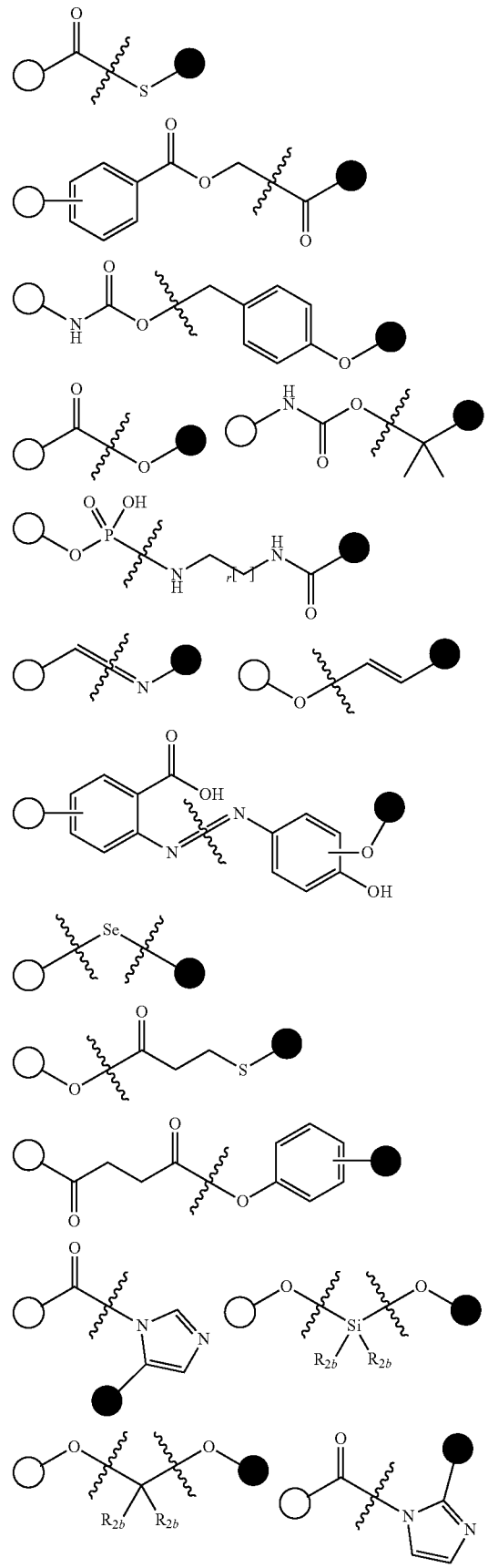

where a wavy line orthogonal to a bond indicates a cleavage site;

a plurality of $R_{2a}$ are the same or different from each other, and are selected from a hydrogen atom or the group consisting of the following substituents;

a symbol of "white circle" indicates a bond to A (or La described below), and a symbol of "black circle" indicates a bond to B (or Lb described below); and when a chemical structure is asymmetrical with respect to the cleavage site, a symbol of "black circle" may indicate a bond to A (or La described below), and a symbol of "white circle" may indicate a bond to B (or Lb described below), for example.

Examples of the cleavable portion of (ii) include an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue.

More specifically, examples of the cleavable portion of (ii) may correspond to any one chemical structure selected from the group consisting of the following:

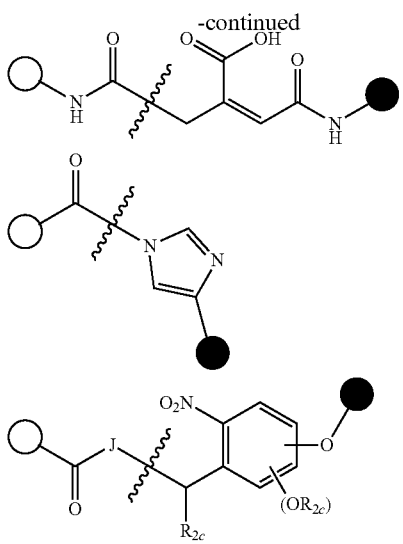

where a wavy line orthogonal to a bond indicates a cleavage site;

a plurality of $R_{2b}$, a plurality of $R_{2c}$, J, and r are selected from a hydrogen atom or the group consisting of the following substituents;

a symbol of "white circle" indicates a bond to A (or La described below), and a symbol of "black circle" indicates a bond to B (or Lb described below); and when a chemical structure is asymmetrical with respect to the cleavage site, a symbol of "black circle" may indicate a bond to A (or La described below), and a symbol of "white circle" may indicate a bond to B (or Lb described below), for example.

In a specific embodiment, the cleavable linker (L) may be represented by any one of the following Formulae (L1) to (L3):

La-C-Lb (L1)

La-C (L2)

C-Lb (L3)

wherein
La and Lb are each a divalent group; and
C is a cleavable portion.

Examples of the divalent group include a divalent hydrocarbon group optionally having a substituent, a divalent heterocyclic group optionally having a substituent, —C(=O)—, —NR$_a$— (R$_a$ indicates a hydrogen atom or a substituent), —O—, —S—, —C(=S)—, and a group consisting of a combination of two or more (e.g., two to eight, preferably two to six, and more preferably two to four) of these.

The divalent hydrocarbon group is a linear, branched, or cyclic divalent hydrocarbon group and preferably a linear or branched divalent hydrocarbon group. Examples of the divalent hydrocarbon group include alkylene, alkenylene, alkynylene, and arylene.

Alkylene is preferably $C_{1-12}$ alkylene, more preferably $C_{1-6}$ alkylene, and particularly preferably $C_{1-4}$ alkylene.

The number of carbon atoms does not comprise the number of carbon atoms of the substituent. Alkylene may be any of linear, branched, or cyclic one and is preferably linear alkylene. Examples of such alkylene include methylene, ethylene, propylene, butylene, pentylene, and hexylene.

Alkenylene is preferably $C_{2-12}$ alkenylene, more preferably $C_{2-6}$ alkenylene, and particularly preferably $C_{2-4}$ alkenylene. The number of carbon atoms does not comprise the number of carbon atoms of the substituent. Alkenylene may be any of linear, branched, or cyclic one and is preferably linear alkenylene. Examples of such alkenylene include ethylenylene, propynylene, butenylene, pentenylene, and hexenylene.

Alkynylene is preferably $C_{2-12}$ alkynylene, more preferably $C_{2-6}$ alkynylene, and particularly preferably $C_{2-4}$ alkynylene. The number of carbon atoms does not comprise the number of carbon atoms of the substituent. Alkynylene may be any of linear, branched, or cyclic one and is preferably linear alkynylene. Examples of such alkynylene include ethynylene, propynylene, butynylene, pentynylene, and hexynylene.

Arylene is preferably $C_{6-24}$ arylene, more preferably $C_{6-18}$ arylene, even more preferably $C_{6-14}$ arylene, and still even more preferably $C_{6-10}$ arylene. The number of carbon atoms does not comprise the number of carbon atoms of the substituent. Examples of arylene include phenylene, naphthylene, and anthracenylene.

The divalent heterocyclic group is a divalent aromatic heterocyclic group or a divalent nonaromatic heterocyclic group. The divalent heterocyclic group preferably comprises, as a hetero atom forming a heterocycle, one or more selected from the group consisting of an oxygen atom, a sulfur atom, a nitrogen atom, a phosphorous atom, a boron atom, and a silicon atom and more preferably comprises one or more selected from the group consisting of an oxygen atom, a sulfur atom, and a nitrogen atom.

The divalent aromatic heterocyclic group is preferably a $C_{3-21}$ divalent aromatic heterocyclic group, more preferably a $C_{3-15}$ divalent aromatic heterocyclic group, even more preferably a $C_{3-9}$ divalent aromatic heterocyclic group, and still even more preferably a $C_{3-6}$ divalent aromatic heterocyclic group. The number of carbon atoms does not comprise the number of carbon atoms of the substituent. More specifically, examples of the divalent aromatic heterocyclic group include pyrenediyl, pyrroldiyl, furandiyl, thiophenediyl, pyridinediyl, pyridazinediyl, pyrimidinediyl, pyrazinediyl, triazinediyl, pyrrolinediyl, piperidinediyl, triazolediyl, purinediyl, anthraquinonediyl, carbazolediyl, fluorenediyl, quinolinediyl, and isoquinolinediyl.

The divalent nonaromatic heterocyclic group is preferably a $C_{3-21}$ nonaromatic heterocyclic group, more preferably a $C_{3-15}$ nonaromatic heterocyclic group, even more preferably a $C_{3-9}$ nonaromatic heterocyclic group, and still even more preferably a $C_{3-6}$ nonaromatic heterocyclic group. The number of carbon atoms does not comprise the number of carbon atoms of the substituent. More specifically, examples of the divalent nonaromatic heterocyclic group include pyrrolidinonediyl, pyrrolinedionediyl, oxiranediyl, aziridinediyl, azetidinediyl, oxetanediyl, thietanediyl, pyrrolidinediyl, dihydrofurandiyl, tetrahydrofurandiyl, dioxolanediyl, tetrahydrothiophenediyl, imidazolidinediyl, oxazolidinediyl, piperidinediyl, dihydropyrandiyl, tetrahydropyrandiyl, tetrahydrothiopyrandiyl, morpholinediyl, thiomorpholinediyl, piperazinediyl, dihydrooxazinediyl, tetrahydrooxazinediyl, dihydropyrimidinediyl, and tetrahydropyrimidinediyl.

The divalent group represented by La and Lb may have e.g., one to five, preferably one to three, and more preferably one or two substituents. Such a substituent is similar to the substituent represented by $R_a$ and $R_b$. Examples of such a substituent include the following:

(i) a halogen atom;
(ii) a monovalent hydrocarbon group;
(iii) aralkyl;
(iv) a monovalent heterocyclic group;
(v) $R_c$—O—, $R_c$—C(=O)—, $R_c$—O—C(=O)—, and $R_c$—C(=O)—O— wherein $R_c$ indicates a hydrogen atom or a monovalent hydrocarbon group;
(vi) $NR_dR_e$—, $NR_dR_e$—C(=O)—, $NR_dR_e$—C(=O)—O—, and $R_d$—C(=O)—$NR_e$— wherein $R_d$ and $R_e$ are the same or different from each other, and each indicate a hydrogen atom or a monovalent hydrocarbon group; and
(vii) a nitro group, a sulfuric acid group, a sulfonic acid group, a cyano group, and a carboxy group.

Examples of the halogen atom include a fluorine atom, a chlorine atom, a bromine atom, and an iodine atom.

Examples of the monovalent hydrocarbon group include a monovalent chain hydrocarbon group, a monovalent alicyclic hydrocarbon group, and a monovalent aromatic hydrocarbon group.

The monovalent chain hydrocarbon group means a hydrocarbon group comprising only a chain structure and does not comprise any cyclic structure in a main chain thereof. Note that the chain structure may be linear or branched. Examples of the monovalent chain hydrocarbon group include alkyl, alkenyl, and alkynyl. Alkyl, alkenyl, and alkynyl may be linear or branched.

Alkyl is preferably $C_{1-12}$ alkyl, more preferably $C_{1-6}$ alkyl, and even more preferably $C_{1-4}$ alkyl. The number of carbon atoms does not comprise the number of carbon atoms of a substituent. Examples of $C_{1-12}$ alkyl include methyl, ethyl, n-propyl, i-propyl, n-butyl, s-butyl, isobutyl, t-butyl, pentyl, hexyl, heptyl, octyl, nonyl, decyl, and dodecyl.

Alkenyl is preferably $C_{2-12}$ alkenyl, more preferably $C_{2-6}$ alkenyl, and even more preferably $C_{2-4}$ alkenyl. The number of carbon atoms does not comprise the number of carbon atoms of a substituent. Examples of $C_{2-12}$ alkenyl include vinyl, propenyl, and n-butenyl.

Alkynyl is preferably $C_{2-12}$ alkynyl, more preferably $C_{2-6}$ alkynyl, and even more preferably $C_{2-4}$ alkynyl. The number of carbon atoms does not comprise the number of carbon atoms of a substituent. Examples of $C_{2-12}$ alkynyl include ethynyl, propynyl, and n-butynyl.

The monovalent chain hydrocarbon group is preferably alkyl.

The monovalent alicyclic hydrocarbon group means a hydrocarbon group comprising only alicyclic hydrocarbon as a cyclic structure and not comprising any aromatic ring, in which alicyclic hydrocarbon may be monocyclic or polycyclic. Note that the monovalent alicyclic hydrocarbon group is not necessarily required to comprise only an alicyclic hydrocarbon but may comprise a chain structure in part thereof. Examples of the monovalent alicyclic hydrocarbon group include cycloalkyl, cycloalkenyl, and cycloalkynyl, which may be monocyclic or polycyclic.

Cycloalkyl is preferably $C_{3-12}$ cycloalkyl, more preferably $C_{3-6}$ cycloalkyl, and even more preferably $C_{5-6}$ cycloalkyl. The number of carbon atoms does not comprise the number of carbon atoms of a substituent. Examples of $C_{3-12}$ cycloalkyl include cyclopropyl, cyclobutyl, cyclopentyl, and cyclohexyl.

Cycloalkenyl is preferably $C_{3-12}$ cycloalkenyl, more preferably $C_{3-6}$ cycloalkenyl, and even more preferably $C_{5-6}$ cycloalkenyl. The number of carbon atoms does not comprise the number of carbon atoms of a substituent. Examples of $C_{3-12}$ cycloalkenyl include cyclopropenyl, cyclobutenyl, cyclopentenyl, and cyclohexenyl.

Cycloalkynyl is preferably $C_{3-12}$ cycloalkynyl, more preferably $C_{3-6}$ cycloalkynyl, and even more preferably $C_{5-6}$ cycloalkynyl. The number of carbon atoms does not comprise the number of carbon atoms of a substituent. Examples of $C_{3-12}$ cycloalkynyl include cyclopropynyl, cyclobutynyl, cyclopentynyl, and cyclohexynyl.

The monovalent alicyclic hydrocarbon group is preferably cycloalkyl.

The monovalent aromatic hydrocarbon group means a hydrocarbon group comprising an aromatic ring structure. Note that the monovalent aromatic hydrocarbon group is not necessarily required to comprise only an aromatic ring and may comprise a chain structure or alicyclic hydrocarbon in part thereof, in which the aromatic ring may be monocyclic or polycyclic. The monovalent aromatic hydrocarbon group is preferably $C_{6-12}$ aryl, more preferably $C_{6-10}$ aryl, and even more preferably $C_6$ aryl. The number of carbon atoms does not comprise the number of carbon atoms of a substituent. Examples of $C_{6-12}$ aryl include phenyl and naphthyl.

The monovalent aromatic hydrocarbon group is preferably phenyl.

Among these, the monovalent hydrocarbon group is preferably alkyl, cycloalkyl, and aryl and more preferably alkyl.

Aralkyl refers to arylalkyl. The definitions, examples, and preferred examples of aryl and alkyl in arylalkyl are as described above. Aralkyl is preferably $C_{3-15}$ aralkyl. Examples of such aralkyl include benzoyl, phenethyl, naphthylmethyl, and naphthylethyl.

The monovalent heterocyclic group refers to a group obtained by removing one hydrogen atom from a heterocycle of a heterocyclic compound. The monovalent heterocyclic group is a monovalent aromatic heterocyclic group or a monovalent nonaromatic heterocyclic group. The monovalent heterocyclic group preferably comprises one or more selected from the group consisting of an oxygen atom, a sulfur atom, a nitrogen atom, a phosphorus atom, a boron atom, and a silicon atom and more preferably comprises one or more selected from the group consisting of an oxygen atom, a sulfur atom, and a nitrogen atom as a hetero atom contained in the heterocyclic group.

The monovalent aromatic heterocyclic group is preferably a $C_{3-15}$ aromatic heterocyclic group, more preferably a $C_{3-9}$ aromatic heterocyclic group, and even more preferably a $C_{3-6}$ aromatic heterocyclic group. The number of carbon atoms does not comprise the number of carbon atoms of a substituent. Examples of the monovalent aromatic heterocyclic group include pyrenyl, pyrrolyl, furanyl, thiophenyl, pyridinyl, pyridazinyl, pyrimidinyl, pyrazinyl, triazinyl, pyrrolinyl, piperidinyl, triazonyl, purinyl, carbazolyl, fluorenyl, quinolinyl, and isoquinolinyl.

The monovalent nonaromatic heterocyclic group is preferably a $C_{3-15}$ nonaromatic heterocyclic group, more preferably a $C_{3-9}$ nonaromatic heterocyclic group, and even more preferably a $C_{3-6}$ nonaromatic heterocyclic group. The number of carbon atoms does not comprise the number of carbon atoms of a substituent. Examples of the monovalent nonaromatic heterocyclic group include oxiranyl, aziridinyl, azetidinyl, oxetanyl, thietanyl, pyrrolidinyl, dihydrofuranyl, tetrahydrofuranyl, dioxolanyl, tetrahydrothiophenyl, imidazolidinyl, oxazolidinyl, piperidinyl, dihydropyranyl, tetrahydropyranyl, tetrahydrothiopyranyl, morpholinyl, thiomorpholinyl, piperazinyl, dihydrooxazinyl, tetrahydrooxazinyl, dihydropyrimidinyl, and tetrahydropyrimidinyl.

Among these, the monovalent heterocyclic group is preferably a five-membered or six-membered heterocyclic group.

The substituent may be preferably the following:
(i') a halogen atom;
(ii') a $C_{1-12}$ alkyl, phenyl, or naphthyl;
(iii') $C_{3-15}$ aralkyl;
(iv') a five-membered or six-membered heterocyclic group;
(v') $R_e$-O—, $R_c$—C(=O)—, $R_c$—O—C(=O)—, or $R_c$—C(=O)—O— wherein $R_e$ indicates a hydrogen atom or $C_{1-12}$ alkyl;
(vi') $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and each indicate a hydrogen atom or $C_{1-12}$ alkyl; or
(vii') the same groups as those enumerated in (vii).

The substituent may be more preferably the following:
(i") a halogen atom;
(ii") $C_{1-12}$ alkyl;
(iii") $R_e$-O—, $R_c$—C(=O)—, $R_c$—O—C(=O)—, or $R_c$—C(=O)—O— wherein $R_e$ indicates a hydrogen atom or $C_{1-12}$ alkyl;
(iv") $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and each indicate a hydrogen atom or $C_{1-12}$ alkyl; or
(v") the same groups as those enumerated in (vii).

The substituent may be even more preferably the following:
(i''') a halogen atom;
(ii''') $C_{1-6}$ alkyl;
(iii''') $R_e$-O—, $R_c$—C(=O)—, $R_c$—O—C(=O)—, or $R_c$—C(=O)—O— wherein $R_e$ indicates a hydrogen atom or $C_{1-6}$ alkyl;
(iv''') $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and each indicate a hydrogen atom or $C_{1-6}$ alkyl; or
(v''') the same groups as those enumerated in (vii).

The substituent may be particularly preferably the following:
(i'''') a halogen atom;
(ii'''') $C_4$ alkyl;
(iii'''') $R_e$—O—, $R_c$—C(=O)—, $R_c$—O—C(=O)—, or $R_c$—C(=O)—O— wherein $R_e$ indicates a hydrogen atom or $C_{1-4}$ alkyl;
(iv'''') $NR_dR_e$—, $NR_dR_e$—C(=O)—, $NR_dR_e$—C(=O)—O—, or $R_d$—C(=O)—$NR_e$— wherein $R_d$ and $R_e$ are the same or different from each other, and each indicate a hydrogen atom or $C_{1-4}$ alkyl; or
(v'''') the same groups as those enumerated in (vii).

In a specific embodiment, La and Lb may be represented by the following (La') and (Lb'), respectively.

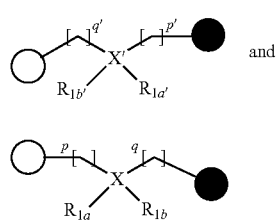

wherein
p and p' are the same or different from each other, and are each any integer of 0 to 10;
q and q' are the same or different from each other, and are each any integer of 0 to 10;
X and X' are the same or different from each other, and are each a carbon atom, a nitrogen atom, or a single bond; wherein when X is a nitrogen atom, $R_{1b}$ is absent; when X' is a nitrogen atom, $R_{1b'}$ is absent; when X is a single bond, $R_{1a}$ and $R_{1b}$ are absent; and when X' is a single bond, $R_{1a'}$ and $R_{1b'}$ are absent; and
$R_{1a}$, $R_{1b}$, $R_{1a'}$, and $R_{1b'}$ are the same or different from each other, and are each a hydrogen atom or selected from the group consisting of the substituents described above.

The letters p and p' are the same or different from each other, and are each any integer of 0 to 10, preferably an integer of 0 to 8, more preferably an integer of 0 to 6, even more preferably an integer of 0 to 4, and particularly preferably 0, 1, or 2. The letters p and p' are preferably the same.

The letters q and q' are the same or different from each other, and are each any integer of 0 to 10, preferably an integer of 0 to 8, more preferably an integer of 0 to 6, even more preferably an integer of 0 to 4, and particularly preferably 0, 1, or 2. The letters q and q' are preferably the same.

X and X' are the same or different from each other, and are each a carbon atom, a nitrogen atom, or a single bond and preferably a carbon atom or a single bond. X and X' are preferably the same.

$R_{1a}$, $R_{1b}$, $R_{1a'}$, and $R_{1b'}$ are the same or different from each other, and are selected from a hydrogen atom or the group consisting of the following substituents. The definition, examples, and preferred examples of the substituent are as described above. $R_{1a}$, $R_{1b}$, $R_{1a}'$, and $R_{1b'}$ are each preferably a hydrogen atom.

1-4. (a) Divalent Group Comprising Bioorthogonal Functional Group or (b) Divalent Group Comprising No Bioorthogonal Functional Group (B)

In Formula (I), B is (a) a divalent group comprising a bioorthogonal functional group or (b) a divalent group comprising no bioorthogonal functional group.

The bioorthogonal functional group refers to a group that does not react with biological components (e.g., amino acids, nucleic acids, lipids, sugars, and phosphoric acids) or has a low reaction rate to biological components but selectively reacts with components other than biological components. The bioorthogonal functional group is well known in the technical field concerned (e.g., refer to Sharpless K. B. et al., Angew. Chem. Int. Ed. 40, 2004 (2015); Bertozzi C. R. et al., Science 291, 2357 (2001); Bertozzi C. R. et al., Nature Chemical Biology 1, 13 (2005)).

When the target of the affinity substance is the soluble protein, the bioorthogonal functional group is a bioorthogonal functional group to proteins. The bioorthogonal functional group to proteins is a group that does not react with side chains of 20 natural amino acid residues forming proteins and reacts with certain functional groups. The 20 natural amino acid residues forming proteins are alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), valine (V), aspartic acid (D), glutamic acid (E), arginine (R), histidine (H), and lysine (L). Among these 20 natural amino acid residues, glycine, which has no side chain (that is, has a hydrogen atom), and alanine, isoleucine, leucine, phenylalanine, and valine, which have a hydrocarbon group as a side chain (that is, comprise no hetero atom selected from the group consisting of a sulfur atom, a nitrogen atom, and an oxygen atom in their side chains) are inactive to normal reactions. Consequently, the bioorthogonal functional group to proteins is a functional group incapable of reacting with, in addition to the side chains of these amino acids having side chains inactive to normal reactions, side chains of asparagine, glutamine, methionine, proline, serine, threonine, tryptophan, tyrosine, aspartic acid, glutamic acid, arginine, histidine, and lysin.

Examples of such a bioorthogonal functional group incapable of reacting with proteins include an azide residue, an aldehyde residue, a thiol residue, an alkene residue (in other words, only required to have a vinylene (ethenylene) portion as the minimum unit having a carbon-carbon double bond; hereinafter the same), an alkyne residue (in other words, only required to have an ethynylene portion as the minimum unit having a carbon-carbon triple bond; hereinafter the same), a halogen residue, a tetrazine residue, a nitron residue, a hydroxyamine residue, a nitrile residue, a hydrazine residue, a ketone residue, a boric acid residue, a cyanobenzothiazole residue, an allyl residue, a phosphine residue, a maleimide residue, a disulfide residue, a thioester residue, an α-halocarbonyl residue (e.g., a carbonyl residue having a fluorine atom, a chlorine atom, a bromine atom, or an iodine atom at the α-position thereof; hereinafter the same), an isonitrile residue, a sydnone residue, and a selenium residue. The proteins include proteins capable of comprising a free thiol (cysteine) (e.g., proteins other than antibodies) and proteins incapable of comprising a free thiol (e.g., antibodies). In the proteins incapable of comprising a free thiol, a thiol functions as a bioorthogonal functional group. Consequently, when the soluble protein as the target of the affinity substance is a protein incapable of comprising a free thiol (e.g., an antibody), the bioorthogonal functional group preferably comprises a thiol. When the soluble protein is a protein capable of comprising a free thiol (e.g., a protein other than antibodies), the bioorthogonal functional group preferably comprises no thiol. The divalent group may comprise one or two or more (e.g., two, three, or four) bioorthogonal functional groups; the divalent group may preferably comprise one bioorthogonal functional group.

In an embodiment, the divalent group comprising a bioorthogonal function group may be a divalent group comprising a bioorthogonal functional group selected from the group consisting of an azide residue, an aldehyde group, a thiol residue, an alkyne residue, an alkene residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue in a main chain thereof.

In another embodiment, the divalent group comprising a bioorthogonal function group may be a divalent group comprising a bioorthogonal function group selected from the group consisting of an azide residue, an aldehyde residue, a thiol residue, an alkyne residue, an alkene residue, a halogen residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue in a side chain thereof.

More specifically, the bioorthogonal functional group may correspond to any one chemical structure selected from the group consisting of the following:

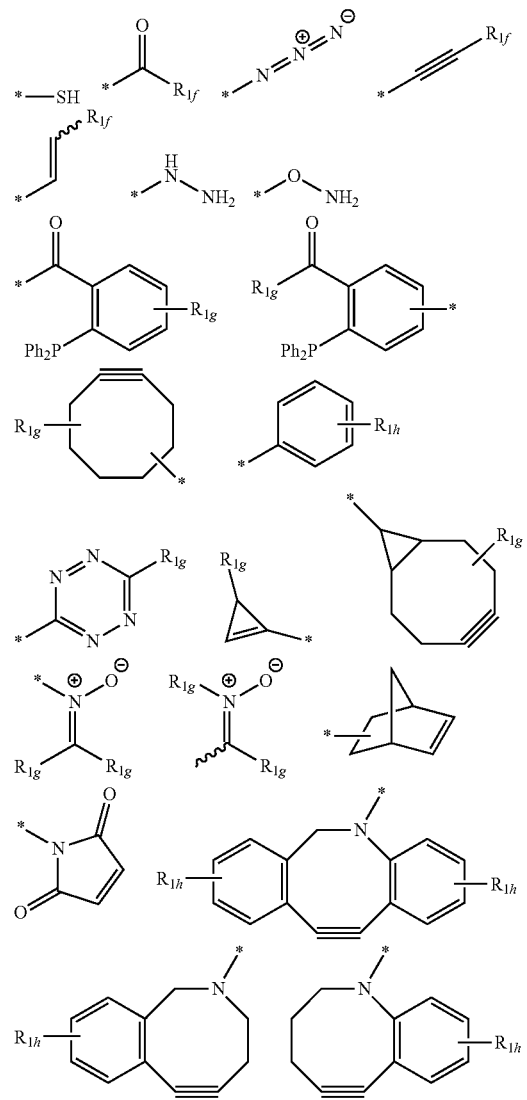

wherein
$R_{1f}$, one or a plurality of Rig, and one or a plurality of $R_{1h}$ are the same or different from each other, and are each an atom or a group selected from the group consisting of (i) to (vii) or an electron-withdrawing group; and
• is a bond.

Examples of the electron-withdrawing group include those described above, in which preferred are a halogen atom, a boronic acid residue, mesyl, tosyl, and triflate.

In an embodiment, B may be (a) the divalent group comprising a bioorthogonal functional group. The divalent group comprises one or a plurality of bioorthogonal functional groups; the number is e.g., one to five, preferably one to three, more preferably one or two, and even more preferably one. When the divalent group comprises a plurality of bioorthogonal functional groups, the bioorthogonal functional groups may be homogeneous or heterogeneous and are preferably homogeneous in view of employing a simple structure and the like.

In a specific embodiment, B may be (a1) a divalent group comprising a bioorthogonal functional group in a main chain thereof. The divalent group comprising a bioorthogonal functional group in a main chain thereof is a bioorthogonal functional group itself selected from the group consisting of an azide residue, an aldehyde group, a thiol residue, an alkyne residue, an alkene residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue as a divalent group or a group in which the divalent group described above is coupled to either one end or both ends of such a divalent orthogonal functional group. The definition, examples, and preferred examples of the divalent group to be coupled are similar to those of the divalent group described above.

In another specific embodiment, B may be (a2) a divalent group comprising a bioorthogonal functional group in a side chain thereof. The divalent group comprising a bioorthogonal functional group in a side chain thereof is a divalent group substituted with a bioorthogonal functional group selected from the group consisting of an azide residue, an aldehyde residue, a thiol residue, an alkyne residue, an alkene residue, a halogen residue, a tetrazine residue, a nitron residue, a hydroxyamine residue, a nitrile residue, a hydrazine residue, a ketone residue, a boronic acid residue, a cyanobenzothiazole residue, an allyl residue, a phosphine residue, a maleimide residue, a disulfide residue, an α-halocarbonyl residue, an isonitrile residue, a sydnone residue, and a selenium residue or a group comprising the bioorthogonal functional group. The definition, examples, and preferred examples of the divalent group to be substituted are similar to those of the divalent group described above.

In another embodiment, B may be (b) the divalent group comprising no bioorthogonal functional group. Such a divalent group may be optionally substituted alkylene, optionally substituted cycloalkylene, optionally substituted aryl, an optionally substituted divalent heterocyclic group, —NR$_a$— (R$_a$ indicates a hydrogen atom or a substituent), —O—, or a group consisting of a combination of two or more (e.g., two to eight, preferably two to six, and more preferably two to four) of these. The substituent in the case of being optionally substituted and the substituent of R$_a$ are each a substituent other than the bioorthogonal functional group. Examples of such a substituent include alkyl, cycloalkyl, aralkyl, a monovalent heterocyclic group, hydroxy, amino, alkyloxy (alkoxy), cycloalkyloxy, and aralkyloxy. The number of such a substituent is e.g., one to five, preferably one to three, more preferably one or two, and even more preferably one.

As to the substituent other than the bioorthogonal functional group, the definitions, examples, and preferred examples of alkyl, cycloalkyl, aralkyl, and the monovalent heterocyclic group are as described above.

As to the substituent other than the bioorthogonal functional group, the definitions, examples, and preferred examples of alkyl in alkyloxy (alkoxy), cycloalkyl in cycloalkyloxy, and aralkyl in aralkyloxy are as described above. More specifically, examples of alkyloxy include methyloxy, ethyloxy, propyloxy (e.g., n-propyloxy and iso-propyloxy), butyloxy (e.g., n-butyloxy, iso-butyloxy, sec-butyloxy, and tert-butyloxy), pentyloxy (e.g., n-pentyloxy), and hexyloxy (e.g., n-hexyloxy). Examples of cycloalkyloxy include cyclopropyloxy, cyclobutyloxy, cyclopentyloxy, and cyclohexyloxy. Examples of aralkyloxy include benzoyloxy, phenethyloxy, naphthylmethyloxy, and naphthylethyloxy.

The divalent group comprising no bioorthogonal functional group may be a group highly inactive to reactions. Consequently, such a divalent group may be a group comprising only carbon atoms and hydrogen atoms. Such a divalent group is alkylene, cycloalkylene, or aryl, and a combination of two or more (e.g., two or three) of these. When the divalent group comprising no bioorthogonal functional group is a group highly inactive to reactions, such a divalent group may have a substituent selected from the group consisting of alkylene, cycloalkylene, and aryl as a substituent highly inactive to reactions. The number of the substituent highly inactive to reactions is e.g., one to five, preferably one to three, and more preferably one or two.

In a specific embodiment, B may be represented by the following Formula (B-1):

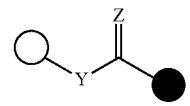

(B-1)

wherein
Y is —NH—, —O—, —CH$_2$—, or the following Formula (B-2):

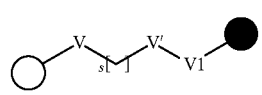

(B-2)

wherein
V and V' are the same or different from each other, and are each —NH—, —O—, —CH$_2$—, or a single bond;
V1 is (a) a divalent group comprising a bioorthogonal functional group or (b) a divalent group comprising no bioorthogonal functional group;
s is any integer of 0 to 10;
a symbol of "white circle" and a symbol of "black circle" in Formula (B-2) have the same orientation as a symbol of "white circle" and a symbol of "black circle" in Formula (B-1), respectively;
Z is an oxygen atom, a sulfur atom, or a hydrogen atom (when Z is a hydrogen atom, —C(=Z)— indicates —CH$_2$—.); and
a symbol of "white circle" in Formula (B-1) indicates a bond to an L-side portion, and a symbol of "black circle" indicates a bond to an R-side portion.
Y is —NH—, —O—, —CH$_2$—, or the group represented by Formula (B-2). In view of simplifying the structure and the like, Y may be —NH—, —O—, or —CH$_2$—. Alternatively, in view of designing a carbon atom-based structure and the like, Y may be —CH$_2$— or the group represented by Formula (B-2)
Z is an oxygen atom, a sulfur atom, or a hydrogen atom and is preferably an oxygen atom or a sulfur atom.
V and V' are each —NH—, —O—, —CH$_2$—, or a single bond and preferably —CH$_2$— or a single bond.
V1 is (a) a divalent group comprising a bioorthogonal functional group or (b) a divalent group comprising no bioorthogonal functional group. Such a divalent group is similar to that described above.

The divalent group in V1 is preferably an optionally substituted divalent hydrocarbon group or an optionally substituted divalent heterocyclic group. The definition, examples, and preferred examples of the divalent hydrocarbon group are similar to those described above; for V1, preferred are alkylene, alkenylene, alkynylene, cycloalkylene, cycloalkenylene, cycloalkynylene, and arylene. In the case of not being substituted at the portion comprising the bioorthogonal functional group, for example, preferred are alkenylene, alkynylene, cycloalkenylene, and cycloalkynylene. On the other hand, in the case of being substituted at the position comprising the bioorthogonal functional group, preferred are alkylene, cycloalkylene, and arylene. Examples and preferred examples of these groups are as described above. The definition, examples, and preferred examples of the divalent heterocyclic group are similar to those described above; for V1, a five-membered or six-membered heterocyclic group is preferred. Examples and preferred examples of the five-membered or six-membered heterocyclic group are similar to those described above. The definition, examples, and preferred examples of the substituent are as described above. V1 may have e.g., one to five, more preferably one to three, even more preferably one or two, and still even more preferably one of (a) the bioorthogonal functional group(s). When the divalent group comprises a plurality of bioorthogonal functional groups, the bioorthogonal functional groups may be homogeneous or heterogeneous. In view employing a simple structure, improving reactivity, and the like, they are preferably homogeneous. In view of ensuring a differentiated reaction and the like, they are preferably heterogeneous. V1 may also have one to five, preferably one to three, and more preferably one or two (of b) the substituents.

The letter s is any integer of 0 to 10, preferably an integer of 0 to 8, more preferably an integer of 0 to 6, even more preferably an integer of 0 to 4, and particularly preferably 0, 1, or 2.

In a specific embodiment, V1 may be a divalent group having, as a side chain, a group represented by the following Formula (B-3):

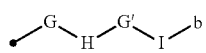

(B-3)

wherein
G and G' are the same or different from each other, and are each —NH—, —O—, —CH$_2$—, a single bond, or a group represented by the following Formula (B-4):

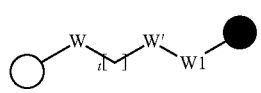

(B-4)

wherein
W and W' are the same or different from each other, and are each —NH—, —O—, —CH$_2$—, or a single bond;
W1 is a (a) a divalent group comprising a bioorthogonal functional group or (b) a divalent group comprising no bioorthogonal functional group;

t is any integer of 0 to 10; and
a symbol of "white circle" in Formula (B-4) indicates a bond to a direction of a bonding arm (.) in Formula (B-3), and a symbol of "black circle" indicates a bond to a direction of a b side;
H is —CH$_2$—, —C=O—, —C=S—, —NH—, or a single bond;
I is a divalent hydrocarbon, a divalent heterocycle, or a single bond; and
b is any one group represented by the following:

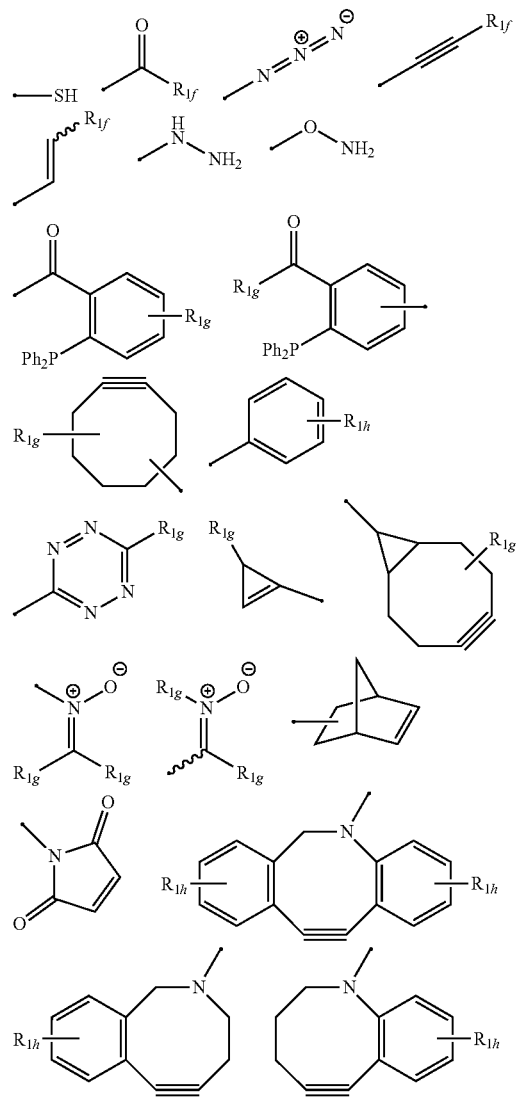

wherein
R$_{1f}$, one or a plurality of R$_{1g}$, and one or a plurality of R$_{1h}$ are the same or different from each other, and are each an atom or a group selected from the group consisting of (i) to (vii) or an electron-withdrawing group; and
• is a bond. Such a divalent group is a divalent hydrocarbon group or a divalent heterocyclic group, preferably an optionally substituted divalent hydrocarbon group, more preferably alkylene, alkenylene, alkynylene, cycloalkylene, cycloalkenylene, cycloalkynylene, or arylene, even more preferably alkylene, cycloalkylene, or arylene, and particularly preferably alkylene. Examples and preferred examples of these groups are as described above. These groups may be substituted with a substituent other than the side chain. The number of such a substituent is one to five, preferably one to three, and more preferably one or two. Examples and preferred examples of the substituent are as described above.

G and G' are the same or different from each other, and are each —NH—, —O—, —CH$_2$—, a single bond, or the group represented by Formula (B-4). In view of simplifying the structure and the like, G and G' may be —NH—, —O—, —CH$_2$—, or a single bond. Alternatively, in view of designing a carbon atom-based structure and the like, G and G' may be —CH$_2$—, a single bond, or the group represented by Formula (B-4).

H is —CH$_2$—, —C=O—, —C=S—, —NH—, or a single bond. H is preferably —CH$_2$— or a single bond.

I is a divalent hydrocarbon group, a divalent heterocycle, or a single bond. The divalent hydrocarbon group and the divalent heterocycle may be substituted or are not necessarily substituted with a substituent. The definitions, examples, and preferred examples of the divalent hydrocarbon group, the divalent heterocycle, and the substituent are similar to those described above for V1.

W and W' are the same or different from each other, and are each —NH—, —O—, —CH$_2$—, or a single bond and preferably —CH$_2$— or a single bond.

W1 is (a) a divalent group comprising a bioorthogonal functional group or (b) a divalent group comprising no bioorthogonal functional group. Such a divalent group is similar to that described above.

The letter t is any integer of 0 to 10, preferably an integer of 0 to 8, more preferably an integer of 0 to 6, even more preferably an integer of 0 to 4, and particularly preferably 0, 1, or 2.

1-5. Reactive Group (R)

In Formula (I), R is a reactive group to the soluble protein. Such a reactive group is a common technical knowledge in the technical field concerned.

The reactive group is a group homogeneous or heterogeneous with respect to the bioorthogonal functional group.

When B is (a) the divalent group comprising a bioorthogonal functional group, for example, the reactive group may be a group heterogeneous with respect to the bioorthogonal functional group. This is because the reactive group being a group homogeneous with respect to the bioorthogonal functional group does not ensure the reaction specificity of the reactive group to the soluble protein. In addition, this is because the bioorthogonal functional group in the first place is a group incapable of reacting with the side chains of the 20 natural amino acid residues forming the soluble protein.

More specifically, among the 20 natural amino acids described above forming proteins, glycine, which has no side chain, and alanine, isoleucine, leucine, phenylalanine, and valine, which have a hydrocarbon group as a side chain, are inactive to normal reactions. Consequently, the reactive group to the protein is a group capable of reacting with side chains of any one or two or more (e.g., two, three, or four) of 14 amino acids consisting of asparagine, glutamine, methionine, proline, serine, threonine, tryptophan, tyrosine, aspartic acid, glutamic acid, arginine, histidine, and lysin. The compound represented by Formula (I) may comprise one or two or more (e.g., two, three, or four) reactive groups in accordance with conditions such as the amino acid composition of the protein; the compound represented by Formula (I) may preferably comprise one reactive group.

The reactive group is preferably a group capable of reacting with a side chain of any one amino acid among the 14 amino acids described above forming proteins.

The reactive group is more preferably a reactive group specific to a side chain of any one amino acid of lysine, tyrosine, tryptophan, and cysteine.

The reactive group is even more preferably a reactive group specific to a side chain of any one amino acid of lysine, tyrosine, and tryptophan.

When the protein is human IgG such as human IgG1, the reactive group is preferably a reactive group specific to a side chain of lysin or tyrosine.

The reactive group specific to a side chain of a lysine residue is a group capable of specifically reacting with an amino group (NH$_2$) present in the side chain of the lysing residue; examples thereof include an activated ester residue (e.g., an N-hydroxysuccinimide residue), a vinylsulfone residue, a sulfonylchloride residue, an isocyanate residue, an isothiocyanate residue, an aldehyde residue, a 1,4,7,10-tetraazacyclododecane-1,4,7,10-tetraacetic acid residue, a 2-imino-2-methoxyethyl residue, and a diazonium terephthalic acid residue.

Examples of a linking portion formed by a reaction between the reactive group specific to a side chain of a lysine residue and the amino group (NH$_2$) present in the side chain of the lysine residue include an amide residue, a urea residue, a pyridine residue, a carbamate residue, and a sulfonamide residue.

More specifically, the reactive group specific to a side chain of a lysine residue may correspond to any one chemical structure selected from the group consisting of the following:

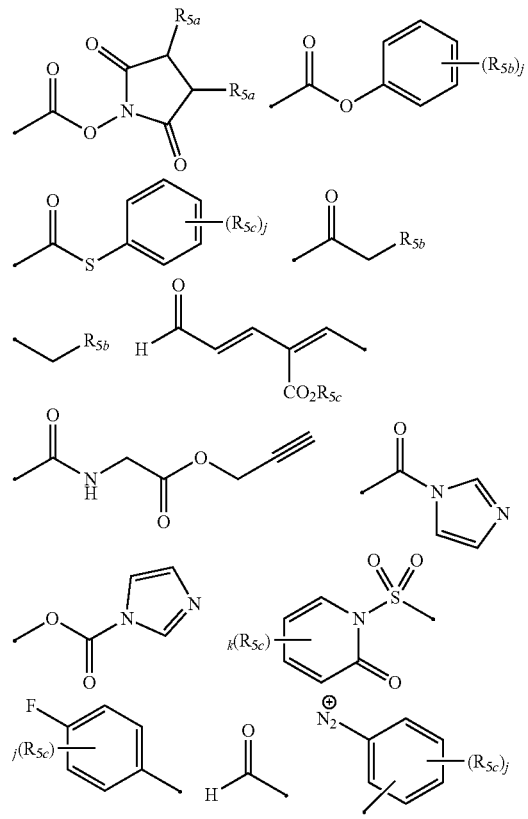

-continued

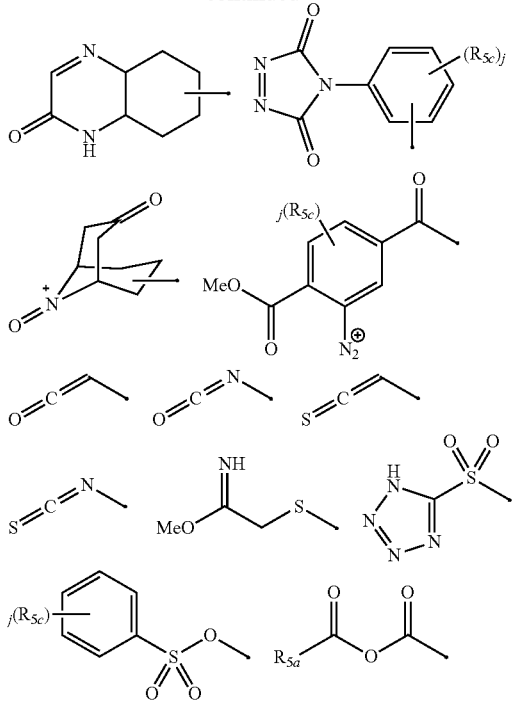

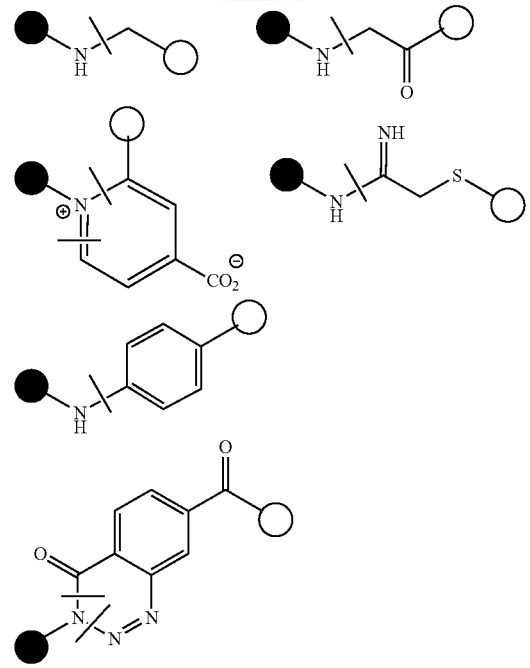

where
R$_{5a}$ and R$_{5c}$ are each a hydrogen atom or the substituent described above;
R$_{5b}$ is an electron-withdrawing group;
j is any integer of 1 to 5; and
k is any integer of 1 to 4.

R$_{5a}$ and R$_{5c}$ are each a hydrogen atom or the substituent described above. The definition, examples, and preferred examples of the substituent are similar to those described above.

R$_{5b}$ is an electron-withdrawing group. Examples of the electron-withdrawing group include those described above; preferred are a halogen atom, a boronic acid residue, mesyl, tosyl, and triflate.

The letter j is any integer of 1 to 5, preferably an integer of 1 to 3, and more preferably 1 or 2.

The letter k is any integer of 1 to 4, preferably an integer of 1 to 3, and more preferably 1 or 2.

The linking portion formed by a reaction between the chemical structure as the reactive group specific to a side chain of a lysine residue and the amino group (NH$_2$) present in the side chain of the lysine residue may correspond to any one chemical structure selected from the group consisting of the following:

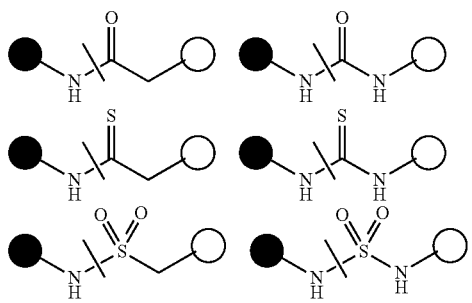

where a symbol of "black circle" indicates a bond to a T-side portion, and a symbol of "white circle" indicates a bond to a B-side portion; and a straight line orthogonal to a bond indicates a bond formed by the reaction.

The reactive group specific to a side chain of a tyrosine residue is a group capable of specifically reacting with an atom at the ortho-position of a phenolic hydroxy group (OH) present in the side chain of the tyrosine residue; examples thereof include a diazonium residue, a diazodicarboxylate residue, and a 2,3-dihydro-1H-pyrazin-6-one residue.

More specifically, the reactive group specific to a side chain of a tyrosine residue may correspond to any one chemical structure selected from the group consisting of the following:

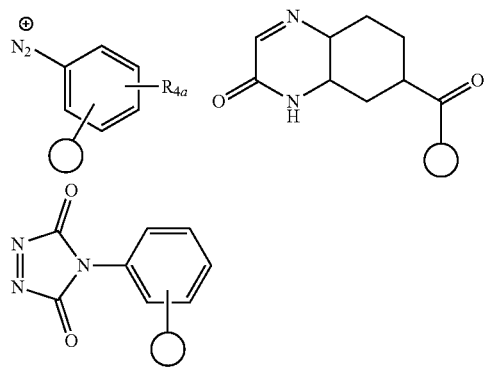

where R$_{4a}$ is a hydrogen atom or the substituent described above; and a symbol of "white circle" indicates a bond to B.

R$_{4a}$ is a hydrogen atom or the substituent described above. The definition, examples, and preferred examples of the substituent are similar to those described above.

A linking portion formed by a reaction between the chemical structure as the reactive group specific to a side chain of a tyrosine residue and the atom at the ortho-position of the phenolic hydroxy group (OH) present in the side chain of the tyrosine residue may correspond to any one chemical structure selected from the group consisting of the following:

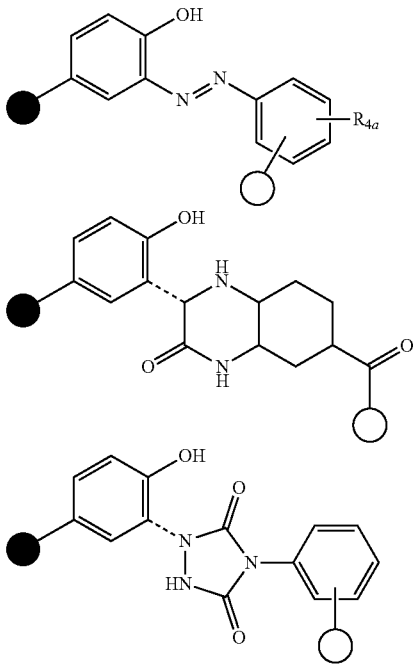

where $R_{4a}$ is a hydrogen atom or the substituent described above; and a symbol of "black circle" indicates a bond to T, and a symbol of "white circle" indicates a bond to B.

$R_{4a}$ is a hydrogen atom or the substituent described above. The definition, examples, and preferred examples of the substituent are similar to those described above.

The reactive group specific to a side chain of a tryptophan residue is a group capable of specifically reacting with a ring-forming atom at the 3-position of an indole group present in the side chain of the tryptophan residue; examples thereof include a 9-azabicyclo[3.3.1]nonan-3-one-N-oxyl residue.

More specifically, the reactive group specific to a side chain of a tryptophan residue may correspond to any one chemical structure selected from the group consisting of the following:

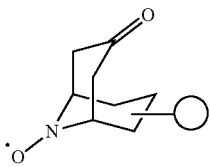

where a symbol of "white circle" indicates a bond to B.

A linking portion formed by a reaction between the chemical structure as the reactive group specific to a side chain of a tryptophan residue and the ring-forming atom at the 3-position of the indole group present in the side chain of the tryptophan residue may correspond to any one chemical structure selected from the group consisting of the following:

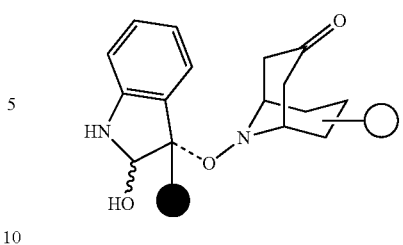

where a symbol of "black circle" indicates a bond to T, and a symbol of "white circle" indicates a bond to B.

The reactive group may be particularly preferably the reactive group specific to a side chain of lysine.

1-6. Partial Structure "L-B"

1-6-1. Length of Main Chain in Partial Structure "L-B" Linking A and R

In Formula (I), the length of a main chain linking A (the affinity substance) and R (the reactive group) (a linear chain portion in L-B) can be designed as appropriate in accordance with various factors such as the types of the soluble protein and the affinity substance and the relation between a target site of the affinity substance in the soluble protein and the positions and the number of the specific amino acid residues in the target region (e.g., the specific position) described above with which R reacts to be bound. The compound represented by Formula (I) can covalently bind to the soluble protein by causing the affinity substance to associate with the soluble protein and then causing the reactive group covalently binding to the affinity substance through L-B to react with a group in a side chain of the specific amino acid residue (e.g., an amino group in a side chain of a lysine residue) present near the target site. In this process, when another specific amino acid residue of the specific amino acid residue is not present in a region near the specific amino acid residue with which R reacts to be bound, a region near the target site, and a region between the specific amino acid residue and the target site, the reactive group can regioselectively bind to the specific amino acid residue without strictly controlling the length of the main chain. It is understood that even when another specific amino acid residue of the specific amino acid residue is present in such regions, the reactive group can regioselectively bind to the specific amino acid residue by controlling the length of the main chain.

The length of the main chain linking A and R, which can vary in accordance with factors such as the types of the soluble protein and the affinity substance thereto and the relation of the positions and the number of the specific amino acid residues in the target site in the soluble protein, may be about 5 angstroms or larger, preferably about 7.5 angstroms or larger, and more preferably about 10.5 angstroms or larger. The length of the main chain may be e.g., about 30 angstroms or smaller, preferably about 23 angstroms or smaller, and more preferably about 16.5 angstroms or smaller. More specifically, the length of the main chain may be e.g., about 5.0 to 30 angstroms, preferably about 7.5 to 23 angstroms, and more preferably about 10.5 to 16.5 angstroms.

By the way, it is a common technical knowledge in the technical field concerned that the relation of interatomic length (distance) is as the table below. Consequently, a person skilled in the art can design the main chain having atoms of the number corresponding to the length (angstrom) of the main chain described above as appropriate with reference to the interatomic lengths in the table below.

TABLE 1

Relationship of length (distance) between carbon atoms present at both end in straight-chain alkylenes

| | Length (Angstrom) |
|---|---|
| straight-chain alkylenes | |
| $CH_2$—$CH_2$ (C2) | about 1.5 |
| $CH_2$—$CH_2$—$CH_2$ (C3) | about 3.0 |
| C4 | about 4.5 |
| C5 | about 6.0 |
| C6 | about 7.5 |
| C7 | about 9.0 |
| C8 | about 10.5 |
| C9 | about 12.0 |
| C10 | about 13.5 |
| straight-chain alkenylene | |
| CH=CH | about 1.5 |

More specifically, the length of the main chain linking A and R can also be defined as the number of atoms forming the main chain (except hydrogen atoms and substituents). The number of atoms forming the main chain may be e.g., four (about 5.0 angstroms) or larger, preferably six (about 7.5 angstroms), and more preferably eight (about 10.5 angstroms) or larger. The number of atoms of the main chain may be e.g., 20 (about 30 angstroms) or smaller, preferably 16 (about 23 angstroms) or smaller, and more preferably 12 (about 16.5 angstroms) or smaller. More specifically, the number of atoms of the main chain may be e.g., 4 to 20, preferably 6 to 16, and more preferably 8 to 12.

When the main chain is a structure comprising no cyclic structure, the number of atoms of the main chain can be determined by counting the number of atoms in a chain structure.

On the other hand, when the main chain is a structure comprising a cyclic structure, the number of atoms of the main chain and the length described above do not necessarily correspond to each other, and the length that can be defined by the number of atoms of the main chain tends to be shorter than the length described above. Even in such a case, in view of defining the length of the main chain, the number of atoms of the main chain can be counted for convenience' sake. Specifically, the number of atoms of the main chain in such a case can be determined by counting the number of atoms of the shortest route connecting two bonds in the cyclic structure in addition to the number of atoms in a chain structure comprising no divalent cyclic structure in the main chain (e.g., refer to the (a) to (d) thick routes below).

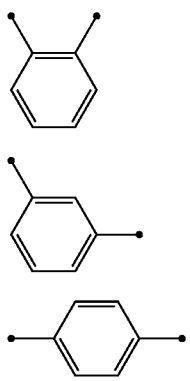

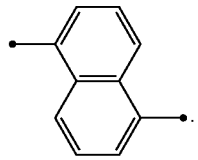

is a bond.

In the case of (a), the shortest route is the thick route, and thus the number of atoms in the divalent cyclic structure counted as the number of atoms of the main chain is two.

In the case of (b), the shortest route is the thick route, and thus the number of atoms in the divalent cyclic structure counted as the number of atoms of the main chain is three.

In the case of (c), any route is the shortest route (the same distance), and thus the number of atoms in the divalent cyclic structure counted as the number of atoms of the main chain is four.

In the case of (d), the route of the condensed site is the shortest route, and thus the number of atoms in the divalent cyclic structure counted as the number of atoms of the main chain is four.

A linking portion of A and R represented by L-B (except a side chain) may be preferably a chain structure comprising no divalent cyclic structure. In this case, L and B can be designed as appropriate such that a linking chain portion of A and R represented by L-B comprises no divalent cyclic group.

1-6-2. Specific Structure of Partial Structure "L-B"

In Formula (I), L and B are structures that can be correlated with each other. Consequently, in Formula (I), L and B can be defined as a partial structure represented by "L-B."

In an embodiment, the cleavable linker may be (i) a cleavable linker which is a divalent group comprising a cleavable portion having the ability to form a bioorthogonal functional group on a reactive group side by cleavage or (ii) a cleavable linker which is a divalent group comprising a cleavable portion having no ability to form a bioorthogonal functional group on a reactive group side by cleavage.

In a specific embodiment, when L is the cleavable linker (i), B is (a) the divalent group comprising a bioorthogonal functional group or (b) the divalent group comprising no bioorthogonal functional group.

When L is the cleavable linker (i), B is preferably (a) the divalent group comprising a bioorthogonal functional group. In this case, the bioorthogonal functional group formed in (i) may be homogeneous or heterogeneous with respect to the bioorthogonal functional group in (a). In view of employing a simpler structure and/or improving reactivity to a single functional substance and the like, the bioorthogonal functional group formed in (i) may be homogeneous with respect to the bioorthogonal functional group in (a). On the other hand, in view of ensuring reactivity differentiated for two or more functional substances, non-use of a partial bioorthogonal functional group in the reaction, and the like, the bioorthogonal functional group formed in (i) may be heterogeneous with respect to the bioorthogonal functional group in (a).

Alternatively, when L is the cleavable linker (i), B may be (b) the divalent group comprising no bioorthogonal functional group. In this case, the compound represented by Formula (I) or a salt thereof has a simpler structure and is thus easily synthesized.

In another specific embodiment, when L is the cleavable linker (ii), B is (a) the divalent group comprising a bioorthogonal functional group.

In a specific embodiment, the partial structure represented by L-B preferably comprises no peptide portion.

In this case, the soluble protein of the present invention (e.g., an antibody drug conjugate) obtained using the compound of the present invention has the advantage that it cannot comprise any peptide portion that can have immunogenicity as a linker.

In a specific embodiment, the partial structure represented by "L-B" may have a symmetrical structure [e.g., a cis form (that is, Z) and a trans form (that is E)] based on an atom present at the central position of the main chain linking A and R (the linear chain portion in L-B) (e.g., when the number of atoms forming the main chain is an odd number) or a bonding site present at the central position of the main chain (e.g., when the number of atoms forming the main chain is an even number). The bonding site present at the central position can be designed as the cleavable portion of the cleavable linker described above, for example. When the partial structure represented by "L-B" has a symmetrical structure, the partial structure represented by "L-B" can be easily synthesized. By reacting the same divalent groups each having a functional group capable of reacting to form a cleavable portion at one end (e.g., chain divalent groups each having an SH group at one end) with each other, a symmetrical structure comprising a cleavable portion at the central position of the main chain (chain divalent group-S-S-chain divalent group) can be achieved, for example.

Consequently, the partial structure represented by "L-B" may be a partial structure represented by "B2-L'-B1" (that is, L is a divalent group represented by B2-L', and B is B1). In this case, the compound represented by Formula (I) can be defined as a compound represented by the following Formula (I'):

A-B2-L'-B1-R    (I')

wherein
A and R are the same as those of Formula (I);
L' is a cleavable linker which is a divalent group comprising a cleavable portion;
B1 and B2 are the same or different from each other, and are each (a) a divalent group comprising a bioorthogonal functional group or (b) a divalent group comprising no bioorthogonal functional group; and
B1 and B2 may have a symmetrical structure with respect to L'.

B1 and B2 are the same or different from each other; the definitions, examples, and preferred examples thereof are similar to those of B.

In a specific embodiment, L' may be represented by any one of the following Formulae (L1') to (L3'):

La'-C'-Lb'    (L1')

La'-C'    (L2')

C'-Lb'    (L3')

wherein
La' and Lb' are each a divalent group; and
C' is a cleavable portion.

The definitions, examples, and preferred examples of the divalent groups represented by La' and Lb' are similar to those of the divalent groups represented by La and Lb, respectively.

The definition, examples, and preferred examples of the cleavable portion represented by C' are similar to those of the cleavable portion represented by C.

In another specific embodiment, a structural unit represented by L-B may be represented by the following Formula (LB'):

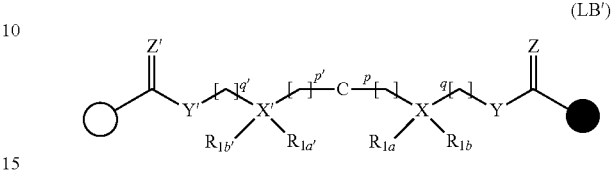

(LB')

wherein
the definitions, examples, and preferred examples of C, p, p', q, q', X, X', $R_{1a}$, $R_{1a'}$, $R_{1b}$, $R_{1b'}$, Y, Y', Z, and Z' are similar to those described above; and
a symbol of "white circle" indicates a bond to A, and a symbol of "black circle" indicates a bond to R.

Consequently, Formula (I) can be defined as the following Formula (I''):

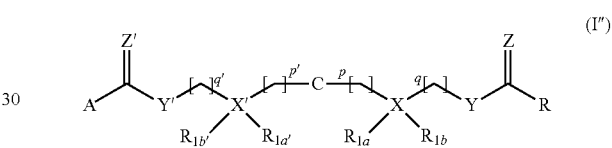

(I'')

wherein
the definitions, examples, and preferred examples of A, R, C, p, p', q, q', X, X', $R_{1a}$, $R_{1b}$, $R_{1a'}$, $R_{1b'}$, Y, Y', Z, and Z' are similar to those described above.

In Formulae (LB') and (I''), the length from C (a carbon atom) in C=Z to C (a carbon atom) in C=Z' is similar to the length of the main chain linking A and R. In these formulae, the length from C in C=Z to C in C=Z' can also be defined as the number of atoms forming a linking chain of a partial structure linking C in C=Z and C in C=Z' (except hydrogen atoms and substituents). The number of atoms is similar to the number of atoms forming the main chain linking A and R. The linking chain of a partial structure linking C in C=Z and C in C=Z' (except hydrogen atoms and substituents) may comprise no cyclic structure or comprise a cyclic structure and preferably comprises no cyclic structure. The linking chain (except hydrogen atoms and substituents) may preferably comprise no peptide portion.

1-8. Method of Production

The compound comprising an affinity substance to a soluble protein, a cleavable portion, and a reactive group or a salt thereof can be prepared as appropriate. The compound comprising an affinity substance to a soluble protein, a cleavable portion, and a reactive group is represented by Formula (I), preferably Formula (I'), and more preferably Formula (I'').

For the affinity substance, one having any functional group can be selected as appropriate. Consequently, using a reactive group capable of reacting with the functional group, the affinity substance is reacted with a structural unit represented by L-B-R or a structural unit represented by R-L-B-R (the two reactive groups are the same or different from each other), whereby a structural unit represented by A-L-B-R can be prepared. Such a reaction can be conducted in an appropriate reaction system such as an organic solvent system or an aqueous solution system at an appropriate temperature (e.g., about 15° C. to 200° C.), for example. The reaction system may comprise an appropriate catalyst. The reaction time is e.g., 1 minute to 20 hours, preferably 10 minutes to 15 hours, more preferably 20 minutes to 10 hours, and even more preferably 30 minutes to 8 hours.

In the reaction system, the molar ratio (Y/X) of the structural unit represented by L-B-R or the structural unit represented by R-L-B-R (Y) to the affinity substance (X) is not limited to a particular ratio because it varies in accordance with the types of the structural unit and the affinity substance, the number of sites in the affinity substance to be modified with the structural unit, and the like; it is e.g., 0.1 to 50, preferably 0.5 to 40, more preferably 1 to 35, even more preferably 2 to 25, and particularly preferably 3 to 15.

Determination of the formation of the soluble protein comprising an affinity substance to a soluble protein and a cleavable portion or a salt thereof, which depends on its specific raw materials and the molecular weight of a product, can be performed by electrophoresis, chromatography (e.g., gel permutation chromatography, ion-exchange chromatography, reversed phase column chromatography, and high-performance liquid chromatography (HPLC)), or mass spectrometry, for example, and preferably mass spectrometry. The soluble protein comprising an affinity substance to a soluble protein and a cleavable portion or a salt thereof can be purified as appropriate by any method such as chromatography (e.g., the pieces of chromatography described above and affinity chromatography).

1-9. Others

In the inventions described below [e.g., the inventions represented by Formulae (II) to (V), formulae having subordinate concepts thereof, and partial structural formulae (e.g., (L1) to (L3), (La'), (Lb'), and (B-1) to (B-4)], any symbols (e.g., A, L, B, and R), terms represented by the symbols, and the details thereof (e.g., the definitions, examples, and preferred examples) are common to those of the invention of the compound represented by Formula (I) or a salt thereof. Specific portions (e.g., a cleavable portion and a portion having the ability to form a bioorthogonal functional group on a reactive group side by cleavage), specific groups (e.g., a bioorthogonal functional group, a divalent group, an alkyl group, a substituent, and an electron-withdrawing group), and specific values that can define the inventions described below and any technical elements such as a salt (e.g., the definitions, examples, and preferred examples) can also be common to those described above. Consequently, these matters can be quoted as appropriate in the inventions described below without any special reference. Similarly, the technical elements of a specific invention described in the inventions described below can be quoted as appropriate as the technical elements of the present invention and other inventions.

2. Soluble Protein Comprising Affinity Substance to Soluble Protein and Cleavable Portion or Salt thereof 2-1. Outline The present invention provides a soluble protein comprising an affinity substance to a soluble protein and a cleavable portion represented by Formula (II) or a salt thereof.

$$A\text{-}L\text{-}B\text{-}R'\text{-}T \qquad (II)$$

wherein
A is an affinity substance to a soluble protein;
L is a cleavable linker which is a divalent group comprising a cleavable portion;
B is (a) a divalent group comprising a bioorthogonal functional group or (b) a divalent group comprising no bioorthogonal functional group; and
R' is a portion formed by a reaction between a soluble protein and a reactive group; and
T is a soluble protein.

2-2. Portion Formed by Reaction Between Soluble Protein and Reactive Group (R')

In the portion formed by a reaction between a soluble protein and a reactive group, the definitions, examples, and preferred examples of the soluble protein and the reactive group are as described above. The portion formed by a reaction between a soluble protein and a reactive group is a common technical knowledge in the technical field concerned and can be determined as appropriate in accordance with the types of the soluble protein and the reactive group.

The portion formed by a reaction between a soluble protein and a reactive group is preferably a portion formed by a reaction between a side chain of any one amino acid of 14 amino acids (asparagine, glutamine, methionine, proline, serine, threonine, tryptophan, tyrosine, aspartic acid, glutamic acid, arginine, histidine, and lysine) that can be contained in the soluble protein and a reactive group thereto.

The portion formed by a reaction between a soluble protein and a reactive group may be more preferably a portion formed by a reaction between a side chain of any one amino acid of lysine, tyrosine, tryptophan, and cysteine and a reactive group specific thereto.

The portion formed by a reaction between a soluble protein and a reactive group may be even more preferably a portion formed by a reaction between a side chain of any one amino acid of lysine, tyrosine, and tryptophan and a reactive group specific thereto. Examples of the portion formed by a reaction between a side chain of any one amino acid of lysine, tyrosine, and tryptophan and a reactive group specific thereto include the linking portion and/or chemical structure described in "1-5. Reactive Group (R)."

The portion formed by a reaction between a soluble protein and a reactive group may be still even more preferably a portion formed by a reaction between a side chain of lysine or tyrosine and a reactive group specific thereto (in particular, when the soluble protein is human IgG such as human IgG1). Examples of the portion formed by a reaction between a side chain of lysine or tyrosine and a reactive group specific thereto include the linking portion and/or chemical structure described in "1-5. Reactive Group (R)."

The portion formed by a reaction between a soluble protein and a reactive group may be particularly preferably a portion formed by a reaction between a side chain of lysine and a reactive group specific thereto.

2-3. Partial Structure "L-B"

The details of the partial structure "L-B" are as described in "1-6. Partial Structure "L-B"."

In a specific embodiment, the partial structure represented by "L-B" may be a partial structure represented by "B2-L'-B1" (that is, L is a divalent group represented by B2-L', and B is B1). In this case, the soluble protein comprising an affinity substance to a soluble protein and a cleavable portion represented by Formula (II) or a salt thereof can be represented by the following Formula (II'):

$$A\text{-}B2\text{-}L'\text{-}B1\text{-}R'\text{-}T \qquad (II')$$

wherein
  A, R', and T are the same as those of Formula (II);
  L' is a cleavable linker which is a divalent group comprising a cleavable portion;
  B1 and B2 are the same or different from each other, and are each (a) a divalent group comprising a bioorthogonal functional group or (b) a divalent group comprising no bioorthogonal functional group; and
  B1 and B2 may have a symmetrical structure with respect to L'.

In Formula (II'), L' may be represented by any one of Formulae (L1') to (L3') described above.

In another specific embodiment, a structural unit represented by L-B may be represented by the following Formula (LB'):

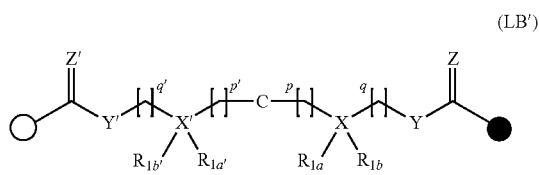

wherein
  the definitions, examples, and preferred examples of C, p, p', q, q', X, X', $R_{1a}$, $R_{1a'}$, $R_{1b}$, $R_{1b'}$, Y, Y', Z, and Z' are the same as those described above;
  a symbol of "white circle" indicates a bond to A, and a symbol of "black circle" indicates a bond to R'.

Consequently, Formula (II) can be defined as the following Formula (II"):

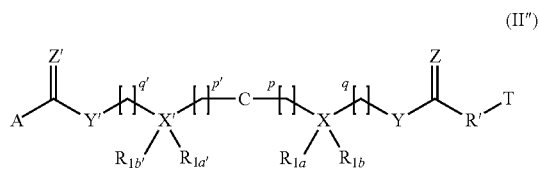

wherein
  the definitions, examples, and preferred examples of A, R', T, C, p, p', q, q', X, X', $R_{1a}$, $R_{1b}$, $R_{1a'}$, $R_{1b'}$, Y, Y', Z, and Z' are the same as those described above.

In Formulae (LB') and (II"), the length from C (a carbon atom) in C=Z to C (a carbon atom) in C=Z' is similar to the length of the main chain linking A and R described above. In these formulae, the length from C in C=Z to C in C=Z' can also be defined as the number of atoms forming a linking chain of a partial structure linking C in C=Z and C in C=Z' (except hydrogen atoms and substituents). The number of atoms is similar to the number of atoms forming the main chain linking A and R. The linking chain of a partial structure linking C in C=Z and C in C=Z' (except hydrogen atoms and substituents) may comprise no cyclic structure or comprise a cyclic structure and preferably comprises no cyclic structure. The linking chain (except hydrogen atoms and substituents) may preferably comprise no peptide portion.

2-4. Binding Site (Regioselectivity) of Partial Structure other than Soluble Protein that Soluble Protein Has A partial structure other than the soluble protein (e.g., A-L-B-R') can be regioselectively bound to the target region described above in the soluble protein (T).

In the present specification, "regioselective" or "regioselectivity" refers to a state in which even though a specific amino acid residue is not present locally at a specific region in the soluble protein, a certain structural unit capable of binding to the specific amino acid residue in the soluble protein is present locally at a specific region in the soluble protein. Consequently, expressions related to regioselectivity such as "regioselectively having," "regioselective binding," and "binding with regioselectivity" mean that the possession rate or the binding rate of a certain structural unit in the target region comprising one or more specific amino acid residues is higher at a significant level than the possession rate or the binding rate of the structural unit in the non-target region comprising a plurality of amino acid residues homogeneous with respect to the specific amino acid residues in the target region. Such regioselective binding or possession can be achieved by the present invention, which enables the certain structural unit to preferentially react with the specific amino acid residues in the target region in the soluble protein, not causing the certain structural unit to randomly react with the specific amino acid residues in the soluble protein.

Specifically, when T comprises one or more specific amino acid residues in a target region consisting of 1 to 50 continuous amino acid residues, and five or more of the specific amino acid residues in a non-target region other than the target region, the partial structure other than the soluble protein can be bound to the one or more specific amino acid residues contained in the target region with 30% or more regioselectivity. The definitions, examples, and preferred examples of the target region and regioselectivity are as described above.

2-5. Number of Partial Structure Other than Soluble Protein that Soluble Protein has The number of the partial structure other than the soluble protein possessed by the soluble protein (T) (e.g., A-L-B-R') can vary. When T is a multimeric protein comprising a plurality of monomeric proteins, for example, T can have the partial structure other than T in a plurality of corresponding target regions in the monomeric proteins. Consequently, T can have a plurality of partial structures other than T. Consequently, the structure represented by Formula (II), (II'), or (II") indicates that T may have one or a plurality of partial structures other than T. The number of partial structures other than T that T has can be adjusted by setting the type of the soluble protein and conditions such as a reaction ratio between the soluble protein and a structural unit to be introduced thereto as appropriate. Such a number, which varies depending on the type of the soluble protein, may be e.g., one to eight, preferably one to four, and more preferably one or two.

In a specific embodiment, when the soluble protein is a multimeric protein comprising a plurality of monomeric proteins, the soluble protein may possess a plurality of partial structures other than the soluble protein. The present invention can introduce a plurality of partial structures other than the soluble protein to the same target region of the monomeric proteins.

In a preferred embodiment, the soluble protein may be an antibody comprising a plurality of heavy chains. The definition, examples, and preferred examples of the antibody are as described above. The number of heavy chains varies depending on the type of the antibody. IgG, IgE, and IgD can have two heavy chains, for example. IgA can have two or four heavy chains. IgM can have eight heavy chains. The number of partial structures other than the antibody possessed by the antibody (the soluble protein) can be considered to have the same meaning as a drug antibody ratio (DAR). In the present invention, the number of partial structures other than the antibody possessed by the antibody may be one or two (preferably two) for IgG, IgE, and IgD, one to four (preferably four) for IgA, and one to eight (preferably eight) for IgM.

2.6 Method of Production

The present invention provides a method for producing a soluble protein comprising an affinity substance to a soluble protein and a cleavable portion or a salt thereof comprising the following:

(A1) reacting a compound comprising an affinity substance to a soluble protein, a cleavable portion, and a reactive group or a salt thereof with a soluble protein to form a soluble protein comprising an affinity substance to a soluble protein and a cleavable portion or a salt thereof.

The compound comprising an affinity substance to a soluble protein, a cleavable portion, and a reactive group is represented by Formula (I), preferably Formula (I'), and more preferably Formula (I"). The soluble protein comprising an affinity substance to a soluble protein and a cleavable portion is represented by Formula (II), preferably Formula (II'), and more preferably Formula (II").

The compound comprising an affinity substance to a soluble protein, a cleavable portion, and a reactive group or a salt thereof has the reactive group and can react with a soluble protein. Such a reaction can be conducted as appropriate under a condition incapable of causing denaturation or decomposition (e.g., cleavage of an amide bond) of proteins (a mild condition). Such a reaction can be conducted in an appropriate reaction system such as a buffer at room temperature (e.g., about 15° C. to 30° C.), for example. The pH of the buffer is e.g., 5 to 9, preferably 5.5 to 8.5, and more preferably 6.0 to 8.0. The buffer may comprise an appropriate catalyst. The reaction time is e.g., 1 minute to 20 hours, preferably 10 minutes to 15 hours, more preferably 20 minutes to 10 hours, and even more preferably 30 minutes to 8 hours. For the details of such a reaction, refer to G. J. L. Bernardes et al., Chem. Rev., 115, 2174 (2015); G. J. L. Bernardes et al., Chem. Asian. J., 4, 630 (2009); B. G. Davies et al., Nat. Commun., 5, 4740 (2014); A. Wagner et al., Bioconjugate. Chem., 25, 825 (2014), for example.

In the reaction system, the molar ratio (Y/X) of the compound comprising an affinity substance to a soluble protein, a cleavable portion, and a reactive group or a salt thereof (Y) to the soluble protein (X) is not limited to a particular ratio because it varies in accordance with the types of the compound comprising an affinity substance to a soluble protein, a cleavable portion, and a reactive group and the soluble protein (e.g., an antibody), the number of sites in the soluble protein to be modified with the compound comprising an affinity substance to a soluble protein, a cleavable portion, and a reactive group (e.g., DAR), and the like; it is e.g., 0.1 to 100, preferably 0.5 to 80, more preferably 1 to 70, even more preferably 2 to 50, and particularly preferably 3 to 30.

Determination of the formation of the soluble protein comprising an affinity substance to a soluble protein and a cleavable portion or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity can be performed by peptide mapping, for example. Peptide mapping can be performed by protease (e.g., trypsin and chymotrypsin) treatment and mass spectrometry, for example. For the protease, an endoprotease is preferred. Examples of such an endoprotease include trypsin, chymotrypsin, Glu-C, Lys-N, Lys-C, and Asp-N. Determination of the number of partial structures other than the soluble protein that the soluble protein has can be performed by electrophoresis, chromatography, or mass spectrometry, for example, and preferably mass spectrometry. The soluble protein comprising an affinity substance to a soluble protein and a cleavable portion or a salt thereof can be purified as appropriate by any method such as chromatography (e.g., the pieces of chromatography described above and affinity chromatography).

3. Conjugate Having Affinity Substance to Soluble Protein, Cleavable Portion, Functional substance, and Soluble Protein or Salt thereof 3-1. Outline The present invention provides a conjugate having an affinity substance to a soluble protein, a cleavable portion, a functional substance(s), and a soluble protein represented by Formula (III) or a salt thereof. A conjugate having an affinity substance to a soluble protein, a cleavable portion, a functional substance(s), and a soluble protein represented by

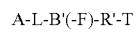

$$A\text{-}L\text{-}B'(\text{-}F)\text{-}R'\text{-}T \tag{III}$$

wherein
A is an affinity substance to a soluble protein;
L is a cleavable linker which is a divalent group comprising a cleavable portion;
B' is a divalent group comprising a portion formed by a reaction between a functional substance and a bioorthogonal functional group;
F is a functional substance;
R' is a portion formed by a reaction between a soluble protein and a reactive group; and
T is a soluble protein; or
a salt thereof.

In Formula (III) or other formulae, R' covalently binds to B' not F.

3-2. Functional Substance (F)

The functional substance is not limited to a particular substance so long as it is a substance imparting any function to the soluble protein; examples thereof include drugs, labelling substances, and stabilizers, and drugs and labelling substances are preferred. The functional substance may be a single functional substance or a substance in which two or more functional substances are coupled to each other.

The drug may be a drug to any disease. Examples of such a disease include cancer (e.g., lung cancer, stomach cancer, colon cancer, pancreatic cancer, renal cancer, liver cancer, thyroid cancer, prostatic cancer, bladder cancer, ovarian cancer, uterine cancer, bone cancer, skin cancer, a brain tumor, and melanoma), autoimmune diseases and inflammatory diseases (e.g., allergic diseases, articular rheumatism, and systemic lupus erythematosus), cranial nerve diseases (e.g., cerebral infarction, Alzheimer's disease, Parkinson disease, and amyotrophic lateral sclerosis), infectious diseases (e.g., microbial infectious diseases and viral infectious diseases), hereditary rare diseases (e.g., hereditary spherocytosis and nondystrophic myotonia), eye diseases (e.g., age-related macular degeneration, diabetic retinopathy, and retinitis pigmentosa), diseases in the bone and orthopedic field (e.g., osteoarthritis), blood diseases (e.g., leukosis and purpura), and other diseases (e.g., diabetes, metabolic diseases such as hyperlipidemia, liver diseases, renal diseases, lung diseases, circulatory system diseases, and digestive system diseases). When the soluble protein is an antibody to a target protein of a certain disease, the drug may be a drug related to the certain disease (e.g., a drug treating the certain disease and a drug relaxing side effects accompanying use of the antibody to the target protein of the certain disease).

More specifically, the drug is an anti-cancer agent. Examples of the anti-cancer agent include chemotherapeutic agents, toxins, and radioisotopes or substances comprising them. Examples of chemotherapeutic agents include DNA injuring agents, antimetabolites, enzyme inhibitors, DNA intercalating agents, DNA cleaving agents, topoisomerase inhibitors, DNA binding inhibitors, tubulin binding inhibitors, cytotoxic nucleosides, and platinum compounds. Examples of toxins include bacteriotoxins (e.g., diphtheria toxin) and phytotoxins (e.g., ricin). Examples of radioisotopes include radioisotopes of a hydrogen atom (e.g., $^3$H), radioisotopes of a carbon atom (e.g., $^{14}$C), radioisotopes of a phosphorous atom (e.g., $^{32}$p), radioisotopes of a sulfur atom (e.g., $^{35}$S), radioisotopes of yttrium (e.g., $^{90}$Y), radioisotopes of technetium (e.g., $^{99m}$Tc), radioisotopes of indium (e.g., $^{111}$In), radioisotopes of an iodide atom (e.g., $^{123}$I, $^{125}$I, $^{129}$I, and $^{131}$I), radioisotopes of samarium (e.g., $^{153}$Sm), radioisotopes of rhenium (e.g., $^{186}$Re), radioisotopes of astatine (e.g., $^{211}$At), and radioisotopes of bismuth (e.g., $^{212}$Bi)

Examples of labelling substances include enzymes (e.g., peroxidase, alkaline phosphatase, luciferase, and β-galactosidase), affinity substances (e.g., streptavidin, biotin, digoxigenin, and aptamer), fluorescent substances (e.g., fluorescein, fluorescein isothiocyanate, rhodamine, green-fluorescent protein, and red-fluorescent protein), luminescent substances (e.g., luciferin, aequorin, acridinium ester, tris(2,2'-bipyridyl)ruthenium, and luminol), and radioisotopes (e.g., those described above) or substances comprising them.

The functional substance is a large compound, a middle compound, or a small compound and is preferably a small compound. The small compound refers to compounds with a molecular weight of 1,500 or lower. The small compound is a natural compound or a synthesized compound. The molecular weight of the small compound may be 1,200 or lower, 1,000 or lower, 900 or lower, 800 or lower, 700 or lower, 600 or lower, 500 or lower, 400 or lower, or 300 or lower. The molecular weight of the small compound may be 30 or higher, 40 or higher, or 50 or higher. The small compound may be any of the drugs or labelling substances described above. Examples of the small compound include amino acids, oligopeptides, vitamins, nucleosides, nucleotides, oligonucleotides, monosaccharides, oligosaccharides, lipids, fatty acids, and salts thereof.

3-3. Divalent Group Comprising Portion Formed by Reaction Between Functional Substance and Bioorthogonal Functional Group (B')

B' is similar to (a) the divalent group comprising a bioorthogonal functional group in B described above except that the bioorthogonal functional group in (a) has reacted with the functional substance. Consequently, the definition, examples, and preferred examples of the divalent group and the bioorthogonal functional group in B' are similar to those in B.

The functional substance has various functional groups corresponding to its structure. When the functional substance has a functional group easily reacting with the bioorthogonal functional group, the functional group of the functional substance and the bioorthogonal functional group can be reacted with each other as appropriate. The function group easily reacting with the bioorthogonal functional group can vary depending on a specific type of the bioorthogonal functional group. A person skilled in the art can select an appropriate functional group as the functional group easily reacting with the bioorthogonal functional group as appropriate. Examples of the functional group easily reacting with the bioorthogonal functional group include, but are not limited to, maleimide and disulfide when the bioorthogonal functional group is a thiol, azides when the bioorthogonal functional group is an alkyne, and hydrazine when the bioorthogonal functional group is an aldehyde or a ketone.

On the other hand, when the functional substance has no functional group easily reacting with the bioorthogonal functional group, a substance derivatized so as to have a desired functional group can be used as the functional substance. When the functional substance is a soluble protein, for example, a substance derivatized so as to have a functional group that the soluble protein does not naturally have can be used. In this case, derivatization of the soluble protein may be performed by the method of the present invention. In this case, a soluble protein derivatized so as to regioselectively have a desired bioorthogonal functional group can be used as the functional substance.

Derivatization is a common technical knowledge in the field concerned (e.g., WO 2004/010957, United States Patent Application Publication No. 2006/0074008, and United States Patent Application Publication No. 2005/0238649). Derivatization may be performed using the cross-linking agent described above, for example. Alternatively, derivatization may be performed using a specific linker having a desired functional group. Such a linker may be able to separate the functional substance and the soluble protein through the cleavage of the linker under an appropriate condition (e.g., intracellular or extracellular), for example. Examples of such a linker include peptidyl linkers decomposed by specific proteases [e.g., intracellular proteases (e.g., proteases present in lysosome or endosome) and extracellular proteases (e.g., secretory proteases)] (e.g., U.S. Pat. No. 6,214,345; Dubowchik et al., Pharm. Therapeutics 83: 67-123 (1999)) and linkers capable of being cleaved at local acidic sites present in living bodies (e.g., U.S. Pat. Nos. 5,622,929, 5,122,368, and 5,824,805). The linker may be self-immolative (e.g., WO 02/083180, WO 04/043493, and WO 05/112919). In the present invention, the derivatized functional substance can also be referred to simply as the "functional substance."

In the divalent group comprising a portion formed by a reaction between a functional substance and a bioorthogonal functional group, the definitions, examples, and preferred examples of the functional substance and the bioorthogonal functional group are as described above. The portion formed by a reaction between a functional substance and a bioorthogonal functional group is a common technical knowledge in the technical field concerned and can be determined as appropriate in accordance with the types of the functional substance (when the functional substance is derivatized, its derivatized portion) and the bioorthogonal functional group.

The divalent group comprising a portion formed by a reaction between a functional substance and a bioorthogonal functional group, which is not limited to a particular group, may be a divalent group comprising a residue selected from the group consisting of a disulfide residue, an acetal residue, a ketal residue, an ester residue, a carbamoyl residue, an alkoxyalkyl residue, an imine residue, a tertiary alkyloxy carbamate residue, a silane residue, a hydrazone-containing residue, a phosphoramidate residue, an aconityl residue, a trityl residue, an azo residue, a vicinal diol residue, a selenium residue, an aromatic ring-containing residue having an electron-withdrawing group, a coumarin-containing residue, a sulfone-containing residue, an unsaturated bond-containing chain residue, and a glycosyl residue, for example.

The divalent group comprising a portion formed by a reaction between a functional substance and a bioorthogonal functional group, which is not limited to a particular group, may be a divalent group comprising a residue corresponding to any one chemical structure selected from the group consisting of the following:

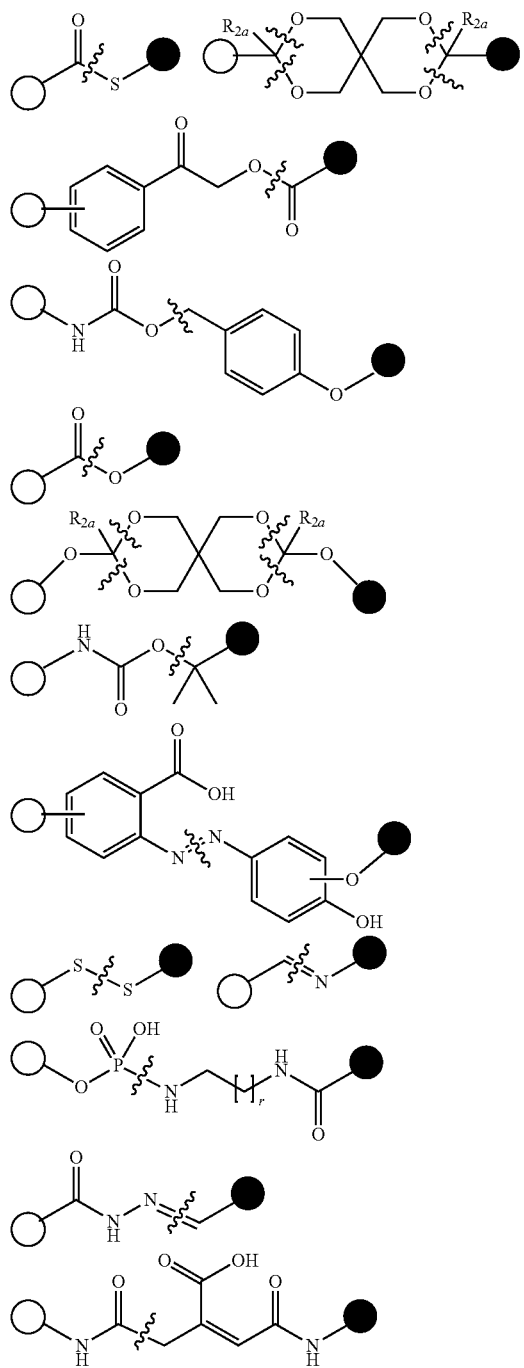

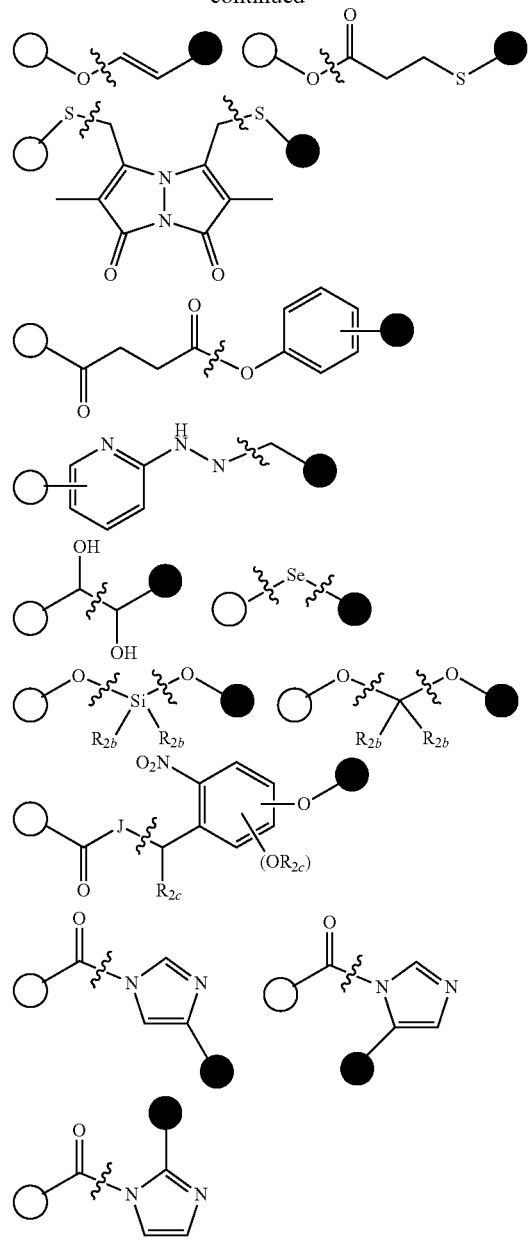

where a wavy line orthogonal to a bond indicates a bond formed by a reaction;

a plurality of $R_{2a}$, a plurality of $R_{2b}$, and a plurality of $R_{2c}$ are the same or different from each other, and are each a hydrogen atom or the substituent described above;

J is —$CH_2$—, —O—, or —S—;

r is any integer of 1 to 4;

a symbol of "white circle" indicates a bond to an F-side portion, and a symbol of "black circle" indicates a bond to a B'-side portion; and when a chemical structure is asymmetrical with respect to the cleavage site, a symbol of "black circle" may indicate a bond to a B'-side portion, and a symbol of "white circle" may indicate a bond to an F-side portion, for example.

3-4. Partial Structure "L-B'(-F)"

The details of a partial structure "L-B'(-F)" are as described in "1-6. Partial Structure "L-B''"" except that B is changed to B'(-F).

In an embodiment, the cleavable linker may be (i) a cleavable linker which is a divalent group comprising a cleavable portion having the ability to form a bioorthogonal functional group on a reactive group side by cleavage or (ii) a cleavable linker which is a divalent group comprising a cleavable portion having no ability to form a bioorthogonal functional group on a reactive group side by cleavage.

In a specific embodiment, the cleavable linker may be the cleavable linker (ii). This is because B' already binds to the functional substance (F), and there is no need to form the bioorthogonal functional group on the reactive group side.

In another specific embodiment, the partial structure represented by L-B'(-F) may be a partial structure represented by B2' (—F2)-L'-B1' (—F1) (that is, L is B2'(—F2)-L', and B' is B1'). In this case, the conjugate having an affinity substance to a soluble protein, a cleavable portion, a functional substance(s), and a soluble protein represented by Formula (III) or a salt thereof can be represented by the following Formula (III'):

A-B2'(—F2)-L'-B1'(—F1)-R'-T    (III')

wherein
A, R', and T are the same as those of Formula (III);
L' is a cleavable linker which is a divalent group comprising a cleavable portion;
B1' and B2' are the same or different from each other, and are each a divalent group comprising a portion formed by a reaction between a functional substance and a bioorthogonal functional group;
F1 and F2 are the same or different from each other, and are each a functional substance; and
B1'(—F1) and B2'(—F2) may have a symmetrical structure with respect to L').
B1' and B2' are the same or different from each other; the definitions, examples, and preferred examples thereof are similar to those of B'

In Formula (III'), L' may be represented by any one of Formulae (L1') to (L3') described above.

In another specific embodiment, a structural unit represented by L-B'(-F) may be represented by the following Formula (LB'(F)'):

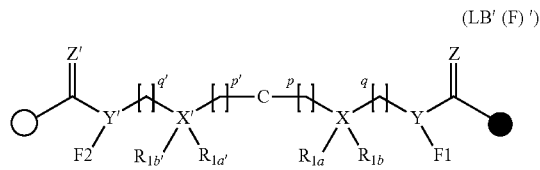

wherein
the definitions, examples, and preferred examples of C, F1, F2, p, p', q, q', X, X', $R_{1a}$, $R_{1a'}$, $R_{1b}$, $R_{1b'}$, Z, and Z' are the same as those described above;
Y and Y' are the same or different from each other, and are each a residue obtained by removing one hydrogen atom from Y of Formula (B-1);
a symbol of "white circle" indicates a bond to A, and a symbol of "black circle" indicates a bond to R'.

More specifically, the residue obtained by removing one hydrogen atom from Y of Formula (B-1) in Y and Y' is N(-)—, —CH(-)—, or a group obtained by removing one hydrogen atom from Formula (B-2). In view of simplifying the structure and the like, Y may be —N(-)- or —CH(-)-. Alternatively, in view of designing a carbon atom-based structure and the like, Y may be —CH(-)- or a group obtained by removing one hydrogen atom from Formula (B-2).

The group obtained by removing one hydrogen atom from Formula (B-2) is a group obtained by removing one hydrogen atom from the following Formula (B-2'):

wherein
V and V' are the same or different from each other, and are each —NH—, —O—, —CH₂—, or a single bond;
V1 is (a) a divalent group comprising a bioorthogonal functional group or (b) a divalent group comprising no bioorthogonal functional group;
s is any integer of 0 to 10; and
a symbol of "white circle" and a symbol of "black circle" in Formula (B-2') have the same orientation as a symbol of "white circle" and a symbol of "black circle" in Formula (B-1), respectively. The definition, examples, and preferred examples of s in Formula (B-2') are similar to those of Formula (B-2). Consequently, in Formula (B-2'), one of V and V' may be —N(-)- or —CH(-)-. Alternatively, in Formula (B-2'), V1 may be a trivalent group obtained by removing one hydrogen atom from the divalent group (a) or (b). Alternatively, in Formula (B-2'), one of s —CH₂— may be —CH(-)-.

In this case, Formula (III) can be defined as the following Formula (III'):

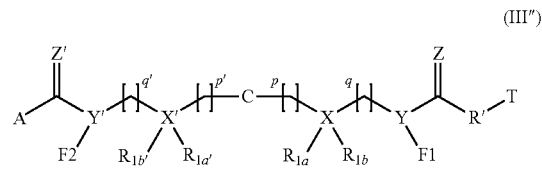

wherein
the definitions, examples, and preferred examples of A, R, C, F1, F2, p, p', q, q', X, X', $R_{1a}$, $R_{1b}$, $R_{1a'}$, $R_{1b'}$, Y, Y', Z, and Z' are the same as those described above.

In Formulae (LB'(F)') and (III'), the length from C (a carbon atom) in C=Z to C (a carbon atom) in C=Z' is similar to the length of the main chain linking A and R described above. In these formulae, the length from C in C=Z to C in C=Z' can also be defined as the number of atoms forming a linking chain of a partial structure linking C in C=Z and C in C=Z' (except hydrogen atoms and substituents). The number of atoms is similar to the number of atoms forming the main chain linking A and R. The linking chain of a partial structure linking C in C=Z and C in C=Z' (except hydrogen atoms and substituents) may comprise no cyclic structure or comprise a cyclic structure and preferably comprises no cyclic structure. The linking chain (except hydrogen atoms and substituents) may preferably comprise no peptide portion.

3-5. Binding Site (Regioselectivity) of Partial Structure other than Soluble Protein that Soluble Protein Has A partial structure other than the soluble protein (e.g., A-L-B'(-F)-R') can be regioselectively bound to the target region described above in the soluble protein (T). Specifically, when T comprises one or more specific amino acid residues in a target region consisting of 1 to 50 continuous amino acid residues, and five or more of the specific amino acid residues in a non-target region other than the target region, the partial structure other than the soluble protein can be bound to the one or more specific amino acid residues contained in the target region with 30% or more regioselectivity. The definitions, examples, and preferred examples of the target region and regioselectivity are as described above.

3-6. Number of Partial Structure Other than Soluble Protein that Soluble Protein has The number of the partial structure other than the soluble protein (e.g., A-L-B'(-F)-R') possessed by the soluble protein (T) can vary. When T is a multimeric protein comprising a plurality of monomeric proteins, for example, T can have the partial structure other than T in a plurality of corresponding target regions in the monomeric proteins. Consequently, T can have a plurality of partial structures other than T. Consequently, the structure represented by Formula (III), (III'), or (III') indicates that T may have one or a plurality of partial structures other than T. The number of partial structures other than T that T has can be adjusted by setting the type of the soluble protein and conditions such as a reaction ratio between the soluble protein and a structural unit to be introduced thereto as appropriate. Such a number, which varies depending on the type of the soluble protein, may be e.g., one to eight, preferably one to four, and more preferably one or two.

In a specific embodiment, when the soluble protein is a multimeric protein comprising a plurality of monomeric proteins, the soluble protein may possess a plurality of partial structures other than the soluble protein. The present invention can introduce a plurality of partial structures other than the soluble protein to the same target region of the monomeric proteins.

In a preferred embodiment, the soluble protein may be an antibody comprising a plurality of heavy chains. The definition, examples, and preferred examples of the antibody are as described above. In the present invention, the number of partial structures other than the antibody possessed by the antibody may be one or two (preferably two) for IgG, IgE, and IgD, one to four (preferably four) for IgA, and one to eight (preferably eight) for IgM.

3-7. Method of Production

The present invention provides a method for producing a conjugate having an affinity substance to a soluble protein, a cleavable portion, a functional substance(s), and a soluble protein or a salt thereof comprising the following:

(B1) reacting a soluble protein comprising an affinity substance to a soluble protein and a cleavable portion or a salt thereof with a functional substance(s) to form a conjugate having an affinity substance to a soluble protein, a cleavable portion, a functional substance(s), and a soluble protein or a salt thereof.

The soluble protein comprising an affinity substance to a soluble protein and a cleavable portion is represented by Formula (II), preferably Formula (II'), and more preferably Formula (II''). The conjugate having an affinity substance to a soluble protein, a cleavable portion, a functional substance(s), and a soluble protein is represented by Formula (III), preferably Formula (III'), and more preferably Formula (III'').

The soluble protein comprising an affinity substance to a soluble protein and a cleavable portion or a salt thereof has a bioorthogonal functional group capable of reacting with a functional substance(s) and can thus react with a functional substance(s). Such a reaction can be conducted as appropriate under a condition incapable of causing denaturation or decomposition (e.g., cleavage of an amide bond) of proteins (a mild condition) described in "2-6. Method of Production."

In the reaction system, the molar ratio (Y/X) of the functional substance (Y) to the soluble protein comprising an affinity substance to a soluble protein and a cleavable portion or a salt thereof (X) is not limited to a particular ratio because it varies in accordance with the types of the soluble protein (e.g., an antibody) and the functional substance, the number of sites in the soluble protein to be modified with the functional substance (e.g., DAR), and the like; it is e.g., 0.1 to 100, preferably 0.5 to 80, more preferably 1 to 70, even more preferably 2 to 50, and particularly preferably 3 to 30.

Determination of the formation of the conjugate having an affinity substance to a soluble protein, a cleavable portion, a functional substance(s), and a soluble protein or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity, determination of the number of partial structures other than the soluble protein, and purification can be performed as appropriate by the methods described in "2-6. Method of Production."

The present invention also provides a method for producing a conjugate having an affinity substance to a soluble protein, a cleavable portion, a functional substance(s), and a soluble protein or a salt thereof comprising the following:

(B2) reacting a compound comprising an affinity substance to a soluble protein, a cleavable portion, and a reactive group or a salt thereof with a soluble protein to form a soluble protein comprising an affinity substance to a soluble protein and a cleavable portion or a salt thereof; and (B3) reacting the soluble protein comprising an affinity substance to a soluble protein and a cleavable portion or a salt thereof with a functional substance(s) to form a conjugate having an affinity substance to a soluble protein, a cleavable portion, a functional substance(s), and a soluble protein or a salt thereof.

The process of (B2) can be performed in a manner similar to the process of (A1) described in "2-6. Method of Production." The process of (B3) can be performed in a manner similar to the process of (B1). The processes of (B2) and (B3) can be separately performed. Alternatively, the processes of (B2) and (B3) can be simultaneously performed in accordance with a combination of a reaction pair of a specific amino acid residue as a reaction target in the soluble protein and the reactive group and a reaction pair of a functional group in the functional substance and the bioorthogonal functional group.

4. Soluble Protein Having Bioorthogonal Functional Group or Salt Thereof 4-1 Outline of Method of Production The present invention provides a method for producing a soluble protein having a bioorthogonal functional group(s) represented by Formula (IV) or a salt thereof.

$$\text{L1-B-R'-T} \tag{IV}$$

wherein
L1 is (i') a monovalent group comprising a bioorthogonal functional group or (ii') a monovalent group comprising no bioorthogonal functional group;
B is (a) a divalent group comprising a bioorthogonal functional group or (b) a divalent group comprising no bioorthogonal functional group;
R' is a portion formed by a reaction between a soluble protein and a reactive group; and
T is a soluble protein.

4-2. (i') Monovalent Group Comprising Bioorthogonal functional group or (ii') Monovalent Group Comprising no Bioorthogonal functional group (L1)

In Formula (IV), L1 is (i') a monovalent group comprising a bioorthogonal functional group or (ii') a monovalent group comprising no bioorthogonal functional group. Such a monovalent group is a monovalent group that can be formed by cleavage of the cleavable linker which is a divalent group comprising a cleavable portion described above. Consequently, L1 may be a monovalent group that can be formed by cleavage of the residue or chemical structure of the cleavable portion described above. More specifically, (i') the monovalent group comprising a bioorthogonal functional group may be a monovalent group that can be formed by cleavage of (i) the cleavable linker which is a divalent group comprising a cleavable portion having the ability to form a bioorthogonal functional group on a reactive group side by cleavage described above; (ii') the monovalent group comprising no bioorthogonal functional group may be a monovalent group that can be formed by cleavage of the cleavable linker (ii) which is a divalent group comprising a cleavable portion having no ability to form a bioorthogonal functional group on a reactive group side by cleavage.

In a specific embodiment, L1 may be represented by any one of the following Formulae (L1-1) and (L1-2):

C1-Lb  (L1-1)

C1  (L1-2)

wherein
Lb is a divalent group; and
C1 is a bioorthogonal functional group or a group other than the bioorthogonal functional group.

Examples of the divalent group include a divalent hydrocarbon group optionally having a substituent, a divalent heterocyclic group optionally having a substituent, —C(=O)—, —NR$_a$— (R$_a$ indicates a hydrogen atom or a substituent), —O—, —S—, —C(=S)—, and a group consisting of a combination of two or more (e.g., two to eight, preferably two to six, and more preferably two to four) of these. The definitions, examples, and preferred examples of the divalent hydrocarbon group, the divalent heterocyclic group, and the substituent are as described above.

The definition, examples, and preferred examples of the bioorthogonal functional group are as described above.

Examples of the group other than the bioorthogonal functional group include, among the substituents described above, those other than the bioorthogonal functional group.

Examples of such a group other than the bioorthogonal functional group include alkyl, cycloalkyl, aralkyl, a monovalent heterocyclic group, hydroxy, amino, alkyloxy (alkoxy), cycloalkyloxy, and aralkyloxy. The definitions, examples, and preferred examples of these groups and the components of these groups (e.g., alkyl in alkyloxy (alkoxy), cycloalkyl in cycloalkyloxy, and aralkyl in aralkyloxy) are similar to those described above.

In a specific embodiment, Lb may be represented by the following (Lb'):

(Lb')

wherein
p is any integer of 0 to 10;
q is any integer of 0 to 10;
X is a carbon atom, a nitrogen atom, or a single bond where when X is a nitrogen atom, R$_{1b}$ is absent; and when X is a single bond, R$_{1a}$ and R$_{1b}$ are absent;
R$_{1a}$ and R$_{1b}$ are the same or different from each other, and are each a hydrogen atom or selected from the group consisting of the substituents described above; and
a symbol of "white circle" indicates a bond to C1, and a symbol of "black circle" indicates a bond to B.

The definitions, examples, and preferred examples of p, q, and X and R$_{1a}$ and R$_{1b}$ (substituents) are as described above.

4-3. Partial Structure "L1-B"

4-3-1. Length of Partial Structure "L1-B" Linking L1 Terminal Portion and R'

In Formula (IV), the length of a partial structure linking an L1 terminal portion (or a C1 terminal portion) formed by cleavage and R' (a linear chain portion in "L1-B") (or the number of atoms of a main chain linking a bioorthogonal functional group and a side chain of a specific amino acid residue in a soluble protein regioselectively having a bioorthogonal functional group or a salt thereof not limited to a specific formula such as Formula (IV); hereinafter the same) can be designed as appropriate in accordance with the various factors described in "I-6-1. Length of Main Chain in Partial Structure "L-B" Linking A and R."

The length of the partial structure linking an L1 terminal portion (or a C1 terminal portion) formed by cleavage and R' may be e.g., about 2.5 angstroms or longer, preferably about 4 angstroms or longer, and more preferably about 5 angstroms or longer. The length of the partial structure may be e.g., about 15 angstroms or shorter, preferably about 12 angstroms or shorter, and more preferably about 8 angstroms or shorter. More specifically, the length of the partial structure may be e.g., about 2.5 to 15 angstroms, preferably about 4 to 12 angstroms, and more preferably about 5 to 8 angstroms.

More specifically, the length of the partial structure linking an L1 terminal portion (or a C1 terminal portion) formed by cleavage and R' can also be defined as the number of atoms forming a linking chain of the partial structure (except hydrogen atoms and substituents). The number of atoms forming the linking chain may be e.g., two (about 2.5 angstroms) or more, preferably three (about 4 angstroms) or more, and more preferably four (about 5 angstroms) or more. The number of atoms forming the linking chain may be e.g., ten (about 15 angstroms) or less, preferably eight (about 12 angstroms) or less, and more preferably six (about 8 angstroms) or less. More specifically, the number of atoms forming the linking chain may be e.g., two to ten, preferably three to eight, and more preferably four to six.

When the linking chain of the partial structure linking an L1 terminal portion (or a C1 terminal portion) formed by cleavage and R' is a chain structure comprising no divalent cyclic structure, the number of atoms of the linking chain can be determined by counting the number of atoms in the linking chain.

On the other hand, when the linking chain of the partial structure linking an L1 terminal portion (or a C1 terminal portion) formed by cleavage and R' is a structure comprising a divalent cyclic structure, the number of atoms of the linking chain and the length described above do not necessarily correspond to each other, and the length that can be defined by the number of atoms of the linking chain tends to be shorter than the length described above. Even in such a case, in view of defining the length of the linking chain by the number of atoms, the number of atoms of the linking chain can be counted for convenience's sake. Specifically, the number of atoms of the linking chain in such a case may be determined by counting the number of atoms of the shortest route connecting two bonds in the divalent cyclic structure in addition to the number of atoms in a chain structure comprising no divalent cyclic structure in the linking chain as described above.

The linking chain of the partial structure linking an L1 terminal portion (or a C1 terminal portion) formed by cleavage and R' may be preferably a chain structure comprising no divalent cyclic structure. In this case, L1-B can be designed as appropriate such that the linking chain of the partial structure linking an terminal portion and R' formed by cleavage comprises no divalent cyclic group.

In a specific embodiment, the partial structure represented by L1-B preferably comprises no peptide portion. In this case, the soluble protein of the present invention (e.g., an antibody drug conjugate) obtained using the soluble protein of the present invention having a bioorthogonal functional group(s) has the advantage that it cannot comprise any peptide portion, which can have immunogenicity, as a linker.

4-3-2. Specific Structure of Partial Structure "L1-B"

In Formula (IV), L1 and B are structures that can be correlated with each other. Consequently, in Formula (IV), L1 and B can be defined as a partial structure represented by "L1-B."

In a specific embodiment, when L1 is (i') the monovalent group comprising a bioorthogonal functional group, B is (a) the divalent group comprising a bioorthogonal functional group or (b) the divalent group comprising no bioorthogonal functional group.

When L1 is (i') the monovalent group comprising a bioorthogonal functional group, B is preferably (a) the divalent group comprising a bioorthogonal functional group. In this case, the bioorthogonal functional group in (i') may be homogeneous or heterogeneous with respect to the bioorthogonal functional group in (a). In view of employing a simpler structure and/or improving reactivity to a single functional substance and the like, the bioorthogonal functional group in (i') may be homogeneous with respect to the bioorthogonal functional group in (a). On the other hand, in view of ensuring reactivity differentiated for two or more functional substances and non-use of a partial bioorthogonal functional group in the reaction, the bioorthogonal functional group in (i') may be heterogeneous with respect to the bioorthogonal functional group in (a).

Alternatively, when L1 is (i') the monovalent group comprising a bioorthogonal functional group, B may be (b) the divalent group comprising no bioorthogonal functional group. In this case, the soluble protein having a bioorthogonal functional group represented by Formula (IV) or a salt thereof has a simpler structure and is thus easily synthesized.

In another specific embodiment, when L1 is (ii') the monovalent group comprising no bioorthogonal functional group, B is (a) the divalent group comprising a bioorthogonal functional group.

In a specific embodiment, a structural unit represented by L1-B may be represented by the following Formula (L1B'):

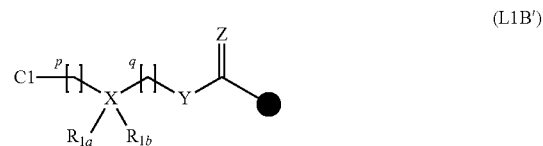

(L1B')

wherein
the definitions, examples, and preferred examples of C1, p, q, X, $R_{1a}$, $R_{1b}$, Y, and Z are the same as those described above; and
a symbol of "black circle" indicates a bond to R'

Consequently, Formula (IV) can be defined as the following Formula (IV'):

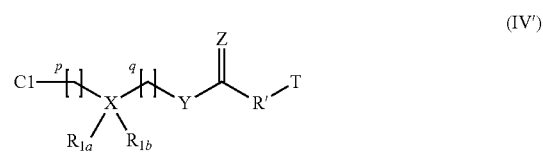

(IV')

wherein
the definitions, examples, and preferred examples of C1, p, q, X, $R_{1a}$, $R_{1b}$, Y, Z, R', and T are the same as those described above.

In Formulae (L1B') and (IV'), the length from C in C=Z to C1 is similar to the length of the partial structure linking an L1 terminal portion (or a C1 terminal portion) formed by cleavage and R'. In these formulae, the length from C in C=Z to C1 can also be defined as the number of atoms forming a linking chain of a partial structure from C in C=Z to C1 (except hydrogen atoms and substituents). The number of atoms is similar to the number of atoms constituting the partial structure linking an L1 terminal portion (or a C1 end) formed by cleavage and R' (except hydrogen atoms and substituents). The linking chain of the partial structure linking C in C=Z and C1 (except hydrogen atoms and substituents) may comprise no cyclic structure or comprise a cyclic structure and preferably comprises no cyclic structure. The linking chain (except hydrogen atoms and substituents) may preferably comprise no peptide portion.

4-4. Binding Site (Regioselectivity) of Partial Structure other than Soluble Protein that Soluble Protein Has A partial structure other than the soluble protein (e.g., L1-B-R') can be regioselectively bound to the target region described above in the soluble protein (T). Specifically, when T comprises one or more specific amino acid residues in a target region consisting of 1 to 50 continuous amino acid residues, and five or more of the specific amino acid residues in a non-target region other than the target region, the partial structure other than the soluble protein can be bound to the one or more specific amino acid residues contained in the target region with 30% or more regioselectivity. The definitions, examples, and preferred examples of the target region and regioselectivity are as described above.

4-5. Number of Partial Structure other than Soluble Protein that Soluble Protein Has The number of the partial structure other than the soluble protein (e.g., L1-B-R') possessed by the soluble protein (T) can vary. When T is a multimeric protein comprising a plurality of monomeric proteins, for example, T can have the partial structure other than T in a plurality of corresponding target regions in the monomeric proteins. Consequently, T can have a plurality of partial structures other than T. Consequently, the structure represented by Formula (IV), (IV'), or (IV'') indicates that T may have one or a plurality of partial structures other than T. The number of partial structures other than T that T has can be adjusted by setting the type of the soluble protein and conditions such as a reaction ratio between the soluble protein and a structural unit to be introduced thereto as appropriate. Such a number, which varies depending on the type of the soluble protein, may be e.g., one to eight, preferably one to four, and more preferably one or two.

In a specific embodiment, when the soluble protein is a multimeric protein comprising a plurality of monomeric proteins, the soluble protein may possess a plurality of partial structures other than the soluble protein. The present invention can introduce a plurality of partial structures other than the soluble protein to the same target region of the monomeric proteins.

In a preferred embodiment, the soluble protein may be an antibody comprising a plurality of heavy chains. The definition, examples, and preferred examples of the antibody are as described above. In the present invention, the number of partial structures other than the antibody possessed by the antibody may be one or two (preferably two) for IgG, IgE, and IgD, one to four (preferably four) for IgA, and one to eight (preferably eight) for IgM.

4-6. Method of Production

The present invention provides a method for producing a soluble protein having a bioorthogonal functional group(s) or a salt thereof comprising the following: (C1) cleaving a cleavable portion of a soluble protein comprising an affinity substance to a soluble protein and a cleavable portion or a salt thereof to form a soluble protein having a bioorthogonal functional group(s) or a salt thereof.

The soluble protein comprising an affinity substance to a soluble protein and a cleavable portion is represented by Formula (II), preferably Formula (II'), and more preferably Formula (II''). The soluble protein having a bioorthogonal functional group(s) is represented by Formula (IV), preferably Formula (IV'), and more preferably Formula (IV'').

The soluble protein comprising an affinity substance to a soluble protein and a cleavable portion or a salt thereof has the cleavable portion cleavable by the cleaving treatment described above and is thus cleavable. Such a cleaving reaction can be conducted as appropriate under a condition incapable of causing denaturation or decomposition (e.g., cleavage of an amide bond) of proteins (a mild condition) described in "2-6. Method of Production."

Examples of the cleaving treatment include (a) treatment with one or more substances selected from the group consisting of an acidic substance, a basic substance, a reducing agent, an oxidizing agent, and an enzyme, (b) treatment by physicochemical stimulus selected from the group consisting of light, and (c) being left when a cleavable linker comprising a self-decomposing cleavable portion is used. Conditions of such cleaving treatment are common technical knowledge in the field concerned (e.g., G. Leriche, L. Chisholm, A. Wagner, Bioorganic & Medicinal Chemistry, 20, 571 (2012); Feng P. et al., Journal of American Chemical Society, 132, 1500 (2010); Bessodes M. et al., Journal of Controlled Release, 99, 423 (2004); DeSimone, J. M., Journal of American Chemical Society, 132, 17928 (2010); Thompson, D. H., Journal of Controlled Release, 91, 187 (2003); Schoenmarks, R. G., Journal of Controlled Release, 95, 291 (2004)).

Determination of the formation of the soluble protein having a bioorthogonal functional group(s) or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity, determination of the number of partial structures other than the soluble protein, and purification can be performed as appropriate by the methods described in "2-6. Method of Production."

The present invention also provides a method for producing a soluble protein having a bioorthogonal functional group(s) or a salt thereof comprising the following:

(C2) reacting a compound comprising an affinity substance to a soluble protein, a cleavable portion, and a reactive group or a salt thereof with a soluble protein to form a soluble protein comprising an affinity substance to a soluble protein and a cleavable portion or a salt thereof; and (C3) cleaving the cleavable portion of the soluble protein comprising the affinity substance to a soluble protein and the cleavable portion or a salt thereof to form a soluble protein having a bioorthogonal functional group(s) or a salt thereof.

The process of (C2) can be performed in a manner similar to the process of (A1) described in "2-6. Method of Production." The process of (C3) can be performed in a manner similar to the process of (C1). The processes of (C2) and (C3) can be separately performed. Alternatively, the processes of (C2) and (C3) can be simultaneously performed in accordance with factors such as a combination of the reactive group and the bioorthogonal functional group that can be formed by cleavage (non-reactivity).

5. Method for Producing Soluble Protein Having Functional substance or Salt thereof 5-1. Outline The present invention provides a method for producing a soluble protein having a functional substance(s) represented by Formula (V) or a salt thereof.

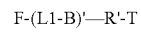

$$F\text{-}(L1\text{-}B)'\text{---}R'\text{-}T \quad\quad\quad (V)$$

wherein

L1 is (i') a monovalent group comprising a bioorthogonal functional group or (ii') a monovalent group comprising no bioorthogonal functional group;

B is (a) a divalent group comprising a bioorthogonal functional group or (b) a divalent group comprising no bioorthogonal functional group;

a structural unit represented by (L1-B') is a divalent structural unit comprising a portion formed by a reaction between a functional substance and either one or both of the bioorthogonal functional groups in (i') and (a);

F is a functional substance;

R' is a portion formed by a reaction between a soluble protein and a reactive group; and T is a soluble protein.

5-2. Partial Structure "F-(L1-B)'"
5-2-1. Length of Partial Structure "L1-B" Linking F and R'

In Formula (V), the length of a partial structure "L1-B" linking F and R' (a linear chain portion in "L1-B") (or the number of atoms of a main chain linking a functional substance and a side chain of a specific amino acid residue in a soluble protein regioselectively having a functional substance(s) or a salt thereof not limited to a specific formula such as Formula (V) or, when the a functional substance(s) binds to the soluble protein through a bioorthogonal functional group, the number of atoms of a main chain linking the bioorthogonal functional group and a side chain of a specific amino acid residue; hereinafter the same) can be designed as appropriate in accordance with the various factors described in "1-6-1. Length of Main Chain in Partial Structure "L-B" Linking A and R."

The length of the partial structure linking F and R' may be e.g., about 2.5 angstroms or longer, preferably about 4 angstroms or longer, and more preferably about 5 angstroms or longer. The length of the partial structure may be e.g., about 15 angstroms or shorter, preferably about 12 angstroms or shorter, and more preferably about 8 angstroms or shorter. More specifically, the length of the partial structure may be e.g., about 2.5 to 15 angstroms, preferably about 4 to 12 angstroms, and more preferably about 5 to 8 angstroms.

More specifically, the length of the partial structure linking F and R' can also be defined as the number of atoms forming a linking chain of the partial structure (except hydrogen atoms and substituents). The number of atoms forming the linking chain may be e.g., two (about 2.5 angstroms) or more, preferably three (about 4 angstroms) or more, and more preferably four (about 5 angstroms) or more. The number of atoms forming the linking chain may be e.g., ten (about 15 angstroms) or less, preferably eight (about 12 angstroms) or less, and more preferably six (about 8 angstroms) or less. More specifically, the number of atoms forming the linking chain may be e.g., two to ten, preferably three to eight, and more preferably four to six.

When the linking chain of the partial structure linking F and R' is a chain structure comprising no divalent cyclic structure, the number of atoms of the linking chain can be determined by counting the number of atoms in the linking chain.

On the other hand, when the linking chain of the partial structure linking F and R' is a structure comprising a divalent cyclic structure, the number of atoms of the linking chain and the length described above do not necessarily correspond to each other, and the length that can be defined by the number of atoms of the linking chain tends to be shorter than the length described above. Even in such a case, in view of defining the length of the linking chain by the number of atoms, the number of atoms of the linking chain can be counted for convenience's sake. Specifically, the number of atoms of the linking chain in such a case may be determined by counting the number of atoms of the shortest route connecting two bonds in the divalent cyclic structure in addition to the number of atoms in a chain structure comprising no divalent cyclic structure in the linking chain as described above.

The linking chain of the partial structure linking F and R' may be preferably a chain structure comprising no divalent cyclic structure. L1-B can be designed as appropriate such that the linking chain of the partial structure linking F and R' comprises no divalent cyclic group.

In a specific embodiment, the partial structure represented by L1-B preferably comprises no peptide portion. In this case, the soluble protein of the present invention (e.g., an antibody drug conjugate) has the advantage that it does not comprise any peptide portion, which can have immunogenicity, as a linker.

5-2-2. Specific Structure of Partial Structure "F-(L1-B)'"

In Formula (V), L1 and B in F-(L1-B)' are structures that can be correlated with each other. Consequently, in Formula (V), L1 and B can be defined as a partial structure represented by "L1-B."

A structural unit represented by F-(L1-B)' is a portion formed by a reaction between a functional substance and either one or both of the bioorthogonal functional groups in (i') and (a). A bioorthogonal functional group used for the reaction is not present in Formula (V). Consequently, in Formula (V), either one or both of the bioorthogonal functional groups in (i') and (a) are not present. The portion formed by a reaction between a functional substance and either one or both of the bioorthogonal functional groups in (i') and (a) is the same as the portion formed by a reaction between a functional substance and a bioorthogonal functional group. Consequently, in the present specification, examples (the names of residues) and specific examples (chemical structures) of the portion formed by a reaction between a functional substance and either one or both of the bioorthogonal functional groups in (i') and (a) are the same as those described above for the portion formed by a reaction between a functional substance and a bioorthogonal functional group.

In an embodiment, when L1 is (i') the monovalent group comprising a bioorthogonal functional group, B is (a) the divalent group comprising a bioorthogonal functional group or (b) the divalent group comprising no bioorthogonal functional group.

In a preferred embodiment, when L1 is (i') the monovalent group comprising a bioorthogonal functional group, B is (a) the divalent group comprising a bioorthogonal functional group. In this case, the bioorthogonal functional group in (i) may be homogeneous or heterogeneous with respect to the bioorthogonal functional group in (a). In view of employing a simpler structure and/or improving reactivity to a single functional substance and the like, the bioorthogonal functional group in (i') may be homogeneous with respect to the bioorthogonal functional group in (a). On the other hand, in view of ensuring reactivity differentiated for two or more functional substances, non-use of a partial bioorthogonal functional group in the reaction, and the like, the bioorthogonal functional group in (i') may be heterogeneous with respect to the bioorthogonal functional group in (a).

In another preferred embodiment, when L1 is (i') the monovalent group comprising a bioorthogonal functional group, B may be (b) the divalent group comprising no bioorthogonal functional group. In this case, the soluble protein having a functional substance(s) represented by Formula (V) or a salt thereof has a simpler structure and is thus easily synthesized.

In another embodiment, when L1 is (ii') the monovalent group comprising no bioorthogonal functional group, B is (a) the divalent group comprising a bioorthogonal functional group.

In a specific embodiment, when the bioorthogonal functional groups in (i') and (a) are heterogeneous, the soluble protein having a functional substance(s) represented by Formula (V) or a salt thereof may be represented by Formula (V1) or (V2).

$$\text{L1-B'(-F)-R'-T} \qquad\qquad (V1)$$

wherein
- L1 is (i') a monovalent group comprising a bioorthogonal functional group or (ii') a monovalent group comprising no bioorthogonal functional group;
- B' is a divalent group comprising a portion formed by a reaction between a functional substance and a bioorthogonal functional group;
- F is a functional substance;
- R' is a portion formed by a reaction between a soluble protein and a reactive group; and
- T is a soluble protein.

F-L1'-B-R'-T    (V2)

wherein
- L1' is a divalent group comprising a portion formed by a reaction between a functional substance and (i') a monovalent group comprising a bioorthogonal functional group;
- B is (a) a divalent group comprising a bioorthogonal functional group or (b) a divalent group comprising no bioorthogonal functional group;
- F is a functional substance;
- R' is a portion formed by a reaction between a soluble protein and a reactive group; and
- T is a soluble protein.

L1' is a divalent group comprising a portion formed by a reaction between a functional substance and (i') a monovalent group comprising a bioorthogonal functional group. The portion formed by a reaction between a functional substance and (i') a monovalent group comprising a bioorthogonal functional group is the same as the portion formed by a reaction between a functional substance and a bioorthogonal functional group. Consequently, in the present specification, examples (the names of residues) and specific examples (chemical structures) of the portion formed by a reaction between a functional substance and (i') a monovalent group comprising a bioorthogonal functional group are the same as those described above for the portion formed by a reaction between a functional substance and a bioorthogonal functional group. Consequently, the functional substance reacts with the bioorthogonal functional group, and thus the divalent group comprising a portion formed by a reaction between a functional substance and (i') a monovalent group comprising a bioorthogonal functional group (L1') can also be represented as a divalent group comprising a portion formed by a reaction between a functional substance and a bioorthogonal functional group (hereinafter the same). The definition, examples, and preferred examples of the divalent group comprising a portion formed by a reaction between a functional substance and a bioorthogonal functional group in L1' may be similar to those of the divalent group comprising a portion formed by a reaction between a functional substance and a bioorthogonal functional group in B'.

In another specific embodiment, when the bioorthogonal functional groups in (i') and (a) are homogeneous or heterogeneous, the soluble protein having a functional substance(s) represented by Formula (V) or a salt thereof may be represented by Formula (V3).

Fa-L1'-B'(-Fb)-R'-T    (V3)

wherein
- L1' is a divalent group comprising a portion formed by a reaction between a functional substance and (i') a monovalent group comprising a bioorthogonal functional group;
- B' is a divalent group comprising a portion formed by a reaction between a functional substance and a bioorthogonal functional group; Fa and Fb are functional substances which are the same or different from each other;
- R' is a portion formed by a reaction between a soluble protein and a reactive group; and
- T is a soluble protein.

In a specific embodiment, in Formula (V1), a structural unit represented by L1-B'(-F) may be represented by the following Formula (FL1'B):

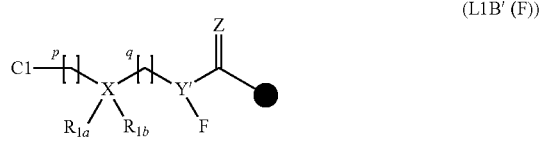

(L1B' (F))

wherein
- the definitions, examples, and preferred examples of F, C1, p, q, X, $R_{1a}$, $R_{1b}$, and Z are the same as those described above;
- Y' is a residue obtained by removing one hydrogen atom from Y of Formula (B-1); and
- a symbol of "black circle" indicates a bond to R'

The definition, examples, and preferred examples of the residue obtained by removing one hydrogen atom from Y of Formula (B-1) are similar to those describes above.

Consequently, Formula (V1) can be defined as the following Formula (V1'):

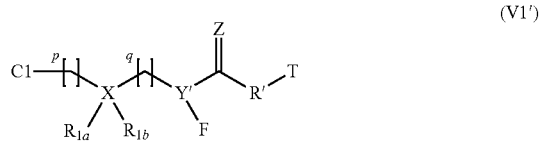

(V1')

wherein
- the definitions, examples, and preferred examples of F, C1, p, q, X, $R_{1a}$, $R_{1b}$, Z, R', and T are the same as those described above; and
- Y' is a residue obtained by removing one hydrogen atom from Y of Formula (B-1).

In a specific embodiment, in Formula (V2), a structural unit represented by F-L1'-B may be represented by the following Formula (FL1'B):

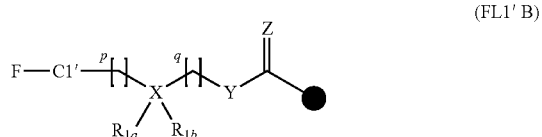

(FL1' B)

wherein
- the definitions, examples, and preferred examples of F, p, q, X, $R_{1a}$, $R_{1b}$, Y, and Z are the same as those described above;
- C1' is a portion formed by a reaction between a functional substance and a bioorthogonal functional group; and
- a symbol of "black circle" indicates a bond to R'.

C1' is a portion formed by a reaction between a functional substance and a bioorthogonal functional group. The definition, examples, and preferred examples of the portion formed by a reaction between a functional substance and a bioorthogonal functional group in C1' are similar to those described in "3-3. Divalent Group Comprising Portion Formed by Reaction between Functional substance and Bioorthogonal functional group (B')" (hereinafter, the same).

Consequently, Formula (V2) can be defined as the following Formula (V2'):

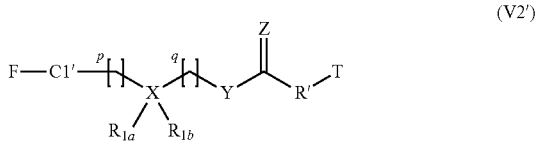

(V2')

wherein
the definitions, examples, and preferred examples of F, p, q, X, $R_{1a}$, $R_{1b}$, Y, Z, R', and T are the same as those described above; and
C1' is a portion formed by a reaction between a functional substance and a bioorthogonal functional group.

In a specific embodiment, in Formula (V3), a structural unit represented by Fa-L1'-B'(-Fb) may be represented by the following Formula (FaL1'B'(Fb)):

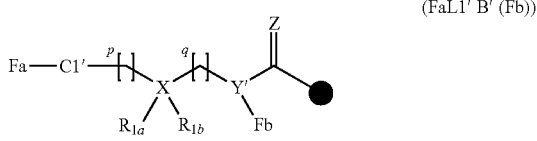

(FaL1' B' (Fb))

wherein
the definitions, examples, and preferred examples of Fa, Fb, p, q, X, $R_{1a}$, $R_{1b}$, and Z are the same as those described above;
C1' is a portion formed by a reaction between a functional substance and a bioorthogonal functional group;
Y' is a residue obtained by removing one hydrogen atom from Y of Formula (B-1); and
a symbol of "black circle" indicates a bond to R'.

Consequently, Formula (V3) can be defined as the following Formula (V3'):

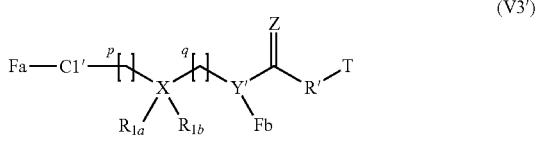

(V3')

wherein
the definitions, examples, and preferred examples of Fa, Fb, p, q, X, $R_{1a}$, $R_{1b}$, Z, R', and T are the same as those described above;
C1' is a portion formed by a reaction between a functional substance and a bioorthogonal functional group; and Y' is a residue obtained by removing one hydrogen atom from Y of Formula (B-1).

In Formulae (L1B'(F), (FL1'B), and (FaL1'B'(F2)) and (V1'), (V2'), and (V3'), the length from C in C=Z to C1 is similar to the length of the partial structure linking an L1 terminal portion (or a C1 terminal portion) formed by cleavage and R'. In these formulae, the length from C in C=Z to C1 can also be defined as the number of atoms forming a linking chain of a partial structure from C in C=Z to C1 (except hydrogen atoms and substituents). The number of atoms is similar to the number of atoms constituting the partial structure linking an L1 terminal portion (or a C1 end) formed by cleavage and R' (except hydrogen atoms and substituents). The linking chain of the partial structure linking C in C=Z and C1 (except hydrogen atoms and substituents) may comprise no cyclic structure or comprise a cyclic structure and preferably comprises no cyclic structure. The linking chain (except hydrogen atoms and substituents) may preferably comprise no peptide portion.

5-3. Binding Site (Regioselectivity) of Partial Structure other than Soluble Protein that Soluble Protein Has A partial structure other than the soluble protein (e.g., F-(L1-B)'—R') can be regioselectively bound to the target region described above in the soluble protein (T). Specifically, when T comprises one or more specific amino acid residues in a target region consisting of 1 to 50 continuous amino acid residues, and five or more of the specific amino acid residues in a non-target region other than the target region, the partial structure other than the soluble protein can be bound to the one or more specific amino acid residues contained in the target region with 30% or more regioselectivity. The definitions, examples, and preferred examples of the target region and regioselectivity are as described above.

5-4. Number of Partial Structure other than Soluble Protein that Soluble Protein Has The number of the partial structure other than the soluble protein (e.g., F-(L1-B)'—R') possessed by the soluble protein (T) can vary. When T is a multimeric protein comprising a plurality of monomeric proteins, for example, T can have the partial structure other than T in a plurality of corresponding target regions in the monomeric proteins. Consequently, T can have a plurality of partial structures other than T. Consequently, the structure represented by Formula (V), (V1), (V2), (V3), (V1'), (V2'), or (V3') indicates that T may have one or a plurality of partial structures other than T. The number of partial structures other than T that T has can be adjusted by setting the type of the soluble protein and conditions such as a reaction ratio between the soluble protein and a structural unit to be introduced thereto as appropriate. Such a number, which varies depending on the type of the soluble protein, may be e.g., one to eight, preferably one to four, and more preferably one or two.

In a specific embodiment, when the soluble protein is a multimeric protein comprising a plurality of monomeric proteins, the soluble protein may possess a plurality of partial structures other than the soluble protein. The present invention can introduce a plurality of partial structures other than the soluble protein to the same target region of the monomeric proteins.

In a preferred embodiment, the soluble protein may be an antibody comprising a plurality of heavy chains. The definition, examples, and preferred examples of the antibody are as described above. In the present invention, the number of partial structures other than the antibody possessed by the antibody may be one or two (preferably two) for IgG, IgE, and IgD, one to four (preferably four) for IgA, and one to eight (preferably eight) for IgM.

5-5. Method of Production

Figures 1, 2:
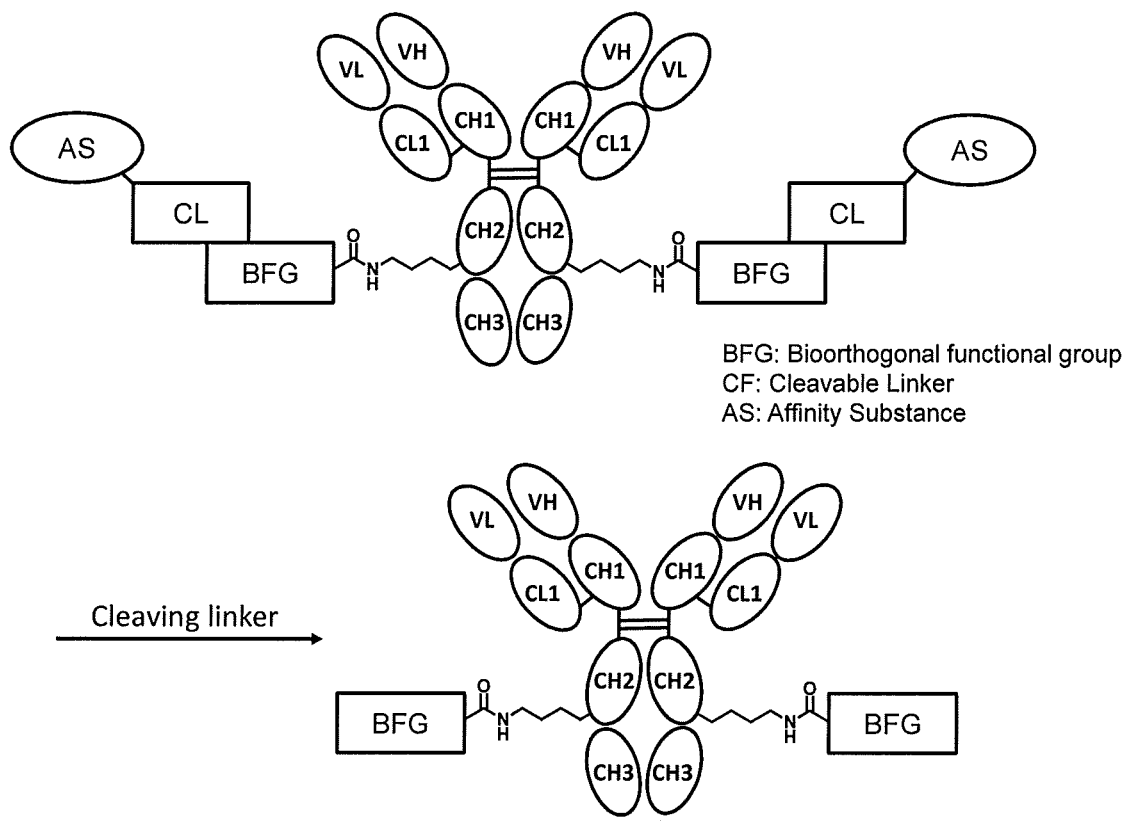

The present invention provides a method for producing a soluble protein having a functional substance(s) or a salt thereof. The present method of production can be classified into (D) a method that uses a conjugate having an affinity substance to a soluble protein, a cleavable portion, a functional substance(s), and a soluble protein or a salt thereof as a raw material (refer to Reaction (3) in FIG. 2) and (E) a method that uses a soluble protein having a bioorthogonal functional group(s) or a salt thereof as a raw material (refer to Reaction (5) in FIG. 2).

(D) The method that uses a conjugate having an affinity substance to a soluble protein, a cleavable portion, a functional substance(s), and a soluble protein or a salt thereof as a raw material comprises the following:

(D1) cleaving the cleavable portion of the conjugate having the affinity substance to a soluble protein, the cleavable portion, the functional substance, and the soluble protein or a salt thereof to form a soluble protein having a functional substance(s) and a salt thereof.

The conjugate having an affinity substance to a soluble protein, a cleavable portion, a functional substance(s), and a soluble protein is represented by Formula (III), preferably (III'), and more preferably (III''). The soluble protein having a functional substance(s) is represented by Formula (V), preferably Formula (V1), (V2), or (V3), and more preferably Formula (V1'), (V2'), or (V3').

The conjugate having an affinity substance to a soluble protein, a cleavable portion, a functional substance(s), and a soluble protein or a salt thereof has the cleavable portion cleavable by the cleaving treatment described above and is thus cleavable. Such a cleaving reaction can be conducted in a manner described in "4-6. Method of Production."

Determination of the formation of the soluble protein having a functional substance(s) or a salt thereof, which depends on its specific raw materials and the molecular weight of a product, can be performed by electrophoresis, chromatography (e.g., gel permutation chromatography, ion-exchange chromatography, reversed phase column chromatography, and HPLC), or mass spectrometry, for example, and preferably mass spectrometry. Determination of regioselectivity, determination of the number of partial structures other than the soluble protein, and purification can be performed as appropriate by the methods described in "2-6. Method of Production."

The present invention also provides a method for producing a soluble protein having a functional substance(s) or a salt thereof comprising the following:

(D2) reacting a soluble protein comprising an affinity substance to a soluble protein and a cleavable portion or a salt thereof with a functional substance(s) to form a conjugate having an affinity substance to a soluble protein, a cleavable portion, a functional substance(s), and a soluble protein or a salt thereof; and (D3) cleaving the cleavable portion of the conjugate having the affinity substance to a soluble protein, the cleavable portion, the functional substance, and the soluble protein or a salt thereof to form a soluble protein having a functional substance(s) or a salt thereof.

The process of (D2) can be performed in a manner similar to the process of (B1) described in "3-7. Method of Production." The process of (D3) can be performed in a manner similar to the process of (D1). The processes of (D2) and (D3) can be separately performed. Alternatively, the processes of (D2) and (D3) can be simultaneously performed in accordance with factors such as a combination of the cleavable portion, the functional substance, and the bioorthogonal functional group.

The present invention further provides a method for producing a soluble protein having a functional substance(s) or a salt thereof comprising the following: (D4) reacting a compound comprising an affinity substance to a soluble protein, a cleavable portion, and a reactive group or a salt thereof with a soluble protein to form a soluble protein comprising an affinity substance to a soluble protein and a cleavable portion or a salt thereof;

(D5) reacting the soluble protein comprising an affinity substance to a soluble protein and a cleavable portion or a salt thereof with a functional substance(s) to form a conjugate having an affinity substance to a soluble protein, a cleavable portion, a functional substance(s), and a soluble protein or a salt thereof; and (D6) cleaving the cleavable portion of the conjugate having the affinity substance to a soluble protein, the cleavable portion, the functional substance, and the soluble protein or a salt thereof to form a soluble protein having a functional substance(s) or a salt thereof.

The process of (D4) can be performed in a manner similar to the process of (A1) described in "2-6. Method of Production." The processes of (D5) and (D6) can be performed in a manner similar to the processes of (D2) and (D3). The process of (D5) can be performed in a manner similar to the process of (B1) described in "3-7. Method of Production." The process of (D6) can be performed in a manner similar to the process of (D1). The processes of (D4) to (D6) can be separately performed. Alternatively, at least part of the processes of (D4) to (D6) can be simultaneously performed in accordance with factors such as a combination of the reactive group, the cleavable portion, the functional substance, and the bioorthogonal functional group.

(E) The method that uses a soluble protein having a bioorthogonal functional group(s) or a salt thereof as a raw material comprises the following:

(E1) reacting the soluble protein having the bioorthogonal functional group or a salt thereof with a functional substance(s) to form a soluble protein having a functional substance(s) or a salt thereof.

The soluble protein having a bioorthogonal functional group(s) is represented by Formula (IV) and preferably Formula (IV'). The soluble protein having a functional substance(s) is represented by Formula (V), preferably Formula (V1), (V2), or (V3), and more preferably Formula (V1'), (V2'), or (V3').

The soluble protein having a bioorthogonal functional group(s) or a salt thereof has the bioorthogonal functional group and can thus react with a functional substance(s). Such a reaction can be conducted in a manner described in "3-7. Method of Production."

Determination of the formation of the soluble protein having a functional substance(s) or a salt thereof can be performed by the method described above. Determination of regioselectivity, determination of the number of partial structures other than the soluble protein, and purification can be performed as appropriate by the methods described in "2-6. Method of Production."

The present invention also provides a method for producing a soluble protein having a functional substance(s) or a salt thereof comprising the following:

(E2) cleaving a cleavable portion of a soluble protein comprising an affinity substance to a soluble protein and a cleavable portion or a salt thereof to form a soluble protein having a bioorthogonal functional group(s) or a salt thereof; and (E3) reacting the soluble protein having the bioorthogonal functional group or a salt thereof with a functional substance(s) to form a soluble protein having a functional substance(s) or a salt thereof.

The process of (E2) can be performed in a manner similar to the process of (C1) described in "4-6. Method of Production." The process of (E3) can be performed in a manner similar to the process of (E1). The processes of (E2) and (E3) can be separately performed. Alternatively, the processes of (E2) and (E3) can be simultaneously performed in accordance with factors such as a combination of the cleavable portion, the functional substance, and the bioorthogonal functional group.

The present invention further provides a method for producing a soluble protein having a functional substance(s) or a salt thereof comprising the following:

(E4) reacting a compound comprising an affinity substance to a soluble protein, a cleavable portion, and a reactive group or a salt thereof with a soluble protein to form a soluble protein comprising an affinity substance to a soluble protein and a cleavable portion or a salt thereof;

(E5) cleaving the cleavable portion of the soluble protein comprising the affinity substance to a soluble protein and the cleavable portion or a salt thereof to form a soluble protein having a bioorthogonal functional group(s) or a salt thereof; and (E6) reacting the soluble protein having the bioorthogonal functional group or a salt thereof with a functional substance(s) to form a soluble protein having a functional substance(s) or a salt thereof.

The process of (E4) can be performed in a manner similar to the process of (A1) described in "2-6. Method of Production." The processes of (E5) and (E6) can be performed in a manner similar to the processes of (E2) and (E3). The processes of (E4) to (E6) can be separately performed. Alternatively, at least part of the processes of (E4) to (E6) can be simultaneously performed in accordance with factors such as a combination of the reactive group, the cleavable portion, the functional substance, and the bioorthogonal functional group.

6. Specific Soluble Protein Regiospecifically Having Bioorthogonal functional group or Salt thereof and Method for Producing Same The present invention also provides a soluble protein regioselectively having a bioorthogonal functional group(s) or a salt thereof. The soluble protein or salt thereof of the present invention regioselectively having a bioorthogonal functional group(s) is a soluble protein regioselectively having a bioorthogonal functional group(s) or a salt thereof, the soluble protein comprising one or more specific amino acid residues in a target region consisting of 1 to 50 continuous amino acid residues and comprising five or more of the specific amino acid residues in a non-target region other than the target region, and the bioorthogonal functional group binding to the one or more specific amino acid residues contained in the target region with 30% or more regioselectivity through a linker comprising no peptide portion.

In a specific embodiment, the soluble protein or salt thereof of the present invention regioselectively having a bioorthogonal functional group(s) may be a soluble protein regioselectively having a bioorthogonal functional group(s) represented by the following Formula (IV):

$$L1\text{-}B\text{-}R'\text{-}T \qquad (IV)$$

wherein

L1 is (i') a monovalent group comprising a bioorthogonal functional group or (ii') a monovalent group comprising no bioorthogonal functional group;

B is (a) a divalent group comprising a bioorthogonal functional group or (b) a divalent group comprising no bioorthogonal functional group;

R' is a portion formed by a reaction between a soluble protein and a reactive group; and T is a soluble protein, the soluble protein comprising one or more specific amino acid residues in a target region consisting of 1 to 50 continuous amino acid residues and comprising five or more of the specific amino acid residues in a non-target region other than the target region, and a structural unit represented by L1-B-R' binding to one or more of the specific amino acid residues contained in the target region of the soluble protein with 30% or more regioselectivity or a salt thereof.

The present invention also provides a method for producing a soluble protein regioselectively having a bioorthogonal functional group(s) or a salt thereof.

Conventional methods cannot produce the soluble protein regioselectively having a bioorthogonal functional group(s) or a salt thereof described above; the method developed by the inventors of the present invention can produce such a soluble protein regioselectively having a bioorthogonal functional group(s) or a salt thereof. The definitions, examples, and preferred examples of elements such as the bioorthogonal functional group, the regioselectivity, the soluble protein, the target region, and the linker, (i') and (ii') in L1, (a) and (b) in B, R', and T, and partial technical elements of those elements are similar to those described above. The details of the process of the method of production are also similar to those described in "4. Method for Producing Soluble Protein Having Bioorthogonal functional group or Salt thereof" except that the regioselectivity and technical elements related thereto (e.g., the target region) are essential elements.

7. Soluble Protein Regioselectively Having Functional Substance or Salt Thereof and Method for Producing Same The present invention also provides a soluble protein regioselectively having a functional substance(s) or a salt thereof. The soluble protein or salt thereof of the present invention regioselectively having a functional substance(s) is a soluble protein regioselectively having a functional substance(s) or a salt thereof, the soluble protein comprising one or more specific amino acid residues in a target region consisting of 1 to 50 continuous amino acid residues and comprising five or more of the specific amino acid residues in a non-target region other than the target region, and the functional substance binding to the one or more specific amino acid residues contained in the target region with 30% or more regioselectivity through a linker comprising no peptide portion.

In a specific embodiment, the soluble protein or salt thereof of the present invention regioselectively having a functional substance(s) may be a soluble protein regioselectively having a functional substance(s) represented by the following Formula (V):

$$F\text{-}(L1\text{-}B)'\text{-}R'\text{-}T \qquad (V)$$

wherein

L1 is (i') a monovalent group comprising a bioorthogonal functional group or (ii') a monovalent group comprising no bioorthogonal functional group;

B is (a) a divalent group comprising a bioorthogonal functional group or (b) a divalent group comprising no bioorthogonal functional group;

a structural unit represented by (L1-B)' is a divalent structural unit comprising a portion formed by a reaction between a functional substance and either one or both of the bioorthogonal functional groups in (i') and (a);

F is a functional substance;

R' is a portion formed by a reaction between a soluble protein and a reactive group; and T is a soluble protein, the soluble protein comprising one or more specific amino acid residues in a target region consisting of 1 to 50 continuous amino acid residues and comprising five or more of the specific amino acid residues in a non-target region other than the target region, and a structural unit represented by F-(L1-B)'—R' binding to the one or more specific amino acid residues contained in the target region of the soluble protein with 30% or more regioselectivity or a salt thereof.

The present invention also provides a method for producing a soluble protein regioselectively having a functional substance or a salt thereof.

Conventional methods cannot produce the soluble protein regioselectively having a functional substance(s) or a salt thereof described above; the method developed by the inventors of the present invention can produce such a soluble protein regioselectively having a functional substance(s) or a salt thereof. The definitions, examples, and preferred examples of elements such as the functional substance, the regioselectivity, the soluble protein, the target region, and the linker, (i') and (ii') in L1, (a) and (b) in B, (L1-B)', F, R', and T, and partial technical elements of those elements are similar to those described above. The details of the process of the method of production are also similar to those described in "5. Method for Producing Soluble Protein Having Functional substance or Salt thereof" except that the regioselectivity and technical elements related thereto (e.g., the target region) are essential elements.

8. Salt

In the present invention, examples of the salt include salts with inorganic acids, salts with organic acids, salts with inorganic bases, salts with organic bases, and salts with amino acids. Examples of salts with inorganic acids include salts with hydrogen chloride, hydrogen bromide, phosphoric acid, sulfuric acid, and nitric acid. Examples of salts with organic acids include salts with formic acid, acetic acid, trifluoroacetic acid, lactic acid, tartaric acid, fumaric acid, oxalic acid, maleic acid, citric acid, succinic acid, malic acid, benzenesulfonic acid, and p-toluenesulfonic acid. Examples of salts with inorganic bases include salts with alkali metals (e.g., sodium and potassium), alkaline-earth metals (e.g., calcium and magnesium), other metals such as zinc and aluminum, and ammonium. Examples of salts with organic bases include salts with trimethylamine, triethylamine, propylenediamine, ethylenediamine, pyridine, ethanolamine, monoalkyl ethanolamine, dialkyl ethanolamine, diethanolamine, and triethanolamine. Examples of salts with amino acids include salts with basic amino acids (e.g., arginine, histidine, lysine, and ornithine) and acidic amino acids (e.g., aspartic acid and glutamic acid). The salt is preferably a salt with an inorganic acid (e.g., hydrogen chloride) or a salt with an organic acid (e.g., trifluoroacetic acid).

9. Uses

The compound or salt thereof of the present invention having an affinity substance to a soluble protein, a cleavable portion, and a reactive group is useful for regioselective modification of a soluble protein, for example. Consequently, the present invention provides a reagent of modifying a soluble protein regioselectively, comprising a compound having an affinity substance to a soluble protein, a cleavable portion, and a reactive group or a salt thereof.

The reagent of the present invention which modifies a soluble protein regioselectively may be provided in the form of a composition further comprising other components. Examples of such other compounds include solutions and stabilizers (e.g., antioxidants and preservatives). Among solutions, aqueous solutions are preferred. Examples of aqueous solutions include water (e.g., distilled water, sterilized distilled water, purified water, and a physiological saline solution) and buffers (e.g., an aqueous phosphoric acid solution, a Tris-hydrochloric acid buffer, a carbonic acid-bicarbonic acid buffer, an aqueous boric acid solution, a glycine-sodium hydroxide buffer, and a citric acid buffer); buffers are preferred. The pH of solutions is e.g., 5.0 to 9.0 and preferably 5.5 to 8.5. The reagent of the present invention can be provided in a liquid form or a powder form (e.g., freeze-dried powder).

The soluble protein or salt thereof of the present invention (regioselectively) having an affinity substance to a soluble protein and a cleavable portion, the conjugate or salt thereof of the present invention (regioselectively) having an affinity substance to a soluble protein, a cleavable portion, a functional substance(s), and a soluble protein, and the soluble protein or salt thereof of the present invention (regioselectively) having a bioorthogonal functional group(s) are useful as intermediates for preparing a soluble protein (regioselectively) having a functional substance(s) or a salt thereof, for example.

The soluble protein or salt thereof of the present invention (regioselectively) having a functional substance(s) is useful as pharmaceuticals or reagents (e.g., diagnostic reagents and reagents for research), for example. When the soluble protein is an antibody in particular, the antibody or salt thereof of the present invention (regioselectively) having a functional substance(s) is suitable for these uses.

In particular, the antibody or salt thereof of the present invention (regioselectively) having a functional substance(s) is useful as pharmaceuticals. It is reported as described above that when the number of bonds and the bond positions of a drug of an antibody drug conjugate (ADC) are changed, pharmacokinetics, a releasing rate of the drug, and effects change. Given these circumstances, next-generation ADCs are required to control the number and positions of a drug to be conjugated. It is believed that when the number and positions are constant, the problems of expected efficacy, variations in conjugate medicines, and lot difference, or what is called regulation, will be solved. The antibody or salt thereof of the present invention having a functional substance(s) can solve such a problem of regulation. Consequently, the antibody or salt thereof of the present invention having a functional substance(s) may be provided in the form of a pharmaceutical composition. The pharmaceutical composition may comprise a pharmaceutically allowable carrier in addition to the soluble protein having a functional substance(s) or a salt thereof. Examples of the pharmaceutically allowable carrier include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrators such as starch, carboxymethylcellulose, hydroxypropyl starch, sodium hydrogencarbonate, calcium phosphate, and calcium citrate; lubricants such as magnesium stearate, Aerosil, talc, sodium lauryl sulfate; aromatics such as citric acid, menthol, glycyl lysine ammonium salts, glycine, and orange powder; preservatives such as sodium benzoate, sodium hydrogen sulfite, methylparaben, and propylparaben; stabilizers such as citric acid, sodium citrate, and acetic acid, suspensions such as methylcellulose, polyvinylpyrrolidone, and aluminum stearate; dispersants such as surfactants; diluents such as water, a physiological saline solution, and orange juice; and base waxes such as cacao butter, polyethylene glycol, and refined kerosene. The antibody or salt thereof of the present invention having a functional substance(s) may also have any modification (e.g., PEGylation) achieving stability.

Examples of preparations suitable for oral administration include liquid medicines dissolving an effective amount of a ligand in a diluted solution such as water, a physiological saline solution, or orange juice; capsules, sachets, and tablets comprising an effective amount of a ligand as a solid or granules; suspension medicines suspending an effective amount of an active ingredient in an appropriate dispersion medium; and emulsions dispersing a solution dissolving an effective amount of an active ingredient in an appropriate dispersion medium to be emulsified.

The pharmaceutical composition is suitable for nonoral administration (e.g., intravenous injection, hypodermic injection, intramuscular injection, local injection, and intraperitoneal administration). Examples of the pharmaceutical composition suitable for such nonoral administration include aqueous or nonaqueous, isotonic, aseptic injection medicines, which may comprise an antioxidant, a buffer, a bacteriostat, a tonicity agent, or the like. Examples thereof also include aqueous or nonaqueous, aseptic suspension medicines, which may comprise a suspension, a solubilizing agent, a thickener, a stabilizer, an antiseptic, or the like.

The dose of the pharmaceutical composition, which varies by the type and activity of an active ingredient, the severity of diseases, an animal type as a subject to be dosed, the drug receptivity, body weight, and age of a subject to be dosed, or the like, can be set as appropriate.

Other features of the invention will become apparent in the course of the following descriptions of exemplary embodiments which are given for illustration of the invention and are not intended to be limiting thereof.

EXAMPLES

Example 1: Synthesis of IgG1 Fc-Binding Peptide (1) Synthesis of IgG1 Fc-Binding Peptide
(1-1) Synthesis of Affinity Substance to Soluble Protein (Peptide of Ac-RGNCAYHKGQLVWCTYH-NH$_2$ (SEQ ID NO: 39))

A peptide of Ac-RGNCAYHKGQLVWCTYH-NH$_2$ (SEQ ID NO: 39) as an affinity substance to a soluble protein was synthesized by Fmoc solid phase synthesis. For a peptide synthesizing apparatus, Syro wave manufactured by Biotage was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration. They were dissolved in a 0.1% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.1% of trifluoroacetic acid, and the fractions were determined by LC-MS. A fraction comprising a product was collected, was concentrated under reduced pressure to remove only acetonitrile, and was freeze-dried.

MS (ESI) m/z: z=3 693 [M+3H]$^{3+}$, z=4 520 [M+4H]$^{4+}$ (1-2) Formation of Intramolecular Disulfide Bond Between Cys at Position 4 and Position 14 in Peptide of Ac-RGNCAYHKGQLVWCTYH-NH$_2$ (SEQ ID NO: 39)

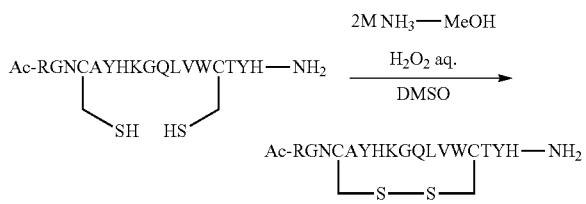

The amino acid sequence is SEQ ID NO: 39.

The peptide synthesized in (1-1) was dissolved in DMSO to be 100 mM, then 2 equivalents of 2M NH$_3$-MeOH and 1 equivalent of a hydrogen peroxide solution were added thereto, and the solution was stirred at room temperature for 12 hours. A 0.1% aqueous trifluoroacetic acid solution was added to the reaction solution to stop the reaction, fractions were eluted by reversed phase preparative chromatography, and then the fractions were determined by LC-MS. A fraction comprising a product was collected, was concentrated under reduced pressure to remove only acetonitrile, and was freeze-dried, giving a scale of 5 mg to 100 mg with a yield of 90% or more in all cases.

MS (ESI) m/z: z=3 692 [M+3H]$^{3+}$, z=4 519 [M+4H]$^{4+}$

Example 2: Synthesis of Cleavable Linker and Coupling Thereof with IgG1 Fc-Binding Peptide (2) Synthesis of Cleavable Linker and Coupling thereof with Peptide
(2-1) Synthesis of Thioester Linker and Coupling thereof with Peptide
(2-1-1) Synthesis of Thioester Linker

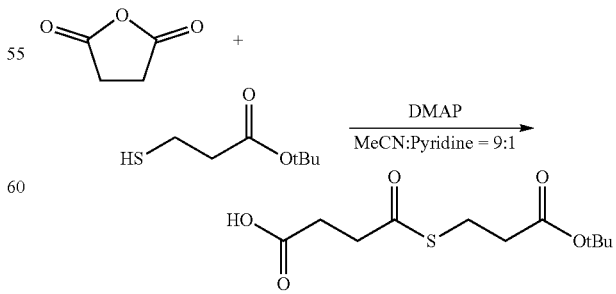

Succinic acid anhydride (0.2 g, 2 mmol) and N,N'-dimethylaminopyridine (12.2 mg, 0.1 mmol) were dissolved in an acetonitrile:pyridine=9:1 solvent and were purged with argon gas. tert-Butyl-3-sulfanyl propanoate (0.3 g, 2.2 mmol) was added thereto, and the solution was stirred at room temperature for 16 hours. The reaction solution was diluted with ethyl acetate and was washed with a 0.1 M aqueous hydrochloric acid solution, water, and brine, and then magnesium sulfate anhydride was added thereto, and allowed to stand for 5 minutes. Magnesium sulfate was removed by filtration, and concentration under reduced pressure was performed to obtain 4-(3-tert-butoxy-3-oxo-propyl)sulfanyl-4-oxo-butanoic acid (0.47 g, 1.8 mmol).

$^1$H NMR (400 MHz, Chloroform-d) δ 3.12 (t, J=7.0 Hz, 2H), 2.91 (t, J=6.9 Hz, 2H), 2.72 (t, J=6.9 Hz, 2H), 2.55 (t, J=7.0 Hz, 2H), 1.46 (s, 9H).

MS (ESI) m/z: 263 [M+H]

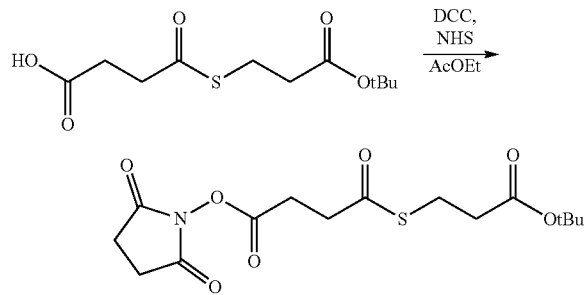

Ethyl acetate in an amount of 5 mL was added to and dissolved in 4-(3-tert-butoxy-3-oxo-propyl)sulfanyl-4-oxo-butanoic acid (0.47 g, 1.8 mmol). Then N,N'-dicyclohexyl-carbodiimide (0.39 g, 1.9 mmol) and N-hydroxysuccinimide (0.22 g, 1.9 mmol) were added thereto, and the solution was stirred for 1 hour. The formed white crystals were filtered, and the mother liquid was concentrated under reduced pressure to obtain (2,5-dioxopyrrolidin-1-yl) 4-(3-tert-butoxy-3-oxo-propyl)sulfanyl-4-oxo-butanoate (0.61 g, 1.7 mmol).

MS (ESI) m/z: 360 [M+H]

(2-1-2) Coupling between Thioester Linker and Peptide

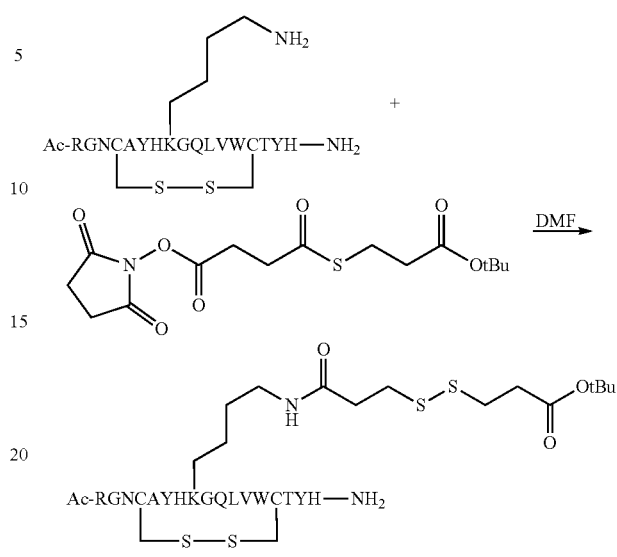

The amino acid sequence is SEQ ID NO: 39.

The peptide of Ac-RGNCAYHKGQLVWCTYH-NH$_2$ (SEQ ID NO: 39) synthesized in Example 1-2 (42 mg, 20.3 µmol, the 4th and 14th of two cysteines form a disulfide bond in the molecule) was dissolved in 1 mL of N,N'-dimethylformamide and was added to a solution dissolving (2,5-dioxopyrrolidin-1-yl) 4-(3-tert-butoxy-3-oxo-propyl) sulfanyl-4-oxo-butanoate (0.61 g, 1.7 mmol) in 1 mL of acetonitrile. The solution was stirred at room temperature for 12 hours, a 0.1% trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled tBu compound (41.7 mg, 18 µmol).

MS (ESI) m/z: z=3 773 [M+3H]$^{3+}$, z=4 580 [M+4H]$^{4+}$

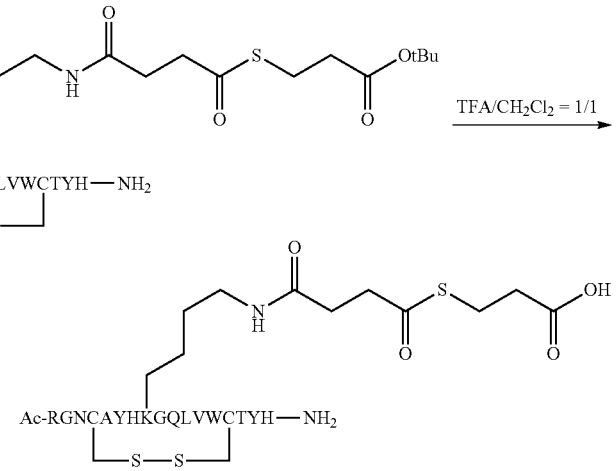

The amino acid sequence is SEQ ID NO: 39.

The peptide- and linker-coupled compound (41.7 mg, 18 µmol) was dissolved in 1.0 mL of dichloromethane, and 1.0 mL of trifluoroacetic acid was added thereto, and the solution was stirred at room temperature for 1 hour. After performing concentration under reduced pressure, a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled carboxylic compound (40.7 mg, 18 µmol).

MS (ESI) m/z: z=3 755 [M+3H]$^{3+}$, z=4 566 [M+4H]$^{4+}$

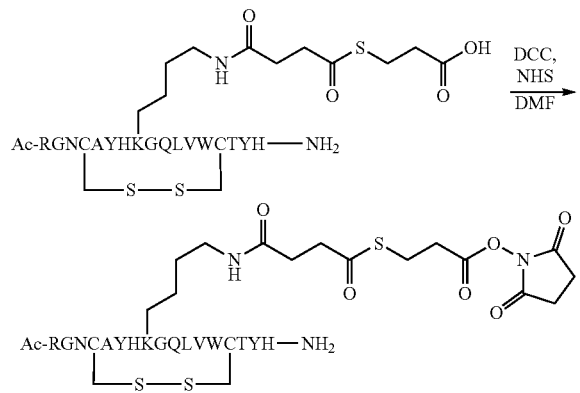

The amino acid sequence is SEQ ID NO: 39.

The peptide- and linker-coupled carboxylic compound (40.7 mg, 18 µmol) was dissolved in 1 mL of N,N'-dimethylformamide, N,N'-dicyclohexylcarbodiimide (37.1 mg, 0.18 mmol) and N-hydroxysuccinimide (20.7 mg, 0.18 mmol) were added thereto, and the solution was stirred for 1 hour. The formed white crystals were filtered, a 0.1% aqueous trifluoroacetic acid solution was added to the mother liquid, and fractions were eluted by reversed phase preparative chromatography. A fraction comprising a product was collected, was concentrated under reduced pressure to remove only acetonitrile, and was freeze-dried to obtain the peptide- and thioester linker-coupled NHS-activation compound (5.2 mg, 2.24 µmol).

MS (ESI) m/z: z=3 787 [M+3H]$^{3+}$, z=4 590 [M+4H]$^{4+}$ (2-2) Coupling between Disulfide Linker and Peptide mmol, the 4th and 14th of two cysteines form a disulfide bond in the molecule) was dissolved in 1 mL of N,N'-dimethylformamide and was added to a solution dissolving di(N-succinimidyl) 3,3'-dithiodipropionate (0.2 g, 0.48 mmol) in 1 mL, and the solution was stirred at room temperature for 12 hours. A 0.5% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and disulfide linker-coupled NHS-activation compound (8.6 mg, 3.63 µmol).

MS (ESI) m/z: z=3 789 [M+3H]$^{3}$, z=4 592 [M+4H]$^{4+}$ (2-3) Synthesis of Acetal Linker and Coupling thereof with Peptide (2-3-1) Synthesis of Acetal Linker

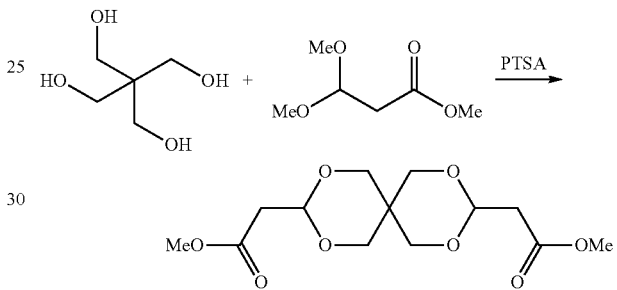

Pentaerythritol (1.98 g, 14.3 mmol), methyl dimethoxypropionate (6.0 g, 31.7 mmol), and p-toluenesulfonic acid monohydrate (33.0 mg, 0.143 mmol) were mixed, and the mixture was stirred at 130° C. for 16 hours. After 16 hours, the temperature was returned to room temperature, and the precipitated crystals were collected by filtration to obtain

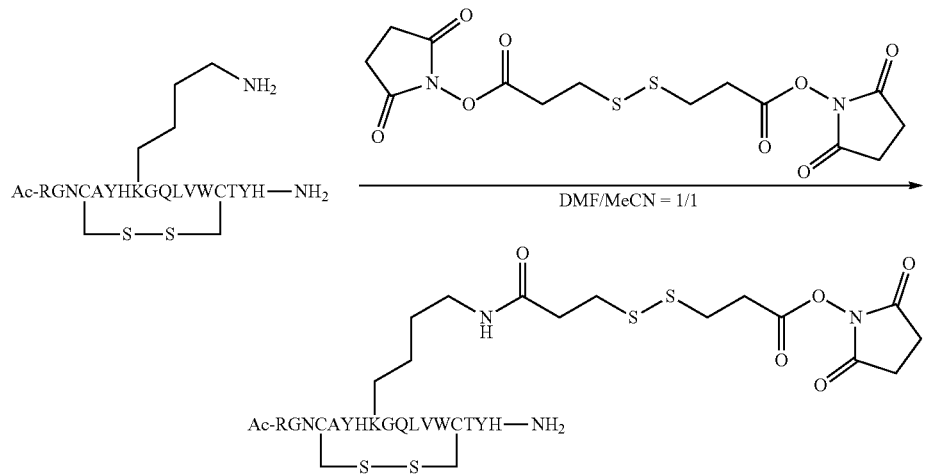

The amino acid sequence is SEQ ID NO: 39.

The peptide of Ac-RGNCAYHKGQLVWCTYH-NH$_2$ (SEQ ID NO: 39) synthesized in Example 1-2 (10 mg, 4.8 methyl 2-[9-(2-methoxy-2-oxo-ethyl)-2,4,8,10-tetraoxospiro[5.5]undecan-3-yl]acetate (3.04 g, 10 mmol).

MS (ESI) m/z: 305 [M+H]$^+$

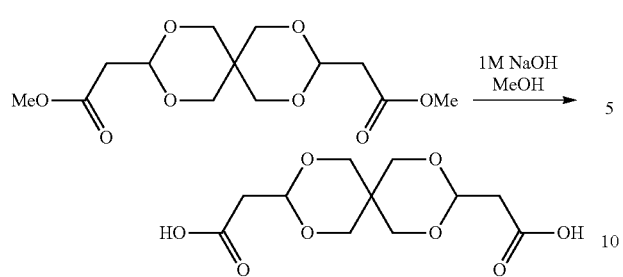

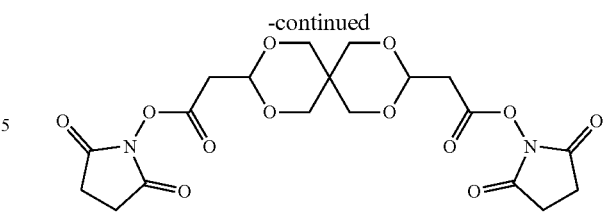

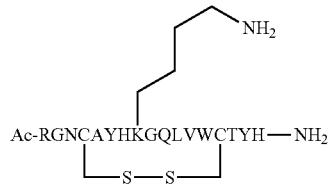

Methyl 2-[9-(2-methoxy-2-oxo-ethyl)-2,4,8,10-tetraoxospiro[5.5]undecan-3-yl]acetate (50 mg, 0.164 mmol) was dissolved in 1 mL of methanol, 0.49 mL of 1 M NaOH aq. was added thereto under ice-cooling, the temperature was raised to room temperature, and the solution was stirred for 2 hours. A cation exchange resin was added to be neutralized, then the resin was removed by filtration to obtain 2-[9-(2-methoxy-2-oxo-ethyl)-2,4,8,10-tetraoxospiro[5.5]undecan-3-yl]acetic acid (32 mg, 0.116 mmol).

$^1$H NMR (400 MHz, DMSO-d$_6$) δ 4.85 (t, J=5.4 Hz, 2H), 4.26 (dd, J=11.3, 2.4 Hz, 2H), 3.67-3.61 (m, 2H), 3.60 (s, 8H), 3.42 (d, J=11.6 Hz, 2H), 2.69-2.56 (m, 4H).

MS (ESI) m/z: 277 [M+H]$^+$

In 1 mL of ethyl acetate, 2-[9-(2-methoxy-2-oxo-ethyl)-2,4,8,10-tetraoxospiro[5.5]undecan-3-yl]acetic acid (32 mg, 0.116 mmol) was dissolved, N,N'-dicyclohexylcarbodiimide (37.1 mg, 0.18 mmol) and N-hydroxysuccinimide (20.7 mg, 0.18 mmol) were added thereto, and the solution was stirred for 1 hour. The formed white crystals were filtered, the mother liquid was concentrated under reduced pressure, then water was added thereto, and fractions were eluted by reversed phase preparative chromatography with neutral acetonitrile and water as solvents. A fraction comprising a product was collected, was concentrated under reduced pressure to remove only acetonitrile, and was freeze-dried to obtain (2,5-dioxopyrrolidin-1-yl) 2-[9-(2-methoxy-2-oxo-ethyl)-2,4,8,10-tetraoxospiro[5.5]undecan-3-yl]acetate (13 mg, 27.6 μmol).

$^1$H NMR (400 MHz, DMSO-d$_6$) δ 4.79 (t, J=5.3 Hz, 2H), 4.24 (dd, J=11.2, 2.3 Hz, 2H), 3.60-3.48 (m, 4H), 3.34 (d, J=11.5 Hz, 2H), 2.33 (d, J=5.3 Hz, 4H).

MS (ESI) m/z: 471 [M+H]

(2-3-2) Coupling between Acetal Linker and Peptide

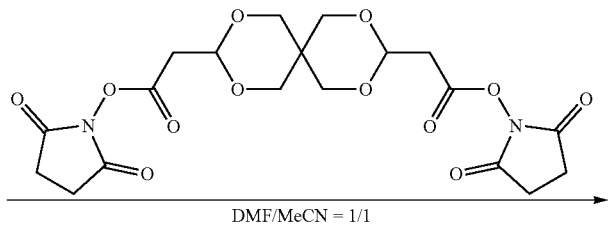

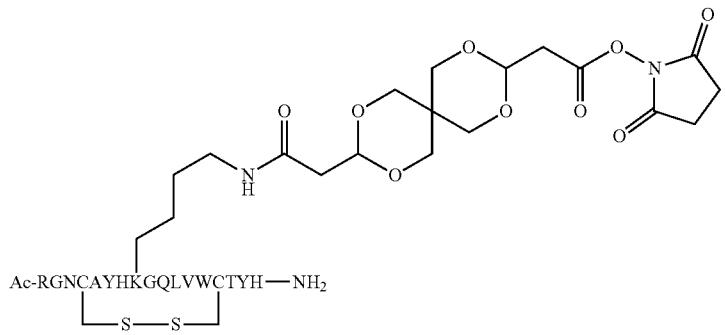

The amino acid sequence is SEQ ID NO: 39.

The peptide of Ac-RGNCAYHKGQLVWCTYH-NH$_2$ (SEQ ID NO: 39) synthesized in Example 1-2 (10 mg, 4.8 μmol, the 4th and 14th of two cysteines form a disulfide bond in the molecule) was dissolved in 1 mL of N,N'-dimethylformamide and was added to a solution dissolving (2,5-dioxopyrrolidin-1-yl) 2-[9-(2-methoxy-2-oxo-ethyl)-2,4,8,10-tetraoxospiro[5.5]undecan-3-yl]acetate (13 mg, 27.6

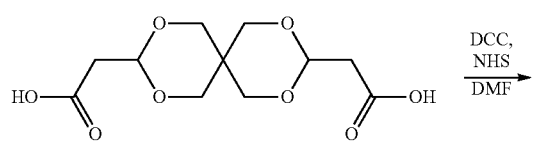

µmol) in 1 mL, and the solution was stirred at room temperature for 12 hours. Water was added thereto, and fractions were eluted by reversed phase preparative chromatography with neutral acetonitrile and water as solvents. A fraction comprising a product was collected, was concentrated under reduced pressure to remove only acetonitrile, and was freeze-dried to obtain the peptide- and acetal linker-coupled NHS-activation compound (8.6 mg, 3.63 µmol).

MS (ESI) m/z: z=3 810 [M+3H]$^3$, z=4 608 [M+4H]$^{4+}$

Example 3: Specific Modification of IgG1 Fc with IgG1 Fc-Binding Peptide Reagent and Analysis Thereof by MALDI-TOFMS (3-1) Specific Modification of IgG1 Fc with Thioester Linker-Binding Peptide Reagent and Analysis Thereof by MALDI-TOFMS For IgG1 Fc, IgG1l Fc, Human, Recombinant, Carrier-free manufactured by R&D (product No: 110-HG-100) was used. The peptide- and thioester linker-coupled NHS-activation compound synthesized in (2-1) of Example 2 was dissolved in N,N'-dimethylformamide to be 0.4 mM. IgG1 Fc in an amount of 15 µg was dissolved in 15 µL of a 0.1 M sodium acetate buffer (pH 4.7), 7 µL of a 0.4 mM peptide reagent (5 equivalents with respect to IgG1 Fc) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by MALDI-TOFMS; for the raw material IgG1 Fc, a peak was observed at m/z 28,270, whereas for a product, a peak was observed at m/z 30,532 with one binding peptide introduced.

(3-2) Specific Modification of IgG1 Fc with Disulfide Linker-Binding Peptide Reagent and Analysis Thereof by MALDI-TOFMS For IgG1 Fc, IgG1 Fc, Human, Recombinant, Carrier-free manufactured by R&D (product No: 110-HG-100) was used. The peptide- and disulfide linker-coupled NHS-activation compound synthesized in (2-2) of Example 2 was dissolved in N,N'-dimethylformamide to be 0.4 mM. IgG1 Fc in an amount of 20 µg was dissolved in 40 µL of a 0.1 M sodium acetate buffer (pH 4.7), 10.7 µL of a 0.4 mM peptide reagent (6 equivalents with respect to IgG1 Fc) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by MALDI-TOFMS; for the raw material IgG1 Fc, a peak was observed at m/z 28,183, whereas for a product, a peak was observed at m/z 30,418 with one binding peptide introduced.

(3-3) Specific Modification of IgG1 Fc with Acetal Linker-Binding Peptide Reagent and Analysis Thereof by MALDI-TOFMS For IgG1 Fc, IgG1 Fc, Human, Recombinant, Carrier-free manufactured by R&D (product No: 110-HG-100) was used. The peptide- and acetal linker-coupled NHS-activation compound synthesized in (2-3) of Example 2 was dissolved in N,N'-dimethylformamide to be 0.4 mM. IgG1 Fc in an amount of 20 g was dissolved in 40 µL of a 0.1 M sodium acetate buffer (pH 4.7), 10.7 µL of a 0.4 mM peptide reagent (6 equivalents with respect to IgG1 Fc) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by MALDI-TOFMS; for the raw material IgG1 Fc, a peak was observed at m/z 28,183, whereas for a product, a peak was observed at m/z 30,541 with one binding peptide introduced.

Example 4: Linker Cleavage of IgG1 Fc-Peptide Conjugate and Analysis Thereof by MALDI-TOFMS (4-1) Cleavage of Thioester Linker and Analysis Thereof by MALDI-TOFMS The IgG1 Fc-peptide thioester linker conjugate synthesized in (3-1) of Example 3 was dissolved in a 0.2 M PBS buffer (pH 7.0) and 40 µL of a 25 mM cysteine solution, and the solution was stirred at room temperature for 16 hours. The reaction solution was subjected to solvent substitution to a 9.57 mM PBS buffer (pH 7.0) with Amicon 10K to stop the reaction. The mass was measured by MALDI-TOFMS; for the conjugate with one binding peptide introduced as the raw material, a peak was observed at m/z 30,541, whereas after reaction, a peak was observed at m/z 28,397.

(4-2) Cleavage of Thioester Linker and Analysis thereof by MALDI-TOFMS

The IgG1 Fc-peptide disulfide linker conjugate synthesized in (3-2) of Example 3 was dissolved in 40 µL of a 0.2 M PBS buffer (pH 7.0), 12.5 µL of 10 mM D,L-dithiothreitol (10 equivalents with respect to Fc) was added thereto, and the solution was stirred at room temperature for 16 hours. The reaction solution was subjected to solvent substitution to a 9.57 mM PBS buffer (pH 7.0) with Amicon 10K to stop the reaction. The mass was measured by MALDI-TOFMS; for the conjugate with one binding peptide introduced as the raw material, a peak was observed at m/z 30,418, whereas after reaction, a peak was observed at m/z 28,183.

(4-3) Cleavage of Acetal Linker and Analysis thereof by MALDI-TOFMS

The IgG1 Fc-peptide acetal linker conjugate synthesized in (3-3) of Example 3 is dissolved in any buffer (pH 3.0 to pH 6.0), and the solution is stirred at room temperature, whereby the acetal structure decomposes to leave an aldehyde on IgG1 Fc; the mass thereof can be measured by MALDI-TOFMS.

Example 5: Specific Modification of Anti-HER2 IgG Antibody Trastuzumab and Anti-CD20 Antibody Rituximab and Analysis Thereof by MALDI-TOFMS and HIC-HPLC (5-1) Specific Modification of Anti-HER2 IgG Antibody Trastuzumab and Analysis Thereof by MALDI-TOFMS The peptide- and disulfide linker-coupled NHS-activation compound synthesized in (2-2) of Example 2 was dissolved in N,N'-dimethylformamide to be 0.4 mM. Anti-HER2 IgG antibody trastuzumab (Chugai Pharmaceutical) in an amount of 500 µg was dissolved in 200 µL of a 50 mM sodium acetate buffer (pH 5.5), 50.7 µL of a 0.4 mM peptide reagent (6 equivalents with respect to the antibody) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by MALDI-TOFMS; for the raw material trastuzumab, a peak was observed at m/z 147,569, whereas for a product, a peak was observed at m/z 151,848 with two binding peptides introduced.

(5-2) HIC-HPLC Analysis of Specific Modification of Anti-HER2 IgG Antibody Trastuzumab The antibody-peptide conjugate produced in (5-1) and a raw material antibody were analyzed by HIC. For a column, Butyl-NPR (TOSOH) 4.6×350 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
- a: trastuzumab+12 equivalents of the peptide reagent (solvent substitution with Amicon 10K after reaction);
- b: trastuzumab+12 equivalents of the peptide reagent;
- c: trastuzumab+6 equivalents of the peptide reagent;
- d: a trastuzumab raw material;
- e: the peptide reagent alone; and
- f: DMF alone.

Figures 1, 2, 3:
Figure 2:
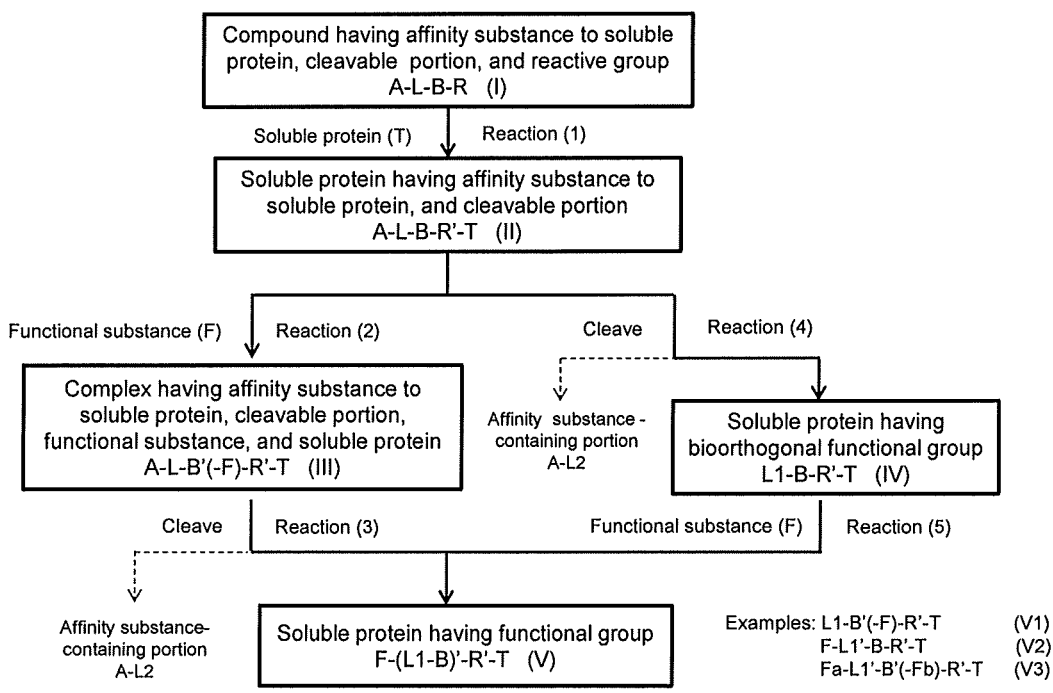
Figure 3:
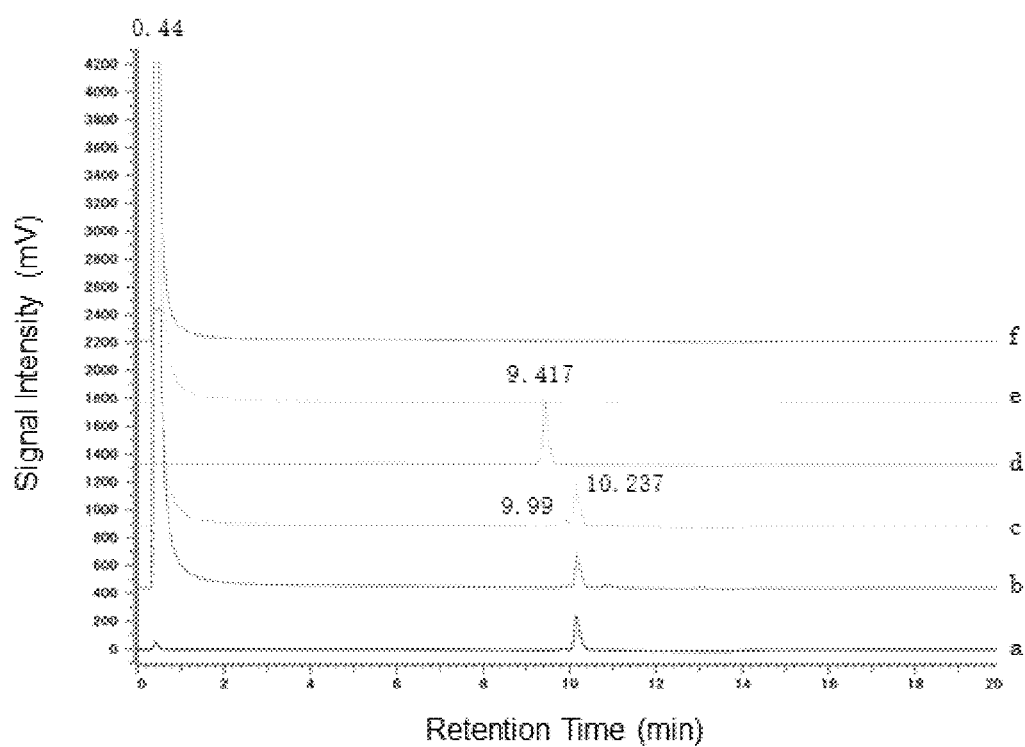
Figure 4:
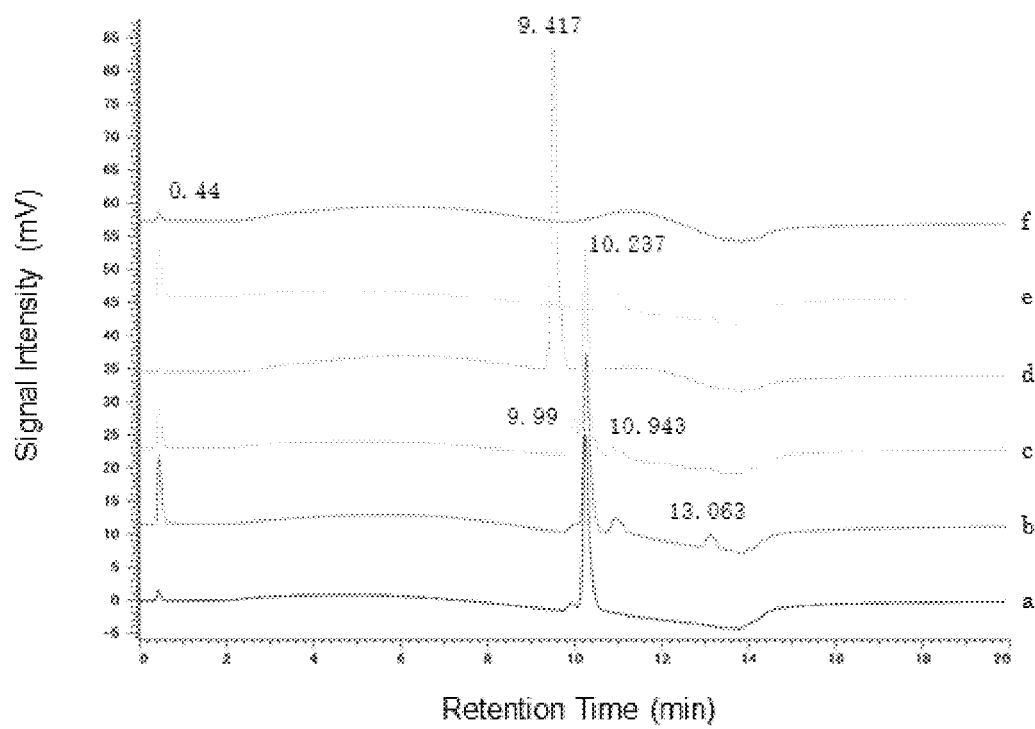
FIG. 4 is a diagram of HIC-HPLC analysis (detection: 280 nm) of anti-HER2 IgG antibody trastuzumab specifically modified with the peptide reagent (the peptide- and disulfide linker-coupled NHS-activation compound). Samples were reacted under conditions similar to those of FIG. 1.

It is revealed that a retention time of 9.417 minutes is attributed to the trastuzumab raw material, those of 10.943 minutes and 13.063 minutes are attributed to peaks derived from the peptide reagent, and that of 0.44 minute is attributed to DMF (FIGS. 3 and 4). When 6 equivalents of the peptide reagent were reacted with trastuzumab, the peak at 9.417 minutes disappeared, and peaks at 9.99 minutes and 10.237 minutes appeared (FIGS. 3 and 4). When 12 equivalents of the peptide reagent were added, the peak at 9.99 minutes disappeared, and it is believed that the peak at 9.99 minutes is attributed to a compound with one peptide introduced to trastuzumab (FIGS. 3 and 4). From analysis of the sample "a" by MALDI-TOFMS, a peak of trastuzumab with two peptide reagents introduced indicating an MS peak of m/z 151848 was observed as illustrated in (5-1) (FIGS. 3 and 4).

(5-3) Specific Modification of Anti-CD20 Antibody Rituximab and Analysis Thereof by MALDI-TOFMS The peptide- and disulfide linker-coupled NHS-activation compound synthesized in (2-2) of Example 2 was dissolved in N,N'-dimethylformamide to be 0.4 mM. Anti-CD20 antibody rituximab in an amount of 500 μg was dissolved in 200 μL of a 50 mM sodium acetate buffer (pH 5.5), 50.7 μL of a 0.4 mM peptide reagent (6 equivalents with respect to the antibody) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by MALDI-TOFMS; for the raw material rituximab, a peak was observed at m/z 144,002, whereas for a product, a peak was observed at m/z 148,169 with two binding peptides introduced.

(5-4) HIC-HPLC Analysis of Specific Modification of Anti-CD20 Antibody Rituximab The antibody-peptide conjugate produced in (5-3) and a raw material antibody were analyzed by HIC. For a column, Butyl-NPR (TOSOH) 4.6×350 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

The samples "a" to "f" were reacted under the following conditions:
- a: rituximab+12 equivalents of the peptide reagent (solvent substitution with Amicon 10K after reaction);
- b: rituximab+12 equivalents of the peptide reagent;
- c: rituximab+6 equivalents of the peptide reagent;
- d: a rituximab raw material;
- e: the peptide reagent alone; and
- f: DMF alone.

Figure 5:
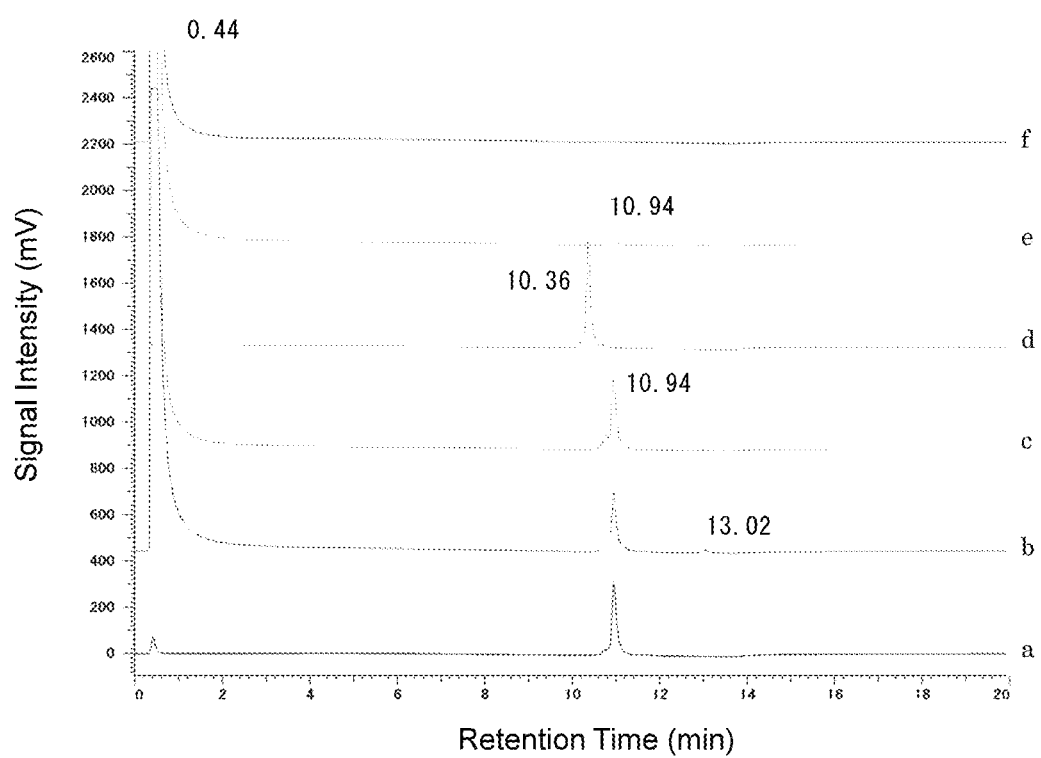
FIG. 5 is a diagram of HIC-HPLC analysis (detection: 225 nm) of anti-CD20 antibody rituximab specifically modified with the peptide reagent (the peptide- and disulfide linker-coupled NHS-activation compound). Samples were reacted under the following conditions: a: rituximab+12 equivalents of the peptide reagent (solvent substitution with Amicon 10K after reaction); b: rituximab+12 equivalents of the peptide reagent; c: rituximab+6 equivalents of the peptide reagent; d: a rituximab raw material; e: the peptide reagent alone; and f: DMF alone.
Figure 6:
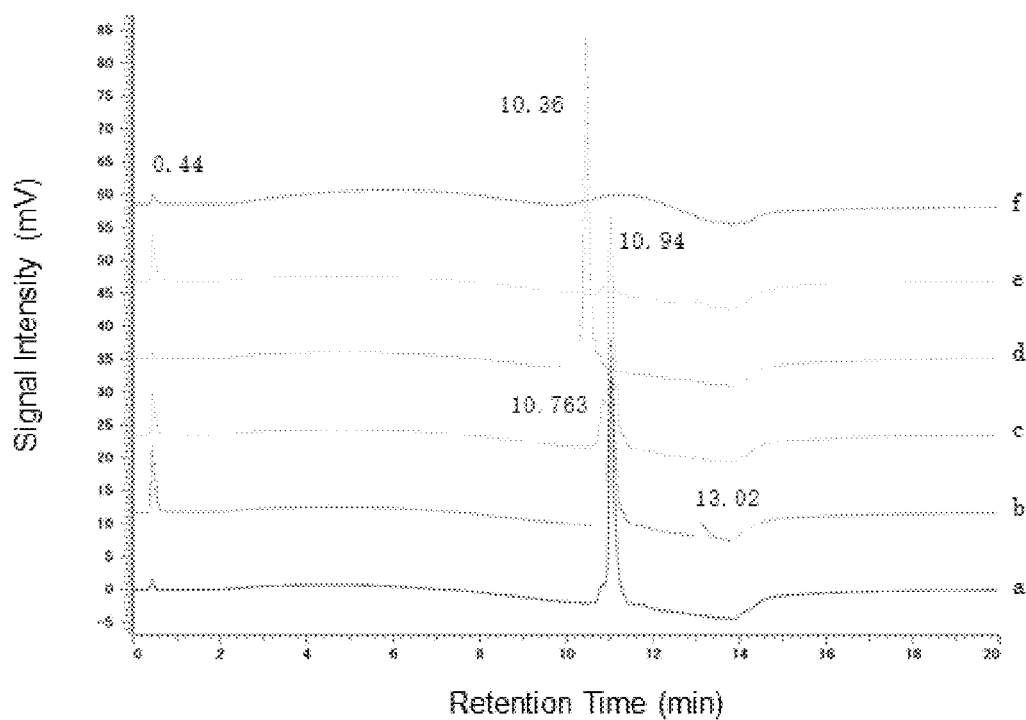
FIG. 6 is a diagram of HIC-HPLC analysis (detection: 280 nm) of anti-CD20 antibody rituximab specifically modified with the peptide reagent (the peptide- and disulfide linker-coupled NHS-activation compound). Samples were reacted under the following conditions: a: rituximab+12 equivalents of the peptide reagent (solvent substitution with Amicon 10K after reaction); b: rituximab+12 equivalents of the peptide reagent; c: rituximab+6 equivalents of the peptide reagent; d: a rituximab raw material; e: the peptide reagent alone; and f: DMF alone.

It is revealed that a retention time of 9.417 minutes is attributed to the rituximab raw material, those of 10.94 minutes and 13.02 minutes are attributed to peaks derived from the peptide reagent, and that of 0.44 minute is attributed to DMF (FIGS. 5 and 6). When 6 equivalents of the peptide reagent were reacted with rituximab, the peak at 10.36 minutes disappeared, and peaks at 10.763 minutes and 10.94 minutes appeared (FIGS. 5 and 6). When 12 equivalents of the peptide reagent were added, the peak at 10.763 minutes disappeared, and it is believed that the peak at 10.763 minutes is attributed to a compound with one peptide introduced to rituximab (FIGS. 5 and 6). From analysis of the sample "a" by MALDI-TOFMS, a peak of rituximab with two peptide reagents introduced which corresponds to m/z 148169 was observed as illustrated in (5-1) (FIGS. 5 and 6).

Example 6: Cleavage and Reoxidation of Trastuzumab-Peptide Conjugate and Rituximab-Peptide Conjugate and Analysis of Products Thereof by MALDI-TOFMS and RP-HPLC (6-1) Linker Cleavage and Reoxidation of Trastuzumab-Peptide Conjugate and Analysis of Product thereof by MALDI-TOFMS First, 400 μg of the trastuzumab-peptide conjugate synthesized in (5-1) of Example 5 was dissolved in a 60 mM phosphate buffer (pH 8.0) to be 72 μM, 10.0 μL of 20 mM D,L-dithiothreitol (60 equivalent with respect to the trastuzumab-peptide conjugate) was added thereto, and the solution was stirred at room temperature for 16 hours to cleave the disulfide bond in the linker.

Next, to again form the disulfide bond in the antibody cleaved together with the disulfide bond in the linker, a process of reoxidation was performed (Jagath R Junutula et al., NATURE BIOTECHNOLOGY, 26(8), 925-932 (2008)). Specifically, the reaction solution was subjected to solvent substitution to a 9.57 mM PBS buffer (pH 7.0) with Amicon 10K to make the concentration of the trastuzumab-peptide conjugate 18 μM, then 6.4 μL of 10 mM dehydroascorbate (20 equivalent with respect to the trastuzumab-peptide conjugate) was added thereto, and the solution was stirred for 3 hours to perform reoxidation. The mass was measured by MALDI-TOFMS; for a product, a peak was observed at m/z 145,329 with two thiopropionyl groups introduced.

(6-2) Analysis of Product Obtained by Linker Cleavage and Reoxidation of Trastuzumab-Peptide Conjugate by RP-HPLC The reaction of (6-1) was analyzed by RP-HPLC. For a column, TSK gel, Protein C4-300 (TOSOH) 4.6×150 mm 3.0 μm was used. Detection was performed with A_Buffer: 0.1% TFA, B_Buffer: 0.1% TFA, 80% ACN, a flow rate of 1.0 ml/min, a gradient of B 20%→60%, 20 minutes (data collection 30 minutes), a column temperature of 60° C., a thermostat temperature of 10° C., and a detector with two wavelengths of UV 225 nm (Ch1) and 280 nm (Ch2).

The samples "a" to "f" were reacted under the following conditions:
- a: trastuzumab;
- b: trastuzumab+6 equivalents of the peptide reagent;
- c: trastuzumab reduced with DTT;
- d: reduced with D,L-dithiothreitol with a buffer pH of 8.0 and an antibody concentration of 72 μM;
- e: after 3 hours of reoxidation of the sample "d" with dehydroascorbate; and f: after 24 hours of reoxidation of the sample "d" with dehydroascorbate.

Figure 7A:
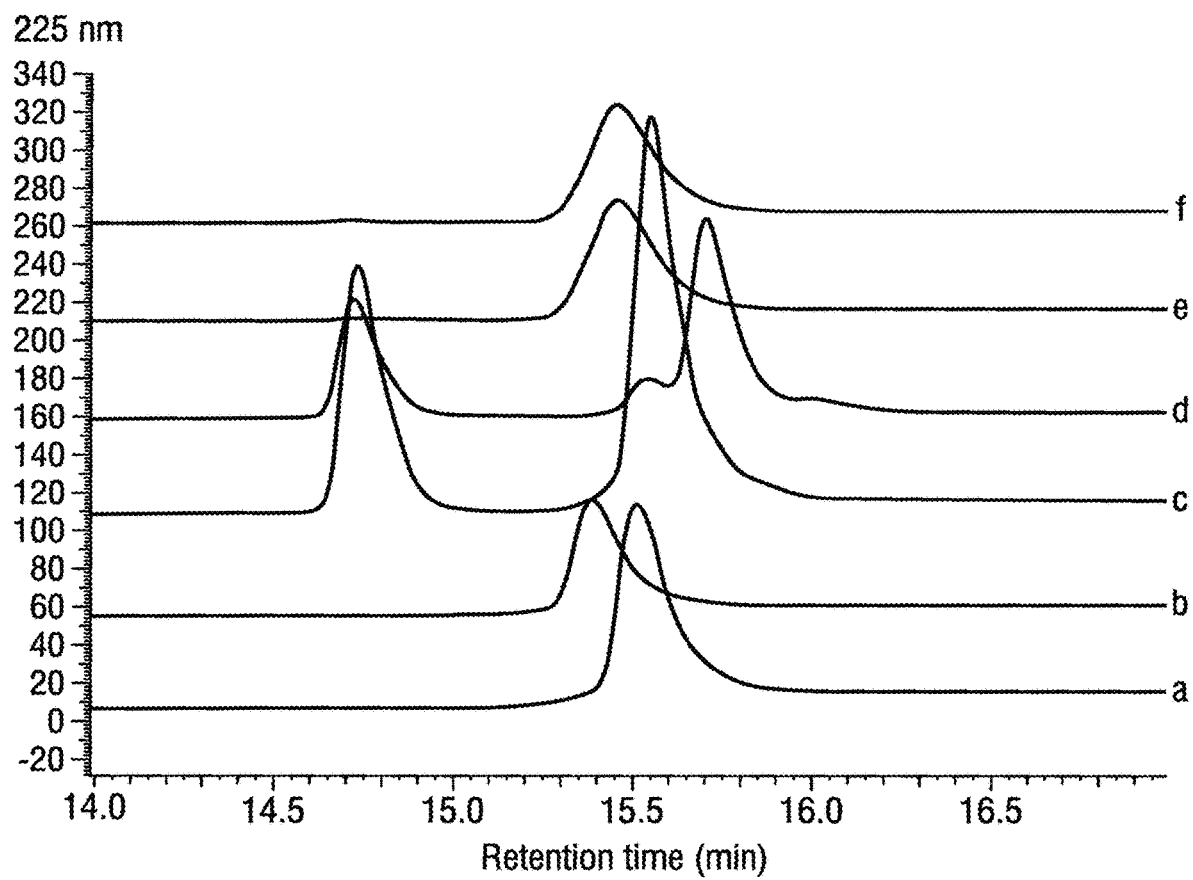
FIG. 7A and FIG. 7B are a diagram of analysis by reversed phase high-performance liquid chromatography (RP-HPLC) (detection: 225 nm and 280 nm) of a product obtained by linker cleavage and reoxidation of a trastuzumab-peptide conjugate: a: trastuzumab; b: trastuzumab+6 equivalents of the peptide reagent; c: trastuzumab reduced with DTT; d: reduced with D,L-dithiothreitol with a buffer pH of 8.0 and an antibody concentration of 72 µM; e: after 3 hours of reoxidation of d with dehydroascorbate; and f: after 24 hours of reoxidation of d with dehydroascorbate.
Figure 7B:
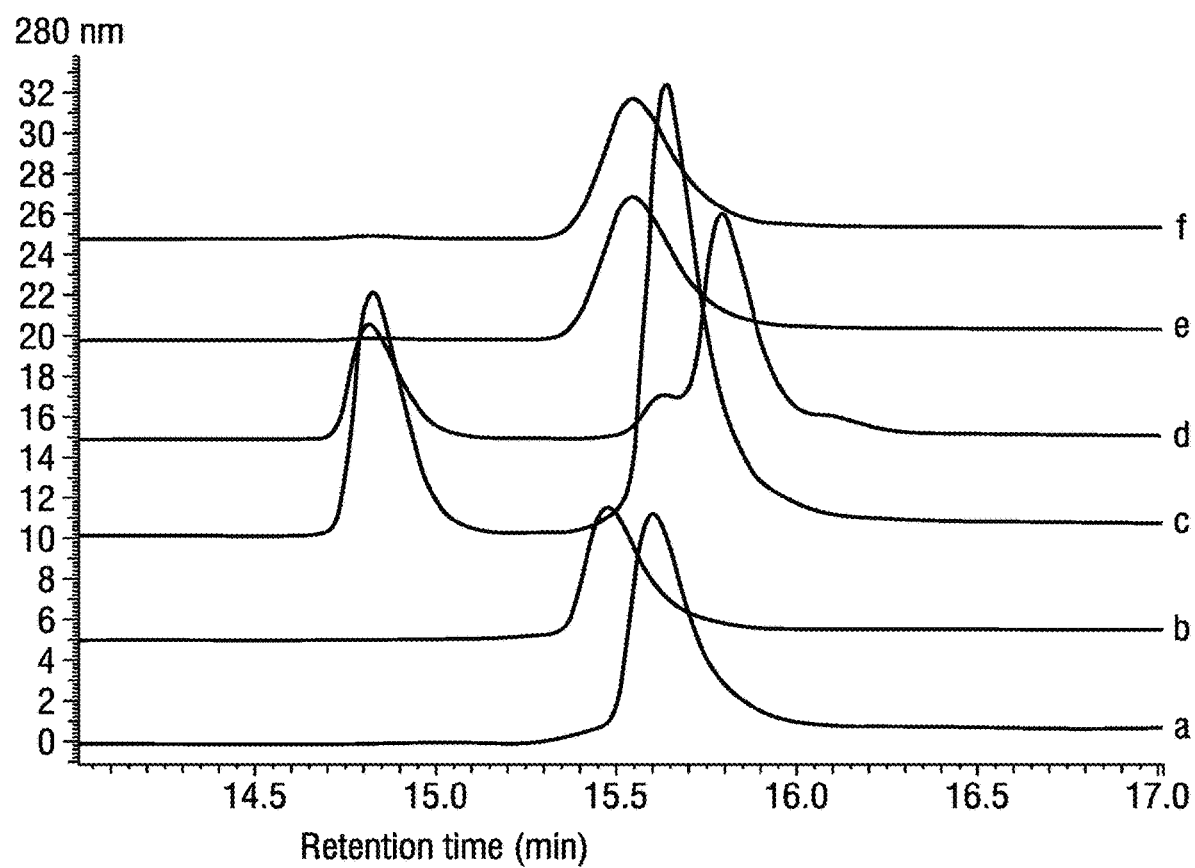

The reactions proceeded in order of the samples "b", "d", and "e" or "f"; after being decomposed into the light chain and the heavy chain (d), reoxidation with dehydroascorbate gave the samples "e" and "f" (FIG. 7A and FIG. 7B). From the retention times of the peaks, the light chain of trastuzumab and the light chain of the modified antibody appear at the same position, whereas the retention times of the heavy chains are different. Therefore, it is revealed that the heavy chain is modified (FIG. 7A and FIG. 7B).

(6-3) Linker Cleavage of Rituximab-Peptide Conjugate and Analysis Thereof by MALDI-TOFMS The rituximab-peptide conjugate synthesized in (5-3) of Example 5 in an amount of 400 µg was dissolved in a 60 mM phosphate buffer (pH 8.0) to be 72 µM, 10.0 µL of 20 mM D,L-dithiothreitol (60 equivalent with respect to the rituximab-peptide conjugate) was added thereto, and the solution was stirred at room temperature for 16 hours. The reaction solution was subjected to solvent substitution to a 9.57 mM PBS buffer (pH 7.0) with Amicon 10K to give a concentration of 18 µM, then 6.4 µL of 10 mM dehydroascorbate (20 equivalent with respect to the rituximab-peptide conjugate) was added thereto, and the solution was stirred for 3 hours to cleave the disulfide bond in the linker. The mass was measured by MALDI-TOFMS; for a product, a peak was observed at m/z 144,783 with two thiopropionyl groups introduced.

Example 7: Fluorescence Labelling of Thiol-Introduced Trastuzumab and Rituximab and Calculation of Fluorescence Labelling Rate (7-1) Fluorescence Labelling of Thiol-Introduced Trastuzumab and Calculation of Fluorescence Labelling Rate The thiol-introduced trastuzumab synthesized in (6-1) of Example 6 was dissolved in a 20 mM PBS buffer to be 0.3 mM, then 20 µL of DyLight 550 manufactured by Thermo Fisher (0.94 mM, dissolved in DMF) was added thereto, and the solution was stirred at room temperature for 12 hours. After reaction, a fluorescent dye was removed with Dye removal Column. Absorbance at 280 nm and 557 nm was measured with DU 800 SPECTROPHOTOMETER manufactured by BECKMAN COULTER. A fluorescence labelling rate was calculated from the absorbance to be 2.

(7-2) Fluorescence Labelling of Thiol-Introduced Rituximab and Calculation of Fluorescence Labelling Rate The thiol-introduced rituximab synthesized in (6-3) of Example 6 was dissolved in a 20 mM PBS buffer to be 0.3 mM, then 20 µL of DyLight 550 manufactured by Thermo Fisher (0.94 mM, dissolved in DMF) was added thereto, and the solution was stirred at room temperature for 12 hours. After reaction, a fluorescent dye was removed with Dye removal Column. Absorbance at 280 nm and 557 nm was measured with DU 800 SPECTROPHOTOMETER manufactured by BECKMAN COULTER. A fluorescence labelling rate was calculated from the absorbance to be 2.

Example 8: Peptide Mapping of Thiol-Introduced IgG1 Fc and Trastuzumab (8-1) Trypsin Treatment for Thiol-Introduced IgG1 Fc, Trastuzumab, and Rituximab A 100 mM ammonium hydrogencarbonate buffer in an amount of 40 µL comprising 8 M urea was dispensed to a 1.5 mL low-adsorptive micro test tube, 2 µL of 2% ProteaseMAX (a protease digestion promoter ProteaseMAX™ Surfactant) dissolving 12 µL of a sample solution in a 100 mM ammonium hydrogencarbonate buffer was added thereto, and the solution was stirred and mixed. Then 20 µL of a 20 mM aqueous dithiothreitol solution was added thereto, the solution was heated at 65° C. for 15 minutes, then 42 µL of a 30 mM aqueous iodoacetic acid solution was added thereto, and the solution was reacted in a dark place at room temperature for 30 minutes. After reaction, 150 µL of a 100 mM ammonium hydrogencarbonate buffer was added thereto, the solution was stirred, 1.4 µL of 2% ProteaseMAX dissolved in a 100 mM ammonium hydrogencarbonate buffer was added thereto, 10 µL of a 100 µg/mL aqueous trypsin solution (Proteomics Grade, Code No. T6567-5×20 µg (SIGMA)) was added thereto, and the solution was subjected to enzyme digestion at 37° C. for 18 hours. After digestion, 15 µL of a 10% aqueous trifluoroacetic acid solution and 4.6 µL of a 0.01% aqueous trifluoroacetic acid solution comprising 2% acetonitrile were added thereto, which was used for LC-MS/MS measurement.

(8-2) Glu-C Treatment for Thiol-Introduced IgG1 Fc and Trastuzumab

A 100 mM ammonium hydrogencarbonate buffer in an amount of 20 µL comprising 8 M urea was dispensed to a 1.5 mL low-adsorptive micro test tube, 8 µL of a sample solution was added thereto, and the solution was stirred and mixed. Then 5 µL of a 100 mM aqueous dithiothreitol solution was added thereto, the solution was heated at 65° C. for 15 minutes, then 6 µL of a 200 mM aqueous iodoacetic acid solution was added thereto, and the solution was reacted in a dark place at room temperature for 30 minutes. After reaction, 2 µL of a 100 mM aqueous dithiothreitol solution was added thereto, 3 µL of a 100 mM ammonium hydrogencarbonate buffer was further added thereto, the solution was stirred, 5 µL of a 200 µg/mL aqueous Glu-C-Protease solution (Pierce™ Glu-C Protease, MS Grade, product No: 90054) was added thereto, and the solution was subjected to enzyme digestion at 37° C. for 18 hours. After digestion, 4 µL of a 10% aqueous trifluoroacetic acid solution was added thereto, which was used for LC-MS/MS measurement.

(8-3) LC-MS/MS Measurement Conditions for IgG1 Fc and Trastuzumab (Analyzer)
  Nano HPLC: EASY-nLC 1000 (Thermo Fisher Scientific)
  Mass Spectrometer: Tribrid Mass Spectrometer Orbitrap Fusion (Thermo Fisher Scientific)

(HPLC Analysis Conditions)
  Trap column: Acclaim PepMap (registered trademark) 100, 75 µm×2 cm, nanoViper (Thermo Fisher Scientific)
  Analysis column: ESI-column (NTCC-360/75-3-125, 75 µm×12.5 cm, 3 µm (Nikkyo Technos Co., Ltd.))
  Mobile Phase A: a 0.1% aqueous formate solution
  Mobile Phase B: a 0.1% formate acetonitrile solution
  Loading solution: a 0.1% aqueous trifluoroacetic acid solution
  Flow rate: 300 nL/min
  Sample injection amount: 2 µL (IgG1 Fc), 3 µL (trastuzumab)
  Gradient condition (B %): 2% (0.0 minute to 0.5 minute), 2%→45% (0.5 minute to 33.5 minutes), 45%→75% (33.5 minutes to 35.5 minutes), and 75% (35.5 minutes to 45.0 minutes).

(Mass Spectrometer Analysis Conditions)
Ionization: ESI, Positive mode
Scan type: Data Dependent Acquisition
Activation Type: Collision Induced Dissociation (CID)
Data acquisition was performed using Xcalibur 3.0 (Thermo Fisher Scientific) and Thermo Orbitrap Fusion Tune Application 2.0 (Thermo Fisher Scientific) as accompanying software.

(8-4) Analysis Condition of Modified Site of IgG1 Fc and Trastuzumab

Modified site analysis of an LC-MS/MS measurement result was performed using Proteome Discoverer version 1.4 (Thermo Fisher Scientific).

For analysis with Proteome Discoverer, Sequest HT was used as a search engine, and the range of precursor ion was set to 350 Da to 5,000 Da. For a digestive enzyme, trypsin or Glu-C was designed as the digestive enzyme in accordance with a sample, and Maximum Missed Cleavage Sites was set to 0. Mass Tolerance was set to 10 ppm and 0.5 Da for precursor and fragment ion, respectively. For Static Modification, Carboxymethyl (+58.005 Da) was set as modification of a cysteine residue with iodoacetic acid. For Dynamic Modifications, oxidation of methionine (+15.995 Da) and a modified compound to a lysine residue (a thiol-introduced portion subjected to carboxymethylation with iodoacetic acid (+146.004 Da)) were set.

As data on amino acid sequences to be searched for a modified site, (1) to (3) illustrated in FIG. 8 were used.

(8-5) Analysis Result of Modified Site of IgG1 Fc and Trastuzumab by LC-MS/MS

Figure 9:
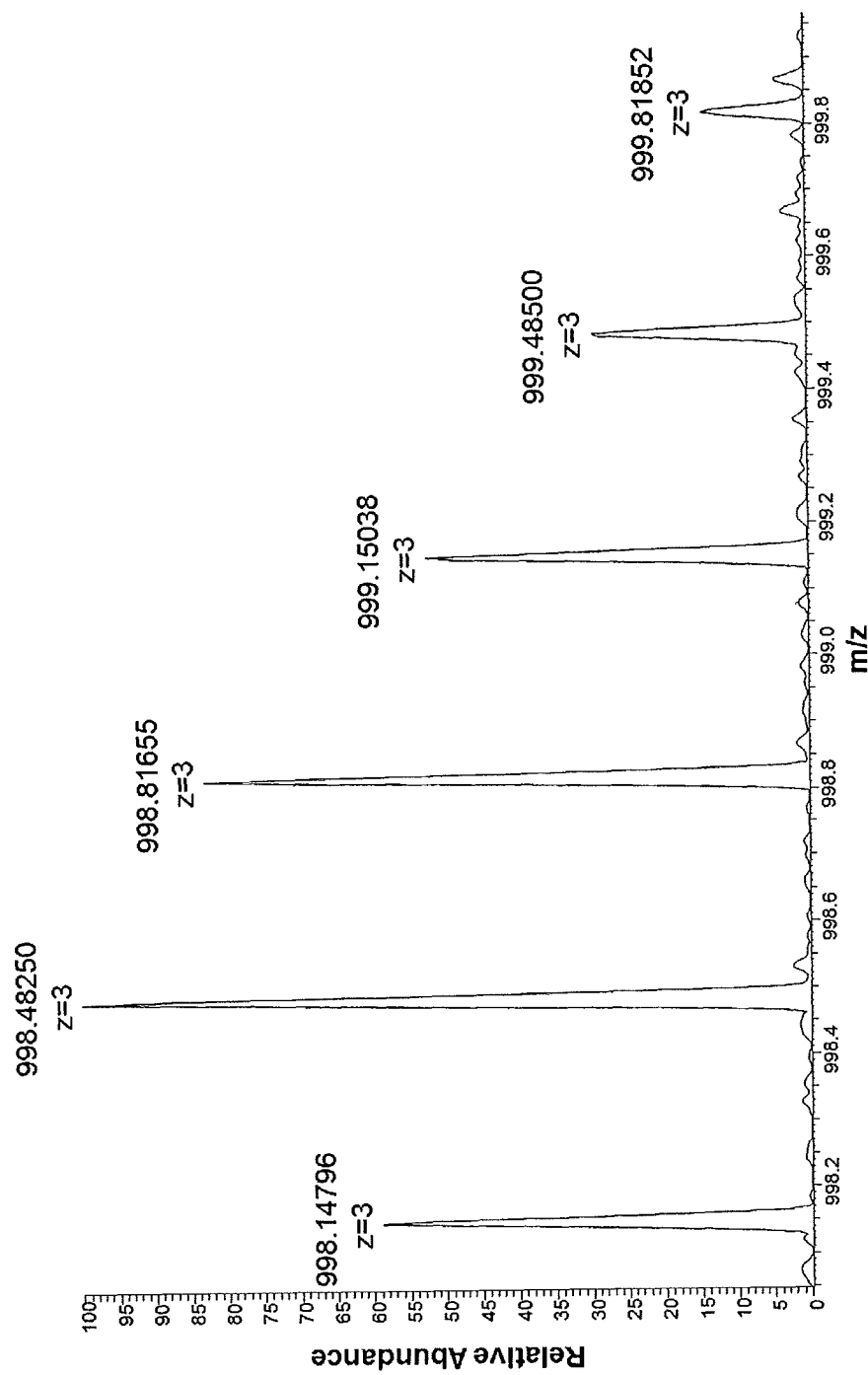
FIG. 9 is a diagram of a mass spectrometry (MS) spectrum of the peptide fragment of THTCPPCPA-PELLGGPSVFLFPPKPK (SEQ ID NO: 5) comprising a modified site to a lysine residue by trypsin digestion of trastuzumab (a thiol-introduced portion subjected to carboxymethylation with iodoacetic acid (+146.004 Da)) (m/z 998.14796, trivalent).
Figure 10:
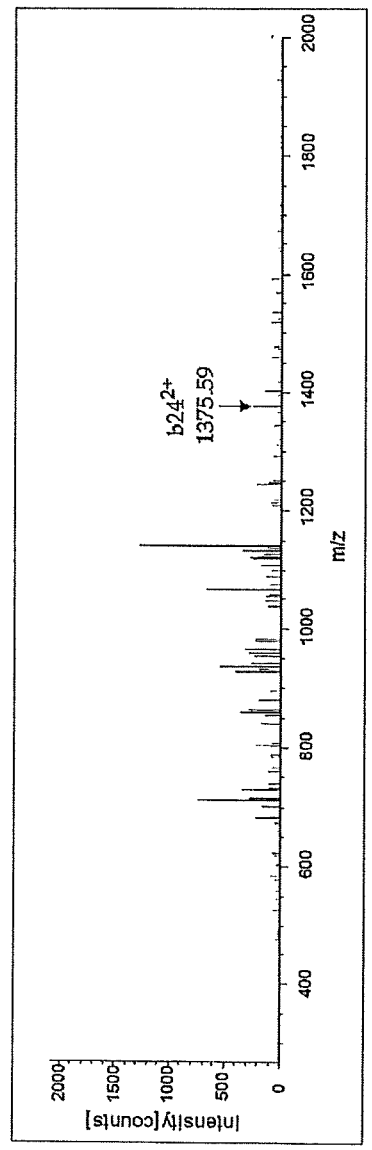
FIG. 10 is a diagram of a collision-induced dissociation (CID) spectrum of the peptide fragment of THTCPPCPA-PELLGGPSVFLFPPKPK (SEQ ID NO: 5) comprising a modified site to a lysine residue by trypsin digestion of trastuzumab (a thiol-introduced portion subjected to carboxymethylation with iodoacetic acid (+146.004 Da)).
Figure 11:
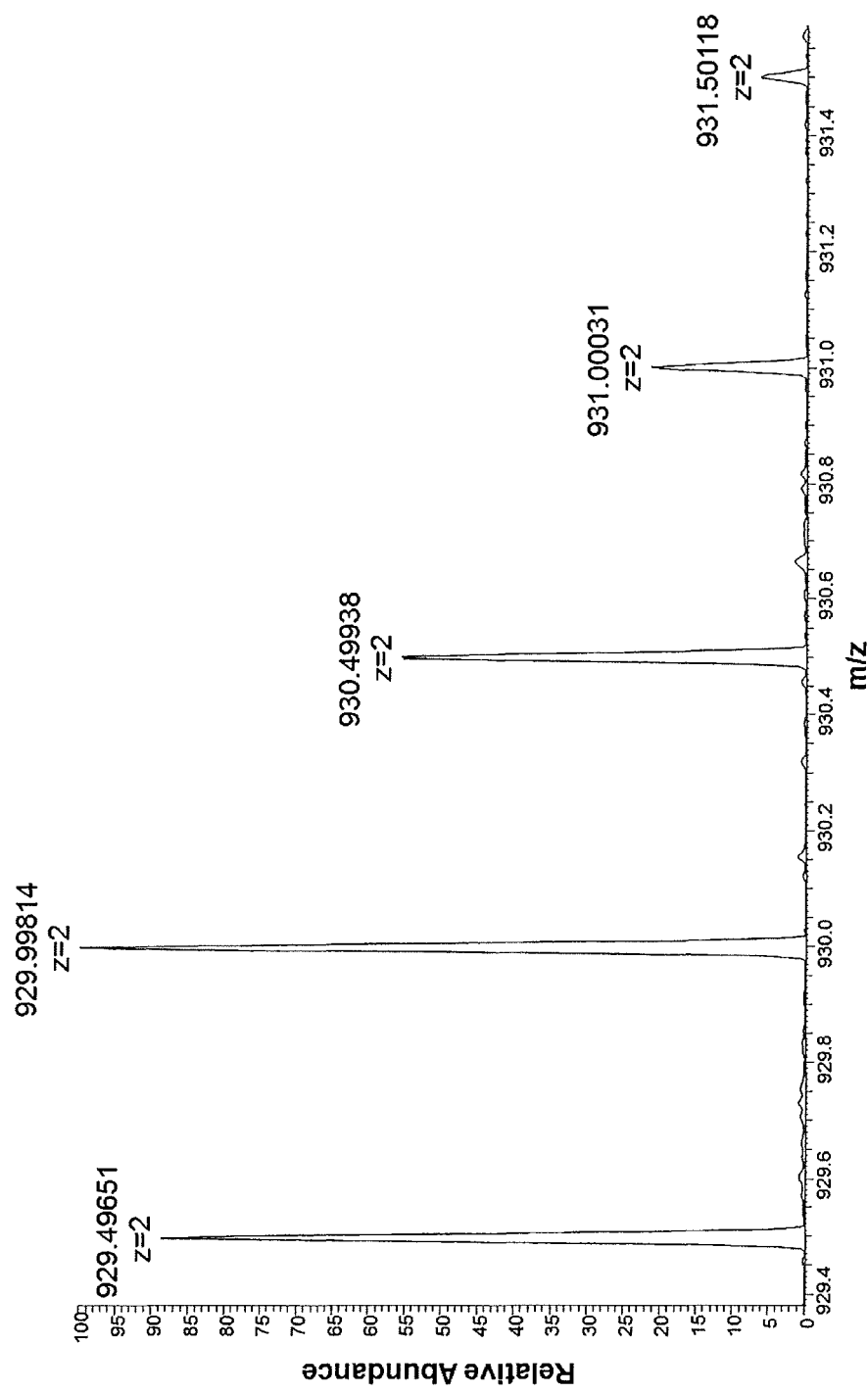
FIG. 11 is a diagram of an MS spectrum of the peptide fragment of LLGGPSVFLFPPKPKD (SEQ ID NO: 6) comprising a modified site to a lysine residue by Glu-C digestion of trastuzumab (a thiol-introduced portion subjected to carboxymethylation with iodoacetic acid (+146.004 Da)) (m/z 929.49651, divalent).
Figure 12:
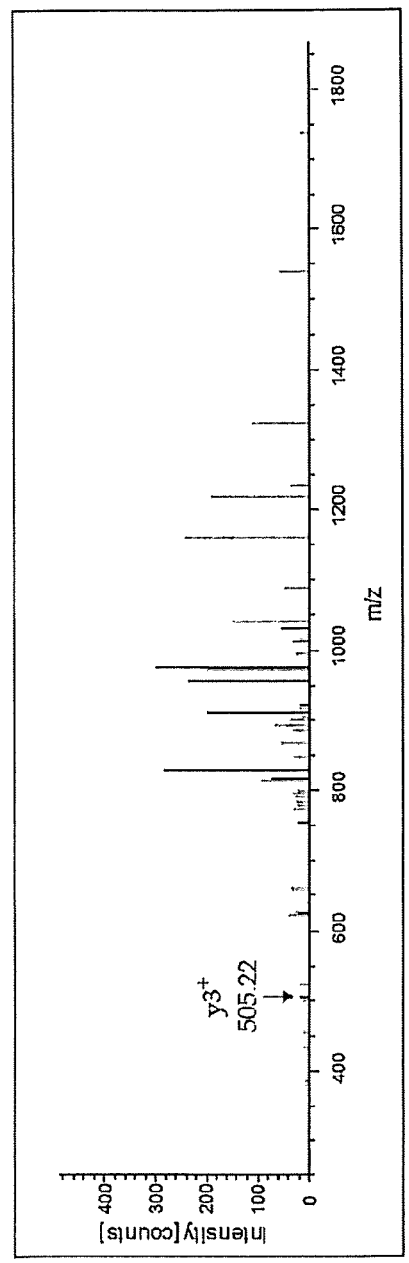
FIG. 12 is a diagram of a CID spectrum of the peptide fragment of LLGGPSVFLFPPKPKD (SEQ ID NO: 6) comprising a modified site to a lysine residue by Glu-C digestion of trastuzumab (a thiol-introduced portion subjected to carboxymethylation with iodoacetic acid (+146.004 Da)).

After analysis using LC/MS/MS, an MS spectrum of the peptide fragment of THTCPPCPAPELLGGPSVFLFPPKPK (SEQ ID NO: 5), which is a peptide consisting of 26 amino acid residues comprising a modified site to a lysine residue by trypsin digestion of trastuzumab (a thiol-introduced portion subjected to carboxymethylation with iodoacetic acid (+146.004 Da)) (measured value: m/z 998.14874; theoretical value: 998.14859; and trivalent) was observed (FIG. 9), and from a collision-induced dissociation (CID) spectrum, a product ion of m/z 1,375.59 (theoretical value: 1,375.14) corresponding to divalent b24 indicating modification of a lysine residue at position 246 in EU numbering of the heavy chain was determined (FIG. 10). An MS spectrum of the peptide fragment of LLGGPSVFLFPPKPKD (SEQ ID NO: 6), which is a peptide consisting of 16 amino acid residues comprising a modified site to a lysine residue by Glu-C Protease digestion of trastuzumab (a thiol-introduced portion subjected to carboxymethylation with iodoacetic acid (+146.004 Da)) (measured value: m/z 929.49573; theoretical value: 929.49527; and divalent) was observed (FIG. 11); and from a CID spectrum, a product ion of m/z 505.22 (theoretical value: 505.20) corresponding to divalent y3 indicating modification of a lysine residue at position 248 in EU numbering of the heavy chain was determined (FIG. 12).

Figure 13:
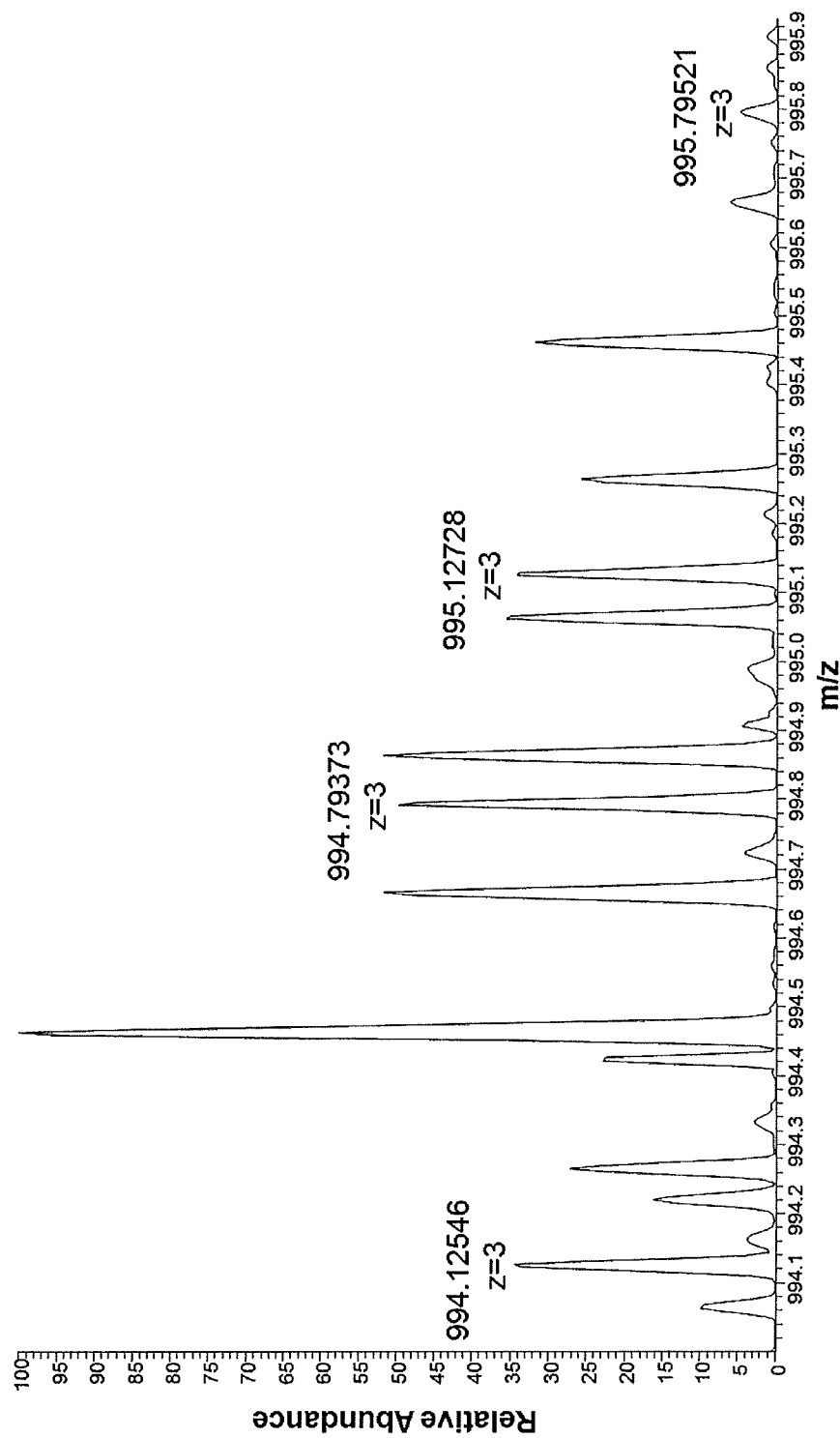
FIG. 13 is a diagram of an MS spectrum of the peptide fragment of THTCPPCPAPEAEGAPSVFLFPPKPK (SEQ ID NO: 7) comprising a modified site to a lysine residue by trypsin digestion of IgG1 Fc (a thiol-introduced portion subjected to carboxymethylation with iodoacetic acid (+146.004 Da)) (m/z 994.12546, trivalent).
Figure 14:
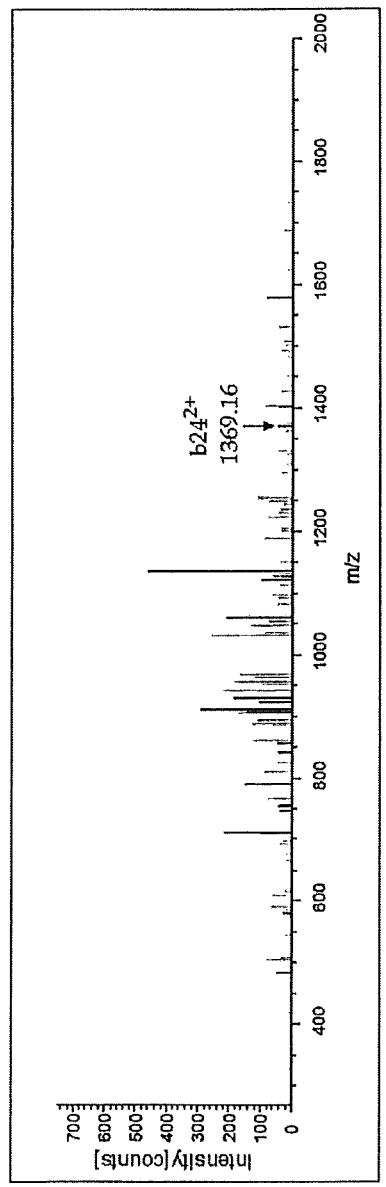
FIG. 14 is a diagram of a CID spectrum of the peptide fragment of THTCPPCPAPEAEGAPSVFLFPPKPK (SEQ ID NO: 7) comprising a modified site to a lysine residue by trypsin digestion of IgG1 Fc (a thiol-introduced portion subjected to carboxymethylation with iodoacetic acid (+146.004 Da)).
Figure 15:
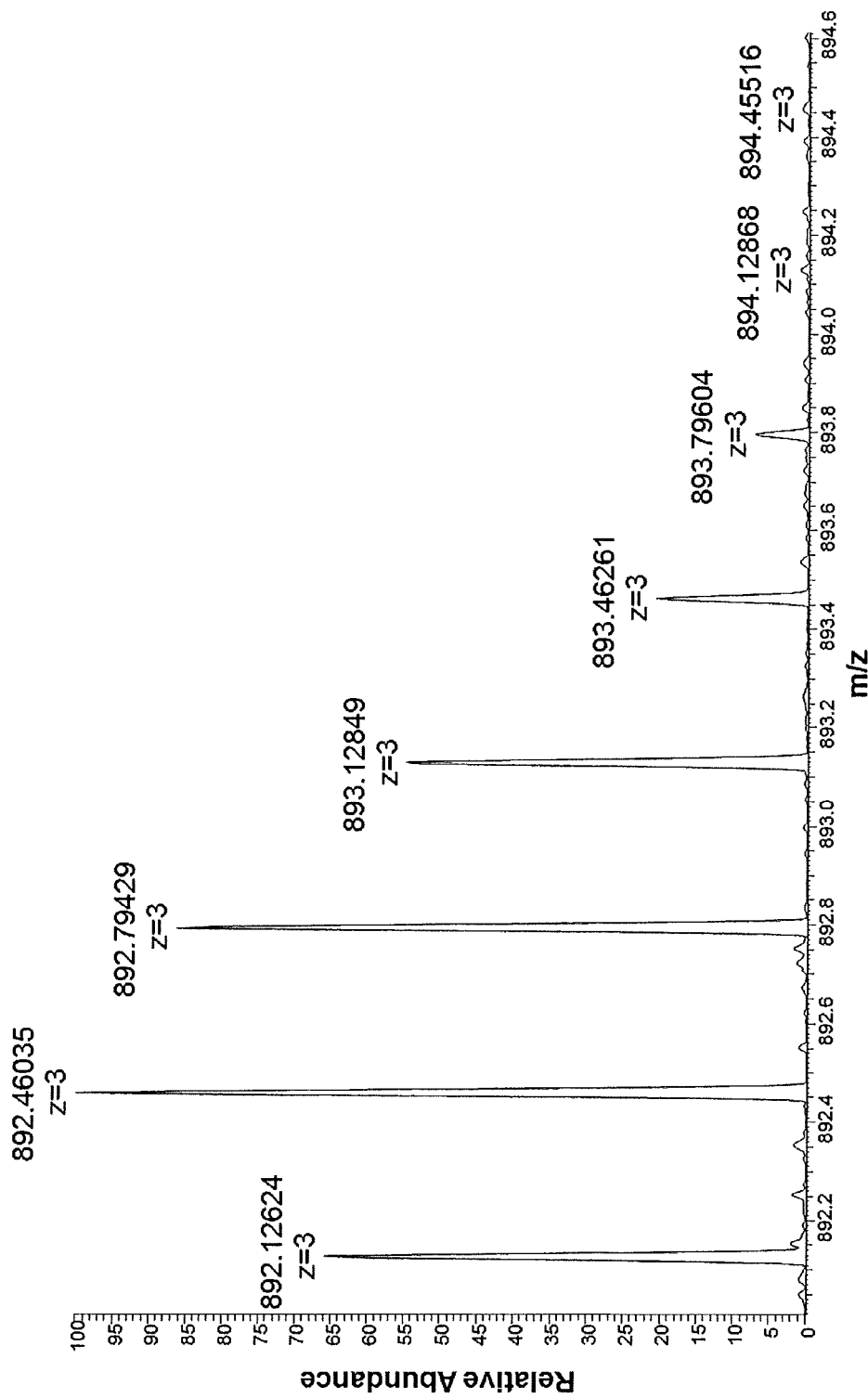
FIG. 15 is a diagram of an MS spectrum of the peptide fragment of GAPSVFLFPPKPKKDTLMISRTPE (SEQ ID NO: 8) comprising a modified site to a lysine residue by Glu-C digestion of IgG1 Fc (a thiol-introduced portion subjected to carboxymethylation with iodoacetic acid (+146.004 Da)) (m/z 892.12624, trivalent).
Figure 16:
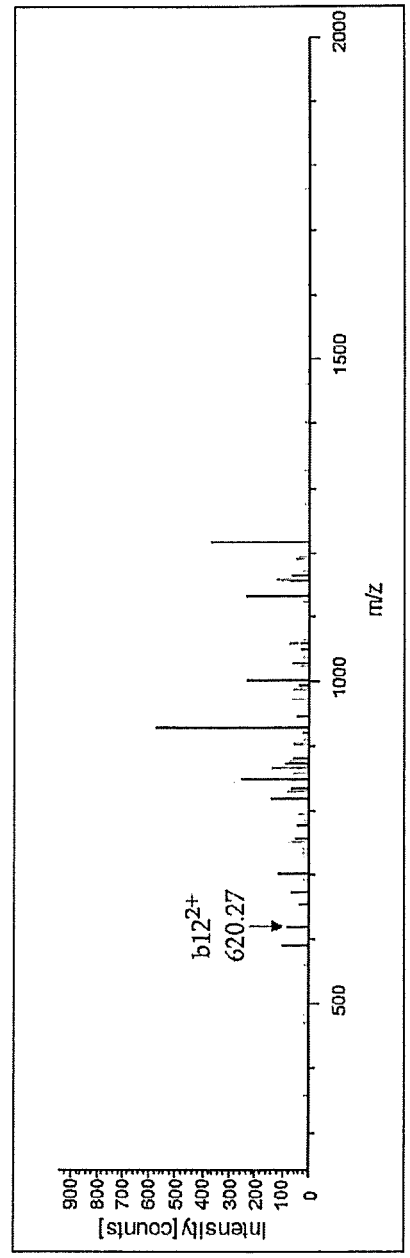
FIG. 16 is a diagram of a CID spectrum of the peptide fragment of GAPSVFLFPPKPKKDTLMISRTPE (SEQ ID NO: 8) comprising a modified site to a lysine residue by Glu-C digestion of IgG1 Fc (a thiol-introduced portion subjected to carboxymethylation with iodoacetic acid (+146.004 Da)).
Figure 20:
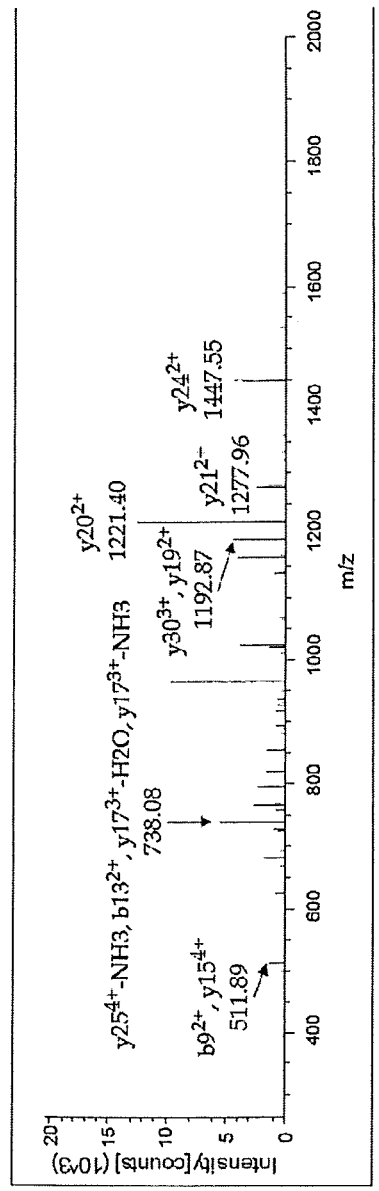
FIG. 20 is a diagram of a CID spectrum of a peptide comprising a modified site of an azide-introduced trastuzumab. This corresponds to a CID spectrum of the peptide of the surrounded portion in FIG. 18. A spectrum having m/z matching theoretical values is illustrated.
Figure 22:
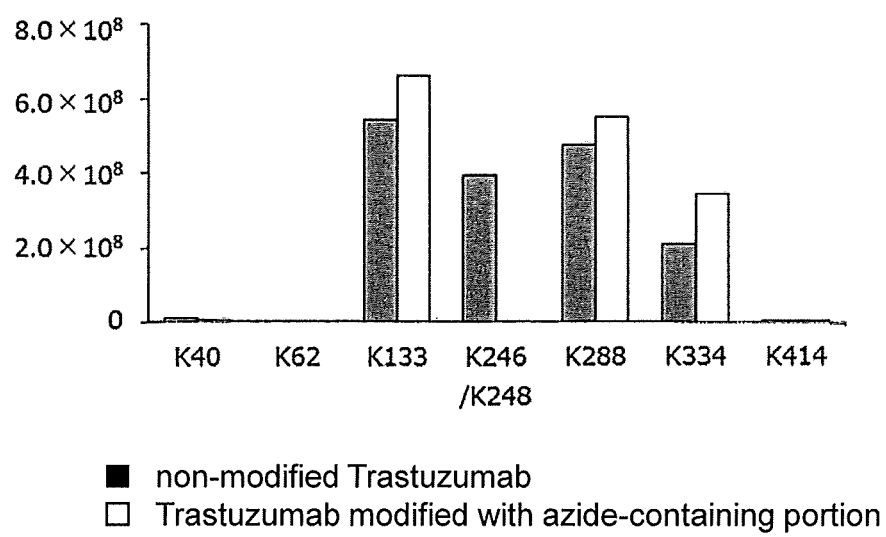
FIG. 22 is a diagram of an area value comparison of modified trastuzumab with non-modified trastuzumab. Based on an estimation that the area value of a non-modified peptide is smaller for a modified site, a comparison with the area value obtained for the non-modified trastuzumab revealed a significant reduction in the area value only in a peptide comprising lysine residues at positions 246 and 248 by EU numbering.

Furthermore, an MS spectrum of the peptide fragment of THTCPPCPAPEAEGAPSVFLFPPKPK (SEQ ID NO: 7), which is a peptide consisting of 26 amino acid residues comprising a modified site to a lysine residue by trypsin digestion of IgG1 Fc (a thiol-introduced portion subjected to carboxymethylation with iodoacetic acid (+146.004 Da)) (measured value: m/z 994.12885; theoretical value: 994.12433; and trivalent) was observed (FIG. 13), and from a CID spectrum, a product ion of m/z 1,369.16 (theoretical value: 1,369.10) corresponding to divalent b24 indicating modification of a lysine residue at position 246 in EU numbering of the heavy chain was determined (FIG. 14). An MS spectrum of the peptide fragment of GAPSVFLFPPKPKDTLMISRTPE (SEQ ID NO: 8), which is a peptide consisting of 23 amino acid residues comprising a modified site to a lysine residue by Glu-C Protease digestion of IgG1 Fc (a thiol-introduced portion subjected to carboxymethylation with iodoacetic acid (+146.004 Da)) (measured value: m/z 892.12604; theoretical value: 892.12611; and trivalent) was observed (FIG. 15), and from a CID spectrum, a product ion of m/z 620.27 (theoretical value: 619.85) corresponding to divalent b12 indicating modification of a lysine residue at position 248 in EU numbering of the heavy chain was determined (FIG. 16).

From the foregoing, modification of the peptide fragments comprising the lysine residues at position 246 and position 248 in EU numbering was determined (FIGS. 9 to 16).

Example 9: Synthesis of Regioselective Trastuzumab-DM1 Conjugate and Analysis of Average DAR (9-1) Synthesis of Regioselective T-DM1*(Trastuzumab-DM1) Conjugate The compound introduced with two bioorthogonal functional groups synthesized in (6-1) of Example 6 in an amount of 0.35 mg was dissolved in 200 µL of 100 mM PBS and a 10 mM EDTA buffer to be 1.75 mg/mL, then 10 µL of N,N'-dimethylformamide and 4.8 µL of a solution obtained by dissolving DM-1 (manufactured by Abzena Ltd.) in N,N'-dimethylformamide to be 5 mM were added thereto, and the solution was stirred at 20° C. for 2 hours. After 2 hours, 1 µL of a solution obtained by dissolving N-acetylcysteine in 100 mM PBS and a 10 mM EDTA buffer to be 50 mM was added thereto, and the solution was further stirred at 20° C. for 1 hour. After reaction, through extraction with a NAP-5 column, DM-1 was removed.

(9-2) Antibody Concentration Measurement after Reaction with SoloVPE

Absorbance at a wavelength of 280 nm was measured, and an antibody concentration was calculated from a molar extinction coefficient to be 0.48 mg/mL. The solution amount was 0.7 mL, and thus the yield can be calculated to be 0.336 mg.

(9-3) Calculation of DAR by Quadrupole Time-Of-Flight Mass Spectrometry (Q-TOFMS)

Figure 23:
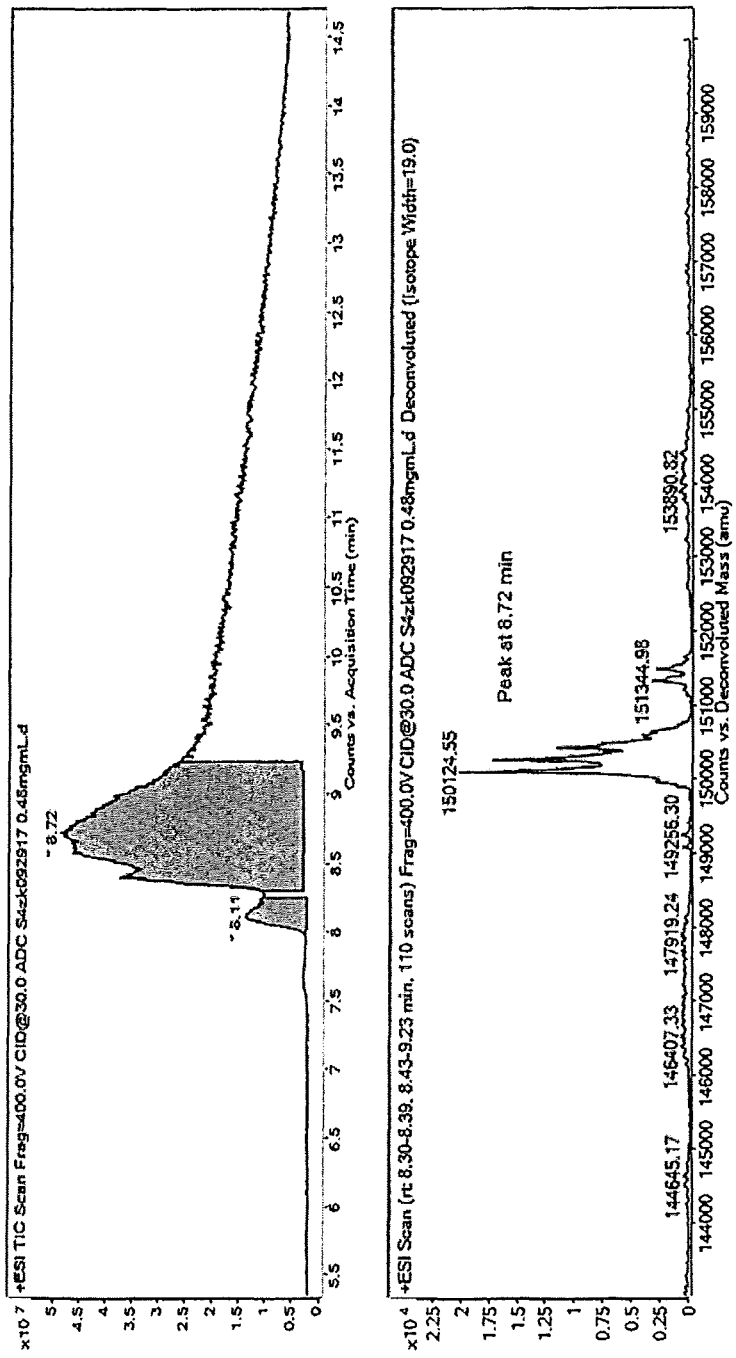
FIG. 23 is diagrams of analysis of a drug antibody ratio (DAR) of the modified trastuzumab by quadruple time-of-flight mass spectrometry (Q-TOFMS). From a peak observation result, an average DAR was 2.

For Q-TOFMS, Agilent 6550 coupled to Agilent 1290 UPLC with DAD detector, Autosampler cooling and Thermostatted column compartment manufactured by Agilent Technologies, Inc. was used. For software, MassHunter was used to calculate DAR. For a product, a peak was observed at 149,945 with two DM-1 introduced, and an average DAR was calculated to be 2 (FIG. 23).

DM1* used in this Example is as follows:

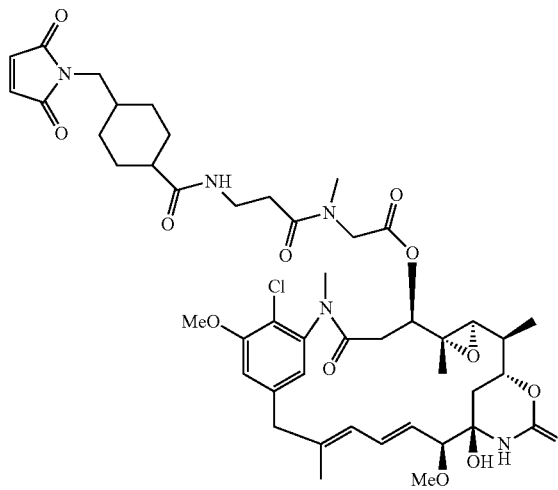

Chemical Formula: C46H60ClN5O13
Exact Mass: 925.3876

Example 10: Evaluation of Binding Property with Biacore (10-1) Evaluation of Binding Property to Antigen HER2 by Enzyme-Linked Immunosorbent Assay (ELISA)

The binding property of the regioselective T-DM1 (trastuzumab-DM1) conjugate synthesized in (9-1) of Example 9 to antigen HER2 was evaluated by ELISA. Kadcyla (T-DM1) was also evaluated as a control. Consequently, the dissociation constant (KD value) of Kadcyla was 6.372±0.76 μM, whereas that of the regioselective T-DM1 (trastuzumab-DM1) conjugate was 6.684±0.17 μM. Consequently, it is believed that the ADC synthesized by this method maintains the antigen binding property.

(10-2) Evaluation of Binding Property to FcRn with Biacore

The binding property of the regioselective T-DM1 (trastuzumab-DM1) conjugate synthesized in (9-1) of Example 9 to neonatal Fc receptor (FcRn) was evaluated by ELISA. It is known that when the binding property of an antibody to FcRn is higher, the antibody has a longer half-life in blood. Kadcyla (T-DM1) was also evaluated as a control. Consequently, the dissociation constant (KD value) of Kadcyla was 1.65±0.05 M, whereas that of the regioselective T-DM1 (trastuzumab-DM1) conjugate was 0.258±0.001 μM. Consequently, it is believed that the ADC synthesized by this method maintains the FcRn binding property, and it has been revealed that it has about six times higher affinity to FcRn than Kadcyla as a conventional ADC.

Example 11: (1) Synthesis of Various Cleavable Linkers and (2) Synthesis of Compounds Having Affinity Substance to Soluble Protein, Cleavable Portion, and Reactive Group (Peptide- and Azide Modified Thioester Linker-Coupled NHS-Activation Compound, Peptide- and Maleimide Modified Thioester Linker-Coupled NHS-Activation Compound, Peptide- and Azide Modified Ester Linker-Coupled NHS-Activation Compound, and Peptide- and Acetal Linker-Coupled NHS-Activation Compound) Through Coupling Between Synthesized Linkers and IgG1 Fc-Binding Peptide (11-1) Synthesis of Thioester Linker and Coupling thereof with Peptide
(11-1-1) Synthesis of Thioester Linker

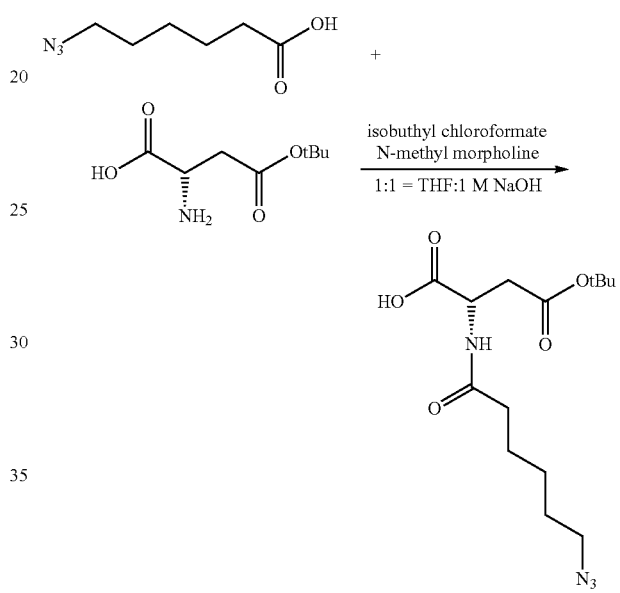

6-Azido-hexanoic acid (300 mg, 1.91 mmol) was dissolved in a THF solvent (20 mL), isobutyl chlorocarbonate (284 μL, 2.10 mmol) and N-methylmorpholine (273 μL, 2.48 mmol) were added thereto at 0° C., and the solution was stirred for 30 minutes to prepare a mixed anhydride of 6-azido-hexanoic acid. At room temperature, 4-(tert-butoxy-oxo)-2-amino-butanoic acid (362 mg, 2.10 mmol) was dissolved in a 1 M aqueous sodium hydroxide solution (2.10 mL), and then the THF solution of the mixed anhydride of 6-azido-hexanoic acid was added dropwise thereto at room temperature. The solution was stirred at room temperature for 16 hours, and then a 6 M aqueous hydrochlorate solution was added thereto to adjust the pH within the system to 3.0. The reaction solution was diluted with ethyl acetate and was washed with water and brine, and then magnesium sulfate anhydride was added thereto, and allowed to stand for 5 minutes. Magnesium sulfate was removed by filtration, and concentration under reduced pressure was performed to obtain a crude product, which was then purified by column chromatography (dichloromethane:methanol=10:1). A fraction comprising a product was collected and was concentrated under reduced pressure to obtain 4-(tert-butoxy-oxo)-2-(6-azidohexyl-1-oxo)amino-butanoic acid (352 mg, 1.07 mmol).

$^1$H NMR (400 MHz, Chloroform-d) δ 6.56 (d, J=7.6 Hz, 1H), 4.76 (ddd, J=7.6, 5.2, 4.8 Hz, 1H), 3.22 (t, 3.6 Hz, 2H), 2.90 (dd, J=17.2, 4.8 Hz, 1H), 2.70 (dd, J=17.2, 5.2 Hz, 1H), 2.22 (t, J=7.2 Hz, 2H), 1.53-1.65 (m, 4H), 1.37 (s, 9H), 1.36-1.31 (m, 2H).

MS (ESI) m/z: 351 [M+Na]$^+$

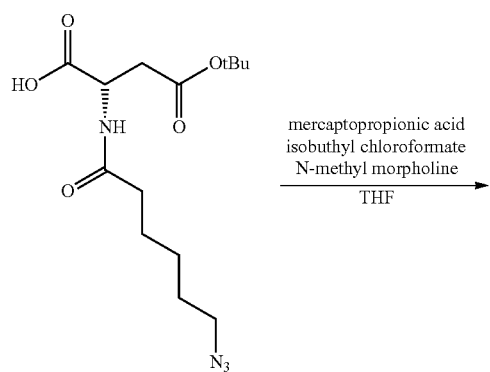

(11-1-2) Coupling between Thioester Linker and Peptide

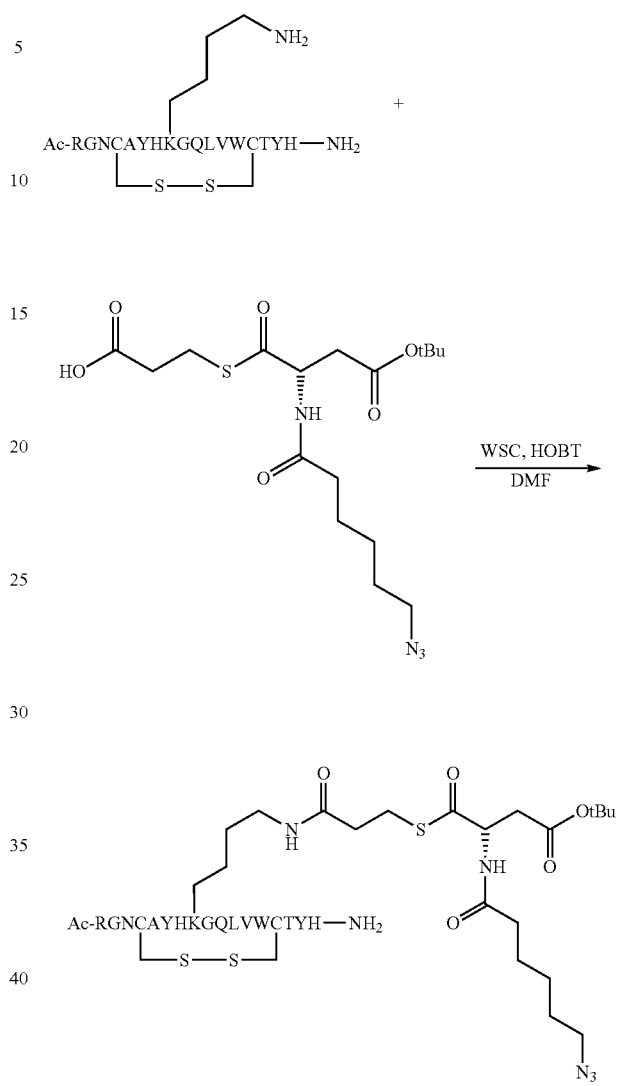

The above-amino acid sequence is SEQ ID NO: 39.

In THF (1.5 mL), 4-(tert-butoxy-oxo)-2-(6-azidohexyl-1-oxo)amino-butanoic acid (50.0 mg, 0.152 mmol) was dissolved, isobutyl chlorocarbonate (30.9 μL, 0.228 mmol) and N-methylmorpholine (28.5 μL, 0.258 mmol) were added thereto at 0° C., and the solution was stirred for 30 minutes to prepare a corresponding mixed anhydride. Mercaptopropionic acid (32.3 mg, 0.456 mmol) was dissolved in THF (ml) at room temperature, then the THF solution of the mixed anhydride was added dropwise thereto at room temperature. The solution was stirred at room temperature for 16 hours, then a 1 M aqueous sodium hydroxide solution was added thereto to adjust the pH within the system to 9.0. The reaction solution was washed with water and ethyl acetate, and an aqueous phase was collected. A 6 M aqueous hydrochlorate solution was added to the aqueous phase to adjust the pH within the system to 3.0, then extraction with ethyl acetate was performed, then an organic phase was washed with brine, and then magnesium sulfate anhydride was added thereto, and allowed to stand for 5 minutes. Magnesium sulfate was removed by filtration, and concentration under reduced pressure was performed to obtain 3-[4-(tert-butoxy-oxo)-2-(6-azidohexyl-1-oxo)amino-1-oxo]sulfanyl-propanoic acid (60.1 mg, 0.144 mmol).

$^1$H NMR (400 MHz, Chloroform-d) δ 6.69 (d, J=9.6 Hz, 1H), 4.89 (dt, J=9.6, 4.4 Hz, 1H), 3.22 (t, 8.5 Hz, 2H), 3.07 (t, 7.2 Hz, 2H), 2.82-2.60 (m, 3H), 2.29-2.22 (m, 3H), 1.70-1.52 (m, 4H), 1.42-1.39 (m, 2H), 1.40 (s, 9H).

MS (ESI) m/z: 439 [M+H]$^+$

The peptide of Ac-RGNCAYHKGQLVWCTYH-NH$_2$ (SEQ ID NO: 39) synthesized in Example 1-2 (20.0 mg, 9.64 μmol, the 4th and 14th of two cysteines form a disulfide bond in the molecule) was dissolved in 1 mL of N,N'-dimethylformamide. Dissolved in 1 mL of DMF were 3-[4-(tert-butoxy-oxo)-2-(6-azidohexyl-1-oxo)amino-1-oxo]-sulfanyl-propanoic acid (60.1 mg, 0.144 mmol), 1-ethyl-3-(3-dimethylaminopropyl)carbodiimide hydrochloride (25.9 mg, 0.135 mmol), and 1-hydroxybenzotriazole (18.2 mg, 0.135 mmol), and the solution was added to the system. The resultant solution was stirred at room temperature for 12 hours, then a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled tBu compound (15 mg, 7.23 μmol).

MS (ESI) m/z: z=2 1,237 [M+2H]$^{2+}$, z=3 824 [M+3H]$^{3+}$

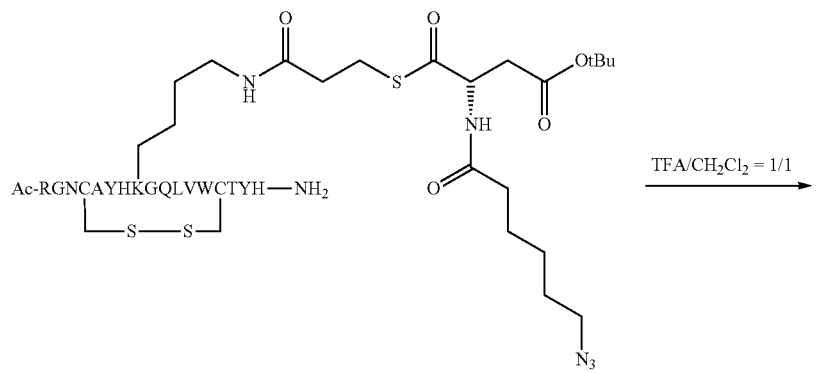

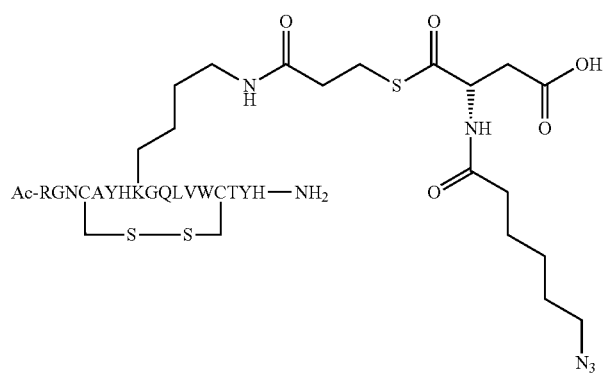

The above-amino acid sequence is SEQ ID NO: 39.

The peptide- and linker-coupled compound (10.0 mg, 4.82 μmol) was dissolved in 0.250 mL of dichloromethane, and 0.250 mL of trifluoroacetic acid was added thereto, and the solution was stirred at room temperature for 1 hour. After performing concentration under reduced pressure, a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled carboxylic compound (6.2 mg, 2.57 μmol).

MS (ESI) m/z: z=2 1,208 [M+2H]$^{2+}$, z=3 806 [M+3H]$^{3+}$

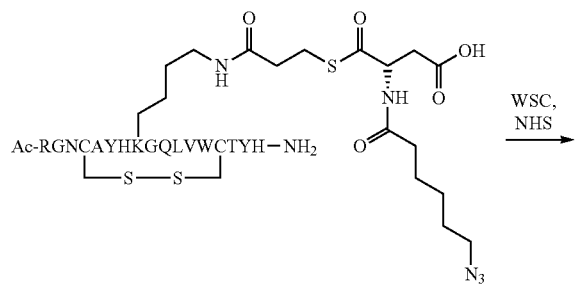

-continued

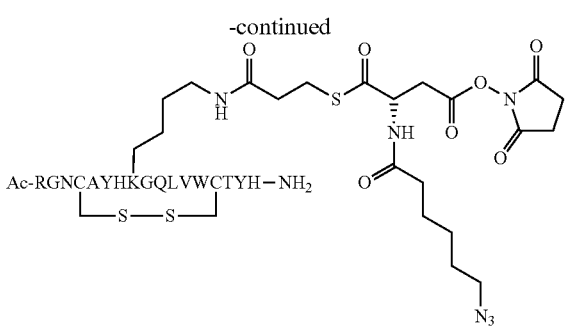

The above-amino acid sequence is SEQ ID NO: 39.

the peptide- and linker-coupled carboxylic compound (5.7 mg, 2.36 μmol) was dissolved in 0.5 mL of N,N'-dimethylformamide, 1-ethyl-3-(3-dimethylaminopropyl)carbodiimide hydrochloride (9.1 mg, 47.2 μmol) and N-hydroxysuccinimide (8.1 mg, 70.8 μmol) were added thereto, and the solution was stirred for 16 hours. A 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and azide modified thioester linker-coupled NHS-activation compound (3.0 mg, 1.19 μmol).

MS (ESI) m/z: z=2 1,257 [M+2H]$^{2+}$, z=3 838 [M+3H]$^{3+}$

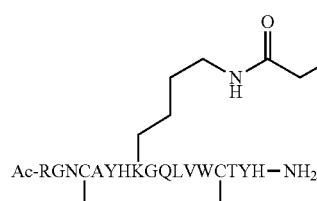
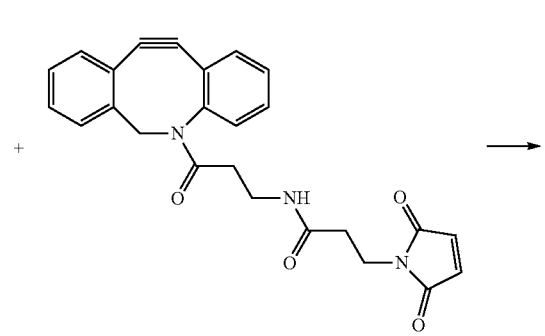

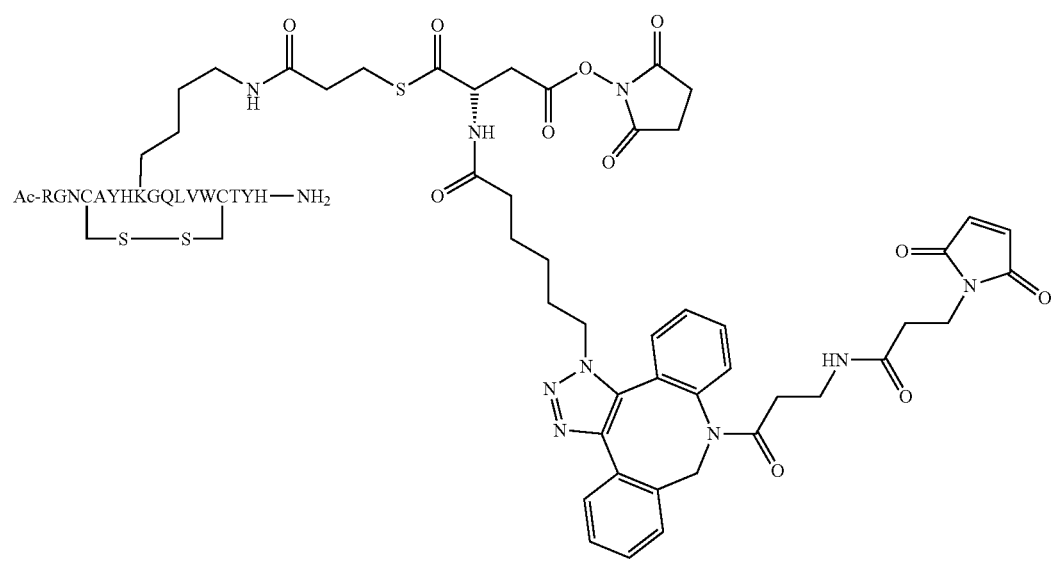

The above-amino acid sequence is SEQ ID NO: 39.

The peptide- and azide modified thioester linker-coupled NHS-activation compound (3.0 mg, 1.20 µmol) was dissolved in 0.5 mL of N,N'-dimethylformamide, dibenzocyclooctyne-maleimide (0.6 mg, 1.20 µmol) was added thereto, and the solution was stirred for 16 hours. A 0.1% aqueous trifluoroacetic acid solution was added to the reaction solution, and fractions were eluted by reversed phase preparative chromatography. A fraction comprising a product was collected, was concentrated under reduced pressure to remove only acetonitrile, and was freeze-dried to obtain the peptide- and maleimide modified thioester linker-coupled NHS-activation compound (2.8 mg, 0.95 µmol).

MS (ESI) m/z: z=2 1,471 [M+2H]$^{2+}$, z=3 981 [M+3H]$^{3+}$ (11-2) Synthesis of Ester Linker and Coupling thereof with Peptide (11-2-1) Synthesis of Ester Linker

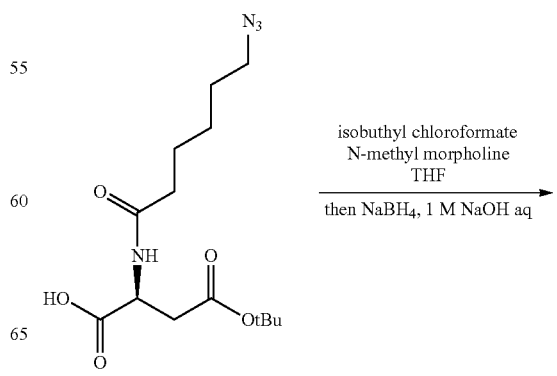

-continued

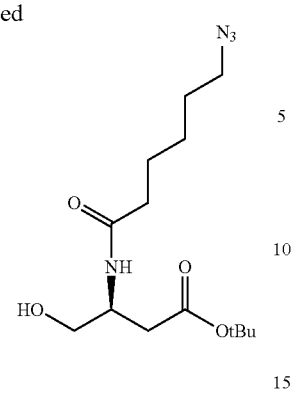

In THF (1.5 mL), 4-(tert-butoxy-oxo)-2-[(6-azidohexyl-1-oxo)amino]-butanoic acid (50 mg, 0.152 mmol) was dissolved, isobutyl chlorocarbonate (22.7 μL, 0.167 mmol) and N-methylmorpholine (21.7 μL, 0.198 mmol) were added thereto at 0° C., and the solution was stirred for 30 minutes to prepare a corresponding mixed anhydride. Sodium borohydride (28.7 mg, 0.76 mmol) was dissolved in a 1 M aqueous sodium hydroxide solution (1.0 ml) at room temperature, and the THF solution of the mixed anhydride was added dropwise thereto at room temperature. The solution was stirred at room temperature for 16 hours, then ethyl acetate was added to the system, and the solution was washed with water and brine, then an organic phase was collected, and magnesium sulfate anhydride was added thereto, and allowed to stand for 5 minutes. Magnesium sulfate was removed by filtration, and concentration under reduced pressure was performed to obtain a crude product, which was then purified by column chromatography (dichloromethane:methanol=10:1). A fraction comprising a product was collected and was concentrated under reduced pressure to obtain tert-butyl-4-hydroxy-3-[(6-azidohexyl-1-oxo)amino]-butanoate (38.1 mg, 0.121 mmol).

$^1$H NMR (400 MHz, Chloroform-d) δ 6.36 (d, J=7.2 Hz, 1H), 4.20 (m, 1H), 3.69 (dt, 12.4, 4.4 Hz, 2H), 3.27 (t, J=6.8 Hz, 2H), 2.50 (d, J=6.0 Hz, 2H), 2.22 (t, J=7.2 Hz, 2H), 1.53-1.72 (m, 4H), 1.41 (s, 9H), 1.40-1.38 (m, 2H).

MS (ESI) m/z: 337 [M+Na]$^+$

-continued

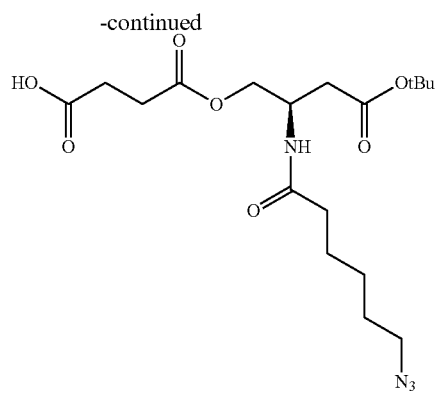

tert-Butyl-4-hydroxy-3-[(6-azidohexyl-1-oxo)amino]-butanoate (70.4 mg, 0.224 mmol) was dissolved in THF (2.2 mL), succinic anhydride (67.3 mg, 0.673 mmol) and N,N-dimethylaminopyridine (82.2 mg, 0.673 mmol) were added thereto at room temperature, and the solution was stirred at room temperature for 16 hours, then a 1 M aqueous sodium hydroxide solution was added thereto to adjust the pH within the system to 9.0. Water and ethyl acetate were added to the reaction solution, a separating operation was performed, and then an aqueous phase was collected. A 6 M aqueous hydrochlorate solution was added to the aqueous phase to adjust the pH within the system to 3.0, then extraction with ethyl acetate was performed, then an organic phase was washed with brine, and then magnesium sulfate anhydride was added thereto, and allowed to stand for 5 minutes. Magnesium sulfate was removed by filtration, and concentration under reduced pressure was performed to obtain 4-[4-(tert-butoxy-oxo)-2-(6-azidohexyl-1-oxo)amino]oxy-4-oxo-propanoic acid (78.9 mg, 0.190 mmol).

$^1$H NMR (400 MHz, Chloroform-d) δ 6.28 (d, J=8.0 Hz, 2H), 4.52 (m, 1H), 4.29 (dd, J=11.2, 4.4, 1H), 4.15 (dd, J=11.2, 5.6), 3.28 (m, 2H), 2.66 (m, 4H), 2.49 (d, J=6.4 Hz, 2H), 2.18 (t, J=7.2, 2H), 1.72-1.50 (m, 4H), 1.42 (s, 9H), 1.41-1.38 (m, 2H).

MS (ESI) m/z: 415 [M+H]

(11-2-2) Coupling between Ester Linker and Peptide

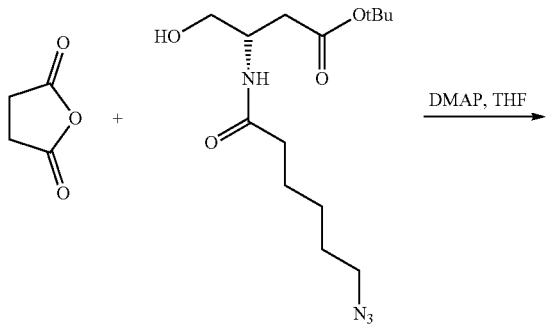

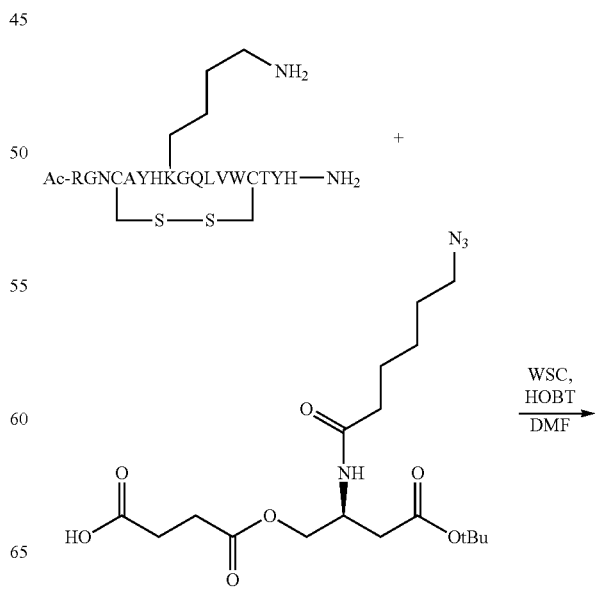

-continued

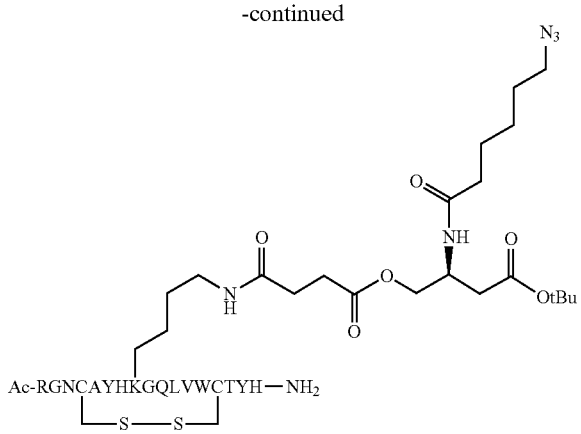

The above-amino acid sequence is SEQ ID NO: 39.

The peptide of Ac-RGNCAYHKGQLVWCTYH-NH$_2$ (SEQ ID NO: 39) synthesized in Example 1-2 (20 mg, 9.63 μmol, the 4th and 14th of two cysteines form a disulfide bond in the molecule) was dissolved in 1 mL of N,N'-dimethylformamide. Dissolved in 1 mL of DMF were 4-[4-(tert-butoxy-oxo)-2-(6-azidohexyl-1-oxo)amino]oxy-4-oxo-propanoic acid (39.9 mg, 96.3 μmol), 1-ethyl-3-(3-dimethylaminopropyl)carbodiimide hydrochloride (25.8 mg, 0.135 mmol), and 1-hydroxybenzotriazole (18.2 mg, 0.135 mmol), and the solution was added to the system. The solution was stirred at room temperature for 12 hours, then a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled tBu compound (18.2 mg, 7.36 μmol).

MS (ESI) m/z: z=2 1,236 [M+2H]$^{2+}$, z=3 824 [M+3H]$^{3+}$

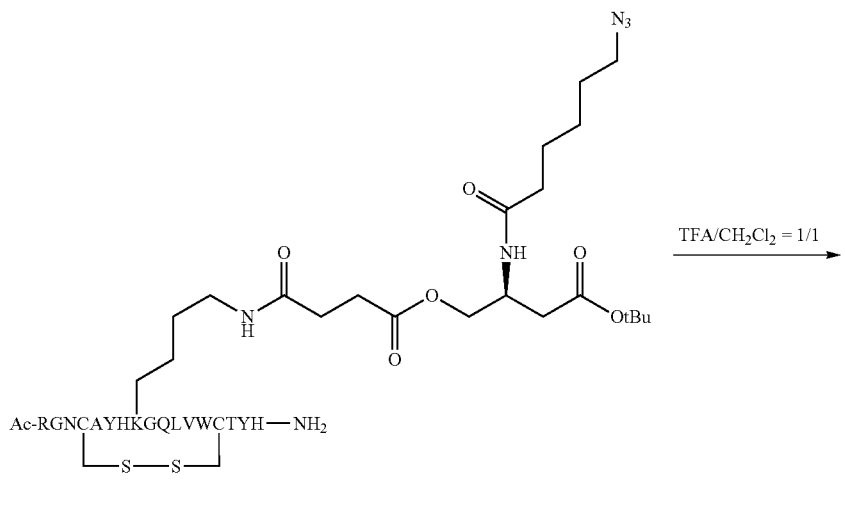

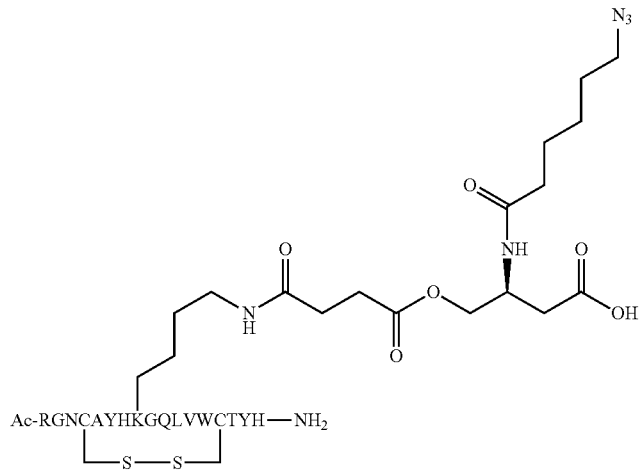

The above-amino acid sequence is SEQ ID NO: 39.

The peptide- and linker-coupled compound (16.5 mg, 6.67 µmol) was dissolved in 1.0 mL of dichloromethane, and 1.0 mL of trifluoroacetic acid was added thereto, and the solution was stirred at room temperature for 1 hour. After performing concentration under reduced pressure, a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled carboxylic compound (15.2 mg, 6.29 µmol).

MS (ESI) m/z: z=2 1,208 [M+2H]$^{2+}$, z=3 805 [M+3H]$^{3+}$

The above-amino acid sequence is SEQ ID NO: 39.

The peptide- and linker-coupled carboxylic compound (3.0 mg, 1.21 µmol) was dissolved in 1 mL of N,N'-dimethylformamide, 1-ethyl-3-(3-dimethylaminopropyl) carbodiimide hydrochloride (4.7 mg, 24.3 µmol) and N-hydroxysuccinimide (4.2 mg, 36.4 µmol) were added thereto, and the solution was stirred for 16 hours. A 0.1% aqueous trifluoroacetic acid solution was added to the reaction solution, and fractions were eluted by reversed phase preparative chromatography. A fraction comprising a product was collected, was concentrated under reduced pressure to remove only acetonitrile, and was freeze-dried to obtain the peptide- and azide modified ester linker-coupled NHS-activation compound (3.0 mg, 1.19 mol).

MS (ESI) m/z: z=2 1,257 [M+2H]$^{2+}$, z=3 837 [M+3H]$^{3+}$ (11-3) Synthesis of Acetal Linker and Coupling thereof with Peptide (11-3-1) Synthesis of Acetal Linker In 20 mL of an 8 M aqueous sodium hydroxide solution, 3,9-bis(2-cyanoethyl)-2,4,8,10-[5.5]tetraoxaspiroundecane (200 mg, 0.752 mmol) was dissolved, and the solution was stirred at 100° C. for 16 hours. After 16 hours, the temperature was returned to room temperature, a 6 M aqueous hydrochlorate solution was added to the aqueous phase to adjust the pH within the system to 7.0, and then acetonitrile and brine were successively added thereto to perform a separating operation. The acetonitrile phase was collected, and then sodium sulfate anhydride was added thereto, and allowed to stand for 5 minutes. Sodium sulfate was removed by filtration, and concentration under reduced pressure was performed to obtain 2,4,8,10-[5.5]tetraoxaspiroundecane-3,9-dipropanoic acid (151 mg, 0.497 mmol).

MS (ESI) m/z: 327 [M+Na]$^+$

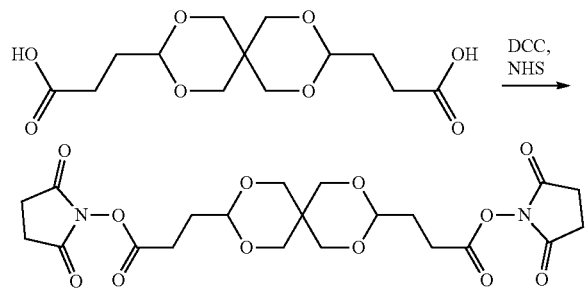

In 0.5 mL of ethyl acetate, 2-[9-(2-methoxy-2-oxo-ethyl)-2,4,8,10-tetraoxospiro[5.5]undecan-3-yl]acetic acid (30.0 mg, 0.099 mmol) was dissolved, N,N'-dicyclohexylcarbodiimide (22.4 mg, 0.109 mmol) and N-hydroxysuccinimide (31.2 mg, 0.271 mmol) were added thereto, and the solution was stirred for 2 hours. The formed white crystals were filtered, and the mother liquid was concentrated under reduced pressure to obtain bis(2,5-dioxopyrrolidin-1-yl)-2,4,8,10-[5.5]tetraoxaspiroundecane-3,9-dipropanoate (15 mg, 31.8 µmol).

MS (ESI) m/z: 521 [M+Na]$^+$ (11-3-2) Coupling Between Acetal Linker and Peptide concentrated under reduced pressure to remove only acetonitrile, and was freeze-dried to obtain the peptide- and acetal linker-coupled NHS-activation compound (2.8 mg, 1.14 µmol).

MS (ESI) m/z: z=2 1,729 [M+2H]$^2$, z=3 819 [M+3H]$^3$

Example 12: Modification of Anti-HER2 IgG Antibody Trastuzumab with Various Compounds and Analysis Thereof by Electron Spray Ionization-Time-OF-Flight Mass Spectrometry (ESI-TOFMS)

(12-1) Specific Modification of IgG Antibody Trastuzumab with Azide-Modified Thioester Linker-Binding Peptide Reagent and Analysis Thereof by ESI-TOFMS The peptide- and azide modified thioester linker-coupled NHS-activation compound synthesized in (11-1-2) of Example 11 was dissolved in N,N'-dimethylformamide to be 4 mM. Anti-HER2 IgG antibody trastuzumab (Chugai Pharmaceutical) in an amount of 120 µg was dissolved in 39.8 µL of a 50 mM sodium acetate buffer (pH 5.5), 2.4 µL of a 4 mM peptide reagent (12 equivalents with respect to the antibody) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by ESI-TOFMS; for the raw material trastuzumab, a peak was observed at 148,225, whereas for a product, a peak was observed at 153,018 with two binding peptides introduced.

(12-2) Determination of Heavy Chain Selectivity of Specifically Modified Compound of Anti-HER2 IgG Antibody Trastuzumab under Reduction Condition by ESI-TOFMS Analysis To the antibody-peptide conjugate PBS solution produced in (12-1), 2.0 µL of a 7 mM tris(2-carboxyethyl)phosphine

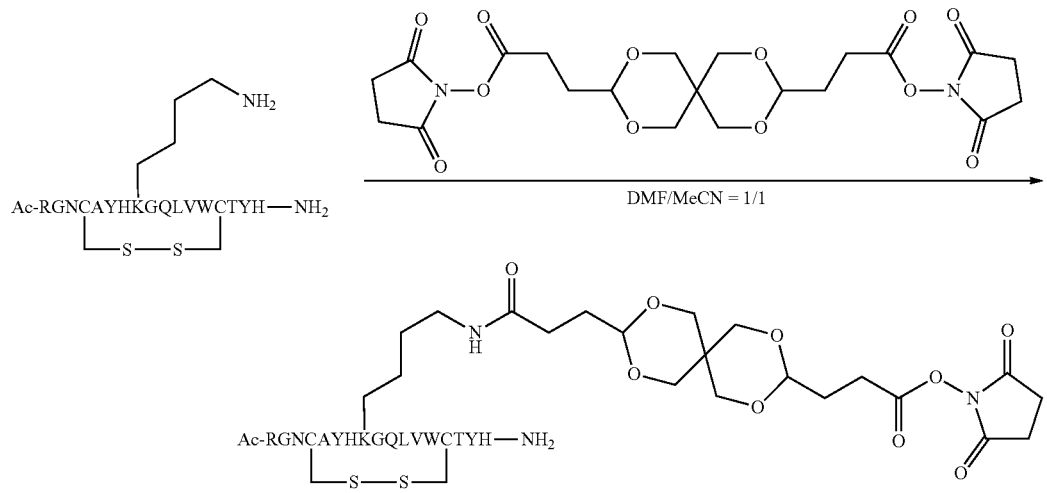

The above-amino acid sequence is SEQ ID NO: 39.

The peptide of Ac-RGNCAYHKGQLVWCTYH-NH$_2$ (SEQ ID NO: 39) synthesized in Example 1-2 (3.0 mg, 1.45 µmol, the 4th and 14th of two cysteines form a disulfide bond in the molecule) was dissolved in 0.3 mL of N,N'-dimethylformamide, bis(2,5-dioxopyrrolidin-1-yl)-2,4,8,10-[5.5]tetraoxaspiroundecane-3,9-dipropanoate (14.4 mg, 28.9 mol) was added thereto, and the solution was stirred at room temperature for 12 hours. Water was added thereto, and fractions were eluted by reversed phase preparative chromatography with neutral acetonitrile and water as solvents. A fraction comprising a product was collected, was hydrochloride solution (100 equivalents with respect to the antibody) was added, and the solution was stirred at room temperature for 20 minutes. The mass was measured by ESI-TOFMS; for the raw material trastuzumab, heavy chain peaks were observed at 50,595 and 50,757, and a light chain peak was observed at 23,440, whereas for a product, peaks were observed at 52,995 and 53,156 with a binding peptide introduced to the heavy chain, and a light chain peak was observed at 23,440, the same as that of the raw material.

(12-3) Specific Modification of IgG Antibody Trastuzumab with Maleimide-Modified Thioester Linker-Binding Peptide Reagent and Analysis Thereof by ESI-TOFMS The peptide- and maleimide modified thioester linker-coupled NHS-activation compound synthesized in (11-1-2) of Example 11 was dissolved in N,N'-dimethylformamide to be 4 mM. Anti-HER2 IgG antibody trastuzumab (Chugai Pharmaceutical) in an amount of 120 µg was dissolved in 39.8 µL of a 50 mM sodium acetate buffer (pH 5.5), 2.4 µL of a 4 mM peptide reagent (12 equivalents with respect to the antibody) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by ESI-TOFMS; for the raw material trastuzumab, a peak was observed at 148,225, whereas for a product, a peak was observed at 153,901 with two binding peptides introduced.

(12-4) Determination of Heavy Chain Selectivity of Specifically Modified Compound of Anti-HER2 IgG Antibody Trastuzumab under Reduction Condition by ESI-TOFMS Analysis To the antibody-peptide conjugate PBS solution produced in (12-3), 2.0 µL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material trastuzumab, heavy chain peaks were observed at 50,594 and 50,757, and a light chain peak was observed at 23,440, whereas for a product, peaks were observed at 53,421 and 53,600 with a binding peptide introduced to the heavy chain, and a light chain peak was observed at 23,440, the same as that of the raw material.

(12-5) Specific Modification of IgG Antibody Trastuzumab with Azide-Modified Ester Linker-Binding Peptide Reagent and Analysis Thereof by ESI-TOFMS The peptide- and azide modified ester linker-coupled NHS-activation compound synthesized in (11-2-2) of Example 11 was dissolved in N,N'-dimethylformamide to be 4 mM. Anti-HER2 IgG antibody trastuzumab (Chugai Pharmaceutical) in an amount of 120 µg was dissolved in 39.8 µL of a 50 mM sodium acetate buffer (pH 5.5), 2.4 µL of a 4 mM peptide reagent (12 equivalents with respect to the antibody) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by ESI-TOFMS; for the raw material trastuzumab, a peak was observed at 148,225, whereas for a product, a peak was observed at 153,028 with two binding peptides introduced.

(12-6) Determination of Heavy Chain Selectivity of Specifically Modified Compound of Anti-HER2 IgG Antibody Trastuzumab under Reduction Condition by ESI-TOFMS Analysis To the antibody-peptide conjugate PBS solution produced in (12-5), 2.0 µL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material trastuzumab, heavy chain peaks were observed at 50,594 and 50,757, and a light chain peak was observed at 23,440, whereas for a product, peaks were determined at 52,994 and 53,154 with a binding peptide introduced to the heavy chain, and a light chain peak was observed at 23,440, the same as that of the raw material.

(12-7) Specific Modification of IgG Antibody Trastuzumab with Acetal Linker-Binding Peptide Reagent and Analysis Thereof by ESI-TOFMS The peptide- and acetal linker-coupled NHS-activation compound synthesized in (11-3-2) of Example 11 was dissolved in N,N'-dimethylformamide to be 4 mM. Anti-HER2 IgG antibody trastuzumab (Chugai Pharmaceutical) in an amount of 120 µg was dissolved in 39.8 µL of a 50 mM sodium acetate buffer (pH 5.5), 2.4 µL of the 4 mM peptide reagent (12 equivalents with respect to the antibody) was added thereto, and the solution was stirred at room temperature for 1 hour. The reaction solution was subjected to solvent substitution to a 9.57 mM PBS buffer (pH 7.4) with Amicon 10K to stop the reaction. The mass was measured by ESI-TOFMS; for the raw material trastuzumab, a peak was observed at 148,238, whereas for a product, a peak was observed at 153,522 with two binding peptides introduced.

(12-8) Determination of Heavy Chain Selectivity of Specifically Modified Compound of Anti-HER2 IgG Antibody Trastuzumab under Reduction Condition by ESI-TOFMS Analysis To the antibody-peptide conjugate PBS solution produced in (12-7), 2.0 µL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material trastuzumab, heavy chain peaks were observed at 50,595 and 50,757, and a light chain peak was observed at 23,440, whereas for a product, peaks were observed at 52,940 and 53,103 with a binding peptide introduced to the heavy chain, and a light chain peak was observed at 23,440, the same as that of the raw material.

Example 13: Cleavage of Trastuzumab-Peptide Conjugate and Analysis of Product Thereof by Esi-Tofms (13-1) Linker Cleavage of Trastuzumab-Peptide Conjugate and Analysis of Product by ESI-TOFMS First, 40 µg of the trastuzumab-peptide conjugate synthesized in (12-1) of Example 12 was dissolved in a 100 mM Tris-hydrochloric acid buffer (pH 8.5) to be 2.0 µM, and then the solution was stirred at room temperature for 48 hours to cleave the thioester bond in the linker. The mass was measured by ESI-TOFMS; for the trastuzumab-peptide conjugate, a peak was observed at 153,018, whereas for a product, a peak was observed at 148,729 with two azides introduced.

(13-2) Determination of Heavy Chain Selectivity of Specifically Modified Compound of Trastuzumab under Reduction Condition by ESI-TOFMS Analysis To the antibody-peptide conjugate produced in (13-1), 2.0 µL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material trastuzumab-peptide conjugate, heavy chain peaks were observed at 52,995 and 53,155, and a light chain peak was observed at 23,440, whereas for a product, peaks were observed at 50,850 and 51,010 with an azide introduced to the heavy chain, and a light chain peak was observed at 23,440, the same as that of the raw material.

(13-3) Linker Cleavage of Trastuzumab-Peptide Conjugate and Analysis of Product by ESI-TOFMS First, 20 µg of the trastuzumab-peptide conjugate synthesized in (12-3) of Example 12 was dissolved in a 100 mM Tris-hydrochloric acid buffer (pH 8.5) to be 2.0 M, and then the solution was stirred at room temperature for 48 hours to cleave the thioester bond in the linker. The mass was measured by ESI-TOFMS; for the trastuzumab-peptide conjugate, a peak was observed at 153,901, whereas for a product, a peak was observed at 149,476 with two maleimides introduced.

(13-4) Determination of Heavy Chain Selectivity of Specifically Modified Compound of Trastuzumab under Reduction Condition by ESI-TOFMS Analysis To the antibody-peptide conjugate produced in (13-3), 2.0 µL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for the trastuzumab-peptide conjugate, heavy chain peaks were observed at 53,421 and 53,600, and a light chain peak was observed at 23,440, whereas for a product, peaks were observed at 51,278 and 51,439 with a maleimide introduced to the heavy chain, and a light chain peak was observed at 23,440, the same as that of the raw material.

(13-5) Cleavage of Ester Linker and Analysis thereof by ESI-TOFMS

The antibody-peptide ester linker conjugate synthesized in (12-5) of Example 12 is dissolved in any buffer (pH 4.5 to 9.0), an esterase-based enzyme is added thereto, and the solution is stirred at room temperature, whereby the ester structure hydrolyzes to leave an azide group on the antibody; the mass thereof can be measured by ESI-TOFMS.

(13-6) Linker Cleavage of Trastuzumab-Peptide Conjugate and Analysis of Product by ESI-TOFMS First, 20 µg of the trastuzumab-peptide conjugate synthesized in (12-7) of Example 12 was dissolved in a 100 mM glycine-hydrochloric acid buffer (pH 2.0) to be 2.0 µM, and then the solution was stirred at room temperature to cleave the acetal bond in the linker. The mass was measured by ESI-TOFMS; for the trastuzumab-peptide conjugate, a peak was observed at 1,535,223, whereas for a product, a peak was observed at 148,452 with two aldehydes introduced.

(13-7) Determination of Heavy Chain Selectivity of Specifically Modified Compound of Trastuzumab under Reduction Condition by ESI-TOFMS Analysis To the antibody-peptide conjugate produced in (13-1), 2.0 µL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material antibody-peptide conjugate, heavy chain peaks were observed at 52,940 and 53,103, and a light chain peak was observed at 23,440, whereas for a product, peaks were observed at 50,683 and 50,845 with an aldehyde introduced to the heavy chain, and a light chain peak was observed at 23,440, the same as that of the raw material.

Example 14: Conjugate of Azide-Introduced Trastuzumab and Small Compound (14-1) Conjugate of Azide-Introduced Trastuzumab and Small Compound The azide-introduced trastuzumab synthesized in (13-1) of Example 13 was dissolved in 20 mM PBS buffer to be 0.3 mM, then 20 µL of Dibenzocyclooctyne-Cy3 manufactured by Sigma Aldrich (0.94 mM, dissolved in DMF) was added thereto, and the solution was stirred at room temperature for 12 hours. The reaction solution was subjected to solvent substitution to a 9.57 mM PBS buffer (pH 7.4) with Amicon 10K to stop the reaction. The mass was measured by ESI-TOFMS; for the raw material azide-introduced trastuzumab, a peak was observed at 148,706, whereas for a product, a peak was observed at 150,688 with two small compounds introduced.

(14-2) Determination of Heavy Chain Selectivity of Trastuzumab-Small Compound Conjugate under Reduction Condition by ESI-TOFMS Analysis To the antibody-small compound conjugate PBS solution produced in (14-1), 2 µL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material azide-introduced trastuzumab, heavy chain peaks were observed at 50,850 and 51,010, and a light chain peak was observed at 23,440, whereas for a product, peaks were observed at 51,834 and 51,990 with a small compound introduced to the heavy chain, and a light chain peak was observed at 23,440, the same as that of the raw material.

Example 15: Peptide Mapping of Azide-Introduced Trastuzumab (15-1) Trypsin Treatment for Azide-Introduced Trastuzumab (Example 14)

Added to a 1.5 mL low-adsorptive micro test tube were 10 µL of a sample solution, a 50 mM ammonium hydrogencarbonate buffer, and 10 µL of a 20 mM aqueous dithiothreitol solution dissolved in 20% trifluoroethanol, the solution was heated at 65° C. for 1 hour, then 10 µL of a 50 mM aqueous iodoacetamide solution was added thereto, and the solution was reacted in a dark place at room temperature while being shaken at 300 rpm for 30 minutes. After reaction, 40 µL of a 50 mM ammonium hydrogencarbonate buffer was added thereto, the solution was stirred, 10 µL of a 20 ng/µL aqueous trypsin solution (Proteomics Grade, Code No. T6567-5×20 µg (SIGMA)) was added thereto, and the solution was subjected to enzyme digestion at 37° C. for 18 hours. After digestion, 2 µL of a 20% aqueous trifluoroacetic acid solution was added thereto to stop the reaction. Then the solution was diluted twofold so as to give an aqueous trifluoroacetic acid solution with a final concentration of 0.25%, which was used for LC-MS/MS measurement.

(15-2) LC-MS/MS Measurement Conditions for Trastuzumab (Analyzer)
Nano HPLC: EASY-nLC 1000 (Thermo Fisher Scientific)
Mass Spectrometer: Tribrid Mass Spectrometer Orbitrap Fusion (Thermo Fisher Scientific)
(HPLC Analysis Conditions)
Trap column: Acclaim PepMap (registered trademark) 100, 75 µm×2 cm, (Thermo Fisher Scientific)
Analysis column: ESI-column (NTCC-360/75-3-125, 75 µm×12.5 cm, 3 µm (Nikkyo Technos Co., Ltd.))
Mobile Phase A: a 0.1% aqueous formate solution
Mobile Phase B: a 0.1% formate acetonitrile solution
Loading solution: a 0.1% aqueous trifluoroacetic acid solution
Flow rate: 300 nL/min
Sample injection amount: 1 µL
Gradient condition (B %): 2% (0.0 minute to 0.5 minute), 2%→30% (0.5 minute to 23.5 minutes), 30% —+75% (23.5 minutes to 25.5 minutes), and 75% (25.5 minutes to 35.0 minutes).
(Mass Spectrometer Analysis Conditions)
Ionization: ESI, Positive mode
Scan type: Data Dependent Acquisition
Activation Type: Collision Induced Dissociation (CID)

Data acquisition was performed using Xcalibur 3.0 (Thermo Fisher Scientific) and Thermo Orbitrap Fusion Tune Application 2.0 (Thermo Fisher Scientific) as accompanying software.

(15-3) Analysis Condition of Modified Site of Trastuzumab

Modified site analysis of an LC-MS/MS measurement result was performed using Proteome Discoverer version 1.4 (Thermo Fisher Scientific).

For analysis with Proteome Discoverer, Sequest HT was used as a search engine, the range of precursor ion was set to 350 Da to 5,000 Da, Total Intensity Threshold was set to 50,000. Trypsin was set as a digestive enzyme, and Maximum Missed Cleavage Sites was set to 3. Mass Tolerance was set to 5 ppm and 0.5 Da for precursor and fragment ion, respectively. For Static Modification, Carbamidomethyl (+57.021 Da) was set as modification of a cysteine residue with iodoacetamide. For Dynamic Modifications, oxidation of methionine (+15.995 Da) and modified compounds to a lysine residue (an azide-introduced portion (+254.102 Da) and an amine-introduced portion (+228.111 Da)) were set. Furthermore, a filter was applied so as to cause Peptide Confidence to be only High.

As data on amino acid sequences to be searched for a modified site, (1) to (3) illustrated in FIG. 24 were used.

(15-4) Analysis Result of Modified Site of Trastuzumab by LC-MS/MS

Figure 25:
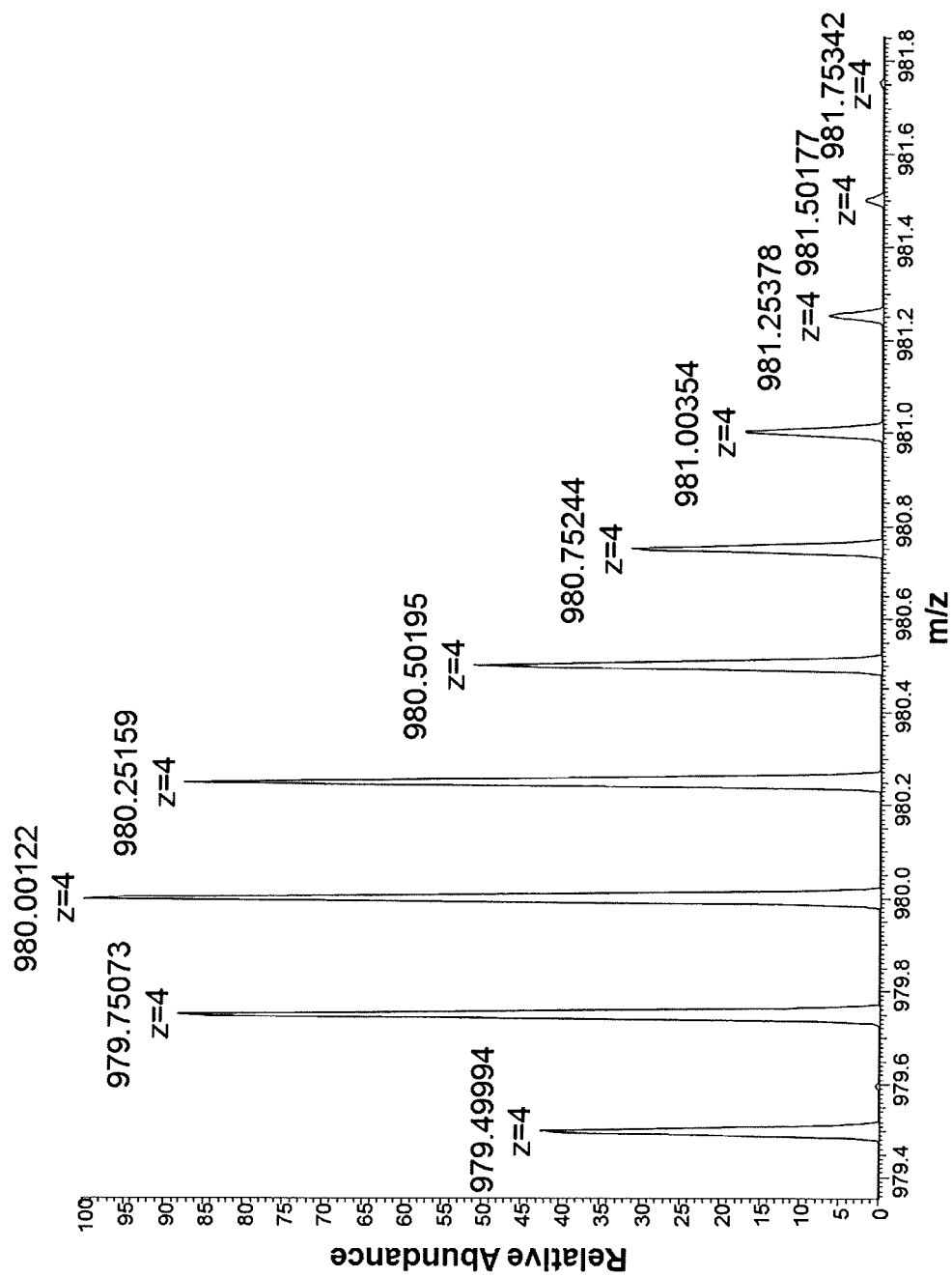
FIG. 25 is a diagram of an MS spectrum (measured value: m/z 979.49982; theoretical value: 979.49975; and tetravalent) of the peptide fragment of THTCPPCPA-PELLGGPSVFLFPPKPKDTLMISR (SEQ ID NO: 40) comprising a modified site to a lysine residue by trypsin digestion of trastuzumab (an azide-introduced portion (+254.102 Da)).
Figure 26:
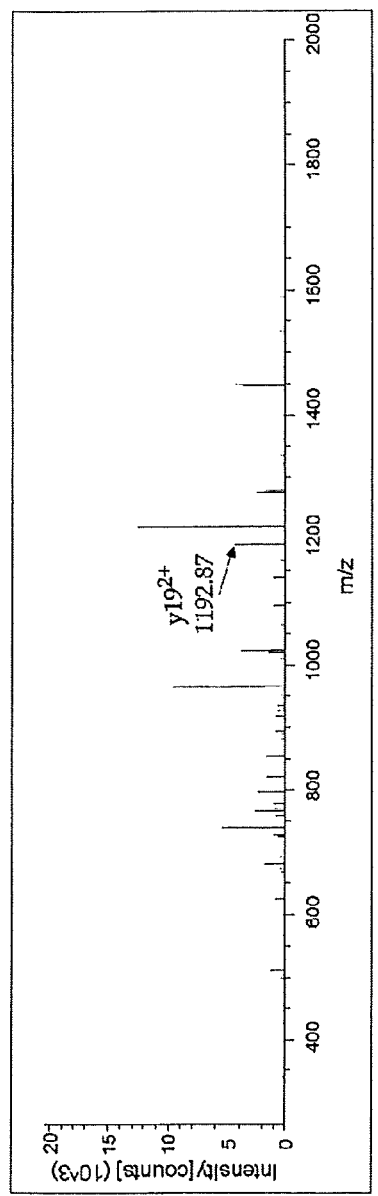
FIG. 26 is a diagram of a CID spectrum of the peptide fragment of THTCPPCPA-PELLGGPSVFLFPPKPKDTLMISR (SEQ ID NO: 40) comprising a modified site to a lysine residue by trypsin digestion of trastuzumab (an azide-introduced portion (+254.102 Da)).

After analysis using LC-MS/MS, an MS spectrum of the peptide fragment of THTCPPCPA-PELLGGPSVFLFPPKPKDTLMISR (SEQ ID NO: 40), which is a peptide consisting of 33 amino acid residues comprising a modified site to a lysine residue by trypsin digestion of trastuzumab (an azide-introduced portion (+254.102 Da)) (measured value: m/z 979.49982; theoretical value: 979.49975; and tetravalent) was observed (FIG. 25); and from a CID spectrum, a product ion of m/z 1,192.87 (theoretical value: 1,192.64) corresponding to divalent y19 indicating modification of a lysine residue at position 246 in EU numbering of the heavy chain was determined (FIG. 26).

Example 16: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (16-1) Synthesis of IgG1 Fc-Binding Peptide The sequence of Ac-RGNCKYHRGQLVWCTYH-NH$_2$ (SEQ ID NO: 42) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration.

They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (36.4 mg, 16.8 μmol).

MS (ESI) m/z: z=3 721.80 [M+3H]$^{3+}$, z=4 541.60 [M+4H]$^{4+}$ (16-2) Formation of Intra-Molecular Disulfide Bond Between Cys at Position 4 and Position 14 of Ac-RGNCKYHRGQLVWCTYH-NH$_2$ (SEQ ID NO: 42)

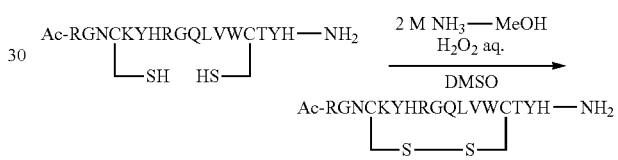

The above-amino acid sequence is SEQ ID NO: 42.

The peptide synthesized in (16-1) (36.4 mg, 16.8 μmol) was dissolved in DMSO (5.00 mL), 2 M NH$_3$-MeOH (17.0 μL, 33.6 μmol) and a hydrogen peroxide solution (34.0 μL, 0.336 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide (20.3 mg, 9.40 mol).

MS (ESI) m/z: z=3 721.25 [M+3H]$^{3}$, z=4 541.20 [M+4H]$^{4+}$ (16-3) Coupling between Disulfide Linker and Peptide

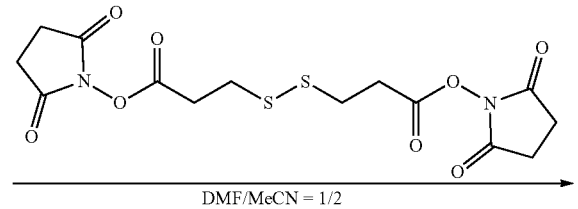

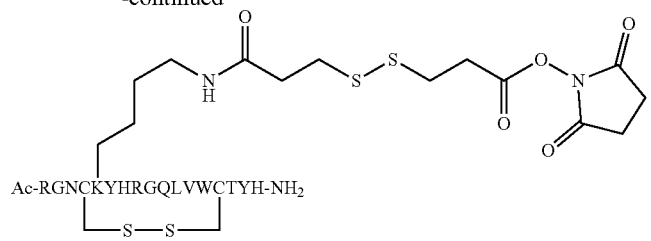

Ac-RGNCKYHRGQLVWCTYH-NH₂ (with S—S disulfide)

The above-amino acid sequence is SEQ ID NO: 42.

Ac-RGNCKYHRGQLVWCTYH-NH$_2$ (SEQ ID NO: 42) synthesized in (16-2) (20.3 mg, 9.40 µmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (228 mg, 0.563 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (6.80 mg, 2.78 µmol).

MS (ESI) m/z: z=3 817.60 [M+3H]$^3$, z=4 613.45 [M+4H]$^{4+}$

HPLC purity: 100%

(16-4) Specific Modification of Anti-HER2 IgG Antibody Trastuzumab and Analysis Thereof by MALDI-TOFMS The peptide- and disulfide linker-coupled NHS-activation compound synthesized in (16-3) was dissolved in N,N'-dimethylformamide to be 21.6 mM. Anti-HER2 IgG antibody trastuzumab (Chugai Pharmaceutical) in an amount of 500 µg was dissolved in 46.9 µL of a 60 mM sodium acetate buffer (pH 4.7), 4.7 µL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by MALDI-TOFMS; no peak derived from the raw material trastuzumab was observed, whereas a peak for a product with one binding peptide introduced was observed at 152,639.

(16-5) HIC-UPLC Analysis of Specific Modification of Anti-HER2 IgG Antibody Trastuzumab The antibody-peptide conjugate produced in (16-4) and a raw material antibody were analyzed by HIC-HPLC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 9.454 minutes is attributed to the trastuzumab raw material, that of 9.845 minutes is attributed to a compound with one peptide introduced to trastuzumab, and that of 10.173 minutes is attributed to a compound with two peptides introduced to trastuzumab. In the case of UV 280 nm, it is believed that a retention time of 9.541 minutes is attributed to the trastuzumab raw material, that of 9.936 minutes is attributed to the compound with one peptide introduced to trastuzumab, and that of 10.254 minutes is attributed to the compound with two peptides introduced to trastuzumab (FIG. 27).

Example 17: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis Thereof (17-1) Synthesis of IgG1 Fc-Binding Peptide The sequence of Ac-RGNCAWHRGKLVWCTYH-NH$_2$ (SEQ ID NO: 43) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (64.8 mg, 30.5 µmol).

MS (ESI) m/z: z=3 710.45 [M+3H]$^{3+}$ (17-2) Formation of Intra-Molecular Disulfide Bond between Cys at Position 4 and Position 14 of Ac-RGN-CAWHRGKLVWCTYH-NH$_2$ (SEQ ID NO: 43)

-continued

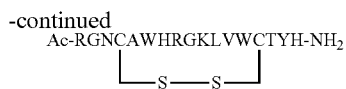

The amino acid sequence is SEQ ID NO: 43.

The peptide synthesized in (17-2) (64.8 mg, 30.5 μmol) was dissolved in DMSO (5.00 mL), 2 M NH$_3$-MeOH (31.0 μL, 61.0 μmol) and a hydrogen peroxide solution (62.0 μL, 610 mol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (35.3 mg, 16.6 μmol).

MS (ESI) m/z: z=3 709.75 [M+3H]$^{3+}$, z=4 532.55 [M+4H]$^{4+}$ (17-3) Coupling between Disulfide Linker and Peptide

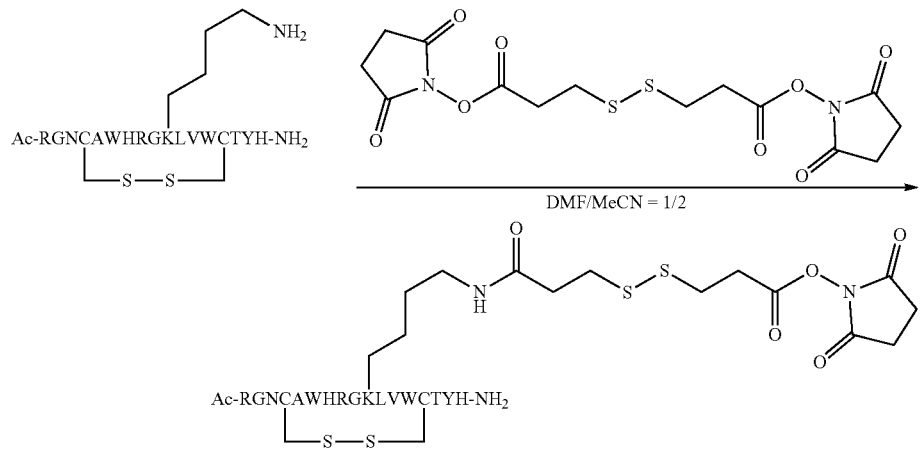

The amino acid sequence is SEQ ID NO: 43.

Ac-RGNCAWHRGKLVWCTYH-NH$_2$ (SEQ ID NO: 43) synthesized in (17-2) (35.3 mg, 16.6 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (269 mg, 0.664 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (17.5 mg, 7.25 μmol).

MS (ESI) m/z: z=3 806.20 [M+3H]$^{3+}$, z=4 604.90 [M+4H]$^{4+}$

HPLC purity: 100%

(17-4) Specific Modification of Anti-HER2 IgG Antibody Trastuzumab and Analysis Thereof by ESI-TOFMS The peptide- and disulfide linker-coupled NHS-activation compound synthesized in (17-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,235, whereas no peak derived from a product with a binding peptide introduced was observed.

(17-5) Determination of Heavy Chain Selectivity of Specifically Modified Compound of Trastuzumab under Reduction Condition by ESI-TOFMS Analysis To the antibody-peptide conjugate produced in (17-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for a product, peaks were observed at 50,594 and 50,753 with a thiopropionyl group introduced to the heavy chain, and a light chain peak was observed at 23,435, the same as that of the raw material.

(17-6) HIC-HPLC Analysis of Specific Modification of Anti-HER2 IgG Antibody Trastuzumab The antibody-peptide conjugate produced in (17-4) and a raw material antibody were analyzed by HIC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 9.469 minutes is attributed to the trastuzumab raw material, whereas that of 10.180 minutes is attributed to a peak derived from the peptide. In the case of UV 280 nm, it is believed that a retention time of 9.563 minutes is attributed to the trastuzumab raw material, whereas that of 10.270 minutes is attributed to a peak derived from the peptide (FIG. 28).

Example 18: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (18-1) Synthesis of IgG1 Fc-Binding Peptide The sequence of Ac-RGNCKWHRGELVWCTYH-NH$_2$ (SEQ ID NO: 44) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (77.8 mg, 35.6 μmol).

MS (ESI) m/z: z=3 729.70 [M+H]$^+$, z=4 547.60 [M+H]

(18-2) Formation of Intra-Molecular Disulfide Bond between Cys at Positions 4 and 14 of Ac-RGNCKWHRGELVWCTYH-NH$_2$ (SEQ ID NO: 44)

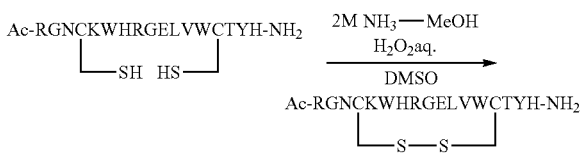

The above-amino acid sequence is SEQ ID NO: 44.

The peptide synthesized in (18-1) (77.8 mg, 35.6 μmol) was dissolved in DMSO (5.00 mL), 2 M NH$_3$-MeOH (71.0 μL, 142 μmol) and a hydrogen peroxide solution (145 μL, 1.42 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (40.0 mg, 18.3 μmol).

MS (ESI) m/z: z=3 729.00 [M+3H]$^{3+}$, z=4 547.05 [M+4H]$^{4+}$ (18-3) Coupling between Disulfide Linker and Peptide

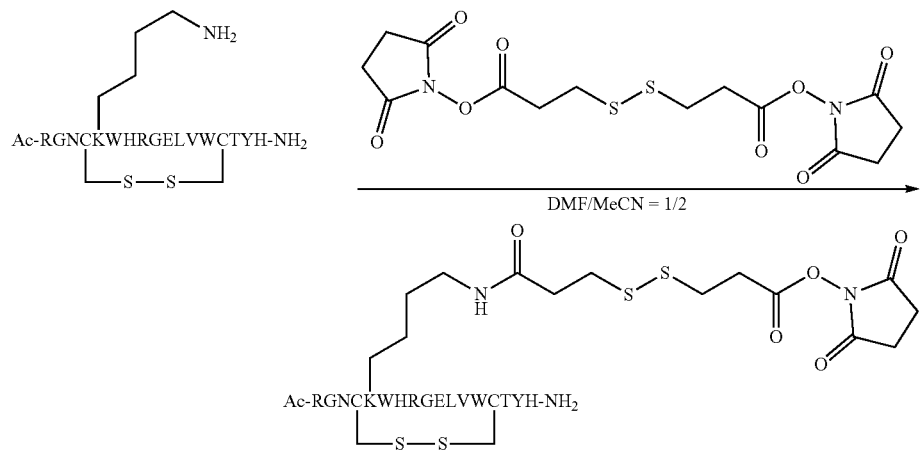

The above-amino acid sequence is SEQ ID NO: 44.

Ac-RGNCKWHRGELVWCTYH-NH$_2$ (SEQ ID NO: 44) synthesized in (18-2) (40.0 mg, 18.3 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (296 mg, 0.733 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (20.0 mg, 8.09 μmol).

MS (ESI) m/z: z=3 825.55 [M+3H]$^{3+}$, z=4 619.45 [M+4H]$^{4+}$

HPLC purity: 31%

(18-4) Specific Modification of Anti-HER2 IgG Antibody Trastuzumab and Analysis Thereof by ESI-TOFMS The peptide- and disulfide linker-coupled NHS-activation compound synthesized in (18-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,222, whereas a peak for a product with one binding peptide introduced was observed at 150,583.

(18-5) Determination of Heavy Chain Selectivity of Specifically Modified Compound of Trastuzumab under Reduction Condition by ESI-TOFMS Analysis To the antibody-peptide conjugate produced in (18-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,680 and 50,719 with a thiopropionyl group introduced to the heavy chain, and a light chain peak was observed at 23,438, the same as that of the raw material.

(18-6) HIC-HPLC Analysis of Specific Modification of Anti-HER2 IgG Antibody Trastuzumab The antibody-peptide conjugate produced in (18-4) and a raw material antibody were analyzed by HIC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:

a: a trastuzumab raw material;

b: trastuzumab+30 equivalents of the peptide- and disulfide linker-coupled NHS-activation compound.

In the case of UV 225 nm, it is believed that a retention time of 9.462 minutes is attributed to the trastuzumab raw material, whereas that of 10.142 minutes is attributed to a compound with one peptide introduced to trastuzumab. In the case of UV 280 nm, it is believed that a retention time of 9.554 minutes is attributed to the trastuzumab raw material, whereas that of 10.230 minutes is attributed to a compound with one peptide introduced to trastuzumab (FIG. 29).

Example 19: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (19-1) Synthesis of IgG1 Fc-Binding Peptide The sequence of Ac-RGNCKWHRGQLVWCTYH-NH$_2$ (SEQ ID NO: 45) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0: 2.5. After cutting out, Resin was removed by filtration, and trifluoroacetic acid was removed. Diethyl ether was added to the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (74.1 mg, 34.0 μmol).

MS (ESI) m/z: z=3 729.40 [M+3H]$^{3+}$, z=4 547.35 [M+4H]$^{4+}$ (19-2) Formation of Intra-Molecular Disulfide Bond between Cys at Positions 4 and 14 of Ac-RGNCK-WHRGQLVWCTYH-NH$_2$ (SEQ ID NO: 45)

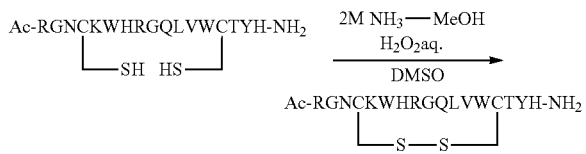

The above-amino acid sequence is SEQ ID NO: 45.

The peptide synthesized in (19-2) (74.1 mg, 34.0 μmol) was dissolved in DMSO (5.00 mL), 2 M NH$_3$-MeOH (67.8 μL, 0.136 mmol) and a hydrogen peroxide solution (139 μL, 1.36 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (38.2 mg, 17.5 μmol).

MS (ESI) m/z: z=3 728.80 [M+3H]$^{3+}$, z=4 546.85 [M+4H]$^{4+}$ (19-3) Coupling Between Disulfide Linker and Peptide

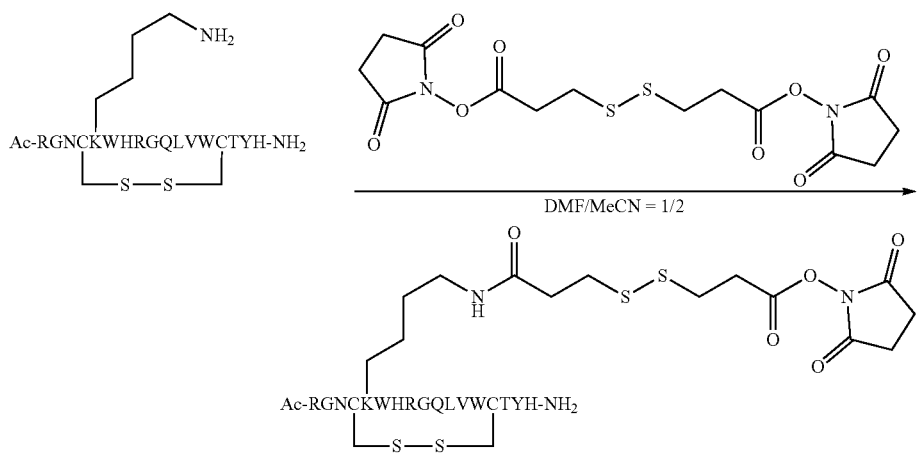

The above-amino acid sequence is SEQ ID NO: 45.

Ac-RGNCKWHRGQLVWCTYH-NH$_2$ (SEQ ID NO: 45) synthesized in (19-2) (38.2 mg, 17.5 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (283 mg, 0.70 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (16.5 mg, 6.68 μmol).

MS (ESI) m/z: z=3 825.25 [M+3H]$^{3+}$, z=4 619.25 [M+4H]$^{4+}$

HPLC purity: 100%

(19-4) Specific Modification of Anti-HER2 IgG Antibody Trastuzumab and Analysis Thereof by ESI-TOFMS The peptide- and disulfide linker-coupled NHS-activation compound synthesized in (19-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,064, whereas a peak for a product with one binding peptide introduced was observed at 150,600.

(19-5) Determination of Heavy Chain Selectivity of Specifically Modified Compound of Trastuzumab under Reduction Condition by ESI-TOFMS Analysis To the antibody-peptide conjugate produced in (19-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,683 and 50,717 with a thiopropionyl group introduced to the heavy chain, and a light chain peak was observed at 23,440, the same as that of the raw material.

(19-6) HIC-HPLC Analysis of Specific Modification of Anti-HER2 IgG Antibody Trastuzumab The antibody-peptide conjugate produced in (19-4) and a raw material antibody were analyzed by HIC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 9.458 minutes is attributed to the trastuzumab raw material, whereas that of 10.137 minutes is attributed to a compound with one peptide introduced to trastuzumab. In the case of UV 280 nm, it is believed that a retention time of 9.550 minutes is attributed to the trastuzumab raw material, whereas that of 10.225 minutes is attributed to a compound with one peptide introduced to trastuzumab (FIG. 30).

Example 20: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (20-1) Synthesis of IgG1 Fc-Binding Peptide The sequence of Ac-RGNCKYHLGELVWCTYH-NH$_2$ (SEQ ID NO: 46) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to

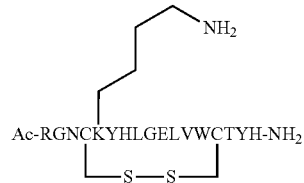

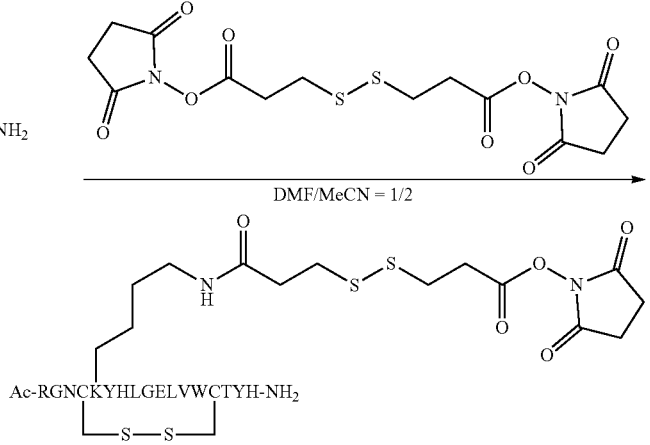

the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (34.5 mg, 16.3 μmol).

MS (ESI) m/z: z=3 707.80 $[M+3H]^{3+}$, z 4 531.10 $[M+4H]^{4+}$ (20-2) Formation of Intra-Molecular Disulfide Bond between Cys at Position 4 and Position 14 of Ac-RGNCKYHLGELVWCTYH-NH$_2$ (SEQ ID NO: 46)

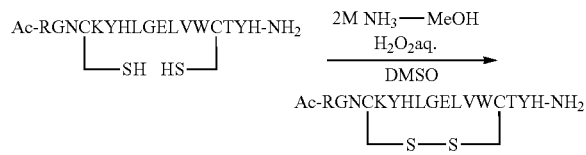

The amino acid sequence is SEQ ID NO: 46.

The peptide synthesized in (20-1) (34.5 mg, 16.3 μmol) was dissolved in DMSO (5.00 mL), 2 M NH$_3$-MeOH (17.0 μL, 32.6 μmol) and a hydrogen peroxide solution (33.0 μL, 0.326 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (15.6 mg, 7.37 μmol).

MS (ESI) m/z: z=3 707.10 $[M+3H]^3$, z=4 530.60 $[M+4H]^{4+}$ (20-3) Coupling between Disulfide Linker and Peptide The amino acid sequence is SEQ ID NO: 46.

Ac-RGNCKYHLGELVWCTYH-NH$_2$ (SEQ ID NO: 46) synthesized in (20-2) (15.6 mg, 7.37 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (119 mg, 0.295 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (5.00 mg, 2.08 μmol).

MS (ESI) m/z: z=2 1,204.85 $[M+2H]^{2+}$, z=3 803.50 $[M+3H]^{3+}$

HPLC purity: 70%

(20-4) Specific Modification of Anti-HER2 IgG Antibody Trastuzumab and Analysis Thereof by ESI-TOFMS The peptide- and disulfide linker-coupled NHS-activation compound synthesized in (20-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer.

(20-5) HIC-HPLC Analysis of Specific Modification of Anti-HER2 IgG Antibody Trastuzumab The antibody-peptide conjugate produced in (20-4) and a raw material antibody were analyzed by HIC-HPLC. For a column, Butyl-NPR (TOSOH) 4.6×350 mm 2.5 μm was used. Detection was performed with A Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, a peak of the trastuzumab raw material was observed at a retention time of 9.581 minutes, whereas a peak was observed at that of 10.089 minutes. In the case of UV 280 nm, a peak of the trastuzumab raw material was observed at a retention time of 9.663 minutes, whereas a peak was observed at that of 10.307 minutes (FIG. 31).

Example 21: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (21-1) Synthesis of IgG1 Fc-Binding Peptide The sequence of Ac-RGNCKYHLGQLVWCTYH-NH$_2$ (SEQ ID NO: 47) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration.

They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (53.0 mg, 25.0 μmol).

MS (ESI) m/z: z=3 707.40 [M+3H]$^{3+}$, z=4 530.80 [M+4H]$^{4+}$ (21-2) Formation of Intra-Molecular Disulfide Bond Between Cys at Positions 4 and 14 of Ac-RGNCKYHLGQLVWCTYH-NH$_2$ (SEQ ID NO: 47)

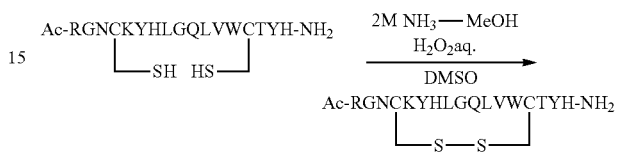

The above-amino acid sequence is SEQ ID NO: 47.

The peptide synthesized in (21-1) (53.0 mg, 25.0 μmol) was dissolved in DMSO (5.00 mL), 2 M NH$_3$-MeOH (25.0 μL, 50.0 μmol) and a hydrogen peroxide solution (51.0 μL, 0.500 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (23.2 mg, 10.9 μmol).

MS (ESI) m/z: z=3 706.75 [M+3H]$^{3+}$, z=4 530.35 [M+4H]$^{4+}$ (21-3) Coupling between Disulfide Linker and Peptide

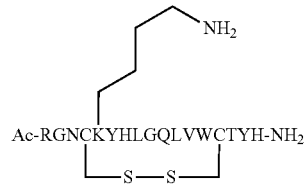

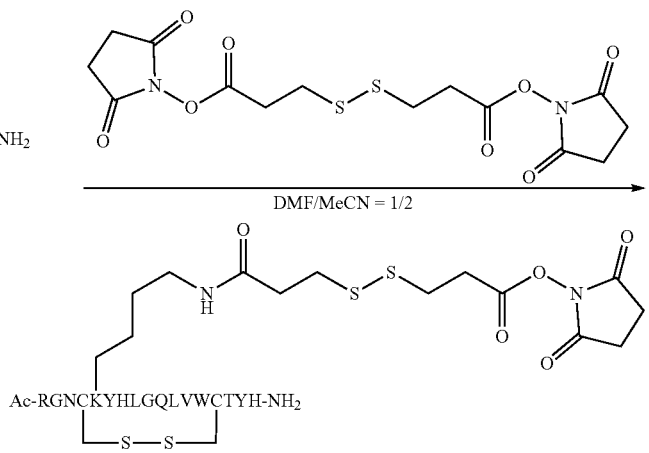

The above-amino acid sequence is SEQ ID NO: 47.

Ac-RGNCKYHLGQLVWCTYH-NH$_2$ (SEQ ID NO: 47) synthesized in (21-2) (23.2 mg, 10.9 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (176 mg, 0.436 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (6.40 mg, 2.66 μmol).

MS (ESI) m/z: z=2 1204.30 $[M+2H]^{2+}$, z=3 803.15 $[M+3H]^{3+}$

HPLC purity: 61%

(21-4) Specific Modification of Anti-HER2 IgG Antibody Trastuzumab and Analysis Thereof by ESI-TOFMS The peptide- and disulfide linker-coupled NHS-activation compound synthesized in (21-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,069, whereas a peak for a product with one binding peptide introduced was observed at 150,515, and a peak for a product with two binding peptides introduced was observed at 152,972.

(21-5) Determination of Heavy Chain Selectivity of Specifically Modified Compound of Trastuzumab under Reduction Condition by ESI-TOFMS Analysis To the antibody-peptide conjugate produced in (21-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,683 and 50,844 with a thiopropionyl group introduced to the heavy chain, and a light chain peak was observed at 23,439, the same as that of the raw material.

(21-6) HIC-HPLC Analysis of Specific Modification of Anti-HER2 IgG Antibody Trastuzumab The antibody-peptide conjugate produced in (21-4) and a raw material antibody were analyzed by HIC. For a column, Butyl-NPR (TOSOH) 4.6×350 mm 2.5 μm was used. Detection was performed with A_Buffer: 0.1 M PiNa, 2.3 M $(NH_4)_2SO_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:

a: a trastuzumab raw material;

b: trastuzumab+30 equivalents of the peptide- and disulfide linker-coupled NHS-activation compound.

In the case of UV 225 nm, it is believed that a retention time of 9.454 minutes is attributed to the trastuzumab raw material, whereas that of 9.877 minutes is attributed to a compound with one peptide introduced to trastuzumab, and that of 10.230 minutes is attributed to a compound with two peptides introduced to trastuzumab. In the case of UV 280 nm, it is believed that a retention time of 9.540 minutes is attributed to the trastuzumab raw material, whereas that of 9.966 minutes is attributed to a compound with one peptide introduced to trastuzumab, and that of 10.317 minutes is attributed to a compound with two peptides introduced to trastuzumab (FIG. 32).

Example 22: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (22-1) Synthesis of IgG1 Fc-Binding Peptide The sequence of Ac-DCKWHLGELVWCT-NH₂ (SEQ ID NO: 48) was synthesized by Fmoc solid phase synthesis, as is similar to Example 1. A target product was obtained (71.1 mg, 43.6 μmol).

MS (ESI) m/z: z=2 816.350 $[M+2H]^2$ (22-2) Formation of Intra-Molecular Disulfide Bond between Cys at Positions 2 and 12 of Ac-DCK-WHLGELVWCT-NH₂ (SEQ ID NO: 48)

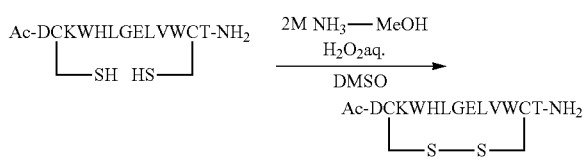

The amino acid sequence is SEQ ID NO: 48.

The peptide synthesized in (22-1) (71.1 mg, 43.6 μmol) was dissolved in DMSO (5.00 mL), 2 M NH₃-MeOH (43.6 μL, 87.2 μmol) and a hydrogen peroxide solution (88.8 μL, 87.2 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (31.6 mg, 19.4 μmol).

MS (ESI) m/z: z=2 815.350 $[M+2H]^{2+}$ (22-3) Coupling between Disulfide Linker and Peptide

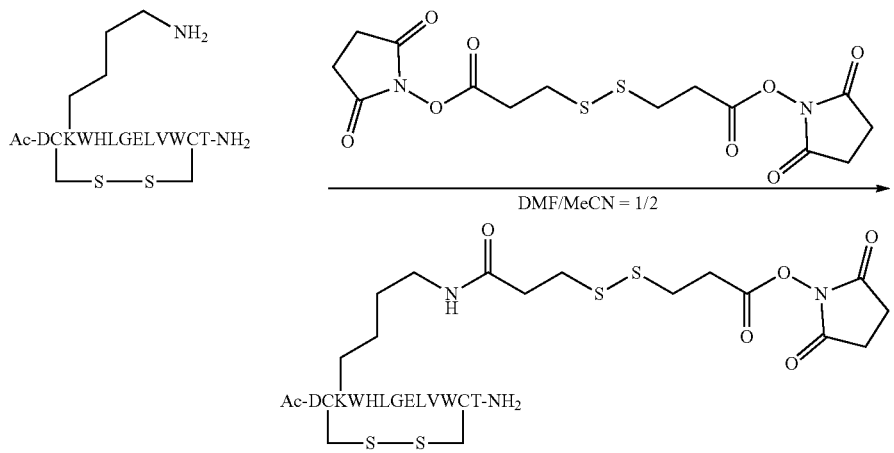

The amino acid sequence is SEQ ID NO: 48.

Ac-DCKWHLGELVWCT-NH₂ (SEQ ID NO: 48) synthesized in (22-2) (31.6 mg, 19.4 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (312 mg, 776 μmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (14.2 mg, 7.40 μmol).

MS (ESI) m/z: z=2 960.05 [M+2H]²⁺

HPLC purity: 70%

(22-4) Specific Modification of Anti-HER2 IgG Antibody Trastuzumab and Analysis Thereof by ESI-TOFMS The peptide- and disulfide linker-coupled NHS-activation compound synthesized in (22-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer.

(22-5) HIC-HPLC Analysis of Specific Modification of Anti-HER2 IgG Antibody Trastuzumab The antibody-peptide conjugate produced in (22-4) and a raw material antibody were analyzed by HIC-HPLC. For a column, Butyl-NPR (TOSOH) 4.6×350 mm 2.5 m was used. Detection was performed with A_Buffer: 0.1 M PiNa, 2.3 M (NH₄)₂SO₄, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, peaks were observed at retention times of 11.193 minutes and 11.981 minutes. In the case of UV 280 nm, peaks were observed at retention times of 11.257 minutes and 12.057 minutes (FIG. 33).

Example 23: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (23-1) Synthesis of IgG1 Fc-Binding Peptide The sequence of Ac-DCKYHLGELVWCT-NH₂ (SEQ ID NO: 49) was synthesized by Fmoc solid phase synthesis, as is similar to Example 1. A target product was obtained (28.0 mg, 17.4 μmol).

MS (ESI) m/z: z=2 804.80 [M+2H]²⁺

(23-2) Formation of Intra-Molecular Disulfide Bond between Cys at Positions 2 and 12 of Ac-DCKYHLGELVWCT-NH₂ (SEQ ID NO: 49)

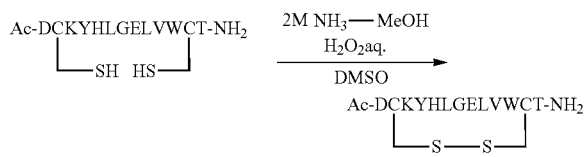

The above-amino acid sequence is SEQ ID NO: 49.

The peptide synthesized in (23-1) (28.0 mg, 17.4 μmol) was dissolved in DMSO (5.00 mL), 2 M NH₃-MeOH (17.4 μL, 34.8 μmol) and a hydrogen peroxide solution (35.4 μL, 348 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (18.0 mg, 11.2 μmol).

MS (ESI) m/z: z=2 803.90 $[M+2H]^{2+}$ (23-3) Coupling between Disulfide Linker and Peptide

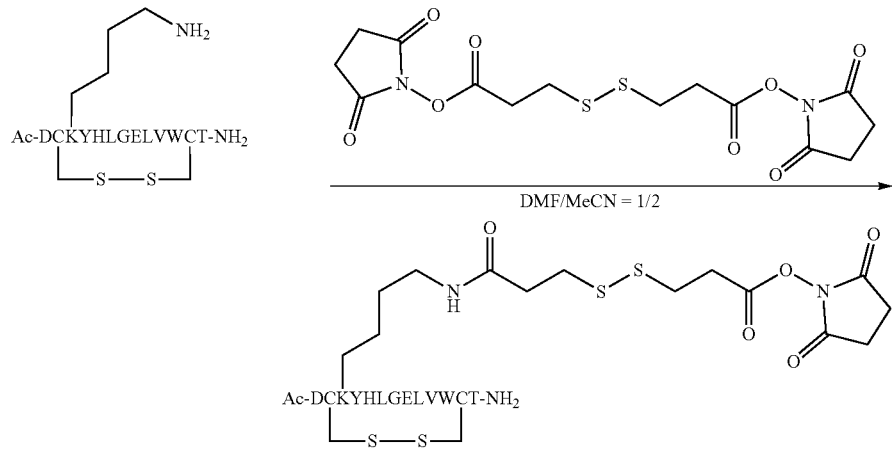

The above-amino acid sequence is SEQ ID NO: 49.

Ac-DCKYHLGELVWCT-NH$_2$ (SEQ ID NO: 49) synthesized in (23-2) (18.0 mg, 11.2 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (181 mg, 448 μmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (2.75 mg, 1.45 μmol).

MS (ESI) m/z: z=2 948.55 $[M+2H]^{2+}$

HPLC purity: 75%

(23-4) Specific Modification of Anti-HER2 IgG Antibody Trastuzumab and Analysis Thereof by ESI-TOFMS The peptide- and disulfide linker-coupled NHS-activation compound synthesized in (23-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; a peak for a product with one binding peptide introduced was observed at 150,001, and a peak for a product with two binding peptides introduced was observed at 151,618.

(23-5) Determination of Heavy Chain Selectivity of Specifically Modified Compound of Trastuzumab under Reduction Condition by ESI-TOFMS Analysis To the antibody-peptide conjugate produced in (23-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,682 and 50,845 with a thiopropionyl group introduced to the heavy chain, and a light chain peak was observed at 23,439, the same as that of the raw material.

(23-6) HIC-HPLC Analysis of Specific Modification of Anti-HER2 IgG Antibody Trastuzumab The antibody-peptide conjugate produced in (23-4) and a raw material antibody were analyzed by HIC. For a column, Butyl-NPR (TOSOH) 4.6×350 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 10.347 minutes is attributed to a compound with one peptide introduced to trastuzumab, and that of 11.015 minutes is attributed to a compound with two peptides introduced to trastuzumab. In the case of UV 280 nm, it is believed that a retention time of 10.434 minutes is attributed to a compound with one peptide introduced to trastuzumab, and that of 11.100 minutes is attributed to a compound with two peptides introduced to trastuzumab (FIG. 34).

Example 24: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (24-1) Synthesis of IgG1 Fc-Binding Peptide The sequence of Ac-DCKWHRGELVWCT-NH$_2$ (SEQ ID NO: 50) was synthesized by Fmoc solid phase synthesis, as is similar to Example 1. A target product was obtained (52.8 mg, 31.5 μmol).

MS (ESI) m/z: z=2 837.85 [M+2H]$^{2+}$, z=3 558.90 [M+3H]$^{3+}$ (24-2) Formation of Intra-Molecular Disulfide Bond between Cys at Positions 2 and 12 of Ac-DCK-WHRGELVWCT-NH$_2$ (SEQ ID NO: 50)

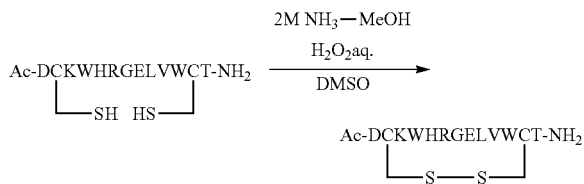

The above-amino acid sequence is SEQ ID NO: 50.

The peptide synthesized in (24-1) (52.8 mg, 31.5 μmol) was dissolved in DMSO (5.00 mL), 2 M NH$_3$-MeOH (31.5 μL, 63.0 μmol) and a hydrogen peroxide solution (64.0 μL, 630 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (26.9 mg, 16.1 μmol).

MS (ESI) m/z: z=2 836.75 [M+2H]$^{2+}$, z=3 558.25 [M+3H]$^{3+}$ (24-3) Coupling between Disulfide Linker and Peptide 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (8.40 mg, 4.28 μmol).

MS (ESI) m/z: z=2 981.50 [M+2H]$^{2+}$, z=3 654.70 [M+3H]$^{3+}$

HPLC purity: 78%

(24-4) Specific Modification of Anti-HER2 IgG Antibody Trastuzumab and Analysis Thereof by ESI-TOFMS The peptide- and disulfide linker-coupled NHS-activation compound synthesized in (24-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; a peak for a product with one binding peptide introduced was observed at 150,268, and a peak for a product with two binding peptides introduced was observed at 152,295.

(24-5) Determination of Heavy Chain Selectivity of Specifically Modified Compound of Trastuzumab under Reduction Condition by ESI-TOFMS Analysis To the antibody-peptide conjugate produced in (24-4), 5 μL of a 7 mM tris(2-carboxyethyl)phosphine hydrochloride

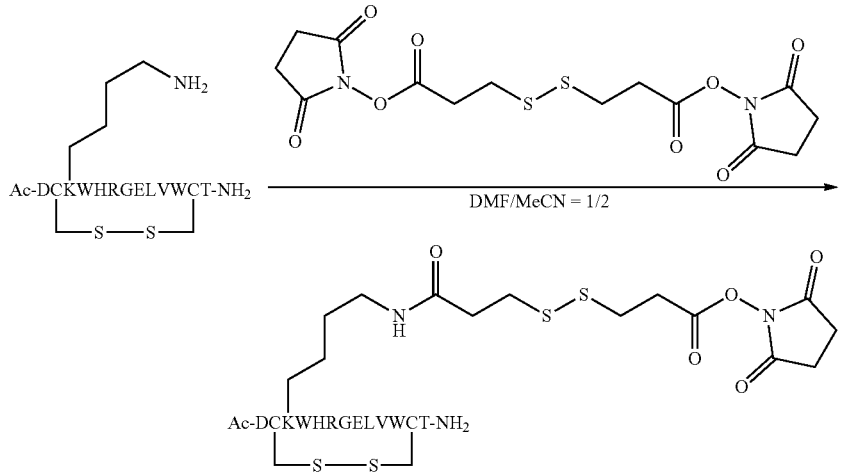

The above-amino acid sequence is SEQ ID NO: 50.

Ac-DCKWHRGELVWCT-NH$_2$ (SEQ ID NO: 50) synthesized in (24-2) (26.9 mg, 16.1 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (260 mg, 644 μmol) in acetonitrile (2.00 mL) was added thereto, and the solution was stirred at room temperature for solution (an equivalent with respect to the antibody) was added, and the solution was stirred at room temperature for 20 minutes. The mass was measured by ESI-TOFMS; for products, peaks were observed at 50,682 and 50,841 with a thiopropionyl group introduced to the heavy chain, and a light chain peak was observed at 23,438, the same as that of the raw material.

(24-6) HIC-HPLC Analysis of Specific Modification of Anti-HER2 IgG Antibody Trastuzumab The antibody-peptide conjugate produced in (24-4) and a raw material antibody were analyzed by HIC. For a column, Butyl-NPR (TOSOH) 4.6×350 mm 2.5 m was used. Detection was performed with A Buffer: 0.1 M PiNa, 2.3 M $(NH_4)_2SO_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:

a: a trastuzumab raw material;

b: trastuzumab+30 equivalents of the peptide- and disulfide linker-coupled NHS-activation compound.

In the case of UV 225 nm, it is believed that a retention time of 10.749 minutes is attributed to a compound with one peptide introduced to trastuzumab, and that of 11.679 minutes is attributed to a compound with two peptides introduced to trastuzumab. In the case of UV 280 nm, it is believed that a retention time of 10.849 minutes is attributed to a compound with one peptide introduced to trastuzumab, and that of 11.782 minutes is attributed to a compound with two peptides introduced to trastuzumab (FIG. 35).

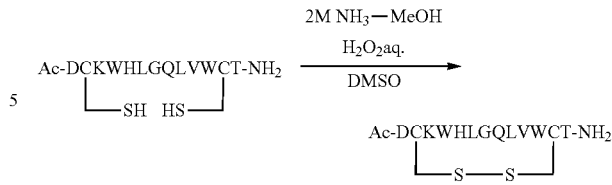

The above-amino acid sequence is SEQ ID NO: 51.

The peptide synthesized in (25-1) (68.5 mg, 42.0 μmol) was dissolved in DMSO (5.00 mL), 2 M $NH_3$-MeOH (42.0 μL, 84.0 μmol) and a hydrogen peroxide solution (85.7 μL, 840 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (30.6 mg, 18.8 μmol).

MS (ESI) m/z: z=2 814.90 $[M+2H]^{2+}$ (25-3) Coupling between Disulfide Linker and Peptide

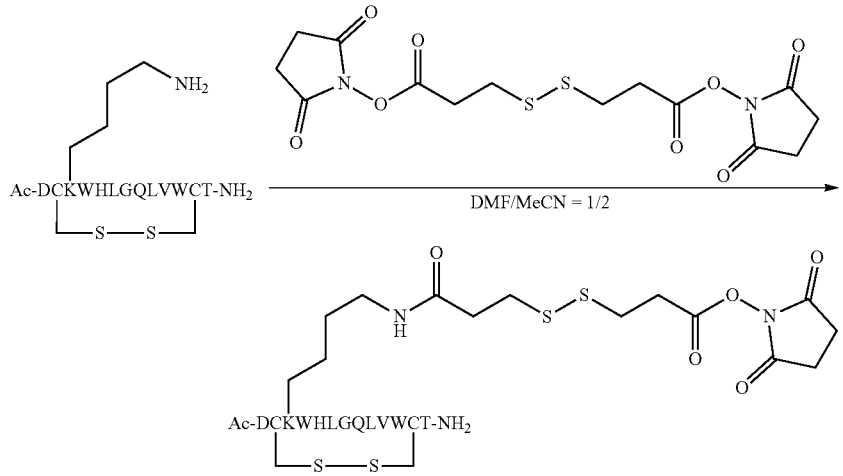

Example 25: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (25-1) Synthesis of IgG1 Fc-Binding Peptide The sequence of Ac-DCKWHLGQLVWCT-NH$_2$ (SEQ ID NO: 51) was synthesized by Fmoc solid phase synthesis, as is similar to Example 1. A target product was obtained (68.5 mg, 42.0 μmol).

MS (ESI) m/z: z=2 815.90 $[M+2H]^{2+}$, z=3 544.25 $[M+3H]^{3+}$ (25-2) Formation of Intra-Molecular Disulfide Bond between Cys at Positions 2 and 12 of Ac-DCK-WHLGQLVWCT-NH$_2$ (SEQ ID NO: 51)

The above-amino acid sequence is SEQ ID NO: 51.

Ac-DCKWHLGQLVWCT-NH$_2$ (SEQ ID NO: 51) synthesized in (25-2) (30.6 mg, 18.8 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (304 mg, 752 μmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (4.10 mg, 2.14 μmol).

MS (ESI) m/z: z=2 959.45 [M+2H]$^{2+}$
HPLC purity: 74%

(25-4) Specific Modification of Anti-HER2 IgG Antibody Trastuzumab and Analysis Thereof by ESI-TOFMS The peptide- and disulfide linker-coupled NHS-activation compound synthesized in (42-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; a peak for a product with one binding peptide introduced was observed at 150,025, and a peak for a product with two binding peptides introduced was observed at 151,878.

(25-5) Determination of Heavy Chain Selectivity of Specifically Modified Compound of Trastuzumab under Reduction Condition by ESI-TOFMS Analysis To the antibody-peptide conjugate produced in (25-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,682 and 50,844 with a thiopropionyl group introduced to the heavy chain, and a light chain peak was observed at 23,439, the same as that of the raw material.

(25-6) HIC-HPLC Analysis of Specific Modification of Anti-HER2 IgG Antibody Trastuzumab The antibody-peptide conjugate produced in (25-4) and a raw material antibody were analyzed by HIC. For a column, Butyl-NPR (TOSOH) 4.6×350 mm 2.5 μm was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 10.761 minutes is attributed to a compound with one peptide introduced to trastuzumab, and that of 11.722 minutes is attributed to a compound with two peptides introduced to trastuzumab. In the case of UV 280 nm, it is believed that a retention time of 10.849 minutes is attributed to a compound with one peptide introduced to trastuzumab, and that of 11.807 minutes is attributed to a compound with two peptides introduced to trastuzumab (FIG. 36).

Example 26: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (26-1) Synthesis of IgG1 Fc-Binding Peptide The sequence of Ac-DCKYHRGELVWCT-NH$_2$ (SEQ ID NO: 52) was synthesized by Fmoc solid phase synthesis, as is similar to Example 1. A target product was obtained (100 mg, 60.8 μmol).

MS (ESI) m/z: z=2 826.35 [M+2H]$^{2+}$, z=3 551.25 [M+3H]$^{3+}$ (26-2) Formation of Intra-Molecular Disulfide Bond between Cys at Positions 2 and 12 of Ac-DCKYHRGELVWCT-NH$_2$ (SEQ ID NO: 52)

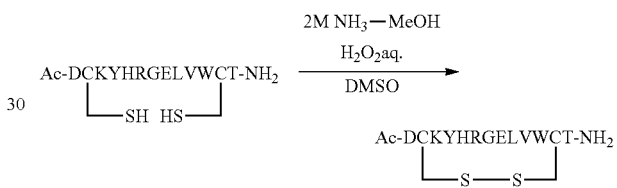

The amino acid sequence is SEQ ID NO: 52.

The peptide synthesized in (26-1) (100 mg, 60.8 μmol) was dissolved in DMSO (5.00 mL), 2 M NH$_3$-MeOH (60.8 μL, 122 μmol) and a hydrogen peroxide solution (125 μL, 1.22 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (74.5 mg, 45.2 μmol).

MS (ESI) m/z: z=2 825.30 [M+2H]$^{2+}$, z=3 550.60 [M+3H]$^{3+}$ (26-3) Coupling Between Disulfide Linker and Peptide

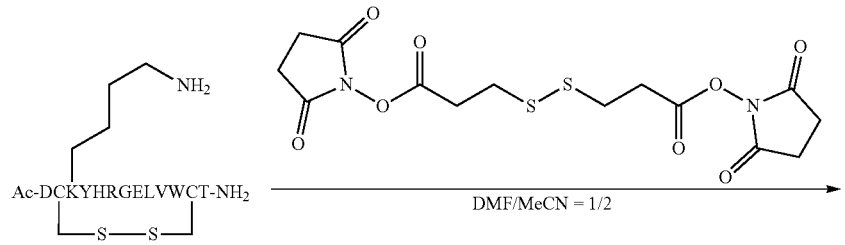

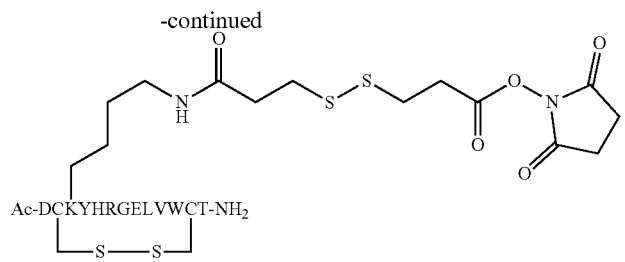

Ac-DCKYHRGELVWCT-NH₂
└─S——S─┘

The amino acid sequence is SEQ ID NO: 52.

Ac-DCKYHRGELVWCT-NH₂ (SEQ ID NO: 52) synthesized in (26-2) (74.5 mg, 45.2 µmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (731 mg, 1.81 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (23.0 mg, 18.9 µmol).

MS (ESI) m/z: z=2 970.00 $[M+2H]^{2+}$

HPLC purity: 69%

(26-4) Specific Modification of Anti-HER2 IgG Antibody Trastuzumab and Analysis Thereof by ESI-TOFMS The peptide- and disulfide linker-coupled NHS-activation compound synthesized in (26-3) was dissolved in N,N'-dimethylformamide to be 21.6 mM. Anti-HER2 IgG antibody trastuzumab (Chugai Pharmaceutical) in an amount of 500 µg was dissolved in 46.9 µL of a 60 mM sodium acetate buffer (pH 4.7), 4.7 µL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 147,074, whereas a peak for a product with one binding peptide introduced was observed at 150,062, and a peak for a product with two binding peptides introduced was observed at 151,873. A peak for a by-product was observed at 154,562.

(26-5) HIC-HPLC Analysis of Specific Modification of Anti-HER2 IgG Antibody Trastuzumab The antibody-peptide conjugate produced in (26-4) and a raw material antibody were analyzed by HIC-HPLC. For a column, Butyl-NPR (TOSOH) 4.6×350 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 9.464 minutes is attributed to the trastuzumab raw material, whereas that of 10.309 minutes is attributed to a compound with one peptide introduced to trastuzumab, and that of 10.962 minutes is attributed to a compound with two peptides introduced to trastuzumab. In the case of UV 280 nm, it is believed that a retention time of 9.564 minutes is attributed to the trastuzumab raw material, whereas that of 10.395 minutes is attributed to a compound with one peptide introduced to trastuzumab, and that of 11.054 minutes is attributed to a compound with two peptides introduced to trastuzumab (FIG. 37).

Example 27: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (27-1) Synthesis of IgG1 Fc-Binding Peptide The sequence of Ac-DCKYHLGQLVWCT-NH₂ (SEQ ID NO: 53) was synthesized by Fmoc solid phase synthesis, as is similar to Example 1. A target product was obtained (85.6 mg, 53.3 µmol).

MS (ESI) m/z: z=2 804.45 $[M+2H]^{2+}$, z=3 536.60 $[M+3H]^{3+}$ (27-2) Formation of Intra-Molecular Disulfide Bond between Cys at Positions 2 and 12 of Ac-DCKYHLGQLVWCT-NH₂ (SEQ ID NO: 53)

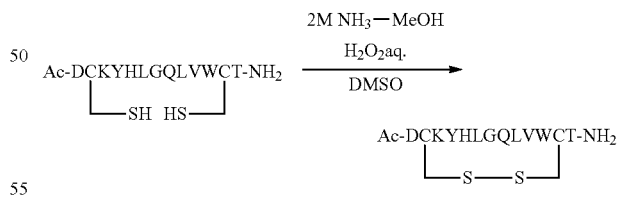

The above-amino acid sequence is SEQ ID NO: 53.

The peptide synthesized in (27-1) (85.6 mg, 53.3 µmol) was dissolved in DMSO (5.00 mL), 2 M NH₃-MeOH (53.5 µL, 107 µmol) and a hydrogen peroxide solution (109 µL, 1.07 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (34.2 mg, 21.3 μmol).

MS (ESI) m/z: z=2 803.40 $[M+2H]^{2+}$ (27-3) Coupling Between Disulfide Linker and Peptide product with two binding peptides introduced was observed at 151,947. A peak for a by-product was observed at 154,885.

(27-5) Determination of Heavy Chain Selectivity of Specifically Modified Compound of Trastuzumab under Reduction Condition by ESI-TOFMS Analysis To the antibody-peptide conjugate produced in (27-4), 5 μL of a 7 mM tris(2-carboxyethyl)phosphine hydrochloride

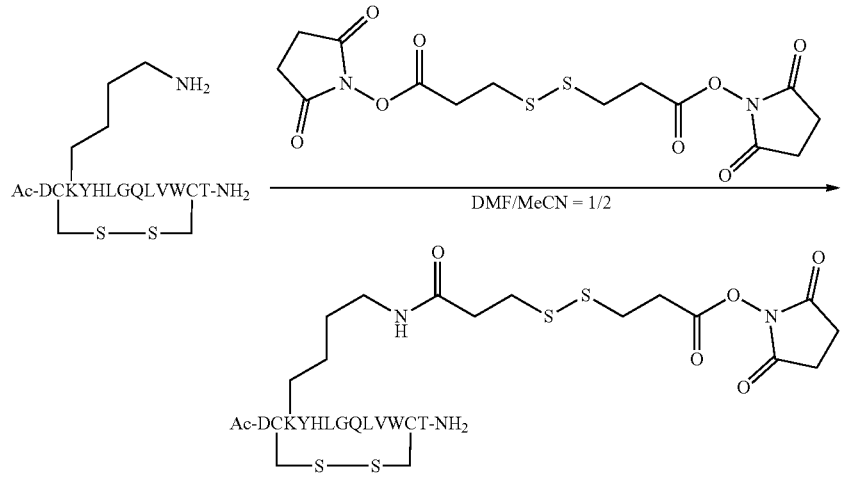

The above-amino acid sequence is SEQ ID NO: 53.

Ac-DCKYHLGQLVWCT-NH$_2$ (SEQ ID NO: 53) synthesized in (27-2) (34.2 mg, 21.3 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (345 mg, 852 μmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (12.0 mg, 6.34 μmol).

MS (ESI) m/z: z=2 948.00 $[M+2H]^{2+}$

HPLC purity: 80%

(27-4) Specific Modification of Anti-HER2 IgG Antibody Trastuzumab and Analysis Thereof by ESI-TOFMS The peptide- and disulfide linker-coupled NHS-activation compound synthesized in (27-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 147,285, whereas a peak for a product with one binding peptide introduced was observed at 150,031, and a peak for a solution (an equivalent with respect to the antibody) was added, and the solution was stirred at room temperature for 20 minutes. The mass was measured by ESI-TOFMS; for products, peaks were observed at 50,685 and 50,847 with a thiopropionyl group introduced to the heavy chain.

(27-6) HIC-HPLC Analysis of Specific Modification of Anti-HER2 IgG Antibody Trastuzumab The antibody-peptide conjugate produced in (27-4) and a raw material antibody were analyzed by HIC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:

a: a trastuzumab raw material;

b: trastuzumab+30 equivalents of the peptide- and disulfide linker-coupled NHS-activation compound.

In the case of UV 225 nm, it is believed that a retention time of 9.468 minutes is attributed to the trastuzumab raw material, whereas that of 10.360 minutes is attributed to a compound with one peptide introduced to trastuzumab, and that of 11.045 minutes is attributed to a compound with two peptides introduced to trastuzumab. In the case of UV 280 nm, it is believed that a retention time of 9.575 minutes is attributed to the trastuzumab raw material, whereas that of 10.449 minutes is attributed to a compound with one peptide introduced to trastuzumab, and that of 11.137 minutes is attributed to a compound with two peptides introduced to trastuzumab (FIG. 38).

Example 28: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (28-1) Synthesis of IgG1 Fc-Binding Peptide The sequence of Ac-DCKWHRGQLVWCT-NH$_2$ (SEQ ID NO: 54) was synthesized by Fmoc solid phase synthesis, as is similar to Example 1. A target product was obtained (89.4 mg, 57.4 μmol).

MS (ESI) m/z: z=2 837.30 [M+2H]$^2$, z=3 558.60 [M+3H]$^{3+}$ (28-2) Formation of Intra-Molecular Disulfide Bond between Cys at Positions 2 and 12 of Ac-DCKWHRGQLVWCT-NH$_2$ (SEQ ID NO: 54)

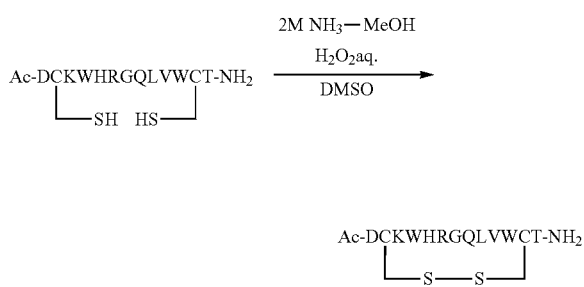

The above-amino acid sequence is SEQ ID NO: 54.

The peptide synthesized in (28-1) (89.4 mg, 57.4 μmol) was dissolved in DMSO (5.00 mL), 2 M NH$_3$-MeOH (53.5 μL, 107 μmol) and a hydrogen peroxide solution (109 μL, 1.07 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (64.4 mg, 38.5 μmol).

MS (ESI) m/z: z=2 836.35 [M+2H]$^{2+}$, z=3 558.00 [M+3H]$^{3+}$ (28-3) Coupling between Disulfide Linker and Peptide

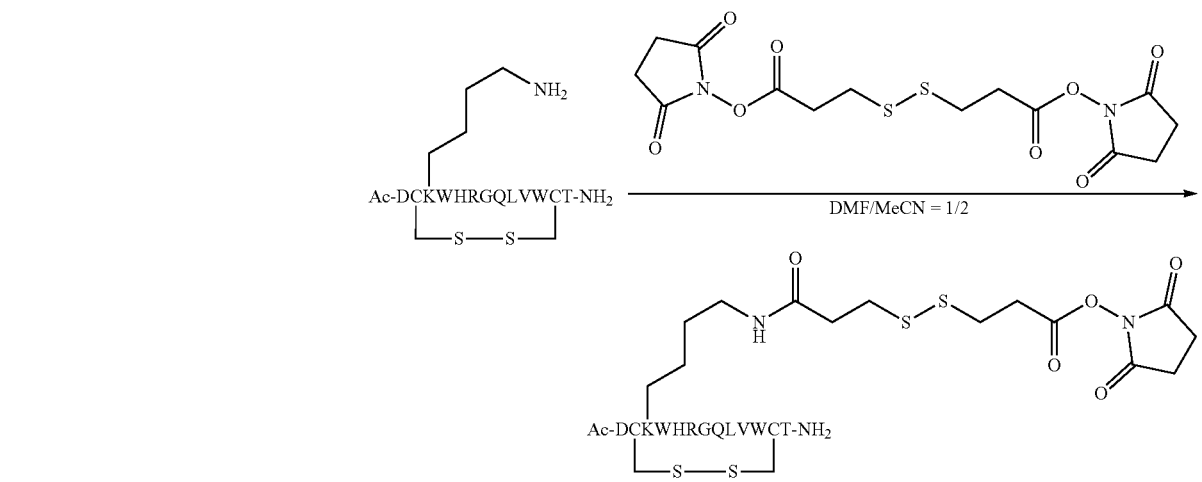

The above-amino acid sequence is SEQ ID NO: 54.

Ac-DCKWHRGQLVWCT-NH$_2$ (SEQ ID NO: 54) synthesized in (28-2) (64.4 mg, 38.5 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (623 mg, 1.54 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (21.8 mg, 11.1 μmol).

MS (ESI) m/z: z=2 981.05 [M+2H]$^{2+}$, z=3 654.25 [M+3H]$^{3+}$

HPLC purity: 82%

(28-4) Specific Modification of Anti-HER2 IgG Antibody Trastuzumab and Analysis Thereof by ESI-TOFMS The peptide- and disulfide linker-coupled NHS-activation compound synthesized in (28-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 147,548, whereas a peak for a product with one binding peptide introduced was observed at 150,261, and a peak for a product with two binding peptides introduced was observed at 152,112. A peak for a by-product was observed at 154,824.

(28-5) Determination of Heavy Chain Selectivity of Specifically Modified Compound of Trastuzumab under Reduction Condition by ESI-TOFMS Analysis To the antibody-peptide conjugate produced in (28-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,684 and 50,845 with a thiopropionyl group introduced to the heavy chain.

(28-6) HIC-HPLC Analysis of Specific Modification of Anti-HER2 IgG Antibody Trastuzumab The antibody-peptide conjugate produced in (28-4) and a raw material antibody were analyzed by HIC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
a: a trastuzumab raw material;
b: trastuzumab+30 equivalents of the peptide- and disulfide linker-coupled NHS-activation compound.

In the case of UV 225 nm, it is believed that a retention time of 9.477 minutes is attributed to the trastuzumab raw material, whereas that of 10.714 minutes is attributed to a compound with one peptide introduced to trastuzumab, and that of 11.650 minutes is attributed to a compound with two peptides introduced to trastuzumab. In the case of UV 280 nm, it is believed that a retention time of 9.573 minutes is attributed to the trastuzumab raw material, whereas that of 10.812 minutes is attributed to a compound with one peptide introduced to trastuzumab, and that of 11.742 minutes is attributed to a by-product (FIG.

Example 29: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (29-1) Synthesis of IgG1 Fc-Binding Peptide The sequence of Ac-DCKYHRGQLVWCT-NH$_2$ (SEQ ID NO: 55) was synthesized by Fmoc solid phase synthesis, as is similar to Example 1. A target product was obtained (93.6 mg, 56.7 μmol).

MS (ESI) m/z: z=2 825.80 [M+2H]$^{2+}$, z=3 550.90 [M+3H]$^{3+}$ (29-2) Formation of Intra-Molecular Disulfide Bond between Cys at Positions 2 and 12 of Ac-DCKYHRGQLVWCT-NH$_2$ (SEQ ID NO: 55)

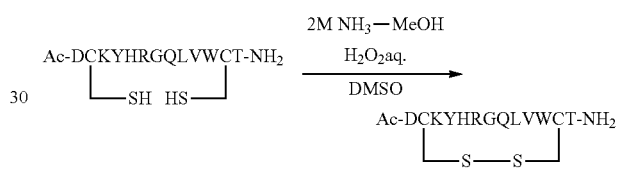

The above-amino acid sequence is SEQ ID NO: 55.

The peptide synthesized in (29-1) (93.6 mg, 56.7 μmol) was dissolved in DMSO (5.00 mL), 2 M NH$_3$-MeOH (56.5 μL, 113 μmol) and a hydrogen peroxide solution (115 μL, 1.13 mmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (71.6 mg, 46.2 μmol).

MS (ESI) m/z: z=2 824.85 [M+2H]$^{2+}$, z=3 550.25 [M+3H]$^{3+}$ (29-3) Coupling between Disulfide Linker and Peptide

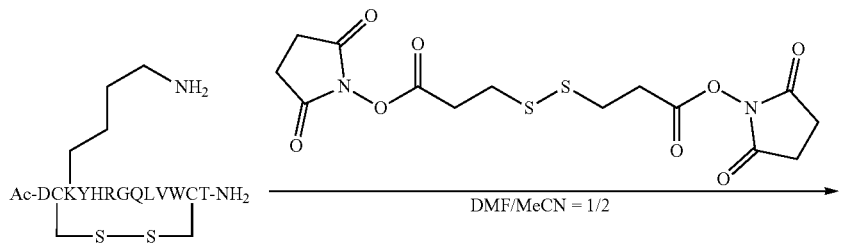

-continued

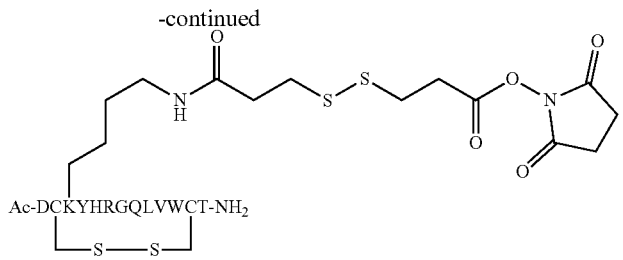

The above-amino acid sequence is SEQ ID NO: 55.

Ac-DCKYHRGQLVWCT-NH$_2$ (SEQ ID NO: 55) synthesized in (29-2) (71.6 mg, 46.2 μmol, the 2nd and 12th of two cysteines form a disulfide bond in the molecule) was dissolved in N,N'-dimethylformamide (1.00 mL), a solution dissolving 3,3'-dithiodipropionic acid di(N-succinimidyl) (747 mg, 1.85 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (25.5 mg, 13.2 μmol).

MS (ESI) m/z: z=2 969.45 [M+2H]$^{2+}$, z=3 646.75 [M+3H]$^{3+}$

HPLC purity: 82%

(29-4) Specific Modification of Anti-HER2 IgG Antibody Trastuzumab and Analysis Thereof by ESI-TOFMS The peptide- and disulfide linker-coupled NHS-activation compound synthesized in (29-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; a peak for a product with one binding peptide introduced was observed at 149,884, and a peak for a product with two binding peptides introduced was observed at 151,873.

(29-5) Determination of Heavy Chain Selectivity of Specifically Modified Compound of Trastuzumab under Reduction Condition by ESI-TOFMS Analysis To the antibody-peptide conjugate produced in (29-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,682 and 50,844 with a thiopropionyl group introduced to the heavy chain.

(29-6) HIC-HPLC Analysis of Specific Modification of Anti-HER2 IgG Antibody Trastuzumab The antibody-peptide conjugate produced in (29-4) and a raw material antibody were analyzed by HIC. For a column, Butyl-NPR (TOSOH) 4.6×350 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:
 a: a trastuzumab raw material;
 b: trastuzumab+30 equivalents of the peptide- and disulfide linker-coupled NHS-activation compound.

In the case of UV 225 nm, it is believed that a retention time of 10.292 minutes is attributed to a compound with one peptide introduced to trastuzumab, and that of 10.949 minutes is attributed to a compound with two peptides introduced to trastuzumab. In the case of UV 280 nm, it is believed that a retention time of 10.381 minutes is attributed to a compound with one peptide introduced to trastuzumab, and that of 11.038 minutes is attributed to a compound with two peptides introduced to trastuzumab (FIG. 40).

Example 30: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (30-1) Synthesis of IgG1 Fc-Binding Peptide The sequence of Ac-RGNCAWHLGQLVWCKYH-NH$_2$ (SEQ ID NO: 56) was synthesized by Fmoc solid phase synthesis, as is similar to Example 1. A target product was obtained (54.2 mg, 25.7 μmol).

MS (ESI) m/z: z=3 705.05 [M+3H]$^3$, z=4 529.10 [M+4H]$^{4+}$ (30-2) Formation of Intra-Molecular Disulfide Bond between Cys at Positions 4 and 14 of Ac-RGN-CAWHLGQLVWCKYH-NH$_2$ (SEQ ID NO: 56)

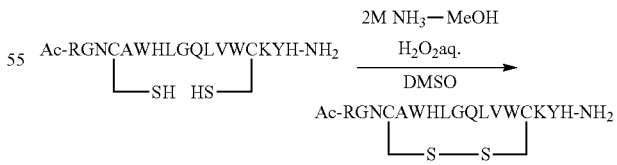

The above-amino acid sequence is SEQ ID NO: 56.

The peptide synthesized in (30-1) (54.2 mg, 25.7 μmol) was dissolved in DMSO (5.00 mL), 2 M NH$_3$-MeOH (25.7 μL, 51.4 μmol) and a hydrogen peroxide solution (52.5 μL, 514 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (13.3 mg, 5.54 μmol).

MS (ESI) m/z: z=3 704.45 [M+3H]$^{3+}$, z=4 528.60 [M+4H]$^{4+}$ (30-3) Coupling between Disulfide Linker and Peptide and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,788, whereas a peak for a product with one binding peptide introduced was observed at 151,375.

(30-5) Determination of Heavy Chain Selectivity of Specifically Modified Compound of Trastuzumab under Reduction Condition by ESI-TOFMS Analysis To the antibody-peptide conjugate produced in (30-4), 5 μL of a 7 mM tris(2-carboxyethyl)phosphine hydrochloride solution (an equivalent with respect to the antibody) was

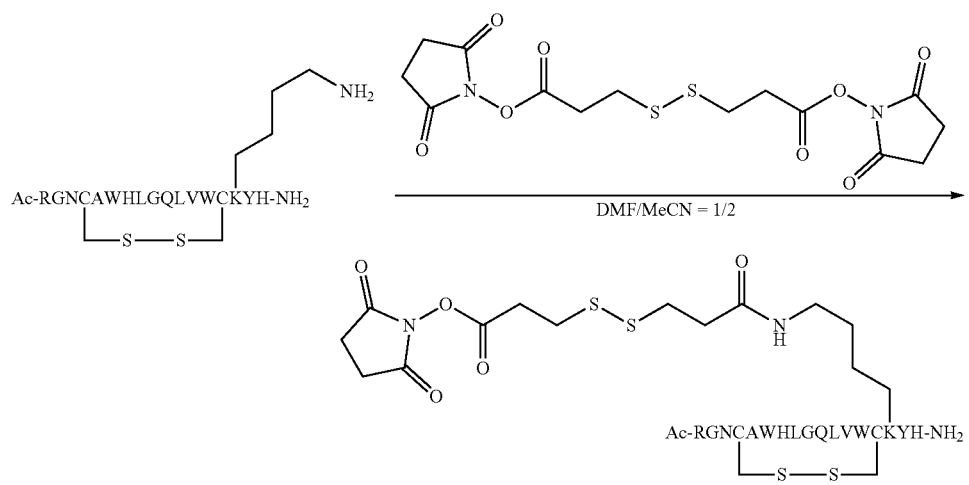

The above-amino acid sequence is SEQ ID NO: 56.

Ac-RGNCAWHLGQLVWCKYH-NH$_2$ (SEQ ID NO: 56) synthesized in (30-2) (13.3 mg, 5.54 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (89.6 mg, 222 μmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (7.00 mg, 2.92 μmol).

MS (ESI) m/z: z=3 800.90 [M+3H]$^{3+}$, z=4 600.80 [M+4H]$^{4+}$

HPLC purity: 69%

(30-4) Specific Modification of Anti-HER2 IgG Antibody Trastuzumab and Analysis Thereof by ESI-TOFMS The peptide- and disulfide linker-coupled NHS-activation compound synthesized in (30-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, added, and the solution was stirred at room temperature for 20 minutes. The mass was measured by ESI-TOFMS; for products, peaks were observed at 50,593 and 50,756 with a thiopropionyl group introduced to the heavy chain, and a light chain peak was observed at 23,337, the same as that of the raw material.

(30-6) HIC-HPLC Analysis of Specific Modification of Anti-HER2 IgG Antibody Trastuzumab The antibody-peptide conjugate produced in (30-4) and a raw material antibody were analyzed by HIC. For a column, Butyl-NPR (TOSOH) 4.6×350 mm 2.5 μm was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 1.0 ml/min, a gradient of B 0%→100%, 12 minutes (data collection 20 minutes), a column temperature of 25° C., a thermostat temperature of RT, and a detector with two wavelengths of UV 225 nm (Ch1) and 280 nm (Ch2).

Samples were reacted under the following conditions:

a: a trastuzumab raw material;

b: trastuzumab+30 equivalents of the peptide- and disulfide linker-coupled NHS-activation compound.

In the case of UV 225 nm, it is believed that a retention time of 9.556 minutes is attributed to the trastuzumab raw material, whereas that of 10.259 minutes is attributed to a compound with one peptide introduced to trastuzumab. In the case of UV 280 nm, it is believed that a retention time of 9.549 minutes is attributed to the trastuzumab raw material, whereas that of 10.382 minutes is attributed to a compound with one peptide introduced to trastuzumab (FIG. 41).

Example 31: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (31-1) Synthesis of IgG1 Fc-Binding Peptide The sequence of Ac-RGNCAWHLGELVWCKYH-NH$_2$ (SEQ ID NO: 57) was synthesized by Fmoc solid phase synthesis, as is similar to Example 1. A target product was obtained (34.0 mg, 16.1 µmol).

MS (ESI) m/z: z=3 705.40 [M+3H]$^{3+}$, z=4 529.30 [M+4H]$^{4+}$ (31-2) Formation of Intra-Molecular Disulfide Bond between Cys at Positions 4 and 14 of Ac-RGN-CAWHLGELVWCKYH-NH$_2$ (SEQ ID NO: 57)

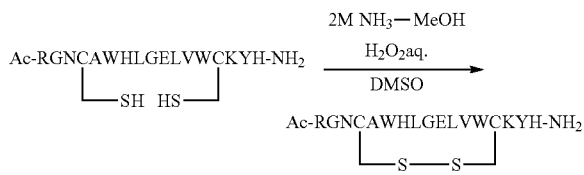

The above-amino acid sequence is SEQ ID NO: 57.

The peptide synthesized in (31-1) (34.0 mg, 16.1 µmol) was dissolved in DMSO (5.00 mL), 2 M NH$_3$-MeOH (16.1 µL, 32.2 µmol) and a hydrogen peroxide solution (32.9 µL, 322 µmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (13.6 mg, 6.40 µmol).

MS (ESI) m/z: z=3 704.85 [M+3H]$^{3+}$, z=4 528.80 [M+4H]$^{4+}$ (31-3) Coupling between Disulfide Linker and Peptide

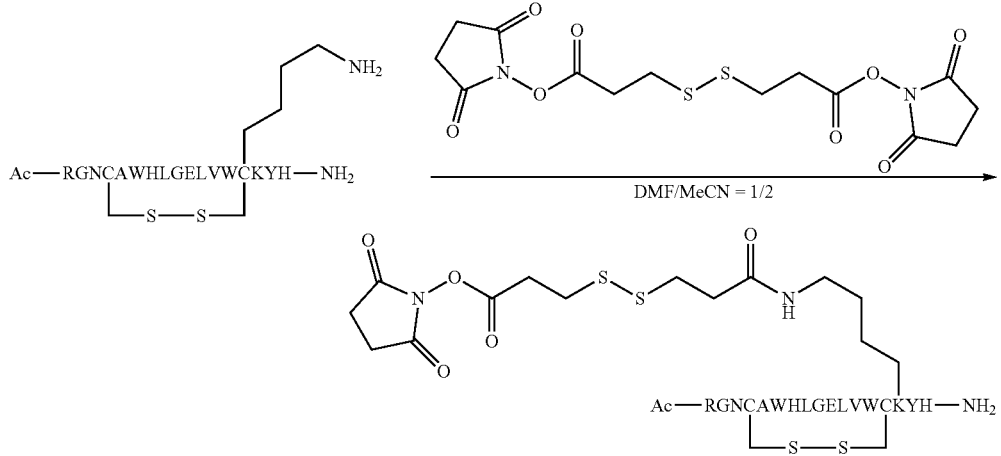

The above-amino acid sequence is SEQ ID NO: 57.

Ac-RGNCAWHLGELVWCKYH-NH$_2$ (SEQ ID NO: 57) synthesized in (31-2) (13.6 mg, 6.40 µmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (104 mg, 256 µmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (1.5 mg, 0.63 µmol).

MS (ESI) m/z: z=3 801.45 [M+3H]$^{3+}$, z=4 601.50 [M+4H]$^{4+}$

HPLC purity: 77%

(31-4) Specific Modification of Anti-HER2 IgG Antibody Trastuzumab and Analysis Thereof by ESI-TOFMS The peptide- and disulfide linker-coupled NHS-activation compound synthesized in (31-3) was dissolved in N,N'-dimethylformamide to be 21.6 mM. Anti-HER2 IgG antibody trastuzumab (Chugai Pharmaceutical) in an amount of 500 µg was dissolved in 46.9 µL of a 60 mM sodium acetate buffer (pH 4.7), 4.7 µL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,219, whereas no peak for a product with a binding peptide introduced was observed.

(31-5) Determination of Heavy Chain Selectivity of Specifically Modified Compound of Trastuzumab under Reduction Condition by ESI-TOFMS Analysis To the antibody-peptide conjugate produced in (31-4), 5 µL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,592 and 50,762 with a thiopropionyl group introduced to the heavy chain, and a light chain peak was observed at 23,338, the same as that of the raw material.

(31-6) HIC-HPLC Analysis of Specific Modification of Anti-HER2 IgG Antibody Trastuzumab The antibody-peptide conjugate produced in (31-4) and a raw material antibody were analyzed by HIC. For a column, Protein-Pak Hi Res HIC Column (Waters) 4.6×100 mm 2.5 μm was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 50% B 50%→A 0% B 100%, 12 minutes (data collection 15 minutes), a column temperature of room temperature, a thermostat temperature of room temperature, and a detector with a wavelength of 280 nm.

Samples were reacted under the following conditions:
a: a trastuzumab raw material;
b: trastuzumab+30 equivalents of the peptide- and disulfide linker-coupled NHS-activation compound.

Figure 42:
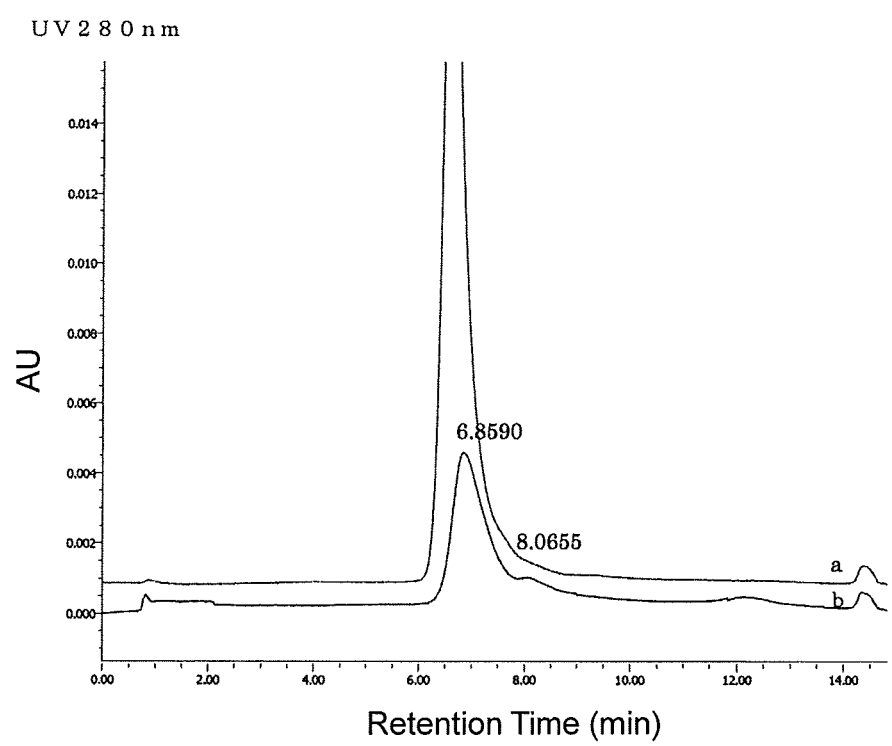
FIG. 42 is a diagram of a result of HIC-UPLC analysis of specific modification of trastuzumab (detection wavelength: UV 280 nm) (Example 31). AU on the vertical axis indicates absorbance (the same for the drawings below)

It is believed that a retention time of 6.8590 minutes is attributed to the trastuzumab raw material, whereas that of 8.0655 minutes is attributed to a peptide (FIG. 42).

Example 32: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (32-1) Synthesis of IgG1 Fc-Binding Peptide The sequence of Ac-RGNCAYHLGQLVWCTKH-NH₂ (SEQ ID NO: 58) was synthesized by Fmoc solid phase

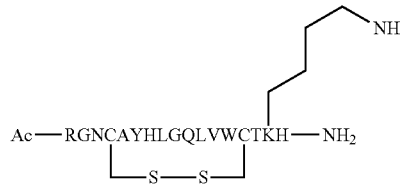

synthesis, as is similar to Example 1. A target product was obtained (36.7 mg, 18.1 μmol).

MS (ESI) m/z: z=3 676.75 $[M+3H]^{3+}$, z=4 507.80 $[M+4H]^{4+}$ (32-2) Formation of Intra-Molecular Disulfide Bond between Cys at Positions 4 and 14 of Ac-RGN-CAYHLGQLVWCTKH-NH₂ (SEQ ID NO: 58)

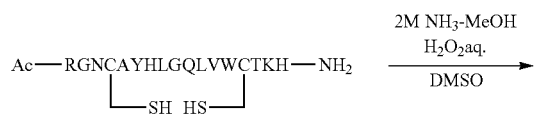

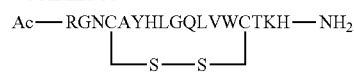

The amino acid sequence is SEQ ID NO: 58.

The peptide synthesized in (32-1) (36.7 mg, 18.1 μmol) was dissolved in DMSO (5.00 mL), 2 M NH₃-MeOH (18.1 μL, 36.2 μmol) and a hydrogen peroxide solution (37.0 μL, 362 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (18.2 mg, 8.99 μmol).

MS (ESI) m/z: z=3 676.00 $[M+3H]^{3+}$, z=4 507.30 $[M+4H]^{4+}$ (32-3) Coupling between Disulfide Linker and Peptide

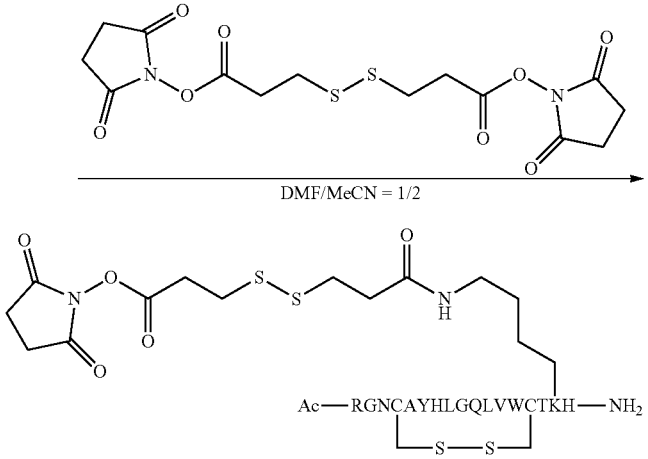

The amino acid sequence is SEQ ID NO: 58.

Ac-RGNCAYHLGQLVWCTKH-NH₂ (SEQ ID NO: 58) synthesized in (32-2) (18.2 mg, 8.99 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (145 mg, 360 μmol) in acetonitrile (1.50 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (3.00 mg, 1.30 μmol).

MS (ESI) m/z: z=3 772.45 [M+3H]$^3$

HPLC purity: 90%

(32-4) Specific Modification of Anti-HER2 IgG Antibody Trastuzumab and Analysis Thereof by ESI-TOFMS The peptide- and disulfide linker-coupled NHS-activation compound synthesized in (32-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,077, whereas a peak for a product with one binding peptide introduced was observed at 150,281.

(32-5) HIC-HPLC Analysis of Specific Modification of Anti-HER2 IgG Antibody Trastuzumab The antibody-peptide conjugate produced in (32-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:

a: a trastuzumab raw material;

b: trastuzumab+30 equivalents of the peptide- and disulfide linker-coupled NHS-activation compound.

Figure 43:
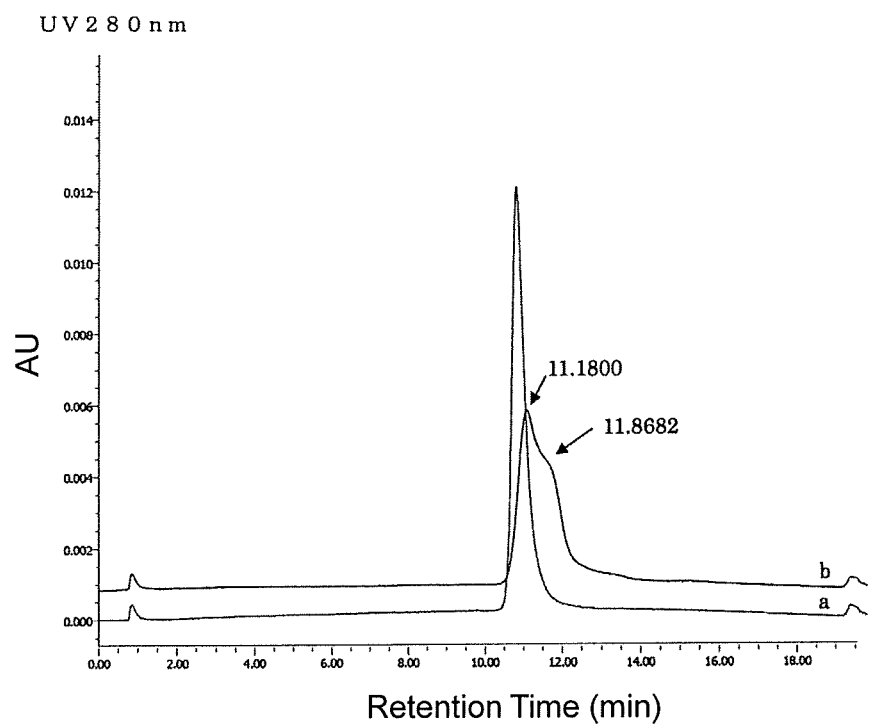
FIG. 43 is a diagram of a result of HIC-UPLC analysis of specific modification of trastuzumab (detection wavelength: UV 280 nm) (Example 32).

It is believed that a retention time of 11.1800 minutes is attributed to the trastuzumab raw material, whereas that of 11.8682 minutes is attributed to a compound with one peptide introduced to trastuzumab (FIG. 43).

Example 33: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (33-1) Synthesis of IgG1 Fc-Binding Peptide The sequence of Ac-RGNCAYHLGQLVWCTYK-NH$_2$ (SEQ ID NO: 59) was synthesized by Fmoc solid phase synthesis, as is similar to Example 1. A target product was obtained (52.1 mg, 25.4 μmol).

MS (ESI) m/z: z=2 1027.3 [M+2H]$^{2+}$, z=3 685.45 [M+3H]$^{3+}$ (33-2) Formation of Intra-Molecular Disulfide Bond between Cys at Positions 4 and 14 of Ac-RGN-CAYHLGQLVWCTYK-NH$_2$ (SEQ ID NO: 59)

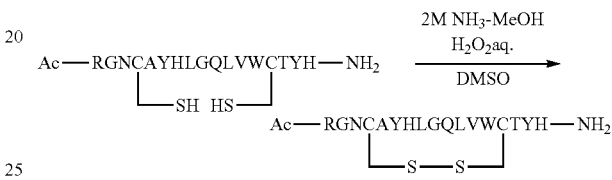

The amino acid sequence is SEQ ID NO: 59.

The peptide synthesized in (33-1) (52.1 mg, 25.4 μmol) was dissolved in DMSO (5.00 mL), 2 M NH$_3$-MeOH (25.4 μL, 50.8 μmol) and a hydrogen peroxide solution (51.9 μL, 508 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (4.70 mg, 2.29 μmol).

MS (ESI) m/z: z=2 1026.5 [M+2H]$^{2+}$, z=3 684.75 [M+3H]$^{3+}$ (33-3) Coupling between Disulfide Linker and Peptide

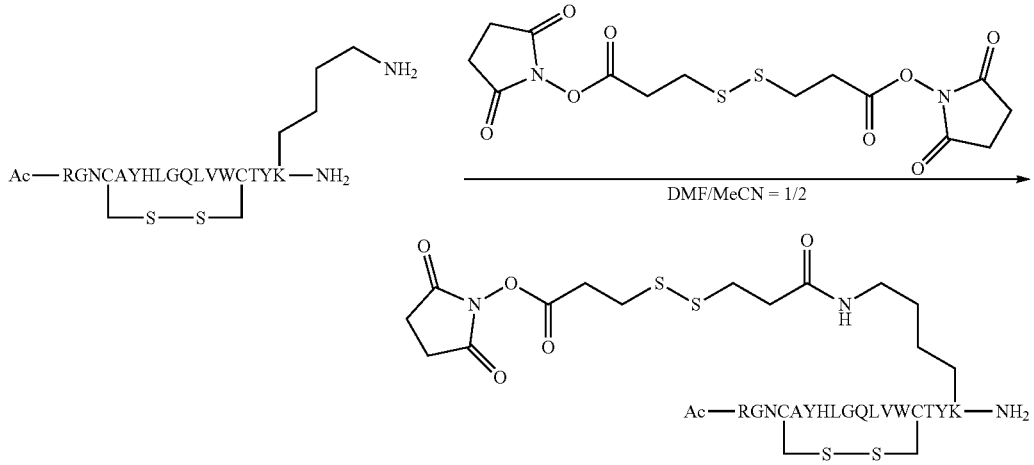

The amino acid sequence is SEQ ID NO: 59.

Ac-RGNCAYHLGQLVWCTYK-NH$_2$ (SEQ ID NO: 59) synthesized in (33-2) (4.70 mg, 2.29 μmol, the 4th and 14th of two cysteines form a disulfide bond in the molecule) was dissolved in N,N'-dimethylformamide (0.50 mL), a solution dissolving 3,3'-dithiodipropionic acid di(N-succinimidyl) (37.0 mg, 91.6 μmol) in acetonitrile (1.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (5.00 mg, 2.14 μmol)

MS (ESI) m/z: z=3 781.20 [M+3H]$^{3+}$

HPLC purity: 79%

(33-4) Specific Modification of Anti-HER2 IgG Antibody Trastuzumab and Analysis Thereof by ESI-TOFMS The peptide- and disulfide linker-coupled NHS-activation compound synthesized in (33-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,223, whereas a peak for a product with one binding peptide introduced was observed at 150,488.

(33-5) HIC-HPLC Analysis of Specific Modification of Anti-HER2 IgG Antibody Trastuzumab The antibody-peptide conjugate produced in (33-4) and a raw material antibody were analyzed by HIC. For a column, Protein-Pak Hi Res HIC Column (Waters) 4.6×100 mm 2.5 μm was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+30 equivalents of the peptide- and disulfide linker-coupled NHS-activation compound.

Figure 44:
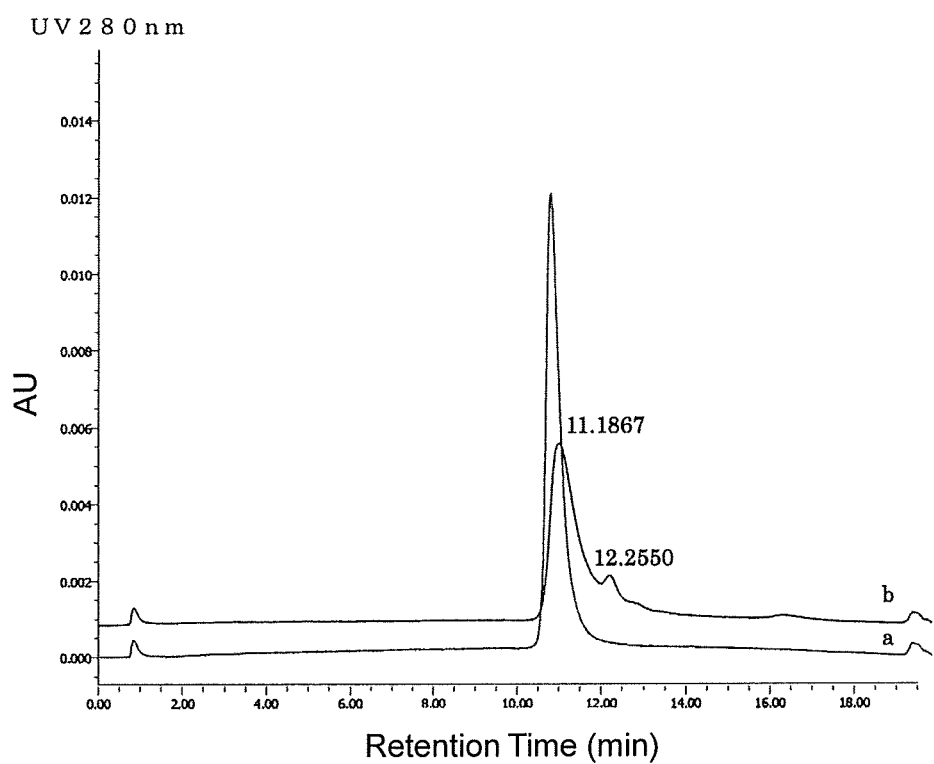
FIG. 44 is a diagram of a result of HIC-UPLC analysis of specific modification of trastuzumab (detection wavelength: UV 280 nm) (Example 33).

It is believed that a retention time of 11.1867 minutes is attributed to the trastuzumab raw material, whereas that of 12.2550 minutes is attributed to a compound with one peptide introduced to trastuzumab (FIG. 44).

Example 34: Synthesis of (Peptide- and Disulfide Linker-Coupled NHS-Activation Compound), Modification of Anti-HER2 IgG Antibody Trastuzumab Using Compound, and Analysis Thereof (34-1) Synthesis of IgG1 Fc-Binding Peptide The sequence of Ac-RGNCAYHRGQLVWCTKH-NH$_2$ (SEQ ID NO: 60) was synthesized by Fmoc solid phase synthesis, as is similar to Example 1. A target product was obtained (66.3 mg, 32.0 μmol).

MS (ESI) m/z: z=3 691.10 [M+3H]$^{3+}$, z=4 518.55 [M+4H]$^{4+}$ (34-2) Formation of Intra-Molecular Disulfide Bond between Cys at Positions 4 and 14 of Ac-RGN-CAYHRGQLVWCTKH-NH$_2$ (SEQ ID NO: 60)

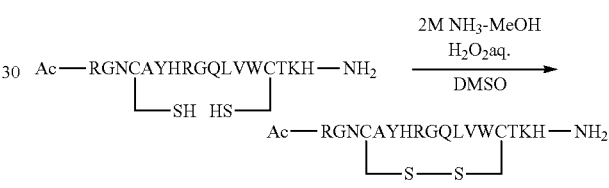

The above-amino acid sequence is SEQ ID NO: 60.

The peptide synthesized in (34-1) (66.3 mg, 32.0 μmol) was dissolved in DMSO (5.00 mL), 2 M NH$_3$-MeOH (32.0 μL, 64.0 μmol) and a hydrogen peroxide solution (65.4 μL, 640 μmol) were added thereto, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the above-peptide (40.0 mg, 19.3 μmol).

MS (ESI) m/z: z=3 690.40 [M+3H]$^{3}$, z=4 518.05 [M+4H]$^{4+}$ (34-3) Coupling between Disulfide Linker and Peptide

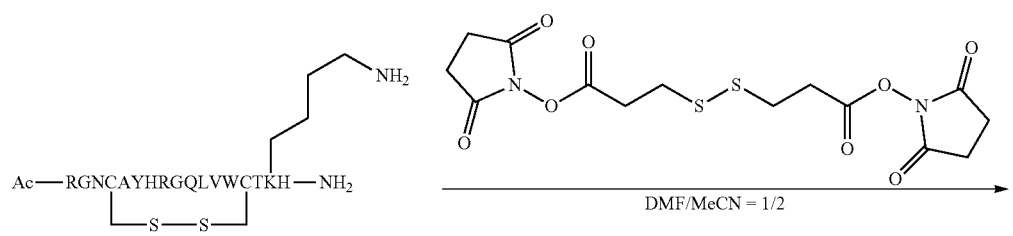

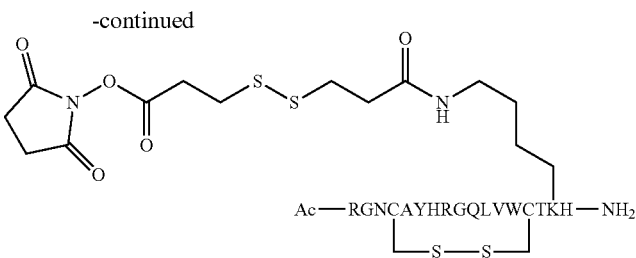

The above-amino acid sequence is SEQ ID NO: 60.

Ac-RGNCAYHRGQLVWCTKH-NH$_2$ (SEQ ID NO: 60) synthesized in (34-2) (40.0 mg, 19.3 μmol, the 4th and 14th of two cysteines form a disulfide bond in the molecule) was dissolved in N,N'-dimethylformamide (1.00 mL), a solution dissolving 3,3'-dithiodipropionic acid di(N-succinimidyl) (312 mg, 772 μmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (4.50 mg, 1.91 μmol).

MS (ESI) m/z: z=3 786.85 [M+3H]$^{3+}$, m/z: z=4 590.45 [M+4H]$^{4+}$

HPLC purity: 78%

(34-4) Specific Modification of Anti-HER2 IgG Antibody Trastuzumab and Analysis Thereof by ESI-TOFMS The peptide- and disulfide linker-coupled NHS-activation compound synthesized in (34-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 60 mM sodium acetate buffer (pH 4.7), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,081.

(34-5) Determination of Heavy Chain Selectivity of Specifically Modified Compound of Trastuzumab under Reduction Condition by ESI-TOFMS Analysis To the antibody-peptide conjugate produced in (34-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,682 and 50,844 with a thiopropionyl group introduced to the heavy chain, and a light chain peak was observed at 23,439, the same as that of the raw material.

(34-6) HIC-HPLC Analysis of Specific Modification of Anti-HER2 IgG Antibody Trastuzumab The antibody-peptide conjugate produced in (34-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:

a: a trastuzumab raw material;

b: trastuzumab+30 equivalents of the peptide- and disulfide linker-coupled NHS-activation compound.

Figure 45:
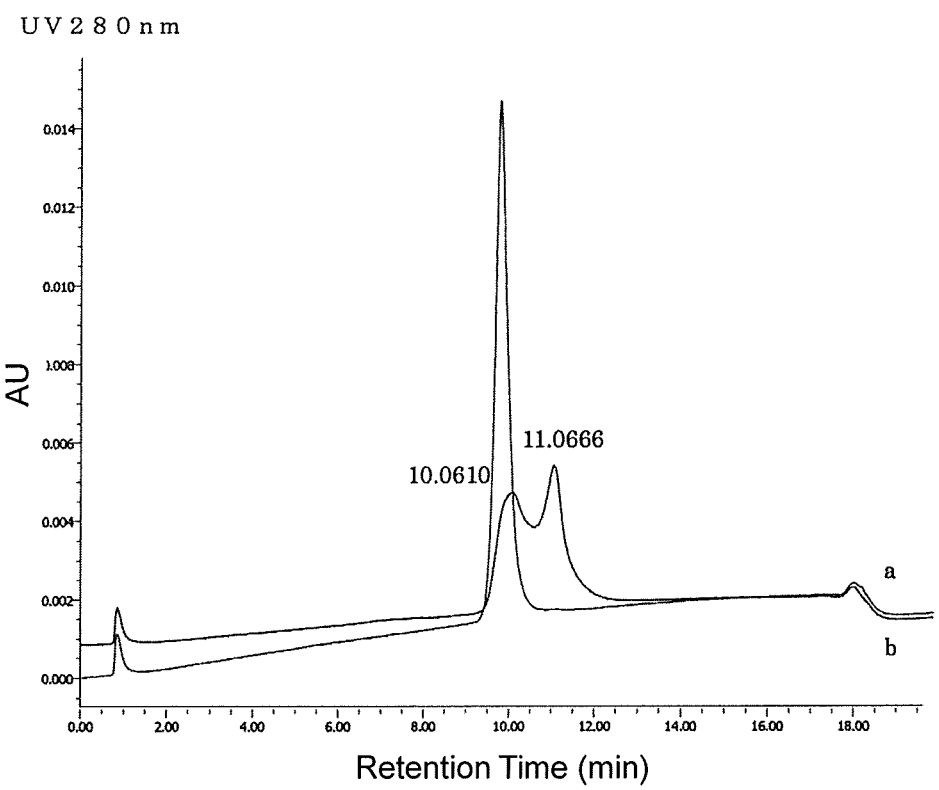
FIG. 45 is a diagram of a result of HIC-UPLC analysis of specific modification of trastuzumab (detection wavelength: UV 280 nm) (Example 34).

It is believed that a retention time of 10.0610 minutes is attributed to the trastuzumab raw material, whereas that of 11.0666 minutes is attributed to a compound with one peptide introduced to trastuzumab (FIG. 45).

Example 35: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (35-1) Synthesis of IgG1 Fc-Binding Peptide The sequence of Ac-KNMQCQRRFYEALHDPNLNE-EQRNARIRSIRDDC-NH$_2$ (SEQ ID NO: 61) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (47.0 mg, 11.0 μmol).

MS (ESI) m/z: z=5 853.35 [M+5H]$^{5+}$, z=6 711.25 [M+6H]$^{6+}$ (35-2) Formation of Intra-Molecular Disulfide Bond between Cys at Positions 5 and 34 of Ac-KNMQCQRRF-YEALHDPNLNEEQRNARIRSIRDDC-NH$_2$ (SEQ ID NO: 61)

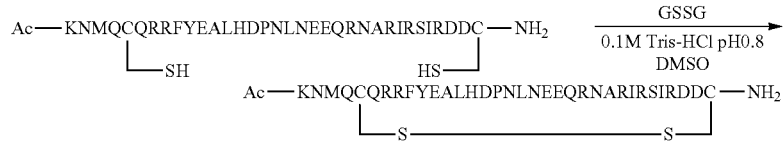

The above-amino acid sequence is SEQ ID NO: 61.

The peptide synthesized in (35-1) (47.0 mg, 11.0 μmol) was dissolved in DMSO (1.10 mL), and 0.1M Tris-HCl, pH 8.0 (11.0 mL) were added thereto. Oxidized glutathione (34.0 mg, 55.0 μmol) was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (18.1 mg, 4.25 μmol).

MS (ESI) m/z: z=5 852.95 [M+5H]$^{5+}$, z=6 710.95 [M+6H]$^{6+}$ (35-3) Coupling between Disulfide Linker and Peptide aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (4.00 mg, 0.80 μmol).

MS (ESI) m/z: z=5 910.85 [M+5H]$^{5+}$, z=6 759.20 [M+6H]$^{6+}$

HPLC purity: 60%

(35-4) Specific Modification of Anti-HER2 IgG Antibody Trastuzumab and Analysis Thereof by ESI-TOFMS The peptide- and disulfide linker-coupled NHS-activation compound synthesized in (35-3) was dissolved in N,N'-dimethylformamide to be 4 mM. Anti-HER2 IgG antibody trastuzumab (Chugai Pharmaceutical) in an amount of 500 μg was dissolved in 171 μL of a 50 mM sodium acetate buffer (pH 5.5), 8.5 μL of a 4 mM peptide reagent (10 equivalents with respect to the antibody) was added thereto, and the solution was stirred at room temperature for 1 hour. The reaction solution was added to a NAP-5 column to stop the reaction and was substituted with a 20 mM PBS buffer.

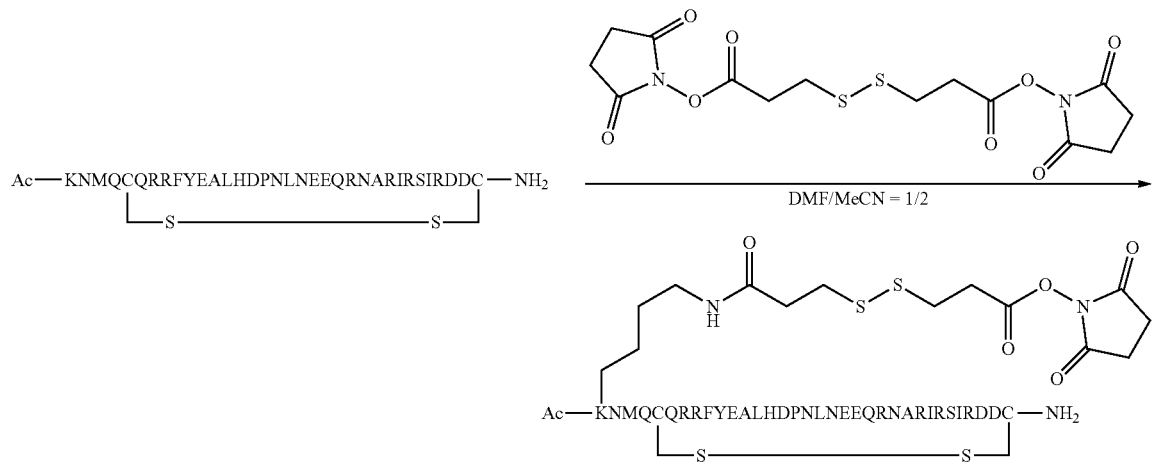

The above-amino acid sequence is SEQ ID NO: 61.

Ac-KNMQCQRRFYEALHDPNLNEEQRNARIR-SIRDDC-NH$_2$ (SEQ ID NO: 61) synthesized in (35-2) (18.1 mg, 4.25 μmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (69.0 mg, 0.170 mmol) in acetonitrile (2.00 mL) was added thereto, and the solution was stirred at room temperature for 24 hours. Concentration under reduced pressure was performed to remove acetonitrile, which was then dissolved in a 0.05%

The mass was measured by ESI-TOFMS; for the raw material trastuzumab, a peak was observed at 148,234, whereas a peak for a product with one binding peptide introduced was observed at 152,672, and a peak for a product with two binding peptides introduced was observed at 157,107.

(35-5) Determination of Heavy Chain Selectivity of Specifically Modified Compound of Trastuzumab under Reduction Condition by ESI-TOFMS Analysis To the antibody-peptide conjugate produced in (35-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,684 and 50,844 with a thiopropionyl group introduced to the heavy chain.

(35-6) HIC-HPLC Analysis of Specific Modification of Anti-HER2 IgG Antibody Trastuzumab The antibody-peptide conjugate produced in (35-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+10 equivalents of the peptide- and disulfide linker-coupled NHS-activation compound.

Figure 46:
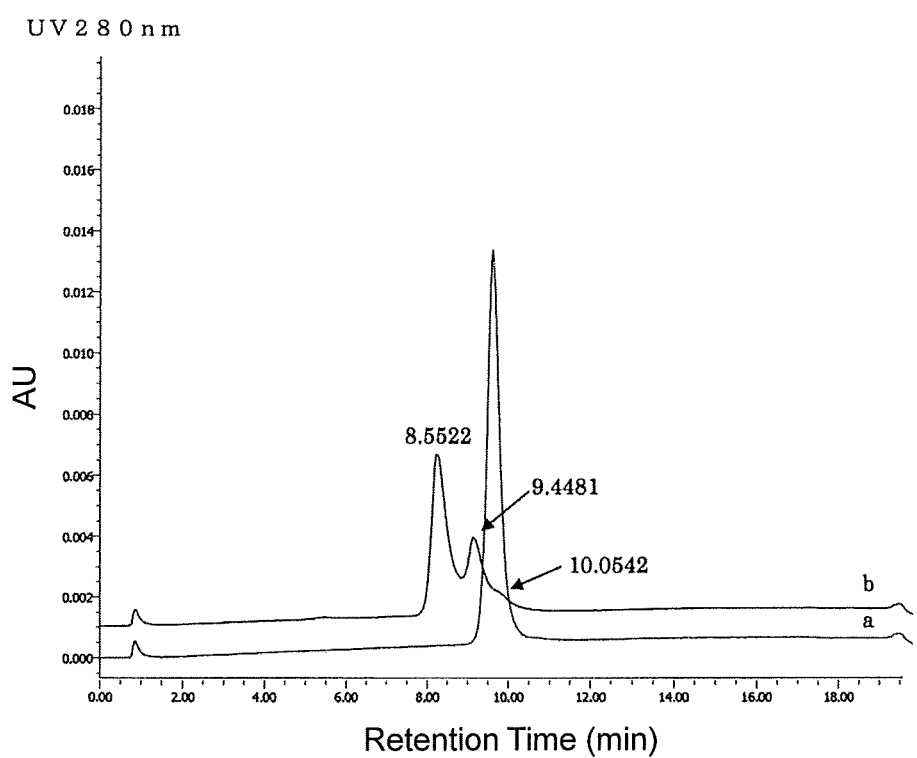
FIG. 46 is a diagram of a result of HIC-UPLC analysis of specific modification of trastuzumab (detection wavelength: UV 280 nm) (Example 35).

It is believed that a retention time of 10.0542 minutes is attributed to the trastuzumab raw material, whereas that of 9.4481 minutes is attributed to a compound with one peptide introduced to trastuzumab, and that of 8.5522 minutes is attributed to a compound with two peptides introduced to trastuzumab (FIG. 46).

Example 36: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (36-1) Synthesis of IgG1 Fc-Binding Peptide The sequence of Ac-FNMQCQKRFYEALHDPNLNEEQRNARIRSIRDDC-$NH_2$ (SEQ ID NO: 62) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (76.3 mg, 18.0 μmol).

MS (ESI) m/z: z=5 851.45 $[M+5H]^{5+}$, z=6 709.75 $[M+6H]^{6+}$ (36-2) Formation of Intra-Molecular Disulfide Bond between Cys at Positions 5 and 34 of Ac-FNMQCQKRFYEALHDPNLNEEQRNARIRSIRDDC-$NH_2$ (SEQ ID NO: 62)

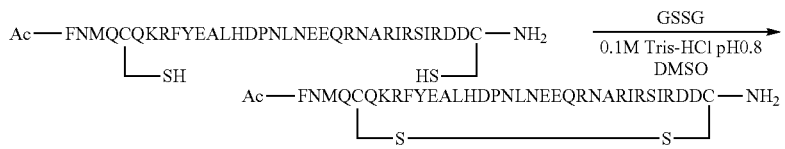

The above-amino acid sequence is SEQ ID NO: 62.

The peptide synthesized in (36-1) (76.3 mg, 18.0 μmol) was dissolved in DMSO (1.80 mL), and 0.1M Tris-HCl, pH 8.0 (18.0 mL) were added thereto. Oxidized glutathione (55.0 mg, 89.5 μmol) was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (28.5 mg, 6.71 μmol).

MS (ESI) m/z: z=5 851.05 $[M+5H]^{5+}$, z=6 709.40 $[M+6H]^{6+}$ (36-3) Coupling between Disulfide Linker and Peptide

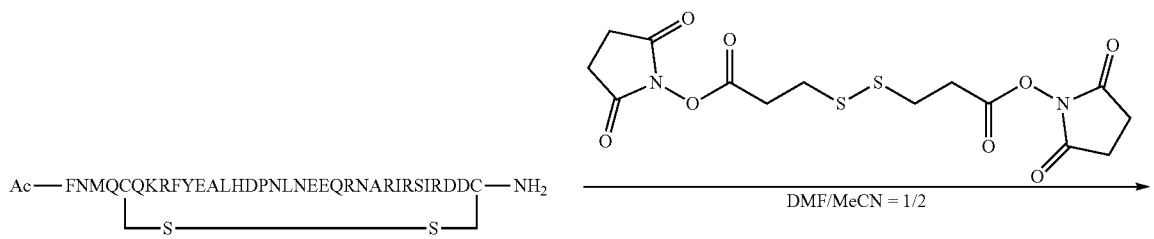

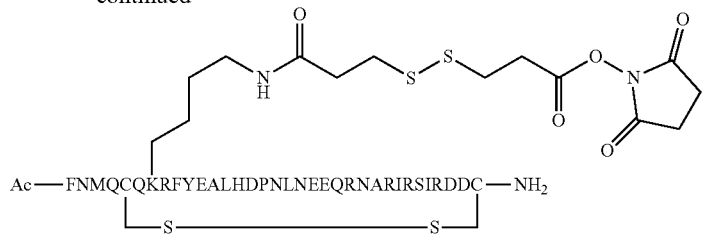

Ac—FNMQCQKRFYEALHDPNLNEEQRNARIRSIRDDC—NH₂

The above-amino acid sequence is SEQ ID NO: 62.

Ac-FNMQCQKRFYEALHDPNLNEEQRNARIR-SIRDDC-NH$_2$ (SEQ ID NO: 62) synthesized in (36-2) (28.5 mg, 6.71 µmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (108 mg, 0.268 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (7.10 mg, 1.56 µmol).

MS (ESI) m/z: z=5 909.05 [M+5H]$^{5+}$, z=6 757.70 [M+6H]$^{6+}$

HPLC purity: 87%

(36-4) Specific Modification of Anti-HER2 IgG Antibody Trastuzumab and Analysis Thereof by ESI-TOFMS The peptide- and disulfide linker-coupled NHS-activation compound synthesized in (36-3) was dissolved in N,N'-dimethylformamide to be 21.6 mM. Anti-HER2 IgG antibody trastuzumab (Chugai Pharmaceutical) in an amount of 500 µg was dissolved in 46.9 µL of a 10 mM sodium acetate buffer (pH 5.5), 4.7 µL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,232, whereas a peak for a product with one binding peptide introduced was observed at 152,664.

(36-5) Determination of Heavy Chain Selectivity of Specifically Modified Compound of Trastuzumab under Reduction Condition by ESI-TOFMS Analysis To the antibody-peptide conjugate produced in (36-4), 5 µL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for a product, a peak was observed at 50,681 with a thiopropionyl group introduced to the heavy chain.

(36-6) HIC-HPLC Analysis of Specific Modification of Anti-HER2 IgG Antibody Trastuzumab The antibody-peptide conjugate produced in (36-4) and a raw material antibody were analyzed by HIC. For a column, Protein-Pak Hi Res HIC Column (Waters) 4.6×100 mm 2.5 µm was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:

a: a trastuzumab raw material;

b: trastuzumab+30 equivalents of the peptide- and disulfide linker-coupled NHS-activation compound.

Figure 47:
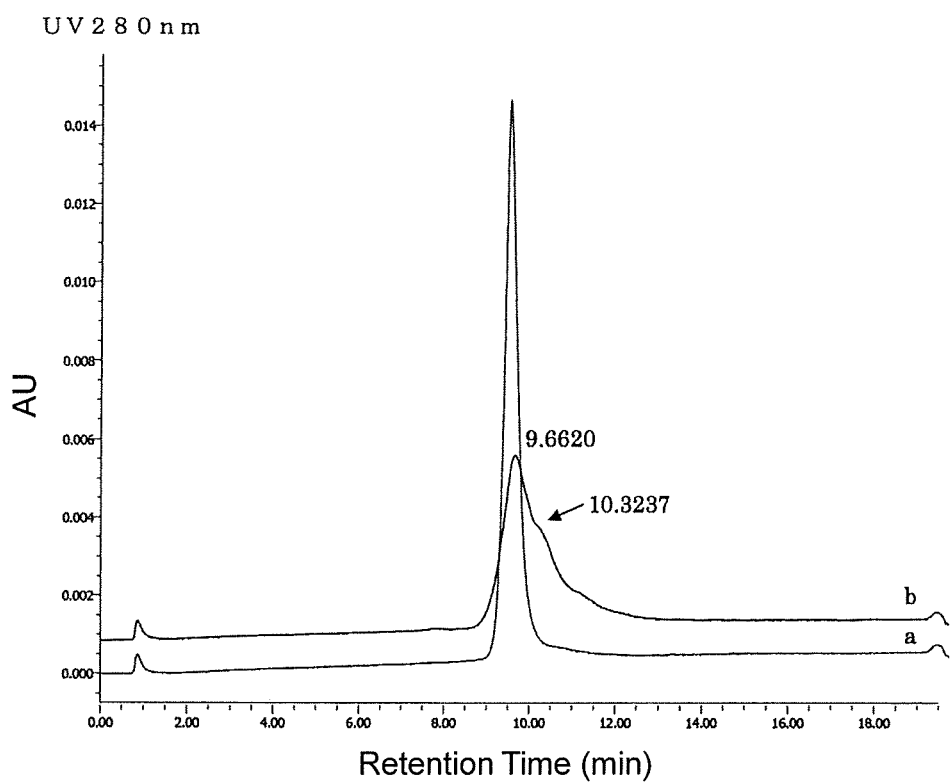
FIG. 47 is a diagram of a result of HIC-UPLC analysis of specific modification of trastuzumab (detection wavelength: UV 280 nm) (Example 36).

It is believed that a retention time of 9.6620 minutes is attributed to the trastuzumab raw material, whereas that of 10.3237 minutes is attributed to a compound with one peptide introduced to trastuzumab (FIG. 47).

Example 37: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (37-1) Synthesis of IgG1 Fc-Binding Peptide The sequence of Ac-FNMQCQRRFYEAKHDPNLNEEQRNARIRSIRDDC-NH$_2$ (SEQ ID NO: 63) was synthesized by Fmoc solid phase synthesis. For a peptide synthesizing apparatus, Liberty Blue manufactured by CEM was used. For all reagents, those manufactured by Watanabe Chemical Industries, Ltd. were used. Resin was Fmoc-NH-SAL-PEG Resin HL. Arginine (R), cysteine (C), and histidine (H) were subjected to double coupling. Cutting out from Resin was performed under a condition with three-hour stirring in a solution of trifluoroacetic acid:water:triisopropylsilane:ethanediol=94:2.5:1.0:2.5. After cutting out, Resin was removed by filtration, and trifluoroacetic acid was removed. Diethyl ether was added to the formed crystals to perform ether precipitation, and the formed white crystals were collected by filtration. They were dissolved in a 0.05% aqueous trifluoroacetic acid solution and were subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (67.4 mg, 15.7 µmol).

MS (ESI) m/z: z=5 860.10 [M+5H]$^{5+}$, z=6 716.95 [M+6H]$^{6+}$ (37-2) Formation of Intra-Molecular Disulfide Bond between Cys at Positions 5 and 34 of Ac-FNMQCQRRF-YEAKHDPNLNEEQRNARIRSIRDDC-NH$_2$ (SEQ ID NO: 63)

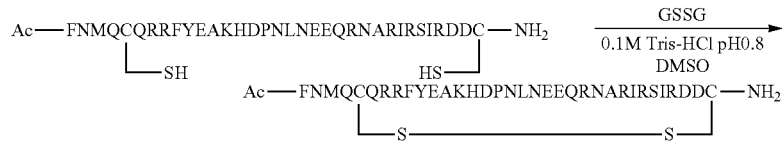

The above-amino acid sequence is SEQ ID NO: 63.

The peptide synthesized in (37-1) (67.4 mg, 15.7 μmol) was dissolved in DMSO (1.50 mL), and 0.1M Tris-HCl, pH 8.0 (15.0 mL) were added thereto. Oxidized glutathione (48.0 mg, 78.5 μmol) was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (16.1 mg, 3.75 μmol).

MS (ESI) m/z: z=5 859.75 $[M+5H]^{5+}$, z=6 716.60 $[M+6H]^{6+}$ (37-3) Coupling between Disulfide Linker and Peptide The above-amino acid sequence is SEQ ID NO: 63.

Ac-FNMQCQRRFYEAKHDPNLNEEQRNARIR-SIRDDC-NH$_2$ (SEQ ID NO: 63) synthesized in (37-2) (16.1 mg, 3.75 μmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (61.0 mg, 0.150 mmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (5.30 mg, 1.16 μmol).

MS (ESI) m/z: z=5 917.60 $[M+5H]^{5+}$, z=6 764.85 $[M+6H]^{6+}$

HPLC purity: 54%

(37-4) Specific Modification of Anti-HER2 IgG Antibody Trastuzumab and Analysis Thereof by ESI-TOFMS The peptide- and disulfide linker-coupled NHS-activation compound synthesized in (37-3) was dissolved in N,N'-dimethylformamide to be 21.6 mM. Anti-HER2 IgG antibody trastuzumab (Chugai Pharmaceutical) in an amount of 500 μg was dissolved in 46.9 μL of a 10 mM sodium acetate buffer (pH 5.5), 4.7 μL of a 21.6 mM peptide reagent (30 equivalents with respect to the antibody) was added thereto, and the solution was stirred at room temperature for 1 hour. The reaction solution was added to a NAP-5 column to stop the reaction and was substituted with a 20 mM PBS buffer.

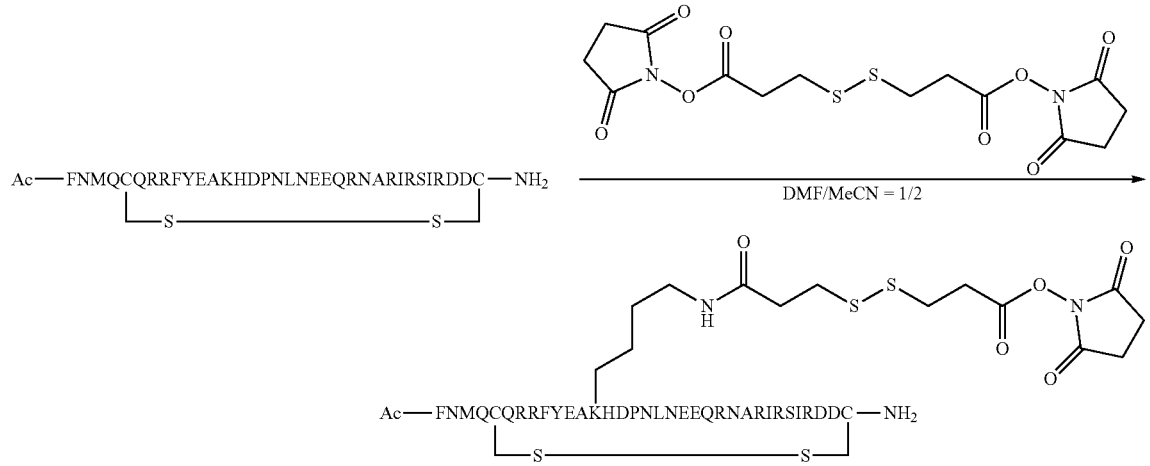

The mass was measured by ESI-TOFMS; for the raw material trastuzumab, a peak was observed at 148,238, whereas a peak for a product with one binding peptide introduced was observed at 152,703.

(37-5) Determination of Heavy Chain Selectivity of Specifically Modified Compound of Trastuzumab under Reduction Condition by ESI-TOFMS Analysis To the antibody-peptide conjugate produced in (37-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for a product, a peak was observed at 50,682 with a thiopropionyl group introduced to the heavy chain.

(37-6) HIC-HPLC Analysis of Specific Modification of Anti-HER2 IgG Antibody Trastuzumab The antibody-peptide conjugate produced in (37-4) and a raw material antibody were analyzed by HIC. For a column, Protein-Pak Hi Res HIC Column (Waters) 4.6×100 mm 2.5 μm was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+30 equivalents of the peptide- and disulfide linker-coupled NHS-activation compound.

Figure 48:
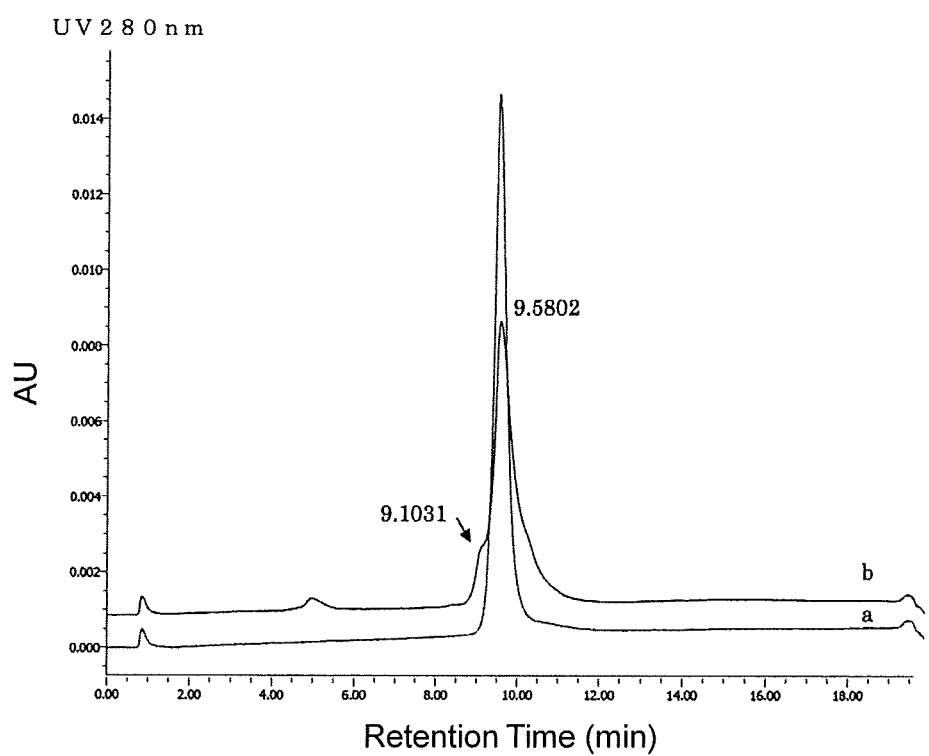
FIG. 48 is a diagram of a result of HIC-UPLC analysis of specific modification of trastuzumab (detection wavelength: UV 280 nm) (Example 37).

It is believed that a retention time of 9.5802 minutes is attributed to the trastuzumab raw material, whereas that of 9.1031 minutes is attributed to a compound with one peptide introduced to trastuzumab (FIG. 48).

Example 38: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (38-1) Synthesis of IgG1 Fc-Binding Peptide The sequence of Ac-FNMQCQRRFYEALHDPNLNE-EQRKARIRSIRDDC-$NH_2$ (SEQ ID NO: 64) was synthesized by Fmoc solid phase synthesis, as is similar to Example 1. The target product was obtained.

(38-2) Formation of Intra-Molecular Disulfide Bond between Cys at Positions 5 and 34 of Ac-FNMQCQRRF-YEALHDPNLNEEQRKARIRSIRDDC-$NH_2$ (SEQ ID NO: 64)

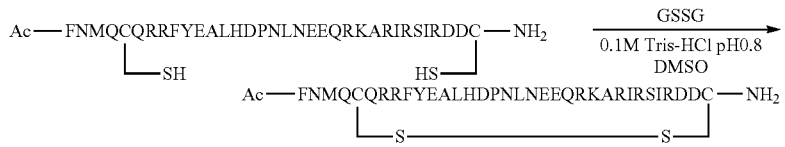

The above-amino acid sequence is SEQ ID NO: 64.

The peptide synthesized in (38-1) was dissolved in DMSO, and 0.1M Tris-HCl (pH 8.0) were added thereto. Oxidized glutathione was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (20.0 mg, 4.66 μmol).

MS (ESI) m/z: z=4 1074.15 $[M+4H]^{4+}$, z=5 859.65 $[M+5H]^{5+}$ (38-3) Coupling between Disulfide Linker and Peptide

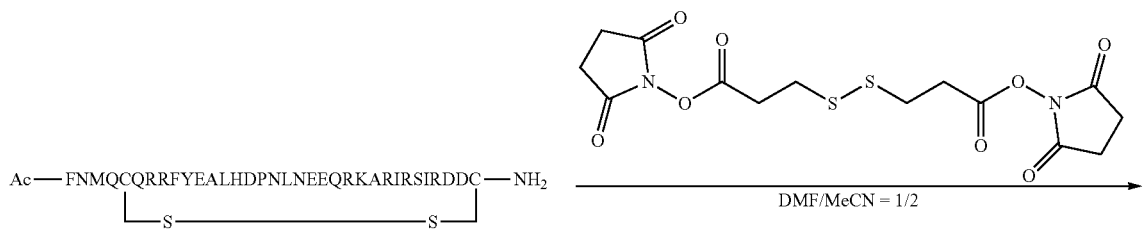

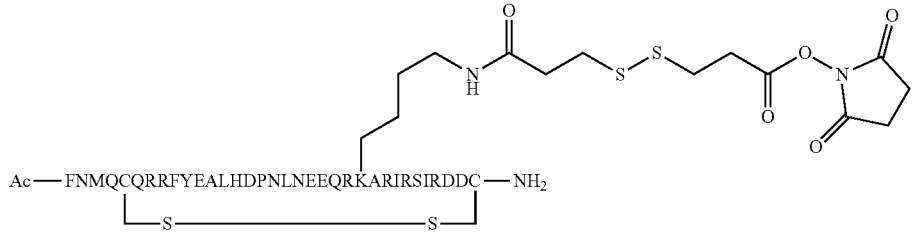

The above-amino acid sequence is SEQ ID NO: 64.

Ac-FNMQCQRRFYEALHDPNLNEEQRKARIR-SIRDDC-NH$_2$ (SEQ ID NO: 64) synthesized in (38-2) (20.0 mg, 4.66 µmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (75.4 mg, 186 µmol) in acetonitrile (2.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (9.00 mg, 1.96 µmol).

MS (ESI) m/z: z=5 917.45 [M+5H]$^{5+}$, z=6 764.65 [M+6H]$^{6+}$

HPLC purity: 100%

(38-4) Specific Modification of Anti-HER2 IgG Antibody Trastuzumab and Analysis Thereof by ESI-TOFMS The peptide- and disulfide linker-coupled NHS-activation compound synthesized in (38-3) was dissolved in N,N'-dimethylformamide to be 4 mM. Anti-HER2 IgG antibody trastuzumab (Chugai Pharmaceutical) in an amount of 500 µg was dissolved in 171 µL of a 50 mM sodium acetate buffer (pH 5.5), 8.5 µL of a 4 mM peptide reagent (10 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,070, whereas a peak for a product with one binding peptide introduced was observed at 152,538, and a peak for a product with two binding peptides introduced was observed at 157,165.

(38-5) Determination of Heavy Chain Selectivity of Specifically Modified Compound of Trastuzumab under Reduction Condition by ESI-TOFMS Analysis To the antibody-peptide conjugate produced in (38-4), 5 µL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,685 and 50,847 with a thiopropionyl group introduced to the heavy chain, and a light chain peak was observed at 23,439, the same as that of the raw material.

(38-6) HIC-HPLC Analysis of Specific Modification of Anti-HER2 IgG Antibody Trastuzumab The antibody-peptide conjugate produced in (38-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+10 equivalents of the peptide- and disulfide linker-coupled NHS-activation compound.

Figure 49:
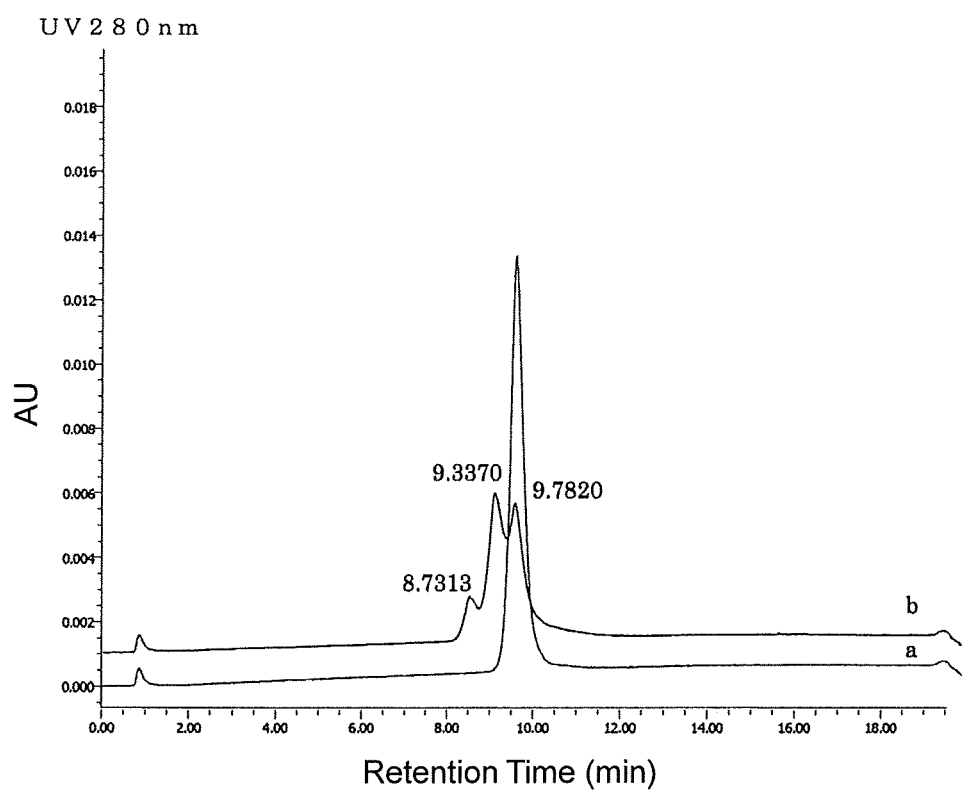
FIG. 49 is a diagram of a result of HIC-UPLC analysis of specific modification of trastuzumab (detection wavelength: UV 280 nm) (Example 38).

It is believed that a retention time of 9.7820 minutes is attributed to the trastuzumab raw material, whereas that of 9.3370 minutes is attributed to a compound with one peptide introduced to trastuzumab, and that of 8.7313 minutes is attributed to a compound with two peptides introduced to trastuzumab (FIG. 49).

Example 39: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (39-1) Synthesis of IgG1 Fc-Binding Peptide The sequence of Ac-FNMQCQRRF-YEALHDPNLNKEQRNARIRSIRDDC-NH$_2$ (SEQ ID NO: 65) was synthesized by Fmoc solid phase synthesis, as is similar to Example 1. The target product was obtained.

(39-2) Formation of Intra-Molecular Disulfide Bond between Cys at Positions 5 and 34 of Ac-FNMQCQRRF-YEALHDPNLNKEQRNARIRSIRDDC-NH$_2$ (SEQ ID NO: 65)

-continued

Ac-FNMQCQRRFYEALHDPNLNKEQRNARIRSIRDDC-NH₂
        |—————S———————S—————|

The above-amino acid sequence is SEQ ID NO: 65.

The peptide synthesized in (39-1) was dissolved in DMSO, and 0.1M Tris-HCl (pH 8.0) were added thereto. Oxidized glutathione was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (23.0 mg, 5.38 µmol).

MS (ESI) m/z: z=4 1070.55 [M+4H]⁴⁺, z=5 856.55 [M+5H]⁵⁺

(39-3) Coupling between Disulfide Linker and Peptide dried to obtain the peptide- and disulfide linker-coupled NHS-activation compound (16.0 mg, 3.50 µmol).

MS (ESI) m/z: z=5 914.45 [M+5H]⁵⁺, z=6 762.15 [M+6H]⁶⁺

HPLC purity: 83%

(39-4) Specific Modification of Anti-HER2 IgG Antibody Trastuzumab and Analysis Thereof by ESI-TOFMS The peptide- and disulfide linker-coupled NHS-activation compound synthesized in (39-3) was dissolved in N,N'-dimethylformamide to be 4 mM. Anti-HER2 IgG antibody trastuzumab (Chugai Pharmaceutical) in an amount of 500 µg was dissolved in 171 µL of a 50 mM sodium acetate buffer (pH 5.5), 8.5 µL of a 4 mM peptide reagent (10 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,065, whereas a peak for a product with one binding peptide

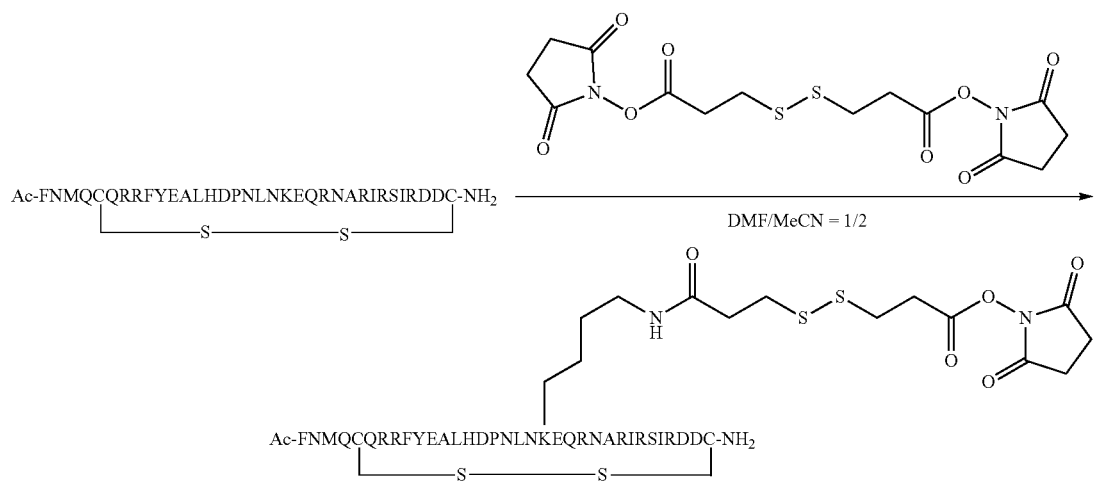

The above-amino acid sequence is SEQ ID NO: 65.

Ac-FNMQCQRRFYEALHDPNLNKEQRNARIRSIRDDC-NH₂ (SEQ ID NO: 65) synthesized in (39-2) (23.0 mg, 5.38 µmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (87.0 mg, 215 µmol) in acetonitrile (1.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freezeintroduced was observed at 152,525, and a peak for a product with two binding peptides introduced was observed at 156,978.

(39-5) HIC-HPLC Analysis of Specific Modification of Anti-HER2 IgG Antibody Trastuzumab The antibody-peptide conjugate produced in (39-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH₄)₂SO₄, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+5 equivalents of the peptide- and disulfide linker-coupled NHS-activation compound.

Figure 50:
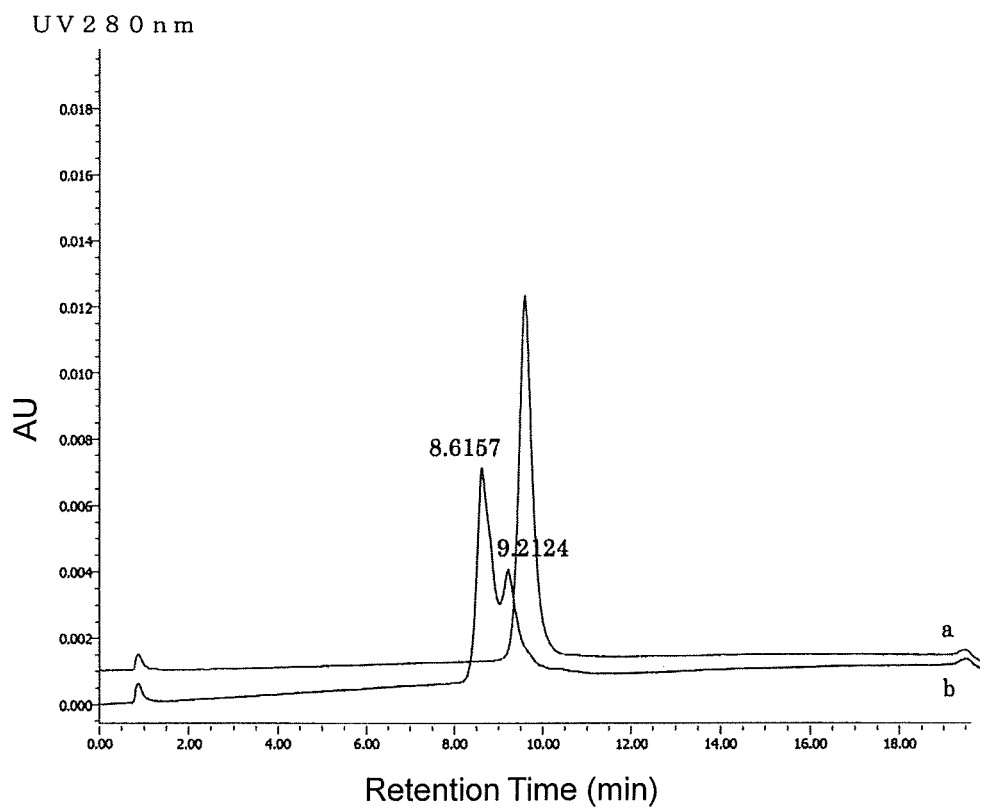
FIG. 50 is a diagram of a result of HIC-UPLC analysis of specific modification of trastuzumab (detection wavelength: UV 280 nm) (Example 39).

It is believed that a retention time of 9.2124 minutes is attributed to the trastuzumab raw material, whereas that of 8.6157 minutes is attributed to a compound with two peptides introduced to trastuzumab (FIG. 50).

Example 40: Peptide Mapping of Thiol-Introduced Compound of Trastuzumab (40-1) Trypsin Treatment for Thiol-Introduced Compound of Trastuzumab Added to a 1.5 mL low-adsorptive micro test tube were 10 μL of a sample solution, a 50 mM ammonium hydrogencarbonate buffer, and 10 μL of a 20 mM aqueous dithiothreitol solution dissolved in 40% trifluoroethanol, the solution was heated at 65° C. for 1 hour, then 10 μL of a 50 mM aqueous iodoacetamide solution was added thereto, and the solution was reacted in a dark place at room temperature while being shaken at 300 rpm for 30 minutes. After reaction, 40 μL of a 50 mM ammonium hydrogencarbonate buffer was added thereto, the solution was stirred, 10 μL of a 20 ng/L aqueous trypsin solution (Proteomics Grade, Code No. T6567-5×20 μg (SIGMA)) was added thereto, and the solution was subjected to enzyme digestion at 37° C. for 18 hours. After digestion, 2 μL of a 20% aqueous trifluoroacetic acid solution was added thereto to stop the reaction, for which LC-MS/MS measurement was performed.

(40-2) LC-MS/MS Measurement Conditions for Trastuzumab (Analyzer)
Nano HPLC: EASY-nLC 1000 (Thermo Fisher Scientific)
Mass Spectrometer: Tribrid Mass Spectrometer Orbitrap Fusion (Thermo Fisher Scientific)
(HPLC Analysis Conditions)
Trap column: Acclaim PepMap (registered trademark) 100, 75 μm×2 cm, (Thermo Fisher Scientific)
Analysis column: ESI-column (NTCC-360/75-3-125, 75 μm×12.5 cm, 3 μm (Nikkyo Technos Co., Ltd.))
Mobile Phase A: a 0.1% aqueous formate solution
Mobile Phase B: a 0.1% formate acetonitrile solution
Loading solution: a 0.1% aqueous trifluoroacetic acid solution
Flow rate: 300 nL/min
Sample injection amount: 1 μL
Gradient condition (B %): 2% (0.0 minute to 0.5 minute), 2%→30% (0.5 minute to 23.5 minutes), 30%→75% (23.5 minutes to 25.5 minutes), and 75% (25.5 minutes to 35.0 minutes).
(Mass Spectrometer Analysis Conditions)
Ionization: ESI, Positive mode
Scan type: Data Dependent Acquisition
Activation Type: Collision Induced Dissociation (CID)
Data acquisition was performed using Xcalibur 3.0 (Thermo Fisher Scientific) and Thermo Orbitrap Fusion Tune Application 2.0 (Thermo Fisher Scientific) as accompanying software.
(40-3) Analysis Condition of Modified Site of Trastuzumab
Modified site analysis of an LC-MS/MS measurement result was performed using Proteome Discoverer version 1.4 (Thermo Fisher Scientific).
For analysis with Proteome Discoverer, Sequest HT was used as a search engine, the range of precursor ion was set to 350 Da to 5,000 Da, and Total Intensity Threshold was set to 50,000. Trypsin was set as a digestive enzyme, and Maximum Missed Cleavage Sites was set to 3. Mass Tolerance was set to 5 ppm and 0.5 Da for a precursor and a fragment ion, respectively. For Static Modification, Carbamidomethyl (+57.021 Da) was set as modification of a cysteine residue with iodoacetamide. For Dynamic Modifications, oxidation of methionine (+15.995 Da) and a modified compound to a lysine residue (a thiol-introduced portion subjected to carbamidomethylation with iodoacetamide (+145.019 Da)) were set. Furthermore, a filter was applied so as to cause Peptide Confidence to be only High.

As data on amino acid sequences to be searched for a modified site, (1) and (3) illustrated in FIG. 8 were used.

(40-4) Analysis Result of Modified Site of Trastuzumab by LC-MS/MS

Figure 51:
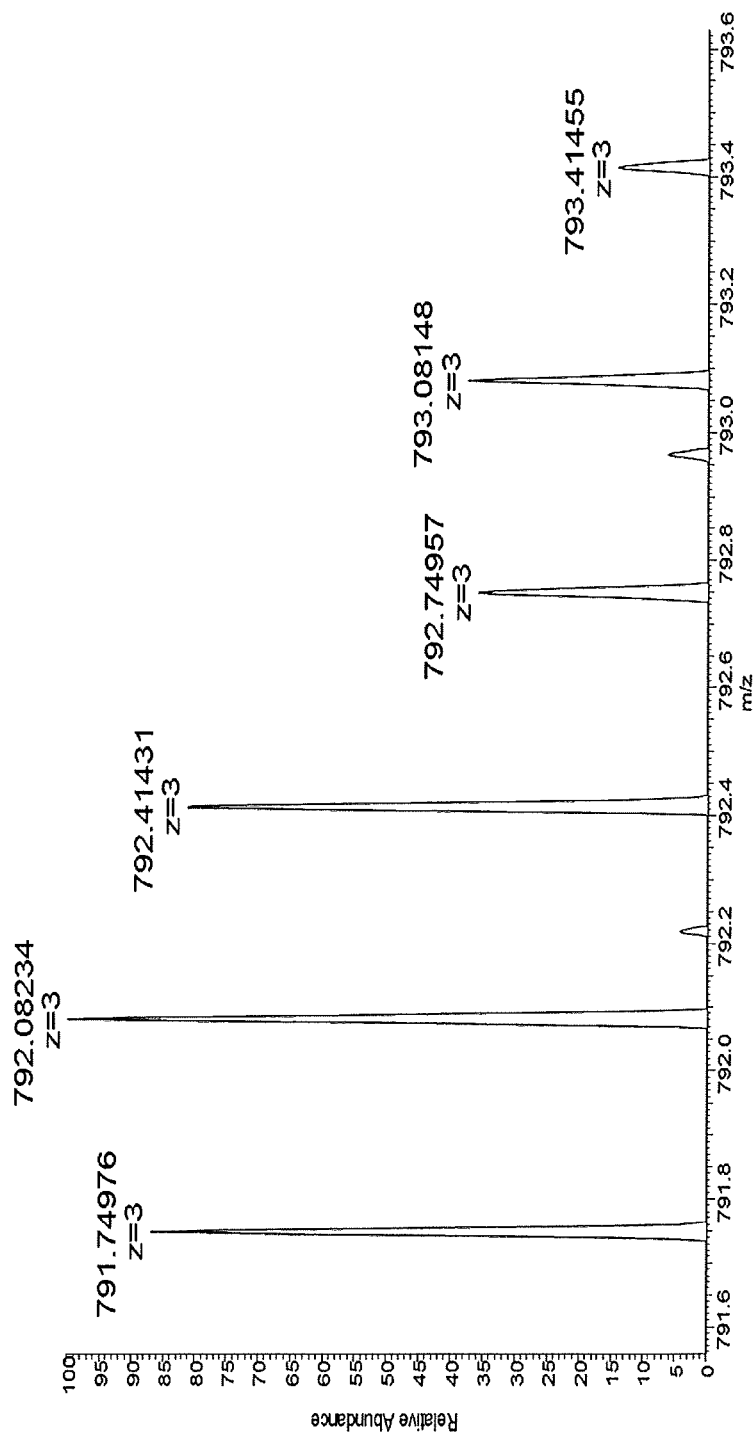
FIG. 51 is a diagram of an MS spectrum of the peptide fragment of VVSVLTVLHQDWLNGKEYK (SEQ ID NO: 66) comprising a modified site to a lysin residue by trypsin digestion of trastuzumab modified using the binder peptide of Example 39 (a thiol-introduced portion subjected to carbamidomethylation with iodoacetamide (+145.019 Da)) (m/z 791.74872, trivalent).
Figure 52:
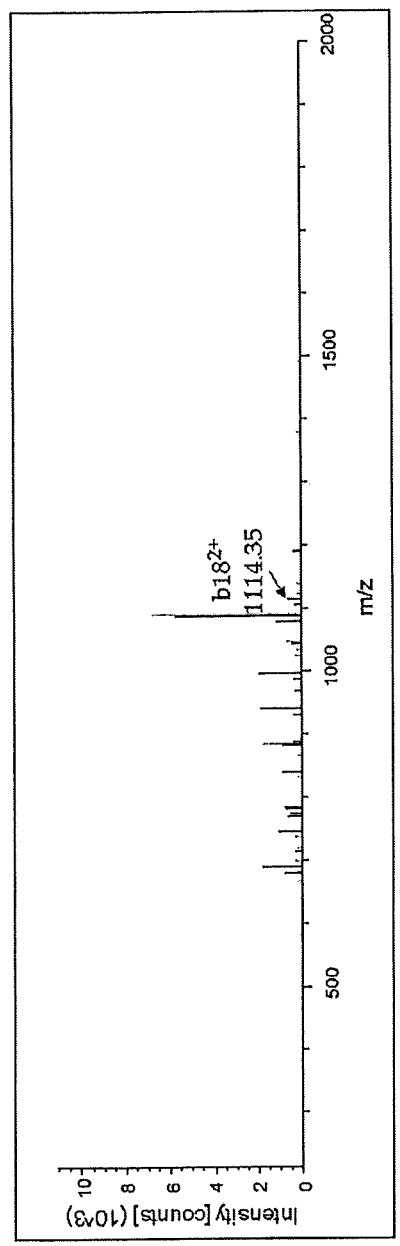
FIG. 52 is a diagram of a CID spectrum of the peptide fragment of VVSVLTVLHQDWLNGKEYK (SEQ ID NO: 66) comprising a modified site to a lysin residue by trypsin digestion of trastuzumab modified using the binder peptide of Example 39 (a thiol-introduced portion subjected to carbamidomethylation with iodoacetamide (+145.019 Da)).
Figure 53:
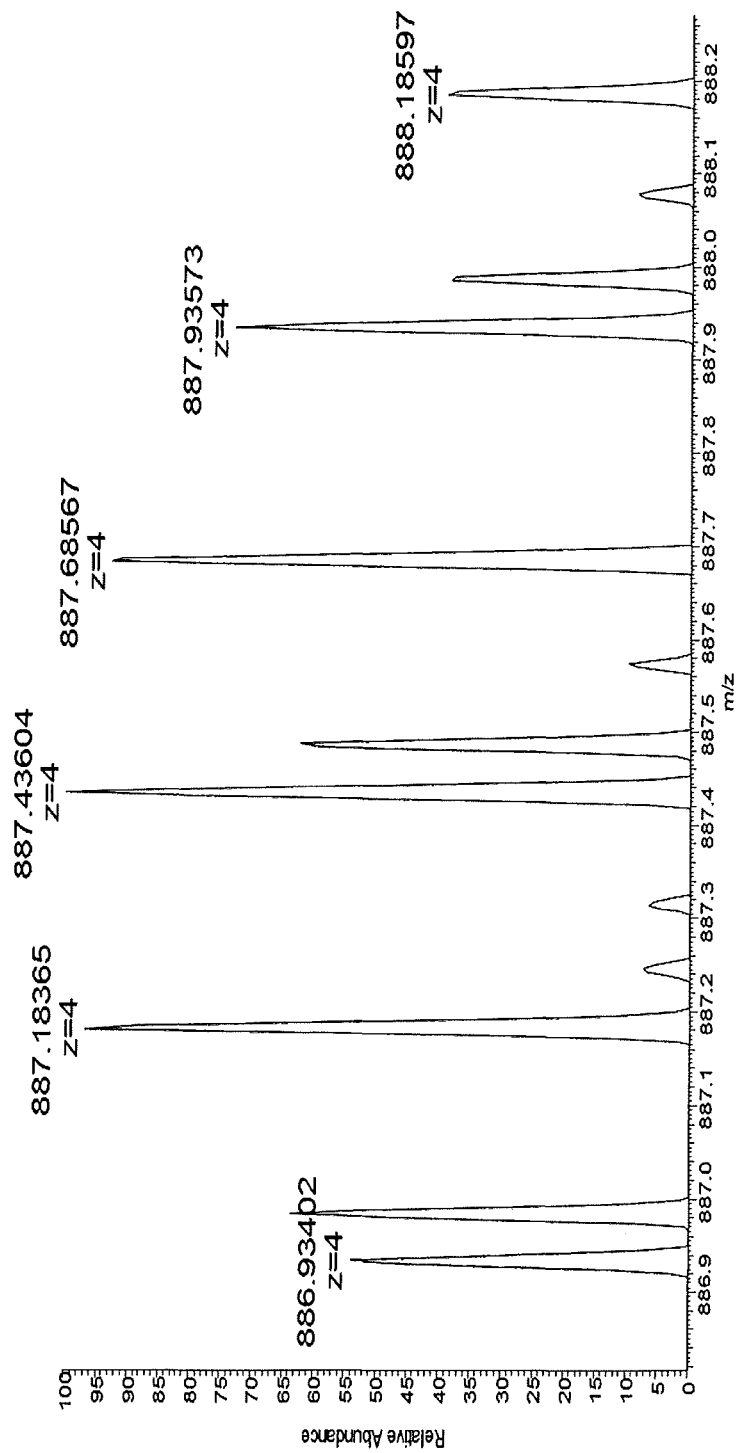
FIG. 53 is an MS spectrum of the peptide fragment of EEQYDSTYRVVSVLTVLHQDWLNGKEYK (SEQ ID NO: 67) comprising a modified site to a lysin residue by trypsin digestion of trastuzumab modified using the binder peptide of Example 39 (a thiol-introduced portion subjected to carbamidomethylation with iodoacetamide (+145.019 Da)) (m/z 886.93408, tetravalent).
Figure 54:
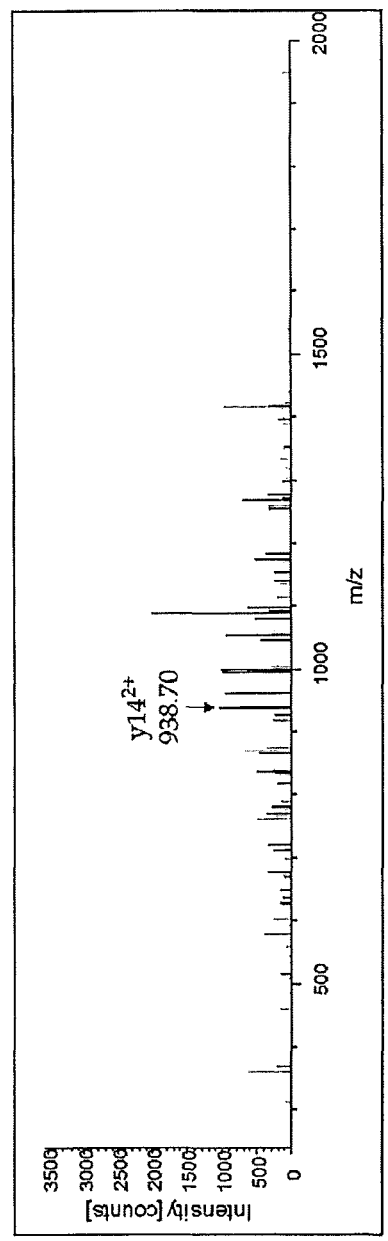
FIG. 54 is a diagram of a CID spectrum of the peptide fragment of EEQYDSTYRVVSVLTVLHQDWLNGKEYK (SEQ ID NO: 67) comprising a modified site to a lysin residue by trypsin digestion of trastuzumab modified using the binder peptide of Example 39 (a thiol-introduced portion subjected to carbamidomethylation with iodoacetamide (+145.019 Da)).

After analysis using LC-MS/MS, an MS spectrum of the peptide fragment of VVSVLTVLHQDWLNGKEYK (SEQ ID NO: 66), which is a peptide consisting of 19 amino acid residues comprising a modified site to a lysin residue by trypsin digestion of trastuzumab modified using the binder peptide of Example 39 (a thiol-introduced portion subjected to carbamidomethylation with iodoacetamide (+145.019 Da)) (measured value: m/z 791.74872; theoretical value: 791.74753; and trivalent) was observed (FIG. 51), and from a CID spectrum, a product ion of m/z 1,114.35 (theoretical value: 1,114.06) corresponding to divalent b18 indicating modification of a lysine residue at position 317 in EU numbering of the heavy chain was determined (FIG. 52). An MS spectrum of the peptide fragment of EEQYDSTYRVVSVLTVLHQDWLNGKEYK (SEQ ID NO: 67), which is a peptide consisting of 28 amino acid residues comprising a modified site to a lysin residue by trypsin digestion (a thiol-introduced portion subjected to carbamidomethylation with iodoacetamide (+145.019 Da)) (measured value: m/z 886.93408; theoretical value: 886.93215; and tetravalent) was observed (FIG. 53), and from a CID spectrum, a product ion of m/z 938.70 (theoretical value: 938.46) corresponding to divalent y14 similarly indicating modification of a lysine residue at position 317 of the heavy chain was determined (FIG. 54).

Example 41: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (41-1) Synthesis of IgG1 Fc-Binding Peptide
The sequence of Ac-FNMQCQRRFYEALHDPNLNEEQRNARIRSIKDDC-NH$_2$ (SEQ ID NO: 68) was synthesized by Fmoc solid phase synthesis, as is similar to Example 1. The target product was obtained.

(41-2) Formation of Intra-Molecular Disulfide Bond between Cys at Positions 5 and 34 of Ac-FNMQCQRRFYEALHDPNLNEEQRNARIRSIKDDC-NH$_2$ (SEQ ID NO: 68)

-continued

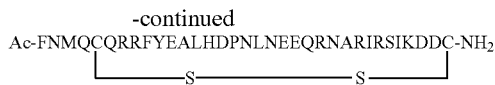

The above-amino acid sequence is SEQ ID NO: 68.

The peptide synthesized in (41-1) was dissolved in DMSO, and 0.1M Tris-HCl (pH 8.0) were added thereto. Oxidized glutathione was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (20.0 mg, 4.70 μmol).

MS (ESI) m/z: z 4 1063.65 $[M+4H]^{4+}$, z=5 851.15 $[M+5H]^5$ (41-3) Coupling between Disulfide Linker and Peptide dried to obtain the peptide- and disulfide linker-coupled NHS-activation compound (12.0 mg, 2.63 μmol).

MS (ESI) m/z: z=5 908.95 $[M+5H]^{5+}$, z=6 757.75 $[M+6H]^{6+}$

HPLC purity: 83%

(41-4) Specific Modification of Anti-HER2 IgG Antibody Trastuzumab and Analysis Thereof by ESI-TOFMS The peptide- and disulfide linker-coupled NHS-activation compound synthesized in (41-3) was dissolved in N,N'-dimethylformamide to be 4 mM. Anti-HER2 IgG antibody trastuzumab (Chugai Pharmaceutical) in an amount of 500 μg was dissolved in 171 μL of a 50 mM sodium acetate buffer (pH 5.5), 8.5 μL of a 4 mM peptide reagent (10 equivalents with respect to the antibody) was added thereto, and the solution was stirred at room temperature for 1 hour. The reaction solution was added to a NAP-5 column to stop the reaction and was substituted with a 20 mM PBS buffer. The mass was measured by ESI-TOFMS; for the raw material trastuzumab, a peak was observed at 148,234, whereas a peak for a product with one binding peptide

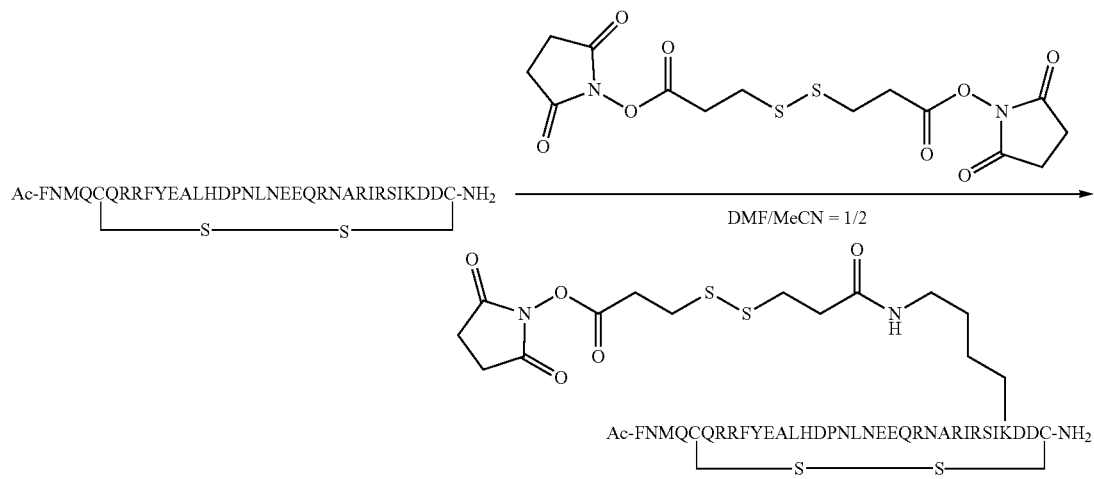

The above-amino acid sequence is SEQ ID NO: 68.

Ac-FNMQCQRRFYEALHDPNLNEEQRNARIR-SIKDDC-NH₂ (SEQ ID NO: 68) synthesized in (41-2) (20.0 mg, 4.70 μmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (76.0 mg, 188 μmol) in acetonitrile (1.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freezeintroduced was observed at 152,648, and a peak for a product with two binding peptides introduced was observed at 157,083.

(41-5) Determination of Heavy Chain Selectivity of Specifically Modified Compound of Trastuzumab under Reduction Condition by ESI-TOFMS Analysis To the antibody-peptide conjugate produced in (41-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,686 and 50,847 with a thiopropionyl group introduced to the heavy chain, and a light chain peak was observed at 23,439, the same as that of the raw material.

(41-6) HIC-HPLC Analysis of Specific Modification of Anti-HER2 IgG Antibody Trastuzumab The antibody-peptide conjugate produced in (41-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+10 equivalents of the peptide- and disulfide linker-coupled NHS-activation compound.

Figure 55:
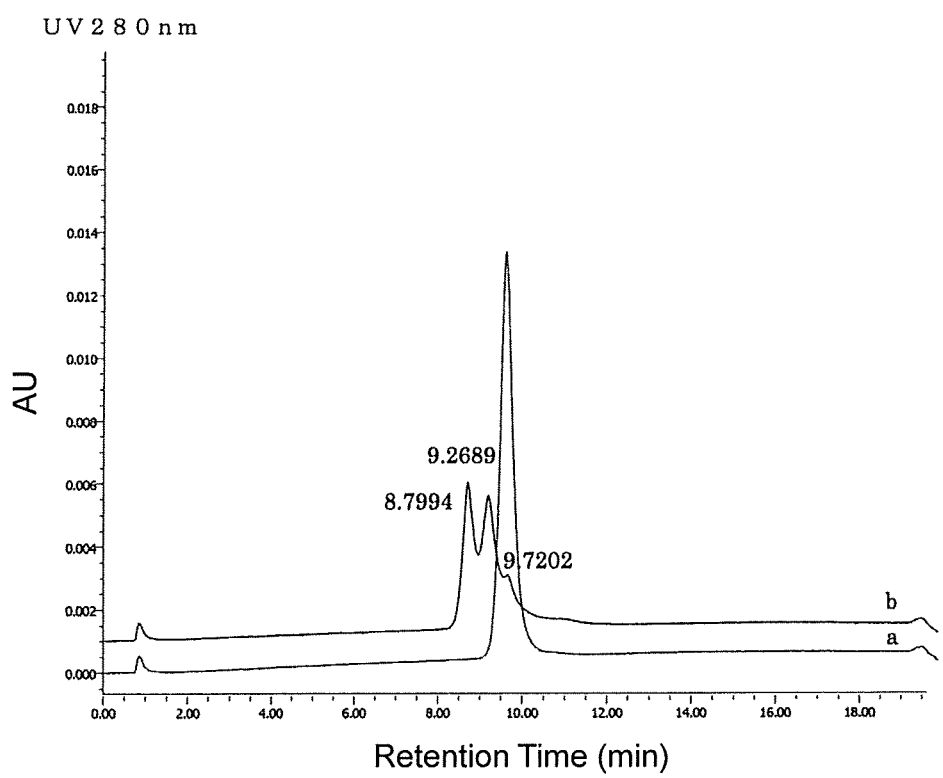
FIG. 55 is a diagram of a result of HIC-UPLC analysis of specific modification of trastuzumab (detection wavelength: UV 280 nm) (Example 40).

It is believed that a retention time of 9.7202 minutes is attributed to the trastuzumab raw material, whereas that of 9.2689 minutes is attributed to a compound with one peptide introduced to trastuzumab, and that of 8.7994 minutes is attributed to a compound with two peptides introduced to trastuzumab (FIG. 55).

Example 42: Peptide Mapping of Thiol-Introduced Compound of Trastuzumab (42-1) Trypsin Treatment for Thiol-Introduced Compound of Trastuzumab The treatments as the same of (40-1) were performed.

(42-2) LC-MS/MS Measurement Conditions for Trastuzumab

The measurement conditions as the same of (40-2) were performed.

(42-3) Analysis Condition of Modified Site of Trastuzumab

The analysis conditions as the same of (40-3) were performed.

(42-4) Analysis Result of Modified Site of Trastuzumab by LC-MS/MS

Figure 56:
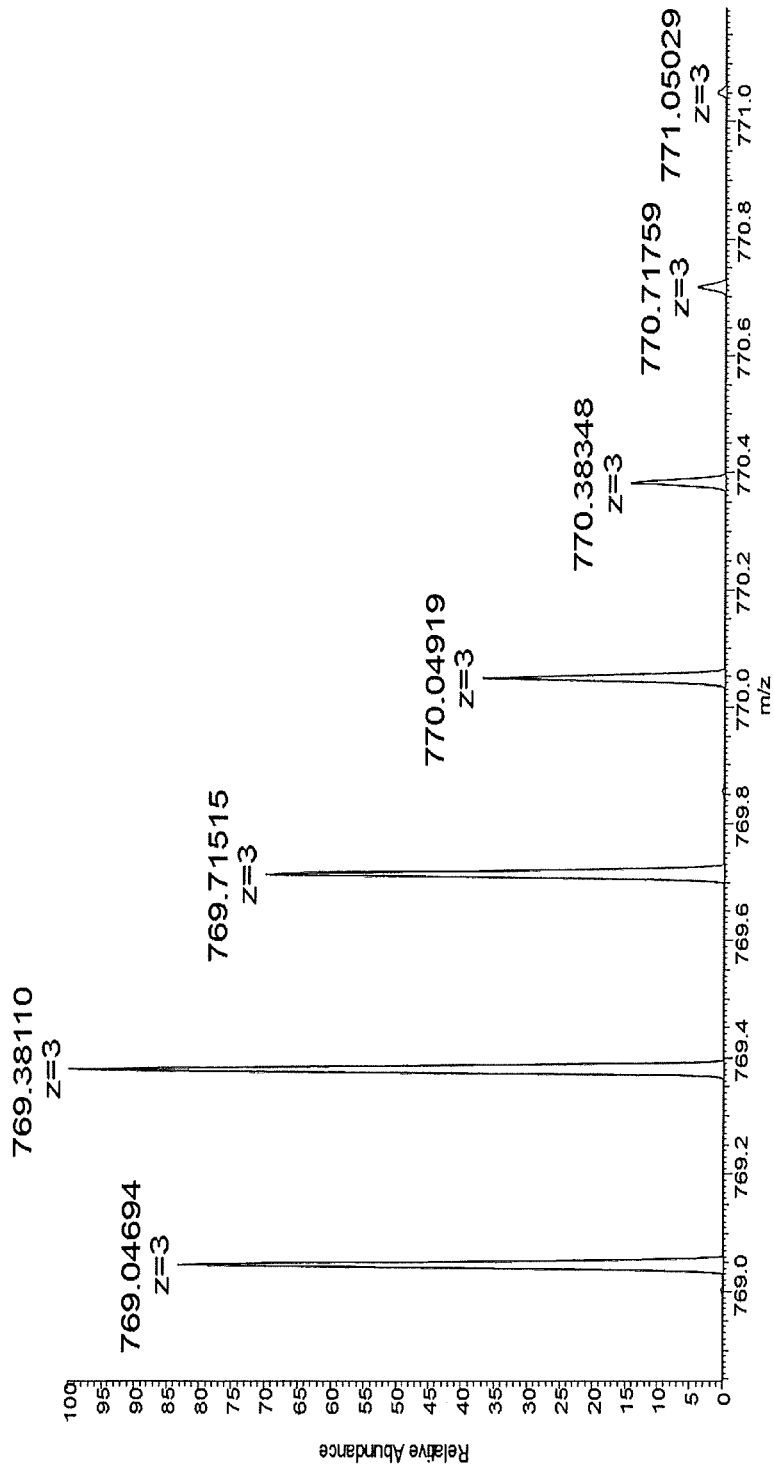
FIG. 56 is an MS spectrum of the peptide fragment of FNWYVDGVEVHNAKTKPR (SEQ ID NO: 69) comprising a modified site to a lysin residue by trypsin digestion of trastuzumab modified using the binder peptide of Example 40 (a thiol-introduced portion subjected to carbamidomethylation with iodoacetamide (+145.019 Da)) (m/z 769.04688, trivalent).
Figure 57:
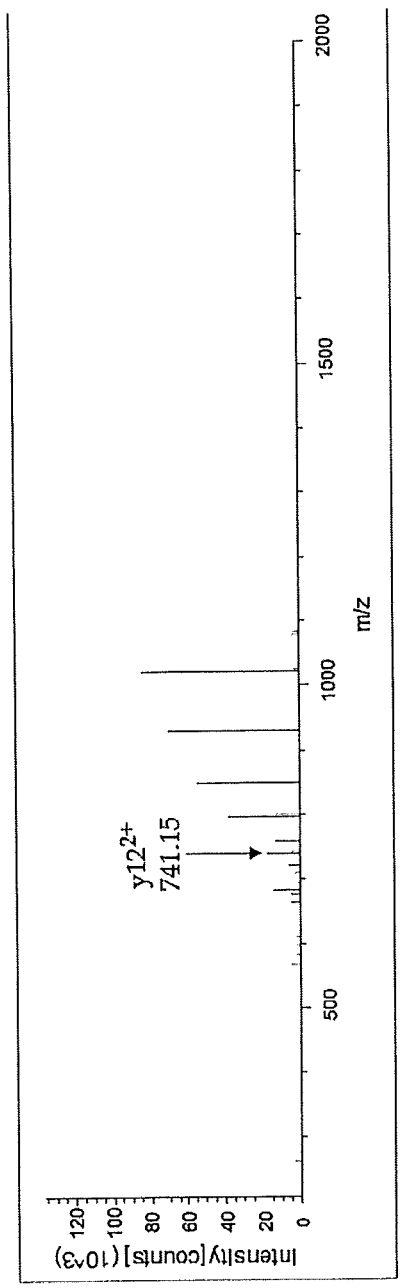
FIG. 57 is a diagram of a CID spectrum of the peptide fragment of FNWYVDGVEVHNAKTKPR (SEQ ID NO: 69) comprising a modified site to a lysin residue by trypsin digestion of trastuzumab modified using the binder peptide of Example 40 (a thiol-introduced portion subjected to carbamidomethylation with iodoacetamide (+145.019 Da)).

After analysis using LC-MS/MS, an MS spectrum of the peptide fragment of FNWYVDGVEVHNAKTKPR (SEQ ID NO: 69), which is a peptide consisting of 18 amino acid residues comprising a modified site to a lysin residue by trypsin digestion of trastuzumab modified using the binder peptide of Example 41 (a thiol-introduced portion subjected to carbamidomethylation with iodoacetamide (+145.019 Da)) (measured value: m/z 769.04688; theoretical value: 769.04457; and trivalent) was observed (FIG. 56), and from a CID spectrum, a product ion of m/z 741.15 (theoretical value: 740.89) corresponding to divalent y12 indicating modification of a lysine residue at position 288 or 290 in EU numbering of the heavy chain was determined (FIG. 57).

Example 43: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (43-1) Synthesis of IgG1 Fc-Binding Peptide The sequence of Ac-FNKQCQRRFYEALHDPNLNE-EQRNARIRSIRDDC-NH$_2$ (SEQ ID NO: 70) was synthesized by Fmoc solid phase synthesis, as is similar to Example 1. The target product was obtained.

(43-2) Formation of Intra-Molecular Disulfide Bond between Cys at Positions 5 and 34 of Ac-FNKQCQRRF-YEALHDPNLNEEQRNARIRSIRDDC-NH$_2$ (SEQ ID NO: 70)

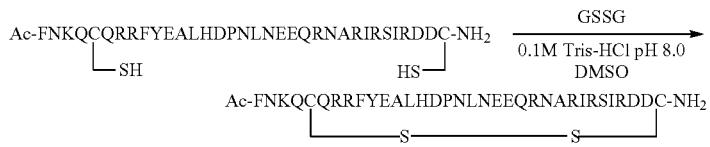

The above-amino acid sequence is SEQ ID NO: 70.

The peptide synthesized in (43-1) was dissolved in DMSO, and 0.1M Tris-HCl (pH 8.0) were added thereto. Oxidized glutathione was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (20.0 mg, 4.67 μmol).

MS (ESI) m/z: z=5 848.30 [M+5H]$^{5+}$, z=6 707.10 [M+6H]$^{6+}$ (43-3) Coupling between Disulfide Linker and Peptide

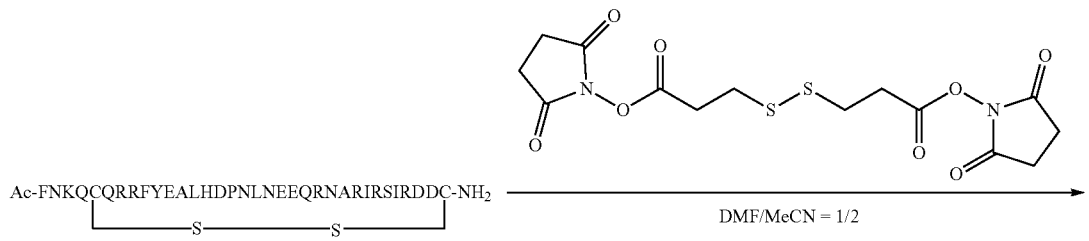

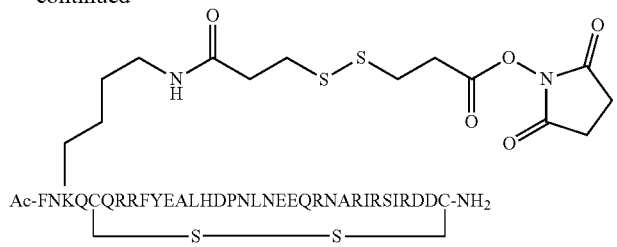

Ac-FNKQCQRRFYEALHDPNLNEEQRNARIRSIRDDC-NH₂

The above-amino acid sequence is SEQ ID NO: 70.

Ac-FNKQCQRRFYEALHDPNLNEEQRNARIRSIRDDC-NH₂ (SEQ ID NO: 70) synthesized in (43-2) (20.0 mg, 4.67 μmol, the 5th and 34th of two cysteines form a disulfide bond in the molecule) was dissolved in N,N'-dimethylformamide (0.50 mL), a solution dissolving 3,3'-dithiodipropionic acid di(N-succinimidyl) (76.0 mg, 188 μmol) in acetonitrile (0.60 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (9.00 mg, 1.97 μmol).

MS (ESI) m/z: z=6 761.85 $[M+6H]^{6+}$

HPLC purity: 85%

(43-4) Specific Modification of Anti-HER2 IgG Antibody Trastuzumab and Analysis Thereof by ESI-TOFMS The peptide- and disulfide linker-coupled NHS-activation compound synthesized in (43-3) was dissolved in N,N'-dimethylformamide to be 4 mM. Anti-HER2 IgG antibody trastuzumab (Chugai Pharmaceutical) in an amount of 1000 μg was dissolved in 342 μL of a 50 mM sodium acetate buffer (pH 5.5), 17.0 μL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS, and a peak for a product with two binding peptides introduced was observed at 156,963.

(43-5) Determination of Heavy Chain Selectivity of Specifically Modified Compound of Trastuzumab under Reduction Condition by ESI-TOFMS Analysis To the antibody-peptide conjugate produced in (43-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,686 and 50,847 with a thiopropionyl group introduced to the heavy chain, and a light chain peak was observed at 23,439, the same as that of the raw material.

(43-6) HIC-HPLC Analysis of Specific Modification of Anti-HER2 IgG Antibody Trastuzumab The antibody-peptide conjugate produced in (43-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+10 equivalents of the peptide- and disulfide linker-coupled NHS-activation compound.

Figure 58:
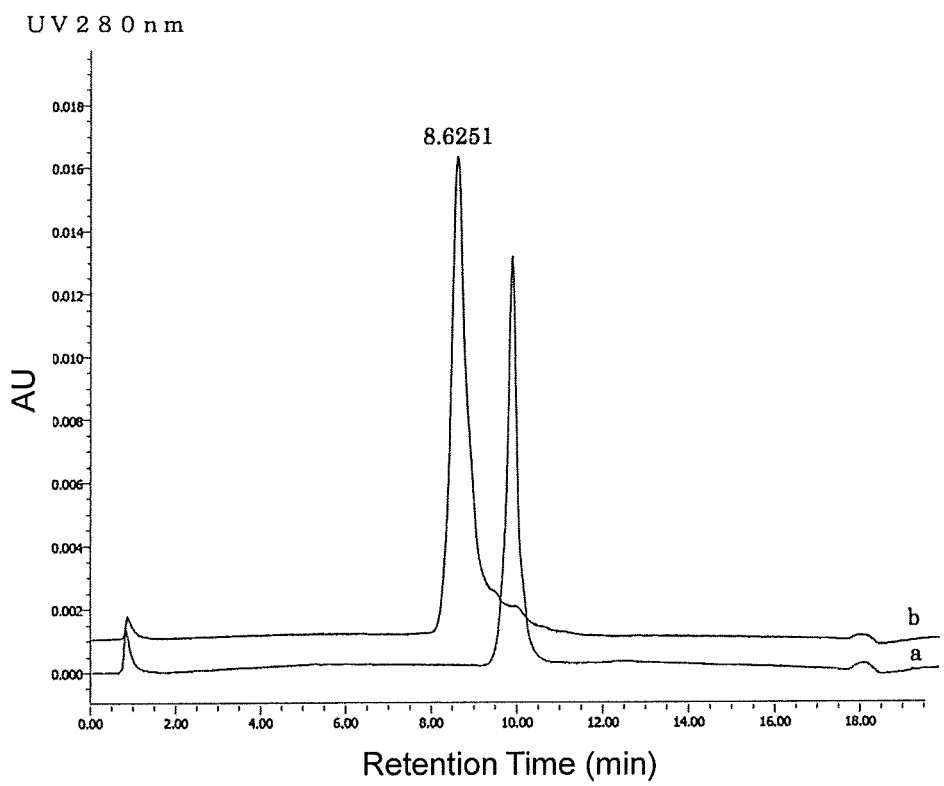
FIG. 58 is a diagram of a result of HIC-UPLC analysis of specific modification of trastuzumab (detection wavelength: UV 280 nm) (Example 41).

It is believed that a retention time of 8.6251 minutes is attributed to a compound with two peptides introduced to trastuzumab (FIG. 58).

Example 44: Peptide Mapping of Thiol-Introduced Compound of Trastuzumab (44-1) Trypsin Treatment for Thiol-Introduced Compound of Trastuzumab Added to a 1.5 mL low-adsorptive micro test tube were 10 μL of a sample solution, a 50 mM ammonium hydrogencarbonate buffer, and 10 μL of a 20 mM aqueous dithiothreitol solution dissolved in 40% trifluoroethanol, the solution was heated at 65° C. for 1 hour, then 10 μL of a 50 mM aqueous iodoacetamide solution was added thereto, and the solution was reacted in a dark place at room temperature while being shaken at 300 rpm for 30 minutes. After reaction, 40 μL of a 50 mM ammonium hydrogencarbonate buffer was added thereto, the solution was stirred, 10 μL of a 20 ng/μL aqueous trypsin solution was added thereto, and the solution was subjected to enzyme digestion at 37° C. for 18 hours. After digestion, 2 μL of a 20% aqueous trifluoroacetic acid solution was added thereto to stop the reaction. Then, the solution was diluted 10 times with a 50 mM ammonium hydrogen carbonate buffer (0.5% trifluoroacetate). The diluted solution was used for LC-MS/MS measurement.

(44-2) LC-MS/MS Measurement Conditions for Trastuzumab (Analyzer)

Nano HPLC: EASY-nLC 1000 (Thermo Fisher Scientific)
Mass Spectrometer: Tribrid Mass Spectrometer Orbitrap Fusion (Thermo Fisher Scientific)

(HPLC Analysis Conditions)

Trap column: Acclaim PepMap (registered trademark) 100, 75 μm×2 cm, (Thermo Fisher Scientific)
Analysis column: ESI-column (NTCC-360/75-3-125, 75 μm×12.5 cm, 3 m (Nikkyo Technos Co., Ltd.))
Mobile Phase A: a 0.1% aqueous formate solution
Mobile Phase B: a 0.1% formate acetonitrile solution
Loading solution: a 0.1% aqueous trifluoroacetic acid solution
Flow rate: 300 nL/min Sample injection amount: 1 μL Gradient condition (B %): 2% (0.0 minute to 0.5 minute), 2%→30% (0.5 minute to 23.5 minutes), 30%→75% (23.5 minutes to 25.5 minutes), and 75% (25.5 minutes to 35.0 minutes).

(Mass Spectrometer Analysis Conditions)

Ionization: ESI, Positive mode

Scan type: Data Dependent Acquisition

Activation Type: Collision Induced Dissociation (CID)

Data acquisition was performed using Xcalibur 3.0 (Thermo Fisher Scientific) and Thermo Orbitrap Fusion Tune Application 2.0 (Thermo Fisher Scientific) as accompanying software.

(44-3) Analysis Condition of Modified Site of Trastuzumab

Modified site analysis of an LC-MS/MS measurement result was performed using Proteome Discoverer version 1.4 (Thermo Fisher Scientific).

For analysis with Proteome Discoverer, Sequest HT was used as a search engine, the range of precursor ion was set to 350 to 5,000 Da. Trypsin was set as a digestive enzyme, and Maximum Missed Cleavage Sites was set to 3. Mass Tolerance was set to 5 ppm and 0.5 Da for a precursor and a fragment ion, respectively. For Static Modification, Carbamidomethyl (+57.021 Da) was set as modification of a cysteine residue with iodoacetamide. For Dynamic Modifications, oxidation of methionine (+15.995 Da) and a modified compound to a lysine residue (a thiol-introduced portion subjected to carbamidomethylation with iodoacetamide (+145.019 Da)) were set. Furthermore, a filter was applied so as to cause Peptide Confidence to be only High. In only Example 32, Total Intensity Threshold was set to 32,000.

As data on amino acid sequences to be searched for a modified site, (1) and (3) illustrated in FIG. 8 were used.

(44-4) Analysis Result of Modified Site of Trastuzumab by LC-MS/MS

Figure 59:
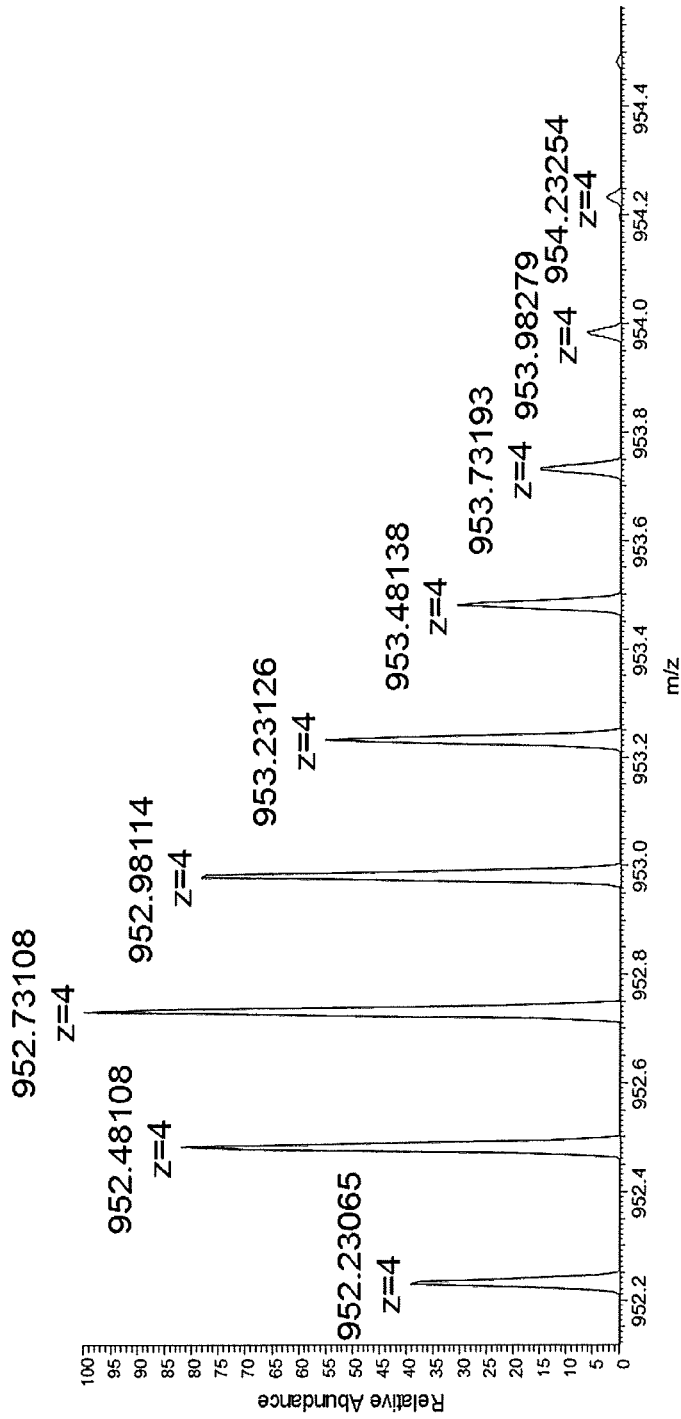
FIG. 59 is an MS spectrum of the peptide fragment of THTCPPCPAPELLGGPSVFLFPPKPKDTLMISR (SEQ ID NO: 40) comprising a modified site to a lysin residue by trypsin digestion of trastuzumab modified using a thiol-introduced compound (a thiol-introduced portion subjected to carbamidomethylation with iodoacetamide (+145.019 Da)) (m/z 952.23145, tetravalent).
Figure 60:
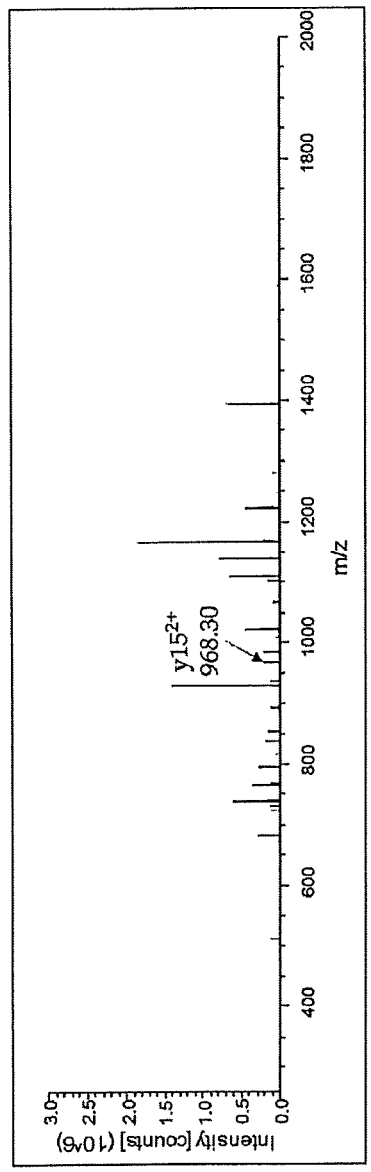
FIG. 60 is a diagram of a CID spectrum of the peptide fragment of THTCPPCPAPELLGGPSVFLFPPKPKDTLMISR (SEQ ID NO: 40) comprising a modified site to a lysin residue by trypsin digestion of trastuzumab modified using a thiol-introduced compound (a thiol-introduced portion subjected to carbamidomethylation with iodoacetamide (+145.019 Da)).

After analysis using LC-MS/MS, an MS spectrum of the peptide fragment of THTCPPCPAPELLGGPSVFLFPPKPKDTLMISR (SEQ ID NO: 40), which is a peptide consisting of 33 amino acid residues comprising a modified site to a lysin residue by trypsin digestion of trastuzumab (a thiol-introduced portion subjected to carbamidomethylation with iodoacetamide (+145.019 Da)) (measured value: m/z 952.23145; theoretical value: 952.22900; and tetravalent) was observed (FIG. 59), and from a CID spectrum, a product ion of m/z 968.30 (theoretical value: 968.01) corresponding to divalent y15 indicating modification of a lysine residue at position 246 in EU numbering of the heavy chain was determined (FIG. 60).

Example 45: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (45-1) Synthesis of IgG1 Fc-Binding Peptide The sequence of Ac-FNMQCKRRFYEALHDPNLNE-EQRNARIRSIRDDC-NH$_2$ (SEQ ID NO: 71) was synthesized by Fmoc solid phase synthesis, as is similar to Example 1. The target product was obtained.

(45-2) Formation of Intra-Molecular Disulfide Bond between Cys at Positions 5 and 34 of Ac-FNMQCKRRF-YEALHDPNLNEEQRNARIRSIRDDC-NH$_2$ (SEQ ID NO: 71)

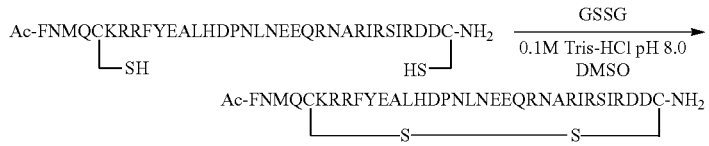

The above-amino acid sequence is SEQ ID NO: 71.

The peptide synthesized in (45-1) was dissolved in DMSO, and 0.1M Tris-HCl (pH 8.0) were added thereto. Oxidized glutathione was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (20.0 mg, 4.67 μmol).

MS (ESI) m/z: z=3 692.70 [M+3H]$^3$, z=4 519.80 [M+4H]$^{4+}$ (45-3) Coupling between Disulfide Linker and Peptide

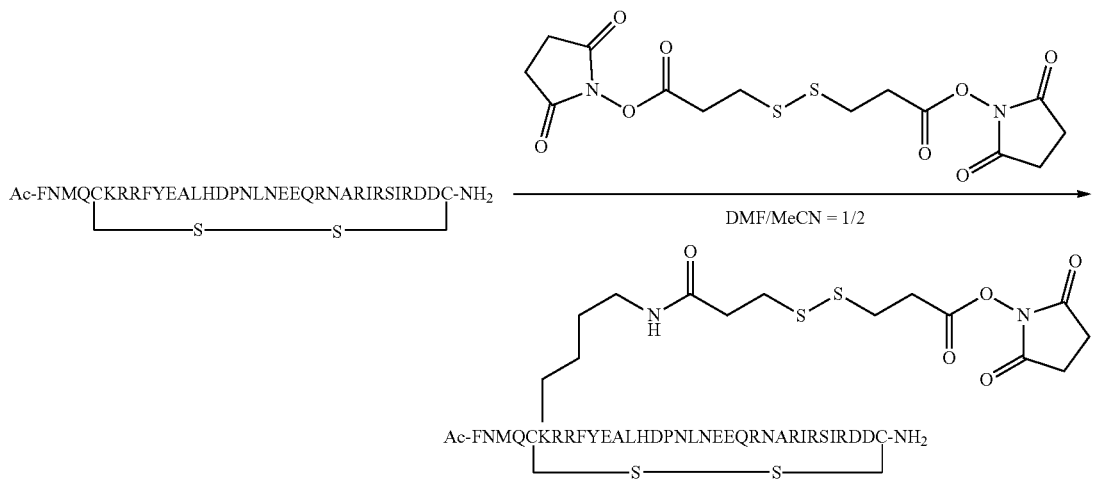

The above-amino acid sequence is SEQ ID NO: 71.

Ac-FNMQCKRRFYEALHDPNLNEEQRNARIR-SIRDDC-NH$_2$ (SEQ ID NO: 71) synthesized in (45-2) (20.0 mg, 4.67 μmol, the 5th and 34th of two cysteines form a disulfide bond in the molecule) was dissolved in N,N'-dimethylformamide (0.50 mL), a solution dissolving 3,3'-dithiodipropionic acid di(N-succinimidyl) (76.0 mg, 188 μmol) in acetonitrile (0.60 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (5.50 mg, 1.20 μmol).

MS (ESI) m/z: z=6 762.40 [M+6H]$^{6+}$

HPLC purity: 100%

(45-4) Specific Modification of Anti-HER2 IgG Antibody Trastuzumab and Analysis Thereof by ESI-TOFMS The peptide- and disulfide linker-coupled NHS-activation compound synthesized in (45-2) was dissolved in N,N'-dimethylformamide to be 4 mM. Anti-HER2 IgG antibody trastuzumab (Chugai Pharmaceutical) in an amount of 500 μg was dissolved in 171 μL of a 50 mM sodium acetate buffer (pH 5.5), 8.5 μL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS; for the raw material trastuzumab, a peak was observed at 148,226, whereas a peak for a product with one binding peptide introduced was observed at 152,662.

(45-5) Determination of Heavy Chain Selectivity of Specifically Modified Compound of Trastuzumab under Reduction Condition by ESI-TOFMS Analysis To the antibody-peptide conjugate produced in (45-3), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,686 and 50,847 with a thiopropionyl group introduced to the heavy chain, and a light chain peak was observed at 23,439, the same as that of the raw material.

(45-6) HIC-HPLC Analysis of Specific Modification of Anti-HER2 IgG Antibody Trastuzumab The antibody-peptide conjugate produced in (45-3) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH$_4$)$_2$SO$_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+10 equivalents of the peptide- and disulfide linker-coupled NHS-activation compound.

Figure 61:
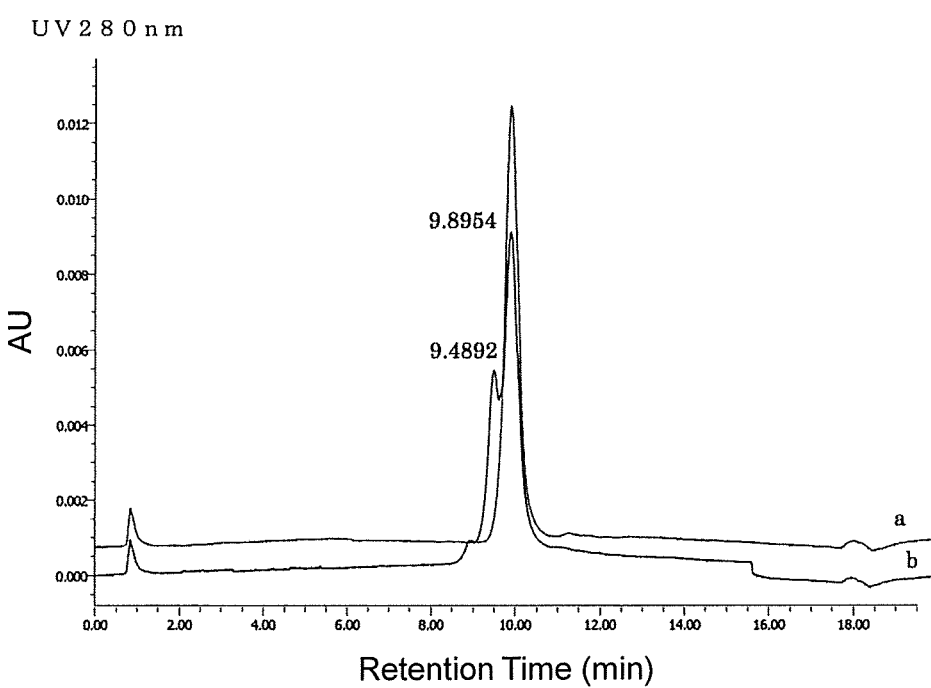
FIG. 61 is a diagram of a result of HIC-UPLC analysis of specific modification of trastuzumab (detection wavelength: UV 280 nm) (Example 42).

It is believed that a retention time of 9.8954 minutes is attributed to the trastuzumab raw material, and a retention time of 9.4892 minutes is attributed to a compound with one peptide introduced to trastuzumab (FIG. 61).

Example 46: Peptide Mapping of Thiol-Introduced Compound of Trastuzumab (46-1) Trypsin Treatment for Thiol-Introduced Compound of Trastuzumab The treatments as the same of (44-1) were performed.

(46-2) LC-MS/MS Measurement Conditions for Trastuzumab

The measurement conditions as the same of (44-2) were performed.

(46-3) Analysis Condition of Modified Site of Trastuzumab

The analysis conditions as the same of (44-3) were performed.

(46-4) Analysis Result of Modified Site of Trastuzumab by LC-MS/MS

Figure 62:
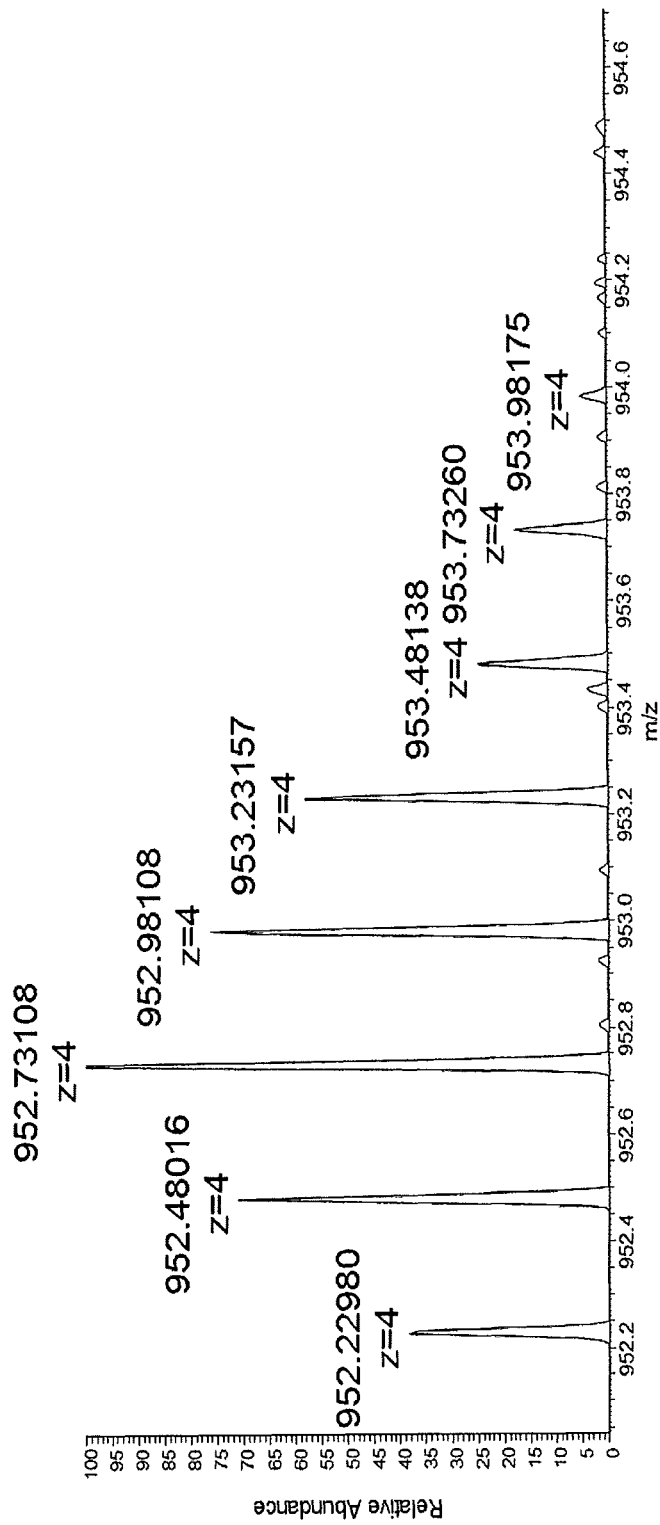
FIG. 62 is an MS spectrum of the peptide fragment of THTCPPCPAPELLGGPSVFLFPPKPKDTLMISR (SEQ ID NO: 40) comprising a modified site to a lysin residue by trypsin digestion of trastuzumab modified using a thiol-introduced compound (a thiol-introduced portion subjected to carbamidomethylation with iodoacetamide (+145.019 Da)) (m/z 952.22968, tetravalent).
Figure 63:
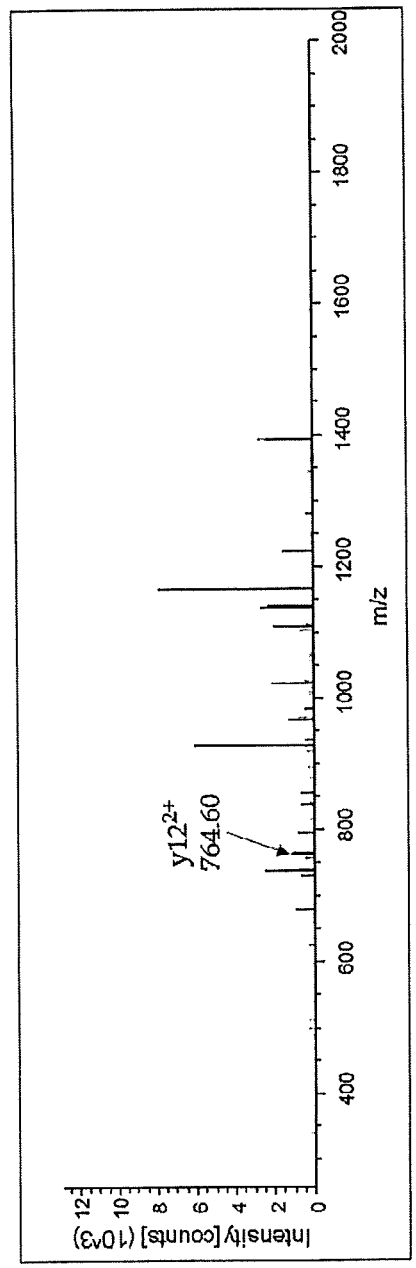
FIG. 63 is a diagram of a CID spectrum of the peptide fragment of THTCPPCPA-PELLGGPSVFLFPPKPKDTLMISR (SEQ ID NO: 40) comprising a modified site to a lysin residue by trypsin digestion of trastuzumab modified using a thiol-introduced compound (a thiol-introduced portion subjected to carbamidomethylation with iodoacetamide (+145.019 Da))

After analysis using LC-MS/MS, an MS spectrum of the peptide fragment of THTCPPCPA-PELLGGPSVFLFPPKPKDTLMISR (SEQ ID NO: 40), which is a peptide consisting of 33 amino acid residues comprising a modified site to a lysin residue by trypsin digestion of trastuzumab (a thiol-introduced portion subjected to carbamidomethylation with iodoacetamide (+145.019 Da)) (measured value: m/z 952.22968; theoretical value: 952.22900; and tetravalent) was observed (FIG. 62), and from a CID spectrum, a product ion of m/z 764.60 (theoretical value: 764.40) corresponding to divalent y12 indicating modification of a lysine residue at position 246 in EU numbering of the heavy chain was determined (FIG. 63).

Example 47: Synthesis of Compound Having Affinity Substance to Soluble Protein, Cleavable Portion, and Reactive Group (Peptide- and Disulfide Linker-Coupled NHS-Activation Compound), Modification of Anti-HER2 IgG Antibody Trastuzumab Using Compound, and Analysis thereof (47-1) Synthesis of IgG1 Fc-Binding Peptide The sequence of Ac-FNMQCQRRFYEALHDPNLNE-EQRNARIRSIRKDC-NH$_2$ (SEQ ID NO: 72) was synthesized by Fmoc solid phase synthesis, as is similar to Example 1. The target product was obtained.

(47-2) Formation of Intra-Molecular Disulfide Bond between Cys at Positions 5 and 34 of Ac-FNMQCQRRF-YEALHDPNLNEEQRNARIRSIRKDC-NH$_2$ (SEQ ID NO: 72)

The above-amino acid sequence is SEQ ID NO: 72.

The peptide synthesized in (47-1) was dissolved in DMSO, and 0.1M Tris-HCl (pH 8.0) were added thereto. Oxidized glutathione was added to this solution, and the solution was stirred at room temperature for 20 hours. A 2 M aqueous trifluoroacetic acid solution was added to the reaction solution to stop the reaction, which was dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the target product (24.5 mg, 5.71 μmol).

MS (ESI) m/z: z=3 692.70 [M+3H]$^{3+}$, z=4 519.80 [M+4H]$^{4+}$ (47-3) Coupling between Disulfide Linker and Peptide

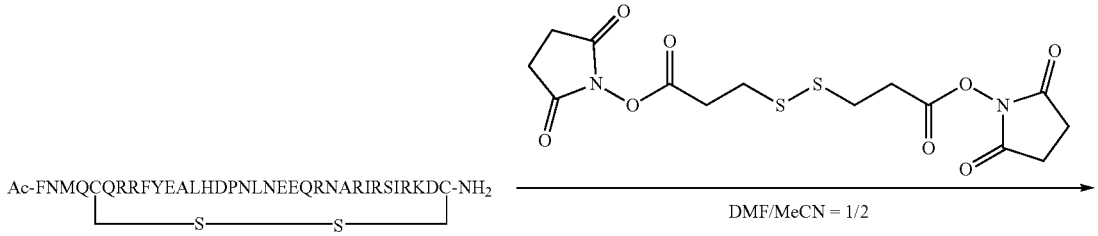

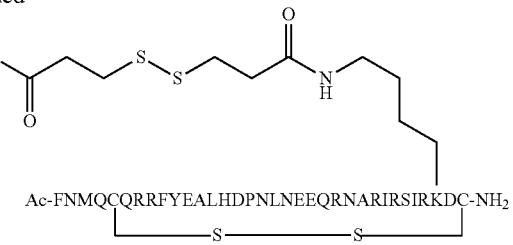

Ac-FNMQCQRRFYEALHDPNLNEEQRNARIRSIRKDC-NH₂ (with S—S bridge)

The above-amino acid sequence is SEQ ID NO: 72.

Ac-FNMQCQRRFYEALHDPNLNEEQRNARIRSIRKDC-NH₂ (SEQ ID NO: 72) synthesized in (47-2) (24.5 mg, 5.71 μmol, the 5th and 34th of two cysteines form a disulfide bond in the molecule) was dissolved in N,N'-dimethylformamide (1.00 mL), a solution dissolving 3,3'-dithiodipropionic acid di(N-succinimidyl) (92.2 mg, 228 μmol) in acetonitrile (1.00 mL) was added thereto, and the solution was stirred at room temperature for 24 hours. Concentration under reduced pressure was performed to remove acetonitrile, which was then dissolved in a 0.05% aqueous trifluoroacetic acid solution and was subjected to reversed phase high-speed liquid chromatography with octadodecyl group-chemically bound type silica gel as a filler, fractions were eluted with a mixed solution of water and acetonitrile containing 0.05% of trifluoroacetic acid, and the fractions were determined by LC-MS. A fraction comprising a product was collected, was concentrated under reduced pressure to remove acetonitrile, and was freeze-dried to obtain the peptide- and disulfide linker-coupled NHS-activation compound (7.50 mg, 1.64 μmol).

MS (ESI) m/z: z=6 762.40 [M+6H]⁶⁺

HPLC purity: 84%

(47-4) Specific Modification of Anti-HER2 IgG Antibody Trastuzumab and Analysis Thereof by ESI-TOFMS The peptide- and disulfide linker-coupled NHS-activation compound synthesized in (47-3) was dissolved in N,N'-dimethylformamide to be 4 mM. Anti-HER2 IgG antibody trastuzumab (Chugai Pharmaceutical) in an amount of 500 μg was dissolved in 171 μL of a 50 mM sodium acetate buffer (pH 5.5), 8.5 μL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS; for the raw material trastuzumab, a peak was observed at 148,087, whereas a peak for a product with one binding peptide introduced was observed at 152,694, and a peak for a product with two binding peptides introduced was observed at 157,160.

(47-5) Determination of Heavy Chain Selectivity of Specifically Modified Compound of Trastuzumab under Reduction Condition by ESI-TOFMS Analysis To the antibody-peptide conjugate produced in (47-4), 5 μL of a 7 mM tris(2-carboxyethyl)phosphine hydrochloride solution (an equivalent with respect to the antibody) was added, and the solution was stirred at room temperature for 20 minutes. The mass was measured by ESI-TOFMS; for products, peaks were observed at 50,686 and 50,847 with a thiopropionyl group introduced to the heavy chain, and a light chain peak was observed at 23,439, the same as that of the raw material.

(47-6) HIC-HPLC Analysis of Specific Modification of Anti-HER2 IgG Antibody Trastuzumab The antibody-peptide conjugate produced in (47-4) and a raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M (NH₄)₂SO₄, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a trastuzumab raw material;
b: trastuzumab+10 equivalents of the peptide- and disulfide linker-coupled NHS-activation compound.

Figure 64:
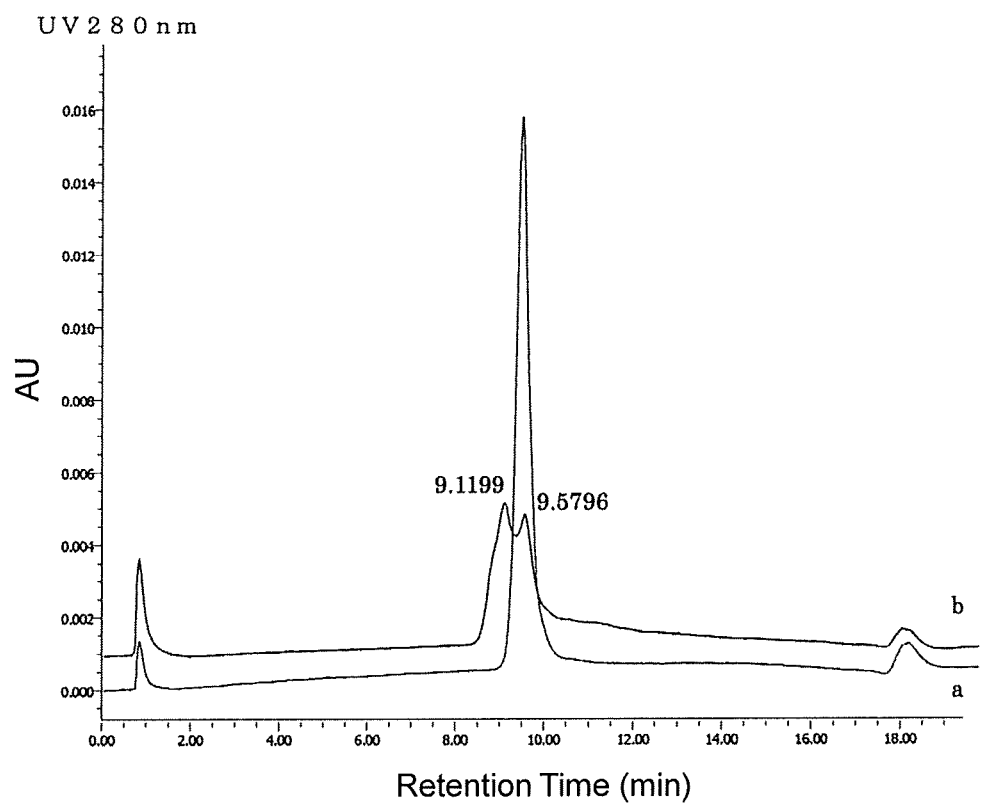
FIG. 64 is a diagram of a result of HIC-UPLC analysis of specific modification of trastuzumab (detection wavelength: UV 280 nm) (Example 43).

It is believed that a retention time of 9.5796 minutes is attributed to the trastuzumab raw material, and a retention time of 9.1199 minutes is attributed to a compound with one peptide introduced to trastuzumab (FIG. 64).

Example 48: Peptide Mapping of Thiol-Introduced Compound of Trastuzumab (48-1) Trypsin Treatment for Thiol-Introduced Compound of Trastuzumab The treatments as the same of (44-1) were performed.

(48-2) LC-MS/MS Measurement Conditions for Trastuzumab

The measurement conditions as the same of (44-2) were performed.

(48-3) Analysis Condition of Modified Site of Trastuzumab

The analysis conditions as the same of (44-3) were performed.

(48-4) Analysis Result of Modified Site of Trastuzumab by LC-MS/MS

Figure 65:
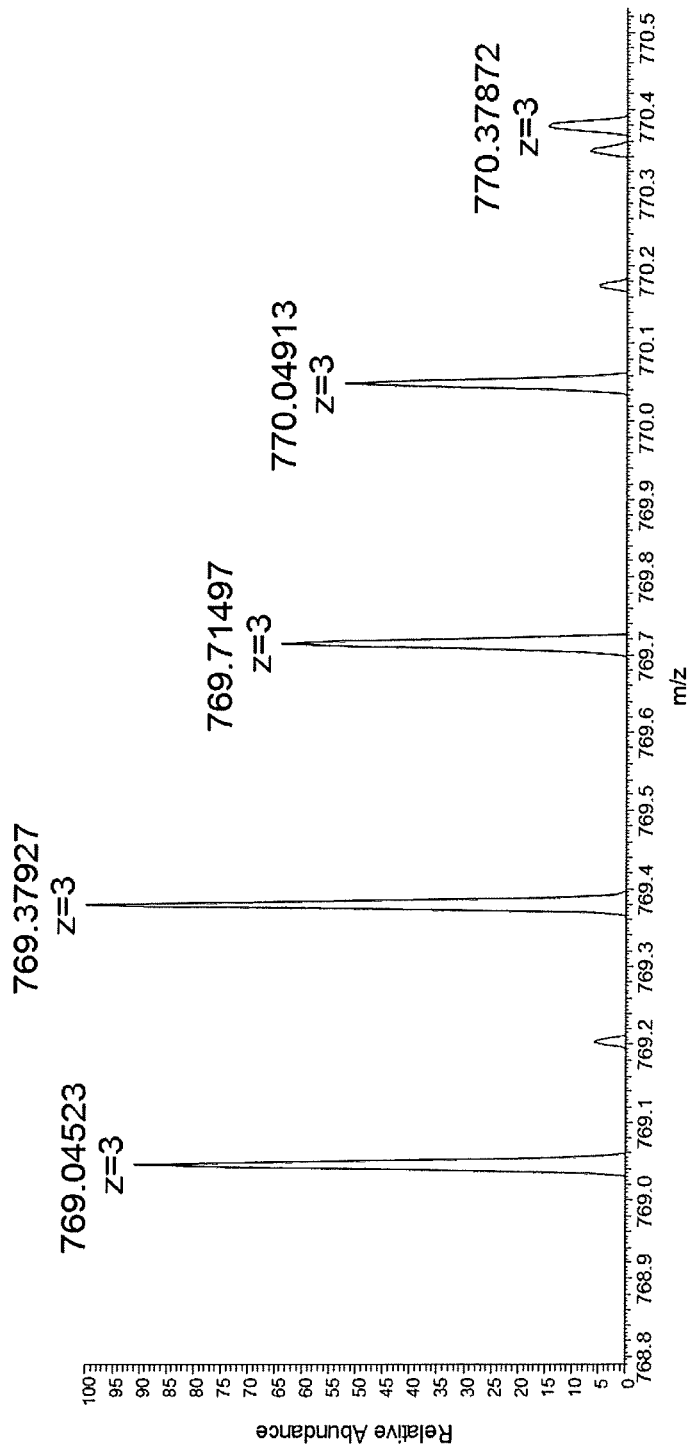
FIG. 65 is an MS spectrum of the peptide fragment of FNWYVDGVEVHNAKTKPR (SEQ ID NO: 69) comprising a modified site to a lysin residue by trypsin digestion of trastuzumab modified using a thiol-introduced compound (a thiol-introduced portion subjected to carbamidomethylation with iodoacetamide (+145.019 Da)) (m/z 769.04529, trivalent).
Figure 66:
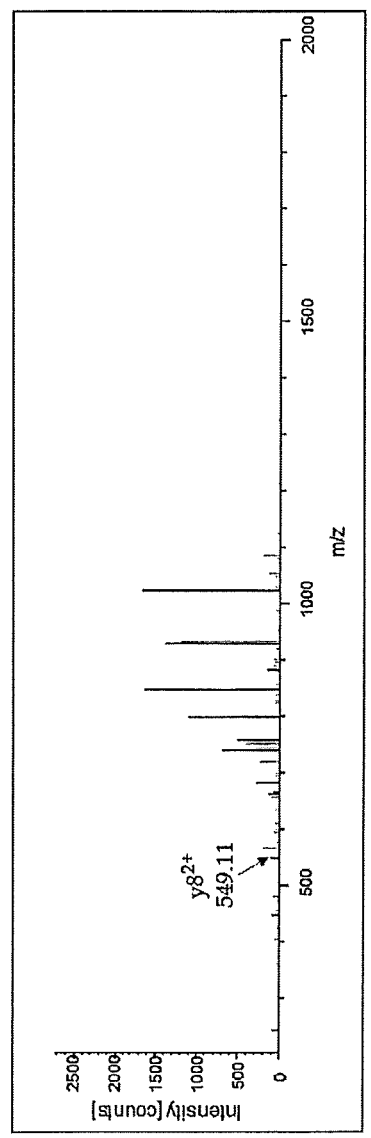
FIG. 66 is a diagram of a CID spectrum of the peptide fragment of FNWYVDGVEVHNAKTKPR (SEQ ID NO: 69) comprising a modified site to a lysin residue by trypsin digestion of trastuzumab modified using a thiol-introduced compound (a thiol-introduced portion subjected to carbamidomethylation with iodoacetamide (+145.019 Da)).

After analysis using LC-MS/MS, an MS spectrum of the peptide fragment of FNWYVDGVEVHNAKTKPR (SEQ ID NO: 69), which is a peptide consisting of 33 amino acid residues comprising a modified site to a lysin residue by trypsin digestion of trastuzumab (a thiol-introduced portion subjected to carbamidomethylation with iodoacetamide (+145.019 Da)) (measured value: m/z 769.04529; theoretical value: 769.04457; and trivalent) was observed (FIG. 65), and from a CID spectrum, a product ion of m/z 549.11 (theoretical value: 548.79) corresponding to divalent y8 indicating modification of a lysine residue at position 290 in EU numbering of the heavy chain was determined (FIG. 66).

Example 49: Modification of Human IgG2 Antibody Using Compound Having Affinity Substance to Soluble Protein, Cleavable Portion, and Reactive Group (Peptide- and Disulfide Linker-Coupled NHS-Activation Compound) and Analysis thereof (49-1) Specific Modification of Human IgG2 Antibody and Analysis Thereof by ESI-TOFMS The peptide- and disulfide linker-coupled NHS-activation compound synthesized in (2-2) was dissolved in N,N'- dimethylformamide to be 4 mM. Human IgG2 antibody (manufactured by RayBiotech, Inc.) in an amount of 500 µg was dissolved in 171 µL of a 50 mM sodium acetate buffer (pH 5.5), 8.5 µL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS; for the raw material IgG2 antibody, a peak was observed at 153,047, whereas for a product with one binding peptide introduced, a peak was observed at 155,129; for a product with two binding peptides introduced, a peak was observed at 157,699.

(49-2) HIC-UPLC Analysis of Specific Modification of Human IgG2 Antibody

The antibody-peptide conjugate produced in (49-1) and the raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a human IgG2 antibody raw material; and
b: human IgG2 antibody+10 equivalents of the peptide- and disulfide linker-coupled NHS-activation compound.

Figure 67:
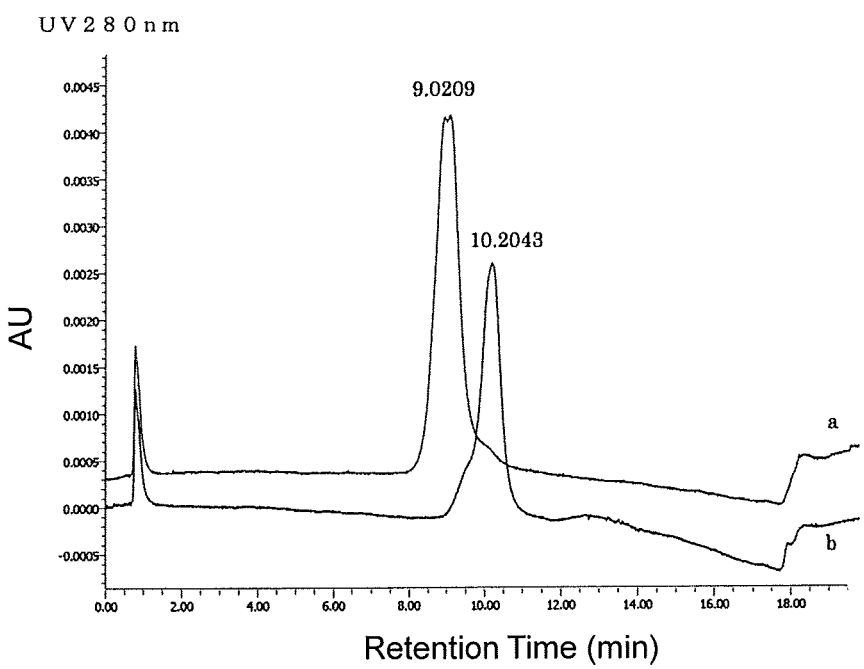
FIG. 67 is a diagram of a result of HIC-UPLC analysis of specific modification of human IgG2 antibody (detection wavelength: UV 280 nm) (Example 2-2).

It is believed that a retention time of 9.0209 minutes is attributed to the human IgG2 antibody raw material, whereas that of 10.2043 minutes is attributed to a compound with one peptide introduced to the human IgG2 antibody (FIG. 67).

Example 50: Modification of Human IgG2 Antibody Using Compound Having Affinity Substance to Soluble Protein, Cleavable Portion, and Reactive Group (Peptide- and Disulfide Linker-Coupled NHS-Activation Compound) and Analysis thereof (50-1) Specific Modification of Human IgG2 Antibody and Analysis Thereof by ESI-TOFMS The peptide- and disulfide linker-coupled NHS-activation compound synthesized in (43-3) was dissolved in N,N'-dimethylformamide to be 4 mM. Human IgG2 antibody (manufactured by RayBiotech, Inc.) in an amount of 500 µg was dissolved in 171 µL of a 50 mM sodium acetate buffer (pH 5.5), 8.5 µL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS; for the raw material IgG2 antibody, a peak was observed at 153,047, whereas for a product with one binding peptide introduced, a peak was observed at 157,652; for a product with two binding peptides introduced, a peak was observed at 165,043.

(50-2) HIC-UPLC Analysis of Specific Modification of Human IgG2 Antibody

The antibody-peptide conjugate produced in (50-1) and the raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a human IgG2 antibody raw material; and
b: human IgG2 antibody+10 equivalents of the peptide- and disulfide linker-coupled NHS-activation compound.

Figure 68:
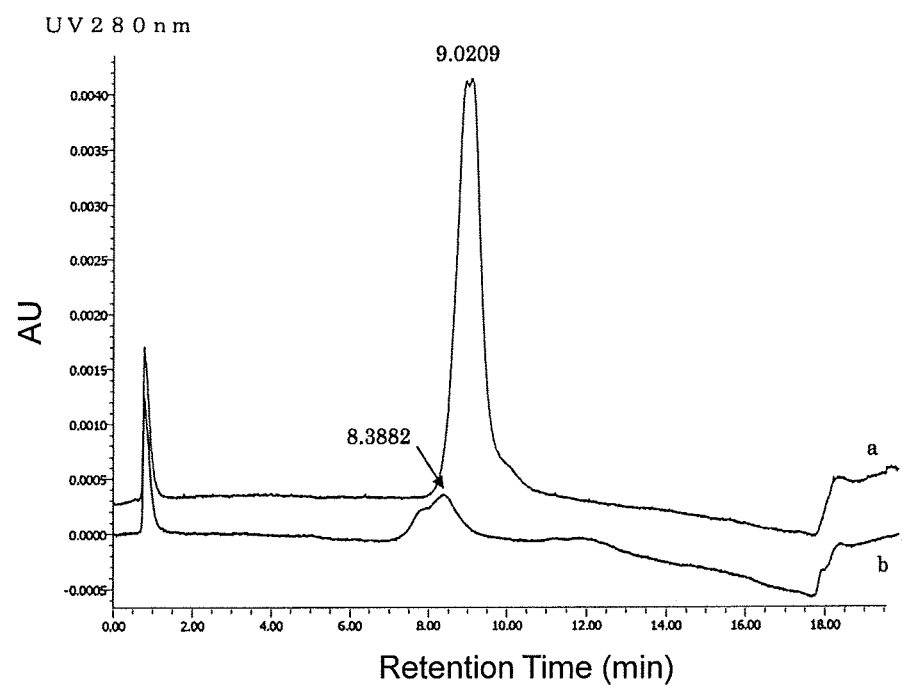
FIG. 68 is a diagram of a result of HIC-UPLC analysis of specific modification of human IgG2 antibody (detection wavelength: UV 280 nm) (Example 43).

It is believed that a retention time of 9.0209 minutes is attributed to the human IgG2 antibody raw material, whereas that of 8.3882 minutes is attributed to a compound with one peptide introduced to the human IgG2 antibody (FIG. 68).

Example 51: Modification of Human IgG4 Antibody Using Compound Having Affinity Substance to Soluble Protein, Cleavable Portion, and Reactive Group (Peptide- and Disulfide Linker-Coupled NHS-Activation Compound) and Analysis thereof (51-1) Specific Modification of Human IgG4 Antibody and Analysis Thereof by ESI-TOFMS The peptide- and disulfide linker-coupled NHS-activation compound synthesized in (2-2) was dissolved in N,N'-dimethylformamide to be 4 mM. Human IgG4 antibody (manufactured by RayBiotech, Inc.) in an amount of 500 µg was dissolved in 171 µL of a 50 mM sodium acetate buffer (pH 5.5), 8.5 µL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS; for the raw material IgG2 antibody, a peak was observed at 154,618, whereas for a product with two binding peptides introduced, a peak was observed at 159,130.

(51-2) HIC-UPLC Analysis of Specific Modification of Human IgG4 Antibody

The antibody-peptide conjugate produced in (51-1) and the raw material antibody were analyzed by HIC. For a column, Protein-Pak Hi Res HIC Column (Waters) 4.6×100 mm 2.5 m was used. Detection was performed with A_Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a human IgG4 antibody raw material; and
b: human IgG4 antibody+10 equivalents of the peptide- and disulfide linker-coupled NHS-activation compound.

Figure 69:
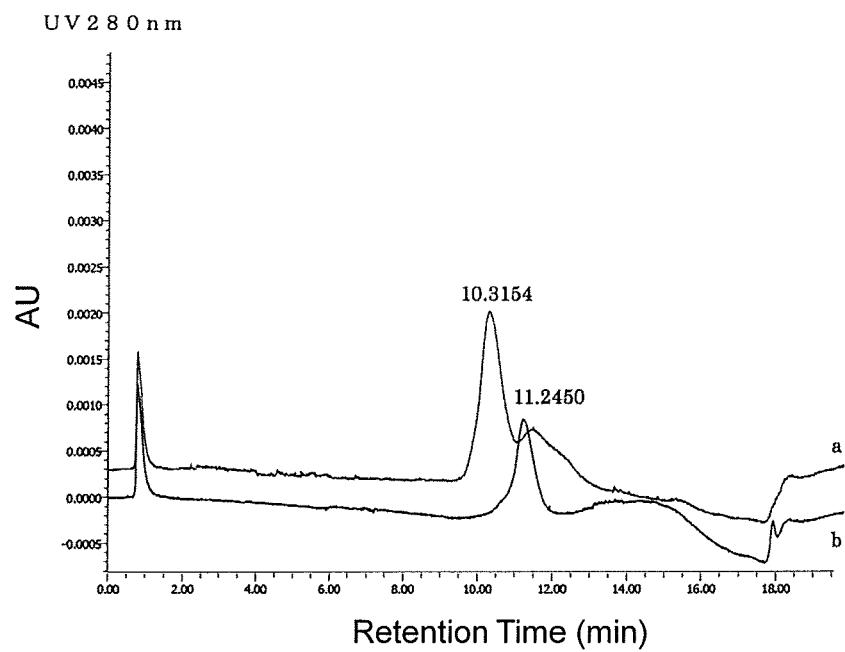
FIG. 69 is a diagram of a result of HIC-UPLC analysis of specific modification of human IgG4 antibody (detection wavelength: UV 280 nm) (Example 2-2).

It is believed that a retention time of 10.3154 minutes is attributed to the human IgG4 antibody raw material,

269 whereas that of 11.2450 minutes is attributed to a compound with one peptide introduced to the human IgG4 antibody (FIG. 69).

Example 52: Modification of Human IgG4 Antibody Using Compound Having Affinity Substance to Soluble Protein, Cleavable Portion, and Reactive Group (Peptide- and Disulfide Linker-Coupled NHS-Activation Compound) and Analysis thereof (52-1) Specific Modification of Human IgG4 Antibody and Analysis Thereof by ESI-TOFMS The peptide- and disulfide linker-coupled NHS-activation compound synthesized in (43-3) was dissolved in N,N'-dimethylformamide to be 4 mM. Human IgG2 antibody (manufactured by RayBiotech, Inc.) in an amount of 500 µg was dissolved in 171 µL of a 50 mM sodium acetate buffer (pH 5.5), 8.5 µL of a 4 mM peptide reagent (10 equivalents with respect to the antibody) was added thereto, and the solution was stirred at room temperature for 1 hour. The reaction solution was substituted with a 100 mM sodium citrate buffer (pH 2.9) to stop the reaction and was further substituted with a 20 mM PBS buffer. The mass was measured by ESI-TOFMS; for the raw material IgG2 antibody, a peak was observed at 154,618, whereas for a product with two binding peptides introduced, a peak was observed at 163,530.

(52-2) HIC-UPLC Analysis of Specific Modification of Human IgG4 Antibody

The antibody-peptide conjugate produced in (52-1) and the raw material antibody were analyzed by HIC. For a column, Protein-Pak Hi Res HIC Column (Waters) 4.6×100 mm 2.5 µm was used. Detection was performed with A Buffer: 0.1 M PiNa, 2.3 M $(NH_4)_2SO_4$, pH 7.0, B_Buffer: 0.1 M PiNa, pH 7.0, a flow rate of 0.6 ml/min, a gradient of A 60% B 40%→A 0% B 100%, 16 minutes (data collection 20 minutes), a column temperature of 40° C., a thermostat temperature of 40° C., and a detector with a wavelength of 280 nm.

Samples were reacted under the following conditions:
a: a human IgG4 antibody raw material; and
b: human IgG4 antibody+10 equivalents of the peptide- and disulfide linker-coupled NHS-activation compound.

Figure 70:
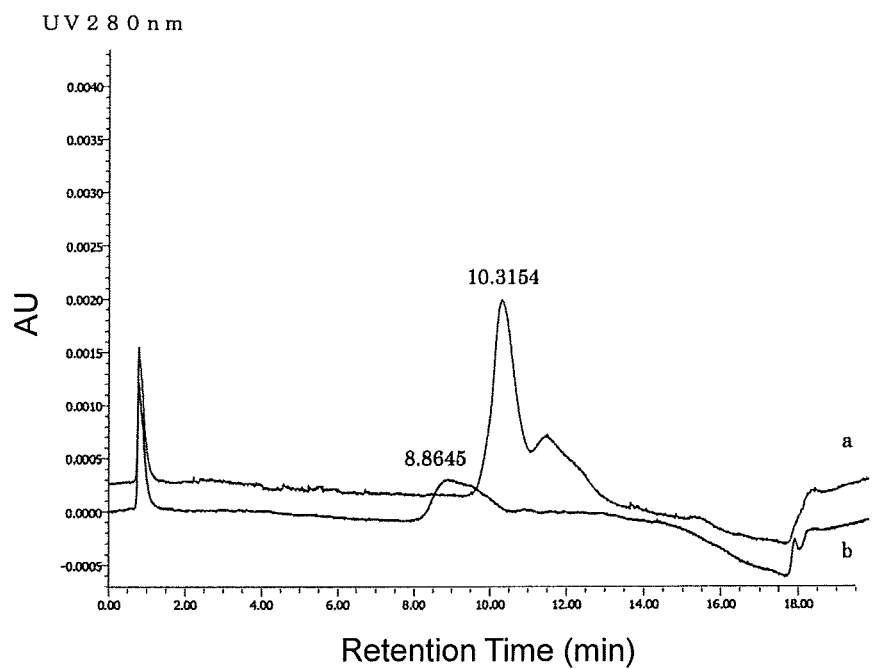
FIG. 70 is a diagram of a result of HIC-UPLC analysis of specific modification of human IgG4 antibody (detection wavelength: UV 280 nm) (Example 43).

It is believed that a retention time of 10.3154 minutes is attributed to the human IgG4 antibody raw material, whereas that of 8.8645 minutes is attributed to a compound with one peptide introduced to the human IgG4 antibody (FIG. 70).

Example 53: (1) Synthesis of Cleavable Linker and (2) Synthesis of Compound Having Affinity Substance to Soluble Protein, Cleavable Portion, and Reactive Group (Peptide- and Azide Modified Thioester Linker-Coupled NHS-Activation Compound) Through Coupling Between Synthesized Linker and IgG1 Fc-Binding Peptide (53-1) Synthesis of Thioester Linker and Coupling thereof with Peptide
(53-1-1) Synthesis of Thioester Linker

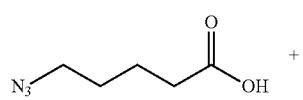

270

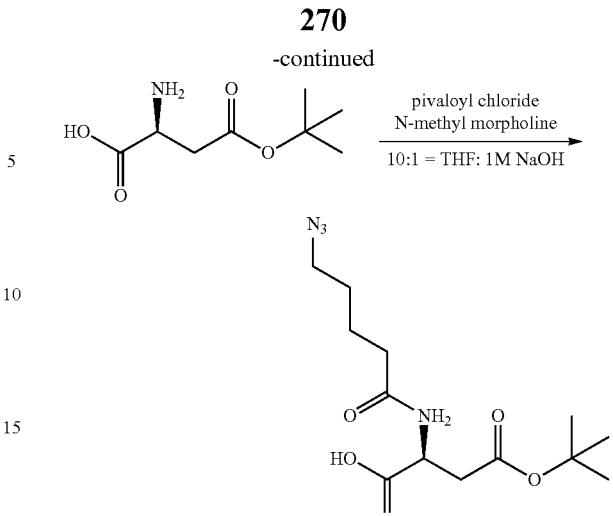

In a THF solvent (12 mL), 5-azido-pentanoic acid (200 mg, 1.40 mmol) was dissolved, pivaloyl chloride (206 µL, 1.68 mmol) and N-methylmorpholine (230 µL, 2.10 mmol) were added thereto at 0° C., and the solution was stirred for 30 minutes to prepare a mixed anhydride of 5-azido-pentanoic acid. At room temperature, 4-(tert-butoxy-oxo)-2-amino-butanoic acid (344 mg, 1.82 mmol) was dissolved in a 1 M aqueous sodium hydroxide solution (1.82 mL), and then the THF solution of the mixed anhydride of 5-azido-pentanoic acid was added dropwise thereto at room temperature. The solution was stirred at room temperature for 16 hours, and then a 6 M aqueous hydrochlorate solution was added thereto to adjust the pH within the system to 3.0. The reaction solution was diluted with ethyl acetate and was washed with water and brine, and then magnesium sulfate anhydride was added thereto, and allowed to stand for 5 minutes. Magnesium sulfate was removed by filtration, and concentration under reduced pressure was performed to obtain a crude product, which was then purified by column chromatography (dichloromethane:methanol=10:1). A fraction comprising a product was collected and was concentrated under reduced pressure to obtain 4-(tert-butoxy-oxo)-2-(5-azidopenta-1-oxo)amino-butanoic acid (320 mg, 1.02 mmol).

MS (ESI) m/z: 337 [M+Na]+

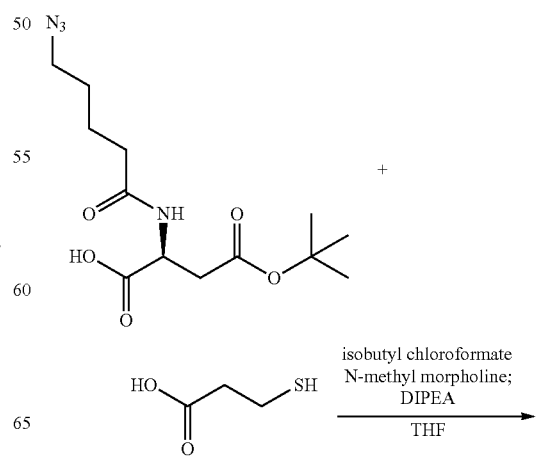

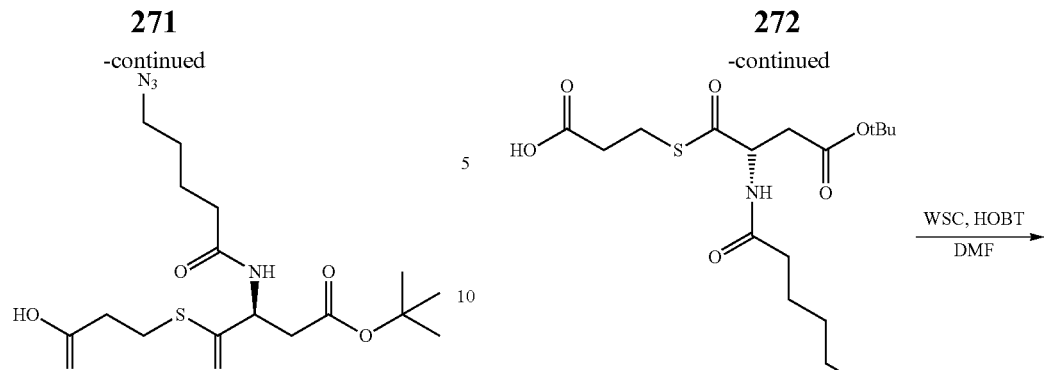

In THF (4.9 mL), 4-(tert-butoxy-oxo)-2-(5-azidopenta-1-oxo)amino-butanoic acid (154 mg, 0.490 mmol) was dissolved, isobutyl chlorocarbonate (83.6 μL, 0.637 mmol) and N-methylmorpholine (108 μL, 0.980 mmol) were added thereto at 0° C., and the solution was stirred for 30 minutes to prepare a corresponding mixed anhydride. The THF solution of the mixed anhydride was added dropwise to mercaptopropionic acid (128 μL, 1.47 mmol) and N,N-diisopropylethylamine (253 μL, 1.47 mmol) at room temperature. The solution was stirred at room temperature for 16 hours, then a 1 M aqueous sodium hydroxide solution was added thereto to adjust the pH within the system to 9.0. The reaction solution was washed with water and ethyl acetate, and an aqueous phase was collected. A 6 M aqueous hydrochlorate solution was added to the aqueous phase to adjust the pH within the system to 3.0, then extraction with ethyl acetate was performed, then organic phase was washed with brine, and then magnesium sulfate anhydride was added thereto, and allowed to stand for 5 minutes. Magnesium sulfate was removed by filtration, and concentration under reduced pressure was performed to obtain 3-[4-(tert-butoxy-oxo)-2-(5-azidopenta-1-oxo)amino-1-oxo]sulfanyl-propanoic acid (108 mg, 0.268 mmol).

MS (ESI) m/z: 403 [M+H]

(53-1-2) Coupling between Thioester Linker and Peptide

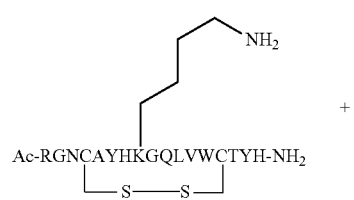

+

The above-amino acid sequence is SEQ ID NO: 39.

The peptide of Ac-RGNCAYHKGQLVWCTYH-NH2 (SEQ ID NO: 39) synthesized in Example 1-2 (31.8 mg, 15.3 μmol, the 4th and 14th of two homocysteines form a disulfide bond in the molecule) was dissolved in 1 mL of N,N'-dimethylformamide. Dissolved in 1 mL of DMF were 3-[4-(tert-butoxy-oxo)-2-(5-azidopenta-1-oxo)amino-1-oxo]-sulfanyl-propanoic acid (61.7 mg, 0.153 mmol), 1-ethyl-3-(3-dimethylaminopropyl)carbodiimide hydrochloride (29.4 mg, 0.153 mmol), and 1-hydroxybenzotriazole (10.4 mg, 0.0766 mmol), which was added to the system. The solution was stirred at room temperature for 2 hours, then a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled tBu compound (2.5 mg, 1.02 μmol).

MS (ESI) m/z: z=2 1,230 [M+2H]$^{2+}$, z=3 820 [M+3H]$^{3+}$

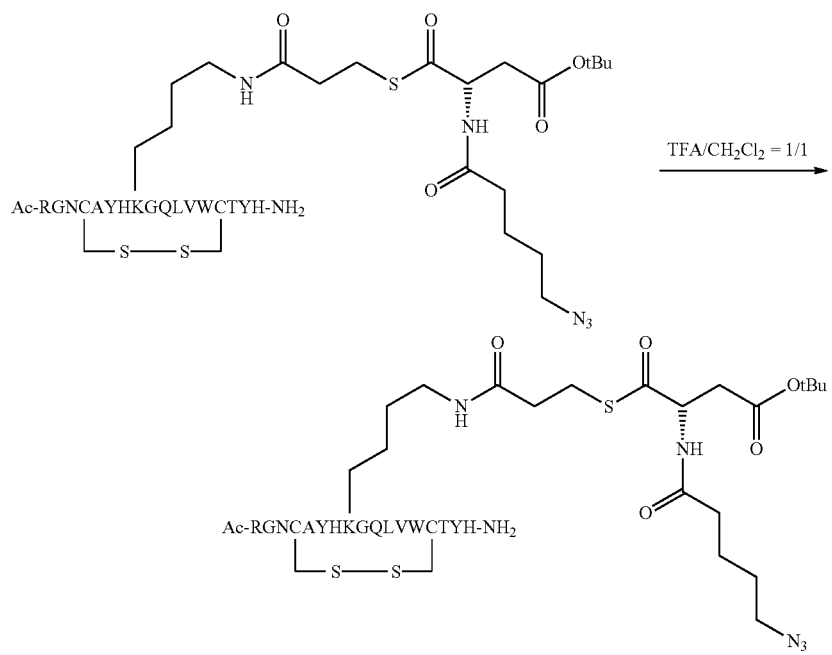

The above-amino acid sequence is SEQ ID NO: 39.

The peptide- and linker-coupled compound (2.5 mg, 1.02 mol) was dissolved in 0.250 mL of dichloromethane, and 0.250 mL of trifluoroacetic acid was added thereto, and the solution was stirred at room temperature for 1 hour. After performing concentration under reduced pressure, a 0.1% aqueous trifluoroacetic acid solution was added thereto, and fractions were eluted by reversed phase preparative chromatography. A fraction comprising a product was collected, was concentrated under reduced pressure to remove only acetonitrile, and was freeze-dried to obtain the peptide- and linker-coupled carboxylic compound.

MS (ESI) m/z: z=2 1,202 [M+2H]$^{2+}$, z=3 802 [M+3H]$^{3+}$

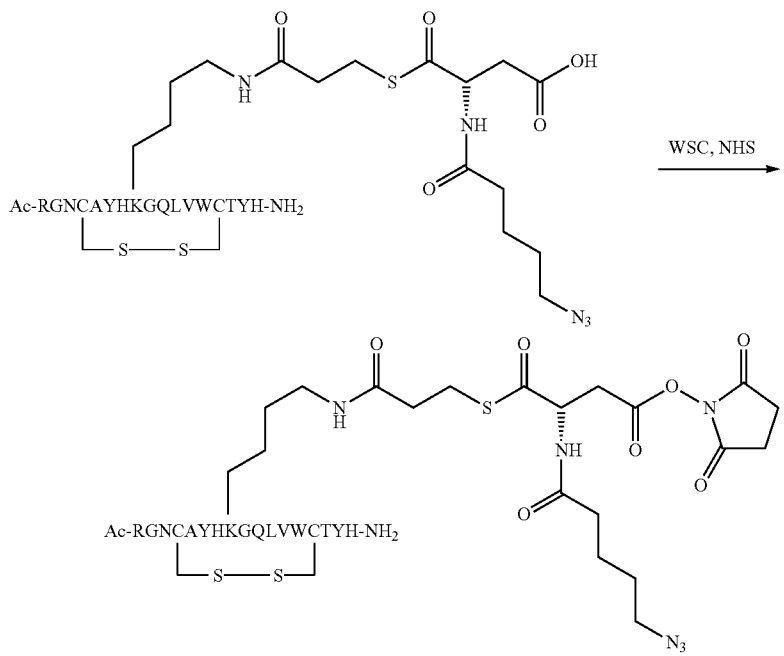

The above-amino acid sequence is SEQ ID NO: 39.

The peptide- and linker-coupled carboxylic compound was dissolved in 0.5 mL of N,N'-dimethylformamide, 1-ethyl-3-(3-dimethylaminopropyl)carbodiimide hydrochloride (2.0 mg, 10.2 µmol) and N-hydroxysuccinimide (1.2 mg, 10.2 µmol) were added thereto, and the solution was stirred for 16 hours. A 0.1% aqueous trifluoroacetic acid solution was added to the reaction solution, and fractions were eluted by reversed phase preparative chromatography. A fraction comprising a product was collected, was concentrated under reduced pressure to remove only acetonitrile, and was freeze-dried to obtain the peptide- and azide modified thioester linker-coupled NHS-activation compound (0.5 mg, 0.2 μmol).

MS (ESI) m/z: z=2 1,251 $[M+2H]^{2+}$, z=3 834 $[M+3H]^{3+}$

Example 54: Specific Modification of Anti-HER2 IgG Antibody Trastuzumab and Analysis Thereof by ESI-TOFMS (54-1) Specific Modification of IgG Antibody Trastuzumab with Azide-Modified Thioester Linker-Binding Peptide Reagent and Analysis Thereof by ESI-TOFMS The peptide- and azide modified thioester linker-coupled NHS-activation compound synthesized in (53-1-2) of Example 53 was dissolved in N,N'-dimethylformamide to be 4 mM. Anti-HER2 IgG antibody trastuzumab (Chugai Pharmaceutical) in an amount of 1.48 mg was dissolved in 555 μL of a 60 mM sodium acetate buffer (pH 4.7), 50 μL of a 4 mM peptide reagent (20 equivalents with respect to the antibody) was added thereto, the solution was stirred at room temperature for 1 hour, and the reaction was stopped with 100 mM citric acid. The reaction solution was subjected to solvent substitution to a 9.57 mM PBS buffer (pH 7.4) with Amicon 10K. The mass was measured by ESI-TOFMS; for the raw material trastuzumab, a peak was observed at 148,225, whereas for a product, a peak was observed at 153,143 with two binding peptides introduced.

(54-2) Determination of Heavy Chain Selectivity of Specifically Modified Compound of Anti-HER2 IgG Antibody Trastuzumab under Reduction Condition by ESI-TOFMS Analysis To the antibody-peptide conjugate PBS solution produced in (54-1), 2.0 μL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material trastuzumab, heavy chain peaks were observed at 50,595 and 50,757, and a light chain peak was observed at 23,440, whereas for products, peaks were observed at 52,981 and 53,143 with a binding peptide introduced to the heavy chain, and a light chain peak was observed at 23,440, the same as that of the raw material.

(54-3) Cleavage of Thioester Linker and Analysis thereof by ESI-TOFMS

The antibody-peptide thioester linker conjugate synthesized in (54-1) is dissolved in any buffer (pH 4.5 to pH 9.0), an aqueous hydroxyamine solution is added thereto, and the solution is stirred at room temperature, whereby the thioester structure hydrolyzes to leave an azide group on the antibody; the mass thereof can be measured by ESI-TOFMS.

(54-4) Linker Cleavage of Trastuzumab-Peptide Conjugate and Analysis of Product by ESI-TOFMS First, 120 μg of the trastuzumab-peptide conjugate synthesized in (54-1) was dissolved in a 0.5 M aqueous hydroxyamine solution (an aqueous solution dissolving 0.5 M hydroxyamine, 9.56 mM PBS, and 4.8 g/mL EDTA in pure water (pH 7.2)), and the solution was stirred at room temperature to cleave the thioester bond in the linker. The mass was measured by ESI-TOFMS; for a product, a peak was observed at 148,469 with two azides introduced.

(54-5) Determination of Heavy Chain Selectivity of Specifically Modified Compound of Trastuzumab under Reduction Condition by ESI-TOFMS Analysis To the antibody-peptide conjugate produced in (54-4), 2.0 μL of a 7 mM tris(2-carboxyethyl)phosphine hydrochloride solution (100 equivalents with respect to the antibody) was added, and the solution was stirred at room temperature for 20 minutes. The mass was measured by ESI-TOFMS; for the raw material antibody-peptide conjugate, heavy chain peaks were observed at 52,981 and 53,143, and a light chain peak was observed at 23,440, whereas for products, peaks were observed at 50,836 and 50,999 with an azide introduced to the heavy chain, and a light chain peak was observed at 23,440, the same as that of the raw material.

Summary

The foregoing results are summarized as follows.

TABLE 2

Summary of affinity peptides

| Amino acid sequence | SEQ ID NO: | Example |
|---|---|---|
| RGNCAYHKGQLVWCTYH | 51 | 1-15 |
| RGNCKYHRGQLVWCTYH | 54 | 16 |
| RGNCAWHRGKLVWCTYH | 55 | 17 |
| RGNCKWHRGELVWCTYH | 56 | 18 |
| RGNCKWHRGQLVWCTYH | 57 | 19 |
| RGNCKYHLGELVWCTYH | 58 | 20 |
| RGNCKYHLGQLVWCTYH | 59 | 21 |
| DCKWHLGELVWCT | 60 | 22 |
| DCKYHLGELVWCT | 61 | 23 |
| DCKWHRGELVWCT | 62 | 24 |
| DCKWHLGQLVWCT | 63 | 25 |
| DCKYHRGELVWCT | 64 | 26 |
| DCKYHLGQLVWCT | 65 | 27 |
| DCKWHRGQLVWCT | 66 | 28 |
| DCKYHRGQLVWCT | 67 | 29 |
| RGNCAWHLGQLVWCKYH | 68 | 30 |
| RGNCAWHLGELVWCKYH | 69 | 31 |
| RGNCAYHLGQLVWCTKH | 70 | 32 |
| RGNCAYHLGQLVWCTYK | 71 | 33 |
| RGNCAYHRGQLVWCTKH | 72 | 34 |
| KNMQCQRRFYEALHDPNLNEEQRNARIRSIRDDC | 73 | 35 |
| FNMQCQRRFYEALHDPNLNEEQRNARIRSIRDDC | 74 | 36 |
| FNMQCQRRFYEAKHDPNLNEEQRNARIRSIRDDC | 75 | 37 |
| FNMQCQRRFYEALHDPNLNEEQRKARIRSIRDDC | 76 | 38 |
| FNMQCQRRFYEALHDPNLKEQRNARIRSIRDDC | 77 | 39 |
| FNMQCQRRFYEALHDPNLNEEQRNARIRSIKDDC | 80 | 41 |
| FNKQCQRRFYEALHDPNLNEEQRNARIRSIRDDC | 82 | 43 |

TABLE 2-continued

Summary of affinity peptides

| Amino acid sequence | SEQ ID NO: | Example |
|---|---|---|
| FNMQCKRRFYEALHDPNLNEEQRNARIRSIRDDC | 83 | 45 |
| FNMQCQRRFYEALHDPNLNEEQRNARIRSIRKDC | 84 | 47 |

It has been demonstrated that for the antibodies regioselective modification of specific amino acid residues is enabled including the lysine residues at position 246 and/or position 248 (e.g., Examples 8, 15, 44, and 46), the lysine residues at position 288 and/or position 290 (e.g., Example 42 and Example 48), and the lysine residue at position 317 (e.g., Example 40).

Furthermore, the following compound having an affinity substance to a soluble protein, a cleavable portion, and a reactive group, which is represented by the following Formula (I), is described with reference to part of Examples as Table 3 below:

$$A\text{-}L\text{-}B\text{-}R \qquad (I)$$

wherein

A is an affinity substance to a soluble protein;

L is a cleavable linker which is a divalent group comprising a cleavable portion;

B is (a) a divalent group comprising a bioorthogonal functional group or (b) a divalent group comprising no bioorthogonal functional group; and R is a reactive group to the soluble protein.

L is (i) a cleavable linker which is a divalent group comprising a cleavable portion having an ability to produce a bioorthogonal functional group on a reactive group side by cleavage or (ii) a cleavable linker which is a divalent group comprising a cleavable portion having no ability to produce a bioorthogonal functional group on a reactive group side by cleavage.

TABLE 3

Relationship between compound having affinity substance to soluble protein, cleavable portion, and reactive group, and soluble protein (antibody) having bioorthogonal functional groups which can be produced by using the same (1)

Specific structure of compound

□ : Affinity substance (A)

⌐ ¬ : Cleavable portion (in L)
└ ┘

○ : Bioorthogonal functional group B(a) or L(ii)

◌ : Reactive group (R)

Example

Soluble protein (antibody) having bioorthogonal functional groups which can be produced by using the compound*

2-1

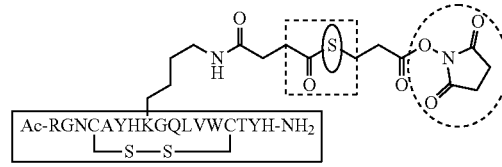

The above-amino acid sequence: SEQ ID NO: 51

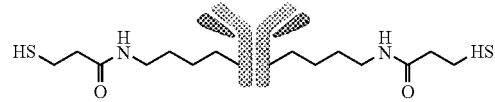

2-2

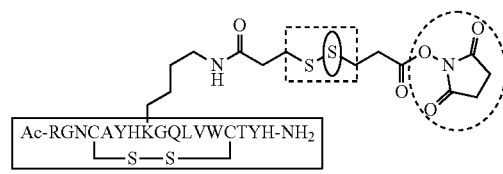

The above-amino acid sequence: SEQ ID NO: 51

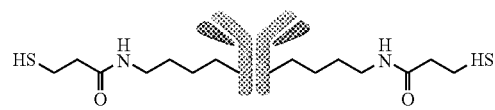

TABLE 3-continued

Relationship between compound having affinity substance to soluble protein, cleavable portion, and reactive group, and soluble protein (antibody) having bioorthogonal functional groups which can be produced by using the same (1)

| Example | Specific structure of compound<br>□ : Affinity substance (A)<br>⌐ ¬ : Cleavable portion (in L)<br>○ : Bioorthogonal functional group B(a) or L(ii)<br>⌐ ¬ : Reactive group (R) | Soluble protein (antibody) having bioorthogonal functional groups which can be produced by using the compound* |
|---|---|---|
| 2-3 | 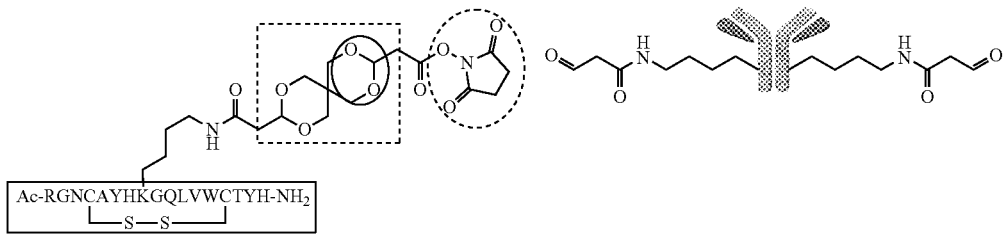<br>Ac-RGNCAYHKGQLVWCTYH-NH₂<br>└─S─S─┘<br>The above-amino acid sequence: SEQ ID NO: 51 | |
| 11-1 | 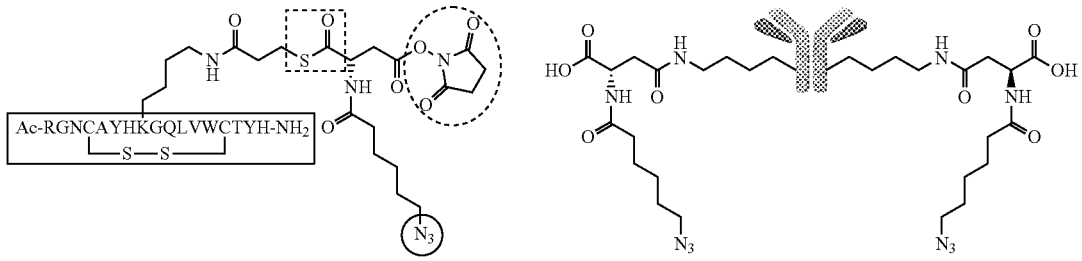<br>Ac-RGNCAYHKGQLVWCTYH-NH₂<br>└─S─S─┘<br>The above-amino acid sequence: SEQ ID NO: 51 | |

*An NH-C4 alkyl portion extending from an antibody is derived from side chain of lysine residue in the antibody (hereafter the same applies).

TABLE 4

Relationship between compound having affinity substance to soluble protein, cleavable portion, and reactive group, and soluble protein (antibody) having bioorthogonal functional groups which can be produced by using the same (2)

Specific structure of compound

☐ : Affinity substance (A)

⬚ : Cleavable portion (in L)

◯ : Bioorthogonal functional group B(a) or L(ii)

◌ : Reactive group (R)

Example

Soluble protein (antibody) having bioorthogonal functional groups which can be produced by using the compound*

11-2

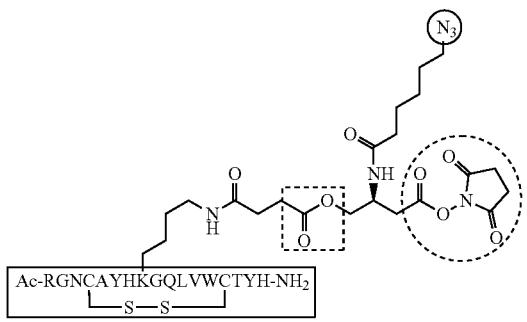

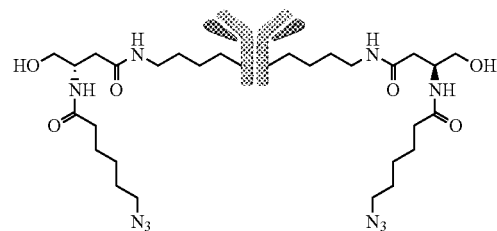

The above-amino acid sequence:
SEQ ID NO: 51

11-3

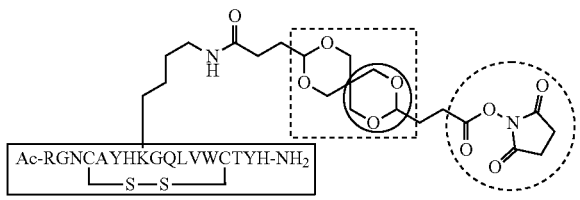

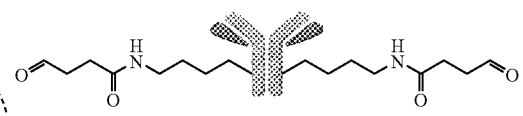

The above-amino acid sequence:
SEQ ID NO: 51

53

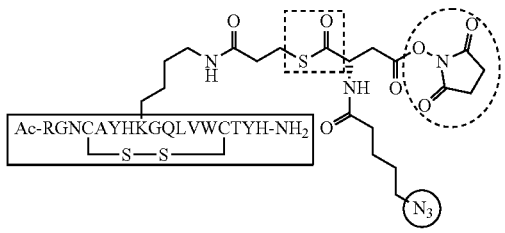

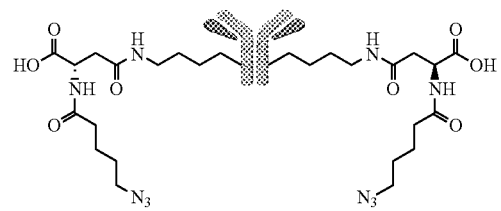

The above-amino acid sequence:
SEQ ID NO: 51

Various compounds having an affinity substance to a soluble protein, a cleavable portion, and a reactive group can be prepared according to well-known methods of organic synthesis by changing the types of (A) the affinity substance to a soluble protein, (L) the cleavable linker which is a divalent group comprising a cleavable portion, (B) (a) the divalent group comprising a bioorthogonal functional group or (b) the divalent group comprising no bioorthogonal functional group, and (R) the reactive group to the soluble protein as appropriate as described above.

The relation between additional examples of the compound having an affinity substance to a soluble protein, a cleavable portion, and a reactive group that can be produced in the present invention and the soluble protein (antibody) having a bioorthogonal functional group(s) that can be produced by using the same is as follows.

TABLE 5

Relationship between additional examples of compound having affinity substance to soluble protein, cleavable portion, and reactive group, and soluble protein (antibody) having bioorthogonal functional groups which can be produced by using the same (1)

Specific structure of compound

☐ : Affinity substance (A)

┌┄┐
┆ ┆ : Cleavable portion (in L)
└┄┘

◯ : Bioorthogonal functional group B(a) or L(ii)

◌ : Reactive group (R)

Soluble protein (antibody) having bioorthogonal functional groups which can be produced by using the compound*

Example

55

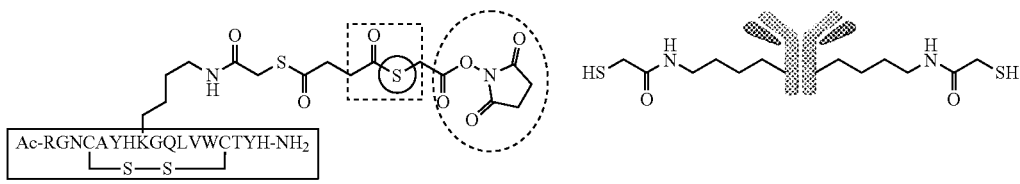

The above-amino acid sequence:
SEQ ID NO: 51

56

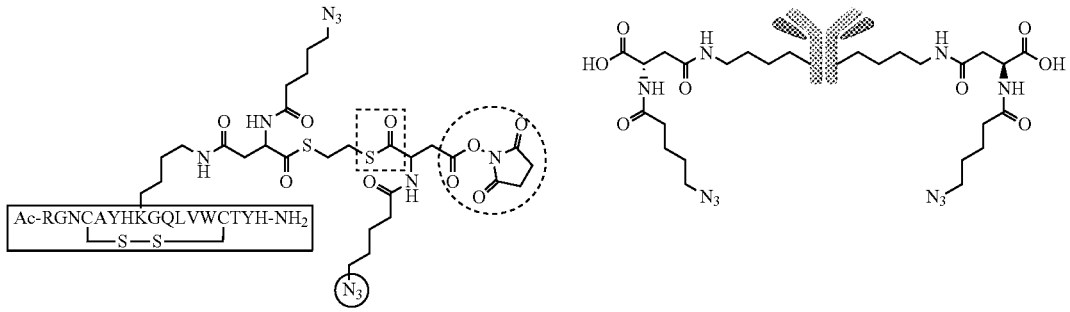

The above-amino acid sequence:
SEQ ID NO: 51

57

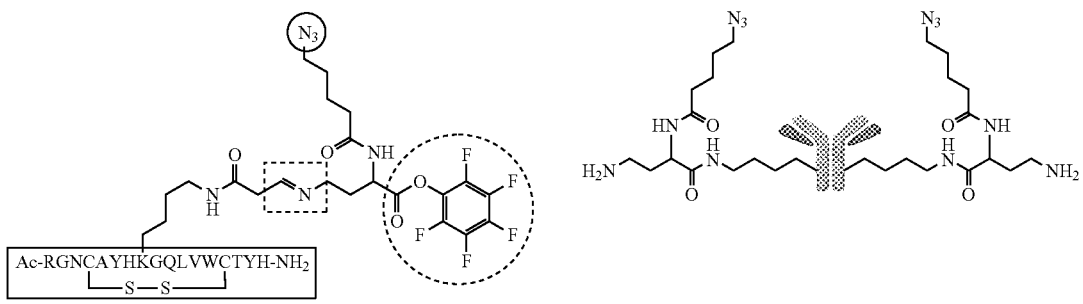

The above-amino acid sequence:
SEQ ID NO: 51

TABLE 5-continued

Relationship between additional examples of compound having affinity substance to soluble protein, cleavable portion, and reactive group, and soluble protein (antibody) having bioorthogonal functional groups which can be produced by using the same (1)

Specific structure of compound

☐ : Affinity substance (A)

⬚ : Cleavable portion (in L)

◯ : Bioorthogonal functional group B(a) or L(ii)

◌ : Reactive group (R)

| Example | | Soluble protein (antibody) having bioorthogonal functional groups which can be produced by using the compound* |
|---|---|---|
| 58 | 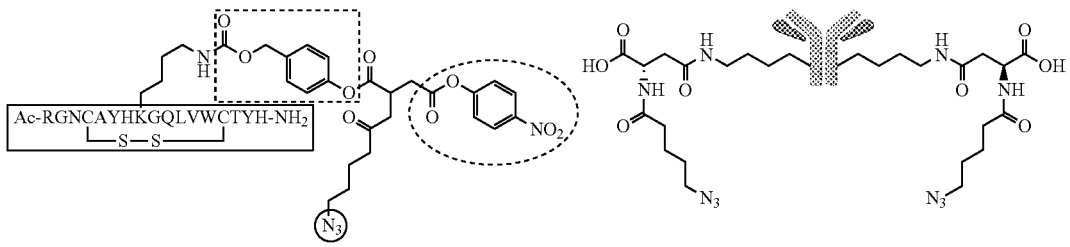 | |

The above-amino acid sequence:
SEQ ID NO: 51

TABLE 6

Relationship between additional examples of compound having affinity substance to soluble protein, cleavable portion, and reactive group, and soluble protein (antibody) having bioorthogonal functional groups which can be produced by using the same (2)

Specific structure of compound

☐ : Affinity substance (A)

⬚ : Cleavable portion (in L)

◯ : Bioorthogonal functional group B(a) or L(ii)

◌ : Reactive group (R)

| Example | | Soluble protein (antibody) having bioorthogonal functional groups which can be produced by using the compound* |
|---|---|---|
| 59 | 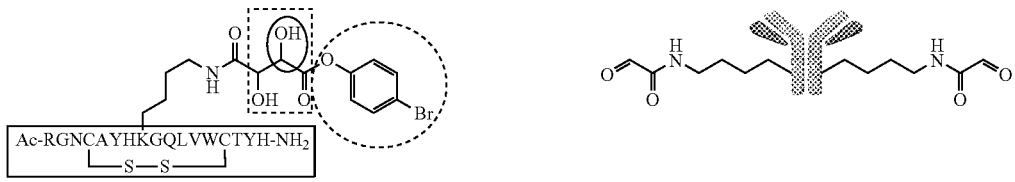 | |

The above-amino acid sequence:
SEQ ID NO: 51

TABLE 6-continued

Relationship between additional examples of compound having affinity substance to soluble protein, cleavable portion, and reactive group, and soluble protein (antibody) having bioorthogonal functional groups which can be produced by using the same (2)

Specific structure of compound

☐ : Affinity substance (A)

┌┈┐
┊ ┊ : Cleavable portion (in L)
└┈┘

◯ : Bioorthogonal functional group B(a) or L(ii)

⌐┈⌐
┊ ┊ : Reactive group (R)
└┈┘

Example

Soluble protein (antibody) having bioorthogonal functional groups which can be produced by using the compound*

60

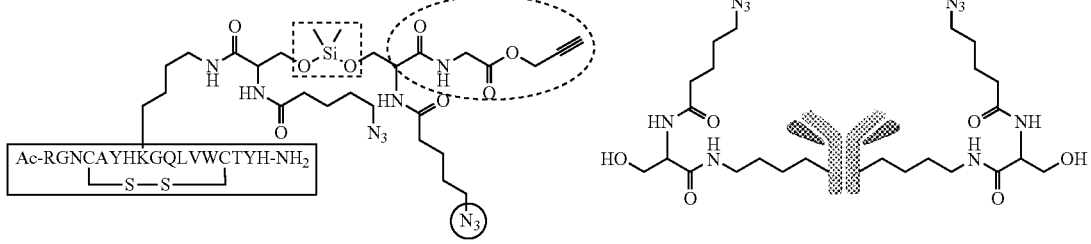

The above-amino acid sequence:
SEQ ID NO: 51

61

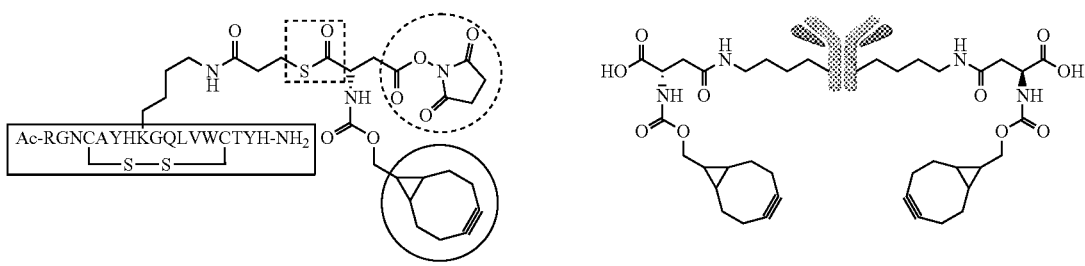

The above-amino acid sequence:
SEQ ID NO: 51

62

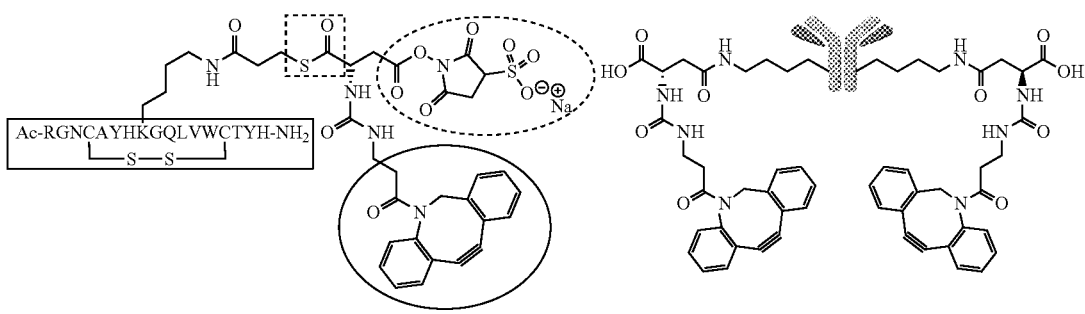

The above-amino acid sequence:
SEQ ID NO: 51

TABLE 7

Relationship between additional examples of compound having affinity substance to soluble protein, cleavable portion, and reactive group, and soluble protein (antibody) having bioorthogonal functional groups which can be produced by using the same (3)

Specific structure of compound

☐ : Affinity substance (A)

▢ : Cleavable portion (in L)

◯ : Bioorthogonal functional group B(a) or L(ii)

◌ : Reactive group (R)

Soluble protein (antibody) having bioorthogonal functional groups which can be produced by using the compound*

Example 63

Ac-RGNCAYHKGQLVWCTYH-NH₂
    └─S─S─┘

The above-amino acid sequence: SEQ ID NO: 51

It has been demonstrated from the foregoing that the antibody can be regioselectively modified by appropriately adjusting factors such as the type of a affinity substance to a soluble protein, the length of a linker between the affinity substance and a reactive group, and the position in the affinity substance to which the linker is introduced in compounds having the affinity substance to a soluble protein, the cleavable portion, and the reactive group.

INDUSTRIAL APPLICABILITY

For example, the present invention is useful for production of a regioselectively modified soluble protein.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An antibody or salt thereof regioselectively having at least one functional substance,
   wherein the antibody comprises one or more lysine residues in a target region consisting of 1 to 50 continuous amino acid residues present in CH2 domain, and five or more lysine residues in a non-target region other than the target region, and
   the at least one functional substance binds to the one or more lysine residues in the target region with 30% or more regioselectivity through a linker comprising no peptide portion,
   wherein the antibody does not comprise an affinity substance to the antibody,
   wherein the at least one functional substance is a drug, a labelling substance, or a stabilizer.

2. An antibody or a salt thereof regioselectively having at least one bioorthogonal functional group,
   wherein the antibody comprises one or more lysine residues in a target region consisting of 1 to 50 continuous amino acid residues present in CH2 domain Fc-region, and five or more lysine residues in a non-target region other than the target region, and
   the at least one bioorthogonal functional group binds to the one or more lysine residues in the target region with 30% or more regioselectivity through a linker comprising no peptide portion,
   wherein the antibody does not comprise an affinity substance to the antibody,
   wherein the at least one bioorthogonal functional group is one or more residues selected from the group consisting of an azide residue, an aldehyde residue, a thiol residue, an alkene residue, an alkyne residue, a halogen residue, a tetrazine residue, a nitron residue, a hydroxyamine residue, a nitrile residue, a hydrazine residue, a ketone residue, a boric acid residue, a cyanobenzothiazole residue, an allyl residue, a phosphine residue, a maleimide residue, a disulfide residue, a thioester residue, an α-halocarbonyl residue, an isonitrile residue, a sydnone residue, and a selenium residue.

3. The antibody or salt thereof according to claim 1, wherein the antibody is a monoclonal antibody.

4. The antibody or salt thereof according to claim 1, wherein the antibody is an IgG antibody.

5. The antibody or salt thereof according to claim 1, wherein the antibody is derived from a human.

6. The antibody or salt thereof according to claim 1, wherein the antibody comprises any one Fc region selected from the group consisting of the following (A) to (C):
   (A) an Fc region comprising the amino acid sequence of SEQ ID NO: 1;

(B) an Fc region comprising an amino acid sequence with one to twenty amino acid residues inserted, added, deleted, or substituted in the amino acid sequence of SEQ ID NO: 1; and (C) an Fc region comprising an amino acid sequence having 90% or more identity to the amino acid sequence of SEQ ID NO: 1.

7. The antibody or salt thereof according to claim 1, wherein the target region is a region consisting of one to three continuous amino acid residues.

8. The antibody or salt thereof according to claim 7, wherein the target region is (a) a region consisting of amino acid residues at positions 246 to 248 in an human IgG Fc region according to EU numbering, (b) a region consisting of amino acid residues at positions 288 to 290 in the human IgG Fc region according to EU numbering, or (c) a region consisting of an amino acid residue at position 317 in the human IgG Fc region according to EU numbering.

9. The antibody or salt thereof according to claim 1, wherein the regioselectivity is 90% or more.

10. The antibody or salt thereof according to claim 1, wherein the antibody is a multimeric protein comprising a plurality of monomeric proteins, and the at least one functional substance is present in positions of the one or more lysine residues in the target regions in a plurality of monomeric proteins such that the multimeric protein has a plurality of functional substances.

11. The antibody or salt thereof according to any one of claims 1,3 to 9, and 10, wherein the antibody is an antibody comprising a plurality of heavy chains, and the functional substances are present in positions of the one or more lysine residues in the target regions in a plurality of heavy chains such that the antibody has a plurality of functional substances.

12. The antibody or salt thereof according to claim 1, wherein the functional substance is a drug, a labelling substance, or a stabilizer.

13. The antibody or salt thereof according to claim 2, wherein the antibody is a multimeric protein comprising a plurality of monomeric proteins, and the at least one bioorthogonal functional groups are present in positions of the one or more lysine residues in the target regions in a plurality of monomeric proteins such that the multimeric protein has a plurality of bioorthogonal functional groups.

14. The antibody or salt thereof according claim 2, wherein the antibody is an antibody comprising a plurality of heavy chains, and the at least one bioorthogonal functional groups are present in positions of the one or more lysine residues in the target regions in a plurality of heavy chains such that the antibody has a plurality of bioorthogonal functional groups.

* * * * *

UNITED STATES PATENT AND TRADEMARK OFFICE
CERTIFICATE OF CORRECTION

PATENT NO. : 12,024,549 B2
APPLICATION NO. : 16/663791
DATED : July 2, 2024
INVENTOR(S) : Kei Yamada et al.

It is certified that error appears in the above-identified patent and that said Letters Patent is hereby corrected as shown below:

In the Claims

Column 351, Line 62, in Claim 2 "Fe-region" after CH2 domain should be deleted.

Signed and Sealed this
Twenty-second Day of October, 2024

Katherine Kelly Vidal
*Director of the United States Patent and Trademark Office*

SEQUENCE LISTING

```
<160> NUMBER OF SEQ ID NOS: 105

<210> SEQ ID NO 1
<211> LENGTH: 230
<212> TYPE: PRT
<213> ORGANISM: Artificial Sequence
<220> FEATURE:
<223> OTHER INFORMATION: Fc region of human IgG1
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
```

```
<220> FEATURE:
<221> NAME/KEY: misc_feature
<222> LOCATION: (177)..(177)
<223> OTHER INFORMATION: Xaa can be any naturally occurring amino acid

<400> SEQUENCE: 1

Pro Lys Ser Cys Asp Lys Thr His Thr Cys Pro Pro Cys Pro Ala Pro
1               5                   10                  15

Glu Xaa Xaa Gly Xaa Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asp Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Xaa Glu Xaa Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Xaa Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly
225                 230

<210> SEQ ID NO 2
<211> LENGTH: 449
<212> TYPE: PRT
<213> ORGANISM: Artificial Sequence
<220> FEATURE:
<223> OTHER INFORMATION: Heavy chain of Trastuzumab (humanized IgG1
      monoclonal antibody)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asp Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly

<210> SEQ ID NO 3
<211> LENGTH: 237
<212> TYPE: PRT
<213> ORGANISM: Artificial Sequence
<220> FEATURE:
<223> OTHER INFORMATION: Fc region of human IgG1 antibody

<400> SEQUENCE: 3
```

-continued

Ile Glu Gly Arg Met Asp Pro Lys Ser Cys Asp Lys Thr His Thr Cys
1               5                   10                  15

Pro Pro Cys Pro Ala Pro Glu Ala Glu Gly Ala Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65              70                  75                  80

Pro Arg Glu Glu Gln Tyr Asp Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Ala Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 4
<211> LENGTH: 214
<212> TYPE: PRT
<213> ORGANISM: Artificial Sequence
<220> FEATURE:
<223> OTHER INFORMATION: Light chain of Trastuzumab (humanized IgG1
      monoclonal antibody)

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 26
<212> TYPE: PRT
<213> ORGANISM: Artificial Sequence
<220> FEATURE:
<223> OTHER INFORMATION: Peptide fragment of Trastuzumab

<400> SEQUENCE: 5

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 6
<211> LENGTH: 16
<212> TYPE: PRT
<213> ORGANISM: Artificial Sequence
<220> FEATURE:
<223> OTHER INFORMATION: Peptide fragment of Trastuzumab

<400> SEQUENCE: 6

Leu Leu Gly Gly Pro Ser Val Phe Leu Phe Pro Pro Lys Pro Lys Asp
1               5                   10                  15

<210> SEQ ID NO 7
<211> LENGTH: 26
<212> TYPE: PRT
<213> ORGANISM: Artificial Sequence
<220> FEATURE:
<223> OTHER INFORMATION: Peptide fragment of Fc region of human IgG1
      antibody

<400> SEQUENCE: 7

Thr His Thr Cys Pro Pro Cys Pro Ala Pro Glu Ala Glu Gly Ala Pro
1               5                   10                  15

Ser Val Phe Leu Phe Pro Pro Lys Pro Lys
            20                  25

<210> SEQ ID NO 8
<211> LENGTH: 24
<212> TYPE: PRT
<213> ORGANISM: Artificial Sequence
<220> FEATURE:
<223> OTHER INFORMATION: Peptide fragment of Fc region of human IgG1
      antibody

<400> SEQUENCE: 8

Gly Ala Pro Ser Val Phe Leu Phe Pro Pro Lys Pro Lys Lys Asp Thr
1               5                   10                  15
```

Leu Met Ile Ser Arg Thr Pro Glu
            20

<210> SEQ ID NO 9
<211> LENGTH: 12
<212> TYPE: PRT
<213> ORGANISM: Artificial Sequence
<220> FEATURE:
<223> OTHER INFORMATION: Peptide having an affinity to CH2 region of
      human IgG

<400> SEQUENCE: 9

Glu Pro Ile His Arg Ser Thr Leu Thr Ala Leu Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 10

Phe Ala Arg Leu Val Ser Ser Ile Arg Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 11

Phe Gly Arg Leu Val Ser Ser Ile Arg Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 12

Thr Trp Lys Thr Ser Arg Ile Ser Ile Phe
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Peptide having an affinity to specific region
      of human IgG

<400> SEQUENCE: 13

Gln Ser Tyr Pro
1

<210> SEQ ID NO 14
<211> LENGTH: 6
<212> TYPE: PRT
<213> ORGANISM: Artificial Sequence

```
<220> FEATURE:
<223> OTHER INFORMATION: Peptide having an affinity to Fc region of
      human IgG

<400> SEQUENCE: 14

His Trp Arg Gly Trp Val
1               5

<210> SEQ ID NO 15
<211> LENGTH: 6
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 15

His Tyr Phe Lys Phe Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 16

His Phe Arg Arg His Leu
1               5

<210> SEQ ID NO 17
<211> LENGTH: 4
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 17

Asp Ala Ala Gly
1

<210> SEQ ID NO 18
<211> LENGTH: 8
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 18

Asn Ala Arg Lys Phe Tyr Lys Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Peptide having an affinity to Fc region of
      human IgG

<400> SEQUENCE: 19

Asn Lys Phe Arg Gly Lys Tyr Lys
1               5
```

```
<210> SEQ ID NO 20
<211> LENGTH: 13
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, aspartic acid, glutamic acid,
      2-amino suberic acid, or diaminopropionic acid

<400> SEQUENCE: 20

Asp Cys Ala Tyr His Xaa Gly Glu Leu Val Trp Cys Thr
1               5                   10

<210> SEQ ID NO 21
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 21

Gly Pro Asp Cys Ala Tyr His Xaa Gly Glu Leu Val Trp Cys Thr Phe
1               5                   10                  15

His

<210> SEQ ID NO 22
<211> LENGTH: 13
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, aspartic acid, glutamic acid,
      2-amino suberic acid, or diaminopropionic acid

<400> SEQUENCE: 22

Arg Cys Ala Tyr His Xaa Gly Glu Leu Val Trp Cys Ser
1               5                   10

<210> SEQ ID NO 23
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 23

Gly Pro Arg Cys Ala Tyr His Xaa Gly Glu Leu Val Trp Cys Ser Phe
1               5                   10                  15

His

<210> SEQ ID NO 24
<211> LENGTH: 17
```

```
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 24

Ser Pro Asp Cys Ala Tyr His Xaa Gly Glu Leu Val Trp Cys Thr Phe
1               5                   10                  15
His

<210> SEQ ID NO 25
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 25

Gly Asp Asp Cys Ala Tyr His Xaa Gly Glu Leu Val Trp Cys Thr Phe
1               5                   10                  15
His

<210> SEQ ID NO 26
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 26

Gly Pro Ser Cys Ala Tyr His Xaa Gly Glu Leu Val Trp Cys Thr Phe
1               5                   10                  15
His

<210> SEQ ID NO 27
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 27

Gly Pro Asp Cys Ala Tyr His Xaa Gly Glu Leu Val Trp Cys Ser Phe
1               5                   10                  15
His

<210> SEQ ID NO 28
```

```
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 28

Gly Pro Asp Cys Ala Tyr His Xaa Gly Glu Leu Val Trp Cys Thr His
1               5                   10                  15

His

<210> SEQ ID NO 29
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 29

Gly Pro Asp Cys Ala Tyr His Xaa Gly Glu Leu Val Trp Cys Thr Phe
1               5                   10                  15

Tyr

<210> SEQ ID NO 30
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 30

Ser Pro Asp Cys Ala Tyr His Xaa Gly Glu Leu Val Trp Cys Thr Phe
1               5                   10                  15

Tyr

<210> SEQ ID NO 31
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 31

Ser Asp Asp Cys Ala Tyr His Xaa Gly Glu Leu Val Trp Cys Thr Phe
1               5                   10                  15

Tyr
```

```
<210> SEQ ID NO 32
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid

<400> SEQUENCE: 32

Arg Gly Asn Cys Ala Tyr His Xaa Gly Gln Leu Val Trp Cys Thr Tyr
1               5                   10                  15

His

<210> SEQ ID NO 33
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (2)..(2)
<223> OTHER INFORMATION: Xaa is homoserine
<220> FEATURE:
<221> NAME/KEY: misc_feature
<222> LOCATION: (8)..(8)
<223> OTHER INFORMATION: Xaa is lysine, aspartic acid, glutamic acid,
      2-amino suberic acid, or diaminopropionic acid
<220> FEATURE:
<221> NAME/KEY: misc_feature
<222> LOCATION: (16)..(16)
<223> OTHER INFORMATION: Xaa is homoserine

<400> SEQUENCE: 33

Gly Xaa Asp Cys Ala Tyr His Xaa Gly Glu Leu Val Trp Cys Thr Xaa
1               5                   10                  15

His

<210> SEQ ID NO 34
<211> LENGTH: 19
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (10)..(10)
<223> OTHER INFORMATION: Xaa is lysine, aspartic acid, glutamic acid,
      2-amino suberic acid, or diaminopropionic acid

<400> SEQUENCE: 34

Arg Arg Gly Pro Asp Cys Ala Tyr His Xaa Gly Glu Leu Val Trp Cys
1               5                   10                  15

Thr Phe His

<210> SEQ ID NO 35
<211> LENGTH: 13
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, aspartic acid, glutamic acid,
      2-amino suberic acid, or diaminopropionic acid
```

```
<400> SEQUENCE: 35

Asp Cys Thr Tyr His Xaa Gly Asn Leu Val Trp Cys Thr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, aspartic acid, glutamic acid,
      2-amino suberic acid, or diaminopropionic acid

<400> SEQUENCE: 36

Asp Cys Ala Tyr His Xaa Gly Asn Leu Val Trp Cys Thr
1               5                   10

<210> SEQ ID NO 37
<211> LENGTH: 13
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, aspartic acid, glutamic acid,
      2-amino suberic acid, or diaminopropionic acid

<400> SEQUENCE: 37

Asp Cys Thr Tyr His Xaa Gly Glu Leu Val Trp Cys Thr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, aspartic acid, glutamic acid,
      2-amino suberic acid, or diaminopropionic acid

<400> SEQUENCE: 38

Asp Cys Ala Trp His Xaa Gly Glu Leu Val Trp Cys Thr
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 39

Arg Gly Asn Cys Ala Tyr His Lys Gly Gln Leu Val Trp Cys Thr Tyr
1               5                   10                  15

His

<210> SEQ ID NO 40
```

```
<211> LENGTH: 33
<212> TYPE: PRT
<213> ORGANISM: Artificial Sequence
<220> FEATURE:
<223> OTHER INFORMATION: peptide fragment of Trastuzumab (humanized IgG1
      monoclonal antibody)

<400> SEQUENCE: 40

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg

<210> SEQ ID NO 41
<211> LENGTH: 449
<212> TYPE: PRT
<213> ORGANISM: Artificial Sequence
<220> FEATURE:
<223> OTHER INFORMATION: Heavy chain of Trastuzumab (humanized IgG1
      monoclonal antibody)

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 42
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 42

Arg Gly Asn Cys Lys Tyr His Arg Gly Gln Leu Val Trp Cys Thr Tyr
1               5                   10                  15

His

<210> SEQ ID NO 43
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 43

Arg Gly Asn Cys Ala Trp His Arg Gly Lys Leu Val Trp Cys Thr Tyr
1               5                   10                  15

His

<210> SEQ ID NO 44
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge -continued

<400> SEQUENCE: 44

Arg Gly Asn Cys Lys Trp His Arg Gly Glu Leu Val Trp Cys Thr Tyr
1               5                   10                  15
His

<210> SEQ ID NO 45
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 45

Arg Gly Asn Cys Lys Trp His Arg Gly Gln Leu Val Trp Cys Thr Tyr
1               5                   10                  15
His

<210> SEQ ID NO 46
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 46

Arg Gly Asn Cys Lys Tyr His Leu Gly Glu Leu Val Trp Cys Thr Tyr
1               5                   10                  15
His

<210> SEQ ID NO 47
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 47

Arg Gly Asn Cys Lys Tyr His Leu Gly Gln Leu Val Trp Cys Thr Tyr
1               5                   10                  15
His

<210> SEQ ID NO 48
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge

<400> SEQUENCE: 48

Asp Cys Lys Trp His Leu Gly Glu Leu Val Trp Cys Thr
1               5                   10

<210> SEQ ID NO 49
<211> LENGTH: 13
<212> TYPE: PRT
<213> ORGANISM: Artificial Sequence
<220> FEATURE:

```
<223> OTHER INFORMATION: Aspartic acid residue at N-terminus may be
      acetylated and two cysteine residues may be linked by disulfide
      bridge

<400> SEQUENCE: 49

Asp Cys Lys Tyr His Leu Gly Glu Leu Val Trp Cys Thr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge

<400> SEQUENCE: 50

Asp Cys Lys Trp His Arg Gly Glu Leu Val Trp Cys Thr
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge

<400> SEQUENCE: 51

Asp Cys Lys Trp His Leu Gly Gln Leu Val Trp Cys Thr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge

<400> SEQUENCE: 52

Asp Cys Lys Tyr His Arg Gly Glu Leu Val Trp Cys Thr
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge

<400> SEQUENCE: 53

Asp Cys Lys Tyr His Leu Gly Gln Leu Val Trp Cys Thr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge
```

```
<400> SEQUENCE: 54

Asp Cys Lys Trp His Arg Gly Gln Leu Val Trp Cys Thr
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Aspartic acid residue at N-terminus may be
      acetylated and two cysteine residues may be linked by disulfide
      bridge

<400> SEQUENCE: 55

Asp Cys Lys Tyr His Arg Gly Gln Leu Val Trp Cys Thr
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 56

Arg Gly Asn Cys Ala Trp His Leu Gly Gln Leu Val Trp Cys Lys Tyr
1               5                   10                  15

His

<210> SEQ ID NO 57
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 57

Arg Gly Asn Cys Ala Trp His Leu Gly Glu Leu Val Trp Cys Lys Tyr
1               5                   10                  15

His

<210> SEQ ID NO 58
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 58

Arg Gly Asn Cys Ala Tyr His Leu Gly Gln Leu Val Trp Cys Thr Lys
1               5                   10                  15

His

<210> SEQ ID NO 59
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
``` bridge

<400> SEQUENCE: 59

Arg Gly Asn Cys Ala Tyr His Leu Gly Gln Leu Val Trp Cys Thr Tyr
1               5                   10                  15

Lys

<210> SEQ ID NO 60
<211> LENGTH: 17
<212> TYPE: PRT
<213> ORGANISM: Artificial Sequence
<220> FEATURE:
<223> OTHER INFORMATION: Arginine residue at N-terminus may be
      acetylated and two cysteine residues may be linked by disulfide
      bridge

<400> SEQUENCE: 60

Arg Gly Asn Cys Ala Tyr His Arg Gly Gln Leu Val Trp Cys Thr Lys
1               5                   10                  15

His

<210> SEQ ID NO 61
<211> LENGTH: 34
<212> TYPE: PRT
<213> ORGANISM: Artificial Sequence
<220> FEATURE:
<223> OTHER INFORMATION: Lysine residue at N-terminus may be acetylated
      and two cysteine residues may be linked by disulfide bridge

<400> SEQUENCE: 61

Lys Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 62
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 62

Phe Asn Met Gln Cys Gln Lys Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 63
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 63

Phe Asn Met Gln Cys Gln Arg Arg Phe Tyr Glu Ala Lys His Asp Pro
1               5                   10                  15

```
Asn Leu Asn Glu Glu Gln Arg Asn Ala Arg Ile Arg Ser Ile Arg Asp
            20                  25                  30

Asp Cys

<210> SEQ ID NO 64
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 64

Phe Asn Met Gln Cys Gln Arg Arg Phe Tyr Glu Ala Leu His Asp Pro
1               5                   10                  15

Asn Leu Asn Glu Glu Gln Arg Lys Ala Arg Ile Arg Ser Ile Arg Asp
            20                  25                  30

Asp Cys

<210> SEQ ID NO 65
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 65

Phe Asn Met Gln Cys Gln Arg Arg Phe Tyr Glu Ala Leu His Asp Pro
1               5                   10                  15

Asn Leu Asn Lys Glu Gln Arg Asn Ala Arg Ile Arg Ser Ile Arg Asp
            20                  25                  30

Asp Cys

<210> SEQ ID NO 66
<211> LENGTH: 19
<212> TYPE: PRT
<213> ORGANISM: Artificial Sequence
<220> FEATURE:
<223> OTHER INFORMATION: Polypeptide fragment

<400> SEQUENCE: 66

Val Val Ser Val Leu Thr Val Leu His Gln Asp Trp Leu Asn Gly Lys
1               5                   10                  15

Glu Tyr Lys

<210> SEQ ID NO 67
<211> LENGTH: 28
<212> TYPE: PRT
<213> ORGANISM: Artificial Sequence
<220> FEATURE:
<223> OTHER INFORMATION: Polypeptide fragment

<400> SEQUENCE: 67

Glu Glu Gln Tyr Asp Ser Thr Tyr Arg Val Val Ser Val Leu Thr Val
1               5                   10                  15

Leu His Gln Asp Trp Leu Asn Gly Lys Glu Tyr Lys
            20                  25

<210> SEQ ID NO 68
```

```
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 68

Phe Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Lys Asp
            20                  25                  30

Asp Cys

<210> SEQ ID NO 69
<211> LENGTH: 18
<212> TYPE: PRT
<213> ORGANISM: Artificial Sequence
<220> FEATURE:
<223> OTHER INFORMATION: Polypeptide fragment

<400> SEQUENCE: 69

Phe Asn Trp Tyr Val Asp Gly Val Glu Val His Asn Ala Lys Thr Lys
1               5                   10                  15

Pro Arg

<210> SEQ ID NO 70
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 70

Phe Asn Lys Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 71
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 71

Phe Asn Met Gln Cys Lys Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 72
<211> LENGTH: 34
<212> TYPE: PRT
<213> ORGANISM: Artificial Sequence
<220> FEATURE:
```

<223> OTHER INFORMATION: Phenylalanine residue at N-terminus may be
      acetylated and two cysteine residues may be linked by disulfide
      bridge

<400> SEQUENCE: 72

Phe Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Lys
            20                  25                  30

Asp Cys

<210> SEQ ID NO 73
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 73

Arg Gly Asn Cys Ala Tyr His Xaa Gly Gln Leu Val Trp Cys Thr Tyr
1               5                   10                  15

His

<210> SEQ ID NO 74
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 74

Arg Gly Asn Cys Ala Trp His Xaa Gly Gln Leu Val Trp Cys Thr Tyr
1               5                   10                  15

His

<210> SEQ ID NO 75
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 75

Arg Gly Asn Cys Ala Trp His Xaa Gly Glu Leu Val Trp Cys Thr Tyr
1               5                   10                  15

His

```
<210> SEQ ID NO 76
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 76

Arg Gly Asn Cys Lys Trp His Xaa Gly Gln Leu Val Trp Cys Thr Tyr
1               5                   10                  15

His

<210> SEQ ID NO 77
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 77

Arg Gly Asn Cys Lys Tyr His Xaa Gly Glu Leu Val Trp Cys Thr Tyr
1               5                   10                  15

His

<210> SEQ ID NO 78
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 78

Arg Gly Asn Cys Lys Tyr His Xaa Gly Gln Leu Val Trp Cys Thr Tyr
1               5                   10                  15

His

<210> SEQ ID NO 79
<211> LENGTH: 13
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (6)..(6)
<223> OTHER INFORMATION: Xaa is arginine, leucine, lysine, aspartic
``` acid, glutamic acid, 2-amino suberic acid, or diaminopropionic acid

<400> SEQUENCE: 79

Asp Cys Lys Trp His Xaa Gly Glu Leu Val Trp Cys Thr
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (6)..(6)
<223> OTHER INFORMATION: Xaa is arginine, leucine, lysine, aspartic
      acid, glutamic acid, 2-amino suberic acid, or diaminopropionic
      acid

<400> SEQUENCE: 80

Asp Cys Lys Tyr His Xaa Gly Glu Leu Val Trp Cys Thr
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 81

Asp Cys Lys Trp His Xaa Gly Glu Leu Val Trp Cys Thr
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (6)..(6)
<223> OTHER INFORMATION: Xaa is arginine, leucine, lysine, aspartic
      acid, glutamic acid, 2-amino suberic acid, or diaminopropionic
      acid

<400> SEQUENCE: 82

Asp Cys Lys Trp His Xaa Gly Gln Leu Val Trp Cys Thr
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Peptide having an affinity to Fc region of human IgG
<220> FEATURE:
<221> NAME/KEY: MISC_FEATURE
<222> LOCATION: (6)..(6)
<223> OTHER INFORMATION: Xaa is arginine, leucine, lysine, aspartic
     acid, glutamic acid, 2-amino suberic acid, or diaminopropionic
     acid

<400> SEQUENCE: 83

Asp Cys Lys Tyr His Xaa Gly Glu Leu Val Trp Cys Thr
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Peptide having an affinity to Fc region of
     human IgG
<220> FEATURE:
<221> NAME/KEY: MISC_FEATURE
<222> LOCATION: (6)..(6)
<223> OTHER INFORMATION: Xaa is arginine, leucine, lysine, aspartic
     acid, glutamic acid, 2-amino suberic acid, or diaminopropionic
     acid

<400> SEQUENCE: 84

Asp Cys Lys Tyr His Xaa Gly Gln Leu Val Trp Cys Thr
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Peptide having an affinity to Fc region of
     human IgG
<220> FEATURE:
<221> NAME/KEY: MISC_FEATURE
<222> LOCATION: (6)..(6)
<223> OTHER INFORMATION: Xaa is arginine, leucine, lysine, aspartic
     acid, glutamic acid, 2-amino suberic acid, or diaminopropionic
     acid

<400> SEQUENCE: 85

Asp Cys Lys Trp His Xaa Gly Gln Leu Val Trp Cys Thr
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Peptide having an affinity to Fc region of
     human IgG
<220> FEATURE:
<221> NAME/KEY: MISC_FEATURE
<222> LOCATION: (6)..(6)
<223> OTHER INFORMATION: Xaa is arginine, leucine, lysine, aspartic
     acid, glutamic acid, 2-amino suberic acid, or diaminopropionic
     acid

<400> SEQUENCE: 86

Asp Cys Lys Tyr His Xaa Gly Gln Leu Val Trp Cys Thr
1               5                   10

<210> SEQ ID NO 87
<211> LENGTH: 17
<212> TYPE: PRT
<213> ORGANISM: Artificial Sequence
<220> FEATURE:

```
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 87

Arg Gly Asn Cys Ala Trp His Xaa Gly Gln Leu Val Trp Cys Lys Tyr
1               5                   10                  15

His

<210> SEQ ID NO 88
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 88

Arg Gly Asn Cys Ala Trp His Xaa Gly Glu Leu Val Trp Cys Lys Tyr
1               5                   10                  15

His

<210> SEQ ID NO 89
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 89

Arg Gly Asn Cys Ala Tyr His Xaa Gly Gln Leu Val Trp Cys Thr Lys
1               5                   10                  15

His

<210> SEQ ID NO 90
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 90

Arg Gly Asn Cys Ala Tyr His Xaa Gly Gln Leu Val Trp Cys Thr Tyr
1               5                   10                  15
```

Lys

<210> SEQ ID NO 91
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid

<400> SEQUENCE: 91

Arg Gly Asn Cys Ala Tyr His Xaa Gly Gln Leu Val Trp Cys Thr Lys
1               5                   10                  15

His

<210> SEQ ID NO 92
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 92

Phe Asn Met Gln Cys Gln Arg Arg Phe Tyr Glu Ala Leu His Asp Pro
1               5                   10                  15

Asn Leu Asn Glu Glu Gln Arg Asn Ala Arg Ile Arg Ser Ile Arg Asp
            20                  25                  30

Asp Cys

<210> SEQ ID NO 93
<211> LENGTH: 34
<212> TYPE: PRT
<213> ORGANISM: Artificial Sequence
<220> FEATURE:
<223> OTHER INFORMATION: Phenylalanine residue at N-terminus may be
      acetylated and two cysteine residues may be linked by disulfide
      bridge

<400> SEQUENCE: 93

Phe Asn Met Gln Cys Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp Cys

<210> SEQ ID NO 94
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature

```
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid
<220> FEATURE:
<221> NAME/KEY: MISC_FEATURE
<222> LOCATION: (10)..(10)
<223> OTHER INFORMATION: Xaa is lysine, glutamine, glutamic acid,
      asparagine, or aspartic acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 94

Xaa Xaa Xaa Cys Xaa Xaa His Xaa Gly Xaa Leu Val Trp Cys Xaa Xaa
1               5                   10                  15

Xaa

<210> SEQ ID NO 95
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is lysine, cystein, aspartic acid, glutamic
      acid, 2-amino suberic acid, or diaminopropionic acid
<220> FEATURE:
<221> NAME/KEY: MISC_FEATURE
<222> LOCATION: (10)..(10)
<223> OTHER INFORMATION: Xaa is glutamic acid, or aspartic acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 95

Xaa Xaa Xaa Cys Xaa Xaa His Xaa Gly Xaa Leu Val Trp Cys Xaa Xaa
1               5                   10                  15

Xaa

<210> SEQ ID NO 96
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
```

```
<221> NAME/KEY: MISC_FEATURE
<222> LOCATION: (8)..(8)
<223> OTHER INFORMATION: Xaa is arginine, or leucine
<220> FEATURE:
<221> NAME/KEY: MISC_FEATURE
<222> LOCATION: (10)..(10)
<223> OTHER INFORMATION: Xaa is lysine, glutamic acid, or aspartic acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 96

Xaa Xaa Xaa Cys Xaa Xaa His Xaa Gly Xaa Leu Val Trp Cys Xaa Xaa
1               5                   10                  15

Xaa

<210> SEQ ID NO 97
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is lysine, cystein, aspartic acid, glutamic
      acid, 2-amino suberic acid, or diaminopropionic acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 97

Xaa Xaa Xaa Cys Xaa Tyr His Xaa Gly Asn Leu Val Trp Cys Xaa Xaa
1               5                   10                  15

Xaa

<210> SEQ ID NO 98
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is arginine, leucine, lysine, cystein,
      aspartic acid, glutamic acid, 2-amino suberic acid, or
      diaminopropionic acid
<220> FEATURE:
<221> NAME/KEY: misc_feature
<222> LOCATION: (15)..(17)
<223> OTHER INFORMATION: Xaa can be any naturally occurring amino acid
```

```
<400> SEQUENCE: 98

Xaa Xaa Xaa Cys Ala Xaa His Xaa Gly Glu Leu Val Trp Cys Xaa Xaa
1               5                   10                  15

Xaa

<210> SEQ ID NO 99
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is alanine, serine, or threonine
<220> FEATURE:
<221> NAME/KEY: MISC_FEATURE
<222> LOCATION: (6)..(6)
<223> OTHER INFORMATION: Xaa is tyrosine, or tryptophan
<220> FEATURE:
<221> NAME/KEY: MISC_FEATURE
<222> LOCATION: (8)..(8)
<223> OTHER INFORMATION: Xaa is lysine, cystein, aspartic acid, glutamic
      acid, 2-amino suberic acid, or diaminopropionic acid
<220> FEATURE:
<221> NAME/KEY: MISC_FEATURE
<222> LOCATION: (10)..(10)
<223> OTHER INFORMATION: Xaa is glutamic acid, or aspartic acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 99

Xaa Xaa Xaa Cys Xaa Xaa His Xaa Gly Xaa Leu Val Trp Cys Xaa Xaa
1               5                   10                  15

Xaa

<210> SEQ ID NO 100
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is lysine, cystein, aspartic acid, glutamic
      acid, 2-amino suberic acid, or diaminopropionic acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 100

Xaa Xaa Xaa Cys Ala Tyr His Xaa Gly Glu Leu Val Trp Cys Xaa Xaa
1               5                   10                  15

Xaa

<210> SEQ ID NO 101
```

```
<211> LENGTH: 13
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (3)..(3)
<223> OTHER INFORMATION: Xaa is alanine, or threonine
<220> FEATURE:
<221> NAME/KEY: MISC_FEATURE
<222> LOCATION: (4)..(4)
<223> OTHER INFORMATION: Xaa is tyrosine, or tryptophan
<220> FEATURE:
<221> NAME/KEY: MISC_FEATURE
<222> LOCATION: (6)..(6)
<223> OTHER INFORMATION: Xaa is lysine, cystein, aspartic acid, glutamic
      acid, 2-amino suberic acid, or diaminopropionic acid
<220> FEATURE:
<221> NAME/KEY: MISC_FEATURE
<222> LOCATION: (8)..(8)
<223> OTHER INFORMATION: Xaa is glutamic acid, or aspartic acid

<400> SEQUENCE: 101

Asp Cys Xaa Xaa His Xaa Gly Xaa Leu Val Trp Cys Thr
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is alanine, or lysine
<220> FEATURE:
<221> NAME/KEY: MISC_FEATURE
<222> LOCATION: (6)..(6)
<223> OTHER INFORMATION: Xaa is tryptophan, or tyrosine
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid
<220> FEATURE:
<221> NAME/KEY: MISC_FEATURE
<222> LOCATION: (10)..(10)
<223> OTHER INFORMATION: Xaa is lysine, glutamine, glutamic acid,
      asparagine, or aspartic acid
<220> FEATURE:
<221> NAME/KEY: MISC_FEATURE
<222> LOCATION: (15)..(15)
<223> OTHER INFORMATION: Xaa is threonine, or lysine
<220> FEATURE:
<221> NAME/KEY: MISC_FEATURE
<222> LOCATION: (16)..(16)
<223> OTHER INFORMATION: Xaa is tyrosine, lysine, or absence
<220> FEATURE:
<221> NAME/KEY: MISC_FEATURE
<222> LOCATION: (17)..(17)
<223> OTHER INFORMATION: Xaa is histidine, lysine, or absence

<400> SEQUENCE: 102

Xaa Xaa Xaa Cys Xaa Xaa His Xaa Gly Xaa Leu Val Trp Cys Xaa Xaa
1               5                   10                  15

Xaa
```

```
<210> SEQ ID NO 103
<211> LENGTH: 15
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (3)..(3)
<223> OTHER INFORMATION: Xaa is alanine, or lysine
<220> FEATURE:
<221> NAME/KEY: MISC_FEATURE
<222> LOCATION: (4)..(4)
<223> OTHER INFORMATION: Xaa is tryptophan, or tyrosine
<220> FEATURE:
<221> NAME/KEY: MISC_FEATURE
<222> LOCATION: (6)..(6)
<223> OTHER INFORMATION: Xaa is arginine, leucine, lysine, aspartic
      acid, glutamic acid, 2-amino suberic acid, or diaminopropionic
      acid
<220> FEATURE:
<221> NAME/KEY: MISC_FEATURE
<222> LOCATION: (8)..(8)
<223> OTHER INFORMATION: Xaa is lysine, glutamine, glutamic acid,
      asparagine, or aspartic acid
<220> FEATURE:
<221> NAME/KEY: MISC_FEATURE
<222> LOCATION: (13)..(13)
<223> OTHER INFORMATION: Xaa is threonine, or lysine
<220> FEATURE:
<221> NAME/KEY: MISC_FEATURE
<222> LOCATION: (14)..(14)
<223> OTHER INFORMATION: Xaa is tyrosine, lysine, or absence
<220> FEATURE:
<221> NAME/KEY: MISC_FEATURE
<222> LOCATION: (15)..(15)
<223> OTHER INFORMATION: Xaa is histidine, lysine, or absence

<400> SEQUENCE: 103

Asp Cys Xaa Xaa His Xaa Gly Xaa Leu Val Trp Cys Xaa Xaa Xaa
1               5                   10                  15

<210> SEQ ID NO 104
<211> LENGTH: 13
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (3)..(3)
<223> OTHER INFORMATION: Xaa is alanine, or lysine
<220> FEATURE:
<221> NAME/KEY: MISC_FEATURE
<222> LOCATION: (4)..(4)
<223> OTHER INFORMATION: Xaa is tryptophan, or tyrosine
<220> FEATURE:
<221> NAME/KEY: MISC_FEATURE
<222> LOCATION: (6)..(6)
<223> OTHER INFORMATION: Xaa is arginine, leucine, lysine, cystein,
      aspartic acid, glutamic acid, 2-amino suberic acid, or
      diaminopropionic acid
<220> FEATURE:
<221> NAME/KEY: MISC_FEATURE
<222> LOCATION: (8)..(8)
<223> OTHER INFORMATION: Xaa is lysine, glutamine, glutamic acid,
      asparagine, or aspartic acid

<400> SEQUENCE: 104

Asp Cys Xaa Xaa His Xaa Gly Xaa Leu Val Trp Cys Thr
1               5                   10
```

```
<210> SEQ ID NO 105
<211> LENGTH: 17
<212> TYPE: PRT
<213> ORGANISM: Artificial Sequence
<220> FEATURE:
<223> OTHER INFORMATION: Peptide having an affinity to Fc region of
      human IgG
<220> FEATURE:
<221> NAME/KEY: MISC_FEATURE
<222> LOCATION: (5)..(5)
<223> OTHER INFORMATION: Xaa is alanine, or lysine
<220> FEATURE:
<221> NAME/KEY: MISC_FEATURE
<222> LOCATION: (6)..(6)
<223> OTHER INFORMATION: Xaa is Tryptophan, or tyrosine
<220> FEATURE:
<221> NAME/KEY: MISC_FEATURE
<222> LOCATION: (8)..(8)
<223> OTHER INFORMATION: Xaa is arginine, leucine, lysine, aspartic
      acid, glutamic acid, 2-amino suberic acid, or diaminopropionic
      acid
<220> FEATURE:
<221> NAME/KEY: MISC_FEATURE
<222> LOCATION: (10)..(10)
<223> OTHER INFORMATION: Xaa is lysine, glutamine, glutamic acid,
      asparagine, or aspartic acid
<220> FEATURE:
<221> NAME/KEY: MISC_FEATURE
<222> LOCATION: (15)..(15)
<223> OTHER INFORMATION: Xaa is threonine, or lysine
<220> FEATURE:
<221> NAME/KEY: MISC_FEATURE
<222> LOCATION: (16)..(16)
<223> OTHER INFORMATION: Xaa is tyrosine, lysine, or absence
<220> FEATURE:
<221> NAME/KEY: MISC_FEATURE
<222> LOCATION: (17)..(17)
<223> OTHER INFORMATION: Xaa is histidine, lysine, or absence

<400> SEQUENCE: 105

Arg Gly Asn Cys Xaa Xaa His Xaa Gly Xaa Leu Val Trp Cys Xaa Xaa
1               5                   10                  15

Xaa
```